United States Patent
Modlin et al.

(10) Patent No.: US 12,258,633 B2
(45) Date of Patent: *Mar. 25, 2025

(54) COMPOSITIONS, METHODS AND KITS FOR DIAGNOSIS OF A GASTROENTEROPANCREATIC NEUROENDOCRINE NEOPLASM

(71) Applicant: Clifton Life Sciences LLC, Charlestown (KN)

(72) Inventors: Irvin Mark Modlin, Woodbridge, CT (US); Mark Kidd, New Haven, CT (US); Ignat Drozdov, Stratford Upon Avon (GB)

(73) Assignee: Clifton Life Sciences LLC, Charlestown (KN)

( * ) Notice: Subject to any disclaimer, the term of this patent is extended or adjusted under 35 U.S.C. 154(b) by 103 days.

This patent is subject to a terminal disclaimer.

(21) Appl. No.: 17/521,205

(22) Filed: Nov. 8, 2021

(65) Prior Publication Data

US 2022/0325351 A1    Oct. 13, 2022

Related U.S. Application Data

(60) Continuation of application No. 16/528,864, filed on Aug. 1, 2019, now Pat. No. 11,168,372, which is a division of application No. 14/855,229, filed on Sep. 15, 2015, now Pat. No. 10,407,730.

(60) Provisional application No. 62/050,465, filed on Sep. 15, 2014.

(51) Int. Cl.
  *C12Q 1/6886* (2018.01)
  *G01N 33/574* (2006.01)

(52) U.S. Cl.
  CPC ..... *C12Q 1/6886* (2013.01); *G01N 33/57407* (2013.01); *C12Q 2600/112* (2013.01); *C12Q 2600/118* (2013.01); *C12Q 2600/158* (2013.01)

(58) Field of Classification Search
  CPC ............ C12Q 1/6886; C12Q 2600/158; C12Q 2600/112; C12Q 2600/118; G01N 33/57407
  See application file for complete search history.

(56) References Cited

U.S. PATENT DOCUMENTS 10,407,730 B2  9/2019  Modlin et al.
11,168,372 B2  11/2021  Modlin et al.

FOREIGN PATENT DOCUMENTS

WO   WO 2009/150469 A2   12/2009
WO   WO 2012/119013 A1    9/2012
WO   WO 2005/020795 A2    3/2015

OTHER PUBLICATIONS

Banck, M. et al., "The genomic landscape of small intestine neuroendocrine tumors" J Clin Invest 2013; 123(6):2502-2508.
Boom, R. et al. (1990) "Rapid and Simple Method for Purification of Nucleic Acids" J Clin Microbiol, 28(3):495-503.
Cai, Y-C. et al., "Cytokeratin 7 and 20 and thyroid transcription factor 1 can help distinguish pulmonary from gastrointestinal carcinoid and pancreatic endocrine tumors," Hum Pathol 2001;32(10):1087-1093.
Chomczynski, P. (2006). "The single-step method of RNA isolation by acid guanidinium thiocyanate-phenol-chloroform extraction: twenty-something years on" Nat Protoc, 1(2):581-585.
Cohen, S.J. et al. "Isolation and characterization of circulating tumor cells in patients with metastatic colorectal cancer" Clin Colorectal Cancer 2006; 6(2):125-132.
Cristofanilli, M. et al., "Circulating tumor cells, disease progression, and survival in metastatic breast cancer", N Engl J Med 2004, 351(8):781-791.
Ćwikla, J.B. et al. (2015) "Circulating Transcript Analysis (NETest) in GEP-NETs Treated With Somatostatin Analogs Defines Therapy" J Clin Endocrinol Metab, 100(11):E1437-E1445.
Danila, D. et al. "Circulating tumor cell number and prognosis in progressive castration-resistant prostate cancer", Clin Cancer Res 2007; 13(23):7053-7058.
Dhawan, M. et al. (2010) "Application of committee kNN classifiers for gene expression profile classification" Int J Bioinform Res Appl, 6(4):344-352.
Drozdov, I. et al. (2010) "Genome-wide expression patterns in physiological cardiac hypertrophy" BMC Genomics, 11:557, 13 pages.
Evgeniou, T. et al. (1999) "Regularization Networks and Support Vector Machines" Advances in Computational Math, 13(1):1-53.
Freeman, T.C. et al. (Oct. 2007) "Construction, visualization, and clustering of transcription networks from microarray expression data" PLoS Comput Biol, 3(10):2032-2042.

(Continued)

*Primary Examiner* — Joseph G. Dauner
(74) *Attorney, Agent, or Firm* — COOLEY LLP

(57) ABSTRACT

Methods are provided for diagnosing, detecting, or prognosticating a GEP-NEN based on the expression level score of biomarkers exhibiting differential expression in subjects having a GEP-NEN relative to a reference or control sample. The invention also provides compositions and kits comprising these biomarkers and methods of using these biomarkers in subsets or panels thereof to diagnose, classify, and monitor GEP-NEN and types of GEP-NEN. The methods and compositions provided herein may be used to diagnose or classify a subject as having a GEP-NEN, to distinguish between different stages of GEP-NENs, e.g., stable or progressive, to provide a measure of risk of developing a progressive GEP-NEN, and to gauge the completeness of treatments for GEP-NEN including, but not limited to surgery and somatostatin therapy.

15 Claims, 47 Drawing Sheets

Specification includes a Sequence Listing.

(56) References Cited

OTHER PUBLICATIONS

Gabriel, K.R. (Dec. 1971) "The Biplot Graphic Display of Matrices with Application to Principal Component Analysis" Biometrika, 58(3):453-467.
Gallant, S.I. (Jun. 1990) "Perceptron-Based Learning Algorithms" IEEE Transactions on Neural Networks, 1(2):179-191.
Glotsos, D. et al. (2005) "Automated diagnosis of brain tumours astrocytomas using probabilistic neural network clustering and support vector machines" Int J Neural Syst, 15(1-2):1-11.
Godfrey, T.E. et al. (May 2000) "Quantitative mRNA Expression Analysis from Formalin-Fixed, Paraffin-Embedded Tissues Using 5' Nuclease Quantitative Reverse Transcription-Polymerase Chain Reaction" Molec Diagnostics, 2(2):84-91.
Hanahan, D and R.A. Weinberg (Mar. 4, 2011) "Hallmarks of cancer: The next generation" Cell, 144(5):646-674.
Hod, Y. (1992) "A Simplified Ribonuclease Protection Assay" Biotechniques, 13(6):852-853.
Hoshikawa et al. "Hypoxia induces different genes in the lungs of rat compared with mice" Physical Genomics 2003; 12:209-219.
Ji, S. and J. Ye (Oct. 2008) "Kernel Uncorrelated and Regularized Discriminant Analysis: A Theoretical and Computational Study" IEEE Transactions on Knowledge and Data Engineering, 20(10):1311-1321.
Kahan, L., "Medical devices; immunology and microbiology devices; classification of the immunomagnetic circulating cancer cell selection and enumeration system", Final rule. Department of Healh and Human Services. Fed Regist May 11, 2004; 69(91):26036-26038.
Kawarazaki, S. et al. (2010) "Conversion of a molecular classifier obtained by gene expression profiling into a classifier based on real-time PCR: a prognosis predictor for gliomas" BMC Med Genomics, 3:52, 8 pages.
Kidd, M. et al. (2005) "Microsatellite instability and gene mutations in transforming growth factor-beta type II receptor are absent in small bowel carcinoid tumors" Cancer, 103(2):229-236.
Kidd, M. et al. (2006) "Isolation, Functional Characterization and transcriptome of the Mastomys ileal enterochromaffin cells," Am J Physiol Gastrointest Liver Physiol, 291:G778-G791.
Kidd, M. et al. (2006) "The Role of Genetic Markers—Nap1L1, MAGE-D2, and MTA1—in Defining Small-Intestinal Carcinoid Neoplasia" Ann Surg Oncol, 13(2):253-262.
Kidd, M. et al. (2007) "GeneChip, geNorm, and Gastrointestinal tumors: novel reference genes for real-time PCR" Physiol Genomics, 30:363-370.
Kidd, M. et al. (2015) "Blood and tissue neuroendocrine tumor gene cluster analysis correlate, define hallmarks and predict disease status" Endocrine-Related Cancer, 22:561-575.
Kinross et al., "Metabonomic profiling: A Novel Approach in Neuroendocrine Neoplasias" Surgery, Dec. 1, 2013, vol. 154, No. 6, pp. 1185-1193.
Kohavi, R. (1995) "A Sudy of Cross-Validation and Bootstrap for Accuracy Estimation and Model Selection" Proceedings of the Fourteenth International Joint Conference on Artificial Intelligence, 2(12):1137-1143.
Lawlor, G, et al. (2011) "Increased Peripheral Blood GATA-3 Expression in Asymptomatic Patients With Active Ulcerative Colitis at Colonoscopy" Gastroenterology, 140(Suppl 1):S-842, Abstract Tu1827.
Lilien, R.H. et al. (2003) "Probabilistic Disease Classification of Expression-Dependent Proteomic Data from Mass Spectrometry of Human Serum" J Comput Biol, 10(6):925-946.
Markey, M.K. et al. (2002) "Perceptron error surface analysis: a case study in breast cancer diagnosis" Comput Biol Med, 32(2):99-109.
Mattfeldt, T. et al. (2003) "Classification of Prostatic Carcinoma with Artificial Neural Networks Using Comparative Genomic Hybridization and Quantitative Stereological Data" Pathol Res Pract, 199(12):773-784.
Mazzaglia, P.J. et al. (2007) "Laparoscopic radiofrequency ablation of neuroendocrine liver metastases: a 10-year experience evaluating predictors of survival" Surgery, 142(1):10-19.

Michiels, et al. (2007) "Interpretation of microarray data in cancer" Br J Cancer, 96(8):1155-1158.
Mimori, K. et al., "A large-scale study of MT1-MMP as a marker for isolated tumor cells in peripheral blood and bone marrow in gastric cancer cases," Ann Surg Oncol 2008; 15(10):2934-2942.
Modlin, I. et al. (2006) "The functional characterization of normal and neoplastic human enterochromaffin cells", J Clin Endocrinol Metab, 91(6):2340-2348.
Modlin, I. et al. (2013) "The Identification of gut neuroendocrine tumor disease by multiple synchronous transcript analysis in blood", Plos One, vol. 8, Issue 5, e63364 (12 pages).
Modlin, I. et al. (2013) "The Identification of gut neuroendocrine tumor disease by multiple synchronous transcript analysis in blood", Plos One, vol. 8, Issue 5, e63364, Supplementary Methods.
Modlin, I.M. et al. (2016) "Blood measurement of neuroendocrine gene transcripts defines the effectiveness of operative resection and ablation strategies" Surgery, 159(1):336-347.
Noble, W.S. (Dec. 2006) "What is a support vector machine?" Nat Biotechnol, 24(12):1565-1567.
Parker, R.M.C. and N.M. Barnes (1999) "mRNA: Detection by In Situ and Northern Hybridization" Methods in Molecular Biology, 106:247-283.
Peng, H. et al. (Aug. 2005) "Feature Selection Based on Mutual Information: Criteria of Max-Dependency, Max-Relevance, and Min-Redundancy" IEEE Transactions on Pattern Analysis and Machine Intelligence, 27(8):1226-1238.
Picon, A. et al. (1998) "A subset of metastatic human colon cancers expresses elevated levels of transforming growth factor beta 1" Cancer Epidemiol Biomarkers Prev, 7(6):497-504.
Pima, I. and M. Aladjem (2004) "Regularized discriminant analysis for face recognition" Pattern Recognition, 37(9):1945-1948.
Pimentel, M. et al. (2011) "Validating a New Genomic Test for Irritable Bowel Syndrome" Gastroenterology, 140(Suppl 1):S-798, Abstract Tu1329.
Pirooznia, M. et al. (2008) "A comparative study of different machine learning methods on microarray gene expression data" BMC Genomics, 9(Suppl 1):S13, 13 pages.
Ross, A.A. et al. "Detection and viability of tumor cells in peripheral blood stem cell collections from breast cancer patients using immunocytochemical and clonogenic assay techniques" Blood 1993; 82(9):2605-2610.
Schimmack et al., "The Clinical Implications and Biologic Relevance of Neurofilament Expression in Gastroenteropancreatic Neuroendocrine Neoplasms", May 15, 2012, Cancer, vol. 118, No. 10, pp. 2763-2775.
Sieuwerts, A.M. et al., "Molecular characterization of circulating tumor cells in large quantities of contaminating leukocytes by a multiplex real-time PCR," Breast Cancer Res Treat 2009; 118(3):455-468.
Simon et al. "Roadmap for Developing and Validating Therapeutically Relevant Genomic Classifiers" Journal of Clinical Oncology 2005; 23(29):7332-7341.
Specht, K. et al. (Feb. 2001) "Quantitative Gene Expression Analysis in Microdissected Archival Formalin-Fixed and Paraffin-Embedded Tumor Tissue" Am J Pathol, 158:419-429.
Tannapfel, A. et al., "BRAF gene mutations are rare events in gastroenteropancreatic neuroendocrine tumors," Am J Clin Pathol 2005; 123(2):256-260.
Urgard, E. et al. (2011) "Metagenes Associated with Survival in Non-Small Cell Lung Cancer" Cancer Inform, 10:175-183.
Van Eeden, S. et al. "Classification of low-grade neuroendocrine tumors of midgut and unknown origin" Hum Pathol 2002; 33(11):1126-1132.
Vandebriel, R.J. et al. (1998) "Altered cytokine (receptor) mRNA expression as a tool in immunotoxicology" Toxicology, 130(1):43-67.
Vandesompele, J. et al. (2002) "Accurate normalization of real-time quantitative RT-PCR data by geometric averaging of multiple internal control genes" Genome Biol, 3(7):research0034.1-0031.11.
Weis, J.H. et al. (Aug. 1992) "Detection of rare mRNAs via quantitative RT-PCT" Trends in Genetics, 8:263-264.

(56) References Cited

OTHER PUBLICATIONS

Whitehead et al. "Variation in tissue-specific gene expression among natural populations" Genome Biology, 2005; 6(2):Article R13.
Wong et al. "Real-time PCR for mRNA quantitation" Bio Techniques, 2005; 39(1):1-11.
Yu, L. et al (2002) "TGF-beta receptor-activated p38 MAP kinase mediates Smad-independent TGF-beta responses" EMBO J, 21(14):3749-3759.
Zampetaki, A. et al. (2010) "Plasma MicroRNA Profiling Reveals Loss of Endothelial MiR-126 and Other MicroRNAs in Type 2 Diabetes" Circ Res, 107(6): 810-817.
Zhang, H. et al (2001) "Recursive Partitioning for Tumor Classification with Gene Expression Microarray Data" Proc Natl Acad Sci USA, 98(12):6730-6735.
Zikusoka, M.N. et al. (2005) "Molecular genetics of gastroenteropancreatic neuroendocrine tumors", Cancer, 104:2292-2309.

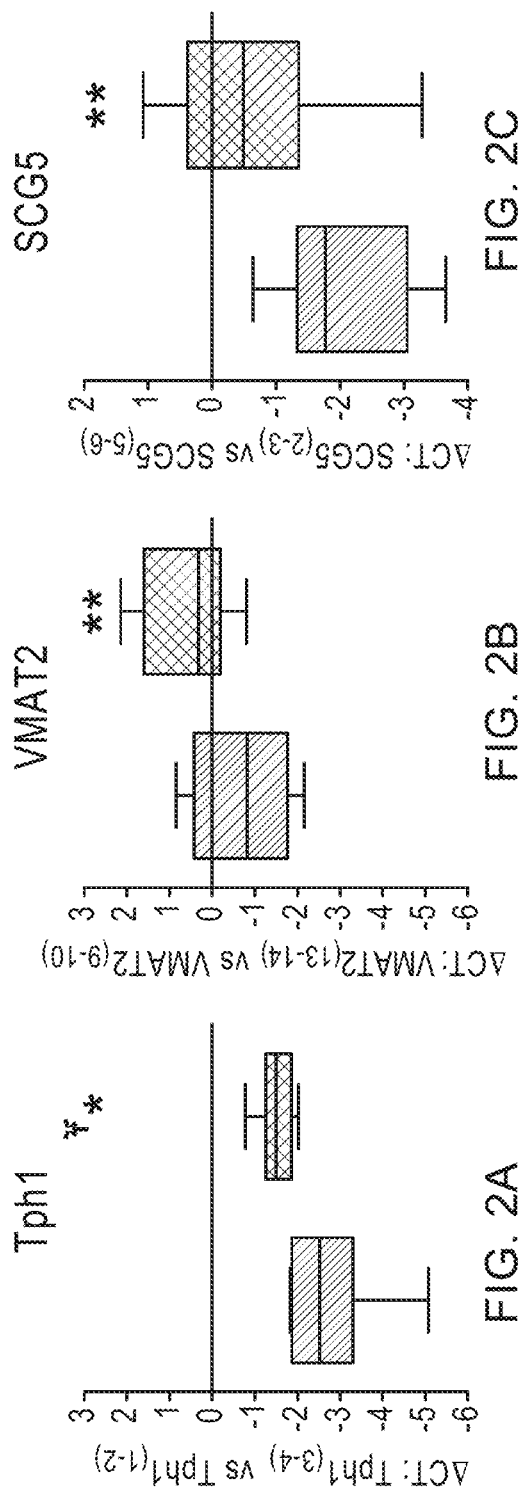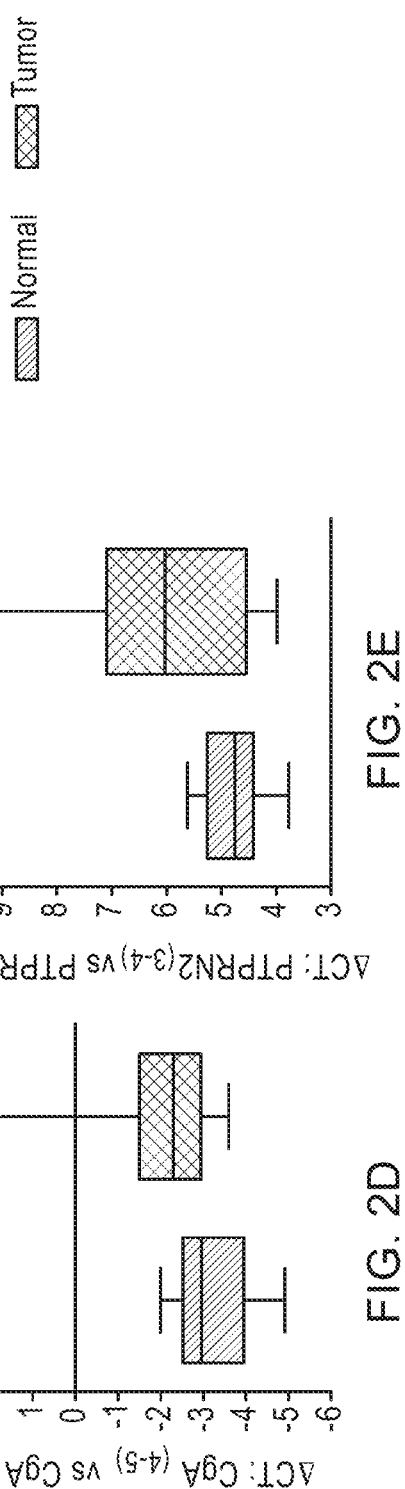

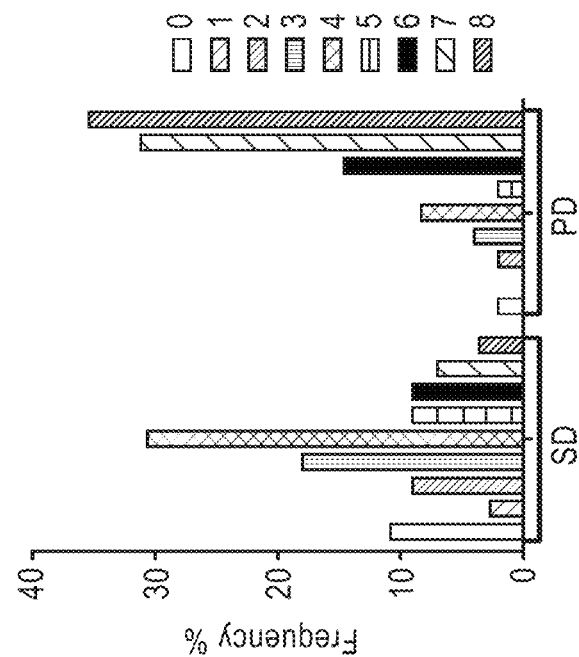
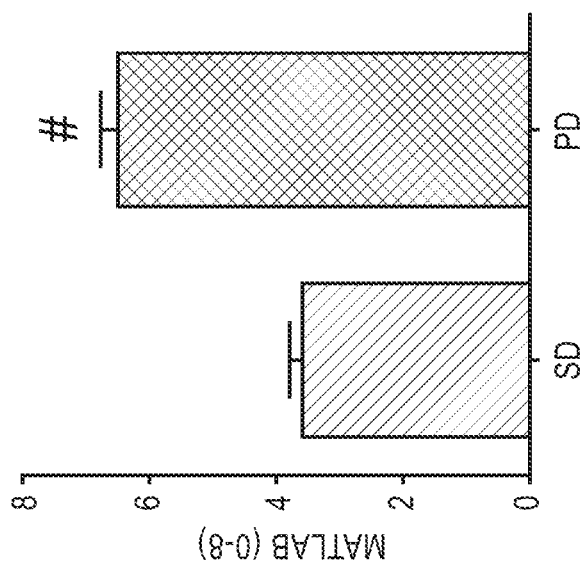
FIG. 6A
FIG. 6B

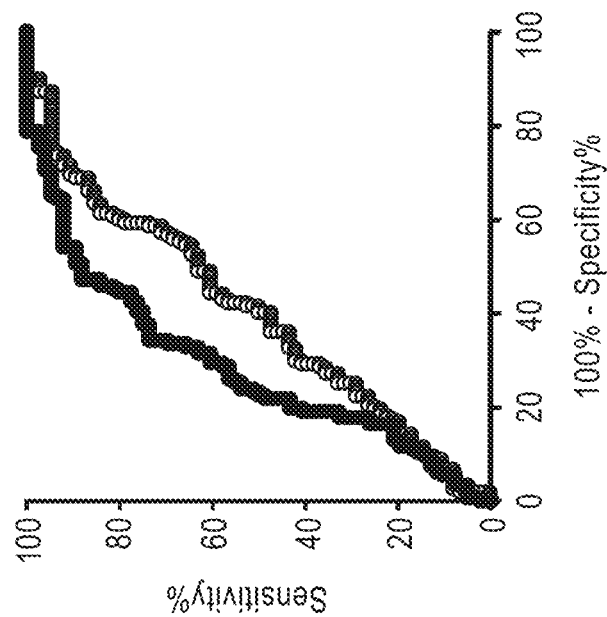
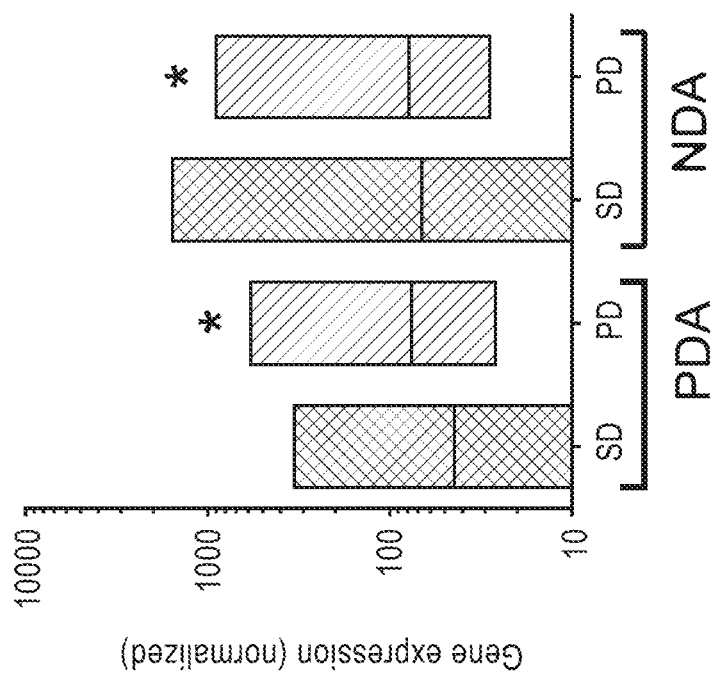
FIG. 20A
FIG. 20B

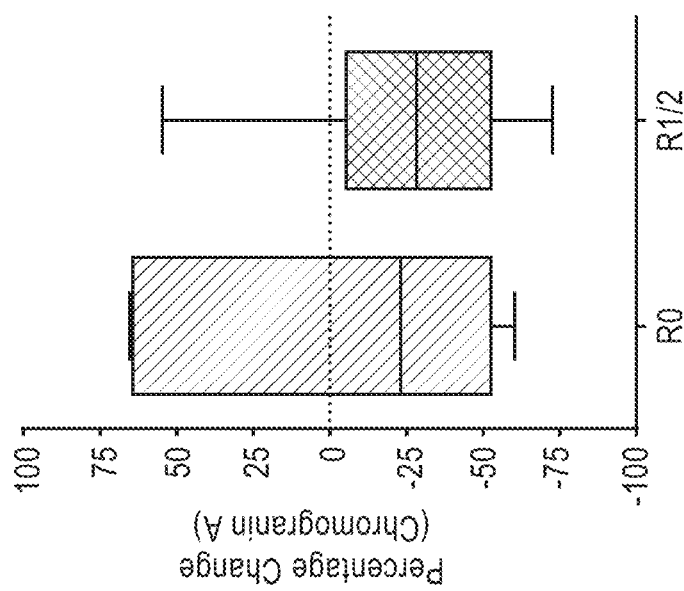
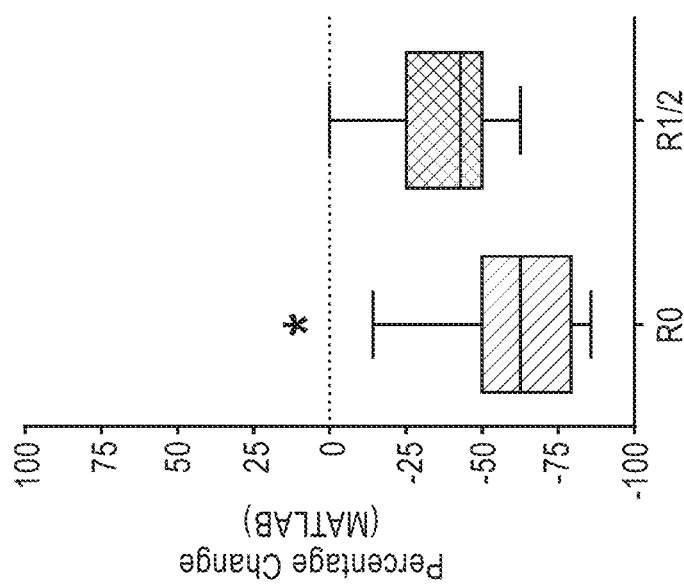
FIG. 25A
FIG. 25B

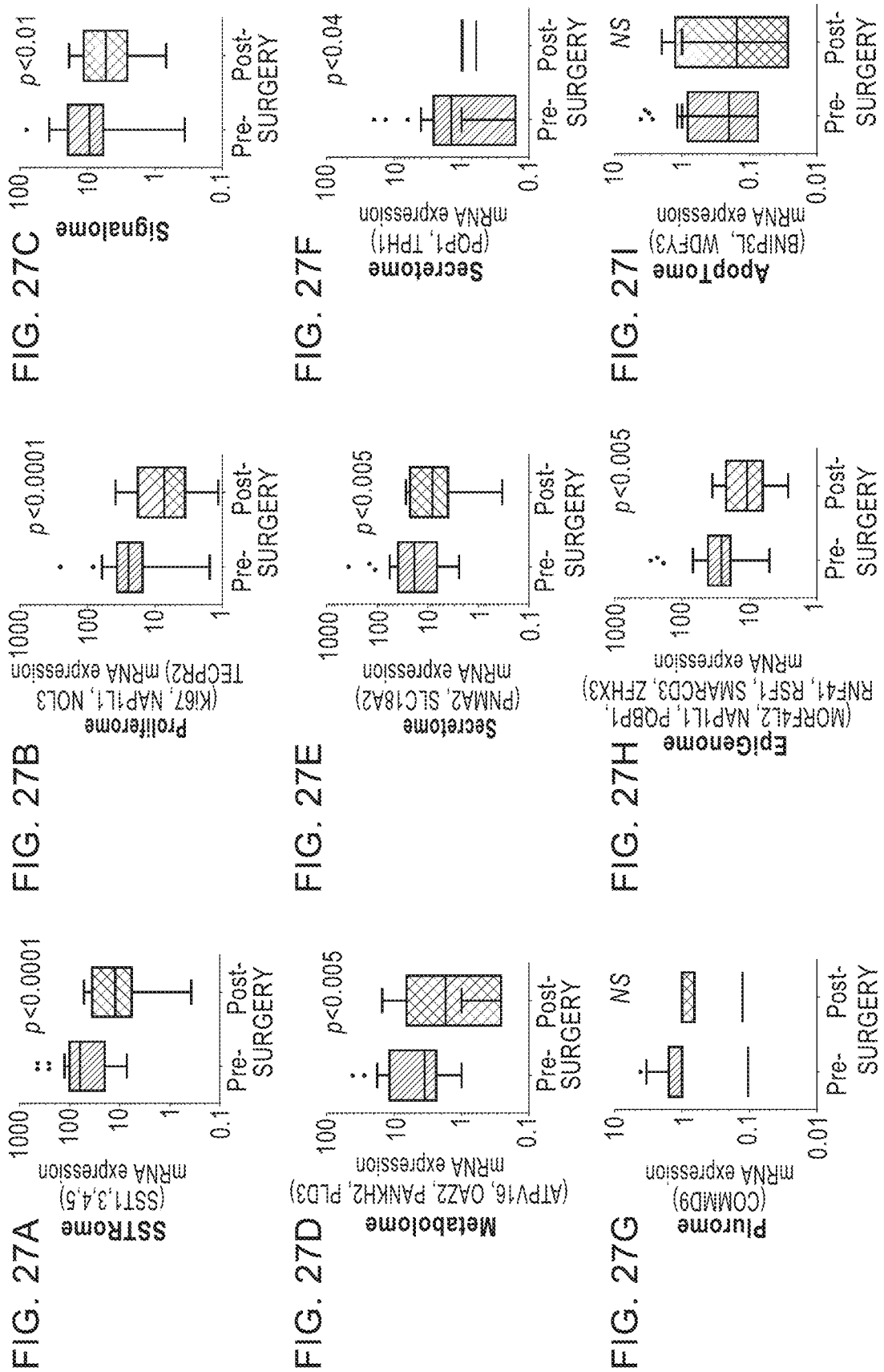

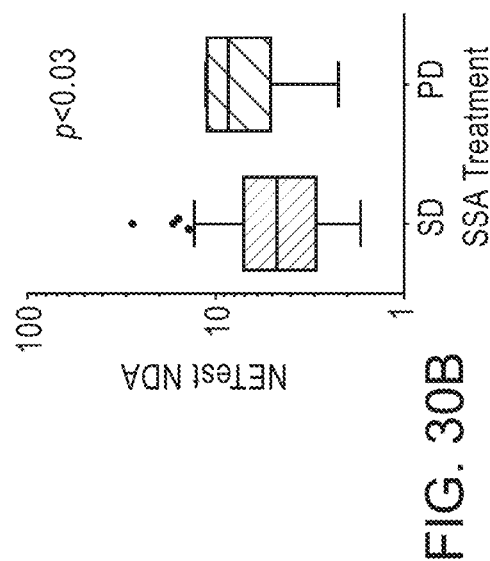
FIG. 30B
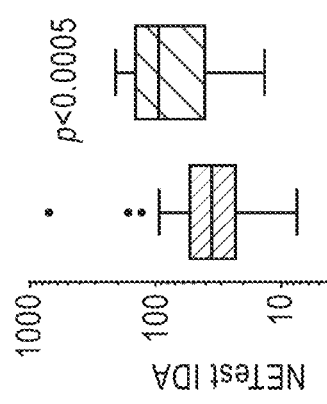
FIG. 30D
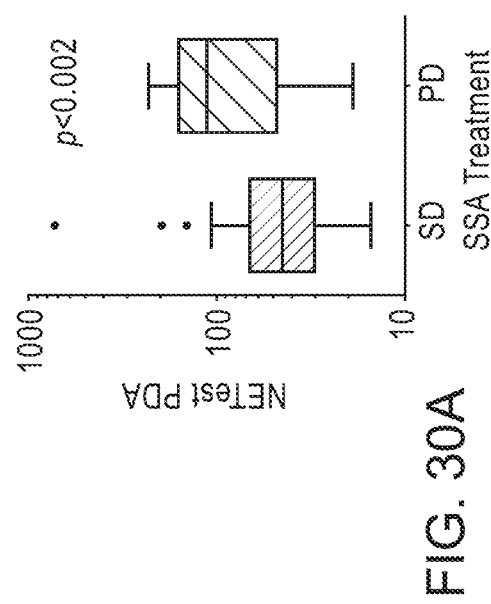
FIG. 30A
FIG. 30C

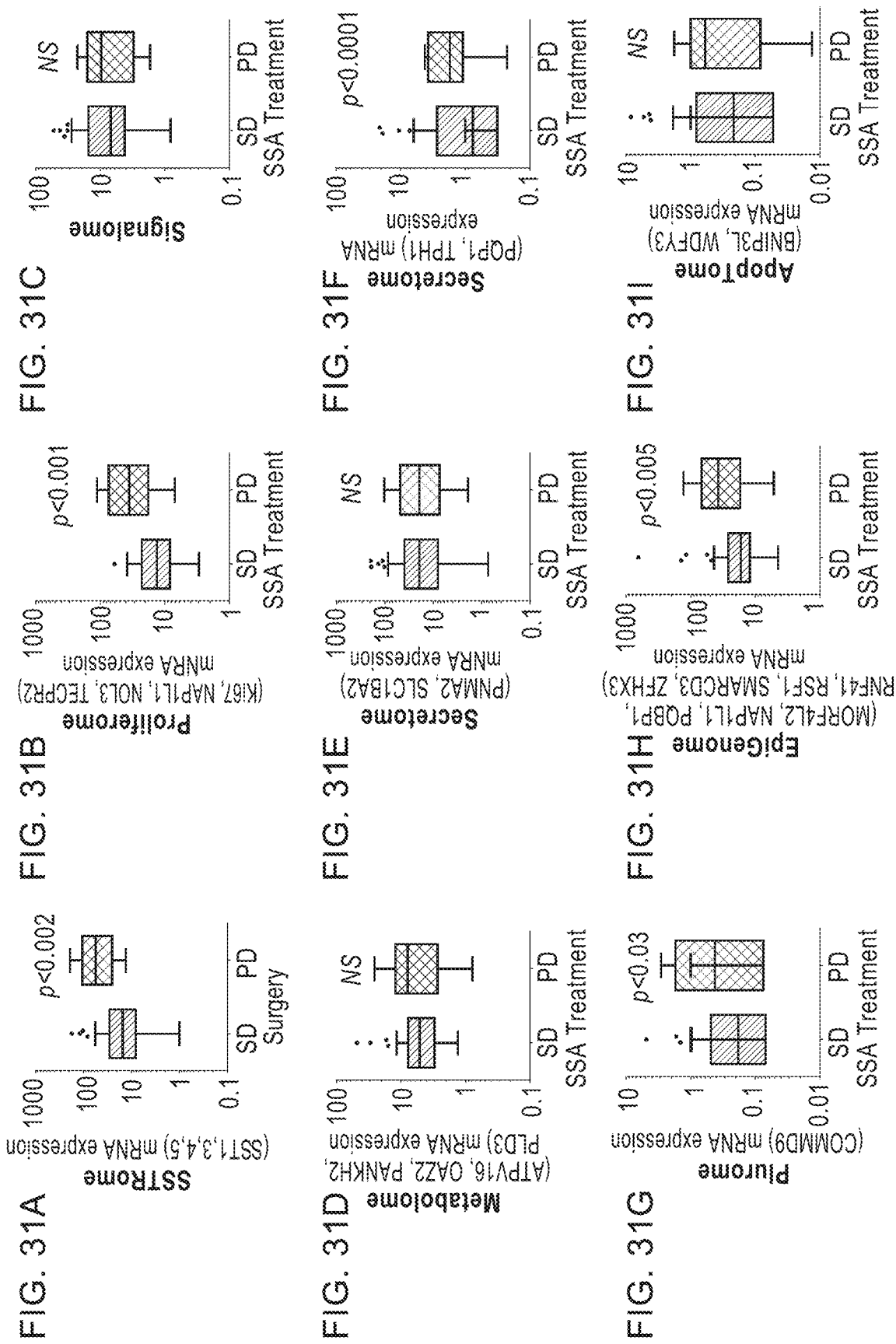

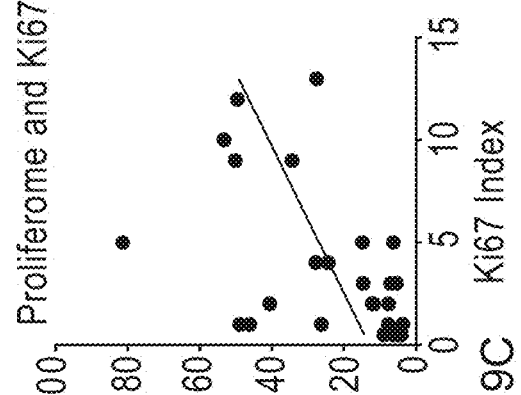
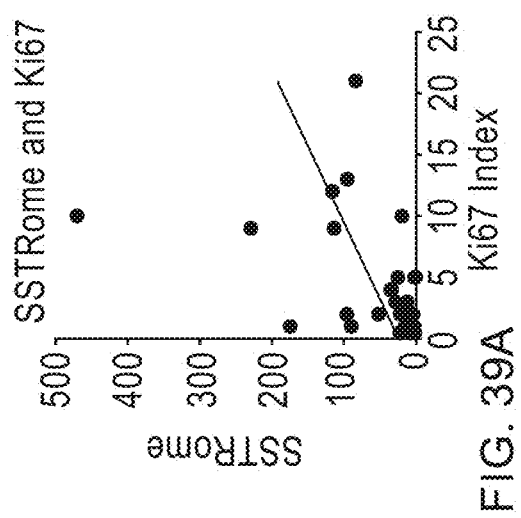
FIG. 39A  FIG. 39B  FIG. 39C  FIG. 39D  FIG. 39E  FIG. 39F

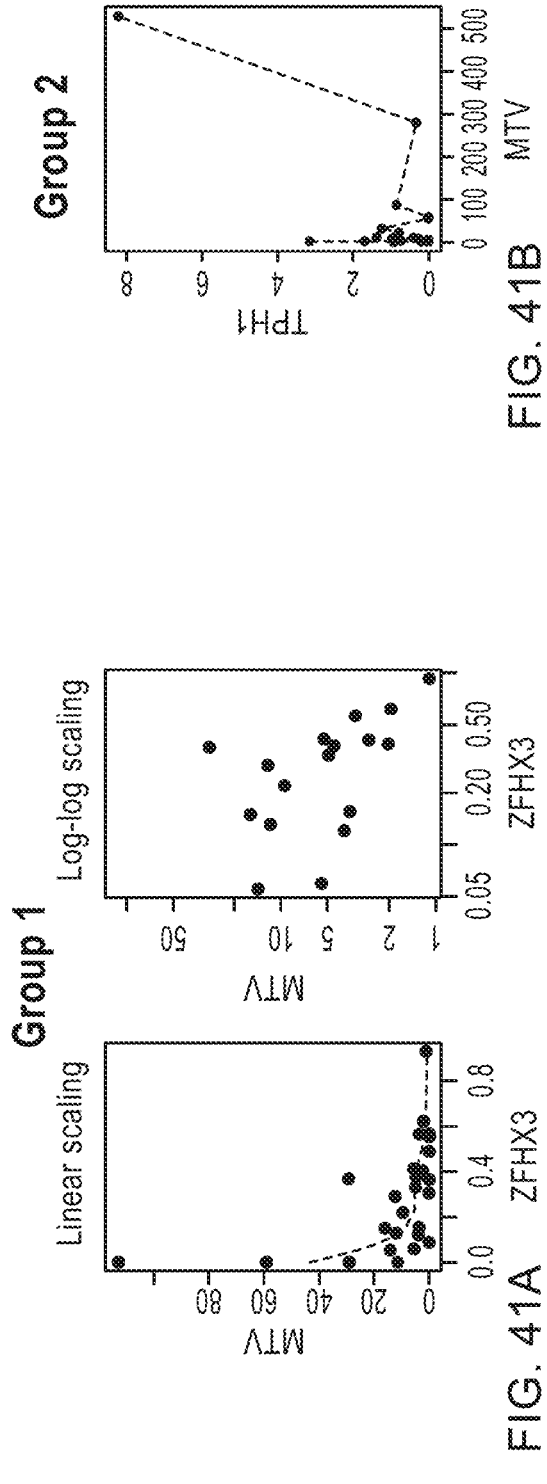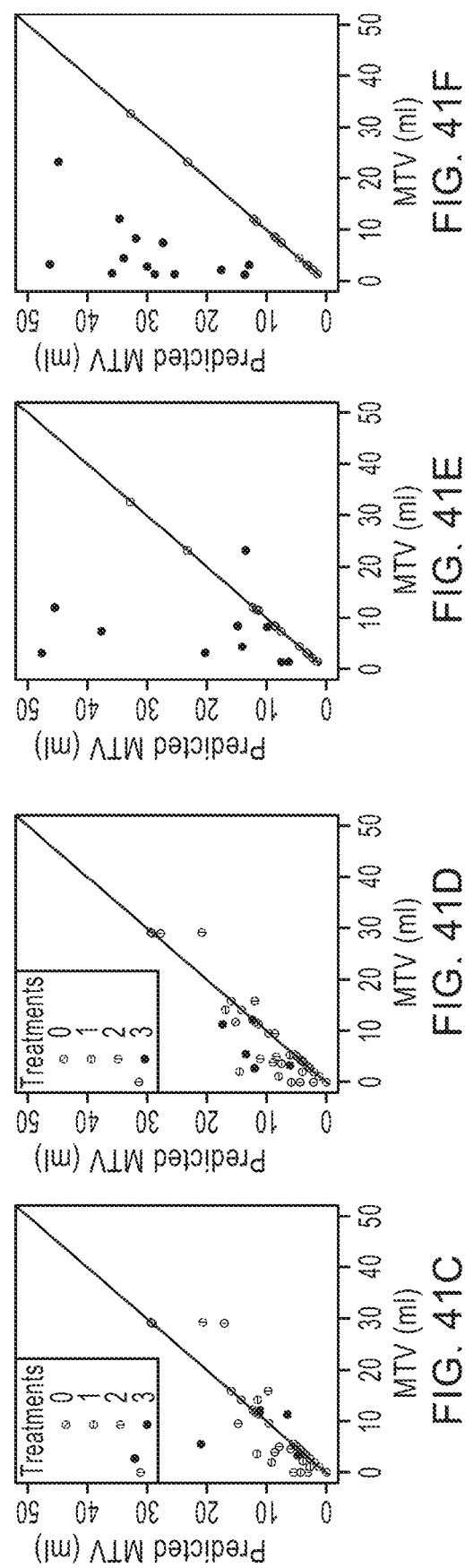

COMPOSITIONS, METHODS AND KITS FOR DIAGNOSIS OF A GASTROENTEROPANCREATIC NEUROENDOCRINE NEOPLASM

CROSS REFERENCE TO RELATED APPLICATIONS

This application is a Continuation of U.S. patent application Ser. No. 16/528,864, filed on Aug. 1, 2019, now U.S. Pat. No. 11,168,372. U.S. patent application Ser. No. 16/528,864 is a Divisional of U.S. patent application Ser. No. 14/855,229, filed on Sep. 15, 2015, now U.S. Pat. No. 10,407,730. U.S. patent application Ser. No. 14/855,229 claims the priority to, and the benefit of, U.S. Provisional Application Ser. No. 62/050,465, filed on Sep. 15, 2014. The contents of each of the aforementioned applications are incorporated by reference in their entireties.

SEQUENCE LISTING

The Sequence Listing associated with this application is provided in text format in lieu of a paper copy and is hereby incorporated by reference into the specification. The name of the text file containing the Sequence Listing is "CLSL-001_C01US_SeqList". The text file is about 298,815 bytes in size, was created on Nov. 5, 2021, and is being submitted electronically via EFS-Web.

BACKGROUND OF THE INVENTION

Gastroenteropancreatic (GEP) neuroendocrine neoplasm (GEP-NEN), also referred to as Gastroenteropancreatic Neuroendocrine Tumor and Neuroendocrine Tumor (NET), is the second most prevalent malignant tumor in the gastrointestinal (GI) tract in the U.S. Incidence and prevalence have increased between 100 and 600 percent in the U.S. over the last thirty years, with no significant increase in survival.

Heterogeneity and complexity of GEP-NENs has made diagnosis, treatment, and classification difficult. These neoplasms lack several mutations commonly associated with other cancers and microsatellite instability is largely absent. See Tannapfel A, Vomschloss S, Karhoff D, et al., "BRAF gene mutations are rare events in gastroenteropancreatic neuroendocrine tumors," *Am J Clin Pathol* 2005; 123(2): 256-60; Banck M, Kanwar R, Kulkarni A A, et al., "The genomic landscape of small intestine neuroendocrine tumors," *J Clin Invest* 2013; 123(6):2502-8; Zikusoka M N, Kidd M, Eick G, et al., Molecular genetics of gastroenteropancreatic neuroendocrine tumors. *Cancer* 2005; 104:2292-309; Kidd M, Eick G, Shapiro M D, et al. Microsatellite instability and gene mutations in transforming growth factor-beta type II receptor are absent in small bowel carcinoid tumors," *Cancer* 2005; 103(2):229-36.

Individual histopathologic subtypes as determined from tissue resources e.g., biopsy, associate with distinct clinical behavior, yet there is no definitive, generally accepted pathologic classification or prediction scheme, hindering treatment assessment and follow-up.

Existing diagnostic and prognostic approaches for GEP-NENs include imaging (e.g., CT or MRI), histology, measurements of circulating hormones and proteins associated with NENs e.g., chromogranin A and detection of some gene products. Available methods are limited, for example, by low sensitivity and/or specificity, inability to detect early-stage disease, or exposure to radiation risk. GEP-NENs often go undiagnosed until they are metastatic and often untreatable. In addition, follow-up is difficult, particularly in patients with residual disease burden.

There is a need for specific and sensitive methods and agents for the detection of GEP-NEN, including stable and progressive GEP-NEN, for example, for use in diagnosis, prognosis, prediction, staging, classification, treatment, monitoring, and risk assessment, and for investigating and understanding molecular factors of pathogenesis, malignancy, and aggressiveness of this disease. For example, such methods and agents are needed that can be repeatedly and directly collected with low risk exposure e.g., non-invasive peripheral blood test, be performed simply, rapidly, and at relatively low cost.

The present application overcomes the above-noted problems by providing novel compositions, methods, and kits for accurately diagnosing, detecting, and monitoring the presence of GEP-NENs and/or the types or stage of GEP-NEN in circulating peripheral blood samples. The described embodiments furthermore may be used to identify a level of risk for a patient to develop a progressive GEP-NEN, and/or to determine the risk of residual or reoccurring progressive GEP-NEN in a post-surgery or post-somatostatin treated human patient. In addition, it can be used as a prognostic for predicting response to therapy e.g., peptide receptor radiotherapy (PRRT).

SUMMARY OF THE INVENTION

In one aspect, the present invention relates to gastroenteropancreatic neuroendocrine neoplasm (GEP-NEN) biomarkers measured in circulating blood, the detection of which may be used in diagnostic, prognostic and predictive methods. Among the provided objects are GEP-NEN biomarkers, feature subsets and panels of the biomarkers, agents for binding and detecting the biomarkers, kits and systems containing such agents, and methods and compositions for detecting the biomarkers, for example, in biological samples e.g., blood, as well as prognostic, predictive, diagnostic, and therapeutic uses thereof.

Provided are agents, sets of agents, and systems containing the agents for GEP-NEN prognosis, detection and diagnosis. Typically, the systems include a plurality of agents (e.g., set of agents), where the plurality specifically binds to and/or detects a plurality of GEP-NEN biomarkers in a panel of GEP-NEN biomarkers. The agents may be isolated polypeptides or polynucleotides which specifically bind to one or more GEP-NEN biomarkers. For example, provided are sets of isolated polynucleotides and polypeptides that bind to a panel of GEP-NEN biomarkers, and methods and uses of the same.

Also provided are prognostic, diagnostic, and predictive methods and uses of the agents, compositions, systems, and kits for GEP-NEN and associated conditions, syndromes and symptoms. For example, provided are methods and uses for detection, diagnosis, classification, prediction, therapeutic monitoring, prognosis, or other evaluation of GEP-NEN or an outcome, stage or level of aggressiveness or risk thereof, or associated condition. In some embodiments, the methods are performed by determining the presence, absence, expression levels, or expression profile of a GEP-NEN biomarker, more typically a plurality of GEP-NEN biomarkers, such as a feature subset chosen from a panel of biomarkers, and/or comparing such information with normal or reference expression levels or profiles or standards. Thus, in some embodiments, the methods are carried out by obtaining a biological test sample and detecting the presence, absence, expression level score, or expression profile of a GEP-NEN biomarker as described herein. For example, the methods can be performed with any of the systems of agents, e.g., polynucleotides or polypeptides, provided herein. For example, the methods generally are carried out using one or more of the provided systems.

Provided are methods, agents and compositions for detection of and distinguishing between a number of different GEP-NEN types or stages. Exemplary GEP-NEN types and stages include stable disease (SD) and progressive (highly active) disease (PD).

In one aspect, the provided methods and compositions may be used to specifically and sensitively detect different stages of GEP-NENs, such as GEP-NENs in a stable disease (SD) or progressive disease (PD) states; in some aspects, the methods and compositions may be used to predict disease progression, treatment response, and metastasis. Methods and compositions provided herein are useful for diagnosis, prognosis, prediction, staging, classification, treatment, monitoring, assessing risk, and investigating molecular factors associated with GEP-NEN disease.

Provided are such methods capable of being carried out quickly, simply, and at relatively low cost, as compared to other diagnostic and prognostic methods.

Provided are methods and compositions that are useful for defining gene expression-based classification of GEP-NENs, and thus are useful for allowing the prediction of malignancy and metastasis, such as in early stage disease or using histologically negative samples, providing accurate staging, facilitating rational therapy, and in developing large validated clinical datasets for GEP-NEN-specific therapeutics.

The GEP-NEN biomarkers may include a subset of biomarkers, the expression of which is different in or is associated with the presence or absence of GEP-NEN, or is different in or is associated with a particular classification, stage, aggressiveness, severity, degree, metastasis, symptom, risk, treatment responsiveness or efficacy, or associated syndrome. The subset of GEP-NEN biomarkers typically includes at least 22 GEP-NEN biomarkers. In some embodiments, the subset of biomarkers includes at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers, or includes at or about 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers.

For example, in some aspects, the subset of biomarkers includes at least 22, or at least 38, or at least 51 biomarkers. In a particular example, the subset contains at least 22 biomarkers, or about 22 biomarkers, or 22 biomarkers, chosen from a panel of 38 biomarkers. In some embodiments, the subset of biomarkers includes at least 22, 23, 24, 25, 26, 27, 28, 29, 30, 31, 32, 33, 34, 35, 36, 37, or 38 biomarkers chosen from a panel of 38 biomarkers.

Because the systems, methods, and kits contain a plurality of agents that specifically bind to or hybridize to the biomarkers in the panel, the number of biomarkers generally relates to the number of agents in a particular system. For example, among the provided methods is a method that contains at least 22 binding agents, which specifically hybridizes to or binds to a subset of at least 22 GEP-NEN biomarkers, respectively.

In some aspects, the subset of biomarkers includes at least 22, 23, 24, 25, 26, 27, 28, 29, 30, 31, 32, 33, 34, 35, 36, 37, and/or all of the following group of gene products, including polynucleotides (e.g. 38 transcripts) and polypeptides: PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and/or GLT8D1 gene products.

In a particular example, the subset of 22 biomarkers includes PNMA2, NAP1L1, FZD7, SLC18A2, NOL3, SSTR5, TPH1, RAF1, RSF1, SSTR3, SSTR1, CD59, ARAF, APLP2, KRAS, MORF4L2, TRMT112, MKI67, SSTR4, CTGF, SPATA7, and ZFHX3 gene products.

Among the provided methods, agents, and systems are those that are able to classify or detect a GEP-NEN in a human blood sample. In some embodiments, the provided systems and methods can identify or classify a GEP-NEN in a human blood sample. In some examples, the systems can provide such information with a specificity, sensitivity, and/or accuracy of at least 75%, 80%, 85%, 90%, 91%, 92%, 93%, 94%, 95%, 96%, 97%, 98%, 99% or 100%, e.g., at least 80%.

In some embodiments, the system can predict treatment responsiveness to, or determine whether a patient has become clinically stable following, or is responsive or non-responsive to, a GEP-NEN treatment, such as a surgical intervention or drug therapy (for example, somatostatin analog therapy). In some cases, the methods and systems do so with a specificity, sensitivity, and/or accuracy of at least 75%, 80%, 85%, 90%, 91%, 92%, 93%, 94%, 95%, 96%, 97%, 98%, 99% or 100%, e.g., with at least 90% accuracy. In some cases, it can differentiate between treated and untreated GEP-NEN with a specificity, sensitivity, and/or accuracy of at least 75%, 80%, 85%, 90%, 91%, 92%, 93%, 94%, 95%, 96%, 97%, 98%, 99% or 100%, e.g., with a sensitivity and specificity of at least 85%.

In some cases, the system can determine diagnostic or prognostic information regarding a subject previously diagnosed with GEP-NEN, for example, whether the subject has a stable disease (SD) or progressive disease (PD) state of GEP-NEN, or is in complete remission, for example, would be clinically categorized as having stable disease, progressive disease, or being in complete remission.

In some embodiments, the agents for detecting the biomarkers, e.g., the sets of polynucleotide or polypeptide agents, and uses thereof, are capable of distinguishing between the presence and absence of GEP-NEN in a biological sample, between GEP-NEN and mucosal samples and GEP-NEN samples, and/or between specific classes or subtypes of GEP-NENs, for example, between aggressive (high activity) and benign (low activity) GEP-NEN samples, In one aspect, the system is able to classify or detect a GEP-NEN in a human blood sample or human saliva sample. In one aspect, the human sample is whole blood or nucleic acid or protein prepared from whole blood, without first sorting or enriching for any particular population of cells. In one aspect, the system includes agents that bind to biomarkers in a subset of at least 22 GEP-NEN biomarkers.

In some embodiments, in addition to the agents that bind the GEP-NEN biomarkers, the provided systems contain one or more agents that bind to gene products for use in normalization or as controls, for example, housekeeping gene products include ALG9 gene products;

In some embodiments, the methods include selecting a subset of at least 22 biomarkers chosen from a panel of 38 biomarkers useful in generating a classifier for GEP-NEN and different stages of GEP-NEN.

In some embodiments, the methods further include contacting a test sample from the human patient with a plurality of agents specific to the biomarkers in the subset.

The biological test sample used with the methods can be any biological sample, such as tissue, biological fluid, or other sample, including blood samples, such as plasma, serum, whole blood, buffy coat, or other blood sample, tissue, saliva, serum, urine, or semen sample. In some aspects, the sample is obtained from blood. Often, the test sample is taken from a GEP-NEN patient.

The agents can be any agents for detection of biomarkers, and typically are isolated polynucleotides or isolated polypeptides or proteins, such as antibodies, for example, those that specifically hybridize to or bind to a subset or panel of GEP-NEN biomarkers including at least 22 GEP-NEN biomarkers.

In some embodiments, the methods are performed by contacting the test sample with one of the provided agents, more typically with a plurality of the provided agents, for example, one of the provided systems, such as a set of polynucleotides that specifically bind to the subset of GEP-NEN biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the GEP-NEN biomarkers, such as expression levels thereof, includes detecting the presence, absence, or amount of RNA. In one example, the RNA is detected by PCR or by hybridization.

In one aspect, the polynucleotides include sense and antisense primers, such as a pair of primers that is specific to each of the GEP-NEN biomarkers in the subset of biomarkers. In one aspect of this embodiment, the detection of the GEP-NEN biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of GEP-NEN biomarkers, and detecting products of the amplification. In some embodiments, the GEP-NEN biomarkers include mRNA, cDNA, or protein.

In some embodiments, the methods further include determining a mathematically-derived expression level score of biomarkers selected in the subset in the test sample. This is the MAARC-NET score (Multi-Analyte Risk Classification for NETs). It has two scales 0-8 and the percentage-derivatives scaled to 100% i.e., 0-100%.

The mathematically-derived MAARC-NET score is the product of a classifier built from predictive classification algorithms, e.g. support vector machines (SVM), linear discriminant analysis (LDA), K-nearest neighbor (KNN) and/or naive Bayes (NB). In some examples, the classifier is generated from a combination of SVM, LDA, KNN, and NB classification algorithms and a 10-fold cross-validation design.

In some embodiments, the methods further include a step of determining a mathematically-derived expression level score of biomarkers in the subset in a normal or reference sample, typically carried out prior to the normalization and comparing steps.

The normal or reference sample may be from a healthy patient or a patient who has GEP-NEN. Where the test sample is from a patient with GEP-NEN, the normal or reference sample or level may be from the same or a different patient. For example, the normal or reference sample may be from the GEP-NEN patient from a tissue, fluid or cell not expected to contain GEP-NEN or GEP-NEN cells. On another aspect, the normal or control sample is from the GEP-NEN patient before or after therapeutic intervention, such as after surgery or chemical intervention. In another aspect, the reference or normal sample is from a tissue or fluid that corresponds to the GEP-NEN or metastasis of the test sample, from a healthy individual, such as normal enterochromaffin cell (EC) preparation or small intestinal (SI) sample, or normal liver, lung, bone, blood, saliva, or other bodily fluid, tissue, or biological sample. In another embodiment, the test sample is from a metastasis, plasma, or whole blood or other fluid of a GEP-NEN patient and the reference sample is from primary tumor or fluorescent activated cell (FAC)-sorted tumor cells.

In other aspects, the test sample is from blood and the test biological sample is from the GEP-NEN patient after treatment and the reference sample is from the same GEP-NEN patient as the test biological sample, prior to treatment; the reference sample is from a tissue or fluid not containing GEP-NEN cells; the reference sample is from a healthy individual; the reference sample is from a cancer other than GEP-NEN; the reference sample is from an EC cell or SI tissue; the test biological sample is from a metastatic GEP-NEN and the reference sample is from a non-metastatic GEP-NEN; or the reference sample is from a GEP-NEN of a different classification compared to the GEP-NEN patient from which the test biological sample is obtained.

In one aspect, the test biological sample is from a GEP-NEN patient prior to treatment and the normal or reference sample is from the GEP-NEN patient after treatment. In another aspect, the normal or reference sample is from a non-metastatic tissue of the GEP-NEN patient.

In some cases, a normalization step is performed to normalize the level of expression score of the biomarkers in the subset in the test sample to the level of expression score of the biomarkers in the subset in the reference sample.

In some cases, a comparison step is performed to determine whether there is a difference, such as a significant difference, between the normalized expression level score and a predetermined cut-off value or score threshold. Certain predetermined cut-off values or score thresholds are indicative of different stages of GEP-NEN, while others are indicative of different levels of risk, i.e. low, intermediate, or high, for developing a progressive GEP-NEN.

In one aspect, the methods include comparing the normalized expression level score with a predetermined cutoff value chosen to exclude a control or reference sample, wherein a normalized expression level above the predetermined cutoff value is indicative of a GEP-NEN, wherein the cutoff value is about 2 (on a scale of 0-8, or 13.4% on a scale of 0-100%).

In another aspect, the methods include comparing the normalized expression level score with a predetermined cutoff value chosen to exclude a non-progressive GEP-NEN, wherein a normalized expression level above the predetermined cutoff value of 5 (on a scale of 0-8, or 43.4% on a scale of 0-100%) is indicative of progressive GEP-NEN.

In another aspect, the methods further include identifying the level of risk for a human patient to develop progressive GEP-NEN, wherein a normalized expression level score below about 5 (or 43.4%) is indicative of a low level of risk for developing a progressive GEP-NEN, a normalized expression level score between about 5 and 7 (43.4%-63.4%) is indicative of an intermediate level of risk for developing progressive GEP-NEN, and a normalized expression level score between about 7 and 8 (>63.4%) is indicative of a high level of risk for developing progressive GEP-NEN.

In some cases, a subsequent determination is performed for the actual expression level (not mathematically-derived expression level score) of individual genes, where identifying the intermediate level of risk for developing progressive GEP-NEN further includes determining a first state of intermediate risk, wherein the normalized expression level score between a non-progressive reference sample and the test sample is about 5 (43.4%), the normalized expression level of SMARCD3 is below a first threshold value, and the expression level of TPH1 is below a second threshold value.

In other cases, identifying the intermediate level of risk for developing progressive GEP-NEN further includes determining a second state of intermediate risk, wherein the normalized expression level score between a non-progressive reference sample and the test sample is about 6 (52.7%), the normalized expression level of VMAT1 is equal to or above 0, and the expression level of PHF21A is equal to or above a first threshold value.

In some cases, identifying the intermediate level of risk for developing progressive GEP-NEN further includes determining a third state of intermediate risk, wherein the normalized expression level score between a non-progressive reference sample and the test sample is about 7 (63.4%), the expression level of VMAT1 is equal to or above 0, and the expression level of PHF21A is equal to or below a first threshold value.

In other cases, identifying the high level of risk for developing progressive GEP-NEN further includes determining the normalized expression level score of ZZZ3, wherein the expression level score of ZZZ3 is equal to or less than 14.

Also provided are methods and uses of the provided biomarkers, agents, systems and detection methods for use in determining the risk of residual or reoccurring progressive GEP-NEN in a post-surgery human patient. In such cases, the level of risk for residual or reoccurring progressive GEP-NEN in the post-surgical test sample is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8>63.4%) is indicative of a high level of risk.

In some cases, identifying the level of risk for residual or reoccurring progressive GEP-NEN further includes determining an elevated expression level score of gene products in at least one gene cluster as determined between a pre-surgical test sample from the patient and the post-surgical test sample.

In some embodiments, the at least one gene cluster includes the proliferome, signalome, secretome I and II, plurome, epigenome, plurome, SSTRome, and combinations thereof.

In other embodiments, the at least one gene cluster includes the PD cluster, the ND cluster, the TD cluster, and the ID cluster. The PD cluster includes the proliferome, signalome, secretome II, plurome, and epigenome. The ND cluster includes the ARAF1, BRAF, KRAS, RAF1, Ki67, NAP1L1, NOL3, GLT8D1, PLD3, PNMA2, VMAT2, TPH1, FZD7, MORF4L2, and ZFHX3. The TD cluster includes the Secretome (I), the Plurome, and the SSTRome. The ID cluster includes the Proliferome, secretome (II), plurome, and epigenome.

In other embodiments, determining the elevated expression of gene products in at least one gene cluster includes evaluating a plurality of gene cluster algorithms including the PDA, NDA, TDA, and IDA algorithms.

In some embodiments, the methods further include treating the patient based on the indication of intermediate or high level of risk for residual or recurring progressive GEP-NEN by one of surgery or therapy.

Also provided are methods and uses of the provided biomarkers, agents, systems and detection methods for use in determining the risk of residual or reoccurring progressive GEP-NEN in a post-somatostatin analog treated patient. In such cases, the level of risk for somatostatin treatment failure is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8 (>63.4%) is indicative of a high level of risk.

The methods may further include determining the difference in expression level score in at least one of the SSTRome and Proliferome gene clusters between a pre-therapy test sample from the human patient and the post-therapy test sample, wherein an increased level of expression score is indicative of increased risk for residual or reoccurring progressive GEP-NEN.

In some cases, a somatostatin analog is administered to the human patient-based on the indication of intermediate or high level of risk for residual or recurring progressive GEP-NEN and an increased level of expression in at least one of the SSTRome and Proliferome gene clusters.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 2A-2E are graphs showing the validation of alternative splicing in marker genes by Reverse transcriptase polymerase chain reaction (RT-PCR). Marker genes (FIG. 2A) Tph1, (FIG. 2B) VMAT2, (FIG. 2C) SCG5, (FIG. 2D) CgA, and (FIG. 2E) PTPRN2 were differentially expressed in NET samples relative to normal mucosa controls.

(FIG. 4A) Frequency distribution for the 0-4 score in the controls, SD and PD; (FIG. 4B) Frequency distribution using a 0-8 score in the same sample set; (FIG. 4C) Correlation assessment for each of the two scores in (FIG. 4A) and (FIG. 4B).

In FIG. 5A, NETs had a significantly elevated score compared to controls, where values for PD were higher than SD. In FIG. 5B, a ROC curve of controls versus GEP-NETS is shown, wherein the AUC was >0.98, p<0.0001. *p<0.05 vs. controls, #p<0.05 vs. SD (2-tailed Mann-Whitney U-test).

FIG. 6A-6B are (FIG. 6A) a graph of MAARC-NET scores in the independent set, wherein Progressive Disease (PD) NETs had a significantly higher elevated score compared to Stable Disease (SD); and (FIG. 6B) a frequency distribution graph for the 0-8 score in SD and PD. #p<0.0001 vs. SD (2-tailed Mann-Whitney U-test).

FIG. 14A shows a delineation of tumor (adenocarcinoma) derived hallmarks from Hanahan D, Weinberg R A: Hallmarks of cancer: the next generation. *Cell* 2011, 144(5): 646-674. FIG. 14B shows NET hallmark based on the Hanahan and Weinberg classification.

FIGS. 20A-20B are graphs showing (FIG. 20A) normalized gene expression of PDA and NDA gene cluster algorithms in the combined set, and (FIG. 20B) a ROC analysis curve of PDA and NDA for differentiating SD from PD, where *p<0.05 vs. SD.

FIGS. 25A-25B are graphs showing the percentage change in (FIG. 25A) mathematically-derived score and (FIG. 25B) Chromogranin A in both R0 (complete resections) and R½ (incomplete sections) conditions.

FIGS. 27A-27I are graphs showing the differences in NETest score for gene-derived clusters, (FIG. 27A) SSTRome, (FIG. 27B) Proliferome, (FIG. 27C) Signalome, (FIG. 27D) Metabolome, (FIG. 27E) Secretome, (FIG. 27F) Secretome, (FIG. 27G) Plurome, (FIG. 27H) EpiGenome, and (FIG. 27I) ApopTome, in pre- and post-surgery conditions.

FIGS. 30A-30D are graphs showing the differences in gene-derived algorithms, (FIG. 30A) PDA, (FIG. 30B) NDA, (FIG. 30C) TDA, and (FIG. 30D) IDA, in stably treated patients (SD) and treatment failure (PD).

FIGS. 31A-31I are graphs showing the differences in gene-derived clusters, specifically (FIG. 31A) SSTrome, (FIG. 31B) Proliferome, (FIG. 31C) Signalome, (FIG. 31D) Metabolome, (FIG. 31E) Secretome, (FIG. 31F) Secretome, (FIG. 31G) Plurome, (FIG. 31H) EpiGenome, and (FIG. 31I) ApopTome, in stably treated patients (SD) and SSA treatment failure (equivalent of PD conditions).

FIGS. 39A-39F are graphs showing the correlations (linear regression) between gene clusters or algorithms, (FIG. 39A) SSTRome and Ki67, (FIG. 39B) TDA and Ki67, (FIG. 39C) Proliferome and Ki67, (FIG. 39D) PDA and Ki67, (FIG. 39E) IDA and Ki67, and (FIG. 39F) PDA and Ki67, each versus the Ki-67 index.

(FIG. 40A) and (FIG. 40C)) and all genes (Group II: (FIG. 40B) and (FIG. 40D)).

FIGS. 41A-41F are graphs modeling MTV (molecular tumor volume–a measure of the tumor burden) in individual genes (FIGS. 41A-41B), SSTRome (FIGS. 41C-41E), and all genes (FIGS. 41D-41F).

(FIG. 44C) change in CgA level versus clinical status at 6M FuP.

DETAILED DESCRIPTION OF THE INVENTION

Figure 1A:
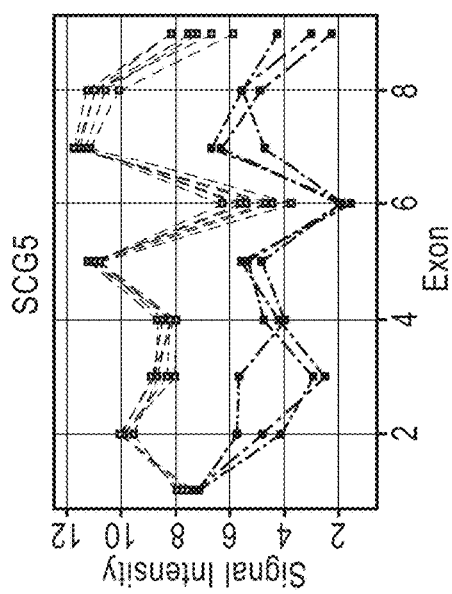
FIGS. 1A-1E are graphs showing differential exon expression in a marker gene panel inferred from an Affymetrix Human Exon 1.0 ST array in neuroendocrine tumor (NET) tissue relative to normal intestinal mucosa controls. RMA-normalized exon expressions of (FIG. 1A) Tph1, (FIG. 1B) VMAT2, (FIG. 1C) SCG5, (FIG. 1D) CgA, and (FIG. 1E) PTPRN2 were visualized in normal (green) and tumor (samples).
Figure 1B:
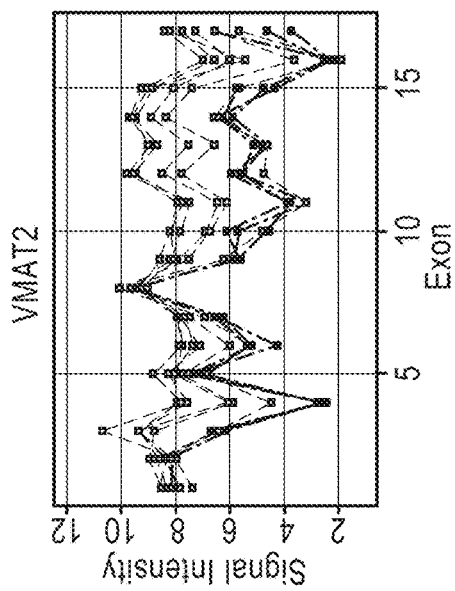
Figure 1C:
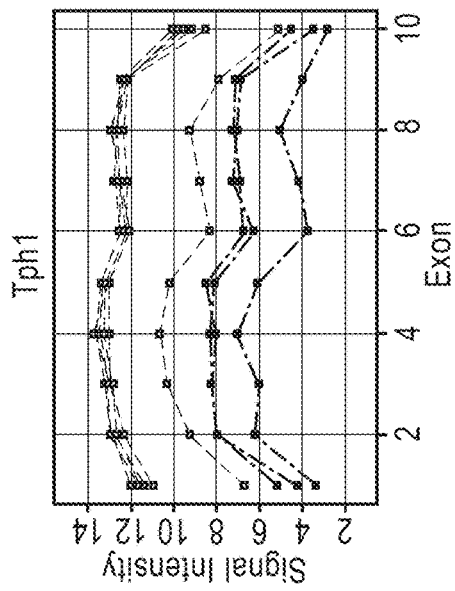
Figure 1D:
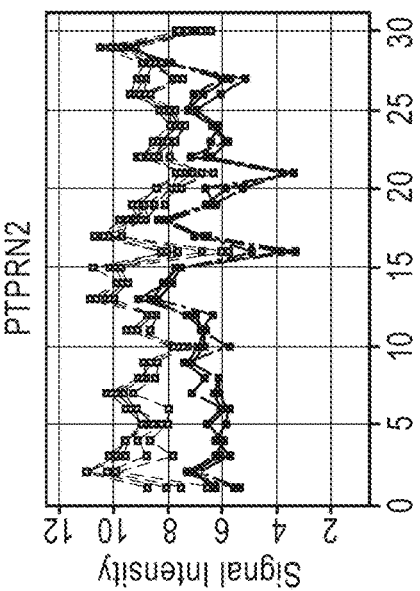
Figure 1E:
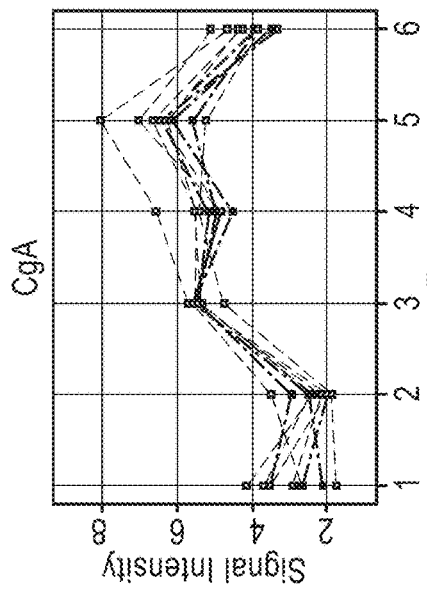

Three-quarters of all human genes undergo alternative splicing. Identifying and defining cancer-specific splice variants is therefore advantageous for the development of biomarker assays. The described embodiments derive from the surprising discovery that particular cancer-specific splice variants of NET marker genes can be used to maximize the difference between neoplasia and normal samples in biomarker diagnostic methods.

The present invention provides a method for detecting a gastroenteropancreatic neuroendocrine neoplasm (GEP-NEN) in a subject in need thereof, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%.

The score is based on a "majority vote" strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naïve Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN.

The at least 22 biomarkers can include APLP2, ARAF, CD59, CTGF, FZD7, KRAS, MKI67/KI67, MORF4L2, NAP1L1, NOL3, PNMA2, RAF1, RSF1, SLC18A2/VMAT2, SMARCD3, SPATA7, SSTR1, SSTR3, SSTR4, SSTR5, TPH1, TRMT112, and ZFHX3.

The methods can further include determining the presence of a progressive GEP-NEN in the subject when the normalized expression level is equal to or higher than the predetermined cutoff value, wherein the predetermined cutoff value is 5 on a scale of 0-8, or less than 55% on a scale of 0-100%.

The methods can further include identifying a level of risk for the subject to develop a progressive GEP-NEN the method further including identifying a low level of risk for developing a progressive GEP-NEN when the normalized expression level is less than a predetermined cutoff value of 5 on a scale of 0-8, or less than 55% on a scale of 0-100%; identifying an intermediate level of risk for developing a progressive GEP-NEN when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk for developing a progressive GEP-NEN when the normalized expression level is equal to or greater than a predetermined cutoff value of 7 on a scale of 0-8, or equal to or greater than 75% on a scale of 0-100%.

The biomarker can be RNA, cDNA, or protein. When the biomarker is RNA, the RNA can be reverse transcribed to produce cDNA (such as by RT-PCR, and the produced cDNA expression level is detected. The expression level of the biomarker can be detected by forming a complex between the biomarker and a labeled probe or primer. When the biomarker is RNA or cDNA, the RNA or cDNA detected by forming a complex between the RNA or cDNA and a labeled nucleic acid probe or primer. The complex between the RNA or cDNA and the labeled nucleic acid probe or primer can be a hybridization complex. When the biomarker is protein, the protein can be detected by forming a complex between the protein and a labeled antibody. The label can be any label for example a fluorescent label, chemiluminescence label, radioactive label, etc.

The test sample can be any biological fluid obtained from the subject. Preferably, the test sample is blood, serum, plasma or neoplastic tissue. The reference sample can be any biological fluid obtained from a subject not having, showing symptoms of or diagnosed with a neoplastic disease. Preferably, the reference sample is blood, serum, plasma or non-neoplastic tissue.

The subject in need thereof can be a subject diagnosed with a GEP-NEN, a subject having at least one GEP-NEN symptom or a subject having a predisposition or familial history for developing a GEP-NEN. The subject can be any mammal. Preferably, the subject is human. The terms subject and patient are used interchangeably herein.

The methods can further include treating a subject identified as having an intermediate level or high level of risk for developing a progressive GEP-NEN with surgery or drug therapy. The drug therapy can be somatostatin analog treatment or peptide receptor radiotherapy therapy (PRRT). The methods can further include treating a subject identified as having a low level of risk for developing a progressive GEP-NEN with regular or periodic monitoring over at least a six month period, a twelve month period, an eighteen month period or twenty four month period.

The present invention also provides a method for differentiating stable and progressive GEP-NEN in a subject comprising determining that the normalized expression level of the at least 22 biomarkers from the test sample from the subject is equal to or greater than a predetermined cutoff value of 5 and less than a predetermined cutoff value of 6, according to the methods of the present invention; detecting an expression level of SMARCD3 and TPH1 from the test sample and from a reference sample by contacting the test sample and the reference sample with a plurality of agents specific to detect the expression of SMARCD3 and the expression of TPH1; normalizing the expression level of SMARCD3 and TPH1 in the test sample to the expression level of SMARCD3 and TPH1 in the reference sample; comparing the normalized expression level of SMARCD3 and TPH1 in the test sample with a first and a second predetermined cutoff value, respectively; and determining the presence of stable GEP-NEN in the subject when the normalized expression level of SMARCD3 is greater than the first predetermined cutoff value and the expression level of TPH1 is equal to or greater than the second predetermined cutoff value, or determining the presence of progressive GEP-NEN in the subject when the normalized expression level of SMARCD3 is equal to or less than the first predetermined cutoff value and the expression level of TPH1 is less than the second predetermined cutoff value wherein the first predetermined cutoff value is 1.3 on a scale of 0-8 and wherein the second predetermined cutoff value is 4 on a scale of 0-8.

The first predetermined cutoff value of 1.3 corresponds to 12% on a scale of 0-100% and wherein the second predetermined cutoff value of 4 corresponds to 41% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 6 and less than a predetermined cutoff value of 7, according to the methods of the present invention; detecting an expression level of VMAT1 and PHF21A from the test sample and from a reference sample by contacting the test sample and reference sample with a plurality of agents specific to detect the expression of VMAT1 and the expression of PHF21A, normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is less than the second predetermined cutoff value, or determining the presence of progressive GEP-NEN in the subject when the normalized expression level of VMAT1 is equal to or greater than the first predetermined cutoff value and the expression level of PHF21A is equal to or greater than the second predetermined cutoff value wherein the first predetermined cutoff value is 0 on a scale of 0-8 and wherein the second predetermined cutoff value is 1.2 on a scale of 0-8.

The first predetermined cutoff value of 0 corresponds to 0% on a scale of 0-100% and wherein the second predetermined cutoff value of 1.2 corresponds to 8% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 7 and less than a predetermined cutoff value of 8, according to the methods of the present invention; detecting an expression level of VMAT1 and PHF21A from the test sample and a reference sample by contacting the test sample and the reference sample with a plurality of agents specific to detect the expression of VMAT1 and the expression of PHF21A; normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is greater than the second predetermined cutoff value, or determining the presence of progressive GEP-NEN in the subject when the normalized expression level of VMAT1 is equal to or greater than the first predetermined cutoff value and the expression level of PHF21A is equal to or less than the second predetermined cutoff value wherein the first predetermined cutoff value is 0 on a scale of 0-8 and wherein the second predetermined cutoff value is 1 on a scale of 0-8.

The first predetermined cutoff value of 0 corresponds to 0% on a scale of 0-100% and wherein the second predetermined cutoff value of 1 corresponds to 7% on a scale of 0-100%.

The present invention also provides a method for differentiating stable and progressive GEP-NEN in a subject comprising determining that the normalized expression level of the at least 22 biomarkers from the test sample from the subject is equal to a predetermined cutoff value of 8, according to the methods of the present invention; detecting an expression level of ZZZ3 from the test sample and a reference sample by contacting the test sample and the reference sample with at least one agent specific to detect the expression of ZZZ3; normalizing the expression level of ZZZ3 in the test sample to the expression level of ZZZ3 in the reference sample; comparing the normalized expression level of ZZZ3 in the test sample with a predetermined cutoff value; and determining the presence of progressive GEP-NEN in the subject when the normalized expression level of ZZZ3 is equal to or less than the predetermined cutoff value, wherein the predetermined cutoff value is 1 on a scale of 0-8.

The predetermined cutoff value of 1 corresponds to 18% on a scale of 0-100%.

The methods of the present invention further include determining the expression level of each of 16 biomarkers from a test sample from the subject and a reference sample by contacting the test sample and the reference sample with a plurality of agents specific to detect the expression of each of the 16 biomarkers, wherein the 16 biomarkers comprise Ki67, NAP1L1, NOL3, TECPR2, ARAF1, BRAF, KRAS, RAF1, PQBP1, TPH1, COMMD9, MORF4L2, RNF41, RSF1, SMARCD3, and ZFHX3; summing the expression level of each of the 16 biomarkers of the test sample to generate a progressive diagnostic I total test value and summing the expression level of each of the 16 biomarkers of the reference sample to generate a progressive diagnostic I total reference value, wherein an increased value of the progressive diagnostic I total test value compared to the progressive diagnostic I total reference value indicates the presence of progressive GEP-NEN in the subject.

The methods of the present invention further include determining the expression level of each of 15 biomarkers from a test sample from the subject and a reference sample by contacting the test sample and the reference sample with a plurality of agents specific to detect the amount of each of the 15 biomarkers, wherein the 15 biomarkers comprise ARAF1, BRAF, KRAS, RAF1, Ki67, NAP1L1, NOL3, GLT8D1, PLD3, PNMA2, VMAT2, TPH1, FZD7, MORF4L2 and ZFHX3; averaging the expression level of each of the 15 biomarkers of the test sample to generate a progressive diagnostic II test value and averaging the expression level of each of the 15 biomarkers of the reference sample to generate a progressive diagnostic II reference value, wherein an increased value of the progressive diagnostic II test value compared to the progressive diagnostic II reference value indicates the presence of progressive GEP-NEN in the subject.

The methods of the present invention further include determining the expression level of each of 7 biomarkers from a test sample from the subject and a reference sample by contacting the test sample and the reference sample with a plurality of agents specific to detect the amount of each of the 7 biomarkers, wherein the 7 biomarkers comprise PNMA2, VMAT2, COMMD9, SSTR1, SSTR3, SSTR4, and SSTR5; summing the expression level of each of the 7 biomarkers of the test sample to generate a progressive diagnostic III total test value and summing the expression level of each of the 7 biomarkers of the reference sample to generate a progressive diagnostic III total reference value, wherein an increased value of the progressive diagnostic III total test value compared to the progressive diagnostic III total reference value indicates the presence of progressive GEP-NEN in the subject.

The methods of the present invention further include determining the expression level of each of 11 biomarkers from a test sample from the subject and a reference sample by contacting the test sample and the reference sample with a plurality of agents specific to detect the amount of each of the 11 biomarkers, wherein the 11 biomarkers comprise Ki67, NAP1L1, NOL3, TECPR2, PQBP1, TPH1, MORF4L2, RNF41, RSF1, SMARCD3, and ZFHX3; summing the expression level of each of the 11 biomarkers of the test sample to generate a progressive diagnostic IV total test value and summing the expression level of each of the 11 biomarkers of the reference sample to generate a progressive diagnostic IV total reference value, wherein an increased value of the progressive diagnostic IV total test value compared to the progressive diagnostic IV total reference value indicates the presence of progressive GEP-NEN in the subject.

The present invention also provides a method for determining the risk of relapsing or reoccurring progressive GEP-NEN in a post-surgery subject, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; identifying an absence of risk of relapsing or reoccurring progressive GEP-NEN post-surgery when the normalized expression level is less than a predetermined cutoff value of 2 on a scale of 0-8, or less than 0% on a scale of 0-100%; identifying a low level of risk of relapsing or reoccurring progressive GEP-NEN post-surgery when the normalized expression level is less than a predetermined cutoff value of 5 on a scale of 0-8, or less than 55% on a scale of 0-100%; identifying an intermediate level of risk of relapsing or reoccurring progressive GEP-NEN post-surgery when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk of relapsing or reoccurring progressive GEP-NEN post-surgery when the normalized expression level is equal to or greater than a predetermined cutoff value of 7 on a scale of 0-8, or equal to or greater than 75% on a scale of 0-100%.

The present invention also provides a method for determining the risk of relapsing or reoccurring progressive GEP-NEN in a subject treated with somatostatin, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; when a GEP-NEN is present, determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise Ki67, NAP1L1, NOL3, TECPR2, SSTR1, SSTR2, SSTR4, and SSTR5; summing the expression level of each of the 8 biomarkers of the test sample to generate a progressive diagnostic V total test value and summing the expression level of each of the 8 biomarkers of the reference sample to generate a progressive diagnostic V total reference value, wherein an increased value of the progressive diagnostic V total test value compared to the progressive diagnostic V total reference value indicates the presence of relapsing or reoccurring progressive GEP-NEN in the subject.

The present invention also provides a method for determining a response of a peptide receptor radionucleotide therapy (PRRT) of a GEP-NEN in a subject in need thereof, including determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise ARAF1, BRAF, KRAS, RAF1, ATP6V1H, OAZ2, PANK2, PLD3; normalizing the expression level of the 8 biomarkers in the test sample to the expression level of the 8 biomarkers in the reference sample; comparing the normalized expression level of the 8 biomarkers in the test sample with a predetermined cutoff value; determining the presence of a PRRT-responsive GEP-NEN in the subject when the normalized expression level of the 8 biomarkers is greater than a predetermined cutoff value, wherein the predetermined cutoff value is 5.9 on a scale of 0-8.

The present invention also provides a method for determining a response of a peptide receptor radionucleotide therapy (PRRT) of a GEP-NEN in a subject in need thereof, including (a) following a first cycle of PRRT therapy: determining the expression level of at least 22 biomarkers from a first cycle test sample from the subject by contacting the first cycle test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the first cycle test sample to the expression level of the at least 22 biomarkers in the reference sample; (b) following a second cycle of PRRT therapy, determining the expression level of at least 22 biomarkers from a second cycle test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the second cycle test sample to the expression level of the at least 22 biomarkers in the reference sample; (c) determining a ratio of change of the normalized expression levels from (a) to the normalized expression levels from (b); (d) determining the presence of a PRRT-responsive GEP-NEN when the ratio of change is greater than a pre-PRRT therapy cutoff value, wherein the pre-PRRT therapy cutoff value is 1 on a scale of 0-8.

The present invention also provides a method for determining a progression of a GEP-NEN in a subject in need thereof, including determining the expression level of ZFHX3 from a test sample from the subject by contacting the test sample with an agent specific to detect the expression of ZFHX3; determining the expression level of ZFHX3 from a reference sample by contacting the reference sample with an agent specific to detect the expression of ZFHX3; normalizing the expression level of ZFHX3 in the test sample to the expression level of ZFHX3 in the reference sample; comparing the normalized expression level of ZFHX3 in the test sample with a predetermined cutoff value; determining the progression of a GEP-NEN in the subject when the normalized expression level is equal to or greater than the predetermined cutoff value, wherein the predetermined cutoff value is 0.5 on a scale of 0-8.

The present invention also provides a method for predicting tumor proliferation of a GEP-NEN in a subject in need thereof, including (a) determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; (b) when a GEP-NEN is present, determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise KRAS, SSTR4 and VPS13C; summing the expression level of each of the 3 biomarkers of the test sample to generate a progressive diagnostic VI total test value and summing the expression level of each of the 3 biomarkers of the reference sample to generate a progressive diagnostic VI total reference value, wherein an increased value of the progressive diagnostic VI total test value compared to the progressive diagnostic VI total reference value indicates the presence of tumor proliferation of a GEP-NEN in the subject.

The method wherein (b) further includes determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise SSTR1, SSTR2 and SSTR5; summing the expression level of each of the 3 biomarkers of the test sample to generate a progressive diagnostic VII total test value and summing the expression level of each of the 3 biomarkers of the reference sample to generate a progressive diagnostic VII total reference value, wherein an increased value of the progressive diagnostic VII total test value compared to the progressive diagnostic VII total reference value indicates the presence of tumor proliferation of a GEP-NEN in the subject.

As used herein, the term "GEP-NEN biomarker" and "NET biomarker" refer synonymously to a biological molecule, such as a gene product, the expression or presence of which (e.g., the expression level or expression profile) on its own or as compared to one or more other biomarkers (e.g., relative expression) differs (i.e., is increased or decreased) depending on the presence, absence, type, class, severity, metastasis, location, stage, prognosis, associated symptom, outcome, risk, likelihood or treatment responsiveness, or prognosis of GEP-NEN disease, or is associated positively or negatively with such factors of the prediction thereof.

As used herein, the term "polynucleotide" or nucleic acid molecule means a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees and temperatures for washing in 0.1×SSC/0.1% SDS are above 55 degrees C., and most preferably to stringent hybridization conditions.

The term "blood biopsy" refers to a diagnostic study of the blood to determine whether a patient presenting with symptoms has a condition that may be classified as either benign (low activity) or malignant (high activity/metastatic).

The term "classifying" as used herein with regard to different types or stages of GEP-NEN refers to the act of compiling and analyzing expression data for using statistical techniques to provide a classification to aid in diagnosis of a stage or type of GEP-NEN.

The term "classifier" as used herein refers to an algorithm that discriminates between disease states with a predetermined level of statistical significance. A two-class classifier is an algorithm that uses data points from measurements from a sample and classifies the data into one of two groups. A multi-class classifier is an algorithm that uses data points from measurements from a sample and classifies the data into one of multiple groups. The "classifier" maximizes the probability of distinguishing a randomly selected cancer sample from a randomly selected benign sample, i.e., the area under a curve (AUC) of receiver operating characteristic (ROC) curve.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression.

The term "condition" as used herein refers generally to a disease, event, or change in health status.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

The term "disease prevalence" refers to the number of all new and old cases of a disease or occurrences of an event during a particular period. Prevalence is expressed as a ratio in which the number of events is the numerator and the population at risk is the denominator.

The term "disease incidence" refers to a measure of the risk of developing some new condition within a specified period of time; the number of new cases during some time period, it is better expressed as a proportion or a rate with a denominator.

The term "stable disease" refers to a diagnosis for the presence of GEP-NEN, however GEP-NEN has been treated and remains in a stable condition, i.e. one that that is not progressive, as determined by imaging data and/or best clinical judgment.

The term "progressive disease" refers to a diagnosis for the presence of a highly active state of GEP-NEN, i.e. one has not been treated and is not stable or has been treated and has not responded to therapy, or has been treated and active disease remains, as determined by imaging data and/or best clinical judgment.

The term "expression level score" or "NETest score" refers to the output of a mathematically-derived classifier algorithm generated from the combination of classification algorithms, i.e. SVM, LDA, KNN, and Bayes. This score ranges between 0 and 100%. The expression level score from a test sample, once compared to the expression level score for a reference or control sample, may be used to diagnose the presence of GEP-NEN, the different stages of GEP-NEN, predict the risk of contracting a stage of GEP-NEN, or determines the risk of recurrence of GEP-NEN in post-therapy human patients. Distinctions between GEP-NEN disease states are based on pre-determined expression level score thresholds and/or ranges as further defined in the present application.

Diagnosis and prognosis of GEP-NEN has been difficult, in part due to the prosaic symptoms and syndromes of the disease, such as carcinoid syndrome, diarrhea, flushing, sweating, bronchoconstriction, gastrointestinal bleeding, cardiac disease, intermittent abdominal pain, which often remain silent for years. Available diagnostic methods include anatomical localization, such as by imaging, e.g., X-ray, gastrointestinal endoscopy, abdominal computed tomography (CT), combined stereotactic radiosurgery (SRS)/CT, and MRI, and detection of some gene products e.g., chromogranin A. Known methods are limited, for example by low specificity and/or sensitivity and/or in the ability to detect early-stage disease.

Detection of single biomarkers has not been entirely satisfactory, for example, to identify malignancy in human blood samples and to predict complex outcomes like fibrosis and metastasis. See Michiels S, Koscielny S, Hill C, "Interpretation of microarray data in cancer," Br J Cancer 2007; 96(8): 1155-8. Limitations in available methods have contributed to difficulties in pathological classification, staging, and prediction, treatment developing and monitoring therapeutic effects. Among the embodiments provided herein are methods and compositions that address these limitations.

In one aspect, the present application relates to the detection and identification of GEP-NEN biomarkers and panels of such biomarkers, for example, in biological samples. Provided are methods and compositions (e.g., agents, such as polynucleotides), for detecting, determining expression levels of, and recognizing or binding to the biomarkers, in biological samples, typically blood samples.

Also provided are models and biomathematical algorithms, e.g., supervised learning algorithms, and methods using the same, for prediction, classification, and evaluation of GEP-NEN and associated outcomes, for example, predicting degree of risk, responsiveness to treatment, metastasis or aggressiveness, and for determining GEP-NEN subtype.

Detection of the biomarkers using the provided embodiments is useful for improving GEP-NEN diagnostics and prognostics, and to inform treatment protocols. In some aspects, detection of the biomarkers and/or expression levels by the provided embodiments confirms or indicates the presence, absence, stage, class, location, sub-type, aggressiveness, malignancy, metastasis, prognosis, or other outcome of GEP-NEN, or a GEP-NEN cell, such as a circulating GEP-NEN cell (CNC). The provided methods and compositions may be used for tumor localization, and for predicting or detecting metastases, micrometastases, and small lesions, and/or for determining degree of risk, likelihood of recurrence, treatment responsiveness or remission, and informing appropriate courses of treatment. For example, detecting the biomarkers, e.g., in circulation may be used to detect early-stage and primary GEP-NENs (e.g., to identify GEP-NEN disease or metastases in a patient previously deemed "negative" by another approach, such as anatomic localization).

The provided methods and compositions may be used for designing, implementing, and monitoring treatment strategies, including patient-specific treatment strategies. In one example, detected expression levels of the GEP-NEN biomarkers serve as surrogate markers for treatment efficacy, e.g., to monitor the effects of surgical therapy, e.g., removal of tumors, targeted medical therapy, e.g., inhibition of tumor secretion/proliferation, and other therapeutic approaches, by detecting remission or recurrence of tumors, even in the form of small micrometastases. The methods also may be used in evaluating clinical symptoms and outcomes, and for histological grading and molecular characterization of GEP-NENs.

The provided biomarkers including GEP-NEN biomarkers, and subsets and panels of the same. Among the provided GEP-NEN biomarkers are gene products, such as DNA, RNA, e.g., transcripts, and protein, which are differentially expressed in GEP-NEN disease, and/or in different stages or sub-types of GEP-NEN, or in different GEP-NEN tumors, such as gene products differentially expressed in metastatic versus non-metastatic tumors, tumors with different degrees of aggressiveness, high versus low-risk tumors, responsive versus non-responsive tumors, tumors exhibiting different pathological classifications and/or likelihood of response to particular courses of treatment, as well as those associated with features of GEP-NEN disease, stage, or type, or with neuroendocrine cells or related cell-types.

For example, the biomarkers include gene products whose expression is associated with or implicated in tumorogenicity, metastasis, or hormone production, or a phenotype of primary or metastatic GEP-NEN, such as adhesion, migration, proliferation, apoptosis, metastasis, and hormone secretion, and those associated with neoplasia or malignancy in general.

Among the biomarkers are GEP-NEN cell secretion products, including hormones and amines, e.g., gastrin, ghrelin, pancreatic polypeptide, substance P, histamine, and serotonin, and growth factors such as tumor growth factor-beta (TGF-β) and connective tissue growth factor (CTGF), which are detectable in the circulation. Secretion products can vary with tumor sub-type and origin.

In one example, the biomarkers are gene products associated with regulatory genotypes (i.e., adhesion, migration, proliferation, apoptosis, metastasis, and/or hormone secretion) that underlay various GEP-NEN subtypes, stages, degrees of aggressiveness, or treatment responsiveness.

A total of 51 differentially expressed biomarker genes have been discovered for the diagnosis, prognosis, and/or monitoring of GEP-NENs. Further details regarding the 51 differentially expressed GEP-NEN biomarkers as well as the housekeeping gene, ALG9, are found in TABLE 1.

TABLE 1

GEP-NEN Biomarker/Houskeeper Sequence Information

| Gene Name | RefSeq Accession | Sequence | SEQ ID NO: |
|---|---|---|---|
| ALG9 | NM_024740.2 | GTCTTTTGTCCCTCGGCGGACACCGTTTGCCAGCCAAAGC<br>TATGTCTGCGCGCTCACCGACTTCATAGGGTGCCGAATTC<br>TTTTTTCCCCAGGCTTGCCATGGCTAGTCGAGGGGCTCGG<br>CAGCGCCTGAAGGGCAGCGGGGCCAGCAGTGGGGATACGG<br>CCCCGGCTGCGGACAAGCTGCGGGAGCTGCTGGGCAGCCG<br>AGAGGCGGGCGGCGCGGAGCACCGGACCGAGTTATCTGGG<br>AACAAAGCAGGACAAGTCTGGGCACCTGAAGGATCTACTG<br>CTTTCAAGTGTCTGCTTTCAGCAAGGTTATGTGCTGCTCT<br>CCTGAGCAACATCTCTGACTGTGATGAAACATTCAACTAC<br>TGGGAGCCAACACACTACCTCATCTATGGGAAGGGTTTC<br>AGACTTGGGAATATTCCCCAGCATATGCCATTCGCTCCTA<br>TGCTTACCTGTTGCTTCATGCCTGGCCAGCTGCATTTCAT<br>GCAAGAATTCTACAAACTAATAAGATTCTTGTGTTTTACT<br>TTTTGCGATGTCTTCTGGCTTTTGTGAGCTGTATTTGTGA<br>ACTTTACTTTTACAAGGCTGTGTGCAAGAAGTTTGGGTTG<br>CACGTGAGTCGAATGATGCTAGCCTTCTTGGTTCTCAGCA<br>CTGGCATGTTTTGCTCATCATCAGCATTCCTTCCTAGTAG<br>CTTCTGTATGTACACTACGTTGATAGCCATGACTGGATGG<br>TATATGGACAAGACTTCCATTGCTGTGCTGGGAGTAGCAG<br>CTGGGGCTATCTTAGGCTGGCCATTCAGTGCAGCTCTTGG<br>TTTACCCATTGCCTTTGATTTGCTGGTCATGAAACACAGG<br>TGGAAGAGTTTCTTTCATTGGTCGCTGATGGCCCTCATAC<br>TATTTCTGGTGCCTGTGGTGGTCATTGACAGCTACTATTA<br>TGGGAAGTTGGTGATTGCACCACTCAACATTGTTTTGTAT<br>AATGTCTTTACTCCTCATGGACCTGATCTTTATGGTACAG<br>AACCCTGGTATTTCTATTTAATTAATGGATTTCTGAATTT<br>CAATGTAGCCTTTGCTTTGGCTCTCCTAGTCCTACCACTG<br>ACTTCTCTTATGGAATACCTGCTGCAGAGATTTCATGTTC | 1 |

TABLE 1-continued

GEP-NEN Biomarker/Houskeeper Sequence Information

| Gene Name | RefSeq Accession | Sequence | SEQ ID NO: |
|---|---|---|---|
| | | AGAATTTAGGCCACCCGTATTGGCTTACCTTGGCTCCAAT<br>GTATATTTGGTTTATAATTTTCTTCATCCAGCCTCACAAA<br>GAGGAGAGATTTCTTTTCCCTGTGTATCCACTTATATGTC<br>TCTGTGGCGCTGTGGCTCTCTCTGCACTTCAGCACAGTTT<br>TCTGTACTTCCAGAAATGTTACCACTTTGTGTTTCAACGA<br>TATCGCCTGGAGCACTATACTGTGACATCGAATTGGCTGG<br>CATTAGGAACTGTCTTCCTGTTTGGGCTCTTGTCATTTTC<br>TCGCTCTGTGGCACTGTTCAGAGGATATCACGGGCCCCTT<br>GATTTGTATCCAGAATTTTACCGAATTGCTACAGACCCAA<br>CCATCCACACTGTCCCAGAAGGCAGACCTGTGAATGTCTG<br>TGTGGGAAAAGAGTGGTATCGATTTCCCAGCAGCTTCCTT<br>CTTCCTGACAATTGGCAGCTTCAGTTCATTCCATCAGAGT<br>TCAGAGGTCAGTTACCAAAACCTTTTGCAGAAGGACCTCT<br>GGCCACCCGGATTGTTCCTACTGACATGAATGACCAGAAT<br>CTAGAAGAGCCATCCAGATATATTGATATCAGTAAATGCC<br>ATTATTTAGTGGATTTGGACACCATGAGAGAAACACCCCG<br>GGAGCCAAAATATTCATCCAATAAAGAAGAATGGATCAGC<br>TTGGCCTATAGACCATTCCTTGATGCTTCTAGATCTTCAA<br>AGCTGCTGCGGGCATTCTATGTCCCCTTCCTGTCAGATCA<br>GTATACAGTGTACGTAAACTACACCATCCTCAAACCCCGG<br>AAAGCAAAGCAAATCAGGAAGAAAAGTGGAGGTTAGCAAC<br>ACACCTGTGGCCCCAAAGGACAACCATCTTGTTAACTATT<br>GATTCCAGTGACCTGACTCCCTGCAAGTCATCGCCTGTAA<br>CATTTGTAATAAAGGTCTTCTGACATGAATACTGGAATCT<br>GGGTGCTCTGGGCTAGTCAAAGTCTATTTCAAAGTCTAAT<br>CAAAGTCACATTTGCTCCCTGTGTGTGTCTCTGTTCTGCA<br>TGTAAACTTTTTGCAGCTAGGCAGAGAAAGGCCCTAAAGC<br>ACAGATAGATATATTGCTCCACATCTCATTGTTTTTCCTC<br>TGTTCAATTATTTACTAGACCGGAGAAGAGCAGAACCAAC<br>TTACAGGAAGAATTGAAAATCCTGGTACTGGATGGCTGTG<br>ATAAGCTGTTCTCCACACTCTGGCCTGGCATCTGAGAACT<br>AGCAAGCCTCTCTTAGGCCATATGGGCTTCTCCACCAAAG<br>CTGTTTGGCAGCTCCTAGCAGACCTTCTTATTGAAATCCT<br>CATGCTGAAAATGAACACAGCCTAGTTGCCAACCCACATG<br>TCCTTTTCACCTCCAGCAAGACTAAGCTTCTTTAAAGCAC<br>TTCACAGGACTAGGACCCTGTCCTGGAGCTATCTCAGGAA<br>AAAGGTGACCATTTGAGGAACTGTGACCTAATTTTATTAT<br>AATGATGCCTCTAATTTTCATTTCCTTTACAACCAACTGT<br>AACTATAAGGTTGTATTGCTTTTTTGTTCAGTTTTAGCAT<br>GCTATTTTTGAATTCTAGACTCCTCCATGTGAAGATATC<br>AACAGACAAAACTACAACTGTATAGGACATATTTGGAGAA<br>AATTCTATCAATTGATACATTTGGATGACATCACATTTTT<br>AAGTAATGTAATCTGAGGCCATTGCTGAGGAAATTAAGAA<br>TTTTCCTTTTTTTTAACCACCCCCAGTGAAAAGGATCAG<br>TGTATATTTATAGCACCTATTTTTTAGTTCTGTCTGTTGT<br>GAGGCACATCCTGCATGGGGCACTTCTAGTCAAATAGGCA<br>ATGATAAGGACCTAATTAAAATGTGATAAGTGTATACTAT<br>TACTTTAAAAGCCTTTACAGTCAGTACTTCAGTTTACAAG<br>GCACTTTCACAGCATCTCGTTTGATCCTCACAGTCACAAC<br>ATGTGGTAGACAAGGCAGGTGATTTTTATCCCCATTTTAC<br>AGATAAGGAAACAGGCTGCGGGTGGGGAGTGAGGGGAGGT<br>AAAGATAGTTAGTTGCCTAAGGTCACACAGCCAGTAAGTA<br>ATAGAGCTGGGACTGGAACCCAGGTTTCCTTACTCTCATC<br>TATTGCTCCTCCATATTCCTCACTCAACCATGAAAACATT<br>ACTTGAAAGGACTGATGAGGTTAACCAGAGACCTAACTGA<br>TATTGTAACTTTCTATTTTAAGGAAGAATTGTGTCTGTAT<br>TTGAGTTCTTTGGAGCCTCCAGTCTGCCTGTGTGTTAGAC<br>CAGCACAGCAGTGCTGTGTGATGCAGCCTGACCTGTGGCA<br>GGAAAGTAGTGCTTCTGTTTGGAAGTCATGTTCTTTTGCA<br>GCCACACAGGATCCAAATATCAGTACTATTCCTGTAGTCA<br>ATCTGGGGTCACATTATAGGTGCCTTATTTCCCTAAGGGT<br>AACTGATCTGAATATCTGCAAATAGGATGAATCTATTTTT<br>CAGAAGTTCCATCTTTCATTTTTCTTTTTTTTTTGAGAC<br>AGAGTCTCATTCTGTCGCCCATGCTGGAGTGCAGTGGCGC<br>GATCTCGGCTCGCTGCAACCTCTGCCTCCCAGGTTGAAGC<br>AATTCTCATGCCTCAGCCACCCGAGTAGCTGGGATTACAG<br>GCATGCGCCATCATGCCCAGCTAATTTATGTATTTTTAGT<br>AGAGTTGGAGTTTCACCATGTTGGCCAGGCTGGTCTTGGA<br>CTCCTGACCTCAGGTCATCCACCCGCCTCAGCCTCCCAAA<br>GTGCTGGTATTACAGGCGTGAGCCACCGCACCCAGCCCCA<br>TCTTTCATTTTCAAAGAGAAGGGCATTCTAATAGGAACTG<br>GTGCCAAGAGAGAAGAAAAGAAGTGATAACAGAAGAAATG<br>GCTAGTTACAATATTAAAAAGCTCCTCTTTGAGATCTCCT<br>CTGCAGGAATATCAGAGACGGAGTTGAAGCGCTGGAGAGG<br>TAATAGGTCTAGACAGTACAGAACAATAACTGGGGAGTGT | |

TABLE 1-continued

GEP-NEN Biomarker/Houskeeper Sequence Information

| Gene Name | RefSeq Accession | Sequence | SEQ ID NO: |
|---|---|---|---|
| | | GTGAGGATAGACTGGGCTCCCCCTTGCTTGAAAGATCTCT<br>GGCATTTAATTCTCAATTCTTGATTACTATTTTCCAGTGT<br>AAAACTAGCACATATGATCTGACTACAGGACAGAGAATTT<br>TAAGTGAAACATTTGCCTTACTTGCAGTAATAATGTGCTG<br>TTCTTCACAGTAGCTAAGGCCCTCTATGTTTCCCAGAGGT<br>AAATAAGAATCCAGGAATGGAGGTCCATCTGTGATGAATG<br>GCTTTTTTCTAATCAAAGTAGTATAATGCTGTTTTATCTG<br>TTTTGTCATCTTGTTTTTTTTTTTTTAAAAAAACAAAA<br>CCTTAATTATAATATAGCGCAAAGAAAGGCCAGGACTGAT<br>GCAGGGATTCCTTGGAAATATCAGTTCCTATCACTTTTAA<br>AACCTGATTTTGGATCTCTCTGTTCTATGTATGTCTTTAG<br>TGAGAGCACAATACATGGCAGAACGCTGTGCCAAATGTTA<br>TAGGTAAGGAATATAGAAATGAATGTTTTTTGTTGTGAAG<br>GTGTTTTCATGTGATATTTTATAAACACATTTTAAAAAAT<br>CTCCATCACTTTTTAGTATAGGAAGGATAGCTTTGCCTGG<br>GAAAAACAGTTTCAACACACCTGCTCAGAGTAGCAGTTCT<br>CCCTCAAAAAAGCAGTGTTCAGCCTGCACTGACTGTTCTG<br>CTTGCCAAAAGGAGGAAGCATGCAAGATACTTATTTCTCC<br>ATAGATTGTGGAGTATAGAGGGATGTGGGACTACAGATTA<br>TTATTTTTTTCCCCGAGACAGAGTCTTGCTCTGTCGCCC<br>AGGTTGGAACACAATGGCACGACCTCAGCTCACTGCAACC<br>TCTGTCTCCCGGGTTCAAGCAATTCTCCTGCTTCAGCCTC<br>CTGAGTAGCTGGGATTACAGGCACACACCACCACCGCACT<br>CAGCTAATTTTTGTATTTTTAGTAGAGGTGGGGTTTTACC<br>ATGTTGGCCAGGCTGGTCTTAAACTCCTGACCTTGTAATC<br>ATCCCGCCTCGGCCTCCTAAAGTGCTAGGATTACAGGCAT<br>GAGCCACCGCACCCGGCCCAGATAATTTTTAATAGCCTTT<br>GATCATGGGGTGAGTGAGGGAGTAGGTATACTTGGCAAAT<br>GCATGGTTCTCTGATTTCTAGCTCTAAAGCAGCCTTATCT<br>GAATCCCCAAATCTTGTGATGCTGAGTACCATTACTGAAC<br>CAGTCTGCACGGTAGGCATCTGCTACCAAAATTTACCTCC<br>TACCTGGTAGGTGTCATCTGATAAGAAAGAAGACAGGTTA<br>TTTTAATTTTTTGAGATAATCACAGAAAATTGCAGCCCAT<br>ACTCTTTATTACCGAATTCAAGTTTGGAAATAGACCCTTT<br>GTTTTAAATCATGATGGGTCTTTATCCCAATCATTTATCT<br>GGGTCATTTTTCCAACTTTGGAGTTCTAGGAAAGAACCTT<br>GAAAACCTGATATGATTCTGCAGCATGAGGTCTACGGTGA<br>CCATTTGGGCAAAGCTCCAGTGGCAATCATTTATTGTGTT<br>TTGCATTTCCTGGGATTTATTGAAATAAGAATTCACTGTG<br>ATTATGTAGTCTTCTGGCTAGTATCAGGCAGCTCTGCTTT<br>TAATTTGGTTAATTTTATTTTCTCTGAAGAGGGAGAAGAG<br>GTACAATTTAATCTTGGCCTCCACAAGCATATTAAAGCTC<br>ACGTGTTAATCAGTGCATTCTTATGCTCCTACATTAAATG<br>CCTTGGGTAAATGGATAAATGGACATGTGCCCAGCTTTAA<br>TTTTTTTTGCAACAGAAAGATCAGACTTCCGTATGGCATC<br>GTTGGATTTCAGAGGCTTTCTGGTGTATCTGTAAATCTGA<br>ATGTTGCCTTCTGCCAGTCTGTATAACCAGGTGATTCATG<br>CTGCAAATGAAATCAGGAAGCAGTAAAGTGTTAAAGCAAG<br>AGTATTGTCCAATTCACTTGTCTTCCTGATCCTTGTACTT<br>TATTTCACGTGTCGGTGTTTACATTACATACTTATATTTC<br>CTGTGAAAGAAAGAGTTAAATAAATTGTAGCAGTTTGA | |
| AKAP8L | NM_014371.3 | ACTGATATGAGGAGGCATAGAGATAGACAGCGGTTCCTTC<br>CAATAGACGTGAAGCCGAGGCCGGTATGAGCCAATGCGGT<br>CGGGAGGCGGGGCTCGGGTGTGTGTGGAGGGGACCCTGTG<br>GTTAGCAGCAGCTATCGCAGCGTCGGATGTTCAGAGCAGC<br>AGAAGCCGGCGTCGTCGGATGTTGTGTTGCCCGCCACCAT<br>GAGCTACACAGGCTTTGTCCAGGGATCTGAAACCACTTTG<br>CAGTCGACATACTCGGATACCAGCGCTCAGCCCACCTGTG<br>ATTATGGATATGGAACTTGGAACTCTGGGACAAATAGAGG<br>CTACGAGGGCTATGGCTATGGCTATGGCTATGGCCAGGAT<br>AACACCACCAACTATGGGTATGGTATGGCCACTTCACACT<br>CTTGGGAAATGCCTAGCTCTGACACAAATGCAAACACTAG<br>TGCCTCGGGTAGCGCCAGTGCCGATTCCGTTTTATCCAGA<br>ATTAACCAGCGCTTAGATATGGTGCCGCATTTGGAGACAG<br>ACATGATGCAAGGAGGCGTGTACGGCTCAGGTGGAGAAAG<br>GTATGACTCTTATGAGTCCTGCGACTCGAGGGCCGTCCTG<br>AGTGAGCGCGACCTGTACCGGTCAGGCTATGACTACAGCG<br>AGCTTGACCCTGAGATGGAAATGGCCTATGAGGGCCAATA<br>CGATGCCTACCGCGACCAGTTCCGCATGCGTGGCAACGAC<br>ACCTTCGGTCCCAGGGCACAGGGCTGGGCCCGGGATGCCC<br>GGAGCGGCCGGCCAATGGCCTCAGGCTATGGGCGCATGTG<br>GGAAGACCCCATGGGGGCCCGGGGCCAGTGCATGTCTGGT<br>GCCTCTCGGCTGCCCTCCCTCTTCTCCCAGAACATCATCC<br>CCGAGTACGGCATGTTCCAGGGCATGCGAGGTGGGGGCGC | 2 |

TABLE 1-continued

GEP-NEN Biomarker/Houskeeper Sequence Information

| Gene Name | RefSeq Accession | Sequence | SEQ ID NO: |
|---|---|---|---|
|  |  | CTTCCCGGGCGGCTCCCGCTTTGGTTTCGGGTTTGGCAAT GGCATGAAGCAGATGAGGCGGACCTGGAAGACCTGGACCA CAGCCGACTTCCGAACCAAGAAGAAGAAGAGAAAGCAGGG CGGCAGTCCTGATGAGCCAGATAGCAAAGCCACCCGCACG GACTGCTCGGACAACAGCGACTCAGACAATGATGAGGGCA CCGAGGGGAAGCCACAGAGGGCCTTGAAGGCACCGAGGC TGTGGAGAAGGGCTCCAGAGTGGACGGAGAGGATGAGGAG GGAAAAGAGGATGGGAGAGAAGAAGGCAAAGAGGATCCAG AGAAGGGGGCCCTAACCACCCAGGATGAAAATGGCCAGAC CAAGCGCAAGTTGCAGGCAGGCAAGAAGAGTCAGGACAAG CAGAAAAAGCGGCAGCGAGACCGCATGGTGGAAAGGATCC AGTTTGTGTGTTCTCTGTGCAAATACCGGACCTTCTATGA GGACGAGATGGCCAGCCATCTTGACAGCAAGTTCCACAAG GAACACTTTAAGTACGTAGGCACCAAGCTCCCTAAGCAGA CGGCTGACTTTCTGCAGGAGTACGTCACTAACAAGACCAA GAAGACAGAGGAGCTCCGAAAAACCGTGGAGGACCTTGAT GGCCTCATCCAGCAAATCTACAGAGACCAGGATCTGACCC AGGAAATTGCCATGGAGCATTTTGTGAAGAAGGTGGAGGC AGCCCATTGTGCAGCCTGCGACCTCTTCATTCCCATGCAG TTTGGGATCATCCAGAAGCATCTGAAGACCATGGATCACA ACCGGAACCGCAGGCTCATGATGGAGCAGTCCAAGAAGTC CTCCCTCATGGTGGCCCGCAGTATTCTCAACAACAAGCTC ATCAGCAAGAAGCTGGAGCGCTACCTGAAGGGCGAGAACC CTTTCACCGACAGCCCCGAGGAGGAGAAGGAGCAGGAGGA GGCTGAGGGCGGTGCCCTGGACGAGGGGGCGCAGGGCGAA GCGGCAGGGATCTCGGAGGGCGCAGAGGGCGTGCCGGCGC AGCCTCCCGTGCCCCCAGAGCCAGCCCCCGGGGCCGTGTC GCCGCCACCGCCGCCGCCCCCAGAGGAGGAGGAGGAGGGC GCCGTGCCCTTGCTGGGAGGGGCGCTGCAACGCCAGATCC GCGGCATCCCGGGCCTCGACGTGGAGGACGACGAGGAGGG CGGCGGGGCGCCCCGTGACCCGAGCTCGGGGCGGGCGGA GCCCGCGTGGCCGAAGCTGGAAACCAAACCTAATAAAGTT TTCCCATCCCACCAAAAAAAAAAAAAAAAAA |  |
| APLP2 | NM_001142276.1 | AGAAGGAGGGCGTGGTAATATGAAGTCAGTTCCGGTTGGT GTAAAACCCCCGGGGCGGCGGCGAACTGGCTTTAGATGCT TCTGGGTCGCGGTGTGCTAAGCGAGGAGTCCGAGTGTGTG AGCTTGAGAGCCGCGCGCTAGAGCGACCCGGCGAGGGATG GCGGCCACCGGGACCGCGGCCGCCGCAGCCACGGGCAGGC TCCTGCTTCTGCTGCTGGTGGGGCTCACGGCGCCTGCCTT GGCGCTGGCCGGCTACATCGAGGCTCTTGCAGCCAATGCC GGAACAGGATTTGCTGTTGCTGAGCCTCAAATCGCAATGT TTTGTGGGAAGTTAAATATGCATGTGAACATTCAGACTGG GAAATGGGAACCTGATCCAACAGGCACCAAGAGCTGCTTT GAAACAAAAGAAGAAGTTCTTCAGTACTGTCAGGAGATGT ATCCAGAGCTACAGATCACAAATGTGATGGAGGCAAACCA GCGGGTTAGTATTGACAACTGGTGCCGGAGGGACAAAAAG CAATGCAAGAGTCGCTTTGTTACACCTTTCAAGTGTCTCG TGGGTGAATTTGTAAGTGATGTCCTGCTAGTTCCAGAAAA GTGCCAGTTTTTCCACAAAGAGCGGATGGAGGTGTGTGAG AATCACCAGCACTGGCACACGGTAGTCAAAGAGGCATGTC TGACTCAGGGAATGACCTTATATAGCTACGGCATGCTGCT CCCATGTGGGGTAGACCAGTTCCATGGCACTGAATATGTG TGCTGCCCTCAGACAAAGATTATTGGATCTGTGTCAAAAG AAGAGGAAGAGGAAGATGAAGAGGAAGAGGAAGAGGAAGA TGAAGAGGAAGACTATGATGTTTATAAAAGTGAATTTCCT ACTGAAGCAGATCTGGAAGACTTCACAGAAGCAGCTGTGG ATGAGGATGATGAGGATGAGGAAGAAGGGGAGGAAGTGGT GGAGGACCGAGATTACTACTATGACACCTTCAAAGGAGAT GACTACAATGAGGAGAATCCTACTGAACCCGGCAGCGACG GCACCATGTCAGACAAGGAAATTACTCATGATGTCAAAGC TGTCTGCTCCCAGGAGGCGATGACGGGGCCTGCCGGGCC GTGATGCCTCGTTGGTACTTCGACCTCTCCAAGGGAAAGT GCGTGCGCTTTATATATGGTGGCTGCGGCGGCAACAGGAA CAATTTTGAGTCTGAGGATTATTGTATGGCTGTGTGTAAA GCGATGATTCCTCCAACTCCTCTGCCAACCAATGATGTTG ATGTGTATTTCGAGACCTCTGCAGATGATAATGAGCATGC TCGCTTCCAGAAGGCTAAGGAGCAGCTGGAGATTCGGCAC CGCAACCGAATGGACAGGGTAAAGAAGGAATGGGAAGAGG CAGAGCTTCAAGCTAAGAACCTCCCCAAAGCAGAGAGGCA GACTCTGATTCAGCACTTCCAAGCCATGGTTAAAGCTTTA GAGAAGGAAGCAGCCAGTGAGAAGCAGCAGCTGGTGGAGA CCCACCTGGCCCGAGTGGAAGCTATGCTGAATGACCGCCG TCGGATGGCTCTGGAGAACTACCTGGCTGCCTTGCAGTCT GACCCGCCACGGCCTCATCGCATTCTCCAGGCCTTACGGC | 3 |

TABLE 1-continued

GEP-NEN Biomarker/Houskeeper Sequence Information

| Gene Name | RefSeq Accession | Sequence | SEQ ID NO: |
|---|---|---|---|
| | | GTTATGTCCGTGCTGAGAACAAAGATCGCTTACATACCAT<br>CCGTCATTACCAGCATGTGTTGGCTGTTGACCCAGAAAAG<br>GCGGCCCAGATGAAATCCCAGGTGATGACACATCTCCACG<br>TGATTGAAGAAAGGAGGAACCAAAGCCTCTCTCTGCTCTA<br>CAAAGTACCTTATGTAGCCCAAGAAATTCAAGAGGAAATT<br>GATGAGCTCCTTCAGGAGCAGCGTGCAGATATGGACCAGT<br>TCACTGCCTCAATCTCAGAGACCCCTGTGGACGTCCGGGT<br>GAGCTCTGAGGAGAGTGAGGAGATCCCACCGTTCCACCCC<br>TTCCACCCCTTCCCAGCCCTACCTGAGAACGAAGGATCTG<br>GAGTGGGAGAGCAGGATGGGGGACTGATCGGTGCCGAAGA<br>GAAAGTGATTAACAGTAAGAATAAAGTGGATGAAAACATG<br>GTCATTGACGAGACTCTGGATGTTAAGGAAATGATTTTCA<br>ATGCCGAGAGAGTTGGAGGCCTCGAGGAAGAGCGGGAATC<br>CGTGGGCCCACTGCGGGAGGACTTCAGTCTGAGTAGCAGT<br>GCTCTCATTGGCCTGCTGGTCATCGCAGTGGCCATTGCCA<br>CGGTCATCGTCATCAGCCTGGTGATGCTGAGGAAGAGGCA<br>GTATGGCACCATCAGCCACGGGATCGTGGAGGTTGATCCA<br>ATGCTCACCCCAGAAGAGCGTCACCTGAACAAGATGCAGA<br>ACCATGGCTATGAGAACCCCACCTACAAATACCTGGAGCA<br>GATGCAGATTTAGGTGGCAGGGAGCGCGGCAGCCCTGGCG<br>GAGGGATGCAGGTGGGCCGGAAGATCCCACGATTCCGATC<br>GACTGCCAAGCAGCAGCCGCTGCCAGGGGCTGCGTCTGAC<br>ATCCTGACCTCCTGGACTGTAGGACTATATAAAGTACTAC<br>TGTAGAACTGCAATTTCCATTCTTTTAAATGGGTGAAAAA<br>TGGTAATATAACAATATATGATATATAAACCTTAAATGAA<br>AAAAATGATCTATTGCAGATATTTGATGTAGTTTTCTTTT<br>TTAAATTAATCAGAAACCCCACTTCCATTGTATTGTCTGA<br>CACATGCTCTCAATATATAATAAATGGGAAATGTCGATTT<br>TCAATAATAGACTTATATGCAGGCTGTCGTTCCGGTTATG<br>TTGTGTAAGTCAACTCTTCAGCCTCATTCACTGTCCTGGC<br>TTTTATTTAAAGAAAAAAAAGGCAGTATTCCCTTTTTAAA<br>TGAGCTTTCAGGAAGTTGCTGAGAAATGGGGTGGAATAGG<br>GAACTGTAATGGCCACTGAAGCACGTGAGAGACCCTCGCA<br>AAATGATGTGAAAGGACCAGTTTCTTGAAGTCCAGTGTTT<br>CCACGGCTGGATACCTGTGTGTCTCCATAAAAGTCCTGTC<br>ACCAAGGACGTTAAAGGCATTTTATTCCAGCGTCTTCTAG<br>AGAGCTTAGTGTATACAGATGAGGGTGTCCGCTGCTGCTT<br>TCCTTCGGAATCCAGTGCTTCCACAGAGATTAGCCTGTAG<br>CTTATATTTGACATTCTTCACTGTCTGTTGTTTACCTACC<br>GTAGCTTTTTACCGTTCACTTCCCCTTCCAACTATGTCCA<br>GATGTGCAGGCTCCTCCTCTCTGGACTTTCTCCAAAGGCA<br>CTGACCCTCGGCCTCTACTTTGTCCCCTCACCTCCACCCC<br>CTCCTGTCACCGGCCTTGTGACATTCACTCAGAGAAGACC<br>ACACCAAGGAGGCGGCCGCTGGCCCAGGAGAGAACACGGG<br>GAGGTTTGTTTGTGTGAAAGGAAAGTAGTCCAGGCTGTCC<br>CTGAAACTGAGTCTGTGGACACTGTGGAAAGCTTTGAACA<br>ATTGTGTTTTCGTCACAGGAGTCTTTGTAATGCTTGTACA<br>GTTGATGTCGATGCTCACTGCTTCTGCTTTTTCTTTCTTT<br>TTATTTTAAATCTGAAGGTTCTGGTAACCTGTGGTGTATT<br>TTTATTTTCCTGTGACTGTTTTGTTTTGTTTTTTCCTT<br>TTTCCTCCCCTTTGACCCTATTCATGTCTCTACCCACTAT<br>GCACAGATTAAACTTCACCTACAAACTCCTTAATATGATC<br>TGTGGAGAATGTACACAGTTTAAACACATCAATAAATACT<br>TTAACTTCCACCGAGAAAAAAAAAAAAAAAA | |
| ARAF1 | NM_001654.4 | CTTGACAGACGTGACCCTGACCCAATAAGGGTGGAAGGCT<br>GAGTCCCGCAGAGCCAATAACGAGAGTCCGAGAGGCGACG<br>GAGGCGGACTCTGTGAGGAAACAAGAAGAGAGGCCCAAGA<br>TGGAGACGGCGGCGGCTGTAGCGGCGTGACAGGAGCCCCA<br>TGGCACCTGCCCAGCCCCACCTCAGCCCATCTTGACAAAA<br>TCTAAGGCTCCATGGAGCCACCACGGGGCCCCCCTGCCAA<br>TGGGGCCGAGCCATCCCGGGCAGTGGGCACCGTCAAGTA<br>TACCTGCCCAACAAGCAACGCACGGTGGTGACTGTCCGGG<br>ATGGCATGAGTGTCTACGACTCTCTAGACAAGGCCCTGAA<br>GGTGCGGGGTCTAAATCAGGACTGCTGTGTGGTCTACCGA<br>CTCATCAAGGGACGAAAGACGGTCACTGCCTGGGACACAG<br>CCATTGCTCCCTGGATGGCGAGGAGCTCATTGTCGAGGT<br>CCTTGAAGATGTCCCGCTGACCATGCACAATTTTGTACGG<br>AAGACCTTCTTCAGCCTGGCGTTCTGTGACTTCTGCCTTA<br>AGTTTCTGTTCCATGGCTTCCGTTGCCAAACCTGTGGCTA<br>CAAGTTCCACCAGCATTGTTCCTCCAAGGTCCCCACAGTC<br>TGTGTTGACATGAGTACCAACCGCCAACAGTTCTACCACA<br>GTGTCCAGGATTTGTCCGGAGGCTCCAGACAGCATGAGGC<br>TCCCTCGAACCGCCCCCTGAATGAGTTGCTAACCCCCCAG<br>GGTCCCAGCCCCCGCACCCAGCACTGTGACCCGGAGCACT | 4 |

TABLE 1-continued

GEP-NEN Biomarker/Houskeeper Sequence Information

| Gene Name | RefSeq Accession | Sequence | SEQ ID NO: |
|---|---|---|---|
| | | TCCCCTTCCCTGCCCCAGCCAATGCCCCCCTACAGCGCAT CCGCTCCACGTCCACTCCCAACGTCCATATGGTCAGCACC ACGGCCCCCATGGACTCCAACCTCATCCAGCTCACTGGCC AGAGTTTCAGCACTGATGCTGCCGGTAGTAGAGGAGGTAG TGATGGAACCCCCCGGGGGAGCCCCAGCCCAGCCAGCGTG TCCTCGGGGAGGAAGTCCCCACATTCCAAGTCACCAGCAG AGCAGCGCGAGCGGAAGTCCTTGGCCGATGACAAGAAGAA AGTGAAGAACCTGGGGTACCGGGACTCAGGCTATTACTGG GAGGTACCACCCAGTGAGGTGCAGCTGCTGAAGAGGATCG GGACGGGCTCGTTTGGCACCGTGTTTCGAGGGCGGTGGCA TGGCGATGTGGCCGTGAAGGTGCTCAAGGTGTCCCAGCCC ACAGCTGAGCAGGCCCAGGCTTTCAAGAATGAGATGCAGG TGCTCAGGAAGACGCGACATGTCAACATCTTGCTGTTTAT GGGCTTCATGACCCGGCCGGGATTTGCCATCATCACACAG TGGTGTGAGGGCTCCAGCCTCTACCATCACCTGCATGTGG CCGACACACGCTTCGACATGGTCCAGCTCATCGACGTGGC CCGGCAGACTGCCCAGGGCATGGACTACCTCCATGCCAAG AACATCATCCACCGAGATCTCAAGTCTAACAACATCTTCC TACATGAGGGGCTCACGGTGAAGATCGGTGACTTTGGCTT GGCCACAGTGAAGACTCGATGGAGCGGGGCCCAGCCCTTG GAGCAGCCCTCAGGATCTGTGCTGTGGATGGCAGCTGAGG TGATCCGTATGCAGGACCCGAACCCCTACAGCTTCCAGTC AGACGTCTATGCCTACGGGGTTGTGCTCTACGAGCTTATG ACTGGCTCACTGCCTTACAGCCACATTGGCTGCCGTGACC AGATTATCTTTATGGTGGGCCGTGGCTATCTGTCCCCGGA CCTCAGCAAAATCTCCAGCAACTGCCCCAAGGCCATGCGG CGCCTGCTGTCTGACTGCCTCAAGTTCCAGCGGGAGGAGC GGCCCCTCTTCCCCCAGATCCTGGCCACAATTGAGCTGCT GCAACGGTCACTCCCCAAGATTGAGCGGAGTGCCTCGGAA CCCTCCTTGCACCGCACCCAGGCCGATGAGTTGCCTGCCT GCCTACTCAGCGCAGCCCGCCTTGTGCCTTAGGCCCCGCC CAAGCCACCAGGGAGCCAATCTCAGCCCTCCACGCCAAGG AGCCTTGCCCACCAGCCAATCAATGTTCGTCTCTGCCCTG ATGCTGCCTCAGGATCCCCCATTCCCCACCCTGGGAGATG AGGGGGTCCCCATGTGCTTTTCCAGTTCTTCTGGAATTGG GGGACCCCCGCCAAAGACTGAGCCCCCTGTCTCCTCCATC ATTTGGTTTCCTCTTGGCTTTGGGGATACTTCTAAATTTT GGGAGCTCCTCCATCTCCAATGGCTGGGATTTGTGGCAGG GATTCCACTCAGAACCTCTCTGGAATTTGTGCCTGATGTG CCTTCCACTGGATTTTGGGGTTCCCAGCACCCCATGTGGA TTTTGGGGGGTCCCTTTTGTGTCTCCCCCGCCATTCAAGG ACTCCTCTCTTTCTTCACCAAGAAGCACAGAATTCTGCTG GGCTTTGCTTGTTTAAAAAAAAAAAAAAAAAAAAAAA AAAAAAAAAAAAAAAAAAAAAAAAAAAAAAAAAAAAA AA | |
| ATP6V1H | NM_015941.3 | AGCAGTCACGTGCCTCCGATCACGTGACCGGCGCCTCTGT CATTCTACTGCGGCCGCCCTGGCTTCCTTCTACCTGTGCG GCCCTCAACGTCTCCTTGGTGCGGGACCCGCTTCACTTTC GGCTCCCGGAGTCTCCCTCCACTGCTCAGACCTCTGGACC TGACAGGAGACGCCTACTTGGCTCTGACGCGGCGCCCCAG CCCGGCTGTGTCCCCGGCGCCCCGGACCACCCTCCCTGCC GGCTTTGGGTGCGTTGTGGGGTCCCGAGGATTCGCGAGAT TTGTTGAAAGACATTCAAGATTACGAAGTTTAGATGACCA AAATGGATATCCGAGGTGCTGTGGATGCTGCTGTCCCCAC CAATATTATTGCTGCCAAGGCTGCAGAAGTTCGTGCAAAC AAAGTCAACTGGCAATCCTATCTTCAGGGACAGATGATTT CTGCTGAAGATTGTGAGTTTATTCAGAGGTTTGAAATGAA ACGAAGCCCTGAAGAGAAGCAAGAGATGCTTCAAACTGAA GGCAGCCAGTGTGCTAAAACATTATAAATCTGATGACTC ATATCTGCAAAGAACAGACCGTTCAGTATATACTAACTAT GGTGGATGATATGCTGCAGGAAAATCATCAGCGTGTTAGC ATTTTCTTTGACTATGCAAGATGTAGCAAGAACACTGCGT GGCCCTACTTTCTGCCAATGTTGAATCGCCAGGATCCCTT CACTGTTCATATGGCAGCAAGAATTATTGCCAAGTTAGCA GCTTGGGGAAAAGAACTGATGGAAGGCAGTGACTTAAATT ACTATTTCAATTGGATAAAAACTCAGCTGAGTTCACAGAA ACTGCGTGGTAGCGGTGTTGCTGTTGAAACAGGAACAGTC TCTTCAAGTGATAGTTCGCAGTATGTGCAGTGCGTGGCCG GGTGTTTGCAGCTGATGCTCCGGGTCAATGAGTACCGCTT TGCTTGGGTGGAAGCAGATGGGGTAAATTGCATAATGGGA GTGTTGAGTAACAAGTGTGGCTTTCAGCTCCAGTATCAAA TGATTTTTTCAATATGGCTCCTGGCATTCAGTCCTCAAAT GTGTGAACACCTGCGGCGCTATAATATCATTCCAGTTCTG TCTGATATCCTTCAGGAGTCTGTCAAAGAGAAAGTAACAA | 5 |

TABLE 1-continued

GEP-NEN Biomarker/Houskeeper Sequence Information

| Gene Name | RefSeq Accession | Sequence | SEQ ID NO: |
|---|---|---|---|
| | | GAATCATTCTTGCAGCATTTCGTAACTTTTTAGAAAAATC<br>AACTGAAAGAGAAACTCGCCAAGAATATGCCCTGGCTATG<br>ATTCAGTGCAAAGTTCTGAAACAGTTGGAGAACTTGGAAC<br>AGCAGAAGTACGATGATGAAGATATCAGCGAAGATATCAA<br>ATTTCTTTTGGAAAAACTTGGAGAGAGTGTCCAGGACCTT<br>AGTTCATTTGATGAATACAGTTCAGAACTTAAATCTGGAA<br>GGTTGGAATGGAGTCCTGTGCACAAATCTGAGAAATTTTG<br>GAGAGAGAATGCTGTGAGGTTAAATGAGAAGAATTATGAA<br>CTCTTGAAAATCTTGACAAAACTTTTGGAAGTGTCAGATG<br>ATCCCCAAGTCTTAGCTGTTGCTGCTCACGATGTTGGAGA<br>ATATGTGCGGCATTATCCACGAGGCAAACGGGTCATCGAG<br>CAGCTCGGTGGGAAGCAGCTGGTCATGAACCACATGCATC<br>ATGAAGACCAGCAGGTCCGCTATAATGCTCTGCTGGCCGT<br>GCAGAAGCTCATGGTGCACAACTGGGAATACCTTGGCAAG<br>CAGCTCCAGTCCGAGCAGCCCCAGACCGCTGCCGCCCGAA<br>GCTAAGCCTGCCTCTGGCCTTCCCCTCCGCCTCAATGCAG<br>AACCAGTAGTGGGAGCACTGTGTTTAGAGTTAAGAGTGAA<br>CACTGTTTGATTTTACTTGGAATTTCCTCTGTTATATAGC<br>TTTTCCCAATGCTAATTTCCAAACAACAACAACAAAATAA<br>CATGTTTGCCTGTTAAGTTGTATAAAAGTAGGTGATTCTG<br>TATTTAAAGAAAATATTACTGTTACATATACTGCTTGCAA<br>TTTCTGTATTTATTGTTCTCTGGAAATAAATATAGTTATT<br>AAAGGATTCTCACTCCAAACATGGCCTCTCTCTTTACTTG<br>GACTTTGAACAAAAGTCAACTGTTGTCTCTTTTCAAACCA<br>AATTGGGAGAATTGTTGCAAAGTAGTGAATGGCAAATAAA<br>TGTTTTAAAATCTATCGCTCTATCAA | |
| BNIP3L | NM_004331.2 | CGTCAGGGGCAGGGGAGGGACGGCGCAGGCGCAGAAAAGG<br>GGGCGGCGGACTCGGCTTGTTGTGTTGCTGCCTGAGTGCC<br>GGAGACGGTCCTGCTGCTGCCGCAGTCCTGCCAGCTGTCC<br>GACAATGTCGTCCCACCTAGTCGAGCCGCCGCCGCCCCTG<br>CACAACAACAACAACAACTGCGAGGAAAATGAGCAGTCTC<br>TGCCCCCGCCGGCCGGCCTCAACAGTTCCTGGGTGGAGCT<br>ACCCATGAACAGCAGCAATGGCAATGATAATGGCAATGGG<br>AAAAATGGGGGGCTGGAACACGTACCATCCTCATCCTCCA<br>TCCACAATGGAGACATGGAGAAGATTCTTTTGGATGCACA<br>ACATGAATCAGGACAGAGTAGTTCCAGAGGCAGTTCTCAC<br>TGTGACAGCCCTTCGCCACAAGAAGATGGGCAGATCATGT<br>TTGATGTGGAAATGCACACCAGCAGGGACCATAGCTCTCA<br>GTCAGAAGAAGAAGTTGTAGAAGGAGAGAAGGAAGTCGAG<br>GCTTTGAAGAAAAGTGCGGACTGGGTATCAGACTGGTCCA<br>GTAGACCCGAAAACATTCCACCCAAGGAGTTCCACTTCAG<br>ACACCCTAAACGTTCTGTGTCTTTAAGCATGAGGAAAAGT<br>GGGAGCCATGAAGAAAGGGGGTATTTTCTCCGCAGAATTTC<br>TGAAGGTGTTCATTCCATCTCTCTTCCTTTCTCATGTTTT<br>GGCTTTGGGGCTAGGCATCTATATTGGAAAGCGACTGAGC<br>ACACCCTCTGCCAGCACCTACTGAGGGAAAGGAAAAGCCC<br>CTGGAAATGCGTGTGACCTGTGAAGTGGTGTATTGTCACA<br>GTAGCTTATTTGAACTTGAGACCATTGTAAGCATGACCCA<br>ACCTACCACCCTGTTTTTACATATCCAATTCCAGTAACTC<br>TCAAATTCAATATTTTATTCAAACTCTGTTGAGGCATTTT<br>ACTAACCTTATACCCTTTTTGGCCTGAAGACATTTTAGAA<br>TTTCCTAACAGAGTTTACTGTTGTTTAGAAATTTGCAAGG<br>GCTTCTTTTCCGCAAATGCCACCAGCAGATTATAATTTTG<br>TCAGCAATGCTATTATCTCTAATTAGTGCCACCAGACTAG<br>ACCTGTATCATTCATGGTATAAATTTTACTCTTGCAACAT<br>AACTACCATCTCTCTCTTAAAACGAGATCAGGTTAGCAAA<br>TGATGTAAAAGAAGCTTTATTGTCTAGTTGTTTTTTTTCC<br>CCCAAGACAAAGGCAAGTTTCCCTAAGTTTGAGTTGATAG<br>TTATTAAAAAGAAAACAAAACAAAAAAAAAAGGCAAGGCA<br>CAACAAAAAAATATCCTGGGCAATAAAAAAAATATTTTAA<br>ACCAGCTTTGGAGCCACTTTTTTGTCTAAGCCTCCTAATA<br>GCGTCTTTTAATTTATAGGAGGCAAACTGTATAAATGATA<br>GGTATGAAATAGAATAAGAAGTAAAATACATCAGCAGATT<br>TTCATACTAGTATGTTGTAATGCTGTCTTTTCTATGGTGT<br>AGAATCTTTCTTTCTGATAAGGAACGTCTCAGGCTTAGAA<br>ATATATGAAATTGCTTTTTGAGATTTTTGCGTGTGTGTTT<br>GATATTTTTTACGATAATTAGCTGCATGTGAATTTTTCAT<br>GACCTTCTTTACATTTTTTATTTTTATTTCTTTATTTTT<br>TTTTCTCTAAGAAGAGGCTTTGGAATGAGTTCCAATTTGT<br>GATGTTAATACAGGCTTCTTGTTTTAGGAAGCATCACCTA<br>TACTCTGAAGCCTTTAAACTCTGAAGAGAATTGTTTCAGA<br>GTTATTCCAAGCACTTGTGCAACTTGGAAAAACAGACTTG<br>GGTTGTGGGAACAGTTGACAGCGTTCTGAAAAGATGCCAT<br>TTGTTTCCTTCTGATCTCTCACTGAATAATGTTTACTGTA | 6 |

TABLE 1-continued

GEP-NEN Biomarker/Houskeeper Sequence Information

| Gene Name | RefSeq Accession | Sequence | SEQ ID NO: |
|---|---|---|---|
| | | CAGTCTTCCCAAGGTGATTCCTGCGACTGCAGGCACTGGT<br>CATTTTCTCATGTAGCTGTCTTTTCAGTTATGGTAAACTC<br>TTAAAGTTCAGAACACTCAACAGATTCCTTCAGTGATATA<br>CTTGTTCGTTCATTTCTAAAATGTGAAGCTTTAGGACCAA<br>ATTGTTAGAAAGCATCAGGATGACCAGTTATCTCGAGTAG<br>ATTTTCTTGGATTTCAGAACATCTAGCATGACTCTGAAGG<br>ATACCACATGTTTTATATATAAATAATTACTGTTTATGAT<br>ATAGACATTGATATTGACTATTTAGAGAACCGTTGTTAAT<br>TTTAAAACTAGCAATCTATAAAGTGCACCAGGTCAACTTG<br>AATAAAAACACTATGACAGACAGGTTTGCCAGTTTGCAGA<br>AACTAACTCTTTTCTCACATCAACATTTGTAAAATTGATG<br>TGTTATAGTGGAAAATAACATATAGATTAAACAAAATTTT<br>TATCTTTTTTCAAGAATATAGCTGGCTATCTTTAAGAAAG<br>ATGATATATCCTAGTTTTGAAAGTAATTTTCTTTTTTCTT<br>TCTAGCATTTGATGTCTAAATAATTTTGGACATCTTTTTC<br>CTAGACCATGTTTCTGTCTTACTCTTAAACCTGGTAACAC<br>TTGATTTGCCTTCTATAACCTATTTATTTCAAGTGTTCAT<br>ATTTGAATTTCTTTGGGAAGAAAGTAAATCTGATGGCTCA<br>CTGATTTTTGAAAAGCCTGAATAAAATTGGAAAGACTGGA<br>AAGTTAGGAGAACTGACTAGCTAAACTGCTACAGTATGCA<br>ATTTCTATTACAATTGGTATTACAGGGGGGAAAAGTAAAA<br>TTACACTTTACCTGAAAGTGACTTCTTACAGCTAGTGCAT<br>TGTGCTCTTTCCAAGTTCAGCAGCAGTTCTATCAGTGGTG<br>CCACTGAAACTGGGTATATTTATGATTTCTTTCAGCGTTA<br>AAAAGAAACATAGTGTTGCCCTTTTCTTAAAGCATCAGT<br>GAAATTATGGAAAATTACTTAAAACGTGAATACATCATCA<br>CAGTAGAATTTATTATGAGAGCATGTAGTATGTATCTGTA<br>GCCCTAACACATGGGATGAACGTTTTACTGCTACACCCAG<br>ATTTGTGTTGAACGAAAACATTGTGGTTTGGAAAGGAGAA<br>TTCAACAATTAATAGTTGAAATTGTGAGGTTAATGTTTAA<br>AAAGCTTTACACCTGTTTACAATTTGGGGACAAAAAGGCA<br>GGCTTCATTTTTCATATGTTTGATGAAAACTGGCTCAAGA<br>TGTTTGTAAATAGAATCAAGAGCAAAACTGCACAAACTTG<br>CACATTGGAAAGTGCAACAAGTTCCCGTGATTGCAGTAAA<br>AATATTTACTATTCTAAAAAAATGAGAATTGAAGACTTAG<br>CCAGTCAGATAAGTTTTTTCATGAACCCGTTGTGGAAATT<br>ATTGGAATTAACTGAGCCAAAGTGATTATGCATTCTTCAT<br>CTATTTTAGTTAGCACTTTGTATCGTTATATACAGTTTAC<br>AATACATGTATAACTTGTAGCTATAAACATTTTGTGCCAT<br>TAAAGCTCTCACAAAACTTTAAAAA | |
| BRAF | NM_004333.4 | CGCCTCCCTTCCCCCTCCCCGCCCGACAGCGGCCGCTCGG<br>GCCCCGGCTCTCGGTTATAAGATGGCGGCGCTGAGCGGTG<br>GCGGTGGTGGCGGCGCGGAGCCGGGCCAGGCTCTGTTCAA<br>CGGGGACATGGAGCCCGAGGCCGGCGCCGGCGCCGGCGCC<br>GCGGCCTCTTCGGCTGCGGACCCTGCCATTCCGGAGGAGG<br>TGTGGAATATCAAACAAATGATTAAGTTGACACAGGAACA<br>TATAGAGGCCCTATTGGACAAATTTGGTGGGGAGCATAAT<br>CCACCATCAATATATCTGGAGGCCTATGAAGAATACACCA<br>GCAAGCTAGATGCACTCCAACAAAGAGAACAACAGTTATT<br>GGAATCTCTGGGGAACGGAACTGATTTTTCTGTTTCTAGC<br>TCTGCATCAATGGATACCGTTACATCTTCTTCCTCTTCTA<br>GCCTTTCAGTGCTACCTTCATCTCTTTCAGTTTTTCAAAA<br>TCCCACAGATGTGGCACGGAGCAACCCCAAGTCACCACAA<br>AAACCTATCGTTAGAGTCTTCCTGCCCAACAAACAGAGGA<br>CAGTGGTACCTGCAAGGTGTGGAGTTACAGTCCGAGACAG<br>TCTAAAGAAAGCACTGATGATGAGAGGTCTAATCCCAGAG<br>TGCTGTGCTGTTTACAGAATTCAGGATGGAGAGAAGAAAC<br>CAATTGGTTGGGACACTGATATTTCCTGGCTTACTGGAGA<br>AGAATTGCATGTGGAAGTGTTGGAGAATGTTCCACTTACA<br>ACACACAACTTTGTACGAAAAACGTTTTTCACCTTAGCAT<br>TTTGTGACTTTTGTCGAAAGCTGCTTTTTCCAGGGTTTCCG<br>CTGTCAAACATGTGGTTATAAATTTCACCAGCGTTGTAGT<br>ACAGAAGTTCCACTGATGTGTGTTAATTATGACCAACTTG<br>ATTTGCTGTTTGTCTCCAAGTTCTTTGAACACCACCCAAT<br>ACCACAGGAAGAGGCGTCCTTAGCAGAGACTGCCCTAACA<br>TCTGGATCATCCCCTTCCGCACCCGCCTCGGACTCTATTG<br>GGCCCCAAATTCTCACCAGTCCGTCTCCTTCAAAATCCAT<br>TCCAATTCCACAGCCCTTCCGACCAGCAGATGAAGATCAT<br>CGAAATCAATTTGGGCAACGAGACCGATCCTCATCAGCTC<br>CCAATGTGCATATAAACAATAGAACCTGTCAATATTGA<br>TGACTTGATTAGAGACCAAGGATTCGTGGTGATGGAGGA<br>TCAACCACAGGTTTGTCTGCTACCCCCCTGCCTCATTAC<br>CTGGCTCACTAACTAACGTGAAAGCCTTACAGAAATCTCC<br>AGGACCTCAGCGAGAAAGGAAGTCATCTTCATCCCTCAGAA | 7 |

TABLE 1-continued

GEP-NEN Biomarker/Houskeeper Sequence Information

| Gene Name | RefSeq Accession | Sequence | SEQ ID NO: |
|---|---|---|---|
| | | GACAGGAATCGAATGAAAACACTTGGTAGACGGGACTCGA<br>GTGATGATTGGGAGATTCCTGATGGGCAGATTACAGTGGG<br>ACAAAGAATTGGATCTGGATCATTTGGAACAGTCTACAAG<br>GGAAAGTGGCATGGTGATGTGGCAGTGAAAATGTTGAATG<br>TGACAGCACCTACACCTCAGCAGTTACAAGCCTTCAAAAA<br>TGAAGTAGGAGTACTCAGGAAAACACGACATGTGAATATC<br>CTACTCTTCATGGGCTATTCCACAAAGCCACAACTGGCTA<br>TTGTTACCCAGTGGTGTGAGGGCTCCAGCTTGTATCACCA<br>TCTCCATATCATTGAGACCAAATTTGAGATGATCAAACTT<br>ATAGATATTGCACGACAGACTGCACAGGGCATGGATTACT<br>TACACGCCAAGTCAATCATCCACAGAGACCTCAAGAGTAA<br>TAATATATTTCTTCATGAAGACCTCACAGTAAAAATAGGT<br>GATTTTGGTCTAGCTACAGTGAAATCTCGATGGAGTGGGT<br>CCCATCAGTTTGAACAGTTGTCTGGATCCATTTTGTGGAT<br>GGCACCAGAAGTCATCAGAATGCAAGATAAAAATCCATAC<br>AGCTTTCAGTCAGATGTATATGCATTTGGAATTGTTCTGT<br>ATGAATTGATGACTGGACAGTTACCTTATTCAAACATCAA<br>CAACAGGGACCAGATAATTTTTATGGTGGGACGAGGATAC<br>CTGTCTCCAGATCTCAGTAAGGTACGGAGTAACTGTCCAA<br>AAGCCATGAAGAGATTAATGGCAGAGTGCCTCAAAAAGAA<br>AAGAGATGAGAGACCACTCTTTCCCCAAATTCTCGCCTCT<br>ATTGAGCTGCTGGCCCGCTCATTGCCAAAAATTCACCGCA<br>GTGCATCAGAACCCTCCTTGAATCGGGCTGGTTTCCAAAC<br>AGAGGATTTTAGTCTATATGCTTGTGCTTCTCCAAAAACA<br>CCCATCCAGGCAGGGGGATATGGTGCGTTTCCTGTCCACT<br>GAAACAAATGAGTGAGAGAGTTCAGGAGAGTAGCAACAAA<br>AGGAAAATAAATGAACATATGTTTGCTTATATGTTAAATT<br>GAATAAAATACTCTCTTTTTTTTTAAGGTGAACCAAAGAA<br>CACTTGTGTGGTTAAAGACTAGATATAATTTTTCCCCAAA<br>CTAAAATTTATACTTAACATTGGATTTTTAACATCCAAGG<br>GTTAAAATACATAGACATTGCTAAAAATTGGCAGAGCCTC<br>TTCTAGAGGCTTTACTTTCTGTTCCGGGTTTGTATCATTC<br>ACTTGGTTATTTTAAGTAGTAAACTTCAGTTTCTCATGCA<br>ACTTTTGTTGCCAGCTATCACATGTCCACTAGGGACTCCA<br>GAAGAAGACCCTACCTATGCCTGTGTTTGCAGGTGAGAAG<br>TTGGCAGTCGGTTAGCCTGGGTTAGATAAGGCAAACTGAA<br>CAGATCTAATTTAGGAAGTCAGTAGAATTTAATAATTCTA<br>TTATTATTCTTAATAATTTTTCTATAACTATTTCTTTTTA<br>TAACAATTTGGAAAATGTGGATGTCTTTTATTTCCTTGAA<br>GCAATAAACTAAGTTTCTTTTTATAAAAA | |
| C21ORF7 | NM_020152.3 | CGCAGCCCCGGTTCCTGCCCGCACCTCTCCCTCCACACCT<br>CCCCGCAAGCTGAGGGAGCCGGCTCCGGCCTCGGCCAGCC<br>CAGGAAGGCGCTCCCACAGCGCAGTGGTGGGCTGAAGGGC<br>TCCTCAAGTGCCGCCAAAGTGGGAGCCCAGGCAGAGGAGG<br>CGCCGAGAGCGAGGGAGGGCTGTGAGGACTGCCAGCACGC<br>TGTCACCTCTCAATAGCAGCCCAAACAGATTAAGACATGG<br>GAGATGTACAAGGGCAGCCGTGGGGCTGGCAACAGCTTCG<br>TAATCCTGGCTTCCTGCTTTCTGGGTCAAAGCCCTGGTGG<br>TGTGTTCTTGATATCGGTCCATCTAGTGGCGTTGTTTGAT<br>TCCTCCCACCTTGCTGATCATTCGTAGTGTAGCCCCCAAG<br>GTGTGGAATAACCCTTAAGCCCTTACCGGGGTCCTTCTGG<br>ACTGAGAATTGTTGTAAAGTAATACTGCTCAGGTGAAAGA<br>CAACTTGAGTGGTTAAATTACTGTCATGCAAAGCGACTAG<br>ATGGTTCAGCTGATTGCACCTTTAGAAGTTATGTGGAACG<br>AGGCAGCAGATCTTAAGCCCCTTGCTCTGTCACGCAGGCT<br>GGAATGCAGTGGTGGAATCATGGCTCACTACAGCCCTGAC<br><u>CTCCTGGGCCCAGAGATGGAGTCTCGCTATTTTGCCCAGG</u><br><u>TTGGTCTT</u>GAACACCTGGCTTCAAGCAGTCCTCCTGCTTT<br>TGGCTTCTTGAAGTGCTTGGATTACAGTATTTCAGTTTTA<br>TGCTCTGCAACAAGTTTGGCCATGTTGGAGGACAATCCAA<br>AGGTCAGCAAGTTGGCTACTGGCGATTGGATGCTCACTCT<br>GAAGCCAAAGTCTATTACTGTGCCCGTGGAAATCCCCAGC<br>TCCCCTCTGGATGATACACCCCCTGAAGACTCCATTCCTT<br>TGGTCTTTCCAGAATTAGACCAGCAGCTACAGCCCCTGCC<br>GCCTTGTCATGACTCCGAGGAATCCATGGAGGTGTTCAAA<br>CAGCACTGCCAAATAGCAGAAGAATACCATGAGGTCAAAA<br>AGGAAATCACCCTGCTTGAGCAAAGGAAGAAGGAGCTCAT<br>TGCCAAGTTAGATCAGGCAGAAAAGGAGAAGGTGGATGCT<br>GCTGAGCTGGTTCGGGAATTCGAGGCTCTGACGAGGAGA<br>ATCGGACGTTGAGGTTGGCCCAGTCTCAATGTGTGGAACA<br>ACTGGAGAAACTTCGAATACAGTATCAGAAGAGGCAGGGC<br>TCGTCCTAACTTTAAATTTTCAGTGTGAGCATACGAGGC<br>TGATGACTGCCCTGTGCTGGCCAAAAGATTTTTATTTTAA<br>ATGAATAGTGAGTCAGATCTATTGCTTCTCTGTATTACCC | 8 |

TABLE 1-continued

GEP-NEN Biomarker/Houskeeper Sequence Information

| Gene Name | RefSeq Accession | Sequence | SEQ ID NO: |
|---|---|---|---|
| | | ACATGACAACTGTCTATAATGAGTTTACTGCTTGCCAGCT TCTAGCTTGAGAGAAGGGATATTTTAAATGAGATCATTAA CGTGAAACTATTACTAGTATATGTTTTTGGAGATCAGAAT TCTTTTCCAAAGATATATGTTTTTTTCTTTTTTAGGAAGA TATGATCATGCTGTACAACAGGGTAGAAAATGATAAAAAT AGACTATTGACTGACCCAGCTAAGAATCGTGGGCTGAGCA GAGTTAAACCATGGGACAAACCCATAACATGTTCACCATA GTTTCACGTATGTGTATTTTTAAATTTCATGCCTTTAATA TTTCAAATATGCTCAAATTTAAACTGTCAGAAACTTCTGT GCATGTATTTATATTTGCCAGAGTATAAACTTTTATACTC TGATTTTTATCCTTCAATGATTGATTATACTAAGAATAAA TGGTCACATATCCTAAAAGCTTCTTCATGAAATTATTAGC AGAAACCATGTTTGTAACCAAAGCACATTTGCCAATGCTA ACTGGCTGTTGTAATAATAAACAGATAAGGCTGCATTTGC TTCATGCCATGTGACCTCACAGTAAACATCTCTGCCTTTG CCTGTGTGTGTTCTGGGGGAGGGGGGACATGGAAAAATAT TGTTTGGACATTACTTGGGTGAGTGCCCATGAAAACATCA GTGAACTTGTAACTATTGTTTTGTTTTGGATTTAAGGAGA TGTTTTAGATCAGTAACAGCTAATAGGAATATGCGAGTAA ATTCAGAATTGAAACAATTTCTCCTTGTTCTACCTATCAC CACATTTTCTCAAATTGAACTCTTTGTTATATGTCCATTT CTATTCATGTAACTTCTTTTTCATTAAACATGGATCAAAA CTGACAAAAAAAAAAAAAA | |
| CD59 | NM_203331.2 | GGGGCCGGGGGCGGAGCCTTGCGGGCTGGAGCGAAAGAA TGCGGGGGCTGAGCGCAGAAGCGGCTCGAGGCTGGAAGAG GATCTTGGGCGCCGCCAGTCTTTAGCACCAGTTGGTGTAG GAGTTGAGACCTACTTCACAGTAGTTCTGTGGACAATCAC AATGGGAATCCAAGGAGGGTCTGTCCTGTTCGGGCTGCTG CTCGTCCTGGCTGTCTTCTGCCATTCAGGTCATAGCCTGC AGTGCTACAACTGTCCTAACCCAACTGCTGACTGCAAAAC AGCCGTCAATTGTTCATCTGATTTTGATGCGTGTCTCATT ACCAAAGCTGGGTTACAAGTGTATAACAAGTGTTGGAAGT TTGAGCATTGCAATTTCAACGACGTCACAACCCGCTTGAG GGAAAATGAGCTAACGTACTACTGCTGCAAGAAGGACCTG TGTAACTTTAACGAACAGCTTGAAATGGTGGGACATCCT TATCAGAGAAAACAGTTCTTCTGCTGGTGACTCCATTTCT GGCAGCAGCCTGGAGCCTTCATCCCTAAGTCAACACCAGG AGAGCTTCTCCCAAACTCCCCGTTCCTGCGTAGTCCGCTT TCTCTTGCTGCCACATTCTAAAGGCTTGATATTTTCCAAA TGGATCCTGTTGGGAAAGAATAAAATTAGCTTGAGCAACC TGGCTAAGATAGAGGGGCTCTGGGAGACTTTGAAGACCAG TCCTGTTTGCAGGGAAGCCCCACTTGAAGGAAGAAGTCTA AGAGTGAAGTAGGTGTGACTTGAACTAGATTGCATGCTTC CTCCTTTGCTCTTGGGAAGACCAGCTTTGCAGTGACAGCT TGAGTGGGTTCTCTGCAGCCCTCAGATTATTTTTCCTCTG GCTCCTTGGATGTAGTCAGTTAGCATCATTAGTACATCTT TGGAGGGTGGGGCAGGAGTATATGAGCATCCTCTCTCACA TGGAACGCTTTCATAAACTTCAGGGATCCCGTGTTGCCAT GGAGGCATGCCAAATGTTCCATATGTGGGTGTCAGTCAGG GACAACAAGATCCTTAATGCAGAGCTAGAGGACTTCTGGC AGGGAAGTGGGGAAGTGTTCCAGATAGCAGGGCATGAAAA CTTAGAGAGGTACAAGTGGCTGAAAATCGAGTTTTTCCTC TGTCTTTAAATTTTATATGGGCTTTGTTATCTTCCACTGG AAAAGTGTAATAGCATACATCAATGGTGTGTTAAAGCTAT TTCCTTGCCTTTTTTTATTGGAATGGTAGGATATCTTGG CTTTGCCACACACAGTTACAGAGTGAACACTCTACTACAT GTGACTGGCAGTATTAAGTGTGCTTATTTTAAATGTTACT GGTAGAAAGGCAGTTCAGGTATGTGTGTATATAGTATGAA TGCAGTGGGACACCCTTTGTGGTTACAGTTTGAGACTTC CAAAGGTCATCCTTAATAACAACAGATCTGCAGGGGTATG TTTTACCATCTGCATCCAGCCTCCTGCTAACTCCTAGCTG ACTCAGCATAGATTGTATAAAATACCTTTGTAACGGCTCT TAGCACACTCACAGATGTTTGAGGCTTTCAGAAGCTCTTC TAAAAAATGATACACACCTTTCACAAGGGCAAACTTTTTC CTTTTCCCTGTGTATTCTAGTGAATGAATCTCAAGATTCA GTAGACCTAATGACATTTGTATTTTATGATCTTGGCTGTA TTTAATGGCATAGGCTGACTTTTGCAGATGGAGGAATTTC TTGATTAATGTTGAAAAAAACCCTTGATTATACTCTGTT GGACAAACCGAGTGCAATGAATGATGCTTTTCTGAAAATG AAATATAACAAGTGGGTGAATGTGGTTATGGCCGAAAAGG ATATGCAGTATGCTTAATGGTAGCAACTGAAAGAAGACAT CCTGAGCAGTGCCAGCTTTCTTCGTTGATGCCGTTCCCT GAACATAGGAAAATAGAAACTTGCTTATCAAACTTAGCA TTACCTTGGTGCTCTGTGTTCTCTGTTAGCTCAGTGTCTT | 9 |

TABLE 1-continued

GEP-NEN Biomarker/Houskeeper Sequence Information

| Gene Name | RefSeq Accession | Sequence | SEQ ID NO: |
|---|---|---|---|
| | | TCCTTACATCAATAGGTTTTTTTTTTTTTTTGGCCTGA GGAAGTACTGACCATGCCCACAGCCACCGGCTGAGCAAAG AAGCTCATTTCATGTGAGTTCTAAGGAATGAGAAACAATT TTGATGAATTTAAGCAGAAAATGAATTTCTGGGAACTTTT TTGGGGGCGGGGGGTGGGGAATTCAGCCACACTCCAGAA AGCCAGGAGTCGACAGTTTTGGAAGCCTCTCTCAGGATTG AGATTCTAGGATGAGATTGGCTTACTGCTATCTTGTGTCA TGTACCCACTTTTTGGCCAGACTACACTGGGAAGAAGGTA GTCCTCTAAAGCAAAATCTGAGTGCCACTAAATGGGGAGA TGGGGCTGTTAAGCTGTCCAAATCAACAAGGGTCATATAA ATGGCCTTAAACTTTGGGGTTGCTTTCTGCAAAAAGTTGC TGTGACTCATGCCATAGACAAGGTTGAGTGCCTGGACCCA AAGGCAATACTGTAATGTAAAGACATTTATAGTACTAGGC AAACAGCACCCCAGGTACTCCAGGCCCTCCTGGCTGGAGA GGGCTGTGGCAATAGAAAATTAGTGCCAACTGCAGTGAGT CAGCCTAGGTTAAATAGAGAGTGTAAGAGTGCTGGACAGG AACCTCCACCCTCATGTCACATTTCTTCAATGTGACCCTT CTGGCCCCTCTCCTCCTGACAGCGGAACAATGACTGCCCC GATAGGTGAGGCTGGAGGAAGAATCAGTCCTGTCCTTGGC AAGCTCTTCACTATGACAGTAAAGGCTCTCTGCCTGCTGC CAAGGCCTGTGACTTTCTAACCTGGCCTCACGCTGGGTAA GCTTAAGGTAGAGGTGCAGGATTAGCAAGCCCACCTGGCT ACCAGGCCGACAGCTACATCCTCCAACTGACCCTGATCAA CGAAGAGGGATTCATGTGTCTGTCTCAGTTGGTTCCAAAT GAAACCAGGGAGCAGGGGAGTTAGGAATCGAACACCAGTC ATGCCTACTGGCTCTCTGCTCGAGAGCCAATACCCTGTGC CCTCCACTCATCTGGATTTACAGGAACTGTCATAGTGTTC AGTATTGGGTGGTGATAAGCCCATTGGATTGTCCCCTTGG GGGGATGAGCTAGGGGTGCAAGGAACACCTGATGAGTAGA TAAGTGGAGCTCATGGTATTTCCTGAAAGATGCTAATCTA TTTGCCAAACTTGGTCTTGAATGTACTGGGGGCTTCAAGG TATGGGTATATTTTTCTTGTGTCCTTGCAGTTAGCCCCCA TGTCTTATGTGTGTCCTGAAAAAATAAGAGCCTGCCCAAG ACTTTGGGCCTCTTGACAGAATTAACCACTTTTATACATC TGAGTTCTCTTGGTAAGTTCTTTAGCAGTGTTCAAAGTCT ACTAGCTCGCATTAGTTTCTGTTGCTGCCAACAGATCTGA ACTAATGCTAACAGATCCCCCTGAGGGATTCTTGATGGGC TGAGCAGCTGGCTGGAGCTAGTACTGACTGACATTCATTG TGATGAGGGCAGCTTTCTGGTACAGGATTCTAAGCTCTAT GTTTTATATACATTTTCATCTGTACTTGCACCTCACTTTA CACAAGAGGAAACTATGCAAAGTTAGCTGGATCGCTCAAG GTCACTTAGGTAAGTTGGCAAGTCCATGCTTCCCACTCAG CTCCTCAGGTCAGCAAGTCTACTTCTCTGCCTATTTTGTA TACTCTCTTTAATATGTGCCTAGCTTTGGAAAGTCTAGAA TGGGTCCCTGGTGCCTTTTTACTTTGAAGAAATCAGTTTC TGCCTCTTTTTGGAAAAGAAAACAAAGTGCAATTGTTTTT TACTGGAAAGTTACCCAATAGCATGAGGTGAACAGGACGT AGTTAGGCCTTCCTGTAAACAGAAAATCATATCAAAACAC TATCTTCCCATCTGTTTCTCAATGCCTGCTACTTTCTTGTA GATATTTCATTTCAGGAGAGCAGCAGTTAAACCCGTGGAT TTTGTAGTTAGGAACCTGGGTTCAAACCCTCTTCCACTAA TTGGCTATGTCTCTGGACAAGTTTTTTTTTTTTTTTT TTAAACCCTTTCTGAACTTTCACTTTCTATGTCTACCTCA AAGAATTGTTGTGAGGCTTGAGATAATGCATTTGTAAAGG GTCTGCCAGATAGGAAGATGCTAGTTATGGATTTACAAGG TTGTTAAGGCTGTAAGAGTCTAAAACCTACAGTGAATCAC AATGCATTTACCCCCACTGACTTGGACATAAGTGAAAACT AGCCAGAAGTCTCTTTTTCAAATTACTTACAGGTTATTCA ATATAAAATTTTTGTAATGGATAATCTTATTTATCTAAAC TAAAGCTTCCTGTTTATACACACTCCTGTTATTCTGGGAT AAGATAAATGACCACAGTACCTTAATTTCTAGGTGGGTGC CTGTGATGGTTCATTGTAGGTAAGGACATTTTCTCTTTTT CAGCAGCTGTGTAGGTCCAGAGCCTCTGGGAGAGGAGGGG GGTAGCATGCACCCAGCAGGGGACTGAACTGGGAAACTCA AGGTTCTTTTTACTGTGGGGTAGTGAGCTGCCTTTCTGTG ATCGGTTTCCCTAGGGATGTTGCTGTTCCCCTCCTTGCTA TTCGCAGCTACATACAACGTGGCCAACCCCAGTAGGCTGA TCCTATATATGATCAGTGCTGGTGCTGACTCTCAATAGCC CCACCCAAGCTGGCTATAGGTTTACAGATACATTAATTAG GCAACCTAAAATATTGATGCTGGTGTTGGTGTGACATAAT GCTATGGCCAGAACTGAAACTTAGAGTTATAATTCATGTA TTAGGGTTCTCCAGAGGGACAGAATTAGTAGGATATATGT ATATATGAAAGGGAGGTTATTAGGGAGAACTGGCTCCCAC AGTTAGAAGGCGAAGTCGCACAATAGGCCGTCTGCAAGCT GGGTTAGAGAGAAGCCAGTAGTGGCTCAGCCTGAGTTCAA | |

TABLE 1-continued

GEP-NEN Biomarker/Houskeeper Sequence Information

| Gene Name | RefSeq Accession | Sequence | SEQ ID NO: |
|---|---|---|---|
| | | AAACCTCAAAACTGGGGAAGCTGACAGTGCAGCCAGCCTT<br>CAGTCTGTGGCCAAAGGCCCAAGAGCCCCTGGCAACCAAC<br>CCACTGGTGCAAGTCCTAGATTCCAAAGGCTGAAGAACCT<br>GGAGTCTGATGTCCAAGAGCAGGAAGAGTGGAAGAAAGCC<br>AGAAGACTCAGCAAACAAGGTAGACAGTGTCTACCACCAT<br>AGTGGCCATACCAAAGAGGCTACCGATTCCTTCCTGCTAC<br>CTGGATCCCTGAAGTTGCCCTGGTCTCTGCACCTTCTAAA<br>CCTAGTTCTTAAGAGCTTTCCATTACATGAGCTGTCTCAA<br>AGCCCTCCAATAAATTCTCAGTGTAAGCTTCTGTTGCTTG<br>TGGACAGAAAATTCTGACAGACCTACCCTATAAGTGTTAC<br>TGTCAGGATAACATGAGAACGCACAACAGTAAGTGGTCAC<br>TAAGTGTTAGCTACGGTTATTTTGCCCAAGGTAGCATGGC<br>TAGTTGATGCCGGTTGATGGGGCTTAAACCCAGCTCCCTC<br>ATCTTCCAGGCCTCTGTACTCCCTATTCCACTAAACTACC<br>TCTCAGGTTTATTTTTTAAATTCTTACTCTGCAAGTACA<br>TAGGACCACATTTACCTGGGAAAACAAGAATAAAGGCTGC<br>TCTGCATTTTTAGAAACTTTTTTGAAAGGGAGATGGGAA<br>TGCCTGCACCCCCAAGTCCAGACCAACACAATGGTTAATT<br>GAGATGAATAATAAAGGAAAGACTGTTCTGGGCTTCCCAG<br>AATAGCTTGGTCCTTAAATTGTGGCACAAACAACCTCCTG<br>TCAGAGCCAGCCTCCTGCCAGGAAGAGGGGTAGGAGACTA<br>GAGGCCGTGTGTGCAGCCTTGCCCTGAAGGCTAGGGTGAC<br>AATTTGGAGGCTGTCCAAACACCCTGGCCTCTAGAGCTGG<br>CCTGTCTATTTGAAATGCCGGCTCTGATGCTAATCGGCGA<br>CCCTCAGGCAAGTTACTTAACCTTACATGCCTCAGTTTTC<br>TCATCTGGAAAATGAGAACCCTAGGTTTAGGGTTGTTAGA<br>AAAGTTAAATGAGTTAAGACAAGTGCCTGGGACACAGTAG<br>CCTCTTGTGTGTGTTTATCATTATGTCCTCAGCAGGTCGT<br>AGAAGCAGCTTCTCAGGTGTGAGGCTGGCGCGATTATCTG<br>GAGTGGGTTGGGTTTTCTAGGATGGACCCCCTGCTGCATT<br>TTCCTCATTCATCCACCAGGGCTTAATGGGGAATCAAGGA<br>ATCCATGTGTAACTGTATAATAACTGTAGCCACACTCCAA<br>TGACCACCTACTAGTTGTCCCTGGCACTGCTTATACATAT<br>GTCCATCAAATCAATCCTATGAAGTAGATACTGTCTTCAT<br>TTTATAGATCAGAGACAATTGGGGTTCAGAGAGCTGATGT<br>GATTTTCCCAGGGTCACAGAGAGTCCCAGATTCAGGCACA<br>ACTCTTGTATTCCAAGACACAACCACTACATGTCCAAAGG<br>CTGCCCAGAGCCACCGGGCACGGCAAATTGTGACATATCC<br>CTAAAGAGGCTGAGCACCTGGTCAGGATCTGATGGCTGAC<br>AGTGTGTCCAGATGCAGAGCTGGAGTGGGGGAGGGGAAGG<br>GGGGCTCCTTGGGACAGAGAAGGCTTTCTGTGCTTTCTCT<br>GAAGGGAGCAGTCTGAGGACCAAGGGAACCCGGCAAACAG<br>CACCTCAGGTACTCCAGGCCCTCCTGGCTGGAGAGGGCTG<br>TGGCAATGGAAAATTAGTGCCAACTGCAATGAGTCAGCCT<br>CGGTTAAATAGAGAGTGAAGAATGCTGGACAGGAACCTCC<br>ACCCTCATGTCACATTTCTTCAGTGTGACCCTTCTGGCCC<br>CTCTCCTCCTGACAGCGGAACAATGACTGCCCCGATAGGT<br>GAGGCTGGAGGAAGAATCAGTCCTGTCCTTGGCAAGCTCT<br>TCACTATGACAGTAAAGGCTCTCTGCCTGCTGCCAAGGCC<br>TGTGACTTTCTAACCTGGCCTCACGCTGGGTAAGCTTAAG<br>GTAGAGGTGCAGGATTAGCAAGCCCACCTGGCTACCAGGC<br>CGACAGCTACATCTTTCAACTGACCCTGATCAACGAAGAG<br>GGACTTGTGTCTCTCAGTTGGTTCCAAATGAAACCAGGGA<br>GCAGGGGCGTTAGGAAGCTCCAACAGGATGGTACTTAATG<br>GGGCATTTGAGTGGAGAGGTAGGTGACATAGTGCTTTGGA<br>GCCCAGGGAGGGAAAGGTTCTGCTGAAGTTGAATTCAAGA<br>CTGTTCTTTCATCACAAACTTGAGTTTCCTGGACATTTGT<br>TTGCAGAAACAACCGTAGGGTTTTGCCTTAACCTCGTGGG<br>TTTATTATTACCTCATAGGGACTTTGCCTCCTGACAGCAG<br>TTTATGGGTGTTCATTGTGGCACTTGAGTTTCTTGCATA<br>CTTGTTAGAGAAACCAAGTTTGTCATCAACTTCTTATTTA<br>ACCCCCTGGCTATAACTTCATGGATTATGTTATAATTAAG<br>CCATCCAGAGTAAAATCTGTTTAGATTATCTTGGAGTAAG<br>GGGGAAAAAATCTGTAATTTTTTCTCCTCAACTAGATATA<br>TACATAAAAAATGATTGTATTGCTTCATTTAAAAAATATA<br>ACGCAAAATCTCTTTTCCTTCTAAAAAAAAAAAAAAAAAA | |
| COMMD9 | NM_001101653.1 | GCTTCCCTGGGTGCCACGGTCATGTGACTTCGGCAAGATG<br>GCTGCCCTGACAGCGGAGCATTTGCAGCACTCCAGAGCC<br>TGCTCAAGCTGCTCCAGGCTGCACCGCCTCACTAGGCT<br>GGTGGCATTCCGTGACCTGTCCTCTGCCGAGGCAATTCTG<br>GCTCTCTTTCCAGAAAATTTCCACCAAAACCTCAAAAACC<br>TGCTGACAAAGATCATCCTAGAACATGTGTCTACTTGGAG<br>AACCGAAGCCCAGGCAAATCAGATCTCTCTGCCACGCCTG<br>GTCGATCTGGACTGGAGAGTGGATATCAAAACCTCCTCAG | 10 |

TABLE 1-continued

GEP-NEN Biomarker/Houskeeper Sequence Information

| Gene Name | RefSeq Accession | Sequence | SEQ ID NO: |
|---|---|---|---|
| | | ACAGCATCAGCCGCATGGCCGTCCCCACCTGCCTGCTCCA<br>GATGAAGATCCAAGAAGATCCCAGCCTATGCGGAGACAAA<br>CCCTCCATCTCAGCTGTCACCGTGGAGCTGAGCAAAGAAA<br>CACTGGACACCATGTTAGATGGCCTGGGCCGCATCCGAGA<br>CCAACTCTCTGCCGTGGCCAGTAAATGATCCAGCCAGCTG<br>CCAGGGCCACTGCCATGACCCAGCTGCTCATGAGTGATAA<br>ATGTCTCCCCATATGCAGGCTGCCCTTGCAGCTGCAGCTG<br>ACAACAGGCAGGATGGTGGGGACAGCAGGGGGCTACTGCC<br>ATCCAGAAGTTACAGTTGGATTGGGAAGAAGCAGCCAGAT<br>CCCCCGCTGTTCTCACTCATCTTCTTTCTCTTTCTGAAGC<br>TGGAGAGCAGAAGCCCCCATCTTTGAAAAGCTCCTGAGTG<br>CAACTTAATTACCACCATGGCAGGGTGAGGGAACATTTGC<br>ATCGTCAGCTGCCTCTGCATAGCTGTTTGAGAAATTCAGG<br>CCCAAATCATGCAGCCTATCCAATAAGTAAGTTTATTTCC<br>AACATTAGCTCTAATTAGTTCATTTCCAATCCCAGAACAC<br>ATGGAGGGAATCGGACAGGTGATGCCAGCAGTTCCTGCTC<br>CTCTGTCAGGGAAGCCAGGCAGAGCCCACAGAGCATGGTC<br>CATCCAGAGTGTTCCCTGAGCCCCCTCCACCATACTGGAA<br>CCCCTCTTCAGTGTAGGAAGTCTGAAATGGGTGCTAATTC<br>CCTTCTTCATGAAACCAGGGCCCTCTTCCTTCATCTAATG<br>CAGCCACTCCTAGGTGAAGAAGTGGGAATAATTGGAAATA<br>AACAACAGTTCTAAAACTTCCATGATTTTTGTAGCTTCTT<br>TTGTCCCCAAGTTGAAGCTTTTGGCCAGTACCTTCTCTAG<br>TTTTTAAAGATGATCCCAACTTCCTAATTCCCAGCTAAGC<br>CCTTGACCCATGGTGTGACATGAAATCAGGCAATTGAATC<br>GCACCACTTTCTGTGTTTTCACCTGTTACGTAGAACAAAA<br>GGAAGCAAGGTGGCCAGGCGCAATGGCTCACGCCTGTAAT<br>CCCAGCACTTTGGGAGGCCGAGGCAGGCAGATCATGAGGT<br>CAGGAGATCGAGACCATGGTGAAACCCCATCTCTACTAAA<br>AATACAAAAAATTAGCTGGGCGCGGTGGCGGGCATCTGTA<br>GTCCCAGCTCCTCGGGAGGCTGAGGCAGGAGAATGGCGTG<br>AACCTGGGAGGCAGAGCTTGCAGTGAGCCGAGATCGTGCC<br>ACTGCACTCCAGTCTGGGTGACAGAGAAGGACTCGTCTCA<br>AAAAATAAAAATAAATAAAAAGGAAGCAAGGCTAATCATC<br>AGTATGTGCTTGTTACAAGAGCTATGATGAAGGCACTCCT<br>TCGAGTTTAACCAAATGAGATCATCTCTGTCATGTGCCTC<br>ACGCCTCACAGGGACTCCATGTGTGAAGATTCCCCCTTCA<br>CTCACCAGATCATCTCCATGGCAACAGCTTGCAGCCTGCT<br>CTTGGAGTGCTTTGTTTTGGCAGCTTCTCTGCTAGTTTGT<br>GTATGGAGTGAATGGAGGAGGTAAATCCACAGATTAAGAA<br>TATGCTGTCAGGAGTCAGGCAGCCAAGGTCAGAAGCCAGC<br>TCTGCTTCTCAGTGGTAAGGTGCTTGACTTCTACATCTCA<br>ATTTTCACCCACTTTGTACTTTTTTCCTAAATTAAATGAG<br>TATAATAGTAGTACCTACTTGATAGGACTTTTGTGAAAAT<br>TAAATGATATAATGCACCTAAAAACAGTACTGTTACAACT<br>AATAGGAAAGGCTTTGATTATTAATGGATGAGAGTAGAAA<br>GCTTGGTGCATTTATTGTCTCATCTACTATAACAGAGTTG<br>GTGTGAGAATTAGTATTATCATCCTCCCTTTATTGACCAG<br>GAAACCAGCTCATTGAGATTGAGTCATCTGCTGGTAAATG<br>GTCTCATTAAGAGGTGGACCCATATTTCTCTAGCTTTCTC<br>TTTACAACACAGGACTTTGCAAGGAACATATAATTCTGTG<br>ACTAGCGCCATTTGGAAAATGTTGAAACTGAAGTAGAGAT<br>GAGAGATCTTACGTCTGCCTACCCAGTGAGATACGAGGAA<br>GGTCAAGGGAAAAAAAATTCCAAGCTCTTCTTTATCTGCT<br>ATAGGAAATGAACATTCAATTTTTTGCATGCAACGACAAG<br>AGGTCAAGGACCCCAGAAGCCAGCCCGCTACTTCCAAGTT<br>GAGAGCCCCTGGTCATACCCTCCAGTTGAGCTCAGATTTG<br>TCACAAATTTACCCCTCTCCTTTCCTTCCATTCCCCATGA<br>CCTGCAGAGAGATGTCAGATACCTTCCTCTTGGCCTCC<br>CATGGGCATCCATAAGAAACTTACTTGAAGCAAGAAGCCC<br>AGTATAGGTGTCTGGGCAGTTGGACATTTCCTCTAGCCAG<br>ATCTGTCCGAATAGAGCCATCTGGGTACATGACGCAGAGG<br>GCATTTGATAAATAACTGGAAAAGTCAATAAATCTTTGCT<br>ACCCTTCAAAAAAAAAAAAAAAAAAAAAAAAAAAAAA | |
| CTGF | NM_001901.2 | AAACTCACACAACAACTCTTCCCCGCTGAGAGGAGACAGC<br>CAGTGCGACTCCACCCTCCAGCTCGACGGCAGCCGCCCCG<br>GCCGACAGCCCCGAGACGACAGCCCGGCGCGTCCCGGTCC<br>CCACCTCCGACCACCGCCAGCGCTCCAGGCCCCGCCGCTC<br>CCCGCTCGCCGCCACCGCGCCCTCCTCCGCTCCGCCCGCAGTG<br>CCAACCATGACCGCCGCCAGTATGGGCCCCGTCCGCGTCG<br>CCTTCGTGGTCCTCCTCGCCCTCTGCAGCCGGCCGGCCGT<br>CGGCCAGAACTGCAGCGGGCCGTGCCGGTGCCCGGACGAG<br>CCGGCGCCGCGCTGCCCGGCGGGCGTGAGCCTCGTGCTGG<br>ACGGCTGCGGCTGCTGCCGCGTCTGCGCCAAGCAGCTGGG | 11 |

TABLE 1-continued

GEP-NEN Biomarker/Houskeeper Sequence Information

| Gene Name | RefSeq Accession | Sequence | SEQ ID NO: |
|---|---|---|---|
| | | CGAGCTGTGCACCGAGCGCGACCCCTGCGACCCGCACAAG<br>GGCCTCTTCTGTGACTTCGGCTCCCCGGCCAACCGCAAGA<br>TCGGCGTGTGCACCGCCAAAGATGGTGCTCCCTGCATCTT<br>CGGTGGTACGGTGTACCGCAGCGGAGAGTCCTTCCAGAGC<br>AGCTGCAAGTACCAGTGCACGTGCCTGGACGGGGCGGTGG<br>GCTGCATGCCCCTGTGCAGCATGGACGTTCGTCTGCCCAG<br>CCCTGACTGCCCCTTCCCGAGGAGGGTCAAGCTGCCCGGG<br>AAATGCTGCGAGGAGTGGGTGTGTGACGAGCCCAAGGACC<br>AAACCGTGGTTGGGCCTGCCCTCGCGGCTTACCGACTGGA<br>AGACACGTTTGGCCCAGACCCAACTATGATTAGAGCCAAC<br>TGCCTGGTCCAGACCACAGAGTGGAGCGCCTGTTCCAAGA<br>CCTGTGGGATGGGCATCTCCACCCGGGTTACCAATGACAA<br>CGCCTCCTGCAGGCTAGAGAAGCAGAGCCGCCTGTGCATG<br>GTCAGGCCTTGCGAAGCTGACCTGGAAGAGAACATTAAGA<br>AGGGCAAAAAGTGCATCCGTACTCCCAAAATCTCCAAGCC<br>TATCAAGTTTGAGCTTTCTGGCTGCACCAGCATGAAGACA<br>TACCGAGCTAAATTCTGTGGAGTATGTACCGACGGCCGAT<br>GCTGCACCCCCACAGAACCACCACCCTGCCGGTGGAGTT<br>CAAGTGCCCTGACGGCGAGGTCATGAAGAAGAACATGATG<br>TTCATCAAGACCTGTGCCTGCCATTACAACTGTCCCGGAG<br>ACAATGACATCTTTGAATCGCTGTACTACAGGAAGATGTA<br>CGGAGACATGGCATGAAGCCAGAGAGTGAGAGACATTAAC<br>TCATTAGACTGGAACTTGAACTGATTCACATCTCATTTTT<br>CCGTAAAAATGATTTCAGTAGCACAAGTTATTTAAATCTG<br>TTTTTCTAACTGGGGGAAAAGATTCCCACCCAATTCAAAA<br>CATTGTGCCATGTCAAACAAATAGTCTATCAACCCCAGAC<br>ACTGGTTTGAAGAATGTTAAGACTTGACAGTGGAACTACA<br>TTAGTACACAGCACCAGAATGTATATTAAGGTGTGGCTTT<br>AGGAGCAGTGGGAGGGTACCAGCAGAAAGGTTAGTATCAT<br>CAGATAGCATCTTATACGAGTAATATGCCTGCTATTTGAA<br>GTGTAATTGAGAAGGAAAATTTTAGCGTGCTCACTGACCT<br>GCCTGTAGCCCCAGTGACAGCTAGGATGTGCATTCTCCAG<br>CCATCAAGAGACTGAGTCAAGTTGTTCCTTAAGTCAGAAC<br>AGCAGACTCAGCTCTGACATTCTGATTCGAATGACACTGT<br>TCAGGAATCGGAATCCTGTCGATTAGACTGGACAGCTTGT<br>GGCAAGTGAATTTGCCTGTAACAAGCCAGATTTTTTAAAA<br>TTTATATTGTAAATATTGTGTGTGTGTGTGTGTGTGTATA<br>TATATATATGTACAGTTATCTAAGTTAATTTAAAGTTG<br>TTTGTGCCTTTTTATTTTTGTTTTTAATGCTTTGATATTT<br>CAATGTTAGCCTCAATTTCTGAACACCATAGGTAGAATGT<br>AAAGCTTGTCTGATCGTTCAAAGCATGAAATGGATACTTA<br>TATGGAAATTCTGCTCAGATAGAATGACAGTCCGTCAAAA<br>CAGATTGTTTGCAAAGGGGAGGCATCAGTGTCCTTGGCAG<br>GCTGATTTCTAGGTAGGAAATGTGGTAGCCTCACTTTTAA<br>TGAACAAATGGCCTTTATTAAAAACTGAGTGACTCTATAT<br>AGCTGATCAGTTTTTTCACCTGGAAGCATTTGTTTCTACT<br>TTGATATGACTGTTTTTCGGACAGTTTATTTGTTGAGAGT<br>GTGACCAAAAGTTACATGTTTGCACCTTTCTAGTTGAAAA<br>TAAAGTGTATATTTTTCTATAAAAAAAAAAAAAAAAA | |
| ENPP4 | NM_014936.4 | AGACGCTCGCCTGGCAGCTGCGCACACTCGGAGCGCCCG<br>AGCGGCGCAGATAGGGACGTTGGGGCTGTGCCCCGCGGCG<br>CGGCGCCTGCCACTGCGCAGGCGCCTCAGGAAGAGCTCGG<br>CATCGCCCCTCTTCCTCCAGGTCCCCCTTCCCCGCAACTT<br>CCCACGAGTGCCAGGTGCCGCGAGCGCCGAGTTCCGCGCA<br>TTGGAAAGAAGCGACCGCGGCGGCTGGAACCCTGATTGCT<br>GTCCTTCAACGTGTTCATTATGAAGTTATTAGTAATACTT<br>TTGTTTTCTGGACTTATAACTGGTTTTAGAAGTGACTCTT<br>CCTCTAGTTTGCCACCTAAGTTACTACTAGTATCCTTTGA<br>TGGCTTCAGAGCTGATTATCTGAAGAACTATGAATTTCCT<br>CATCTCCAGAATTTTATCAAAGAAGGTGTTTTGGTAGAGC<br>ATGTTAAAAATGTTTTATCACAAAAACATTTCCAAACCA<br>CTACAGTATTGTGACAGGCTTGTATGAAGAAAGCCATGGC<br>ATTGTGGCTAATTCCATGTATGATGCAGTCACAAAGAAAC<br>ACTTTTCTGACTCTAATGACAAGGATCCTTTTTGGTGGAA<br>TGAGGCAGTACCTATTTGGGTGACCAATCAGCTTCAGGAA<br>AACAGATCAAGTGCTGCTGCTATGTGGCCTGGTACTGATG<br>TACCCATTCACGATACCATCTCTTCCTATTTTATGAATTA<br>CAACTCCTCAGTGTCATTTGAGGAAAGACTAAATAATATT<br>ACTATGTGGCTAAACAATTCGAACCCACCAGTCACCTTTG<br>CAACACTATATTGGGAAGAACCAGATGCAAGTGGCCACAA<br>ATACGGACCTGAAGATAAAGAAAACATGAGCAGAGTGTTG<br>AAAAAAATAGATGATCTTATCGGTGACTTAGTCCAAAGAC<br>TCAAGATGTAGGGCTATGGGAAAATCTTAATGTGATCAT<br>TACAAGTGATCATGGGATGACCCAGTGTTCTCAGGACAGA | 12 |

TABLE 1-continued

GEP-NEN Biomarker/Houskeeper Sequence Information

| Gene Name | RefSeq Accession | Sequence | SEQ ID NO: |
|---|---|---|---|
| | | CTGATAAACCTGGATTCCTGCATCGATCATTCATACTACA | |
| | | CTCTTATAGATTTGAGCCCAGTTGCTGCAATACTTCCCAA | |
| | | AATAAATAGAACAGAGGTTTATAACAAACTGAAAAACTGT | |
| | | AGCCCTCATATGAATGTTTATCTCAAAGAAGACATTCCTA | |
| | | ACAGATTTTATTACCAACATAATGATCGAATTCAGCCCAT | |
| | | TATTTTGGTTGCCGATGAAGGCTGGACAATTGTGCTAAAT | |
| | | GAATCATCACAAAAATTAGGTGACCATGGTTATGATAATT | |
| | | CTTTGCCTAGTATGCATCCATTTCTAGCTGCCCACGGACC | |
| | | TGCATTTCACAAAGGCTACAAGCATAGCACAATTAACATT | |
| | | GTGGATATTTATCCAATGATGTGCCACATCCTGGGATTAA | |
| | | AACCACATCCCAATAATGGGACCTTTGGTCATACTAAGTG | |
| | | CTTGTTAGTTGACCAGTGGTGCATTAATCTCCCAGAAGCC | |
| | | ATCGCGATTGTTATCGGTTCACTCTTGGTGTTAACCATGC | |
| | | TAACATGCCTCATAATAATCATGCAGAATAGACTTTCTGT | |
| | | ACCTCGTCCATTTTCTCGACTTCAGCTACAAGAAGATGAT | |
| | | GATGATCCTTTAATTGGGTGACATGTGCTAGGGCTTATAC | |
| | | AAAGTGTCTTTGATTAATCACAAAACTAAGAATACATCCA | |
| | | AAGAATAGTGTTGTAACTATGAAAAAGAATACTTTGAAAG | |
| | | ACAAAGAACTTAGACTAAGCATGTTAAAATTATTACTTTG | |
| | | TTTTCCTTGTGTTTTGTTTCGGTGCATTTGCTAATAAGAT | |
| | | AACGCTGACCATAGTAAAATTGTTAGTAAATCATTAGGTA | |
| | | ACATCTTGTGGTAGGAAATCATTAGGTAACATCAATCCTA | |
| | | ACTAGAAATACTAAAAATGGCTTTTGAGAAAAATACTTCC | |
| | | TCTGCTTGTATTTTGCGATGAAGATGTGATACATCTTTAA | |
| | | ATGAAAATATACCAAAATTTAGTAGGCATGTTTTTCTAAT | |
| | | AAATTTATATATTTGTAAAGAAAACAACAGAAATCTTTAT | |
| | | GCAATTTGTGAATTTTGTATATTAGGGAGGAAAAGCTTCC | |
| | | TATATTTTTATATTTACCTTTAATTAGTTTGTATCTCAAG | |
| | | TACCCTCTTGAGGTAGGAAATGCTCTGTGATGGTAAATAA | |
| | | AATTGGAGCAGACAGAAAAGATATAGCAAATGAAGAAATA | |
| | | TTTTAAGGAAACCTATTTGAAAAAAAAAGCAAAGACCATT | |
| | | TGATAAAAGCCTGAGTTGTCACCATTATGTCTTAAGCTGT | |
| | | TAGTCTTAAAGATTATTGTTAAAAAATTCAGAAGAAAAGA | |
| | | GAGACAAGTGCTCTTCTCTCTATCTATGCTTAATGCCTTT | |
| | | ATGTAAGTTACTTAGTTGTTTGCGTGTGCCTGTGCAAGTG | |
| | | TGTTTGTGTGTGGTTGTGTGGACATTATGTGATTTACTAT | |
| | | ATAAGGAGGTCAGAGATGGACTGTGGCCAGGCTTCCACAT | |
| | | TCCTGAAGCACACAGATCTCAGGAAAGGTTATTTTTGCAC | |
| | | TTCATATTTGTTTACTTTCTCCTAACTCACAAGTTAAAAT | |
| | | CATAACTTAATTTCATTAACTTTTATCATTTAACTCTCTC | |
| | | ATGTTTGTTGTAACCTGAGGTATCCAAATGCTACAGAAAA | |
| | | ATTTATGACCCAAATACAAATCTCAATTTGACTGGGACAG | |
| | | AATGAGGAATGGAGATTTTTGTATTTATCTTTGGGACTTT | |
| | | ATGCCTTACTTTTTAGGCTATAGAATAGTTAAGAAATTTT | |
| | | AAACAAAATTTAGTATCTTTTGGTCTTTCACACCATTCAT | |
| | | ATGTTAAGTGGCAGAATAGCCTTAGTGCTACCTCCACTTT | |
| | | TTTCTCCAGTATTTGCATCACAGAAATAATCCCTCTGTTT | |
| | | AACATGTTTGTTCAGAGCCAAGGGTTTATTGTGAAGAACT | |
| | | GTCATCCTGCCTTTGCTAGCTGGTACCTTCTAGTAATCAA | |
| | | AATTAATATGAAGAAACTAGGTTGTGACAGACTAGATTAT | |
| | | ATTTAGTAGGGGAAAAATTGGGCTCAAGAACCATTCATCA | |
| | | GTACGTGAGACAAGCAGTTAATAGTATGATCTTTAAAGTT | |
| | | TTGACAATATAAAATAAACTTGGTAACTGTTTTACAAATA | |
| | | TAAAAGTATAATAAATATGCAGCCCAGTTAAATATTGATT | |
| | | ATCTGTGATGGTAAAGAACAACAGTGGTGCCAGTCATCAA | |
| | | ACATACAGTGCGTCCTATTGAGTCACTGCTAATTTCTTGA | |
| | | GCCTGGTATTTGCTGCCTATTGTATTTGTGGTTGTTGAGA | |
| | | GGCATTTTCAAACCCTGTATAAATAATCCATGCTGTTGGT | |
| | | CATAAGTTAACTGTATTAAGAACAGTAAAATAAATAAAAA | |
| | | CCAATAGTACTAATTTTGCTTTAAAAAAATTTCTAATTTT | |
| | | TTTCACATAAAACAATTATCCTAAAGGTTAATAGTTGATC | |
| | | GAAACAGAATAATAGAAAAATTCTACTTTAATTTCCATTA | |
| | | AAAAGCAAATAGCATTGACACATTTAAAGCTTTTCATTTA | |
| | | AAGTAGTGGATGTTTTGAAGTATCTAAAATAGTAGCAGA | |
| | | ATATTTTATACTTGGTCCTTGCAATGGTGTGAGTTTTAAT | |
| | | GATTGCATTATCGTGATTGGTGGTTATGAGTTTCAGAAAT | |
| | | CTATACTTGGCATCCAACTCATGAGTGGATTTTATATAGG | |
| | | ATGGAACAGGAAGGTATGTCCTGTCAGTATCTTAACCCTT | |
| | | TCAACAAGACATTTACCTATTTGTCTTTCCTTACGTTCTC | |
| | | AAAATATTAACTCGAATTGTAAATTAAGCAAAAATTTAAA | |
| | | AAGTATATGTTGATGGGACAAGAAGAATAGTATTTATTTA | |
| | | ATAAAACATATATTATATTGAACTATGTGTTAATTCATTT | |
| | | GTATCTTTTAAAAAATTATCACTGTTAAAGCCATTGACTC | |
| | | CTTTAGTACACTGAGAAAAATCTTATAGTAAAACTAGCCT | |
| | | TTCACATTAAGGTTTTGGTGTGTATTTTGTTAAATAACTA | |

TABLE 1-continued

GEP-NEN Biomarker/Houskeeper Sequence Information

| Gene Name | RefSeq Accession | Sequence | SEQ ID NO: |
|---|---|---|---|
| | | ACATGCTGCTCTATTTTCTGGGTGTAGAAAGTATTTGGCT<br>CTAGGAAACATTTACTTGTTTGTGAAAACAATACCCCAAG<br>GTAATAGGAAAAGTTTGAGTTAAGTGTTTTTAATTCAGTC<br>AGTGAATTCAGAATAAGTACATTCATGTATAACATAGGGA<br>CAGTTCTGCTGCTGTTATTTATATGCAATTCTTCTGGTAA<br>ATAGCAATAGAATAAAACATATTTCAATGTTTGTGTATAG<br>GTTTTATATTATTATTCCACTAGGAATGGCATAAGAATTT<br>ATAGATAAATTCTTGTAACATTAAAGGATTAAAATGTTTT<br>TACATTGTTTTTGGGTGTCTCCTTCTTGTGCCCATATCTG<br>ATAAGCTTTATGGATTATTGCATTTAATTCCTTTTATTTG<br>GAGGGTTTTACTTCCTTGTTAACATATAAAGTTATAAATG<br>AAGGACAAGGAGGAGATGGAAAATGTGTATTTATTGTTAA<br>TTCTTAAAATAGTGTGTAAATAAAATAACATCAGTGTGCT<br>TTAAAGAAATGTGTATGTAGTGCCTTAATTTAAATTAAAA<br>TATTTTTGACTGTTACTTGAGTTCAGAATTAATGACTTTG<br>TTCATGATTTTTAAAATGTGTGTGAATAAAATCTACCAAA<br>AAATTCTTACTGTAATTATTAAATATAAAGTTCAGTGTCA<br>AAAAAAAAAAAAAAAA | |
| FAM131A | NM_001171093.1 | ACCGGCCCGGTTCCCTCTCCGGGGAGCGGCGGCGGACGCG<br>CGGCTCCCACCCCTCCCCTCTCACGGGCTCTCCCCTCCCC<br>AGTGTGGCCGCGACCCTACCCTCTGCAAGGCGATGGCCCG<br>CGCCCCGAGCGCAGGCTAGCGTGCCTGGGTGCCCGGCCAT<br>GGGCTGTATCGGCTCTCGGAGCCCGGCGGGTCAGGCATTT<br>CTGGGGACCAACAGCTGGCCGAGGCTCAGGGATAGAGACG<br>GCTGCTCCAGCTAAAGGTGAATGTTGGAGACACAGTCGCG<br>ATGCTGCCCAAGTCCCGGCGAGCCCTAACTATCCAGGAGA<br>TCGCTGCGCTGGCCAGGTCCTCCCTGCATGGTATTTCCCA<br>GGTGGTGAAGGACCACGTGACCAAGCCTACCGCCATGGCC<br>CAGGGCCGAGTGGCTCACCTCATTGAGTGGAAGGGCTGGA<br>GCAAGCCGAGTGACTCACCTGCTGCCCTGGAATCAGCCTT<br>TTCCTCCTATTCAGACCTCAGCGAGGGCGAACAAGAGGCT<br>CGCTTTGCAGCAGGAGTGGCTGAGCAGTTTGCCATCGCGG<br>AAGCCAAGCTCCGAGCATGGTCTTCGGTGGATGGCGAGGA<br>CTCCACTGATGACTCCTATGATGAGGACTTTGCTGGGGGA<br>ATGGACACAGACATGGCTGGGCAGCTGCCCCTGGGGCCGC<br>ACCTCCAGGACCTGTTCACCGGCCACCGGTTCTCCCGGCC<br>TGTGCGCCAGGGCTCCGTGGAGCCTGAGAGCGACTGCTCA<br>CAGACCGTGTCCCAGACACCCTGTGCTCTAGTCTGTGCA<br>GCCTGGAGGATGGGTTGTTGGGCTCCCCGGCCCGGCTGGC<br>CTCCCAGCTGCTGGGCGATGAGCTGCTTCTCGCCAAACTG<br>CCCCCCAGCCGGGAAAGTGCCTTCCGCAGCCTGGGCCCAC<br>TGGAGGCCCAGGACTCACTCTACAACTCGCCCCTCACAGA<br>GTCCTGCCTTTCCCCCGCGGAGGAGGAGCCAGCCCCCTGC<br>AAGGACTGCCAGCCACTCTGCCCACCACTAACGGGCAGCT<br>GGGAACGGCAGCGGCAAGCCTCTGACCTGGCCTCTTCTGG<br>GGTGGTGTCCTTAGATGAGGATGAGGCAGAGCCAGAGGAA<br>CAGTGACCCACATCATGCCTGGCAGTGGCATGCATCCCCC<br>GGCTGCTGCCAGGGGCAGAGCCTCTGTGCCCAAGTGTGGG<br>CTCAAGGCTCCCAGCAGAGCTCCACAGCCTAGAGGGCTCC<br>TGGGAGCGCTCGCTTCTCCGTTGTGTGTTTTGCATGAAAG<br>TGTTTGGAGAGGAGGCAGGGGCTGGGCTGGGGGCGCATGT<br>CCTGCCCCCACTCCCGGGGCTTGCCGGGGGTTGCCCGGGG<br>CCTCTGGGGCATGGCTACAGCTGTGGCAGACAGTGATGTT<br>CATGTTCTTAAAATGCCACACACACATTTCCTCCTCGGAT<br>AATGTGAACCACTAAGGGGGTTGTGACTGGGCTGTGTGAG<br>GGTGGGGTGGGAGGGGGCCCAGCAACCCCCCACCCTCCCC<br>ATGCCTCTCTCTTCTCTGCTTTTCTTCTCACTTCCGAGTC<br>CATGTGCAGTGCTTGATAGAATCACCCCCACCTGGAGGGG<br>CTGGCTCCTGCCCTCCCGGAGCCTATGGGTTGAGCCGTCC<br>CTCAAGGGCCCCTGCCCAGCTGGGCTCGTGCTGTGCTTCA<br>TTCACCTCTCCATCGTCTCTAAATCTTCCTCTTTTTTCCT<br>AAAGACAGAAGGTTTTTGGTCTGTTTTTTCAGTCGGATCT<br>TCTCTTCTCTGGGAGGCTTTGGAATGATGAAAGCATGTAC<br>CCTCCACCCTTTTCCTGGCCCCCTAATGGGGCCTGGGCCC<br>TTTCCCAACCCCTCCTAGGATGTGCGGGCAGTGTGCTGGC<br>GCCTCACAGCCAGCCGGGCTGCCCATTCACGCAGAGCTCT<br>CTGAGCGGGAGGTGGAAGAAAGGATGGCTCTGGTTGCCAC<br>AGAGCTGGGACTTCATGTTCTTCTAGAGAGGGCCACAAGA<br>GGGCCACAGGGGTGGCCGGGAGTTGTCAGCTGATGCCTGC<br>TGAGAGGCAGGAATTGTGCCAGTGAGTGACAGTCATGAGG<br>GAGTGTCTCTTCTTGGGGAGGAAAGAAGGTAGAGCCTTTC<br>TGTCTGAATGAAAGGCCAAGGCTACAGTACAGGGCCCCAC<br>CCCAGCCAGGGTGTTAATGCCCACGTAGTGGAGGCCTCTG<br>GCAGATCCTGCATTCCAAGGTCACTGGACTGTACGTTTTT | 13 |

TABLE 1-continued

GEP-NEN Biomarker/Houskeeper Sequence Information

| Gene Name | RefSeq Accession | Sequence | SEQ ID NO: |
|---|---|---|---|
| | | ATGGTTGTGGGAAGGGTGGGTGGCTTTAGAATTAAGGGCC<br>TTGTAGGCTTTGGCAGGTAAGAGGGCCCAAGGTAAGAACG<br>AGAGCCAACGGGCACAAGCATTCTATATATAAGTGGCTCA<br>TTAGGTGTTTATTTTGTTCTATTTAAGAATTTGTTTTATT<br>AAATTAATATAAAAATCTTTGTAAATCTCTAAAAAAAAAA<br>AAAAAAAA | |
| FLJ10357 | NM_018071.4 | GGAGCGGGCCGAGCCGCCACCGCGGCCGGAGCTGTCCCTT<br>AGCCAGACCCGGCGAGACACGAGCGGCGGGAGGGAGGCGG<br>TGGCGCGCCCGGCCCCGCCCGCCCGACCAAGCGTCGGACG<br>CGGCCCGGCGCCGAGCCATGGAGCCTGAGCCAGTGGAGGA<br>CTGTGTGCAGAGCACTCTCGCCGCCCTGTATCCACCCTTT<br>GAGGCAACAGCCCCCACCCTGTTGGGCCAGGTGTTCCAGG<br>TGGTGGAGAGGACTTATCGGGAGGACGCACTGAGGTACAC<br>GCTGGACTTCCTGGTACCAGCCAAGCACCTGCTTGCCAAG<br>GTCCAGCAGGAAGCCTGTGCCCAATACAGTGGATTCCTCT<br>TCTTCCATGAGGGGTGGCCGCTCTGCCTGCATGAACAGGT<br>GGTGGTGCAGCTAGCAGCCCTACCCTGGCAACTGCTGCGC<br>CCAGGAGACTTCTATCTGCAGGTGGTGCCCTCAGCTGCCC<br>AAGCACCCCGACTAGCACTCAAGTGTCTGGCCCCTGGGGG<br>TGGGCGGGTGCAGGAGGTTCCTGTGCCCAATGAGGCTTGT<br>GCCTACCTATTCACACCTGAGTGGCTACAAGGCATCAACA<br>AGGACCGGCCAACAGGTCGCCTCAGTACCTGCCTACTGTC<br>TGCGCCCTCTGGGATTCAGCGGCTGCCCTGGGCTGAGCTC<br>ATCTGTCCACGATTTGTGCACAAAGAGGGCCTCATGGTTG<br>GACATCAGCCAAGTACACTGCCCCCAGAACTGCCCTCTGG<br>ACCTCCAGGGCTTCCCAGCCCTCCACTTCCTGAGGAGGCG<br>CTGGGTACCCGGAGTCCTGGGGATGGGCACAATGCCCCTG<br>TGGAAGGACCTGAGGGCGAGTATGTGGAGCTGTTAGAGGT<br>GACGCTGCCCGTGAGGGGGAGCCCAACAGATGCTGAAGGC<br>TCCCCAGGCCTCTCCAGAGTCCGGACGGTACCCACCCGCA<br>AGGGCGCTGGAGGGAAGGGCCGCCACCGGAGACACCGGGC<br>GTGGATGCACCAGAAGGGCCTGGGGCCTCGGGGCCAGGAT<br>GGAGCACGCCCACCCGGCGAGGGGAGCAGCACCGGAGCCT<br>CCCCTGAGTCTCCCCCAGGAGCTGAGGCTGTCCCAGAGGC<br>AGCAGTCTTGGAGGTGTCTGAGCCCCCAGCAGAGGCTGTG<br>GGAGAAGCCTCCGGATCTTGCCCCCTGAGGCCAGGGGAGC<br>TTAGAGGAGGAGGAGGAGGAGGCCAGGGGGCTGAAGGACC<br>ACCTGGTACCCCTCGGAGAACAGGCAAAGGAAACAGAAGA<br>AAGAAGCGAGCTGCAGGTCGAGGGGCTCTTAGCCGAGGAG<br>GGGACAGTGCCCCACTGAGCCCTGGGGACAAGGAAGATGC<br>CAGCCACCAAGAAGCCCTTGGCAATCTGCCCTCACCAAGT<br>GAGCACAAGCTTCCAGAATGCCACCTGGTTAAGGAGGAAT<br>ATGAAGGCTCAGGGAAGCCAGAATCTGAGCCAAAAGAGCT<br>CAAAACAGCAGGCGAGAAAGAGCCTCAGCTCTCTGAAGCC<br>TGTGGGCCTACAGAAGAGGGGGCCGGAGAGAGAGAGCTGG<br>AGGGGCCAGGCCTGCTGTGTATGGCAGGACACACAGGCCC<br>AGAAGGCCCCCTGTCTGACACTCCAACACCTCCGCTGGAG<br>ACTGTGCAGGAAGGAAAAGGGGACAACATTCCAGAAGAGG<br>CCCTTGCAGTCTCCGTCTCTGATCACCCTGATGTAGCTTG<br>GGACTTGATGGCATCTGGATTCCTCATCCTGACGGGAGGG<br>GTGGACCAGAGTGGGCGAGCTCTGCTGACCATTACCCCAC<br>CGTGCCCTCCTGAGGAGCCCCCACCCTCCCGAGACACGCT<br>GAACACAACTCTTCATTACCTCCACTCACTGCTCAGGCCT<br>GATCTACAGACACTGGGGCTGTCCGTCCTGCTGGACCTTC<br>GTCAGGCACCTCCACTGCCTCCAGCACTCATTCCTGCCTT<br>GAGCCAACTTCAGGACTCAGGAGATCCTCCCCTTGTTCAG<br>CGGCTGCTGATTCTCATTCATGATGACCTTCCAACTGAAC<br>TCTGTGGATTTCAGGGTGCTGAGGTGCTGTCAGAGAATGA<br>TCTGAAAAGAGTGGCCAAGCCAGAGGAGCTGCAGTGGGAG<br>TTAGGAGGTCACAGGGACCCCTCTCCCAGTCACTGGGTAG<br>AGATACACCAGGAAGTGGTAAGGCTATGTCGCCTGTGCCA<br>AGGTGTGCTGGGCTCGGTACGGCAGGCCATTGAGGAGCTG<br>GAGGGAGCAGCAGAGCCAGAGGAAGAGGAGGCAGTGGGAA<br>TGCCCAAGCCACTGCAGAAGGTGCTGGCAGATCCCCGGCT<br>GACGGCACTGCAGAGGGATGGGGGGGCCATCCTGATGAGG<br>CTGCGCTCCACTCCCAGCAGCAAGCTGGAGGGCCAAGGCC<br>CAGCTACACTGTATCAGGAAGTGGACGAGGCCATTCACCA<br>GCTTGTGCGCCTCTCCAACCTGCACGTGCAGCAGCAAGAG<br>CAGCGGCAGTGCCTGCGGCGACTCCAGCAGGTGTTGCAGT<br>GGCTCTCGGGCCCAGGGGAGGAGCAGCTGGCAAGCTTTGC<br>TATGCCTGGGGACACCTTGTCTGCCCTGCAGGAGACAGAG<br>CTGCGATTCCGTGCTTTCAGCGCTGAGGTCCAGGAGCGCC<br>TGGCCCAGGCACGGGAGGCCCTGGCTCTGGAGGAGAATGC<br>CACCTCCCAGAAGGTGCTGGATATCTTTGAACAGCGGCTG | 14 |

TABLE 1-continued

GEP-NEN Biomarker/Houskeeper Sequence Information

| Gene Name | RefSeq Accession | Sequence | SEQ ID NO: |
|---|---|---|---|
| | | GAGCAGGTTGAGAGTGGCCTCCATCGGGCCCTGCGGCTAC | |
| | | AGCGCTTCTTCCAGCAGGCACATGAATGGGTGGATGAGGG | |
| | | CTTTGCTCGGCTGGCAGGAGCTGGGCCGGGTCGGGAGGCT | |
| | | GTGCTGGCTGCACTGGCCCTGCGGCGGGCCCCAGAGCCCA | |
| | | GTGCCGGCACCTTCCAGGAGATGCGGGCCCTGGCCCTGGA | |
| | | CCTGGGCAGCCCAGCAGCCCTGCGAGAATGGGGCCGCTGC | |
| | | CAGGCCCGCTGCCAAGAGCTAGAGAGGAGGATCCAGCAAC | |
| | | ACGTGGGAGAGGAGGCGAGCCCACGGGGCTACCGACGACG | |
| | | GCGGGCAGACGGTGCCAGCAGTGGAGGGGCCCAGTGGGGG | |
| | | CCCCGCAGCCCTCGCCCAGCCTCAGCTCCTTGCTGCTCC | |
| | | CCAGCAGCCCTGGGCCACGGCCAGCCCCATCCCATTGCTC | |
| | | CCTGGCCCCATGTGGAGAGGACTATGAGGAAGAGGGCCCT | |
| | | GAGCTGGCTCCAGAAGCAGAGGGCAGGCCCCAAGAGCTG | |
| | | TGCTGATCCGAGGCCTGGAGGTCACCAGCACTGAGGTGGT | |
| | | AGACAGGACGTGCTCACCACGGGAACACGTGCTGCTGGGC | |
| | | CGGGCTAGGGGGCCAGACGGACCCTGGGGAGTAGGCACCC | |
| | | CCCGGATGGAGCGCAAGCGAAGCATCAGTGCCCAGCAGCG | |
| | | GCTGGTGTCTGAGCTGATTGCCTGTGAACAAGATTACGTG | |
| | | GCCACCTTGAGTGAGCCAGTGCCACCCCCTGGGCCTGAGC | |
| | | TGACGCCTGAACTTCGGGGCACCTGGGCTGCTGCCCTGAG | |
| | | TGCCCGGGAAAGGCTTCGCAGCTTCCACCGGACACACTTT | |
| | | CTGCGGGAGCTTCAGGGCTGCGCCACCCACCCCCTACGCA | |
| | | TTGGGGCCTGCTTCCTTCGCCACGGGGACCAGTTCAGCCT | |
| | | TTATGCACAGTACGTGAAGCACCGACACAAACTGGAGAAT | |
| | | GGTCTGGCTGCGCTCAGTCCCTTAAGCAAGGGCTCCATGG | |
| | | AGGCTGGCCCTTACCTGCCCCGAGCCCTGCAGCAGCCTCT | |
| | | GGAACAGCTGACTCGGTATGGGCGGCTCCTGGAGGAGCTC | |
| | | CTGAGGGAAGCTGGGCCTGAGCTCAGTTCTGAGTGCCGGG | |
| | | CCCTTGGGGCTGCTGTACAGCTGCTCCGGGAACAAGAGGC | |
| | | CCGTGGCAGAGACCTGCTGGCCGTGGAGGCGGTGCGTGGC | |
| | | TGTGAGATAGATCTGAAGGAGCAGGGACAGCTCTTGCATC | |
| | | GAGACCCCTTCACTGTCATCTGTGGCCGAAAGAAGTGCCT | |
| | | TCGCCATGTCTTTCTCTTCGAGCATCTCCTCCTGTTCAGC | |
| | | AAGCTCAAGGGCCCTGAAGGGGGGTCAGAGATGTTTGTTT | |
| | | ACAAGCAGGCCTTTAAGACTGCTGATATGGGGCTGACAGA | |
| | | AAACATCGGGGACAGCGGACTCTGCTTTGAGTTGTGGTTT | |
| | | CGGCGGCGGCGTGCACGAGAGGCATACACTCTGCAGGCAA | |
| | | CCTCACCAGAGATCAAACTCAAGTGGACAAGTTCTATTGC | |
| | | CCAGCTGCTGTGGAGACAGGCAGCCCACAACAAGGAGCTC | |
| | | CGAGTGCAGCAGATGGTGTCCATGGGCATTGGGAATAAAC | |
| | | CCTTCCTGGACATCAAAGCCCTTGGGGAGCGGACGCTGAG | |
| | | TGCCCTGCTCACTGGAAGAGCCGCCCGCACCCGGGCCTCC | |
| | | GTGGCCGTGTCATCCTTTGAGCATGCCGGCCCCTCCCTTC | |
| | | CCGGCCTTTCGCCGGGAGCCTGCTCCCTGCCTGCCCGCGT | |
| | | CGAGGAGGAGGCCTGGGATCTGGACGTCAAGCAAATTTCC | |
| | | CTGGCCCCAGAAACACTTGACTCTTCTGGAGATGTGTCCC | |
| | | CAGGACCAAGAAACAGCCCCAGCCTGCAACCCCCCCACCC | |
| | | TGGGAGCAGCACTCCCACCCTGGCCAGTCGAGGGATCTTA | |
| | | GGGCTATCCCGACAGAGTCATGCTCGAGCCCTGAGTGACC | |
| | | CCACCACGCCTCTGTGACCTGGAGAAGATCCAGAACTTGC | |
| | | GTGCAGCTTCTCCTCTCAGCACACTTTGGGCTGGGATGGC | |
| | | AGTGGGGCATAATGGAGCCCTGGGCGATCGCTGAATTTCT | |
| | | TCCCTCTGCTTCCTGGACACAGAGGAGGTCTAACGACCAG | |
| | | AGTATTGCCCTGCCACCACTATCTCTAGTCTCCCTAGCTT | |
| | | GGTGCCTTCTCCTGCAGGAGTCAGAGCAGCCACATTGCTT | |
| | | GCCTTCATACCCTGGAGGTGGGGAAGTTATCCCTCTTCCG | |
| | | GTGCTTTCCCATCCTGGGCCACTGTATCCAGGACATCACT | |
| | | CCCATGCCAGCCCTCCCTGGCAGCCCATGTTCTCCTCTTT | |
| | | TCTCACCCCCTGACTTTCCCTGAGAAGAATCATCTCTGCC | |
| | | AGGTCAACTGGAGTCCCTGGTGACTCCATTCTGAGGTGTC | |
| | | ACAAGCAATGAAGCTATGCAAACAATAGGAGGGTGTGACA | |
| | | GGGGAACCGTAGACTTTATATATGTAATTACTGTTATTAT | |
| | | AATACTATTGTTATATTAAATGTATTTACTCACACTTTGC | |
| | | CTCTAAGGAGCTAGAGTAGTCCTCTGGATTAAGGTGATAA | |
| | | ATAACTTGAGCACTTTCCCTCAACCAGCCCTTAACTAGAA | |
| | | CACAGAAAATAAAACCAAGACTGGAAGGTCCCCTCTACCC | |
| | | CTCCCAGGCCCAGAGCTAGCTGACTGTGTATGAGCCTGGG | |
| | | AGAATGTGTCTCCTCCACAGTGGCTCCCAGAGGTTCCACA | |
| | | CACTCTCTGAAGCTCCTTCTCCCACACTGCACCTACTCCT | |
| | | TGAGGCTGAACTGGTCACAGACAAACTGGGATCCAGCACA | |
| | | GTCCAGCAGTTCTCAAAATGAGGTCCTCAGGCCACAGTGC | |
| | | GTGAGAACTTCTTGGCTGTTTGTTAAATGCTAATTCTTG | |
| | | GGCCCCATCAGAGCTACTGCATCGAAACCTGGGGGTAAAA | |
| | | CCCAATATTCTGCATTTCTTATCAAACTCTTTGGGTGATA | |
| | | ACTAAGTGTCTGAAGAGGTGACTATTTCCTGACAGAAGGA | |

TABLE 1-continued

GEP-NEN Biomarker/Houskeeper Sequence Information

| Gene Name | RefSeq Accession | Sequence | SEQ ID NO: |
|---|---|---|---|
| | | CCCAAAGAGGGAAGCAGGACATAGGTAGGCAGACAGACAC AGGGCCCTGTGCCTCAAGACACCTGTTTATTGGGGACACG ACTCTGCAATAGGGATGACAGGAATCGTACCAAAAATAGC GACGTCTACAGGGCCCCTGATGGGGCTAGAAGGGTACAGT GCCCCCCACCCTCACCCCTTGTACAAAAATAAACTCTCAC GCCTATGGACCAGCAAAAAAAAAAAAAA | |
| FZD7 | NM_003507.1 | CTCTCCCAACCGCCTCGTCGCACTCCTCAGGCTGAGAGCA CCGCTGCACTCGCGGCCGGCGATGCGGGACCCCGGCGCGG CCGCTCCGCTTTCGTCCCTGGGCCTCTGTGCCCTGGTGCT GGCGCTGCTGGGCGCACTGTCCGCGGGCGCCGGGGCGCAG CCGTACCACGGAGAGAAGGGCATCTCCGTGCCGGACCACG GCTTCTGCCAGCCCATCTCCATCCCGCTGTGCACGGACAT CGCCTACAACCAGACCATCCTGCCCAACCTGCTGGGCCAC ACGAACCAAGAGGACGCGGGCCTCGAGGTGCACCAGTTCT ACCCGCTGGTGAAGGTGCAGTGTTCTCCCGAACTCCGCTT TTTCTTATGCTCCATGTATGCGCCCGTGTGCACCGTGCTC GATCAGGCCATCCCGCCGTGTCGTTCTCTGTGCGAGCGCG CCCGCCAGGGCTGCGAGGCGCTCATGAACAAGTTCGGCTT CCAGTGGCCCGAGCGGCTGCGCTGCGAGAACTTCCCGGTG CACGGTGCGGGCGAGATCTGCGTGGGCCAGAACACGTCGG ACGGCTCCGGGGGCCCAGGCGGCGGCCCCACTGCCTACCC TACCGCGCCCTACCTGCCGGACCTGCCCTTCACCGCGCTG CCCCCGGGGGCCTCAGATGGCAGGGGGCGTCCCGCCTTCC CCTTCTCATGCCCCCGTCAGCTCAAGGTGCCCCCGTACCT GGGCTACCGCTTCCTGGGTGAGCGCGATTGTGGCGCCCCG TGCGAACCGGGCCGTGCCAACGGCCTGATGTACTTTAAGG AGGAGGAGAGGCGCTTCGCCCGCCTCTGGGTGGGCGTGTG GTCCGTGCTGTGCTGCGCCTCGACGCTCTTTACCGTTCTC ACCTACCTGGTGGACATGCGGCGCTTCAGCTACCCAGAGC GGCCCATCATCTTCCTGTCGGGCTGCTACTTCATGGTGGC CGTGGCGCACGTGGCCGGCTTCCTTCTAGAGGACCGCGCC GTGTGCGTGGAGCGCTTCTCGGACGATGGCTACCGCACGG TGGCGCAGGGCACCAAGAAGGAGGGCTGCACCATCCTCTT CATGGTGCTCTACTTCTTCGGCATGGCCAGCTCCATCTGG TGGGTCATTCTGTCTCTCACTTGGTTCCTGGCGGCCGGCA TGAAGTGGGGCCACGAGGCCATCGAGGCCAACTCGCAGTA CTTCCACCTGGCCGCGTGGGCCGTGCCCGCCGTCAAGACC ATCACTATCCTGGCCATGGGCCAGGTAGACGGGGACCTGC TGAGCGGGGTGTGCTACGTTGGCCTCTCCAGTGTGGACGC GCTGCGGGGCTTCGTGCTGGCGCCTCTGTTCGTCTACCTC TTCATAGGCACGTCCTTCTTGCTGGCCGGCTTCGTGTCCC TCTTCCGTATCCGCACCATCATGAAACACGACGGCACCAA GACCGAGAAGCTGGAGAAGCTCATGGTGCGCATCGGCGTC TTCAGCGTGCTCTACACAGTGCCCGCCACCATCGTCCTGG CCTGCTACTTCTACGAGCAGGCCTTCCGCGAGCACTGGGA GCGCACCTGGCTCCTGCAGACGTGCAAGAGCTATGCCGTG CCCTGCCCGCCCGGCCACTTCCCGCCCATGAGCCCCGACT TCACCGTCTTCATGATCAAGTACCTGATGACCATGATCGT CGGCATCACCACTGGCTTCTGGATCTGGTCGGGCAAGACC CTGCAGTCGTGGCGCCGCTTCTACCACAGACTTAGCCACA GCAGCAAGGGGGAGACTGCGGTATGAGCCCCGGCCCCTCC CCACCTTTCCCACCCCAGCCCTCTTGCAAGAGGAGAGGCA CGGTAGGGAAAAGAACTGCTGGGTGGGGGCCTGTTTCTGT AACTTTCTCCCCCTCTACTGAGAAGTGACCTGGAAGTGAG AAGTTCTTTGCAGATTTGGGGCGAGGGGTGATTTGGAAAA GAAGACCTGGGTGGAAAGCGGTTTGGATGAAAAGATTTCA GGCAAAGACTTGCAGGAAGATGATGATAACGGCGATGTGA ATCGTCAAAGGTACGGGCCAGCTTGTGCCTAATAGAAGGT TGAGACCAGCAGAGACTGCTGTGAGTTTCTCCCGGCTCCG AGGCTGAACGGGGACTGTGAGCGATCCCCCTGCTGCAGGG CGAGTGGCCTGTCCAGACCCCTGTGAGGCCCCGGGAAAGG TACAGCCCTGTCTGCGGTGGCTGCTTTGTTGGAAAGAGGG AGGGCCTCCTGCGGTGTGCTTGTCAAGCAGTGGTCAAACC ATAATCTCTTTTCACTGGGGCCAAACTGGAGCCCAGATGG GTTAATTTCCAGGGTCAGACATTACGGTCTCTCCTCCCCT GCCCCCTCCCGCCTGTTTTTCCTCCCGTACTGCTTTCAGG TCTTGTAAAATAAGCATTTGGAAGTCTTGGGAGGCCTGCC TGCTAGAATCCTAATGTGAGGATGCAAAAGAAATGATGAT AACATTTTGAGATAAGGCCAAGGAGACGTGGAGTAGGTAT TTTTGCTACTTTTTCATTTTCTGGGGAAGGCAGGAGGCAG AAAGACGGGTGTTTATTTGGTCTAATACCCTGAAAAGAA GTGATGACTTGTTGCTTTTCAAAACAGGAATGCATTTTTC CCCTTGTCTTTGTTGTAAGAGACAAAAGAGGAAACAAAG TGTCTCCCTGTGGAAAGGCATAACTGTGACGAAAGCAACT | 15 |

TABLE 1-continued

GEP-NEN Biomarker/Houskeeper Sequence Information

| Gene Name | RefSeq Accession | Sequence | SEQ ID NO: |
|---|---|---|---|
| | | TTTATAGGCAAAGCAGCGCAAATCTGAGGTTTCCCGTTGG<br>TTGTTAATTTGGTTGAGATAAACATTCCTTTTTAAGGAAA<br>AGTGAAGAGCAGTGTGCTGTCACACACCGTTAAGCCAGAG<br>GTTCTGACTTCGCTAAAGGAAATGTAAGAGGTTTTGTTGT<br>CTGTTTTAAATAAATTTAATTCGGAACACATGATCCAACA<br>GACTATGTTAAAATATTCAGGGAAATCTCTCCCTTCATTT<br>ACTTTTTCTTGCTATAAGCCTATATTTAGGTTTCTTTTCT<br>ATTTTTTTCTCCCATTTGGATCCTTTGAGGTAAAAAAACA<br>TAATGTCTTCAGCCTCATAATAAAGGAAAGTTAATTAAAA<br>AAAAAAAGCAAAGAGCCATTTTGTCCTGTTTTCTTGGTTC<br>CATCAATCTGTTTATTAAACATCATCCATATGCTGACCCT<br>GTCTCTGTGTGGTTGGGTTGGGAGGCGATCAGCAGATACC<br>ATAGTGAACGAAGAGGAAGGTTTGAACCATGGGCCCCATC<br>TTTAAAGAAAGTCATTAAAGAAGGTAAACTTCAAAGTGA<br>TTCTGGAGTTCTTTGAAATGTGCTGGAAGACTTAAATTTA<br>TTAATCTTAAATCATGTACTTTTTTTCTGTAATAGAACTC<br>GGATTCTTTTGCATGATGGGGTAAAGCTTAGCAGAGAATC<br>ATGGGAGCTAACCTTTATCCCACCTTTGACACTACCCTCC<br>AATCTTGCAACACTATCCTGTTTCTCAGAACAGTTTTTAA<br>ATGCCAATCATAGAGGGTACTGTAAAGTGTACAAGTTACT<br>TTATATATGTAATGTTCACTTGAGTGGAACTGCTTTTTAC<br>ATTAAAGTTAAAATCGATCTTGTGTTTCTTCAACCTTCAA<br>AACTATCTCATCTGTCAGATTTTTAAAACTCCAACACAGG<br>TTTTGGCATCTTTTGTGCTGTATCTTTTAAGTGCATGTGA<br>AATTTGTAAAATAGAGATAAGTACAGTATGTATATTTTGT<br>AAATCTCCCATTTTTGTAAGAAAATATATATTGTATTTAT<br>ACATTTTTACTTTGGATTTTTGTTTTGTTGGCTTTAAAGG<br>TCTACCCCACTTTATCACATGTACAGATCACAAATAAATT<br>TTTTTAAATAC | |
| GLT8D1 | NM_001010983.2 | GACGGGCCGGTACAGCCCGTGTCCCGCCCCGCGCCATCG<br>CTAGGCGACGTGCGCTTTTGCCGCGCCGTGCTGCCCGCGA<br>GGGCAGCTGAGGTGGTGGTGGCGGCCGCCTTGTCGAGGCA<br>TCGCGCGCCCGTGAAGTGTTCGCCGTCAGTGCTGTTGGGT<br>GCCTGGAGCCGCGTCCCCCGTCCCGAAAACTGTCCTTGAC<br>AGTACTTGCGCGGCCCAACGGCCGCCGGCGCCCCCGCGTC<br>TCCATGGCGACGGCCTTTTTCCCTGCGAGGACCCCGGCGG<br>CAGGGCTGCCCCGCGGCGCCTGCTTGGCGCGACGCTCTAG<br>CGGTTACCGCTGCGGGCTGGCTGGGCGTAGTGGGGCTGCG<br>CGGCTGCCACGGAGCTAGAGGGCAAGTGTGCTCGGCCCAG<br>CGTGCAGGGAACGCGGGCGGCCAGACAACGGGCTGGGCTC<br>CGGGGCCTGCGGCGCGGGCGCTGAGCTGGCAGGGCGGGTC<br>GGGGCGCGGGCTGCATCCGCATCTCCTCCATCGCCTGCAG<br>TAAGGGCGGCCGCGGCGAGCCTTTGAGGGGAACGACTTGT<br>CGGAGCCCTAACCAGGGGTATCTCTGAGCCTGGTGGGATC<br>CCCGGAGCGTCACATCACTTTCCGATCACTTCAAAGTACA<br>GCAGACCGAGGACACGGTTGTTACCAAGACCAGGCTGTTG<br>CCTTGGAAGAGCCCAGAGCGTGTCAAGGGAGACAGCCACA<br>TCACGCCAGAAATACATGACAGCTGGATTAGCCCTGGGAG<br>AGGGAGGCCCAGATGTGGGAGCTCAGGGGAGGTGCAGCTC<br>AACGTGGAGTTTGGAGGAGGCTACCTTGACCTTTGAATGC<br>CAAGTGGGAGCCAGCCAGATGAAAGGGGTTAAAAACTAAT<br>ATTTATATGACAGAAGAAAAAGATGTCATTCCGTAAAGTA<br>AACATCATCATCTTGGTCCTGGCTGTTGCTCTCTTCTTAC<br><u>TGGTTTTGCACCATAACTTCCTCAGCTTGAGCAGTTTGTT<br>AAGGAATGAGGTTACAGATTCAGGAATTGTAGGGCCTCA</u><br>CCTATAGACTTTGTCCCAAATGCTCTCCGACATGCAGTAG<br>ATGGGAGACAAGAGGAGATTCCTGTGGTCATCGCTGCATC<br>TGAAGACAGGCTTGGGGGGCCATTGCAGCTATAAACAGC<br>ATTCAGCACAACACTCGCTCCAATGTGATTTTCTACATTG<br>TTACTCTCAACAATACAGCAGACCATCTCCGGTCCTGGCT<br>CAACAGTGATTCCCTGAAAAGCATCAGATACAAAATTGTC<br>AATTTTGACCCTAAACTTTTGGAAGGAAAAGTAAAGGAGG<br>ATCCTGACCAGGGGGAATCCATGAAACCTTTAACCTTTGC<br>AAGGTTCTACTTGCCAATTCTGGTTCCCAGCGCAAAGAAG<br>GCCATATACATGGATGATGATGTAATTGTGCAAGGTGATA<br>TTCTTGCCCTTTACAATACAGCACTGAAGCCAGGACATGC<br>AGCTGCATTTTCAGAAGATTGTGATTCAGCCTCTACTAAA<br>GTTGTCATCCGTGGAGCAGGAAACCAGTACAATTACATTG<br>GCTATCTTGACTATAAAAAGGAAATTCGTAAGCTTTC<br>CATGAAAGCCAGCACTTGCTCATTTAATCCTGGAGTTTTT<br>GTTGCAAACCTGACGGAATGGAAACGACAGAATATAACTA<br>ACCAACTGGAAAAATGGATGAAACTCAATGTAGAAGAGGG<br>ACTGTATAGCAGAACCCTGGCTGGTAGCATCACAACACCT<br>CCTCTGCTTATCGTATTTTATCAACAGCACTCTACCATCG | 16 |

TABLE 1-continued

GEP-NEN Biomarker/Houskeeper Sequence Information

| Gene Name | RefSeq Accession | Sequence | SEQ ID NO: |
|---|---|---|---|
| | | ATCCTATGTGGAATGTCCGCCACCTTGGTTCCAGTGCTGG<br>AAAACGATATTCACCTCAGTTTGTAAAGGCTGCCAAGTTA<br>CTCCATTGGAATGGACATTTGAAGCCATGGGGAAGGACTG<br>CTTCATATACTGATGTTTGGGAAAAATGGTATATTCCAGA<br>CCCAACAGGCAAATTCAACCTAATCCGAAGATATACCGAG<br>ATCTCAAACATAAAGTGAAACAGAATTTGAACTGTAAGCA<br>AGCATTTCTCAGGAAGTCCTGGAAGATAGCATGCGTGGGA<br>AGTAACAGTTGCTAGGCTTCAATGCCTATCGGTAGCAAGC<br>CATGGAAAAGATGTGTCAGCTAGGTAAAGATGACAAACT<br>GCCCTGTCTGGCAGTCAGCTTCCCAGACAGACTATAGACT<br>ATAAATATGTCTCCATCTGCCTTACCAAGTGTTTTCTTAC<br>TACAATGCTGAATGACTGGAAAGAAGAACTGATATGGCTA<br>GTTCAGCTAGCTGGTACAGATAATTCAAAACTGCTGTTGG<br>TTTTAATTTTGTAACCTGTGGCCTGATCTGTAAATAAAAC<br>TTACATTTTTCAATAGGTAAAAAAAAAAAAAAAAA | |
| HDAC9 | NM_001204144.1 | GCAGCGCGCACCGAGCCGGCCGCGCCGCGCCCGCCGCTCT<br>CGCCGCTTTCGCCGCGGTCTCCTCCTCTAGCGCCCGCCGC<br>GGCCGGTAAATCTCGGCTGGAGGAGCAGCGGCGGCCCCCG<br>AGTCAACTTTCATTCCCTTTTTGCTTCTGCCTCACCATTC<br>TCTTCTCCTCCTCGAAAGATGGCTGTTTGGAGAAGGGGGA<br>GAAGTTAAGAGGTCGCCAGCGCGGAGCGAAGGAGGGCGCG<br>ATAGCCTCAGCAGGAGCGGGCGGAGGTTTCTCCTCTGCCA<br>ACCCCTCCTGGACCATTGTCAGCAGTTGAACGACAAAGGC<br>TGTGAATCTGCATCCTAGTCTTAGCAGTCCCTCTGATTCT<br>CATGATGAGCTCACCTGCACAGCCTGACCTCATGTGGAAC<br>CTTGTACCATGGGTGCTATTCTGTGGCTGCTGTAGGATCT<br>TCCCAGATGGGGTGGCTGGACGAGAGCAGCTCTTGGCTCA<br>GCAAAGAATGCACAGTATGATCAGCTCAGTGGATGTGAAG<br>TCAGAAGTTCCTGTGGGCCTGGAGCCCATCTCACCTTTAG<br>ACCTAAGGACAGACCTCAGGATGATGATGCCCGTGGTGGA<br>CCCTGTTGTCCGTGAGAAGCAATTGCAGCAGGAATTACTT<br>CTTATCCAGCAGCAGCAACAAATCCAGAAGCAGCTTCTGA<br>TAGCAGAGTTTCAGAAACAGCATGAGAACTTGACACGGCA<br>GCACCAGGCTCAGCTTCAGGAGCATATCAAGGAACTTCTA<br>GCCATAAAACAGCAACAAGAACTCCTAGAAAAGGAGCAGA<br>AACTGGAGCAGCAGAGGCAAGAACAGGAAGTAGAGAGGCA<br>TCGCAGAGAACAGCAGCTTCCTCCTCTCAGAGGCAAAGAT<br>AGAGGACGAGAAAGGGCAGTGGCAAGTACAGAAGTAAAGC<br>AGAAGCTTCAAGAGTTCCTACTGAGTAAATCAGCAACGAA<br>AGACACTCCAACTAATGGAAAAAATCATTCCGTGAGCCGC<br>CATCCCAAGCTCTGGTACACGGCTGCCCACCACACATCAT<br>TGGATCAAAGCTCTCCACCCCTTAGTGGAACATCTCCATC<br>CTACAAGTACACATTACCAGGAGCACAAGATGCAAAGGAT<br>GATTTCCCCCTTCGAAAAACTGAATCCTCAGTCAGTAGCA<br>GTTCTCCAGGCTCTGGTCCCAGTTCACCAAACAATGGGCC<br>AACTGGAAGTGTTACTGAAAATGAGACTTCGGTTTTGCCC<br>CCTACCCCTCATGCCGAGCAAATGGTTTCACAGCAACGCA<br>TTCTAATTCATGAAGATTCCATGAACCTGCTAAGTCTTTA<br>TACCTCTCCTTCTTTGCCCAACATTACCTTGGGGCTTCCC<br>GCAGTGCCATCCCAGCTCAATGCTTCGAATTCACTCAAAG<br>AAAAGCAGAAGTGTGAGACGCAGACGCTTAGGCAAGGTGT<br>TCCTCTGCCTGGGCAGTATGGAGGCAGCATCCCGGCATCT<br>TCCAGCCACCCTCATGTTACTTTAGAGGGAAAGCCACCCA<br>ACAGCAGCCACCAGGCTCTCCTGCAGCATTTATTATTGAA<br>AGAACAAATGCGACAGCAAAAGCTTCTTGTAGCTGGTGGA<br>GTTCCCTTACATCCTCAGTCTCCCTTGGCAACAAAAGAGA<br>GAATTTCACCTGGCATTAGAGGTACCCACAAATTGCCCCG<br>TCACAGACCCCTGAACCGAACCCAGTCTGCACCTTTGCCT<br>CAGAGCACGTTGGCTCAGCTGGTCATTCAACAGCAACACC<br>AGCAATTCTTGGAGAAGCAGAAGCAATACCAGCAGCAGAT<br><u>CCACATGAACAAACTGCTTTCGAAATCTATTGAACAACTG</u><br><u>AAGCAACCAGGCAGTCACCTTGAGGAAGCAGAGGAAGAGC</u><br><u>TTC</u>AGGGGACCAGGCGATGCAGGAAGACAGAGCGCCCTC<br>TAGTGGCAACAGCACTAGGAGCGACAGCAGTGCTTGTGTG<br>GATGACACACTGGGACAAGTTGGGGCTGTGAAGGTCAAGG<br>AGGAACCAGTGGACAGTGATGAAGATGCTCAGATCCAGGA<br>AATGGAATCTGGGGAGCAGGCTGCTTTTATGCAACAGGTA<br>ATAGGCAAAGATTTAGCTCCAGGATTTGTAATTAAAGTCA<br>TTATCTGAACATGAAATGCATTGCAGGTTTGGTAAATGGA<br>TATGATTTCCTATCAGTTTATATTTCTCTATGATTTGAGT<br>TCAGTGTTTAAGGATTCTACCTAATGCAGATATATGTATA<br>TATCTATATAGAGGTCTTTCTATATACTGATCTCTATATA<br>GATATCAATGTTTCATTGAAAATCCACTGGTAAGGAAATA<br>CCTGTTATACTAAAATTATGATACATAATATCTGAGCAGT | 17 |

TABLE 1-continued

GEP-NEN Biomarker/Houskeeper Sequence Information

| Gene Name | RefSeq Accession | Sequence | SEQ ID NO: |
|---|---|---|---|
| | | TAATAGGCTTTAAATTTATCCCAAAGCCTGCTACACCAAT TACTTCTAAAGAAAACAAATTCACTGTTATTTTGAGTTTA TGTGTTGAGATCAGTGACTGCTGGATAGTCTCCCAGTCTG ATCAATGAAGCATTCGATTAGTTTTTGATTTTTTGCAACA TCTAGAATTTAATTTTCACATCACTGTACATAATGTATCA TACTATAGTCTTGAACACTGTTAAAGGTAGTCTGCCCCTT CCTTCCTCTCTCTTTTTTAGTTAAGTAGAAATGTTCTGG TCACCATGCCAGTAGTCCTAGGTTATTGTGTAGGTTGCAA TTGAACATATTAGGAATACAGGTGGTTTTAAATATATAGA TGCAAATTGCAGCACTACTTTAAATATTAGATTATGTCTC ACATAGCACTGCTCATTTTACTTTTATTTTGTGTAATTTG ATGACACTGTCTATCAAAAAAGAGCAAATGAAGCAGATGC AAATGTTAGTGAGAAGTAATGTGCAGCATTATGGTCCAAT CAGATACAATATTGTGTCTACAATTGCAAAAAACACAGTA ACAGGATGAATATTATCTGATATCAAGTCAAAATCAGTTT GAAAAGAAGGTGTATCATATTTTATATTGTCACTAGAATC TCTTAAGTATAATTCCATAATGACATGGGCATATACCGTA ACATTCTGGCAAATAACAATTAGAAAAGATAGGTTTAACA AAAAAATTTACTTGTATATAATGCACCTTCAGGAGGACTA TGTCCTTTGATGCTATAAAATACAAACAACTTTGAAGGCA ACAGAAGACACTGTTTATTCAAGTCAGTTCTTTGTCAGGT TCCTGCTGTTCTCCTACAGAAAGTGATTCTGTGAGGGTG AACAGGAAATGCCTTGTGGAAACAGGAAGTCCAAGTGATT CATGTACTGAGGAATGTAGGAAAAAAAATCTGAGGATAGT GCTTTACTCTTTCTGTTTTTAAAGGGCACTCTATGAATTG ATTTATTGTCTAAGAAAATAACACCACAAGTAGGGAAATT GTTACGGAAGCTTTTCACTGGAACATTTCCTTCATATTCC CTTTTGATATGTTTACCTTGTTTTATAGGTTTACTTTTGT TAAGCTAGTTAAAGGTTCGTTGTATTAAGACCCCTTTAAT ATGGATAATCCAAATTGACCTAGAATCTTTGTGAGGTTTT TTCTATTAAAATATTTATATTTCTAAATCCGAGGTATTTC AAGGTGTAGTATCCTATTTCAAAGGAGATATAGCAGTTTT GCCAAATGTAGACATTGTTCAACTGTATGTTATTGGCACG TGTTGTTTACATTTTGCTGTGACATTTAAAAATATTTCTT TAAAAATGTTACTGCTAAAGATACATTATCCTTTTTTAAA AAGTCTCCATTCAAATTAAATTAACATAACTAGAAGTTAG AAAGTTTAAAAGTTTTCCACATAATGAAAGTCCTTCTGAT AATTTGACAAATAGCTATAATAGGAACACTCCCTATCACC AACATATTTTGGTTAGTATATTCCTTCATATTAAAATGAC TTTTTGTCAGTTGTTTTGCATTAAAAATATGGCATGCCTA AGATAAAATTGTATATTTTTTCCATCTCATAAATATTCAT TTTCTTCAAAGTCTTTTTTCAATCTCATAAAAAAGGGATA GTGCATCTTTTAAAATACATTTTATTTGGGGAGGAACATG TGGCTGAGCAGACTTTTGTATAATATTACTTCAAAGATAT GTAATCACAAACAAAAAAACTATTTTTTATAATGTCATT TGAGAGAGTTTCATCAGTACAGTTGGTGGACGTTAATTGT TTGAATTTGATAGTCTTTGAATTTAATCAAGAAACTACCT GGAACCAGTGAAAGGAAAGCTGGACTTAAATAATCTTAG AATTAATTGATAAATGTCTCTTTTAAAATCTACTGTATTT ATTATAATTTACACCCTTGAAGGTGATCTCTTGTTTTGTG TTGTAAATATATTGTTTGTATGTTTCCCTTCTTGCCTTCT GTTATAAGTCTCTTCCTTTCTCAAATAAAGTTTTTTTAA AAGAAAAAAAAAAAAAAAAAAA | |
| HSF2 | NM_004506.3 | ACTTGTCCGTCACGTGCGGCCGCCCGGCCTCTCGGCCTTG CCGCGCGCCTGGCGGGGTTGGGGGGGCGGGGACCAAGATC TGCTGCGCCTGCGTTGTGGGCGTTCTCGGGGAGCTGCTGC CGTAGCTGCCGCCGCCGCTACCACCGCGTTCGGGTGTAGA ATTTGGAATCCCTGCGCCGCGTTAACAATGAAGCAGAGTT CGAACGTGCCGGCTTTCCTCAGCAAGCTGTGGACGCTTGT GGAGGAAACCCACACTAACGAGTTCATCACCTGGAGCCAG AATGGCCAAAGTTTTCTGGTCTTGGATGAGCAACGATTTG CAAAAGAAATTCTTCCCAAATATTTCAAGCACAATAATAT GGCAAGCTTTGTGAGGCAACTGAATATGTATGGTTTCCGT AAAGTAGTACATATCGACTCTGGAATTGTAAAGCAAGAAA GAGATGGTCCTGTAGAATTTCAGCATCCTTACTTCAAACA AGGACAGGATGACTTGTTGGAGAACATTAAAAGGAAGGTT TCATCTTCAAAACCAGAAGAAATAAATTCGTCAGGAAG ATTTAACAAAAATTATAAGTAGTGCTCAGAAGGTTCAGAT AAAACAGGAAACTATTGAGTCCAGGCTTTCTGAATTAAAA AGTGAGAATGAGTCCCTTTGGAAGGAGGTGTCAGAATTAC GAGCAAAGCATGCACAACAGCAACAAGTTATTCGAAAGAT TGTCCAGTTTATTGTTACATTGGTTCAAAATAACCAACTT GTGAGTTTAAAACGTAAAAGGCCTCTACTTCTAAACACTA ATGGAGCCCAAAAGAAGAACCTGTTTCAGCACATAGTCAA | 18 |

TABLE 1-continued

GEP-NEN Biomarker/Houskeeper Sequence Information

| Gene Name | RefSeq Accession | Sequence | SEQ ID NO: |
|---|---|---|---|
| | | AGAACCAACTGATAATCATCATCATAAAGTTCCACACAGT<br>AGGACTGAAGGTTTAAAGCCAAGGGAGAGGATTTCAGATG<br>ACATCATTATTTATGATGTTACTGATGATAATGCAGATGA<br>AGAAAATATCCCAGTTATTCCAGAAACTAATGAGGATGTT<br>ATATCTGATCCCTCCAACTGTAGCCAGTACCCTGATATTG<br>TCATCGTTGAAGATGACAATGAAGATGAGTATGCACCTGT<br>CATTCAGAGTGGAGAGCAGAATGAACCAGCCAGAGAATCC<br>CTAAGTTCAGGCAGTGATGGCAGCAGCCCTCTCATGTCTA<br>GTGCTGTCCAGCTAAATGGCTCATCCAGTCTGACCTCAGA<br>AGATCCAGTGACCATGATGGATTCCATTTTGAATGATAAC<br>ATCAATCTTTTGGGAAAGGTTGAGCTGTTGGATTATCTTG<br>ACAGTATTGACTGCAGTTTAGAGGACTTCCAGGCCATGCT<br>ATCAGGAAGACAATTTAGCATAGACCCAGATCTCCTGGTT<br>GATCTTTTCACTAGTTCTGTGCAGATGAATCCCACAGATT<br>ACATCAATAATACAAAATCTGAGAATAAAGGATTAGAAAC<br>TACCAAGAACAATGTAGTTCAGCCAGTTTCGGAAGAGGGA<br>AGAAAATCTAAATCCAAACCAGATAAGCAGCTTATCCAGT<br>ATACCGCCTTTCCACTTCTTGCATTCCTCGATGGGAACCC<br>TGCTTCTTCTGTTGAACAGGCGAGTACAACAGCATCATCA<br>GAAGTTTTGTCCTCTGTAGATAAACCCATAGAAGTTGATG<br>AGCTTCTGGATAGCAGCCTAGACCCAGAACCAACCCAAAG<br>TAAGCTTGTTCGCCTGGAGCCATTGACTGAAGCTGAAGCT<br>AGTGAAGCTACACTGTTTTATTTATGTGAACTTGCTCCTG<br>CACCTCTGGATAGTGATATGCCACTTTTAGATAGCTAAAT<br>CCCCAGGAAGTGGACTTTACATGTATATATTCATCAAAAT<br>GATGAACTATTTATTTTAAAGTATCATTTGGTACTTTTTT<br>TGTAAATTGCTTTGTTTTGTTTAATCAGATACTGTGGAAT<br>AAAAGCACCTTTTGCTTTTCTCACTAACCACACACTCTTG<br>CAGAGCTTTCAGGTGTTACTCAGCTGCATAGTTACGCAGA<br>TGTAATGCACATTATTGGCGTATCTTTAAGTTGGATTCAA<br>ATGGCCATTTTTCTCCAATTTTGGTAAATTGGATATCTTT<br>TTTTTACAAATACGACCATTAACCTCAGTTAAATTTTTGT<br>TTGTTTTCCTGTTTGATGCTGTCTATTTGCATTGAGTGTA<br>AGTCATTTGAACTAATGGTATAACTCCTAAAGCTTTCTCT<br>GCTCCAGTTATTTTTATTAAATATTTTTCACTTGGCTTAT<br>TTTTAAAACTGGGAACATAAAGTGCCTGTATCTTGTAAAA<br>CTTCATTTGTTTCTTTTGGTTCAGAGAAGTTCATTTATGT<br>TCAAAGACGTTTATTCATGTTCAACAGGAAAGACAAAGTG<br>TACGTGAATGCTCGCTGTCTGATAGGGTTCCAGCTCCATA<br>TATATAGAAAGATCGGGGGTGGGATGGGATGGAGTGAGCC<br>CCATCCAGTTAGTTGGACTAGTTTTAAATAAAGGTTTTCC<br>GGTTTGTGTTTTTTTGAACCATACTGTTTAGTAAAATAAA<br>TACAATGAATGTTGAGTACTAGTGTCTGTTATGTGTCTTC<br>TTTAGAGGTGACACTCACATGAAACAATTTTTTCTTCTCA<br>TAGGAAGCAGTAGCTTTAAACTGTCTGTGGTTCATTATTC<br>TCAATATGAATCATACCAAGATATTTGTGCCTCATCTCGA<br>AAATATATTGTATATTG | |
| Ki-67 | NM_001145966.1 | TACCGGGCGGAGGTGAGCGCGGCGCCGGCTCCTCCTGCGG<br>CGGACTTTGGGTGCGACTTGACGAGCGGTGGTTCGACAAG<br>TGGCCTTGCGGGCCGGATCGTCCCAGTGGAAGAGTTGTAA<br>ATTTGCTTCTGGCCTTCCCCTACGGATTATACCTGGCCTT<br>CCCCTACGGATTATACTCAACTTACTGTTTAGAAAATGTG<br>GCCCACGAGACGCCTGGTTACTATCAAAAGGAGCGGGGTC<br>GACGGTCCCCACTTTCCCCTGAGCCTCAGCACCTGCTTGT<br>TTGGAAGGGGTATTGAATGTGACATCCGTATCCAGCTTCC<br>TGTTGTGTCAAAACAACATTGCAAAATTGAAATCCATGAG<br>CAGGAGGCAATATTACATAATTTCAGTTCCACAAATCCAA<br>CACAAGTAAATGGGTCTGTTATTGATGAGCCTGTACGGCT<br>AAAACATGGAGATGTAATAACTATTATTGATCGTTCCTTC<br>AGGTATGAAATGAAAGTCTTCAGAATGGAAGGAAGTCAA<br>CTGAATTTCCAAGAAAAATACGTGAACAGGAGCCAGCACG<br>TCGTGTCTCAAGATCTAGCTTCTCTTCTGACCCTGATGAG<br>AGTGAGGGAATACCTTTGAAAAGAAGGCGTGTGTCCTTTG<br>GTGGGCACCTAAGACCTGAACTATTTGATGAAAACTTGCC<br>TCCTAATACGCCTCTCAAAAGGGGAGAAGCCCCAACCAAA<br>AGAAAGTCTCTGGTAATGCACACTCCACCTGTCCTGAAGA<br>AAATCATCAAGGAACAGCCTCAACCATCAGGAAAACAAGA<br>GTCAGGTTCAGAAATCCATGTGGAAGTGAAGGCACAAAGC<br>TTGGTTATAAGCCCTCCAGCTCCTAGTCCTAGGAAAACTC<br>CAGTTGCCAGTGATCAACGCCGTAGGTCCTGCAAAACAGC<br>CCCTGCTTCCAGCAGCAAATCTCAGACAGAGGTTCCTAAG<br>AGAGGAGGGAGAAAGAGTGGCAACCTGCCTTCAAAGAGAG<br>TGTCTATCAGCCGAAGTCAACATGATATTTTACAGATGAT<br>ATGTTCCAAAAGAAGAAGTGGTGCTTCGGAAGCAAATCTG | 19 |

TABLE 1-continued

GEP-NEN Biomarker/Houskeeper Sequence Information

| Gene Name | RefSeq Accession | Sequence | SEQ ID NO: |
|---|---|---|---|
| | | ATTGTTGCAAAATCATGGGCAGATGTAGTAAAACTTGGTG<br>CAAAACAAACACAAACTAAAGTCATAAAACATGGTCCTCA<br>AAGGTCAATGAACAAAAGGCAAAGAAGACCTGCTACTCCA<br>AAGAAGCCTGTGGGCGAAGTTCACAGTCAATTTAGTACAG<br>GCCACGCAAACTCTCCTTGTACCATAATAATAGGGAAAGC<br>TCATACTGAAAAAGTACATGTGCCTGCTCGACCCTACAGA<br>GTGCTCAACAACTTCATTTCCAACCAAAAAATGGACTTTA<br>AGGAAGATCTTTCAGGAATAGCTGAAATGTTCAAGACCCC<br>AGTGAAGGAGCAACCGCAGTTGACAAGCACATGTCACATC<br>GCTATTTCAAATTCAGAGAATTTGCTTGGAAAACAGTTTC<br>AAGGAACTGATTCAGGAGAAGAACCTCTGCTCCCACCTC<br>AGAGAGTTTTGGAGGAAATGTGTTCTTCAGTGCACAGAAT<br>GCAGCAAAACAGCCATCTGATAAATGCTCTGCAAGCCCTC<br>CCTTAAGACGGCAGTGTATTAGAGAAAATGGAAACGTAGC<br>AAAAACGCCCAGGAACACCTACAAAATGACTTCTCTGGAG<br>ACAAAAACTTCAGATACTGAGACAGAGCCTTCAAAAACAG<br>TATCCACTGCAAACAGGTCAGGAAGGTCTACAGAGTTCAG<br>GAATATACAGAAGCTACCTGTGGAAAGTAAGAGTGAAGAA<br>ACAAATACAGAAATTGTTGAGTGCATCCTAAAAAGAGGTC<br>AGAAGGCAACACTACTACAACAAAGGAGAGAAGGAGAGAT<br>GAAGGAAATAGAAAGACCTTTTGAGACATATAAGGAAAAT<br>ATTGAATTAAAAGAAAACGATGAAAAGATGAAAGCAATGA<br>AGAGATCAAGAACTTGGGGGCAGAAATGTGCACCAATGTC<br>TGACCTGACAGACCTCAAGAGCTTGCCTGATACAGAACTC<br>ATGAAAGACACGGCACGTGGCCAGAATCTCCTCCAAACCC<br>AAGATCATGCCAAGGCACCAAAGAGTGAGAAAGGCAAAAT<br>CACTAAAATGCCCTGCCAGTCATTACAACCAGAACCAATA<br>AACACCCCAACACACACAAAACAACAGTTGAAGGCATCCC<br>TGGGGAAAGTAGGTGTGAAAGAAGAGCTCCTAGCAGTCGG<br>CAAGTTCACACGGACGTCAGGGGAGACCACGCACACGCAC<br>AGAGAGCCAGCAGGAGATGGCAAGAGCATCAGAACGTTTA<br>AGGAGTCTCCAAAGCAGATCCTGGACCCAGCAGCCCGTGT<br>AACTGGAATGAAGAAGTGGCCAAGAACGCCTAAGGAAGAG<br>GCCCAGTCACTAGAAGACCTGGCTGGCTTCAAAGAGCTCT<br>TCCAGACACCAGGTCCCTCTGAGGAATCAATGACTGATGA<br>GAAAACTACCAAAATAGCCTGCAAATCTCCACCACCAGAA<br>TCAGTGGACACTCCAACAAGCACAAAGCAATGGCCTAAGA<br>GAAGTCTCAGGAAAGCAGATGTAGAGGAAGAATTCTTAGC<br>ACTCAGGAAACTAACACCATCAGCAGGGAAAGCCATGCTT<br>ACGCCCAAACCAGCAGGAGGTGATGAGAAAGACATTAAAG<br>CATTTATGGGAACTCCAGTGCAGAAACTGGACCTGGCAGG<br>AACTTTACCTGGCAGCAAAAGACAGCTACAGACTCCTAAG<br>GAAAAGGCCCAGGCTCTAGAAGACCTGGCTGGCTTTAAAG<br>AGCTCTTCCAGACTCCTGGTCACACCGAGGAATTAGTGGC<br>TGCTGGTAAAACCACTAAAATACCCTGCGACTCTCCACAG<br>TCAGACCCAGTGGACACCCCAACAAGCACAAAGCAACGAC<br>CCAAGAGAAGTATCAGGAAAGCAGATGTAGAGGGAGAACT<br>CTTAGCGTGCAGGAATCTAATGCCATCAGCAGGCAAAGCC<br>ATGCACACGCCTAAACCATCAGTAGGTGAAGAGAAAGACA<br>TCATCATATTTGTGGGAACTCCAGTGCAGAAACTGGACCT<br>GACAGAGAACTTAACCGGCAGCAAGAGACGGCCACAAACT<br>CCTAAGGAAGAGGCCCAGGCTCTGGAAGACCTGACTGGCT<br>TTAAAGAGCTCTTCCAGACCCCTGGTCATACTGAAGAAGC<br>AGTGGCTGCTGGCAAAACTACTAAAATGCCCTGCGAATCT<br>TCTCCACCAGAATCAGCAGACACCCCAACAAGCACAAGAA<br>GGCAGCCCAAGACACCTTTGGAGAAAAGGGACGTACAGAA<br>GGAGCTCTCAGCCCTGAAGAAGCTCACACAGACATCAGGG<br>GAAACCACACACAGATAAAGTACCAGGAGGTGAGGATA<br>AAAGCATCAACGCGTTTAGGGAAACTGCAAAACAGAAACT<br>GGACCCAGCAGCAAGTGTAACTGGTAGCAAGAGGCACCCA<br>AAAACTAAGGAAAAGGCCCAACCCCTAGAAGACCTGGCTG<br>GCTTGAAAGAGCTCTTCCAGACACCAGTATGCACTGACAA<br>GCCCACGACTCACGAGAAAACTACCAAAATAGCCTGCAGA<br>TCACAACCAGACCCAGTGGACACACCAACAAGCTCCAAGC<br>CACAGTCCAAGAGAAGTCTCAGGAAAGTGGACGTAGAAGA<br>AGAATTCTTCGCACTCAGGAAACGAACACCATCAGCAGGC<br>AAAGCCATGCACACACCCAAACCAGCAGTAAGTGGTGAGA<br>AAAACATCTACGCATTTATGGGAACTCCAGTGCAGAAACT<br>GGACCTGACAGAGAACTTAACTGGCAGCAAGAGACGGCTA<br>CAAACTCCTAAGGAAAAGGCCCAGGCTCTAGAAGACCTGG<br>CTGGCTTTAAAGAGCTCTTCCAGACACGAGGTCACACTGA<br>GGAATCAATGACTAACGATAAAACTGCCAAAGTAGCCTGC<br>AAATCTTCACAACCAGACCCAGACAAAAACCCAGCAAGCT<br>CCAAGCGACGGCTCAAGACATCCCTGGGGAAAGTGGGCGT<br>GAAAGAAGAGCTCCTAGCAGTTGGCAAGCTCACACAGACA | |

TABLE 1-continued

GEP-NEN Biomarker/Houskeeper Sequence Information

| Gene Name | RefSeq Accession | Sequence | SEQ ID NO: |
|---|---|---|---|
| | | TCAGGAGAGACTACACACACACACAGAGCCAACAGGAG | |
| | | ATGGTAAGAGCATGAAAGCATTTATGGAGTCTCCAAAGCA | |
| | | GATCTTAGACTCAGCAGCAAGTCTAACTGGCAGCAAGAGG | |
| | | CAGCTGAGAACTCCTAAGGGAAAGTCTGAAGTCCCTGAAG | |
| | | ACCTGGCCGGCTTCATCGAGCTCTTCCAGACACCAAGTCA | |
| | | CACTAAGGAATCAATGACTAACGAAAAAACTACCAAAGTA | |
| | | TCCTACAGAGCTTCACAGCCAGACCTAGTGGACACCCCAA | |
| | | CAAGCTCCAAGCCACAGCCCAAGAGAAGTCTCAGGAAAGC | |
| | | AGACACTGAAGAAGAATTTTTAGCATTTAGGAAACAAACG | |
| | | CCATCAGCAGGCAAAGCCATGCACACACCCAAACCAGCAG | |
| | | TAGGTGAAGAGAAAGACATCAACACGTTTTTGGGAACTCC | |
| | | AGTGCAGAAACTGGACCAGCCAGGAAATTTACCTGGCAGC | |
| | | AATAGACGGCTACAAACTCGTAAGGAAAAGGCCCAGGCTC | |
| | | TAGAAGAACTGACTGGCTTCAGAGAGCTTTTCCAGACACC | |
| | | ATGCACTGATAACCCCACGACTGATGAGAAAACTACCAAA | |
| | | AAAATACTCTGCAAATCTCCGCAATCAGACCCAGCGGACA | |
| | | CCCCAACAAACACAAAGCAACGGCCCAAGAGAAGCCTCAA | |
| | | GAAAGCAGACGTAGAGGAAGAATTTTTAGCATTCAGGAAA | |
| | | CTAACACCATCAGCAGGCAAAGCCATGCACACGCCTAAAG | |
| | | CAGCAGTAGGTGAAGAGAAAGACATCAACACATTTGTGGG | |
| | | GACTCCAGTGGAGAAACTGGACCTGCTAGGAAATTTACCT | |
| | | GGCAGCAAGAGACGGCCACAAACTCCTAAAGAAAAGGCCA | |
| | | AGGCTCTAGAAGATCTGGCTGGCTTCAAAGAGCTCTTCCA | |
| | | GACACCAGGTCACACTGAGGAATCAATGACCGATGACAAA | |
| | | ATCACAGAAGTATCCTGCAAATCTCCACAACCAGACCCAG | |
| | | TCAAAACCCCAACAAGCTCCAAGCAACGACTCAAGATATC | |
| | | CTTGGGGAAAGTAGGTGTGAAAGAAGAGGTCCTACCAGTC | |
| | | GGCAAGCTCACACAGACGTCAGGGAAGACCCACACAGACAC | |
| | | ACAGAGAGACAGCAGGAGATGGAAAGAGCATCAAAGCGTT | |
| | | TAAGGAATCTGCAAAGCAGATGCTGGACCCAGCAAACTAT | |
| | | GGAACTGGGATGGAGAGGTGGCCAAGAACACCTAAGGAAG | |
| | | AGGCCCAATCACTAGAAGACCTGGCCGGCTTCAAAGAGCT | |
| | | CTTCCAGACACCAGACCACACTGAGGAATCAACAACTGAT | |
| | | GACAAAACTACCAAAATAGCCTGCAAATCTCCACCACCAG | |
| | | AATCAATGGACACTCCAACAAGCACAAGGAGGCGGCCCAA | |
| | | AACACCTTTGGGGAAAAGGGATATAGTGGAAGAGCTCTCA | |
| | | GCCCTGAAGCAGCTCACACAGACCACACACACAGACAAAG | |
| | | TACCAGGAGATGAGGATAAAGGCATCAACGTGTTCAGGGA | |
| | | AACTGCAAAACAGAAACTGGACCCAGCAGCAAGTGTAACT | |
| | | GGTAGCAAGAGGCAGCCAAGAACTCCTAAGGGAAAAGCCC | |
| | | AACCCCTAGAAGACTTGGCTGGCTTGAAAGAGCTCTTCCA | |
| | | GACACCAATATGCACTGACAAGCCCACGACTCATGAGAAA | |
| | | ACTACCAAAATAGCCTGCAGATCTCCACAACCAGACCCAG | |
| | | TGGGTACCCCAACAATCTTCAAGCCACAGTCCAAGAGAAG | |
| | | TCTCAGGAAAGCAGACGTAGAGGAAGAATCCTTAGCACTC | |
| | | AGGAAACGAACACCATCAGTAGGGAAAGCTATGGACACAC | |
| | | CCAAACCAGCAGGAGGTGATGAGAAAGACATGAAAGCATT | |
| | | TATGGGAACTCCAGTGCAGAAATTGGACCTGCCAGGAAAT | |
| | | TTACCTGGCAGCAAAAGATGGCCACAAACTCCTAAGGAAA | |
| | | AGGCCCAGGCTCTAGAAGACCTGGCTGGCTTCAAAGAGCT | |
| | | CTTCCAGACACCAGGCACTGACAAGCCCACGACTGATGAG | |
| | | AAAACTACCAAAATAGCCTGCAAATCTCCACAACCAGACC | |
| | | CAGTGGACACCCCAGCAAGCACAAAGCAACGGCCCAAGAG | |
| | | AAACCTCAGGAAAGCAGACGTAGAGGAAGAATTTTTAGCA | |
| | | CTCAGGAAACGAACACCATCAGCAGGCAAAGCCATGGACA | |
| | | CACCAAAACCAGCAGTAAGTGATGAGAAAAATATCAACAC | |
| | | ATTTGTGGAAACTCCAGTGCAGAAACTGGACCTGCTAGGA | |
| | | AATTTACCTGGCAGCAAGAGACAGCCACAGACTCCTAAGG | |
| | | AAAAGGCTGAGGCTCTAGAGGACCTGGTTGGCTTCAAAGA | |
| | | ACTCTTCCAGACACCAGGTCACACTGAGGAATCAATGACT | |
| | | GATGACAAAATCACAGAAGTATCCTGTAAATCTCCACAGC | |
| | | CAGAGTCATTCAAAACCTCAAGAAGCTCCAAGCAAAGGCT | |
| | | CAAGATACCCCTGGTGAAAGTGGACATGAAAGAAGAGCCC | |
| | | CTAGCAGTCAGCAAGCTCACACGGACATCAGGGGAGACTA | |
| | | CGCAAACACACACAGAGCCAACAGGAGATAGTAAGAGCAT | |
| | | CAAAGCGTTTAAGGAGTCTCCAAAGCAGATCCTGGACCCA | |
| | | GCAGCAAGTGTAACTGGTAGCAGGAGGCAGCTGAGAACTC | |
| | | GTAAGGAAAAGGCCCGTGCTCTAGAAGACCTGGTTGACTT | |
| | | CAAAGAGCTCTTCTCAGCACCAGGTCACACTGAAGAGTCA | |
| | | ATGACTATTGACAAAAACACAAAATTCCCTGCAAATCTC | |
| | | CCCCACCAGAACTAACAGACACTGCCACGAGCACAAAGAG | |
| | | ATGCCCCAAGACACGTCCCAGGAAAGAAGTAAAAGAGGAG | |
| | | CTCTCAGCAGTTGAGAGGCTCACGCAAACATCAGGGCAAA | |
| | | GCACACACACACAAAGAACCAGCAAGCGGTGATGAGGG | |
| | | CATCAAAGTATTGAAGCAACGTGCAAAGAAGAAACCAAAC | |

TABLE 1-continued

GEP-NEN Biomarker/Houskeeper Sequence Information

| Gene Name | RefSeq Accession | Sequence | SEQ ID NO: |
|---|---|---|---|
| | | CCAGTAGAAGAGGAACCCAGCAGGAGAAGGCCAAGAGCAC<br>CTAAGGAAAAGGCCCAACCCCTGGAAGACCTGGCCGGCTT<br>CACAGAGCTCTCTGAAACATCAGGTCACACTCAGGAATCA<br>CTGACTGCTGGCAAAGCCACTAAAATACCCTGCGAATCTC<br>CCCCACTAGAAGTGGTAGACACCACAGCAAGCACAAAGAG<br>GCATCTCAGGACACGTGTGCAGAAGGTACAAGTAAAAGAA<br>GAGCCTTCAGCAGTCAAGTTCACACAAACATCAGGGGAAA<br>CCACGGATGCAGACAAAGAACCAGCAGGTGAAGATAAAGG<br>CATCAAAGCATTGAAGGAATCTGCAAAACAGACACCGGCT<br>CCAGCAGCAAGTGTAACTGGCAGCAGGAGACGGCCAAGAG<br>CACCCAGGGAAAGTGCCCAAGCCATAGAAGACCTAGCTGG<br>CTTCAAAGACCCAGCAGCAGGTCACACTGAAGAATCAATG<br>ACTGATGACAAAACCACTAAAATACCCTGCAAATCATCAC<br>CAGAACTAGAAGACACCGCAACAAGCTCAAAGAGACGGCC<br>CAGGACACGTGCCCAGAAAGTAGAAGTGAAGGAGGAGCTG<br>TTAGCAGTTGGCAAGCTCACACAAACCTCAGGGGAGACCA<br>CGCACACCGACAAAGAGCCGGTAGGTGAGGGCAAAGGCAC<br>GAAAGCATTTAAGCAACCTGCAAAGCGGAAGCTGGACGCA<br>GAAGATGTAATTGGCAGCAGGAGACAGCCAAGAGCACCTA<br>AGGAAAAGGCCCAACCCCTGGAAGATCTGGCCAGCTTCCA<br>AGAGCTCTCTCAAACACCAGGCCACACTGAGGAACTGGCA<br>AATGGTGCTGCTGATAGCTTTACAAGCGCTCCAAAGCAAA<br>CACCTGACAGTGGAAAACCTCTAAAAATATCCAGAAGAGT<br>TCTTCGGGCCCCTAAAGTAGAACCCGTGGGAGACGTGGTA<br>AGCACCAGAGACCCTGTAAAATCACAAAGCAAAAGCAACA<br>CTTCCCTGCCCCCACTGCCCTTCAAGAGGGGAGGTGGCAA<br>AGATGGAAGCGTCACGGGAACCAAGAGGCTGCGCTGCATG<br>CCAGCACCAGAGGAAATTGTGGAGGAGCTGCCAGCCAGCA<br>AGAAGCAGAGGGTTGCTCCCAGGGCAAGAGGCAAATCATC<br>CGAACCCGTGGTCATCATGAAGAGAAGTTTGAGGACTTCT<br>GCAAAAAGAATTGAACCTGCGGAAGAGCTGAACAGCAACG<br>ACATGAAAACCAACAAAGAGGAACACAAATTACAAGACTC<br>GGTCCCTGAAAATAAGGGAATATCCCTGCGCTCCAGACGC<br>CAAAATAAGACTGAGGCAGAACAGCAAATAACTGAGGTCT<br>TTGTATTAGCAGAAAGAATAGAAATAAACAGAAATGAAAA<br>GAAGCCCATGAAGACCTCCCCAGAGATGGACATTCAGAAT<br>CCAGATGATGGAGCCCGGAAACCCATACCTAGAGACAAAG<br>TCACTGAGAACAAAAGGTGCTTGAGGTCTGCTAGACAGAA<br>TGAGAGCTCCCAGCCTAAGGTGGCAGAGGAGAGCGGAGGG<br>CAGAAGAGTGCGAAGGTTCTCATGCAGAATCAGAAAGGGA<br>AAGGAGAAGCAGGAAATTCAGACTCCATGTGCCTGAGATC<br>AAGAAAGACAAAAAGCCAGCCTGCAGCAAGCACTTTGGAG<br>AGCAAATCTGTGCAGAGAGTAACGCGGAGTGTCAAGAGGT<br>GTGCAGAAAATCCAAAGAAGGCTGAGGACAATGTGTGTGT<br>CAAGAAAATAAGAACCAGAAGTCATAGGGACAGTGAAGAT<br>ATTTGACAGAAAAATCGAACTGGGAAAAATATAATAAAGT<br>TAGTTTTGTGATAAGTTCTAGTGCAGTTTTTGTCATAAAT<br>TACAAGTGAATTCTGTAAGTAAGGCTGTCAGTCTGCTTAA<br>GGGAAGAAAACTTTGGATTTGCTGGGTCTGAATCGGCTTC<br>ATAAACTCCACTGGGAGCACTGCTGGGCTCCTGGACTGAG<br>AATAGTTGAACACCGGGGGCTTTGTGAAGGAGTCTGGGCC<br>AAGGTTTGCCCTCAGCTTTGCAGAATGAAGCCTTGAGGTC<br>TGTCACCACCCACAGCCACCCTACAGCAGCCTTAACTGTG<br>ACACTTGCCACACTGTGTCGTCGTTTGTTTGCCTATGTCC<br>TCCAGGGCACGGTGGCAGGAACAACTATCCTCGTCTGTCC<br>CAACACTGAGCAGGCACTCGGTAAACACGAATGAATGGAT<br>GAGCGCACGGATGAATGGAGCTTACAAGATCTGTCTTTCC<br>AATGGCCGGGGGCATTTGGTCCCCAAATTAAGGCTATTGG<br>ACATCTGCACAGGACAGTCCTATTTTTGATGTCCTTTCCT<br>TTCTGAAAATAAAGTTTTGTGCTTTGGAGAATGACTCGTG<br>AGCACATCTTTAGGGACCAAGAGTGACTTTCTGTAAGGAG<br>TGACTCGTGGCTTGCCTTGGTCTCTTGGGAATACTTTTCT<br>AACTAGGGTTGCTCTCACCTGAGACATTCTCCACCCGCGG<br>AATCTCAGGGTCCCAGGCTGTGGGCCATCACGACCTCAAA<br>CTGGCTCCTAATCTCCAGCTTTCCTGTCATTGAAAGCTTC<br>GGAAGTTTACTGGCTCTGCTCCCGCCTGTTTTCTTTCTGA<br>CTCTATCTGGCAGCCCGATGCCACCCAGTACAGGAAGTGA<br>CACCAGTACTCTGTAAAGCATCATCATCCTTGGAGAGACT<br>GAGCACTCAGCACCTTCAGCCACGATTTCAGGATCGCTTC<br>CTTGTGAGCCGCTGCCTCCGAAATCTCCTTTGAAGCCCAG<br>ACATCTTTCTCCAGCTTCAGACTTGTAGATATAACTCGTT<br>CATCTTCATTTACTTTCCACTTTGCCCCCTGTCCTCTCTG<br>TGTTCCCCAAATCAGAGAATAGCCCGCCATCCCCCAGGTC<br>ACCTGTCTGGATTCCTCCCCATTCACCCACCTTGCCAGGT<br>GCAGGTGAGGATGGTGCACCAGACAGGGTAGCTGTCCCCC | |

TABLE 1-continued

GEP-NEN Biomarker/Houskeeper Sequence Information

| Gene Name | RefSeq Accession | Sequence | SEQ ID NO: |
|---|---|---|---|
| | | AAAATGTGCCCTGTGCGGGCAGTGCCCTGTCTCCACGTTT<br>GTTTCCCCAGTGTCTGGCGGGGAGCCAGGTGACATCATAA<br>ATACTTGCTGAATGAATGCAGAAATCAGCGGTACTGACTT<br>GTACTATATTGGCTGCCATGATAGGGTTCTCACAGCGTCA<br>TCCATGATCGTAAGGGAGAATGACATTCTGCTTGAGGGAG<br>GGAATAGAAAGGGGCAGGGAGGGGACATCTGAGGGCTTCA<br>CAGGGCTGCAAAGGGTACAGGGATTGCACCAGGGCAGAAC<br>AGGGGAGGGTGTTCAAGGAAGAGTGGCTCTTAGCAGAGGC<br>ACTTTGGAAGGTGTGAGGCATAAATGCTTCCTTCTACGTA<br>GGCCAACCTCAAAACTTTCAGTAGGAATGTTGCTATGATC<br>AAGTTGTTCTAACACTTTAGACTTAGTAGTAATTATGAAC<br>CTCACATAGAAAAATTTCATCCAGCCATATGCCTGTGGAG<br>TGGAATATTCTGTTTAGTAGAAAAATCCTTTAGAGTTCAG<br>CTCTAACCAGAAATCTTGCTGAAGTATGTCAGCACCTTTT<br>CTCACCCTGGTAAGTACAGTATTTCAAGAGCACGCTAAGG<br>GTGGTTTTCATTTTACAGGGCTGTTGATGATGGGTTAAAA<br>ATGTTCATTTAAGGGCTACCCCCGTGTTTAATAGATGAAC<br>ACCACTTCTACACAACCCTCCTTGGTACTGGGGAGGGAG<br>AGATCTGACAAATACTGCCCATTCCCCTAGGCTGACTGGA<br>TTTGAGAACAAATACCCACCCATTTCCACCATGGTATGGT<br>AACTTCTCTGAGCTTCAGTTTCCAAGTGAATTTCCATGTA<br>ATAGGACATTCCCATTAAATACAAGCTGTTTTTACTTTTT<br>CGCCTCCCAGGGCTGTGGGATCTGGTCCCCCAGCCTCTC<br>TTGGGCTTTCTTACACTAACTCTGTACCTACCATCTCCTG<br>CCTCCCTTAGGCAGGCACCTCCAACCACCACACACTCCCT<br>GCTGTTTTCCCTGCCTGGAACTTTCCCTCCTGCCCCACCA<br>AGATCATTTCATCCAGTCCTGAGCTCAGCTTAAGGGAGGC<br>TTCTTGCCTGTGGGTTCCCTCACCCCCATGCCTGTCCTCC<br>AGGCTGGGGCAGGTTCTTAGTTTGCCTGGAATTGTTCTGT<br>ACCTCTTTGTAGCACGTAGTGTTGTGGAAACTAAGCCACT<br>AATTGAGTTTCTGGCTCCCCTCCTGGGGTTGTAAGTTTTG<br>TTCATTCATGAGGGCCGACTGCATTTCCTGGTTACTCTAT<br>CCCAGTGACCAGCCACAGGAGATGTCCAATAAAGTATGTG<br>ATGAAATGGTCTTAAAAAAAAAAAAAA | |
| KRAS | NM_004985.4 | TCCTAGGCGGCGGCCGCGGCGGCGGAGGCAGCAGCGGCGG<br>CGGCAGTGCCGGCGGCGAAGGTGGCGGCGGCTCGGCCAGT<br>ACTCCCGGCCCCCGCCATTTCGGACTGGGAGCGAGCGCGG<br>CGCAGGCACTGAAGGCGGCGGCGGGGCCAGAGGCTCAGCG<br>GCTCCCAGGTGCGGGAGAGAGGCCTGCTGAAAATGACTGA<br>ATATAAACTTGTGGTAGTTGGAGCTGGTGGCGTAGGCAAG<br>AGTGCCTTGACGATACAGCTAATTCAGAATCATTTTGTGG<br>ACGAATATGATCCAACAATAGAGGATTCCTACAGGAAGCA<br>AGTAGTAATTGATGGAGAAACCTGTCTCTTGGATATTCTC<br>GACACAGCAGGTCAAGAGGAGTACAGTGCAATGAGGGACC<br>AGTACATGAGGACTGGGGAGGGCTTTCTTTGTGTATTTGC<br>CATAAATAATACTAAATCATTTGAAGATATTCACCATTAT<br>AGAGAACAAATTAAAAGAGTTAAGGACTCTGAAGATGTAC<br>CTATGGTCCTAGTAGGAAATAAATGTGATTTGCCTTCTAG<br>AACAGTAGACACAAAACAGGCTCAGGACTTAGCAAGAAGT<br>TATGGAATTCCTTTTATTGAAACATCAGCAAAGACAAGAC<br><u>AGGGTGTTGATGATGCCTTCTATACATTAGTTCGAGAAAT</u><br><u>TCGAAAACATAAAGAAAAGATGAGCAAAGATGGTAAAAAG</u><br>AAGAAAAAGAAGTCAAAGACAAAGTGTGTAATTATGTAAA<br>TACAATTTGTACTTTTTTCTTAAGGCATACTAGTACAAGT<br>GGTAATTTTTGTACATTACACTAAATTATTAGCATTTGTT<br>TTAGCATTACCTAATTTTTTTCCTGCTCCATGCAGACTGT<br>TAGCTTTTACCTTAAATGCTTATTTTAAAATGACAGTGGA<br>AGTTTTTTTTTCCTCTAAGTGCCAGTATTCCCAGAGTTTT<br>GGTTTTTGAACTAGCAATGCCTGTGAAAAAGAAACTGAAT<br>ACCTAAGATTTCTGTCTTGGGGTTTTTGGTGCATGCAGTT<br>GATTACTTCTTATTTTTCTTACCAATTGTGAATGTTGGTG<br>TGAAACAAATTAATGAAGCTTTTGAATCATCCCTATTCTG<br>TGTTTTATCTAGTCACATAAATGGATTAATTACTAATTTC<br>AGTTGAGACCTTCTAATTGGTTTTTACTGAAACATTGAGG<br>GAACACAAATTTATGGGCTTCCTGATGATGATTCTTCTAG<br>GCATCATGTCCTATAGTTTGTCATCCCTGATGAATGTAAA<br>GTTACACTGTTCACAAAGGTTTTGTCTCCTTTCCACTGCT<br>ATTAGTCATGGTCACTCTCCCCAAAATATTATATTTTTC<br>TATAAAAAGAAAAAAATGGAAAAAAATTACAAGGCAATGG<br>AAACTATTATAAGGCCATTTCCTTTTCACATTAGATAAAT<br>TACTATAAAGACTCCTAATAGCTTTTCCTGTTAAGGCAGA<br>CCCAGTATGAAATGGGGATTATTATAGCAACCATTTTGGG<br>GCTATATTTACATGCTACTAAATTTTTATAATAATTGAAA<br>AGATTTTAACAAGTATAAAAAAATTCTCATAGGAATTAAAT | 20 |

TABLE 1-continued

GEP-NEN Biomarker/Houskeeper Sequence Information

| Gene Name | RefSeq Accession | Sequence | SEQ ID NO: |
|---|---|---|---|
| | | GTAGTCTCCCTGTGTCAGACTGCTCTTTCATAGTATAACT<br>TTAAATCTTTTCTTCAACTTGAGTCTTTGAAGATAGTTTT<br>AATTCTGCTTGTGACATTAAAAGATTATTTGGGCCAGTTA<br>TAGCTTATTAGGTGTTGAAGAGACCAAGGTTGCAAGGCCA<br>GGCCCTGTGTGAACCTTTGAGCTTTCATAGAGAGTTTCAC<br>AGCATGGACTGTGTCCCCACGGTCATCCAGTGTTGTCATG<br>CATTGGTTAGTCAAAATGGGGAGGGACTAGGGCAGTTTGG<br>ATAGCTCAACAAGATACAATCTCACTCTGTGGTGGTCCTG<br>CTGACAAATCAAGAGCATTGCTTTTGTTTCTTAAGAAAAC<br>AAACTCTTTTTTAAAAATTACTTTTAAATATTAACTCAAA<br>AGTTGAGATTTTGGGGTGGTGGTGTGCCAAGACATTAATT<br>TTTTTTTTAAACAATGAAGTGAAAAAGTTTTACAATCTCT<br>AGGTTTGGCTAGTTCTCTTAACACTGGTTAAATTAACATT<br>GCATAAACACTTTTCAAGTCTGATCCATATTTAATAATGC<br>TTTAAAATAAAAATAAAAACAATCCTTTTGATAAATTTAA<br>AATGTTACTTATTTTAAAATAAATGAAGTGAGATGGCATG<br>GTGAGGTGAAAGTATCACTGGACTAGGAAGAAGGTGACTT<br>AGGTTCTAGATAGGTGTCTTTTAGGACTCTGATTTTGAGG<br>ACATCACTTACTATCCATTTCTTCATGTTAAAAGAAGTCA<br>TCTCAAACTCTTAGTTTTTTTTTTTACAACTATGTAATT<br>TATATTCCATTTACATAAGGATACACTTATTTGTCAAGCT<br>CAGCACAATCTGTAAATTTTTAACCTATGTTACACCATCT<br>TCAGTGCCAGTCTTGGGCAAAATTGTGCAAGAGGTGAAGT<br>TTATATTTGAATATCCATTCTCGTTTTAGGACTCTTCTTC<br>CATATTAGTGTCATCTTGCCTCCCTACCTTCCACATGCCC<br>CATGACTTGATGCAGTTTTAATACTTGTAATTCCCCTAAC<br>CATAAGATTTACTGCTGCTGTGGATATCTCCATGAAGTTT<br>TCCCACTGAGTCACATCAGAAATGCCCTACATCTTATTTC<br>CTCAGGGCTCAAGAGAATCTGACAGATACCATAAAGGGAT<br>TTGACCTAATCACTAATTTTCAGGTGGTGGCTGATGCTTT<br>GAACATCTCTTTGCTGCCCAATCCATTAGCGACAGTAGGA<br>TTTTTCAAACCTGGTATGAATAGACAGAACCCTATCCAGT<br>GGAAGGAGAATTTAATAAAGATAGTGCTGAAAGAATTCCT<br>TAGGTAATCTATAACTAGGACTACTCCTGGTAACAGTAAT<br>ACATTCCATTGTTTTAGTAACCAGAAATCTTCATGCAATG<br>AAAAATACTTTAATTCATGAAGCTTACTTTTTTTTTTGG<br>TGTCAGAGTCTCGCTCTTGTCACCCAGGCTGGAATGCAGT<br>GGCGCCATCTCAGCTCACTGCAACCTCCATCTCCCAGGTT<br>CAAGCGATTCTCGTGCCTCGGCCTCCTGAGTAGCTGGGAT<br>TACAGGCGTGTGCCACTACACTCAACTAATTTTTGTATTT<br>TTAGGAGAGACGGGGTTTCACCCTGTTGGCCAGGCTGGTC<br>TCGAACTCCTGACCTCAAGTGATTCACCCACCTTGGCCTC<br>ATAAACCTGTTTTGCAGAACTCATTTATTCAGCAAATATT<br>TATTGAGTGCCTACCAGATGCCAGTCACCGCACAAGGCAC<br>TGGGTATATGGTATCCCCAAACAAGAGACATAATCCCGGT<br>CCTTAGGTAGTGCTAGTGTGGTCTGTAATATCTTACTAAG<br>GCCTTTGGTATACGACCCAGAGATAACACGATGCGTATTT<br>TAGTTTTGCAAAGAAGGGGTTTGGTCTCTGTGCCAGCTCT<br>ATAATTGTTTTGCTACGATTCCACTGAAACTCTTCGATCA<br>AGCTACTTTATGTAAATCACTTCATTGTTTTAAAGGAATA<br>AACTTGATTATATTGTTTTTTTATTTGGCATAACTGTGAT<br>TCTTTTAGGACAATTACTGTACACATTAAGGTGTATGTCA<br>GATATTCATATTGACCCAAATGTGTAATATTCCAGTTTTC<br>TCTGCATAAGTAATTAAAATATACTTAAAAATTAATAGTT<br>TTATCTGGGTACAAATAAACAGGTGCCTGAACTAGTTCAC<br>AGACAAGGAAACTTCTATGTAAAAATCACTATGATTTCTG<br>AATTGCTATGTGAAACTACAGATCTTTGGAACACTGTTTA<br>GGTAGGGTGTTAAGACTTACACAGTACCTCGTTTCTACAC<br>AGAGAAAGAAATGGCCATACTTCAGGAACTGCAGTGCTTA<br>TGAGGGGATATTTAGGCCTCTTGAATTTTTGATGTAGATG<br>GGCATTTTTTAAGGTAGTGGTTAATTACCTTTATGTGAA<br>CTTTGAATGGTTTAACAAAAGATTTGTTTTTGTAGAGATT<br>TTAAAGGGGGAGAATTCTAGAAATAAATGTTACCTAATTA<br>TTACAGCCTTAAAGACAAAAATCCTTGTTGAAGTTTTTTT<br>AAAAAAAGCTAAATTACATAGACTTAGGCATTAACATGTT<br>TGTGGAAGAATATAGCAGACGTATATTGTATCATTTGAGT<br>GAATGTTCCCAAGTAGGCATTCTAGGCTCTATTTAACTGA<br>GTCACACTGCATAGGAATTTAGAACCTAACTTTTATAGGT<br>TATCAAAACTGTTGTCACCATTGCACAATTTTGTCCTAAT<br>ATATACATAGAAACTTTGTGGGGCATGTTAAGTTACAGTT<br>TGCACAAGTTCATCTCATTTGTATTCCATTGATTTTTTTT<br>TTCTTCTAAACATTTTTTCTTCAAACAGTATATAACTTTT<br>TTTAGGGGATTTTTTTTAGACAGCAAAAACTATCTGAAG<br>ATTTCCATTTGTCAAAAAGTAATGATTTCTTGATAATTGT<br>GTAGTAATGTTTTTTAGAACCCAGCAGTTACCTTAAAGCT | |

TABLE 1-continued

GEP-NEN Biomarker/Houskeeper Sequence Information

| Gene Name | RefSeq Accession | Sequence | SEQ ID NO: |
|---|---|---|---|
| | | GAATTTATATTTAGTAACTTCTGTGTTAATACTGGATAGC<br>ATGAATTCTGCATTGAGAAACTGAATAGCTGTCATAAAAT<br>GAAACTTTCTTTCTAAAGAAAGATACTCACATGAGTTCTT<br>GAAGAATAGTCATAACTAGATTAAGATCTGTGTTTTAGTT<br>TAATAGTTTGAAGTGCCTGTTTGGGATAATGATAGGTAAT<br>TTAGATGAATTTAGGGGAAAAAAAAGTTATCTGCAGATAT<br>GTTGAGGGCCCATCTCTCCCCCCACACCCCCACAGAGCTA<br>ACTGGGTTACAGTGTTTTATCCGAAAGTTTCCAATTCCAC<br>TGTCTTGTGTTTTCATGTTGAAAATACTTTTGCATTTTTC<br>CTTTGAGTGCCAATTTCTTACTAGTACTATTTCTTAATGT<br>AACATGTTTACCTGGAATGTATTTTAACTATTTTTGTATA<br>GTGTAAACTGAAACATGCACATTTTGTACATTGTGCTTTC<br>TTTTGTGGGACATATGCAGTGTGATCCAGTTGTTTTCCAT<br>CATTTGGTTGCGCTGACCTAGGAATGTTGGTCATATCAAA<br>CATTAAAAATGACCACTCTTTTAATTGAAATTAACTTTTA<br>AATGTTTATAGGAGTATGTGCTGTGAAGTGATCTAAAATT<br>TGTAATATTTTTGTCATGAACTGTACTACTCCTAATTATT<br>GTAATGTAATAAAAATAGTTACAGTGACTATGAGTGTGTA<br>TTTATTCATGAAATTTGAACTGTTTGCCCCGAAATGGATA<br>TGGAATACTTTATAAGCCATAGACACTATAGTATACCAGT<br>GAATCTTTTATGCAGCTTGTTAGAAGTATCCTTTATTTCT<br>AAAAGGTGCTGTGGATATTATGTAAAGGCGTGTTTGCTTA<br>AACTTAAAACCATATTTAGAAGTAGATGCAAAACAAATCT<br>GCCTTTATGACAAAAAAATAGGATAACATTATTTATTTAT<br>TTCCTTTTATCAAAGAAGGTAATTGATACACAACAGGTGA<br>CTTGGTTTTAGGCCCAAAGGTAGCAGCAGCAACATTAATA<br>ATGGAAATAATTGAATAGTTAGTTATGTATGTTAATGCCA<br>GTCACCAGCAGGCTATTTCAAGGTCAGAAGTAATGACTCC<br>ATACATATTATTTATTTCTATAACTACATTTAAATCATTA<br>CCAGG | |
| LEO1 | NM_138792.3 | CGTAAAGAGAGGCCGGGAGCTGCCCCTAACCGAGGCAGCA<br>GCGGACGTGAGCGATAATGGCGGATATGGAGGATCTCTTC<br>GGGAGCGACGCCGACAGCGAAGCTGAGCGTAAAGATTCTG<br>ATTCTGGATCTGACTCAGATTCTGATCAAGAGAATGCTGC<br>CTCTGGCAGTAATGCCTCTGGAAGTGAAAGTGATCAGGAT<br>GAAAGAGGTGATTCAGGACAACCAAGTAATAAGGAACTGT<br>TTGGAGATGACAGTGAGGACGAGGGAGCTTCACATCATAG<br>TGGTAGTGATAATCACTCTGAAAGATCAGACAATAGATCA<br>GAAGCTTCTGAGCGTTCTGACCATGAGGACAATGACCCCT<br>CAGATGTAGATCAGCACAGTGGATCAGAAGCCCCTAATGA<br>TGATGAAGACGAAGGTCATAGATCGGATGGAGGGAGCCAT<br>CATTCAGAAGCAGAAGGTTCTGAAAAAGCACATTCAGATG<br>ATGAAAAATGGGGCAGAGAAGATAAAAGTGACCAGTCAGA<br>TGATGAAAAGATACAAAATTCTGATGATGAGGAGAGGGCA<br>CAAGGATCTGATGAAGATAAGCTGCAGAATTCTGACGATG<br>ATGAGAAAATGCAGAACACAGATGATGAGGAGAGGCCTCA<br>GCTTTCCGATGATGAGAGACAACAGCTATCTGAGGAGGAA<br>AAGGCTAATTCTGATGATGAACGGCCGGTAGCTTCTGATA<br>ATGATGATGAGAAACAGAATTCTGATGATGAAGAACAACC<br>ACAGCTGTCTGATGAAGAGAAAATGCAAAATTCTGATGAT<br>GAAAGGCCACAGGCCTCAGATGAAGAACACAGGCATTCAG<br>ATGATGAAGAGGAACAGGATCATAAATCAGAATCTGCAAG<br>AGGCAGTGATAGTGAAGATGAAGTTTTACGAATGAAACGC<br>AAGAATGCGATTGCATCTGATTCAGAAGCGGATAGTGACA<br>CTGAGGTGCCAAAAGATAATAGTGGAACCATGGATTTATT<br>TGGAGGTGCAGATGATATCTCTTCAGGGAGTGATGGAGAA<br>GACAAACCACCTACTCCAGGACAGCCTGTTGATGAAAATG<br>GATTGCCTCAGGATCAACAGGAAGAGGAGCCAATTCCTGA<br>GACCAGAATAGAAGTAGAAATACCCAAAGTAAACACTGAT<br>TTAGGAAACGACTTATATTTTGTTAAACTGCCCAACTTTC<br>TCAGTGTAGAGCCCAGACCTTTTGATCCTCAGTATTATGA<br>AGATGAATTTGAAGATGAAGAAATGCTGGATGAAGAAGGT<br>AGAACCAGGTTAAAATTAAAGGTAGAAAATACTATAAGAT<br>GGAGGATACGCCGAGATGAAGAAGGAAATGAAATTAAAGA<br>AAGCAATGCTCGGATAGTCAAGTGGTCAGATGGAAGCATG<br>TCCCTGCATTTAGGCAATGAAGTGTTTGATGTGTACAAAG<br>CCCCACTGCAGGGCGACCACAATCATCTTTTTATAAGACA<br>AGGTACTGGTCTACAGGGACAAGCAGTCTTTAAAACGAAA<br>CTCACCTTCAGACCTCACTCTACGGACAGTGCCACACATA<br>GAAAGATGACTCTGTCACTTGCAGATAGGTGTTCAAAGAC<br>ACAGAAGATTAGAATCTTGCCAATGGCTGGTCGTGATCCT<br>GAATGCCAACGCACAGAAATGATTAAGAAAGAAGAAGAAC<br>GTTTGAGGGCTTCCATACGTAGGGAATCTCAGCAGCGCCG<br>AATGAGAGAGAAACAGCACCAGCGGGGGCTGAG<u>CGCCAGT</u> | 21 |

TABLE 1-continued

GEP-NEN Biomarker/Houskeeper Sequence Information

| Gene Name | RefSeq Accession | Sequence | SEQ ID NO: |
|---|---|---|---|
| | | TACCTGGAACCTGATCGATACGATGAGGAGGAGGAAGGCG AGGAGTCCATCAGCTTGGCTGCCATTAAAAACCGATATAA AGGGGGCATTCGAGAGGAACGAGCCAGAATCTATTCATCA GACAGTGATGAGGGATCAGAAGAAGATAAAGCTCAAAGAT TACTCAAAGCAAAGAAACTTACCAGTGATGAGGAAGGTGA ACCTTCCGGAAAGAGAAAAGCAGAAGATGATGATAAAGCA AATAAAAAGCATAAGAAGTATGTGATCAGCGATGAAGAGG AAGAAGATGATGATTGAAGTATGAAATATGAAAACATTTT ATATATTTTATTGTACAGTTATAAATATGTAAACATGAGT TATTTTGATTGAAATGAATCGATTTGCTTTTGTGTAATTT TAATTGTAATAAAACAATTTAAAAGCAAAAAAAAAAAAAA AA | |
| MORF4L2 | NM_001142418.1 | TTGATTATGGAACATTCTAAAACTTAGACAAGACGATTGT GATTGGCTGAAGGGCATACGCCCTCCTCCAGGGTGACGTG TCTGCCTATGGATATCAGTTGCCAGAGAAACCTGGCTTTA CTATGGCGGTTGGAGGAACGGCAGTGATCACACGTCGGCT GCTGGGAAGATCTGGATTCTCGTTTCAGGTCACCATCAGA AAAGCTAAGTTTGCTGTATAGTGAGGATCAGGAGATCTGA TCCTGATTGCAGAACCTTCCCTGATTACAGAATCTTGGGA TTGTTGAGAGGATTACATGTAAAGTACCAGGACAGTGCAT GGCACATATGATTTCACAAAAGTTCATCTTCATTGCAGAT ACCTGCCTTTCTTTCTAGGTTGTATCTCCCACTTCACCCT TCTAGACCATCCCAGAAGATCTATAAGATTTCATCTGGGA AATCACTAGGAGTTCTTGGAAGGGAAAGAAGGAAGATTGT TGGTTGGAATAAAAACAGGGTTGAATGAGTTCCAGAAAGC AGGGTTCTCAACCTCGTGGACAGCAATCTGCAGAAGAAGA GAACTTCAAAAAACCAACTAGAAGCAACATGCAGAGAAGT AAAATGAGAGGGGCCTCCTCAGGAAAGAAGACAGCTGGTC CACAGCAGAAAAATCTTGAACCAGCTCTCCCAGGAAGATG GGGTGGTCGCTCTGCAGAGAACCCCCCTTCAGGATCCGTG AGGAAGACCAGAAAGAACAAGCAGAAGACTCCTGGAAACG GAGATGGTGGCAGTACCAGCGAAGCACCTCAGCCCCCTCG GAAGAAAAGGGCCCGGGCAGACCCCACTGTTGAAAGTGAG GAGGCGTTTAAGAATAGAATGGAGGTTAAAGTGAAGATTC CTGAAGAATTAAAACCATGGCTTGTTGAGGACTGGGACTT AGTTACCAGGCAGAAGCAGCTGTTTCAACTCCCTGCCAAG AAAAATGTAGATGCAATTCTGGAGGAGTATGCAAATTGCA AGAAATCGCAGGGAAATGTTGATAATAAGGAATATGCGGT TAATGAAGTTGTGCAGGAATAAAAGAATATTTCAATGTG ATGTTGGGCACTCAGCTGCTCTACAAATTTGAGAGGCCCC AGTATGCTGAAATCCTCTTGGCTCACCCTGATGCTCCAAT GTCCCAGGTTTATGGAGCACCACACCTACTGAGATTATTT GTAAGAATTGGAGCAATGTTGGCCTATACGCCCCTTGATG AGAAAAGCCTTGCATTATTGTTGGGCTATTTGCATGATTT CCTAAAAATATCTGGCAAAGAATTCTGCATCTCTCTTTACT GCCAGTGATTACAAAGTGGCTTCTGCTGAGTACCACCGCA AAGCCCTGTGAGCGTCTACAGACAGCTCACCATTTTTGTC CTGTATCTGTAAACACTTTTTGTTCTTAGTCTTTTTCTTG TAAAATTGATGTTCTTTAAAATCGTTAATGTATAACAGGG CTTATGTTTCAGTTTGTTTTCCGTTCTGTTTTAAACAGAA AATAAAAGGAGTGTAAGCTCCTTTTCTCATTTCAAAGTTG CTACCAGTGTATGCAGTAATTAGAACAAAGAAGAAACATT CAGTAGAAACATTTTATTGCCTAGTTGACAACATTGCTTGA ATGCTGGTGGTTCCTATCCCTTTGACACTACACAATTTTC TAATATGTGTTAATGCTATGTGACAAAACGCCCTGATTCC TAGTGCCAAAGGTTCAACTTAATGTATATACCTGAAAACC CATGCATTTGTGCTCTTTTTTTTTTTTATGGTGCTTGAA GTAAAACAGCCCATCCTCTGCAAGTCCATCTATGTTGTTC TTAGGCATTCTATCTTTGCTCAAATTGTTGAAGGATGGTG ATTTGTTTCATGGTTTTTGTATTTGAGTCTAATGCACGTT CTAACATGATAGAGGCAATGCATTATTGTGTAGCCACGGT TTTCTGGAAAAGTTGATATTTTAGGAATTGTATTTCAGAT CTTAAATAAAATTTGTTTCTAAATTTCAAAGCAAAAAAAA AAAAAA | 22 |
| NAP1L1 | NM_139207.2 | AAAAGATATGGTGGGTGCTTAACAGAGGAGGTTAGACAC CGGCGGGAACCAGAGGAGCCCAAGCGCGGCGCCTGGGCCT CGGGGCTGCAGGAGTCCTCGGTGGGGTATGGAGGTCGCC GGGGAAGGAGGACGGTTCAGTTGCTAGGCAACCCGGCCTG GACCCGCCTCTCGCTCGCGTTGCTGGGAGACTACAAGGCC GGGAGGAGGGCGGCGAAAGGGCCCTACGTGCTGACGCTAA TTGTATATGAGCGCGAGCGGCGGGCTCTTGGGTCTTTTTT AGCGCCATCTGCTCGCGGCGCCGCCTCCTGCTCCTCCCGC TGCTGCTGCCGCTGCCGCCCTGAGTCACTGCCTGCGCAGC | 23 |

TABLE 1-continued

GEP-NEN Biomarker/Houskeeper Sequence Information

| Gene Name | RefSeq Accession | Sequence | SEQ ID NO: |
|---|---|---|---|
| | | TCCGGCCGCCTGGCTCCCCATACTAGTCGCCGATATTTGG<br>AGTTCTTACAACATGGCAGACATTGACAACAAAGAACAGT<br>CTGAACTTGATCAAGATTTGGATGATGTTGAAGAAGTAGA<br>AGAAGAGGAAACTGGTGAAGAAACAAAACTCAAAGCACGT<br>CAGCTAACTGTTCAGATGATGCAAAATCCTCAGATTCTTG<br>CAGCCCTTCAAGAAAGACTTGATGGTCTGGTAGAAACACC<br>AACAGGATACATTGAAAGCCTGCCTAGGGTAGTTAAAAGA<br>CGAGTGAATGCTCTCAAAAACCTGCAAGTTAAATGTGCAC<br>AGATAGAAGCCAAATTCTATGAGGAAGTTCACGATCTTGA<br>AAGGAAGTATGCTGTTCTCTATCAGCCTCTATTTGATAAG<br>CGATTTGAAATTATTAATGCAATTTATGAACCTACGGAAG<br>AAGAATGTGAATGGAAACCAGATGAAGAAGATGAGATTTC<br>GGAGGAATTGAAAGAAAAGGCCAAGATTGAAGATGAGAAA<br>AAAGATGAAGAAAAGAAGACCCCAAAGGAATTCCTGAAT<br>TTTGGTTAACTGTTTTTAAGAATGTTGACTTGCTCAGTGA<br>TATGGTTCAGGAACACGATGAACCTATTCTGAAGCACTTG<br>AAAGATATTAAAGTGAAGTTCTCAGATGCTGGCCAGCCTA<br>TGAGTTTTGTCTTAGAATTTCACTTTGAACCCAATGAATA<br>TTTTACAAATGAAGTGCTGACAAAGACATACAGGATGAGG<br>TCAGAACCAGATGATTCTGATCCCTTTTCTTTTGATGGAC<br>CAGAAATTATGGGTTGTACAGGGTGCCAGATAGATTGGAA<br>AAAAGGAAAGAATGTCACTTTGAAAACTATTAAGAAGAAG<br>CAGAAACACAAGGGACGTGGGACAGTTCGTACTGTGACTA<br>AAACAGTTTCCAATGACTCTTTCTTTAACTTTTTTGCCCC<br>TCCTGAAGTTCCTGAGAGTGGAGATCTGGATGATGATGCT<br>GAAGCTATCCTTGCTGCAGACTTCGAAATTGGTCACTTTT<br>TACGTGAGCGTATAATCCCAAGATCAGTGTTATATTTTAC<br>TGGAGAAGCTATTGAAGATGATGATGATTATGATGAA<br>GAAGGTGAAGAAGCGGATGAGGAAGGGGAAGAAGAAGGAG<br>ATGAGGAAAATGATCCAGACTATGACCCAAAGAAGGATCA<br>AAACCCAGCAGAGTGCAAGCAGCAGTGAAGCAGGATGTAT<br>GTGGCCTTGAGGATAACCTGCACTGGTCTACCTTCTGCTT<br>CCCTGGAAAGGATGAATTTACATCATTTGACAAGCCTATT<br>TTCAAGTTATTTGTTGTTTGTTTGCTTGTTTTTGTTTTTG<br>CAGCTAAAATAAAAATTTCAAATACAATTTTAGTTCTTAC<br>AAGATAATGTCTTAATTTTGTACCAATTCAGGTAGAAGTA<br>GAGGCCTACCTTGAATTAAGGGTATACTCAGTTTTTAAC<br>ACATTGTTGAAGAAAAGGTACCAGCTTTGGAACGAGATGC<br>TATACTAATAAGCAAGTGTAAAAAAAAAAAAAAAAGAGGA<br>AGAAAATCTTAAGTGATTGATGCTGTTTTCTTTTAAAAAA<br>AAAAAAAAAAATTCATTTTCTTTGGGTTAGAGCTAGAGAG<br>AAGGCCCCAAGCTTCTATGGTTTCTTCTAATTCTTATTGC<br>TTAAAGTATGAGTATGTCACTTACCCGTGCTTCTGTTTAC<br>TGTGTAATTAAAATGGGTAGTACTGTTTACCTAACTACCT<br>CATGGATGTGTTAAGGCATATTGAGTTAAATCTCATATAA<br>TGTTTCTCAATCTTGTTAAAAGCTCAAAATTTTGGGCCTA<br>TTTGTAATGCCAGTGTGACACTAAGCATTTTGTTCACACC<br>ACGCTTTGATAACTAAACTGGAAAACAAAGGTGTTAAGTA<br>CCTCTGTTCTGGATCTGGGCAGTCAGCACTCTTTTTAGAT<br>CTTTGTGTGGCTCCTATTTTTATAGAAGTGGAGGGATGCA<br>CTATTTCACAAGGTCCAAGATTTGTTTTCAGATATTTTTG<br>ATGACTGTATTGTAAATACTACAGGGATAGCACTATAGTA<br>TTGTAGTCATGAGACTTAAAGTGGAAATAAGACTATTTTT<br>GACAAAAGATGCCATTAAATTTCAGACTGTAGAGCCACAT<br>TTACAATACCTCAGGCTAATTACTGTTAATTTTGGGGTTG<br>AACTTTTTTTTGACAGTGAGGGTGGATTATTGGATTGTCA<br>TTAGAGGAAGGTCTAGATTTCCTGCTCTTAATAAAATTAC<br>ATTGAATTGATTTTTAGAGGTAATGAAAACTTCCTTTCTG<br>AGAAGTTAGTGTTAAGGTCTTGGAATGTGAACACATTGTT<br>TGTAGTGCTATCCATTCCTCTCCTGAGATTTAACTTACT<br>ACTGGAAATCCTTAACCAATTATAATAGCTTTTTTTCTTT<br>ATTTTCAAAATGATTTCCTTTGCTTTGATTAGACACTATG<br>TGCTTTTTTTTTTAACCATAGTTCATCGAAATGCAGCTT<br>TTTCTGAACTTCAAAGATAGAATCCCATTTTTAATGAACT<br>GAAGTAGCAAAATCATCTTTTCATTCTTTAGGAAATAGC<br>TATTGCCAAAGTGAAGGTGTAGATAATACCTAGTCTTGTT<br>ACATAAAGGGGATGTGGTTTGCAGAAGAATTTTCTTTATA<br>AAATTGAAGTTTTAAGGGACGTCAGTGTTTATGCCATTTT<br>TCCAGTTCCAAAATGATTCCATTCCATTCTAGAAATTTGA<br>AGTATGTAACCTGAAATCCTTAATAAAATTTGGATTTAAT<br>TTTATAAAATGTACTGGTGATATTTTGGGTGTTTTTTTTT<br>AAATGAATGTATATACTTTTTTTTGAAGAGTGGAGAGTA<br>GTGATGTCTAGAGGGAGCTATTTTGTGCTGAGGCCACTAT<br>GTTCTGTAAATATATAATTTTAAGAGCAACCTCACAATCC<br>CTGCTAAGTGGAGTTTATTATTTGAAGACTAAAATGGAAT | |

TABLE 1-continued

GEP-NEN Biomarker/Houskeeper Sequence Information

| Gene Name | RefSeq Accession | Sequence | SEQ ID NO: |
|---|---|---|---|
| | | TCCATAGTTCCTGATAGGTTATATTCTGGGTTATTATTCT<br>GAGTTATCTACAAACATTTTTGAGATTTGTCTTTACACTC<br>TGATTGTAGTTTCCAGCAGCCCATGCACACTGCCAAGTAA<br>GTCTCATTTTTTCCTGTTAGAAATGGTGAAATATCATATA<br>ATCACTTATAAAGAAAACTGATATGAAAAAATTTTAGAGT<br>TGTTTGCTTTATGGTCACTCAAGTAGGGTAAGTGTTCCAC<br>AAATTCCACAAGTTGATAGTTTAACATGGATGTCTGAAAG<br>CCACATATATAATTTCTTAGGATTCTTAAATTAGTAAATC<br>TAGCTTACTGAAGCAGTATTAGCATCACTATTTTAGATTG<br>CAAAAATACCTTAATTGTGTGGAACTGGCTTGTAGAGTGG<br>TACTTAAGAAAAATGGGATTCTACCTCTATTTCTGTTTTA<br>GCACACTTAATCAGGAAAGGATATATTAACTTTCATAAAA<br>ATATTTTTGTTGTGTGAATAGGTTAATGATATGGTAAGGC<br>CCCTAAAATAACTGAATTAATTGTTTATTGTAATTGTAGG<br>CCATTCCCATTATTAAAAATAAAGACAAAACTTGAAGTAA<br>CTGAAAATCTTATCGTGCTATGTAGAAATATTGAACTAAT<br>ATTCAAATATTTGAATGCTTTGGTTTCAGGGATTGGTTTA<br>AAATTGGAGTCCTTTTTTATGGGTTAGTCTTACAAAAATT<br>TAAGCCTTTATATTTTTGACTTTAAATCAAAACAAATGTT<br>ATTTTAAATGTACAGAATAGATTGGTAGTGCAGAAGAGTG<br>TAAGTTCTTCATAGGAGCTTTAGAAAAGAGAAATATGTGC<br>TAATTCAGTTTTTTTTTAATCTGCACTGTACATATATACT<br>TGGTAATTATGAGCTTGATTTTGTTTTTGGAAATATGTGT<br>TCATAATTTAGGTAATTTGCTACTTAAAGCACTAAGTCTC<br>TGATACCTGAAAAGTACATGTAAATGGTGATGGTGAAATA<br>ATACTGCAGTTAACTTAATAGATGTATACTGGTGATTTTT<br>GTATGCTGGATTAAAACTCCAGATATTAAAATATAACCTG<br>GATAAAAAGCC | |
| NOL3 | NM_001185057.2 | GGCATTCAGAGAGTAGATGCCAGTCCTGGGAAAGGCAGGG<br>GAGGAGAGGAGAGCCACGGCTGACGCTTGGGGACAGAAGG<br>AGGAGCCTGAGGAGGAGACAGGACAGAGCGTCTGGAGAGG<br>CAGGAGGACACCGAGTTCCCCGTGTTGGCCTCCAGGTCCT<br>GTGCTTGCGGAGCCGTCCGGCGGCTGGGATCGAGCCCCGA<br>CAATGGGCAACGCGCAGGAGCGGCCGTCAGAGACTATCGA<br>CCGCGAGCGGAAACGCCTGGTCGAGACGCTGCAGGCGGAC<br>TCGGGACTGCTGTTGGACGCGCTGCTGGCGCGGGGCGTGC<br>TCACCGGGCCAGAGTACGAGGCATTGGATGCACTGCCTGA<br>TGCCGAGCGCAGGGTGCGCCGCCTACTGCTGCTGGTGCAG<br>GGCAAGGGCGAGGCCGCCTGCCAGGAGCTGCTACGCTGTG<br>CCCAGCGTACCGCGGGCGCGCCGGACCCCGCTTGGGACTG<br>GCAGCACGCTACCGGGACCGCAGCTATGACCCTCCATGCC<br>CAGGCCACTGGACGCCGGAGGCACCCGGCTCGGGGACCAC<br>ATGCCCCGGGTTGCCCAGAGCTTCAGACCCTGACGAGGCC<br>GGGGGCCCTGAGGGCTCCGAGGCGGTGCAATCCGGGACCC<br>CGGAGGAGCCAGAGCCAGAGCTGGAAGCTGAGGCCTCTAA<br>AGAGGCTGAACCGGAGCCGGAGCCAGAGCCAGAGCTGGAA<br>CCCGAGGCTGAAGCAGAACCAGAGCCGGAACTGGAGCCAG<br>AACCGGACCCAGAGCCCGAGCCCGACTTCGAGGAAAGGGA<br>CGAGTCCGAAGATTCCTGAAGGCCAGAGCTCTGACAGGCG<br>GTGCCCCGCCCATGCTGGATAGGACCTGGGATGCTGCTGG<br>AGCTGAATCGGATGCCACCAAGGCTCGGTCCAGCCCAGTA<br>CCGCTGGAAGTGAATAAACTCCGGAGGGTCGGACGGGACC<br>TGGGCTCTCTCCACGATTCTGGCTGTTTGCCCAGGAACTT<br>AGGGTGGGTACCTCTGAGTCCCAGGGACCTGGGCAGGCCC<br>AAGCCCACCACGAGCATCATCCAGTCCTCAGCCCTAATCT<br>GCCCTTAGGAGTCCAGGCTGCACCCTGGAGATCCCAAACC<br>TAGCCCCCTAGTGGGACAAGGACCTGACCCTCCTGCCCGC<br>ATACACAACCCATTTCCCCTGGTGAGCCACTTGGCAGCAT<br>ATGTAGGTACCAGCTCAACCCCACGCAAGTTCCTGAGCTG<br>AACATGGAGCAAGGGGAGGGTGACTTCTCTCCACATAGGG<br>AGGGCTTAGAGCTCACAGCCTGGGAAGTGAGACTAGAAG<br>AGGGGAGCAGAAAGGGACCTTGAGTAGACAAAGGCCACAC<br>ACATCATTGTCATTACTGTTTTAATTGTCTGGCTTCTCTC<br>TGGACTGGGAGCTCAGTGAGGATTCTGACCAGTGACTTAC<br>ACAAAAGGCGCTCTATACATATTATAATATATTCGCTTAC<br>TAAATGAATAAGGACTTTCCAAAAAAAAAAAAAAAAAAA<br>AAAAAAAAA | 24 |
| NUDT3 | NM_006703.3 | GGTGCAGCCTTACGCCGCTGACGCATCGCGCCCAAGATGG<br>CGGCGCGGTCGTCGTCGGGGGTGGCGGCGGCAGAGGGGGC<br>GGCGGCCCTGGCGGCAGCGGAGACGGCAGCCGTGACGGTG<br>GCAGCGGCGGCGCGGGACCTGGGCCTGGGGGAATGAGGCG<br>GCCGCGGCGGGCCAGCGGCGGAGCCGTGTAGCGGAGAAGC<br>TCCCCCTCCCTGCTTCCCTTGGCCGAGCCGGGGGCGCGCG | 25 |

TABLE 1-continued

GEP-NEN Biomarker/Houskeeper Sequence Information

| Gene Name | RefSeq Accession | Sequence | SEQ ID NO: |
|---|---|---|---|
| | | CGCACGCGGCCGTCCAGAGCGGGCTCCCCACCCCTCGACT CCTGCGACCCGCACCGCACCCCCACCCGGGCCCGGAGGAT GATGAAGCTCAAGTCGAACCAGACCCGCACCTACGACGGC GACGGCTACAAGAAGCGGGCCGCATGCCTGTGTTTCCGCA GCGAGAGCGAGGAGGAGGTGCTACTCGTGAGCAGTAGTCG CCATCCAGACAGATGGATTGTCCCTGGAGGAGGCATGGAG CCCGAGGAGGAGCCAAGTGTGGCAGCAGTTCGTGAAGTCT GTGAGGAGGCTGGAGTAAAAGGGACATTGGGAAGATTAGT TGGAATTTTTGAGAACCAGGAGAGGAAGCACAGGACGTAT GTCTATGTGCTCATTGTCACTGAAGTGCTGGAAGACTGGG AAGATTCAGTTAACATTGGAAGGAAGAGGGAATGGTTTAA AATAGAAGACGCCATAAAAGTGCTGCAGTATCACAAACCC GTGCAGGCATCATATTTTGAAACATTGAGGCAAGGCTACT CAGCCAACAATGGCACCCCAGTCGTGGCCACCACATACTC GGTTTCTGCTCAGAGCTCGATGTCAGGCATCAGATGACTG AAGACTTCCTGTAAGAGAAATGGAAATTGGAAACTAGACT GAAGTGCAAATCTTCCCTCTCACCCTGGCTCTTTCCACTT CTCACAGGCCTCCTCTTTCAAATAAGGCATGGTGGGCAGC AAAGAAAGGGTGTATTGATAATGTTGCTGTTTGGTGTTAA GTGATGGGGCTTTTTCTTCTGTTTTTATTGAGGGTGGGGG TTGGGTGTGTAATTTGTAAGTACTTTTGTGCATGATCTGT CCCTCCCTCTTCCCACCCCTGCAGTCCTCTGAAGAGAGGC CAACAGCCTTCCCCTGCCTTGGATTCTGAAGTGTTCCTGT TTGTCTTATCCTGGCCCTGGCCAGACGTTTTCTTTGATTT TTAATTTTTTTTTTTATTAAAAGATACCAGTATGAGATG AAAACTTCCAATAATTTGTCCTATAATGTGCTGTACAGTT CAGTAGAGTGGTCACTTTCACTGCAGTATACATTTATCTA CACATTATATATCGGACATATAATATGTAAATAAATGACT TCTAGAAAGAGAAATTTGTTTAATTTTTCAAGGTTTTTTT CTCTTTTAATTTGGGCATTTCTAGAATTGAGAGCCTCACA ATTAACATACCTTTTGTTTTCGATGCTAGTGGCTGGGCA GGTTGCCCTGTCCTTTCTCTATTTCCCAGTCATTGACTGT AGATATGGGAAGAGTTTAGCTACCTTCATAGTGCTCCCAG GACTCATGGCCTTTCCTTCTTTAAGCTGTATTTCCCTGCC CAGAAAGAAACAGGAAGAAACCTTTTTTATTTTTTTATT TTTTTTTAACCAAGCAAGGAGCAAATGGCCTCAGCCCAGA TCTGTAAAAACAATGATAGAAATTGAATTCTGCCCCACAT GTTGACAGTAGAGTTGGAACTGGATTCTTGGGATTACTTA TCTAAAAAACTGGAGCATCAGGTCCATTTCTGTTCTGCTG GTTTGGAATCTTTTCCGTAATGCTATTTATTGCCAACAAT GGCCTCTCTTTGTGTCCATATATGCCTTACACCGTGCTGA CCTGGGTATCATCCATGTGCTCTGAAGCATCCAACTTTAC TTTGCAGGTGCATCAATGTAGTCCTGTCCCTGAACTGAGT AACCGTGTTCCTGAAAAGTACACTAGGGAAATTCACCTGC TTGCTTGTCTTTGTATTGGCATGGCACTTGTGATTGCACC ATGGAGCATGCTCAGAGCTATTAAATTGGTCTCCCATCTC CCACCAGGATATGAAAGGTCCATATGGGAGGCCACGTAAT CACTTATTACAGTGGTTACATAATACACTGGCTCACTGCA GACTCTCTTGTTTTTTGATACAGTTTCGTGCTGGCTTCAT TTGCCAATTGTGTTGTTTAGTTCGGAAGTAAGAGGGTCTT GAGATTGAGGGGTAGGGAGGGCTACACTGACTGATCCGTG GCTTAAGACAGGAGATTATCTCTGTACTCCAGTGGCATCT CCTTAGCCAAGATGTGAAATTAAAATCATAGTTCGCCTCA TTTAAAAATTCTAATAAAGCACTCAAACTTTGAAAAAAAA AAAAAAAAA | |
| OAZ2 | NM_002537.3 | ATGCAGATGAGGCACTCGGGGGCGGGGCGGCGGCGGCGGC GGCGGCGGTGGCGGCCGGGGAGGGTCAGTTGGAGGCAGGC GCTCGCTGAGGCAAAAGGAGGCGCTCGGCCCGCGGCCTGA CAGGGACTTAGCCCGCAGAGATCGACCCCGCGCGCGTGAC CCCACACCCACCCACTCATCCATCTATCCACTCCCTGCGC CGCCTCCTCCCACCCTGAGCAGAGCCGCCGAGGATGATAA ACACCCAGGACAGTAGTATTTTGCCTTTGAGTAACTGTCC CCAGCTCCAGTGCTGCAGGCACATTGTTCCAGGGCCTCTG TGGTGCTCCTGATGCCCTCACCCACTGTCGAAGATCCCC GGTGGGCGAGGGGCGGCAGGGATCCTTCTCTCTCAGCTC TAATATATAAGGACGAGAAGCTCACTGTGACCCAGGACCT CCCTGTGAATGATGGAAAACCTCACATCGTCCACTTCCAG TATGAGGTCACCGAGGTGAAGGTCTCTTCTTGGGATGCAG TCCTGTCCAGCCAGAGCCTGTTTGTAGAAATCCCAGATGG ATTATTAGCTGATGGGAGCAAAGAAGGATTGTTAGCACTG CTAGAGTTTGCTGAAGAGAAGATGAAAGTGAACTATGTCT TCATCTGCTTCAGGAAGGGCCGAGAAGACAGAGCTCCACT CCTGAAGACCTTCAGCTTCTTGGGCTTTGAGATTGTACGT CCAGGCCATCCCTGTGTCCCCTCTCGGCCAGATGTGATGT | 26 |

TABLE 1-continued

GEP-NEN Biomarker/Houskeeper Sequence Information

| Gene Name | RefSeq Accession | Sequence | SEQ ID NO: |
|---|---|---|---|
| | | TCATGGTTTATCCCCTGGACCAGAACTTGTCCGATGAGGA<br>CTAATAGTCATAGAGGATGCTTTACCCAAGAGCCACAGTG<br>GGGGAAGAGGGGAAGTTAGGCAGCCCTGGGACAGACGAGA<br>GGGCTCCTCGCTGTCTAGGGAAGGACACTGAGGGGCTCAG<br>GGTGAGGGTTGCCTATTGTGTTCTCGGAGTTGACTCGTTG<br>AAATTGTTTTCCATAAAGAACAGTATAAACATATTATTCA<br>CATGTAATCACCAATAGTAAATGAAGATGTTTATGAACTG<br>GCATTAGAAGCTTTCTAAACTGCGCTGTGTGATGTGTTCT<br>ATCTAGCCTAGGGGAGGACATTGCCTAGAGGGGAGGGAC<br>TGTCTGGGTTCAGGGGCATGGCCTGGAGGGCTGGTGGGCA<br>GCACTGTCAGGCTCAGGTTTCCCTGCTGTTGGCTTTCTGT<br>TTTGGTTATTAAGACTTGTGTATTTTCTTTCTTTGCTTCC<br>TGTCACCCCAGGGGCTCCTGAGTATAGGCTTTTCAGTCCC<br>TGGGCAGTGTCCTTGAGTTGTTTTTTGACACTCTTACCTG<br>GGCTTCTCTGTGTGCATTTGCGTCTGGCCTGGAGTAAGCA<br>GGTCCGACCCCTCCTTCTTTACAGCTTAGTGTTATTCTGG<br>CATTTGGTTAAGCTGGCTTAATCTGTTTAATGTTATCAGT<br>ACATTTTAAATAGGGGCATTGAAATTTACTCCCACCACCA<br>GGGCTTTTTTGGGGGATGCCTGGGCCTTTAAAACACTAGC<br>CAAACTCTAATTAATTCTCAAATCACTGCCAGGAGTTCTT<br>GCTCCTGGCTGCAGGCCCAGGCCCCAAGGTCTCCTTCTTG<br>GGGTCACAAACAGCAGTAAGGAAGAGGAATATATAGCAAC<br>TCAGGGCCTGGGAATTGTGGGCAATCCGTTCTTAGGGAC<br>TGGATACTTCTGGCTGGCTGAGTATAGTACTAGCTGCCTC<br>CCCACCAGGTTCCGAGTAGTGTCTGAGACTCTGCTCTGCA<br>GGGCCTAGGGTAGCGCTGGGAGTGTAGAAGTGGCCTGCCC<br>TTAACTGTTTTCACTAAACAGCTTTTTCTAAGGGGAGAGC<br>AAGGGGGAGAGATCTAGATTGGGTGAGGGGGACGGGGATG<br>TCAGGGAGGCAAGTGTGTTGTGTTACTGTGTCAATAAACT<br>GATTTAAAGTTGTGAAAAAAAAAAAAA | |
| PANK2 | NM_024960.4 | ATGCTGGGGGAGGGGCTGGCGGCCTCGACGGCAGCTGCGG<br>AACTAGGCCGAGGGACAAAGGCTAAGTTTTTCCATGGTTT<br>GGACTGGATATCGGTGGAACTCTGGTCAAGCTGGTATATT<br>TTGAACCCAAAGACATCACTGCTGAAGAAGAAGAGGAAGA<br>AGTGGAAAGTCTTAAAAGCATTCGGAAGTACCTGACCTCC<br>AATGTGGCTTATGGGTCTACAGGCATTCGGGACGTGCACC<br>TCGAGCTGAAGGACCTGACTCTGTGTGGACGCAAAGGCAA<br>TCTGCACTTTATACGCTTTCCCACTCATGACATGCCTGCT<br>TTTATTCAAATGGGCAGAGATAAAAACTTCTCGAGTCTCC<br>ACACTGTCTTTTGTGCCACTGGAGGTGGAGCGTACAAATT<br>TGAGCAGGATTTTCTCACAATAGGTGATCTTCAGCTTTGC<br>AAACTGGATGAACTAGATTGCTTGATCAAAGGAATTTTAT<br>ACATTGACTCAGTCGGATTCAATGGACGGTCACAGTGCTA<br>TTACTTTGAAAACCCTGCTGATTCTGAAAAGTGTCAGAAG<br>TTACCATTTGATTTGAAAAATCCGTATCCTCTGCTTCTGG<br>TGAACATTGGCTCAGGGGTTAGCATCTTAGCAGTATATTC<br>CAAAGATAATTACAAACGGGTCACAGGTACTAGTCTTGGA<br>GGAGGAACTTTTTTTGGTCTCTGCTGTCTTCTTACTGGCT<br>GTACCACTTTTGAAGAAGCTCTTGAAATGGCATCTCGTGG<br>AGATAGCACCAAAGTGGATAAACTAGTACGAGATATTTAT<br>GGAGGGGACTATGAGAGGTTTGGACTGCCAGGCTGGGCTG<br>TGGCTTCAAGCTTTGGAAACATGATGAGCAAGGAGAAGCG<br>AGAGGCTGTCAGTAAAGAGGACCTGGCCAGAGCGACTTTG<br>ATCACCATCACCAACAACATTGGCTCAATAGCAAGAATGT<br>GTGCCCTTAATGAAAACATTAACCAGGTGGTATTTGTTGG<br>AAATTTCTTGAGAATTAATACGATCGCCATGCGGCTTTTG<br>GCATATGCTTTGGATTATTGGTCCAAGGGGCAGTTGAAAG<br>CACTTTTTTCGGAACACGAGGGTTATTTTGGAGCTGTTGG<br>AGCACTCCTTGAGCTGTTGAAGATCCCGTGATCATTACCT<br>GGGGAGGGGTTCCTGAAACCTTCCACAATGGGATCTGTGG<br>ACTTTCATTTTTTAAGAGACTTACTCAATTTCATGACTG<br>TACTACCTGAAACAAAGTGAGAAAGGACAGGTGTATTTTT<br>CTAAGTCATCAAGATAAATCCTTAAGAATTCAGTCTAAAT<br>TAGCAACCAGGAAGGAAAAATATATTAAAAACAACAAAAA<br>AGTGGCACATGTCCAGGCAGTGTGAGGATTTGCTGTATAT<br>AAGTTGCCTGCTTTGTATTTTTGAAATCTCTGCATCACTC<br>ATTGGAAGTGCTTCTGAAGAGAGCTGCTCTGTGTTCAGTT<br>GACTGGTTTTGTGTCCTGTTTGAACTTGCTGAATGTAAGG<br>CAGGCTACTATGCGTTATAATCTAATCACAATTTGTCAAT<br>ATGGTCTTGGCAATCATCTGTGCATTACTCTGGTTTGCAT<br>TAAGCCTGTGTGTGAACTTACTGTAAAACATGTTTTATTT<br>CAAGGTTCTGCAAAATTAATTGGGCAGGTTAATTGTGTAC<br>CTGAAACTTAACAAGCAGTTTTTGGAAGGGCA | 27 |

TABLE 1-continued

GEP-NEN Biomarker/Houskeeper Sequence Information

| Gene Name | RefSeq Accession | Sequence | SEQ ID NO: |
|---|---|---|---|
| PHF21A | NM_001101802.1 | GGTGAATGGGCTGGTGGTGCTCGCTGCTGCTGCTGAGAGG<br>AGGAGGAGGATGAAGAGTTGGGCTTGTTTGTCTCCTACAG<br>TTTCTCTCCTGCTGCTCTGATTCCCCCCTCCCGATTCCGG<br>CCCGGGGCCTGTGTGTGTCCCTCCTGGAGGAGGAGGAGGA<br>TCCAGTTCCTCCCCCCAACCCCCTCCTCCCCACCCCCCCT<br>TGCCTGGGGAAGAGGAGGAAAGAAACAGCCCAGAGAGAGA<br>GAGAGAGAGAGAGTGAGTGAGAGAGAGAGGAGAGGAGAGG<br>AGGAGGAGGAGGAGGGAGAAGGGAACAACCTACCATCTTA<br>ACACACTAATATCTAAAAAGTGCGAGAGGCCCAGAGCAGC<br>AGCAGAAGCAGCAGCAGCAGCTCCAGCTTCTTCCCTCCCT<br>CCCCATGAAGAAGAGTTCCCTCCTCCTCCTCCTCCTGCTT<br>CTCCTGCTCAGAGTTCCTGCCTCCAGCTGCCAGGGGGGAC<br>AGCCAGCCAGCAGCAGGAGGGGGCTAGAGAGCTGAAGGA<br>GAGCCAGTTTCCCCAAAATTGCTGCAGTGAGAAGAGGAGT<br>TTGTTACTTTAAACAGAGGCTGAAGAAACTATAGAATTAG<br>CAGAGAAAGTGGAGAAGGTAGAGGATGGAGTTGCAGACTC<br>TACAGGAGGCTCTTAAAGTGGAAATTCAGGTTCACCAGAA<br>ACTGGTTGCTCAAATGAAGCAGGATCCACAGAATGCTGAC<br>TTAAAGAAACAGCTTCATGAACTCCAAGCCAAAATCACAG<br>CTTTGAGTGAGAAACAGAAAAGAGTAGTTGAACAGCTACG<br>GAAGAACCTGATAGTAAAGCAAGAACAACCGGACAAGTTC<br>CAAATACAGCCATTGCCACAATCTGAAAACAAACTACAAA<br>CAGCACAGCAGCAACCACTACAGCAACTACAACAACAGCA<br>GCAGTACCACCACCACCACGCCCAGCAGTCAGCTGCAGCC<br>TCTCCCAACCTGACTGCTTCACAGAAGACTGTAACTACAG<br>CTTCTATGATTACCACAAAGACACTACCTCTCGTCTTGAA<br>AGCAGCAACTGCGACCATGCCTGCCTCTGTGGTGGGCCAG<br>AGACCTACCATTGCTATGGTGACCGCCATCAACAGTCAGA<br>AGGCTGTGCTCAGCACTGATGTGCAGAACACACCAGTCAA<br>CCTCCAGACGTCTAGTAAGGTCACTGGGCCTGGGGCAGAG<br>GCTGTCCAAATTGTGGCAAAAAACACAGTCACTCTGGTTC<br>AGGCAACACCTCCTCAGCCCATCAAAGTACCACAGTTTAT<br>CCCCCCTCCTAGACTCACTCCACGTCCAAACTTTCTTCCA<br>CAGGTTCGACCCAAGCCTGTGGCCCAGAATAACATTCCTA<br>TTGCCCCAGCACCACCTCCCATGCTCGCAGCTCCTCAGCT<br>TATCCAGAGGCCCGTCATGCTGACCAAGTTCACCCCCACA<br>ACCCTTCCCACATCCCAGAATTCCATCCACCCCGTCCGTG<br>TCGTCAATGGGCAGACTGCAACCATAGCCAAAACGTTCCC<br>CATGGCCCAGCTCACCAGCATTGTGATAGCTACTCCAGGG<br>ACCAGACTCGCTGGACCTCAAACTGTACAGCTTAGCAAGC<br>CAAGTCTTGAAAAACAGACAGTTAAATCTCACACAGAAAC<br>AGATGAGAAACAAACAGAGAGCCGCACCATCACCCCACCT<br>GCTGCACCCAAACCAAAACGGGAGGAGAACCCTCAGAAAC<br>TTGCCTTCATGGTGTCTCTAGGGTTGGTAACACATGACCA<br>TCTAGAAGAAATCCAAAGCAAGAGGCAAGAGCGAAAAAGA<br>AGAACAACAGCAAATCCGGTCTACAGTGGAGCAGTCTTTG<br>AGCCAGAGCGTAAGAAGAGTGCAGTGACATACCTAAACAG<br>CACAATGCACCCTGGGACCCGGAAGAGAGGTCGTCCTCCA<br>AAATACAATGCAGTGCTGGGGTTTGGAGCCCTTACCCCAA<br>CATCCCCCCAATCCAGTCATCCTGACTCCCCTGAAAATGA<br>AAAGACAGAGACCACATTCACTTTCCCTGCACCTGTTCAG<br>CCTGTGTCCCTGCCCAGCCCCACCTCCACAGACGGTGATA<br>TTCATGAGGATTTTTGCAGCGTTTGCAGAAAAAGTGGCCA<br>GTTACTGATGTGCGACACATGTTCCCGTGTATATCATTTG<br>GACTGCTTAGACCCCCCTCTGAAAACAATTCCCAAGGGCA<br>TGTGGATCTGTCCCAGATGTCAGGACCAGATGCTGAAGAA<br>GGAAGAAGCAATTCCATGGCCTGGAACTTTAGCAATTGTT<br><u>CATTCCTATATTGCCTACAAAGCAGCAAAAGAAGAAGAGA</u><br><u>AACAGAAGTTACTTAAATGGAGTTCAGATTTAAAACAAGA</u><br><u>ACGAGAACAACTAGAGCAAAAGGTGAAACAGCTCAGCAAT</u><br>TCCATAAGTAAATGCATGGAAATGAAGAACACCATCCTGG<br>CCCGGCAGAAGGAGATGCACAGCTCCCTGGGAGAAGGTAAA<br>ACAGCTGATTCGCCTCATCCACGGCATCGACCTCTCCAAA<br>CCTGTAGACTCTGAGGCCACTGTGGGGGCCATCTCCAATG<br>GCCCGGACTGCACCCCCCTGCCAATGCCGCCACCTCCAC<br>GCCGGCCCCTTCCCCCTCCTCCCAGAGCTGCACAGCGAAC<br>TGTAACCAGGGGAAGAGACTAAATAACAGAGCCCCTCTA<br>GGAGAAGCCACGGGATCCCGGCGGCAAGGAGAACAGAACA<br>CTGAAGACTCTAGAAAAGCAAAGCCGGATTTCTGGAAAGT<br>GCAGAATTCTTTTGGTTCTTTGGTTCCAGAGAGAGAGAAG<br>ATGCTTGTGCCAGGTGGCACCAGAGTTTGCCAATTGATCC<br>TTCTTATTCTGTGTGTACATGCAAAGATTGGACCATGTTA<br>CATGAAATAGTGCCAGCTGGAGGTTCTTTGCCAGCACCAT<br>GCCAAGTGAAATAATATATTTACTCTCTCTATTATACACC<br>AGTGTGTGCCTGCAGCAGCCTCCACAGCCACGATGGGTTT | 28 |

TABLE 1-continued

GEP-NEN Biomarker/Houskeeper Sequence Information

| Gene Name | RefSeq Accession | Sequence | SEQ ID NO: |
|---|---|---|---|
| | | GTTTCTGTTTTCTTGGGTGGGGAGCAGGGACGGGCGGAGG | |
| | | GAGGAGAGCAGGTTTCAGATCCTTACTTGCCGAGCCGTTT | |
| | | GTTTAGGTAGAGAAGACAAGTCCAAAGAGTGTGTGGGCTT | |
| | | TCCTGTTTCTAAACTTTCGCTACTATAAAACCAAAAAAAG | |
| | | GAATTGAGATTTCACCAACCCCAGTGCCCAGAAGAGGGAA | |
| | | GGGGAGTGGCTGGAGGGAGCAGGGGGTGGGACAGTGTATC | |
| | | AAATAAGCAGTATTTAATCACCTCTGGCGGGGGCCTCGTG | |
| | | CAAGGGGAGACTGACACCAAGAACAGCCAGTAGGTTCTTC | |
| | | TCCCCTGCACTCTGCTCCCTGCGCGGTAACCCCACCACTC | |
| | | CTGAAGCCTGCCCAGTCTCCTTCCTTCCCTGCTTGGTGAG | |
| | | TCGCGCATCTCCGTGGTTATCCCGCTGTCTCCTCTCCAAG | |
| | | AACAAGCAGAGCCCGGGCCACTGGCCCTTGCCCAAGGCAG | |
| | | GGAAGAAGGATGTGTGTGTCCAGGAAGGAAAAAAAGGTGG | |
| | | ATCAGTGATTTTACTTGAAAACAAGCTCCATCCCTTTTCT | |
| | | ATATTTATAAGAAGAGAAGATCTTGAGTGAAGCAGCACGC | |
| | | GACCCAGGTGTGTGTGAATTGAATGGAGACGTTTCTTTTC | |
| | | TCTTTCTTTAATTTTTGTTTTTGTTCTTTTTTTCTTTAAG | |
| | | GAAAGTTTTATTTTACTGTTCATTTTACTTTCTTGGTAAC | |
| | | AAAAACTAAAATAAGGAATAGAAAAGCTGTTTTTCAGGCT | |
| | | GACAGTCCAATTAAGGGTAGCCAAGACCTTGCATGGTAGA | |
| | | GTAGGAATCATAGTGTCAGTGAGGTCCCGTGAGTCTTTGT | |
| | | GAGTCCTTGTGTCATCGTTCGGGCACTGTTTTTTATGCA | |
| | | AGGGCAAAAATCTTTGTATCTGGGGAAAAAAAACTTTTTT | |
| | | TTAAATTAAAAAGGAAAATAAAAGATATTGAGGTCTTCCT | |
| | | AGTGTTACTTAAATTAAGATCAAGGTAAGAAACATTGTAA | |
| | | AAAAAAATTACAAAAGTGCTATTTGTTTCCTAAAAACAGT | |
| | | GATTTCTATTAAAAAGGTGTCAGAACTGGAGAAAATGCCG | |
| | | TGTAGTTATAATTTTTTAGCACAGACCCTGCTGATCACGA | |
| | | TGACATTTTGCCGTGTGTGTGTCTCTAGACTGGTGGGCCA | |
| | | GTCTCCTTGAAGGACAGAGGCGGAGCTCCCCACCCTTCTC | |
| | | TCTCCTCAGAAAAGACCGTGCTCTCTTCTTGGTGCAGGGA | |
| | | TCTTGTCTCCTGTTGTGAAGCCCAAATGGAAGCGTGGATG | |
| | | GTATCAGGGCCCTACCCGTGGTCTTCTCAGATTCTGCTAG | |
| | | AGCAAAAGGCTGGTGCCTAAATAAGATCCCTTCCTTTGGT | |
| | | GCTGCTTTTGGTCTTTCAGCCACCAGCATTATGAGTGCCT | |
| | | GGGGGACACCTCCGAGGGAACTGGCCAGCGGAGCTCTGTG | |
| | | GTGCGCACGCACCCTGGCCGTGACAGGAGGGTGCGGGAGT | |
| | | ACAGGCTGGCTGCATCAGCCCTTGGTGCTTAGAACAGAGG | |
| | | AGGAGTGACATGTTTTGAGGGTACGTCTCTGAGACAGAGC | |
| | | CCCAGCGTGGCCTTCGCTCTGTCTTGCCTTTGGGGAGAGG | |
| | | TCTGAAGCTCCCACTCCTTTCTCTGCCTGTTGGCTCCAGG | |
| | | CACCAGAAATTTACTCCACTCCACCCACCCACAAGCCTCC | |
| | | TGGGTGACCCTGGGCTAGAATTGCTGCGCTTGCCTCGGCT | |
| | | TGGCCGGTTGTGGCCTCTCCTTGAGAAAACCAGGGTTGTG | |
| | | AAAGACTCAGACCATTCTCTCATCTTGCCTTGTCAGAAGT | |
| | | AAATTGTGTCAGATTTGTGCTCTCGCTGGAGACCTTTGCC | |
| | | CCTTGCGTGCCCCTGGCCGATGGGAGGGCGGTGGAGGCTC | |
| | | TGTACCCTGGCCCTGCTGGAGCATCTCCCCCAAGCCCACT | |
| | | CCAGGCCCTGGGAATGGCCAGAGTCTAGGAGAGGTAGAAA | |
| | | CGATCCTATCAGCTTCTCTCCCACCCAATTAGGCCCAGAG | |
| | | AGACAAAGACAGATCTGAAAGCAAATGCAACAGAGAAGAG | |
| | | ACACTTCTTAGAGTAAAATGTGTCTCATCTCTATCAGCCA | |
| | | TCGCCTTTCATCTTCCCAGGGGCCTCAGAAGAAGGAATTA | |
| | | AGTTAGGCTGAACAGGCCTCAGAGTTAGGCCCTGGCTGCT | |
| | | TGATTGGCTGAGGGGGAAAGAGTTCCCTTTTCTCATTCAG | |
| | | AAACCAAGGTGCTGTGTCTAGTCAGGGAGCCTTGGAGATG | |
| | | CCTGGACTAGTTGGAGGAATCGTTGGCAGAGGATCAGAGA | |
| | | CCAGCAGCAGGCTGTCTGCCCTGTCTAGAGCTCTTCCCCT | |
| | | CAACTTGTCTGGGCCCATCTGGGGGTTGCCACACAACACC | |
| | | TAACTTACCTTTTCCTGAAAGAAGTTGGGAAACCATCATC | |
| | | ACTAGAGGCCTTTGCTCAGAGAGGAGCTGCCTTAGGAGTC | |
| | | TTGGGTCGGAGGACGGGGCTAGGAATTGACCAGGGCTTTG | |
| | | CCTGCCGCCCTCAGCAGTGTCGGGTACATTCTGACCTCGC | |
| | | CTGCAGCTGGGCTGTGGATTCTTCCTGACATTCAGATGTG | |
| | | AGCTGTTTGGGAGTCAGCTAGTATGGAGTACGAGATGCA | |
| | | ACCCAGCCCCCAAACCTACATTCTGCACTCAAATTCCAAA | |
| | | ACACTGCTTTACTGTAAAGAAGAGGCCCCTGGCACCCAAT | |
| | | CTCCCTGTCCTTCACTGTCCCCTCAGACCTGGGCGGGGAG | |
| | | GGGGGGGGGCCTGTGACCACCTGAGACATACGCTCGTGAC | |
| | | ACTGCCCCACCCCAGCCACCTCCACTTGCTTCCTCCTCCT | |
| | | TCCCTCCGCTGCTCTTTCCCCACGGCCCAGAATTTAGCTG | |
| | | CTCTGACAGCCACTTTTGAGACCAGCTGGCTTTGTAGTCA | |
| | | CTTCAGAGAGCTGGAGCGGCTGCCCACTGGGCCCTGACTG | |
| | | GGAGTCCCCTGCCAGCTCCTGATCAGGCGCTGCGCCCTGG | |
| | | TGGCAGTGATGACTGGGAGTCCCCTGCCAGCTCCTGTCCA | |

TABLE 1-continued

GEP-NEN Biomarker/Houskeeper Sequence Information

| Gene Name | RefSeq Accession | Sequence | SEQ ID NO: |
|---|---|---|---|
| | | GGCGCTGCATCCTGGTAACAGTGAGGCCATGTTGCTGTCA<br>TCTCCACCTCTGCATTCTTGCTGCCTGTGGGTCCTTTTTC<br>TTTCATGGAGCCTGCTGGGTCTTGTCTCACCTGTGCTGAG<br>CTCCTCTGGGGTTTTGATTTCTTCCTTCCTTATCAGGCCC<br>TTTGGGGTAAGCCTGCTGGTTGTACCTGACATAGGGAGGC<br>AGTTAGGGGCAGTCCCTGGTGGGGCCGCCCTGGCAGCCTC<br>CAGCTGGCACCATCGTGTGCCTGGTTTCCCTGCAACACCT<br>GCCTCTCTGTCCCTGCTGCTGCTTGGCTCAGGCCCAACAG<br>GCAGCCGTGCATGGAGGTGGTTACACACAGCTGTTTCCGTG<br>AGGGTGACCGTGTCTGCAGCACGCTTCCGTCTCCGCATGC<br>ACGGCTGCCTCTCCAGCCACCTCTGATACTTCTCTCTTGG<br>GGCCATCAGAGCCTCCCTTGGGCTGTCACCTCCCAGCTCA<br>CACACACTCTTCAGTGGTTTCCTCTCTTCATTCTCTTATA<br>GGGCGTGGTCCTTCTTATTTATCTAAAGGGCTGAATTTAG<br>GAGACTTTTTACCCAGGGGCAAAAGGCTCTTAGGGTAATG<br>AGATGGATGGTGGCCAGGTGCATTTTCAGGGCCTGGGT<br>TCTCCAGATCCCGTGGCTTCTGTTGAGTGGAGGCAACTTT<br>GCTCTGTGTGAACCTCGCCCTGTCCCTCTGCCGGGCACC<br>CCTGGCAGGAAGCAGGACTCCCATCCTCACCCTGACTTAG<br>ACTGTCCTCTGAGTCAGCTCCTCTCCAAGACAGGAGTGGG<br>CAGCCCTGGGCAGTCTTCTGGCCCCTTGCTAAAGTGAGGG<br>GCAGGAAGCTGGGGCTGCCCTCCAGAAAGCCGGGGTAGGA<br>ACTCTGAAAAATACCTCCTCTAAACGGAAGCAGGGCTCTC<br>CAGTTCCACTTGGCGCCCCCTCCCACAAGGCCCTTCCTCC<br>CTGAGGACCCCACCCCCCTACCCCTTCCCCAGCAGCCTTT<br>GGACCCTCACCTCTCCGGTGTCCGTGGGTCCTCAGCCC<br>AGGGTGAGCTGCAGTCAGGCGGGATGGGACGGGCAGGCCA<br>GAGGTCAGCCAGCTCCTAGCAGAGAAGAGCCAGCCAGACC<br>CCAACCCTGTCTCTTGTCCATGCCCTTTGTGATTTCAGTC<br>TTGGTAGACTTGTATTTGGAGTTTTGTGCTTCAAAGTTTT<br>TGTTTTTGTTTGTTTGGTTTTTGTTTTGAGGGGGTGGGGG<br>GGGATACAGAGCAGCTGATCAATTTGTATTTATTTATTTT<br>AACATTTTACTAAATAAAGCCAAATAAAGCCTCTCAAAAA<br>AAAAAAAAAAAA | |
| PKD1 | NM_000296.3 | GCACTGCAGCGCCAGCGTCCGAGCGGGCGGCCGAGCTCCC<br>GGAGCGGCCTGGCCCCGAGCCCCGAGCGGGCGTCGCTCAG<br>CAGCAGGTCGCGGCCGCAGCCCCATCCAGCCCCGCGCCCG<br>CCATGCCGTCCGCGGGCCCCGCCTGAGCTGCGGCCTCCGC<br>GCGCGGGCGGGCCTGGGGACGGCGGGGCCATGCGCGCGCT<br>GCCCTAACGATGCCGCCCGCCGCGCCCGCCCGCCTGGCGC<br>TGGCCCTGGGCCTGGGCCTGTGGCTCGGGGCGCTGGCGGG<br>GGGCCCCGGGCGCGGCTGCGGGCCCTGCGAGCCCCCCTGC<br>CTCTGCGGCCCAGCGCCCGGCGCCGCCTGCCGCGTCAACT<br>GCTCGGGCCGCGGGCTGCGGACGCTCGGTCCCGCGCTGCG<br>CATCCCCGCGGACGCCACAGCGCTAGACGTCTCCCACAAC<br>CTGCTCCGGGCGCTGGACGTTGGGCTCCTGGCGAACCTCT<br>CGGCGCTGGCAGAGCTGGATATAAGCAACAACAAGATTTC<br>TACGTTAGAAGAAGGAATATTTGCTAATTTATTTAATTTA<br>AGTGAAATAAACCTGAGTGGGAACCCGTTTGAGTGTGACT<br>GTGGCCTGGCGTGGCTGCCGCGATGGGCGGAGGAGCAGCA<br>GGTGCGGGTGGTGCAGCCCGAGGCAGCCACGTGTGCTGGG<br>CCTGGCTCCCTGGCTGGCCAGCCTCTGCTTGGCATCCCCT<br>TGCTGGACAGTGGCTGTGGTGAGGAGTATGTCGCCTGCCT<br>CCCTGACAACAGCTCAGGCACCGTGGCAGCAGTGTCCTTT<br>TCAGCTGCCCACGAAGGCCTGCTTCAGCCAGAGGCCTGCA<br>GCGCCTTCTGCTTCTCCACCGGCCAGGGCCTCGCAGCCCT<br>CTCGGAGCAGGGCTGGTGCCTGTGTGGGGCGGCCCAGCCC<br>TCCAGTGCCTCCTTTGCCTGCCTGTCCCTCTGCTCCGGCC<br>CCCCGCCACCTCCTGCCCCCACCTGTAGGGGCCCCACCCT<br>CCTCCAGCACGTCTTCCCTGCCTCCCCAGGGGCCACCCTG<br>GTGGGGCCCCACGGACCTCTGGCCTCTGGCCAGCTAGCAG<br>CCTTCCACATCGCTGCCCCGCTCCCTGTCACTGCCACACG<br>CTGGGACTTCGGAGACGGCTCCGCCGAGGTGGATGCCGCT<br>GGGCCGGCTGCCTCGCATCGCTATGTGCTGCCTGGGCGCT<br>ATCACGTGACGGCCGTGCTGGCCCTGGGGGCCGGCTCAGC<br>CCTGCTGGGGACAGACGTGCAGGTGGAAGCGGCACCTGCC<br>GCCCTGGAGCTCGTGTGCCCGTCCTCGGTGCAGAGTGACG<br>AGAGCCTTGACCTCAGCATCCAGAACCGCGGTGGTTCAGG<br>CCTGGAGGCCGCTACAGCATCGTGGCCCTGGGCGGAGGAG<br>CCGGCCCGAGCGGTGCACCCGCTCTGCCCCTCGGACACGG<br>AGATCTTCCCTGGCAACGGGCACTGCTACCGCCTGGTGGT<br>GGAGAAGGCGGCCTGGCTGCAGGCGCAGGAGCAGTGTCAG<br>GCCTGGGCCGGGGCCGCCCTGGCAATGGTGGACAGTCCCG<br>CCGTGCAGCGCTTCCTGGTCTCCCGGGTCACCAGGAGCCT | 29 |

TABLE 1-continued

GEP-NEN Biomarker/Houskeeper Sequence Information

| Gene Name | RefSeq Accession | Sequence | SEQ ID NO: |
|---|---|---|---|
| | | AGACGTGTGGATCGGCTTCTCGACTGTGCAGGGGGTGGAG | |
| | | GTGGGCCCAGCGCCGCAGGGCGAGGCCTTCAGCCTGGAGA | |
| | | GCTGCCAGAACTGGCTGCCCGGGGAGCCACACCCAGCCAC | |
| | | AGCCGAGCACTGCGTCCGGCTCGGGCCCACCGGGTGGTGT | |
| | | AACACCGACCTGTGCTCAGCGCCGCACAGCTACGTCTGCG | |
| | | AGCTGCAGCCCGGAGGCCCAGTGCAGGATGCCGAGAACCT | |
| | | CCTCGTGGGAGCGCCCAGTGGGGACCTGCAGGGACCCCTG | |
| | | ACGCCTCTGGCACAGCAGGACGGCCTCTCAGCCCCGCACG | |
| | | AGCCCGTGGAGGTCATGGTATTCCCGGGCCTGCGTCTGAG | |
| | | CCGTGAAGCCTTCCTCACCACGGCCGAATTTGGGACCCAG | |
| | | GAGCTCCGGCGGCCCGCCCAGCTGCGGCTGCAGGTGTACC | |
| | | GGCTCCTCAGCACAGCAGGGACCCCGGAGAACGGCAGCGA | |
| | | GCCTGAGAGCAGGTCCCCGGACAACAGGACCCAGCTGGCC | |
| | | CCCGCGTGCATGCCAGGGGGACGCTGGTGCCCTGGAGCCA | |
| | | ACATCTGCTTGCCGCTGGACGCCTCCTGCCACCCCCAGGC | |
| | | CTGCGCCAATGGCTGCACGTCAGGGCCAGGGCTACCCGGG | |
| | | GCCCCCTATGCGCTATGGAGAGAGTTCCTCTTCTCCGTTC | |
| | | CCGCGGGGCCCCCCGCGCAGTACTCGGTCACCCTCCACGG | |
| | | CCAGGATGTCCTCATGCTCCCTGGTGACCTCGTTGGCTTG | |
| | | CAGCACGACGCTGGCCCTGGCGCCCTCCTGCACTGCTCGC | |
| | | CGGCTCCCGGCCACCCTGGTCCCCAGGCCCCGTACCTCTC | |
| | | CGCCAACGCCTCGTCATGGCTGCCCCACTTGCCAGCCCAG | |
| | | CTGGAGGGCACTTGGGCCTGCCCTGCCTGTGCCCTGCGGC | |
| | | TGCTTGCAGCCACGGAACAGCTCACCGTGCTGCTGGGCTT | |
| | | GAGGCCCAACCCTGGACTGCGGCTGCCTGGGCGCTATGAG | |
| | | GTCCGGGCAGAGGTGGGCAATGGCGTGTCCAGGCACAACC | |
| | | TCTCCTGCAGCTTTGACGTGGTCTCCCCAGTGGCTGGGCT | |
| | | GCGGGTCATCTACCCTGCCCCCCGCGACGGCCGCCTCTAC | |
| | | GTGCCCACCAACGGCTCAGCCTTGGTGCTCCAGGTGGACT | |
| | | CTGGTGCCAACGCCACGGCCACGGCTCGCTGGCCTGGGGG | |
| | | CAGTGTCAGCGCCCGCTTTGAGAATGTCTGCCCTGCCCTG | |
| | | GTGGCCACCTTCGTGCCCGGCTGCCCCTGGGAGACCAACG | |
| | | ATACCCTGTTCTCAGTGGTAGCACTGCCGTGGCTCAGTGA | |
| | | GGGGGAGCACGTGGTGGACGTGGTGGTGGAAAACAGCGCC | |
| | | AGCCGGGCCAACCTCAGCCTGCGGGTGACGGCGGAGGAGC | |
| | | CCATCTGTGGCCTCCGCGCCACGCCCAGCCCCGAGGCCCG | |
| | | TGTACTGCAGGGAGTCCTAGTGAGGTACAGCCCCGTGGTG | |
| | | GAGGCCGGCTCGGACATGGTCTTCCGGTGGACCATCAACG | |
| | | ACAAGCAGTCCCTGACCTTCCAGAACGTGGTCTTCAATGT | |
| | | CATTTATCAGAGCGCGGCGGTCTTCAAGCTCTCACTGACG | |
| | | GCCTCCAACCACGTGAGCAACGTCACCGTGAACTACAACG | |
| | | TAACCGTGGAGCGGATGAACAGGATGCAGGGTCTGCAGGT | |
| | | CTCCACAGTGCCGGCCGTGCTGTCCCCAATGCCACGCTA | |
| | | GCACTGACGGCGGGCGTGCTGGTGGACTCGGCCGTGGAGG | |
| | | TGGCCTTCCTGTGGACCTTTGGGGATGGGGAGCAGGCCCT | |
| | | CCACCAGTTCCAGCCTCCGTACAACGAGTCCTTCCCGGTT | |
| | | CCAGACCCCTCGGTGGCCCAGGTGCTGGTGGAGCACAATG | |
| | | TCATGCACACCTACGCTGCCCAGGTGAGTACCTCCTGAC | |
| | | CGTGCTGGCATCTAATGCCTTCGAGAACCTGACGCAGCAG | |
| | | GTGCCTGTGAGCGTGCGCGCCTCCCTGCCCTCCGTGGCTG | |
| | | TGGGTGTGAGTGACGGCGTCCTGGTGGCCGGCCGGCCCGT | |
| | | CACCTTCTACCCGCACCCGCTGCCCTCGCCTGGGGGTGTT | |
| | | CTTTACACGTGGGACTTCGGGGACGGCTCCCCTGTCCTGA | |
| | | CCCAGAGCCAGCCGGCTGCCAACCACACCTATGCCTCGAG | |
| | | GGGCACCTACCACGTGCGCCTGGAGGTCAACAACACGGTG | |
| | | AGCGGTGCGGCGGCCCAGGCGGATGTGCGCGTCTTTGAGG | |
| | | AGCTCCGCGGACTCAGCGTGGACATGAGCCTGGCCGTGGA | |
| | | GCAGGGCGCCCCCGTGGTGGTCAGCGCCGCGGTGCAGACG | |
| | | GGCGACAACATCACGTGGACCTTCGACATGGGGGACGGCA | |
| | | CCGTGCTGTCGGGCCCGGAGGCAACAGTGGAGCATGTGTA | |
| | | CCTGCGGGCACAGAACTGCACAGTGACCGTGGGTGCGGCC | |
| | | AGCCCCGCCGGCCACCTGGCCCGGAGCCTGCACGTGCTGG | |
| | | TCTTCGTCCTGGAGGTGCTGCGCGTTGAACCCGCCGCCTG | |
| | | CATCCCACGCAGCCTGACGCGCGGCTCACGGCCTACGTC | |
| | | ACCGGGAACCCGGCCCACTACCTCTTCGACTGGACCTTCG | |
| | | GGGATGGCTCCTCCAACACGACCGTGCGGGGGTGCCCGAC | |
| | | GGTGACACACAACTTCACGCGGAGCGGCACGTTCCCCCTG | |
| | | GCGCTGGTGCTGTCCAGCCGCGTGAACAGGGCGCATTACT | |
| | | TCACCAGCATCTGCGTGGAGCCAGAGGTGGGCAACGTCAC | |
| | | CCTGCAGCCAGAGAGGCAGTTTGTGCAGCTCGGGGACGAG | |
| | | GCCTGGCTGGTGGCATGTGCCTGGCCCCGTTCCCCTACC | |
| | | GCTACACCTGGGACTTTGGCACCGAGGAAGCCGCCCCCAC | |
| | | CCGTGCCAGGGGCCCTGAGGTGACGTTCATCTACCGAGAC | |
| | | CCAGGCTCCTATCTTGTGACAGTCACCGCGTCCAACAACA | |
| | | TCTCTGCTGCCAATGACTCAGCCCTGGTGGAGGTGCAGGA | |

TABLE 1-continued

GEP-NEN Biomarker/Housekeeper Sequence Information

| Gene Name | RefSeq Accession | Sequence | SEQ ID NO: |
|---|---|---|---|
| | | GCCCGTGCTGGTCACCAGCATCAAGGTCAATGGCTCCCTT | |
| | | GGGCTGGAGCTGCAGCAGCCGTACCTGTTCTCTGCTGTGG | |
| | | GCCGTGGGCGCCCCGCCAGCTACCTGTGGGATCTGGGGGA | |
| | | CGGTGGGTGGCTCGAGGGTCCGGAGGTCACCCACGCTTAC | |
| | | AACAGCACAGGTGACTTCACCGTTAGGGTGGCCGGCTGGA | |
| | | ATGAGGTGAGCCGCAGCGAGGCCTGGCTCAATGTGACGGT | |
| | | GAAGCGGCGCGTGCGGGGGCTCGTCGTCAATGCAAGCCGC | |
| | | ACGGTGGTGCCCCTGAATGGGAGCGTGAGCTTCAGCACGT | |
| | | CGCTGGAGGCCGGCAGTGATGTGCGCTATTCCTGGGTGCT | |
| | | CTGTGACCGCTGCACGCCCATCCCTGGGGGTCCTACCATC | |
| | | TCTTACACCTTCCGCTCCGTGGGCACCTTCAATATCATCG | |
| | | TCACGGCTGAGAACGAGGTGGGCTCCGCCCAGGACAGCAT | |
| | | CTTCGTCTATGTCCTGCAGCTCATAGAGGGGCTGCAGGTG | |
| | | GTGGGCGGTGGCCGCTACTTCCCCACCAACCACACGGTAC | |
| | | AGCTGCAGGCCGTGGTTAGGGATGGCACCAACGTCTCCTA | |
| | | CAGCTGGACTGCCTGGAGGGACAGGGGCCCGGCCCTGGCC | |
| | | GGCAGCGGCAAAGGCTTCTCGCTCACCGTGCTCGAGGCCG | |
| | | GCACCTACCATGTGCAGCTGCGGGCCACCAACATGCTGGG | |
| | | CAGCGCCTGGGCCGACTGCACCATGGACTTCGTGGAGCCT | |
| | | GTGGGGTGGCTGATGGTGGCCGCCTCCCCGAACCCAGCTG | |
| | | CCGTCAACACAAGCGTCACCCTCAGTGCCGAGCTGGCTGG | |
| | | TGGCAGTGGTGTCGTATACACTTGGTCCTTGGAGGAGGGG | |
| | | CTGAGCTGGGAGACCTCCGAGCCATTTACCACCCATAGCT | |
| | | TCCCCACACCCGGCCTGCACTTGGTCACCATGACGGCAGG | |
| | | GAACCCGCTGGGCTCAGCCAACGCCACCGTGGAAGTGGAT | |
| | | GTGCAGGTGCCTGTGAGTGGCCTCAGCATCAGGGCCAGCG | |
| | | AGCCCGGAGGCAGCTTCGTGGCGGCCGGGTCCTCTGTGCC | |
| | | CTTTTGGGGGCAGCTGGCCACGGGCACCAATGTGAGCTGG | |
| | | TGCTGGGCTGTGCCCGGCGGCAGCAGCAAGCGTGGCCCTC | |
| | | ATGTCACCATGGTCTTCCCGGATGCTGGCACCTTCTCCAT | |
| | | CCGGCTCAATGCCTCCAACGCAGTCAGCTGGGTCTCAGCC | |
| | | ACGTACAACCTCACGGCGGAGGAGCCCATCGTGGGCCTGG | |
| | | TGCTGTGGGCCAGCAGCAAGGTGGTGGCGCCCGGGCAGCT | |
| | | GGTCCATTTTCAGATCCTGCTGGCTGCCGGCTCAGCTGTC | |
| | | ACCTTCCGCCTGCAGGTCGGCGGGGCCAACCCCGAGGTGC | |
| | | TCCCCGGGCCCCGTTTCTCCCACAGCTTCCCCCGCGTCGG | |
| | | AGACCACGTGGTGAGCGTGCGGGGCAAAAACCACGTGAGC | |
| | | TGGGCCCAGGCGCAGGTGCGCATCGTGGTGCTGGAGGCCG | |
| | | TGAGTGGGCTGCAGGTGCCCAACTGCTGCGAGCCTGGCAT | |
| | | CGCCACGGGCACTGAGAGGAACTTCACAGCCCGCGTGCAG | |
| | | CGCGGCTCTCGGGTCGCCTACGCCTGGTACTTCTCGCTGC | |
| | | AGAAGGTCCAGGGCGACTCGCTGGTCATCCTGTCGGGCCG | |
| | | CGACGTCACCTACACGCCCGTGGCCGCGGGGCTGTTGGAG | |
| | | ATCCAGGTGCGCGCCTTCAACGCCCTGGGCAGTGAGAACC | |
| | | GCACGCTGGTGCTGGAGGTTCAGGACGCCGTCCAGTATGT | |
| | | GGCCCTGCAGAGCGGCCCCTGCTTCACCAACCGCTCGGCG | |
| | | CAGTTTGAGGCCGCCACCAGCCCCAGCCCCCGGCGTGTGG | |
| | | CCTACCACTGGGACTTTGGGGATGGGTCGCCAGGGCAGGA | |
| | | CACAGATGAGCCCAGGGCCGAGCACTCCTACCTGAGGCCT | |
| | | GGGGACTACCGCGTGCAGGTGAACGCCTCCAACCTGGTGA | |
| | | GCTTCTTCGTGGCGCAGGCCACGGTGACCGTCCAGGTGCT | |
| | | GGCCTGCCGGGAGCCGGAGGTGGACGTGGTCCTGCCCCTG | |
| | | CAGGTGCTGATGCGGCGGATCACAGCGCAACTACTTGGAGG | |
| | | CCCACGTTGACCTGCGCGACTGCGTCACCTACCAGACTGA | |
| | | GTACCGCTGGGAGGTGTATCGCACCGCCAGCTGCCAGCGG | |
| | | CCGGGGCGCCCAGCGCGTGTGGCCCTGCCCGGCGTGGACG | |
| | | TGAGCCGGCCTCGGCTGGTGCTGCCGCGGCTGGCGCTGCC | |
| | | TGTGGGGCACTACTGCTTTGTGTTTGTCGTGTCATTTGGG | |
| | | GACACGCCACTGACACAGAGCATCCAGGCCAATGTGACGG | |
| | | TGGCCCCCGAGCGCCTGGTGCCCATCATTGAGGGTGGCTC | |
| | | ATACCGCGTGTGGTCAGACACACGGGACCTGGTGCTGGAT | |
| | | GGGAGCGAGTCCTACGACCCCAACCTGGAGGACGGCGACC | |
| | | AGACGCCGCTCAGTTTCCACTGGGCCTGTGTGGCTTCGAC | |
| | | ACAGAGGGAGGCTGCGGGTGTGCGCTGAACTTTGGGCCC | |
| | | CGCGGGAGCAGCACGGTCACCATTCCACGGGAGCGGCTGG | |
| | | CGGCTGGCGTGGAGTACACCTTCAGCCTGACCGTGTGGAA | |
| | | GGCCGGCCGCAAGGAGGAGGCCACCAACCAGACGGTGCTG | |
| | | ATCCGGAGTGGCCGGGTGCCCATTGTGTCCTTGGAGTGTG | |
| | | TGTCCTGCAAGGCACAGGCCGTGTACGAAGTGAGCCGCAG | |
| | | CTCCTACGTGTACTTGGAGGGCCGCTGCCTCAATTGCAGC | |
| | | AGCGGCTCCAAGCGAGGGCGGTGGGCTGCACGTACGTTCA | |
| | | GCAACAAGACGCTGGTGCTGGATGAGACCACCACATCCAC | |
| | | GGGCAGTGCAGGCATGCGACTGGTGCTGCGGCGGGGCGTG | |
| | | CTGCGGGACGGCGAGGGATACACCTTCACGCTCACGGTGC | |
| | | TGGGCCGCTCTGGCGAGGAGGAGGGCTGCGCCTCCATCCG | |

TABLE 1-continued

GEP-NEN Biomarker/Houskeeper Sequence Information

| Gene Name | RefSeq Accession | Sequence | SEQ ID NO: |
|---|---|---|---|
| | | CCTGTCCCCCAACCGCCCGCCGCTGGGGGGCTCTTGCCGC | |
| | | CTCTTCCCACTGGGCGCTGTGCACGCCCTCACCACCAAGG | |
| | | TGCACTTCGAATGCACGGGCTGGCATGACGCGGAGGATGC | |
| | | TGGCGCCCCGCTGGTGTACGCCCTGCTGCTGCGGCGCTGT | |
| | | CGCCAGGGCCACTGCGAGGAGTTCTGTGTCTACAAGGGCA | |
| | | GCCTCTCCAGCTACGGAGCCGTGCTGCCCCCGGGTTTCAG | |
| | | GCCACACTTCGAGGTGGGCCTGGCCGTGGTGGTGCAGGAC | |
| | | CAGCTGGGAGCCGCTGTGGTCGCCCTCAACAGGTCTTTGG | |
| | | CCATCACCCTCCCAGAGCCCAACGGCAGCGCAACGGGGCT | |
| | | CACAGTCTGGCTGCACGGGCTCACCGCTAGTGTGCTCCCA | |
| | | GGGCTGCTGCGGCAGGCCGATCCCCAGCACGTCATCGAGT | |
| | | ACTCGTTGGCCCTGGTCACCGTGCTGAACGAGTACGAGCG | |
| | | GGCCCTGGACGTGGCGGCAGAGCCCAAGCACGAGCGGCAG | |
| | | CACCGAGCCCAGATACGCAAGAACATCACGGAGACTCTGG | |
| | | TGTCCCTGAGGGTCCACACTGTGGATGACATCCAGCAGAT | |
| | | CGCTGCTGCGCTGGCCCAGTGCATGGGGCCCAGCAGGGAG | |
| | | CTCGTATGCCGCTCGTGCCTGAAGCAGACGCTGCACAAGC | |
| | | TGGAGGCCATGATGCTCATCCTGCAGGCAGAGACCACCGC | |
| | | GGGCACCGTGACGCCCACCGCCATCGGAGACAGCATCCTC | |
| | | AACATCACAGGAGACCTCATCCACCTGGCCAGCTCGGACG | |
| | | TGCGGGCACCACAGCCCTCAGAGCTGGGAGCCGAGTCACC | |
| | | ATCTCGGATGGTGGCGTCCCAGGCCTACAACCTGACCTCT | |
| | | GCCCTCATGCGCATCCTCATGCGCTCCCGCGTGCTCAACG | |
| | | AGGAGCCCCTGACGCTGGCGGGCGAGGAGATCGTGGCCCA | |
| | | GGGCAAGCGCTCGGACCCGCGGAGCCTGCTGTGCTATGGC | |
| | | GGCGCCCCAGGGCCTGGCTGCCACTTCTCCATCCCCGAGG | |
| | | CTTTCAGCGGGGCCCTGGCCAACCTCAGTGACGTGGTGCA | |
| | | GCTCATCTTTCTGGTGGACTCCAATCCCTTTCCCTTTGGC | |
| | | TATATCAGCAACTACACCGTCTCCACCAAGGTGGCCTCGA | |
| | | TGGCATTCCAGACACAGGCCGGCGCCCAGATCCCCATCGA | |
| | | GCGGCTGGCCTCAGAGCGCGCCATCACCGTGAAGGTGCCC | |
| | | AACAACTCGGACTGGGCTGCCCGGGGCCACCGCAGCTCCG | |
| | | CCAACTCCGCCAACTCCGTTGTGGTCCAGCCCCAGGCCTC | |
| | | CGTCGGTGCTGTGGTCACCCTGGACAGCAGCAACCCTGCG | |
| | | GCCGGGCTGCATCTGCAGCTCAACTATACGCTGCTGGACG | |
| | | GCCACTACCTGTCTGAGGAACCTGAGCCCTACCTGGCAGT | |
| | | CTACCTACACTCGGAGCCCCGGCCCAATGAGCACAACTGC | |
| | | TCGGCTAGCAGGAGGATCCGCCCAGAGTCACTCCAGGGTG | |
| | | CTGACCACCGGCCCTACACCTTCTTCATTTCCCGGGGAG | |
| | | CAGAGACCCAGCGGGGAGTTACCATCTGAACCTCTCCAGC | |
| | | CACTTCCGCTGGTCGGCGCTGCAGGTGTCCGTGGGCCTGT | |
| | | ACACGTCCCTGTGCCAGTACTTCAGCGAGGAGGACATGGT | |
| | | GTGGCGGACAGAGGGGCTGCTGCCCCTGGAGGAGACCTCG | |
| | | CCCCGCCAGGCCGTCTGCCTCACCCGCCACCTCACCGCCT | |
| | | TCGGCGCCAGCCTCTTCGTGCCCCCAAGCCATGTCCGCTT | |
| | | TGTGTTTCCTGAGCCGACAGCGGATGTAAACTACATCGTC | |
| | | ATGCTGACATGTGCTGTGTGCCTGGTGACCTACATGGTCA | |
| | | TGGCCGCCATCCTGCACAAGCTGGACCAGTTGGATGCCAG | |
| | | CCGGGGCCGCGCCATCCCTTTCTGTGGGCAGCGGGGCCGC | |
| | | TTCAAGTACGAGATCCTCGTCAAGACAGGCTGGGGCCGGG | |
| | | GCTCAGGTACCACGGCCCACGTGGGCATCATGCTGTATGG | |
| | | GGTGGACAGCCGGAGCGGCCACCGGCACCTGGACGGCGAC | |
| | | AGAGCCTTCCACCGCAACAGCCTGGACATCTTCCGGATCG | |
| | | CCACCCCGCACAGCCTGGGTAGCGTGTGGAAGATCCGAGT | |
| | | GTGGCACGACAACAAAGGGCTCAGCCCTGCCTGGTTCCTG | |
| | | CAGCACGTCATCGTCAGGGACCTGCAGACGGCACGCAGCG | |
| | | CCTTCTTCCTGGTCAATGACTGGCTTTCGGTGGAGACGGA | |
| | | GGCCAACGGGGCCTGGTGGAGAAGGAGGTGCTGGCCGCG | |
| | | AGCGACGCAGCCCTTTTGCGCTTCCGGCGCCTGCTGGTGG | |
| | | CTGAGCTGCAGCGTGGCTTCTTTGACAAGCACATCTGGCT | |
| | | CTCCATATGGGACCGGCCGCCTCGTAGCCGTTTCACTCGC | |
| | | ATCCAGAGGGCCACCTGCTGCGTTCTCCTCATCTGCCTCT | |
| | | TCCTGGGCGCCAACGCCGTGTGGTACGGGGCTGTTGGCGA | |
| | | CTCTGCCTACAGCACGGGGCATGTGTCCAGGCTGAGCCCG | |
| | | CTGAGCGTCGACACAGTCGCTGTTGGCCTGGTGTCCAGCG | |
| | | TGGTTGTCTATCCCGTCTACCTGGCCATCCTTTTCTCTT | |
| | | CCGGATGTCCCGGAGCAAGGTGGCTGGGAGCCCGAGCCCC | |
| | | ACACCTGCCGGGCAGCAGGTGCTGGACATCGACAGCTGCC | |
| | | TGGACTCGTCCGTGCTGGACAGCTCCTTCCTCACGTTCTC | |
| | | AGGCCTCCACGCTGAGGCCTTTGTTGGACAGATGAAGAGT | |
| | | GACTTGTTCTGGATGATTCTAAGAGTCTGGTGTGCTGGC | |
| | | CCTCCGGCGAGGGAACGCTCAGTTGGCCGGACCTGCTCAG | |
| | | TGACCCGTCCATTGTGGGTAGCAATCTGCGGCAGCTGGCA | |
| | | CGGGGCCAGGCGGGCCATGGGCTGGGCCCAGAGGAGGACG | |
| | | GCTTCTCCCTGGCCAGCCCCTACTCGCCTGCCAAATCCTT | |

TABLE 1-continued

GEP-NEN Biomarker/Houskeeper Sequence Information

| Gene Name | RefSeq Accession | Sequence | SEQ ID NO: |
|---|---|---|---|
| | | CTCAGCATCAGATGAAGACCTGATCCAGCAGGTCCTTGCC GAGGGGGTCAGCAGCCCAGCCCCTACCCAAGACACCCACA TGGAAACGGACCTGCTCAGCAGCCTGTCCAGCACTCCTGG GGAGAAGACAGAGACGCTGGCGCTGCAGAGGCTGGGGGAG CTGGGGCCACCCAGCCCAGGCCTGAACTGGGAACAGCCCC AGGCAGCGAGGCTGTCCAGGACAGGACTGGTGGAGGGTCT GCGGAAGCGCCTGCTGCCGGCCTGGTGTGCCTCCCTGGCC CACGGGCTCAGCCTGCTCCTGGTGGCTGTGGCTGTGGCTG TCTCAGGGTGGGTGGGTGCGAGCTTCCCCCCGGGCGTGAG TGTTGCGTGGCTCCTGTCCAGCAGCGCCAGCTTCCTGGCC TCATTCCTCGGCTGGGAGCCACTGAAGGTCTTGCTGGAAG CCCTGTACTTCTCACTGGTGGCCAAGCGGCTGCACCCGGA TGAAGATGACACCCTGGTAGAGAGCCCGGCTGTGACGCCT GTGAGCGCACGTGTGCCCCGCGTACGGCCACCCCACGGCT TTGCACTCTTCCTGGCCAAGGAAGAAGCCCGCAAGGTCAA GAGGCTACATGGCATGCTGCGGAGCCTCCTGGTGTACATG CTTTTTCTGCTGGTGACCCTGCTGGCCAGCTATGGGGATG CCTCATGCCATGGGCACGCCTACCGTCTGCAAAGCGCCAT CAAGCAGGAGCTGCACAGCCGGGCCTTCCTGGCCATCACG CGGTCTGAGGAGCTCTGGCCATGGATGGCCCACGTGCTGC TGCCCTACGTCCACGGGAACCAGTCCAGCCCAGAGCTGGG GCCCCCACGGCTGCGGCAGGTGCGGCTGCAGGAAGCACTC TACCCAGACCCTCCCGGCCCCAGGGTCCACACGTGCTCGG CCGCAGGAGGCTTCAGCACCAGCGATTACGACGTTGGCTG GGAGAGTCCTCACAATGGCTCGGGGACGTGGGCCTATTCA GCGCCGGATCTGCTGGGGGCATGGTCCTGGGGCTCCTGTG CCGTGTATGACAGCGGGGGCTACGTGCAGGAGCTGGGCCT GAGCCTGGAGGAGAGCCGCGACCGGCTGCGCTTCCTGCAG CTGCACAACTGGCTGGACAACAGGAGCCGCGCTGTGTTCC TGGAGCTCACGCGCTACAGCCCGGCCGTGGGGCTGCACGC CGCCGTCACGCTGCGCCTCGAGTTCCCGGCGGCCGGCCGC GCCCTGGCCGGCCCTCAGCGTCCGCCCCTTTGCGCTGCGCC GCCTCAGCGCGGGCCTCTCGCTGCCTCTGCTCACCTCGGT GTGCCTGCTGCTGTTCGCCGTGCACTTCGCCGTGGCCGAG GCCCGTACTTGGCACAGGGAAGGGCGCTGGCGCGTGCTGC GGCTCGGAGCCTGGGCGCGGTGGCTGCTGGTGGCGCTGAC GGCCGGCCACGGCACTGGTACGCCTCGCCCAGCTGGGTGCC GCTGACCGCCAGTGGACCCGTTTCGTGCGCGGCCGCCCGC GCCGCTTCACTAGCTTCGACCAGGTGGCGCAGCTGAGCTC CGCAGCCCGTGGCCTGGCGGCCTCGCTGCTCTTCCTGCTT TTGGTCAAGGCTGCCCAGCAGCTACGCTTCGTGCGCCAGT GGTCCGTCTTTGGCAAGACATTATGCCGAGCTCTGCCAGA GCTCCTGGGGGTCACCTTGGGCCTGGTGGTGCTCGGGGTA GCCTACGCCCAGCTGGCCATCCTGCTCGTGTCTTCCTGTG TGGACTCCCTCTGGAGCGTGGCCCAGGCCCTGTTGGTGCT GTGCCCTGGGACTGGGCTCTCTACCCTGTGTCCTGCCGAG TCCTGGCACCTGTCACCCCTGCTGTGTGTGGGGCTCTGGG CACTGCGGCTGTGGGGCGCCCTACGGCTGGGGGCTGTTAT TCTCCGCTGGCGCTACCACGCCTTGCGTGGAGAGCTGTAC CGGCCGGCCTGGGAGCCCCAGGACTACGAGATGGTGGAGT TGTTCCTGCGCAGGCTGCGCCTCTGGATGGGCCTCAGCAA GGTCAAGGAGTTCCGCCACAAAGTCCGCTTTGAAGGGATG GAGCCGCTGCCCTCTCGCTCCTCCAGGGGGCTCCAAGGTAT CCCCGGATGTGCCCCCACCCAGCGCTGGCTCCGATGCCTC GCACCCCTCCACCTCCTCCAGCCAGCTGGATGGGCTGAGC GTGAGCCTGGGCCGGCTGGGGACAAGGTGTGAGCCTGAGC CCTCCCGCCTCCAAGCCGTGTTCGAGGCCCTGCTCACCCA GTTTGACCGACTCAACCAGGCCACAGAGGACGTCTACCAG CTGGAGCAGCAGCTGCACAGCCTGCAAGGCCGCAGGAGCA GCCGGGCGCCCGCCGGATCTTCCCGTGGCCCATCCCCGGG CCTGCGGCCAGCACTGCCCAGCCGCCTTGCCCGGGCCAGT CGGGGTGTGGACCTGGCCACTGGCCCCAGCAGGACACCCC TTCGGGCCAAGAACAAGGTCCACCCCAGCAGCACTTAGTC CTCCTTCCTGGCGGGGTGGGCCGTGGAGTCGGAGTGGAC ACCGCTCAGTATTACTTTCTGCCGCTGTCAAGGCCGAGGG CCAGGCAGAATGGCTGCACGTAGGTTCCCCAGAGAGCAGG CAGGGGCATCTGTCTGTCTGTGGGCTTCAGCACTTTAAAG AGGCTGTGTGGCCAACCAGGACCCAGGGTCCCCTCCCCAG CTCCCTTGGGAAGGACACAGCAGTATTGGACGGTTTCTAG CCTCTGAGATGCTAATTTATTTCCCCGAGTCCTCAGGTAC AGCGGGCTGTGCCCGGCCCCACCCCCTGGGCAGATGTCCC CCACTGCTAAGGCTGCTGGCTTCAGGGAGGGTTAGCCTGC ACCGCCGCCACCCTGCCCCTAAGTTATTACCTCTCCAGTT CCTACCGTACTCCCTGCACCGTCTCACTGTGTGTCTCGTG TCAGTAATTTATATGGTGTTAAAATGTGTATATTTTTGTA | |

TABLE 1-continued

GEP-NEN Biomarker/Houskeeper Sequence Information

| Gene Name | RefSeq Accession | Sequence | SEQ ID NO: |
|---|---|---|---|
| | | TGTCACTATTTTCACTAGGGCTGAGGGGCCTGCGCCCAGA<br>GCTGGCCTCCCCCAACACCTGCTGCGCTTGGTAGGTGTGG<br>TGGCGTTATGGCAGCCCGGCTGCTGCTTGGATGCGAGCTT<br>GGCCTTGGGCCGGTGCTGGGGGCACAGCTGTCTGCCAGGC<br>ACTCTCATCACCCCAGAGGCCTTGTCATCCTCCCTTGCCC<br>CAGGCCAGGTAGCAAGAGAGCAGCGCCCAGGCCTGCTGGC<br>ATCAGGTCTGGGCAAGTAGCAGGACTAGGCATGTCAGAGG<br>ACCCCAGGGTGGTTAGAGGAAAAGACTCCTCCTGGGGGCT<br>GGCTCCCAGGGTGGAGGAAGGTGACTGTGTGTGTGTGTGT<br>GTGCGCGCGCACGCGCGAGTGTGCTGTATGGCCCAGGC<br>AGCCTCAAGGCCCTCGGAGCTGGCTGTGCCTGCTTCTGTG<br>TACCACTTCTGTGGGCATGGCCGCTTCTAGAGCCTCGACA<br>CCCCCCCAACCCCCGCACCAAGCAGACAAAGTCAATAAAA<br>GAGCTGTCTGACTGC | |
| PLD3 | NM_001031696.3 | GCATCCTCTCACCGCCGGAAGCTGAACTGACTCGTCCGCG<br>GCCGCTCTACCCCAACAGGCCGCCACCAGCGAGAGTGCGG<br>CCATAACCATCACGTGACCGCCCACCGACACCAGCGAGAG<br>TGCAGTCGTAACCGTCACGTGACCGCCCACCGTCGGCCCG<br>GCGCTCCCCTCCGCCCGAAGCTAGCAAGCGGCGCGGCCAA<br>TGAGAAAGGCGCATGCCTGGCCCCCGCCGGCCTGCAGTCT<br>AGCCGTAGTGCGCCTGCGCGCGGCTAGGAGGGGCCGTCAG<br>GCGGGGATACAGCCTGGAAGGTAATGCATGTCCATGGTAC<br>ACAAATTCACAAGTTTGGAGACCCTGACACACCCACCTTC<br>TCACCTGGGCTCTGCGTATCCCCCAGCCTTGAGGGAAGAT<br>GAAGCCTAAACTGATGTACCAGGAGCTGAAGGTGCCTGCA<br>GAGGAGCCCGCCAATGAGCTGCCCATGAATGAGATTGAGG<br>CGTGGAAGGCTGCGGAAAAGAAAGCCCGCTGGGTCCTGCT<br>GGTCCTCATTCTGGCGGTTGTGGGCTTCGGAGCCCTGATG<br>ACTCAGCTGTTTCTATGGGAATACGGCGACTTGCATCTCT<br>TTGGGCCCAACCAGCGCCCAGCCCCCTGCTATGACCCTTG<br>CGAAGCAGTGCTGGTGGAAAGCATTCCTGAGGGCCTGGAC<br>TTCCCCAATGCCTCCACGGGGAACCCTTCCACCAGCCAGG<br>CCTGGCTGGGCCTGCTCGCCGGTGCGCACAGCAGCCTGGA<br>CATCGCCTCCTTCTACTGG<u>ACCCTCACCAACAATGACACC</u><br><u>CACACGCAGGAGCCCTCTGCCCAGCAGGGTGAGGAGGTCC</u><br><u>TCCGGCAGCTGCAGACCCTGGCACCAAAGGGCGTGAACGT</u><br><u>CCGCATCGCTGTGAGCAAGCCCAGCGGGCCCCAGCCACAG</u><br>GCGGACCTGCAGGCTCTGCTGCAGAGCGGTGCCCAGGTCC<br>GCATGGTGGACATGCAGAAGCTGACCCATGGCGTCCTGCA<br>TACCAAGTTCTGGGTGGTGGACCAGACCCACTTCTACCTG<br>GGCAGTGCCAACATGGACTGGCGTTCACTGACCCAGGTCA<br>AGGAGCTGGGCGTGGTCATGTACAACTGCAGCTGCCTGGC<br>TCGAGACCTGACCAAGATCTTTGAGGCCTACTGGTTCCTG<br>GGCCAGGCAGGCAGCTCCATCCCATCAACTTGGCCCCGGT<br>TCTATGACACCCGCTACAACCAAGAGACACCAATGGAGAT<br>CTGCCTCAATGGAACCCCTGCTCTGGCCTACCTGGCGAGT<br>GCGCCCCCACCCCTGTGTCCAAGTGGCCGCACTCCAGACC<br>TGAAGGCTCTACTCAACGTGGTGGACAATGCCCGGAGTTT<br>CATCTACGTCGCTGTCATGAACTACCTGCCCACTCTGGAG<br>TTCTCCCACCCTCACAGGTTCTGGCCTGCCATTGACGATG<br>GGCTGCGGCGGGCCACCTACGAGCGTGGCGTCAAGGTGCG<br>CCTGCTCATCAGCTGCTGGGGACACTCGGAGCCATCCATG<br>CGGGCCTTCCTGCTCTCTCTGGCTGCCCTGCGTGACAACC<br>ATACCCACTCTGACATCCAGGTGAAACTCTTTGTGGTCCC<br>CGCGGATGAGGCCCAGGCTCGAATCCCATATGCCCGTGTC<br>AACCACAACAAGTACATGGTGACTGAACGCGCCACCTACA<br>TCGGAACCTCCAACTGGTCTGGCAACTACTTCACGGAGAC<br>GGCGGGCACCTCGCTGCTGGTGACGCAGAATGGGAGGGGC<br>GGCCTGCGGAGCCAGCTGGAGGCATTTTCCTGAGGGACT<br>GGGACTCCCCTTACAGCCATGACCTTGACACCTCAGCTGA<br>CAGCGTGGGCAACGCCTGCCGCCTGCTCTGAGGCCCGATC<br>CAGTGGGCAGGCCAAGGCCTGCTGGGCCCCCGCGGACCCA<br>GGTGCTCTGGGTCACGGTCCCTGTCCCCGCGCCCCCGCTT<br>CTGTCTGCCCATTGTGGCTCCTCAGGCTCTCTCCCCTGC<br>TCTCCCACCTCTACCTCCACCCCCACCGGCCTGACGCTGT<br>GGCCCCGGGACCCAGCAGAGCTGGGGGAGGGATCAGCCCC<br>CAAAGAAATGGGGGTGCATGCTGGGCCTGGCCCCCTGGCC<br>CACCCCCACTTTCCAGGGCAAAAAGGGCCCAGGGTTATAA<br>TAAGTAAATAACTTGTCTGTACAGCCTGAAAAAAAAAAAA<br>AAAAAAA | 30 |
| PNMA2 | NM_007257.5 | GAGCGGTGCTCAGGGGAGGGCTGGAGGGGAGGGAAGGAGA<br>GAGAGAGGGGAGGGCGGCACCGCCCCTAGCCCCGCGCTCC<br>GGAAGTGAAGCGGCCAGACCACCAGCTAATGGATGCGGAG | 31 |

TABLE 1-continued

GEP-NEN Biomarker/Houskeeper Sequence Information

| Gene Name | RefSeq Accession | Sequence | SEQ ID NO: |
|---|---|---|---|
| | | CGGAGGGCCCGCTGACCGCTCTCCGCGCCTGGAGCAGCTT GGCTTGGCTGGAGCTAAGAGCCAGACACACCACTGTGTGG AGGTGGGTGATGTCTTCCTGTGCTAAAAGGTGAATAAATA AGCTCCTCACCTCTCGCGGAACACTCGGGAACACATCAAC AGGGGTCCAAGCCGCCCTGCTGGGAGGCTTCTCTTCAAGA GTTCTGGGTCCCAGAGTGGAAGGCATTTTCCCATCAACTG GAGAGAGACGAAACATCAGAGACCAGGAGGCTGTGGAGAA AGCAGCTGTCCCAGGTGCCTCAACTATCAGAGAAGGGTCA GCGTCACGTGGCTGCCAGCATCTTTGAGAAAATCACTGGC AATCGGACTTCAGAGCTGCGGGCACAGGTGTGGTTAGAAC TGAGATACGACCTGCCCACCTGGGTCAGGCCTAAAGACAA GAAGTCCTGAGTTCTTGCCACTGAGTAGGCCAGGGTCATT TGTCCAGAAAACTTTGTGACTGTCTTTGAGTGACCTAGTC TGGGACCCATTCATTGGTGGGTTCTAAGGTTAGAAGCTCA TCCAGGATATTTTCAATATTAAGTCAGTGCATAGCTGCAC CACTAACAAATTGGTGCCTGTAGAGTCAGAGTGGGTCAAT TCTTAGGACAATGGCGCTGGCACTGTTAGAGGACTGGTGC AGGATAATGAGTGTGGATGAGCAGAAGTCACTGATGGTTA CGGGGATACCGGCGGACTTTGAGGAGGCTGAGATTCAGGA GGTCCTTCAGGAGACTTTAAAGTCTCTGGGCAGGTATAGA CTGCTTGGCAAGATATTCCGGAAGCAGGAGAATGCCAATG CTGTCTTACTAGAGCTTCTGGAAGATACTGATGTCTCGGC CATTCCCAGTGAGGTCCAGGGAAAGGGGGGTGTCTGGAAG GTGATCTTTAAGACCCCTAATCAGGACACTGAGTTTCTTG AAAGATTGAACCTGTTTCTAGAAAAAGAGGGGCAGACGGT CTCGGGTATGTTTCGAGCCCTGGGGCAGGAGGGCGTGTCT CCAGCCACAGTGCCCTGCATCTCACCAGAATTACTGGCCC ATTTGTTGGGACAGGCAATGGCACATGCGCCTCAGCCCCT GCTACCCATGAGATACCGGAAACTGCGAGTATTCTCAGGG AGTGCTGTCCCAGCCCCAGAGGAAGAGTCCTTTGAGGTCT GGTTGGAACAGGCCACGGAGATAGTCAAAGAGTGGCCAGT AACAGAGGCAGAAAAGAAAAGGTGGCTGGCGGAAAGCCTG CGGGGCCCTGCCCTGGACCTCATGCACATAGTGCAGGCAG ACAACCCGTCCATCAGTGTAGAAGAGTGTTTGGAGGCCTT TAAGCAAGTGTTTGGGAGCCTAGAGAGCCGCAGGACAGCC CAGGTGAGGTATCTGAAGACCTATCAGGAGGAAGGAGAGA AGGTCTCAGCCTATGTGTTACGGCTAGAAACCCTGCTCCG GAGAGCGGTGGAGAAACGCGCCATCCCTCGGCGTATTGCG GACCAGGTCCGCCTGGAGCAGGTCATGGCTGGGGCCACTC TTAACCAGATGCTGTGGTGCCGGCTTAGGGAGCTGAAGGA TCAGGGCCCGCCCCCCAGCTTCCTTGAGCTAATGAAGGTA ATACGGGAAGAAGAGGAGGAAGAGGCCTCCTTTGAGAATG AGAGTATCGAAGAGCCAGAGGAACGAGATGGCTATGGCCG CTGGAATCATGAGGGAGACGACTGAAAACCACCTGGGGGC AGGACCCACAGCCAGTGGGCTAAGACCTTTAAAAAATTTT TTTCTTTAATGTATGGGACTGAAATCAAACCATGAAAGCC AATTATTGACCTTCCTTCCTTCCTTCCTTCCCTCCCTTCC TCCTTCTCTCCTTCTCTCCTCCTCTCTCCTCTCCTCTCCT CTCTTTCCTTCCTTCCTTCCTTTTTCTTTTTCTCTTTCT TCTTTATTTCTTGGGTCTCACTCTCATCACCCAGGCTAGA GTGCAGTGGCACAAAAATCTCGGCTCACTGCAGCCTTGAC TTCCCAGGCTCAGGCTCAGGTGATCCTCACACCTTAGCCT CCCAAGTACCTGGGACTACAGGCACGCACCACCATGCCTA GCTATTCTTTTGTATTTTTGGTAGAGACAGGGTTTTGCTG TGTTGCTCAGGCTGGTCTGGAACCCCTAGGCTCAAATGAT GTGCCCAACTCGGCCTCCCAAAGTGCTGGGATTACAGGCA TGAACCGCCATGCCTGGCCCTTGATTTTTCTTTTTAAGAA AAAAATATCTAGGAGTTTCTTAGACCCCTATGTAGATTATT AATGAACAAAAGATTAAACTCCAAATATTAAATAGTAAGC CTGAAGGAATCTGAAACACTTGTACTTCCAATTTTCTTTA AATAATCCCAAATAGACCAGAATTGGCCCATACCATAGAA GAAAGAATTGGCAGTCAAAAAAAAAATACCTTTTGTAAT GTTTGAAAAATAAAGCTGTTTGACTTGTCAGGTGTTTTCC TTTCTCAAATCAGCAAATTCTCTCTGAGTGCCTGGCTTTG TGAGACACTGTACAAGGAGTTACAAGACTACAGCTATAAC CTGCAGTTGAGCAGTTATAAACCTACAAAATGGGCCCTGC CCTCAGAGAGGTTCCAGTCTAGATGAGGAGCTGATCTAGA CAGGTAAAAGGCTAACTAACCCTTTGTGTAAATAAGTTCA TCACCCCAGTAAAAGTGTCATCACCCAGTGAATAGGACCA CCTCTGCCTGCAGATTTTTGTTGTTGTTGTTGTCATTGTT GTTGTTGTTTAACCTGGGAAGTGTTCTTCCTGCCTTTCT GCTAGGTGTCAGATAGATGGTCCCAGAGCTAGGTGCTGTG TCAGGCCCTGAAGACACAGATGACTCAACCTAAGCTTTAC TTTCCAGAGGTCCACAGCCTGAGAGGTGTCCCCAAAGAAA GGGGGACATGAGGGGACTGCATGCTTGAGAGCAGGGTTGT | |

TABLE 1-continued

GEP-NEN Biomarker/Houskeeper Sequence Information

| Gene Name | RefSeq Accession | Sequence | SEQ ID NO: |
|---|---|---|---|
| | | TTAGGGCAGGTTTGGATTTAGTGAGCAGGCTGGTTTGCTT<br>AGAGAAGGCTTTTAGTGGCAACAAAGGATGAAGAGGAGAG<br>AAAAGGAACTCACATTTATTGAGGGCCTACTGTGTGCAAA<br>GTGTTTCATGTATATCTCATTGAATGTATACAGCCACCCT<br>GTTGTGGTATAATTTTGCTCTTTATAAAGAGAAAGACCGA<br>AGCTCAGATGAGTTAAGTGGTCTCCTCAACACCAAAATGC<br>CAAGAAGTGATGGAGCCTAGACAGAAGCCCAGAACTTTCT<br>GACTCACACTAGTCCATCCTCTACCATCACGATGACTTTC<br>AAATTGTGCTCTGCAGTTCTGCAGATTTTCTAGCAGTGCC<br>ATCTCCAAAATGTGTTTTAAACTCTTTATTTTTTTAATTA<br>TTATTAGTATTATTTTGAGACTGAGTCTTGCTCTATCACC<br>CAGGCTGGAGTGCAGTGGTGCAATCTCAGCTCACTGCAAC<br>CTCCGCCTCCCAGGTTCAAGCGATTTCGTGCCTCAGCCTC<br>CCGAGTAGCTGGGATTACAGGCACCCACCACCACGCCCAG<br>CTAATTTTTGTATTTTTAGTAGAAATGGGGTTTCACCATG<br>TTGGCCAGGCTGGTCTCGAACTCCTGACCTCAAGTGATCC<br>ACTCACCTCGGCCTCCCAAAGTGCTGGGATTACAGGTGTG<br>AGCCACCATGCCTGGGCTAAACTCTTTAAGTCTCTAGTAA<br>ATGCAGCTAGATTCAAATGGGCTGATAACCAAATTTTAAC<br>ACATCAGCATTCACCACCAGGTTTACTTTTATTTTCAGAT<br>TGGCTCATTTTGTGCAGACCTTAGAGCAAAGTTTCCTTTA<br>TGGTATCTGTGTACGTATCCAAACTTCTTTTAATTGTTCA<br>CAGATTTTAAAAGCGGTAGCACCACATGGTTGTGTAGATC<br>AGACCTGTGTATTTAGATCAGACCTGTGTATCACGTAAGT<br>GTGTGAGTGCAGTGCAGATGAGCACCATTTAGTTATATGT<br>GCTAGGCAAATCTCCAACACAGTTGATGTGTAGTCTTGTG<br>GTAGATTTGTGCATACTGTAAGCAAATTGCTTAGCTTCTC<br>TAGACATCAGTTTCCACATCTGAAAAATAAGAAGATGAGA<br>GTACACGGTTGTTATGAACAAATGACTTAATGCTTTTTAA<br>GCACGTTGCATGACATCTGGAACACAGAAAGCCCTCAATA<br>CATTGAAGCTCTTAGGATTTTCACGATGTTCCTGTCTGCT<br>CAATGCATGCTTTCTTTATTGTTCTGACAGTTGTGTGGTA<br>ACAAGCTAATATGCTTCCAGTTGACTTCCAGTCTACCCTG<br>GTGTTAGAAACCGTTTCATCTCTTATTGTAAATTTGAGTG<br>CTTGTTGTTTTTATATTTGTGATGACTCTTCCAGCAGTT<br>GTTGACAATTGTTAGAGGTTTGACTTTTAAATAATTACTT<br>ATTTTTTCTGATTGTGGTTCAGTTTAACTGAAGAATATCC<br>TGAGATTGTAAGAAAAGCATTTTTTAAAAGGTATCACTTG<br>TGATCATTTATCTTTCTAAATTCTATTTTTAATACTGTTC<br>CACCCAAAGTGATGCAGTGGTTACCATGACACCCTAATTTC<br>ATGTGTTTTTGTATTTATGAAAATAGTTTCATTGTCATTT<br>ATTGGCGGTATACAAAGTAAAATGTTATAAATGTGAAGTT<br>ATAAAATAAATATATGCTAATAAAATCCTGAGTTTTTCTG<br>TTTCCT | |
| PQBP1 | NM_001032381.1 | TGCCTCCTGAGCGTAGTCCAGTTACTTTCAGGCTCGGGGA<br>GTGAAGGCCTCGTTGAGAGAAGGTCTCATTCGGTGTTTTG<br>GGAAGAGAGTCGTGTGGGCCCAGGTCTGTCTGCTATCAGC<br>TATGCCGCTGCCCGTTGCGCTGCAGACCCGCTTGGCCAAG<br>AGAGGCATCCTCAAACATCTGGAGCCTGAACCAGAGGAAG<br>AGATCATTGCCGAGGACTATGACGATGATCCTGTGGACTA<br>CGAGGCCACCAGGTTGGAGGGCCTACCACCAAGCTGGTAC<br>AAGGTGTTCGACCCTTCCTGCGGGCTCCCTTACTACTGGA<br>ATGCAGACACAGACCTTGTATCCTGGCTCTCCCCACATGA<br>CCCCAACTCCGTGGTTACCAAATCGGCCAAGAAGCTCAGA<br>AGCAGTAATGCAGATGCTGAAGAAAAGTTGGACCGGAGCC<br>ATGACAAGTCGGACAGGGGCCATGACAAGTCGGACCGCAG<br>CCATGAGAAACTAGACAGGGGCCACGACAAGTCAGACCGG<br>GGCCACGACAAGTCTGACAGGGATCGAGAGCGTGGCTATG<br>ACAAGGTAGACAGAGAGAGAGCGAGACAGGGAACGGGA<br>TCGGGACCGCGGGTATGACAAGGCAGACCGGGAAGAGGGC<br>AAAGAACGGCGCCACCATCGCCGGGAGGAGCTGGCTCCCT<br>ATCCCAAGAGCAAGAAGGCAGTAAGCCGAAAGGATGAAGA<br>GTTAGACCCCATGGACCCTAGCTCATACTCAGACGCCCCC<br>CGGGGCACGTGGTCAACAGGACTCCCCAAGCGGAATGAGG<br>CCAAGACTGGCGCTGACACCACAGCAGCTGGGCCCTCTT<br>CCAGCAGCGGCCGTATCCATCCCAGGGGCTGTGCTCCGG<br>GCCAATGCAGAGGCCTCCCGAACCAAGCAGCAGGATTGAA<br>GCTTCGGCCTCCCTGGCCCTGGGTTAAAATAAAAGCTTTC<br>TGGTGATCCTGCCCACCAAAAAAAAAAAAAAAAAAAAAAA<br>AAAAAAAAAAAAAA | 32 |
| RAF1 | NM_002880.3 | AGAATCGGAGAGCCGGTGGCGTCGCAGGTCGGGAGGACGA<br>GCACCGAGTCGAGGGCTCGCTCGTCTGGGCCGCCCGAGAG<br>TCTTAATCGCGGGCGCTTGGGCCGCCATCTTAGATGGCGG | 33 |

TABLE 1-continued

GEP-NEN Biomarker/Houskeeper Sequence Information

| Gene Name | RefSeq Accession | Sequence | SEQ ID NO: |
|---|---|---|---|
| | | GAGTAAGAGGAAAACGATTGTGAGGCGGGAACGGCTTTCT<br>GCTGCCTTTTTGGGCCCCGAAAAGGGTCAGCTGGCCGGG<br>CTTTGGGGCGCGTGCCCTGAGGCGCGGAGCGCGTTTGCTA<br>CGATGCGGGGCTGCTCGGGGCTCCGTCCCCTGGGCTGGG<br>GACGCGCCGAATGTGACCGCCTCCCGCTCCCTCACCCGCC<br>GCGGGGAGGAGGAGCGGGCGAGAAGCTGCCGCCGAACGAC<br>AGGACGTTGGGGCGGCCTGGCTCCCTCAGGTTTAAGAATT<br>GTTTAAGCTGCATCAATGGAGCACATACAGGGAGCTTGGA<br>AGACGATCAGCAATGGTTTTGGATTCAAAGATGCCGTGTT<br>TGATGGCTCCAGCTGCATCTCCTACAATAGTTCAGCAG<br>TTTGGCTATCAGCGCCGGGCATCAGATGATGGCAAACTCA<br>CAGATCCTTCTAAGACAAGCAACACTATCCGTGTTTTCTT<br>GCCGAACAAGCAAAGAACAGTGGTCAATGTGCGAAATGGA<br>ATGAGCTTGCATGACTGCCTTATGAAAGCACTCAAGGTGA<br>GGGGCCTGCAACCAGAGTGCTGTGCAGTGTTCAGACTTCT<br>CCACGAACACAAAGGTAAAAAAGCACGCTTAGATTGGAAT<br>ACTGATGCTGCGTCTTTGATTGGAGAAGAACTTCAAGTAG<br>ATTTCCTGGATCATGTTCCCCTCACAACACACAACTTTGC<br>TCGGAAGACGTTCCTGAAGCTTGCCTTCTGTGACATCTGT<br>CAGAAATTCCTGCTCAATGGATTTCGATGTCAGACTTGTG<br>GCTACAAATTTCATGAGCACTGTAGCACCAAAGTACCTAC<br>TATGTGTGTGGACTGGAGTAACATCAGACAACTCTTATTG<br>TTTCCAAATTCCACTATTGGTGATAGTGGAGTCCCAGCAC<br>TACCTTCTTTGACTATGCGTCGTATGCGAGAGTCTGTTTC<br>CAGGATGCCTGTTAGTTCTCAGCACAGATATTCTACACCT<br>CACGCCTTCACCTTTAACACCTCCAGTCCCTCATCTGAAG<br>GTTCCCTCTCCCAGAGGCAGAGGTCGACATCCACACCTAA<br>TGTCCACATGGTCAGCACCACCCTGCCTGTGGACAGCAGG<br>ATGATTGAGGATGCAATTCGAAGTCACAGCGAATCAGCCT<br>CACCTTCAGCCCTGTCCAGTAGCCCCAACAATCTGAGCCC<br>AACAGGCTGGTCACAGCCGAAAACCCCCGTGCCAGCACAA<br>AGAGAGCGGGCACCAGTATCTGGGACCCAGGAGAAAAACA<br>AAATTAGGCCTCGTGGACAGAGAGATTCAAGCTATTATTG<br>GGAAATAGAAGCCAGTGAAGTGATGCTGTCCACTCGGATT<br>GGGTCAGGCTCTTTTGGAACTGTTTATAAGGGTAAATGGC<br>ACGGAGATGTTGCAGTAAAGATCCTAAAGGTTGTCGACCC<br>AACCCCAGAGCAATTCCAGGCCTTCAGGAATGAGGTGGCT<br>GTTCTGCGCAAAACACGGCATGTGAACATTCTGCTTTTCA<br>TGGGGTACATGACAAAGGACAACCTGGCAATTGTGACCCA<br>GTGGTGCGAGGGCAGCAGCCTCTACAAACACCTGCATGTC<br>CAGGAGACCAAGTTTCAGATGTTCCAGCTAATTGACATTG<br>CCCGGCAGACGGCTCAGGGAATGGACTATTTGCATGCAAA<br>GAACATCATCCATAGAGACATGAAATCCAACAATATATTT<br>CTCCATGAAGGCTTAACAGTGAAAATTGGAGATTTTGGTT<br>TGGCAACAGTAAAGTCACGCTGGAGTGGTTCTCAGCAGGT<br>TGAACAACCTACTGGCTCTGTCCTCTGGATGGCCCCAGAG<br>GTGATCCGAATGCAGGATAACAACCCATTCAGTTTCCAGT<br>CGGATGTCTACTCCTATGGCATCGTATTGTATGAACTGAT<br>GACGGGGAGCTTCCTTATTCTCACATCAACAACCGAGAT<br>CAGATCATCTTCATGGTGGGCCGAGGATATGCCTCCCCAG<br>ATCTTAGTAAGCTATATAAGAACTGCCCCAAAGCAATGAA<br>GAGGCTGGTAGCTGACTGTGTGAAGAAAGTAAAGGAAGAG<br>AGGCCTCTTTTTCCCCAGATCCTGTCTTCCATTGAGCTGC<br>TCCAACACTCTCTACCGAAGATCAACCGGAGCGCTTCCGA<br>GCCATCCTTGCATCGGGCAGCCCACACTGAGGATATCAAT<br>GCTTGCACGCTGACCACGTCCCCGAGGCTGCCTGTCTTCT<br>AGTTGACTTTGCACCTGTCTTCAGGCTGCCAGGGGAGGAG<br>GAGAAGCCAGCAGGCACCACTTTTCTGCTCCCTTTCTCCA<br>GAGGCAGAACACATGTTTTCAGAGAAGCTGCTGCTAAGGA<br>CCTTCTAGACTGCTCACAGGGCCTTAACTTCATGTTGCCT<br>TCTTTTCTATCCCTTTGGGCCCTGGGAGAAGGAAGCCATT<br>TGCAGTGCTGGTGTGTCCTGCTCCCTCCCCACATTCCCCA<br>TGCTCAAGGCCCAGCCTTCTGTAGATGCGCAAGTGGATGT<br>TGATGGTAGTACAAAAAGCAGGGGCCCAGCCCCAGCTGTT<br>GGCTACATGAGTATTTAGAGGAAGTAAGGTAGCAGGCAGT<br>CCAGCCCTGATGTGGAGACACATGGGATTTTGGAAATCAG<br>CTTCTGGAGGAATGCATGTCACAGGCGGGACTTTCTTCAG<br>AGAGTGGTGCAGCGCCAGACATTTTGCACATAAGGCACCA<br>AACAGCCCAGGACTGCCGAGACTCTGGCCGCCCGAAGGAG<br>CCTGCTTTGGTACTATGGAACTTTTCTTAGGGGACACGTC<br>CTCCTTTCACAGCTTCTAAGGTGTCCAGTGCATTGGGATG<br>GTTTTCCAGGCAAGGCACTCGGCCAATCCGCATCTCAGCC<br>CTCTCAGGGAGCAGTCTTCCATCATGCTGAATTTTGTCTT<br>CCAGGAGCTGCCCCTATGGGGCGGGGCCGCAGGGCCAGCC<br>TTGTTTCTCTAACAAACAAACAAACAGCCTTGTTTC | |

TABLE 1-continued

GEP-NEN Biomarker/Houskeeper Sequence Information

| Gene Name | RefSeq Accession | Sequence | SEQ ID NO: |
|---|---|---|---|
| | | TCTAGTCACATCATGTGTATACAAGGAAGCCAGGAATACA<br>GGTTTTCTTGATGATTTGGGTTTTAATTTTGTTTTTATTG<br>CACCTGACAAAATACAGTTATCTGATGGTCCCTCAATTAT<br>GTTATTTTAATAAAATAAATTAAATTTAGGTGTAAAAAAA<br>AAAAAAAAAA | |
| RNF41 | NM_001242826.1 | GATGTCCCAGGGGTATTGGGCGGGGGGTTGAAATAACTG<br>GGGTTCAGGAGGAGGGATGGTGGTAGAGATAAAAATGTGA<br>GAAGGGAGCAGCACTGGCGAGGAGTCGGGAGAGTACTCCT<br>GATTGTGACATCACATTCATCCCCTGGGCGATGGAGCTTG<br>TCACTGGGAAGGAATACTCAGTCGGAGAATAGCCAACAAG<br>ATGGGTTACTGGGAGAATCTCTTCAGTGGCACTGAGTGGA<br>GGCATCAGGGGGTTGGAGCCTTGTGAACAGGGAACCTGCC<br>CCCCAACACTTGGAAGGACCTGGGTTTCAGTGATGAGACA<br>TGGGGTATGATGTAACCCGTTTCCAGGGGGATGTTGACGA<br>AGATCTTATCTGCCCTATTTGCAGTGGAGTCTTGGAGGAG<br>CCAGTACAGGCACCTCATTGTGAACATGCTTTCTGCAACG<br>CCTGCATCACCCAGTGGTTCTCTCAGCAACAGACATGTCC<br>AGTGGACCGTAGTGTTGTGACGGTCGCCCATCTGCGCCCA<br>GTACCTCGGATCATGCGGAACATGTTGTCAAAGCTGCAGA<br>TTGCCTGTGACAACGCTGTGTTCGGCTGTAGTGCCGTTGT<br>CCGGCTTGACAACCTCATGTCTCACCTCAGCGACTGTGAG<br>CACAACCCGAAGCGGCCTGTGACCTGTGAACAGGGCTGTG<br>GCCTGGAGATGCCCAAAGATGAGCTGCCCAACCATAACTG<br>CATTAAGCACCTGCGCTCAGTGGTACAGCAGCAGCAGACA<br>CGCATCGCAGAGCTGGAGAAGACGTCAGCTGAACACAAAC<br>ACCAGCTGGCGGAGCAGAAGCGAGACATCCAGCTGCTAAA<br>GGCATACATGCGTGCAATCCGCAGTGTCAACCCCAACCTT<br>CAGAACCTGGAGGAGACAATTGAATACAACGAGATCCTAG<br>AGTGGGTGAACTCCCTTCAGCCAGCAAGAGTGACCCGCTG<br>GGGAGGGATGATCTCGACTCCTGATGCTGTGCTCCAGGCT<br>GTAATCAAGCGCTCCCTGGTGGAGAGTGGCTGTCCTGCTT<br>CTATTGTCAACGAGCTGATTGAAAATGCCCACGAGCGTAG<br>CTGGCCCCAGGGTCTGGCCACACTAGAGACTAGACAGATG<br>AACCGACGCTACTATGAGAACTACGTGGCCAAGCGCATCC<br>CTGGCAAGCAGGCTGTTGTCGTGATGGCCTGTGAGAACCA<br>GCACATGGGGGATGACATGGTGCAAGAGCCAGGCCTTGTC<br>ATGATATTTGCGCATGGCGTGGAAGAGATATAAGAGAACT<br>CGACTGGCTATCAGGAAGAGATGGAAATCAGAAAATCCCA<br>TCACTCCAGCAGCTGGGACCTGAGTCCTACCCACCATTCT<br>TAATACTGTGGCTTATACCTGAGCCACACATCTCCCTGCC<br>CTTCTGGCACTGAAGGGCCTTGGGGTAGTTTGCTCAGCCT<br>TTCAGGTGGGAAACCCAGATTTCCTCCCTTTGCCATATTC<br>CCCTAAAATGTCTATAAATTATCAGTCTGGGTGGGAAAGC<br>CCCCACCTCCATCCATTTTCCTGCTTAGGGTCCCTGGTTC<br>CAGTTATTTTCAGAAAGCACAAAGAGATTCAATTTCCCTG<br>GAGGATCAGGACAGAGGAAGGAATCTCTAATCGTCCCTCT<br>CCTCCAAAACCAGGGAATCAGAGCAGTCAGGCCTGTTGAC<br>TCTAAGCAGCAGACATCCTGAAGAAATGGTAAGGGTGGAG<br>CCAAATCTCTAGAAATAAGTAGTGAGGCCGTTAATTGGCC<br>ATCACTGATGGCCCTTAGGGAAAGACTGGACCTCTGTGCC<br>AAGCAGTATCCCTGTTCAGCCCACCTTAAAGGTGTAGGCA<br>CCCACTGGGTCTACCAGTATGCAGGTTGGGATACTGAAAA<br>TTTCCAGATGAGCTCTTCTTTCCTACAAGTTTTCATAATT<br>AGGGAATGCCAGGGTTTAGGGTAGGGGTTAATCTGTTGGG<br>GGTTGATGTGTTTAGCAAGAAGCTACTCCTAGCTTTTGCT<br>AAAATATGGTTGGCACTGCCTCTTGTGGCACAGGCCATAA<br>TTGTTCCATAGACCCCTCTCTAGCCCTGTGACTGTAGTTA<br>GTTACTTTGATAATTTTCTTTGGCCATTGTTTGTTTATAT<br>TTCACAAACTCCACCTACTGCCCCCCCCCCTCTTTTTTTT<br>AAGAATGGCCTGATCATGGCTATCTCAGCCACATTGTTGG<br>CAATTTAATTTATTTACTTCCTTTTTTTTTTTTAAGAAA<br>GGAAAAAGAAAAAAAAATCAAACTTGAAACTTTTCTTTT<br>GATGTTCCTATTGTGGGGGTTCTGGATAGGGTGGGACAGG<br>GATGGGGGTGTGTTTTATATTTTTCCTTTTCAGCACAAC<br>CTTTGGCTTTAATATAGGAAGAGCCAAGGGAGTCCTCGGC<br>TGAACTTACGATATCTGCCCCAAACCTCTGTAACCCCAAC<br>TGAAATGAGGAGCTTCCTCTCTTCCTGTGAAGGATATGAC<br>AGTCCAGCATCGATGCCTGTGCCCTCTGGAAAAATTTCCT<br>CCTAGCCCTTCCAGGGCCTTATCATAAAACTCTGGATTTA<br>GAGTATTCATTTTGAAGGCAACTCCCCCTTCCCCAAGTTT<br>CCTTGGAGCTGTATAGCTGGGTTCTAAGCTTCACCATGCA<br>AATCAGAAATTTTATCTCTAAGTACAGGCTGTGCCGTGTC<br>TCACCCACACCCCCTGGGGACTTCAGTTCCATTTCAGGT<br>TACCTGGGGTATACCTTGATCCCTAGAGTGACTGGCAGAG | 34 |

TABLE 1-continued

GEP-NEN Biomarker/Houskeeper Sequence Information

| Gene Name | RefSeq Accession | Sequence | SEQ ID NO: |
|---|---|---|---|
| | | TAAGAGAAGGGGAGAGATAATAGGTGTGATTATTTTAATA<br>TGGAGGTGGGAGTGTGGTTGGAGATAGAAAGGCTCCTCCC<br>CACCATGTAATGGCTTCCTCTCAGAATTTTATTCCAGGCT<br>AGCTTGCTGCAGGTCTGGGTAGTTGGATCATGGCTCCACT<br>GGGATTGGGGTGGAAAGCTTGAGGGGAGTAGGGTTCCAGC<br>TCTGGGACATTGTGCTCAGGAATTTGAAAACGCTGCTATA<br>CTTACTCTGGTTACTACATTTCTTCCACTCCCCTTTCCCC<br>TACCTGCCTTAACCAAGGCTCATACTGTCCTGTCCTTACC<br>CTCAGATGGAGCCAGGAAGCTCAGTGAAAGGCTTCCCTAC<br>CCTTTGCACTAGTGTCTCTGCAGGTTGCTGGTTGTGTTGT<br>ATGTGCTGTTCCATGGTGTTGACTGCACTAATAATAAACC<br>TTTTACTCAACTCTCTAAATTCTTCAGCATTACTCCCTTT<br>CTTGAGAAGGTTTCCCCTCTGCTTTTGCCTTTCTCTCACC<br>TTAATTCCCTTTCTTCCTTACTTTGTTACCTACCCTTATC<br>TTAGTGCTAACTTCTCTTTCAGGAGGATGTCTGGGAGTAG<br>TGTGCACTTCACAGCTGCTTTCCCATGTACCCTCCTGCAT<br>TCTTCCCTCCTATCTCCTGTTCTGTAGCAGCCAAAGCTCT<br>CTAGTGATCTGAACTGTGTGCTTCCCAGGGTCTGCCTTTA<br>TCCTAAATTCCATGTCTTCCCTGAGTGGTCCTGAGTTTTT<br>GGGATAATTTCTACAGAAGATATGTATATATCTTTTTCCT<br>TTGTCCCACAAGCAACTTTGCTTTAGAATCTAGAATTCCT<br>TTGCAGGCAGAGAAGTCTCTACCTCCCAGTGTTTCCTAGC<br>TAAGAACGTAAATGTGAGGAGGGAAATGTACTTGCAGAGG<br>TTTCATAATTATTTACTTATAAAAATAGTCTTCATAGCCG<br>GGCGCGGTGGCTCACGCCTGTAATCCCAGCACTTTGGGAG<br>GCCGAGGTGGGTGGATCACAAGGTCAGGAGTTCGAGACCA<br>TCCTGGCTAACACAGTGAAACCCCGTCTCTACTAAAAATA<br>CAAAAAATTAGCCGGGCGTGGTGGCAGGCACCTGTAGTCC<br>CAGCTACTTAGGAGGCTGAGGCAGGAGAATGGCGTGAACC<br>CGGGAGGCAGAGCTTGCAGTGAGCAGAGATTGGGCCACTG<br>CATTCCAGCCTGGGCGACAGAGCAAGGCTCCGTCTAAAAA<br>AAAAAAAAAAAAAAAAAAGTCTTCATAGGCCGGGCACGGTG<br>GCTCACGTCTGTAATCCCAGCACTTTGGGAGGCCAAGGTG<br>GGTGGATCACAACGTCAGGAGATCGAGACCATCCTGGCTA<br>ACATGGTGAAACCCTGTCTCTACTAAAAATATAAATAAAT<br>TAGCCGGACAGGCGCCTGTCCTCCCAGCTACTCAGGAGGC<br>TGAGGCAGGAGAATGGTGTGAACCTGGGAGGCGGAGCTTG<br>CAGTGAGCTGAGATCACGCCACTGCACTCCAGCCTGGGCA<br>ACAGAGCAAGACTCCGTCTCAAAAAAAAAAAAAAAAAAAC<br>CAGTCTTCATAAGTATTTGCTGCTACCTTTCCCTGTCATA<br>AGAAAAAGGATAGCCAGACATGGTGGGACGCCACTATGAT<br>CCCAGCTCCTTGGAAGGCTAAGGCACAAGAATCGCTTGAA<br>CCTGGGAGGTGGAGGTTGCAGTGAGCTGAGATCATGCCAC<br>TGCACTCCAGCCTGGTGACAGAGCAAGAGCCTGTCTCAAA<br>AAAAAAAAAGAAAAGAAAAAGGGATATCTTTTCCT<br>CCTCCCAGAAGTTTGTTTTAAATTTGAGCATTTATCATGC<br>ACCTGATGTAAACCTAATAGTACTCTTGATACTCTAGTGG<br>CTTGAAAAAAAAAAAAAGGCATTTCTGTGCTGAGTCTGC<br>GCTTCTATGCACACAAGGTATGTTTATAAAATACTGATAA<br>GCATGTCACAGTATAGAGCATAAGAGGCAATGTATGTATC<br>CTAGTGACATTAGCAGTGCTTTTCCCCCCTTAAACTCCTT<br>TAAAATTACTTTTAGAACTTGCTGCTCATTCTTGTGAATG<br>TTATGAATGGTGTCATATTGTCCTTTTACAGAAGATACGA<br>TTTTTAGAAACAAATATTCATTGAATGTCTGCCCTGTGAG<br>ATACTCACTAGAGTGAACATGAGGAGGCTTATGTAGCAAA<br>ATGGCACCTACCTGCAAAGAACTTAGTCCCTAATGGAGAT<br>GAATATATAATAAGGGATCATAAATGTGCTAAGTGGATTT<br>ACTAGTAATATGTGAGCCAAGGACGATAAAGCTCCTGATT<br>CTGATGGGTATCAGGAAAGGCTTTTCAGGAAGTGTTACTT<br>GTTATAGGTCAGAGGTCAGCAAACTACAGGTTACAACCCC<br>ACTGCCTGCTTTTGTAAAAAACTTTATTGGAATACAGTTA<br>TGCCCACTTGTTTATA | |
| RSF1 | NM_016578.3 | GATCCGCAGAGGAGCCCACTTGAGAGCGCCTCCTGTCGTC<br>TGTAAGGTTGCCTTGCCATCCCTCGGCACCCCAACTTCCC<br>CCGCCCCCCCATCGCCTCCTCCTCCATCCTTCCAGTTCAAA<br>ATGGCGACGGCGGCGGCAGCGGCGGCGGTGATGGCTCCTC<br>CGGGCTGCCCGGGTTCGTGCCCCAACTTCGCCGTAGTCTG<br>CTCCTTCTTGGAGCGCTACGGGCCGCTGCTAGACCTGCCT<br>GAGTTGCCGTTCCCTGAGCTGGAGCGGGTGCTGCAGGCGC<br>CGCCGCCGGACGTCGGCAACGGAGAAGTACCAAAAGAATT<br>GGTGGAGCTCCATTTGAAGCTGATGAGGAAAATTGGCAAA<br>TCTGTTACTGCAGACAGATGGGAAAAATATTTGATCAAGA<br>TATGCCAAGAGTTTAACAGTACCTGGGCATGGGAGATGGA<br>GAAGAAGGGCTATCTTGAAATGAGTGTTGAATGCAAACTA | 35 |

TABLE 1-continued

GEP-NEN Biomarker/Houskeeper Sequence Information

| Gene Name | RefSeq Accession | Sequence | SEQ ID NO: |
|---|---|---|---|
| | | GCACTCTTAAAGTACCTCTGTGAGTGTCAGTTTGATGACA ATCTCAAATTCAAGAATATTATTAATGAGGAGGATGCCGA TACTATGCGTCTCCAGCCAATTGGTCGAGACAAAGATGGC CTCATGTACTGGTACCAATTGGATCAAGATCACAATGTCA GAATGTACATAGAAGAACAAGATGATCAAGATGGCTCTTC ATGGAAATGCATTGTCAGAAATCGAAACGAGTTGGCTGAG ACTCTTGCACTCCTGAAAGCACAAATTGATCCTGTACTAT TGAAAAACTCTAGCCAACAAGACAACTCTTCTCGGGAAAG TCCCAGCTTAGAGGATGAGGAGACTAAAAAAGAGGAAGAA ACACCTAAACAAGAGGAACAGAAAGAAAGTGAAAAGATGA AAAGTGAGGAGCAGCCTATGGATTTAGAAAACCGTTCTAC AGCCAATGTTCTAGAAGAGACTACTGTGAAAAAAGAAAAA GAAGATGAAAAGGAACTTGTGAAACTGCCAGTCATAGTGA AGCTAGAAAAACCTTTGCCAGAAAATGAAGAAAAAAAGAT TATCAAAGAAGAAAGTGATTCCTTCAAGGAAAATGTCAAA CCCATTAAAGTTGAGGTGAAGGAATGTAGAGCAGATCCTA AAGATACCAAAAGTAGCATGGAGAAGCCAGTGGCACAGGA GCCTGAAAGGATCGAATTTGGTGGCAATATTAAATCTTCT CACGAAATTACTGAGAAATCTACTGAAGAAACTGAGAAAC TTAAAAATGACCAGCAGGCCAAGATACCACTAAAAAAACG AGAAATTAAACTGAGTGATGATTTTGACAGTCCAGTCAAG GGACCTTTGTGTAAATCAGTTACTCCAACAAAAGAGTTTT TGAAAGATGAAATAAAACAAGAGGAAGAGACTTGTAAAAG GATCTCTACAATCACTGCTTTGGGTCATGAAGGGAAACAG CTGGTAAATGGAGAAGTTAGTGATGAAAGGGTAGCTCCAA ATTTTAAGACAGAACCAATAGAGACAAAGTTTTATGAGAC AAAGGAAGAGAGCTATAGCCCCTCTAAGGACAGAAATATC ATCACGGAGGGAAATGGAACAGAGTCCTTAAATTCTGTCA TAACAAGTATGAAAACAGGTGAGCTTGAGAAAGAAACAGC CCCTTTGAGGAAAGATGCAGATAGTTCAATATCAGTCTTA GAGATCCATAGTCAAAAAGCACAAATAGAGGAACCCGATC CTCCAGAAATGGAAACTTCTCTTGATTCTTCTGAGATGGC AAAAGATCTCTCTTCAAAAACTGCTTTATCTTCCACCGAG TCGTGTACCATGAAAGGTGAAGAGAAGTCTCCCAAAACTA AGAAGGATAAGCGCCCACCAATCCTAGAATGTCTTGAAAA GTTAGAGAAGTCCAAAAAGACTTTTCTTGATAAGGACGCA CAAAGATTGAGTCCAATACCAGAAGAAGTTCCAAAGAGTA CTCTAGAGTCAGAAAAGCCTGGCTCTCCTGAGGCAGCTGA AACTTCTCCACCATCTAATATCATTGACCACTGTGAGAAA CTAGCCTCAGAAAAAGAAGTGGTAGAATGCCAGAGTACAA GTACTGTTGGTGGCCAGTCTGTGAAAAAAGTAGACCTAGA AACCCTAAAAGAGGATTCTGAGTTCACAAAGGTAGAAATG GATAATCTGGACAATGCCCAGACCTCTGGCATAGAGGAGC CTTCTGAGACAAAGGGTTCTATGCAAAAAAGCAAATTCAA ATATAAGTTGGTTCCTGAAGAAGAAACCACTGCCTCAGAA AATACAGAGATAACCTCTGAAAGGCAGAAAGAGGGCATCA AATTAACAATCAGGATATCAAGTCGGAAAAAGAAGCCCGA TTCTCCCCCCAAAGTTCTAGAACCAGAAAACAAGCAAGAG AAGACAGAAAAGGAAGAGGAGAAAACAAATGTGGGTCGTA CTTTAAGAAGATCTCCAAGAATATCTAGACCCACTGCAAA AGTGGCTGAGATCAGAGATCAGAAAGCTGATAAAAAAAGA GGGGAAGGAGAAGATGAGGTGGAAGAAGAGTCAACAGCTT TGCAAAAAACTGACAAAAAGGAAATTTTGAAAAAATCAGA GAAAGATACAAATTCTAAAGTAAGCAAGGTAAAACCCAAA GGCAAAGTTCGATGGACTGGTTCTCGGACACGTGGCAGAT GGAAATATTCCAGCAATGATGAAAGTGAAGGGTCTGGCAG TGAAAAAATCATCTGCAGCTTCAGAAGAGGAGGAAGAAAAG GAAAGTGAAGAAGCCATCCTAGCAGATGATGATGAACCAT GCAAAAAATGTGGCCTTCCAAACCATCCTGAGCTAATTCT TCTGTGTGACTCTTGCGATAGTGGATACCATACTGCCTGC CTTCGCCCTCCTCTGATGATCATCCCAGATGGAGAATGGT TCTGCCCACCTTGCCAACATAAACTGCTCTGTGAAAAATT AGAGGAACAGTTCAGGATTTGGATGTTGCCTTAAAGAAG AAAGAGCGTGCCGAACGAAGAAAAGAACGCTTGGTGTATG TTGGTATCAGTATTGAAAACATCATTCCTCCACAAGAGCC AGACTTTTCTGAAGATCAAGAAGAAAGAAAAAAAGATTCA AAAAAATCCAAAGCAAACTTGCTTGAAAGGAGGTCAACAA GAACAAGGAAATGTATAAGCTACAGATTTGATGAGTTTGA TGAAGCAATTGATGAAGCTATTGAAGATGACATCAAAGAA GCCGATGGAGGAGGAGTTGGCCGAGGAAAAGATATCTCCA CCATCACAGGTCATCGTGGGAAAGACATCTCTACTATTTT GGATGAAGAAAGAAAGAAATAAACGACCCCAGAGGGCA GCTGCTGCTCGAAGGAAGAAACGCCGGCGATTAAATGATC TGGACAGTGATAGCAACCTGGATGAAGAAGAGAGCGAGGA TGAATTCAAGATCAGTGATGGATCTCAAGATGAGTTTGTT | |

TABLE 1-continued

GEP-NEN Biomarker/Houskeeper Sequence Information

| Gene Name | RefSeq Accession | Sequence | SEQ ID NO: |
|---|---|---|---|
| | | GTGTCTGATGAAAACCCAGATGAAAGTGAAGAAGATCCGC<br>CATCTAATGATGACAGTGACACTGACTTTTGTAGCCGTAG<br>ACTGAGGCGACACCCCTCTCGGCCAATGAGGCAGAGCAGG<br>CGTTTGCGAAGAAAGACCCCAAAGAAAAAATATTCCGATG<br>ATGATGAAGAGGAGGAATCTGAGGAGAATAGTAGAGACTC<br>TGAAAGTGACTTCAGTGATGATTTTAGTGATGATTTTGTA<br>GAAACTCGGCGAAGGCGGTCAAGGAGAAATCAGAAAAGAC<br>AAATTAACTACAAAGAAGACTCAGAAAGTGACGGTTCCCA<br>GAAGAGTTTGCGACGTGGTAAAGAAATAAGGCGAGTACAC<br>AAGCGAAGACTTTCCAGCTCAGAGAGTGAAGAGAGCTATT<br>TGTCCAAGAACTCTGAAGATGATGAGCTAGCTAAAGAATC<br>AAAGCGGTCAGTTCGAAAGCGGGGCCGAAGCACAGACGAG<br>TATTCAGAAGCAGATGAGGAGGAGGAGGAAGAGGAAGGCA<br>AACCATCCCGCAAACGGCTACACCGGATTGAGACGGATGA<br>GGAGGAGAGTTGTGACAATGCTCATGGAGATGCAAATCAG<br>CCTGCCCGTGACAGCCAGCCTAGGGTCCTGCCCTCAGAAC<br>AAGAGAGCACCAAGAAGCCCTACCGGATAGAAAGTGATGA<br>GGAAGAGGACTTTGAAAATGTAGGCAAAGTGGGGAGCCCA<br>TTGGACTATAGCTTAGTGGACTTACCTTCAACCAATGGAC<br>AGAGCCCTGGCAAAGCCATTGAGAACTTGATTGGCAAGCC<br>TACTGAGAAGTCTCAGACCCCCAAGGACAACAGCACAGCC<br>AGTGCAAGCCTAGCCTCCAATGGGACAAGTGGTGGGCAGG<br>AGGCAGGAGCACCAGAAGAGGAGGAAGATGAGCTTTTGAG<br>AGTGACTGACCTTGTTGATTATGTCTGTAACAGTGAACAG<br>TTATAAGACTTTTTTTCCATTTTTGTGCTAATTTATTCCA<br>CGGTAGCTCTCACACCAGCGGGCCAGTTATTAAAAGCTGT<br>TTAATTTTTCCTAGAAAACTCCACTACAGAATGACTTTTA<br>GAAGAAAAATTTCAACAAATCCTGAAGTCTTTCTGTGAAG<br>TGACCAGTTCTGAACTTTGAAGATAAATAATTGCTGTAAA<br>TTCCTTTTGATTTTCTTTTTCCAGGTTCATGGTCCTTGGT<br>AATTTCATTCATGGAAAAAAATCTTATTATAATAACAACA<br>AAGATTTGTATATTTTTGACTTTATATTTCCTGAGCTCTC<br>CTGACTTTGTGAAAAAGGGTGGATGAAAATGCATTCCGAA<br>TCTGTGAGGGCCCAAAACAGAATTTAGGGGTGGGTGAAAG<br>CACTTGTGCTTTAGCTTTTTCATATTAAATATATATTATA<br>TTTAAACATTCATGGCATAGATGATGATTTACAGACAATT<br>TAAAAGTTCAAGTCTGTACTGTTACAGTTTGAGAATTGTA<br>GATAACATCATACATAAGTCATTTAGTAACAGCCTTTGTG<br>AAATGAACTTGTTTACTATTGGAGATAACCACACTTAATA<br>AAGAAGAGACAGTGAAAGTACCATCATAATTAACCTAAAT<br>TTTTGTTATAGCAGAGTTTCTTGTTTAAAAAAAAATAAAA<br>TCATCTGAAAAGCAAAAA | |
| RTN2 | NM_005619.4 | CGCGCGCTGCAGTGCCTTCCCCACCTCGGCCCCGCCCGCC<br>CCCGCCGAGCCGAGCACCAGGGCGGCGGCGGCGGCGGCGG<br>CGGCGGCGGCGGCTGGAGCAGCCCGGGAGGAGGAGGCGGC<br>GAGAATGGCAGCGGCGTCGTGGGCGCGGCGGAGATGAGCG<br>CCCGCGACCCCGGGCCCAGGGCGGCACAGCCGGAGTGGGC<br>GGGGGTCCCGATGCAGGCCCGAGGGGGGCCATGGGGCAGG<br>TCCTGCCGGTCTTCGCCCACTGCAAAGAAGCTCCGTCTAC<br>AGCCTCCTCAACTCCTGATTCCACAGAAGGAGGGAACGAC<br>GACTCTGATTTTCGAGAGCTGCACACAGCCCGGGAATTCT<br>CAGAGGAGGACGAGGAGGAGACCACGTCGCAGGACTGGGG<br>CACCCCCCGGGAGCTGACCTTCTCCTACATCGCCTTTGAT<br>GGTGTAGTGGGCTCCGGGGGCCGCAGGGATTCAACTGCCC<br>GCCGCCCCGCCCCAGGGCCGCTCAGTCTCGGAACCACG<br>AGACCAGCACCCTCAGCCCAGCCTGGGCGACAGCTTGGAG<br>AGCATCCCCAGCCTGAGCCAATCCCCGGAGCCTGGACGAC<br>GGGGTGATCCTGACACCGCGCCTCCATCCGAGCGCCCTCT<br>GGAAGACCTGAGGCTTCGGTTGGACCATCTGGGCTGGGTG<br>GCCCGGGGAACGGGATCCGGGGAGGACTCTTCCACCAGCA<br>GCTCCACCCCGCTGGAAGACGAAGAACCCCAAGAACCCAA<br>CAGATTGGAGACAGGAGAAGCTGGGGAAGAACTGGACCTA<br>CGACTCCGACTTGCTCAGCCCTCATCGCCCGAGGTCTTGA<br>CTCCCCAGCTCAGTCCGGGCTCTGGGACACCCCAGGCCGG<br>TACTCCGTCCCCATCCCGATCGCGAGATTCGAACTCTGGG<br>CCCGAAGAGCCATTGCTGGAAGAGGAAGAAAAGCAGTGGG<br>GGCCACTGGAGCGAGAGCCAGTAAGGGGACAGTGCCTCGA<br>TAGCACGGACCAATTAGAATTCACGGTGGAGCCACGCCTT<br>CTAGGAACAGCTATGGAATGGTTAAAGACATCATTGCTTT<br>TGGCTGTTTACAAGACGGTTCCAATTTTGGAATTGTCCCC<br>ACCTCTGTGGACAGCCATTGGCTGGGTCCAAAGGGGCCCC<br>ACCCCCCTACTCCTGTCCTCCGGGTTCTACTGAAGTGGG<br>CAAAATCCCCGAGAAGCAGCGGTGTCCCCAGCCTCTCACT<br>CGGAGCCGATATGGGGAGTAAAGTGGCGGACCTGCTGTAC | 36 |

TABLE 1-continued

GEP-NEN Biomarker/Houskeeper Sequence Information

| Gene Name | RefSeq Accession | Sequence | SEQ ID NO: |
|---|---|---|---|
| | | TGGAAGGACACGAGGACGTCAGGAGTGGTCTTCACAGGCC<br>TGATGGTCTCCCTCCTCTGCCTCCTGCACTTTAGCATCGT<br>GTCCGTGGCCGCGCACTTGGCTCTGTTGCTGCTCTGCGGC<br>ACCATCTCTCTCAGGGTTTACCGCAAAGTGCTGCAGGCCG<br>TGCACCGGGGGATGGAGCCAACCCTTTCCAGGCCTACCT<br>GGATGTGGACCTCACCCTGACTCGGGAGCAGACGGAACGT<br>TTGTCCCACCAGATCACCTCCCGCGTGGTCTCGGCGGCCA<br>CGCAGCTGCGGCACTTCTTCCTGGTAGAAGACCTCGTGGA<br>TTCCCTCAAGCTGGCCCTCCTCTTCTACATCTTGACCTTC<br>GTGGGTGCCATCTTCAATGGTTTGACTCTTCTCATTCTGG<br>GAGTGATTGGTCTATTCACCATCCCCCTGCTGTACCGGCA<br>GCACCAGGCTCAGATCGACCAATATGTGGGGTTGGTGACC<br>AATCAGTTGAGCCACATCAAAGCTAAGATCCGAGCTAAAA<br>TCCCAGGGACCGGAGCCCTGGCCTCTGCAGCAGCCGCAGT<br>CTCCGGATCCAAAGCCAAAGCCGAATGAGAACGGTGTCTC<br>TGCCCGCAGGACGCCTGCCCCCAGCCCCCGCAGCCCTCTG<br>GCCCCCTCCATCTCTTGTCCGTTCCCACCCACCCCCCTCC<br>TCGGCCCGAGCCTTTTCCCGGTGGGTGTCAGGATCACTCC<br>CACTAGGGACTCTGCGCTAATTACCTGAGCGACCAGGACT<br>ACATTTCCCAAGAGGCTCTGCTCCAGGAGTCCAGGAAAGA<br>CGAGGCACCTTGGCCGCGGGGCCTGCTGGGACTTGTAGTT<br>GCCTAGACAGGGCACCACCCTGCACTTCCGGACCCGCCGC<br>TGGAGGCGCCGTGAGGCGTTGGTGTCTCCTGGATGCTACT<br>AGCCCCAACGCCGGGGCTTTGCATGGGGCCCAGGGGAGGC<br>CTGAGCTTGGATTTACACTGTAATAAAGACTCCTGTGGAA<br>AACCCGAG | |
| SMARCD3 | NM_001003801.1 | AGCAGGACTCAGAGGGGAGAGTTGGAGGAAAAAAAAAGGC<br>AGAAAAGGGAAAGAAAGAGGAAGAGAGAGAGAGTGAGA<br>GGAGCCGCTGAGCCCACCCCGATGGCCGCGGACGAAGTTG<br>CCGGAGGGGCGCGCAAAGCCACGAAAAGCAAACTTTTTGA<br>GTTTCTGGTCCATGGGGTGCGCCCCGGGATGCCGTCTGGA<br>GCCCGGATGCCCCACCAGGGGCGCCCATGGGCCCCCCGG<br>GCTCCCCGTACATGGGCAGCCCCGCCGTGCGACCCGGCCT<br>GGCCCCCGCGGGCATGGAGCCCGCCCGCAAGCGAGCAGCG<br>CCCCCGCCCGGGCAGAGCCAGGCACAGAGCCAGGGCCAGC<br>CGGTGCCCACCGCCCCCGCGCGGAGCCGCAGTGCCAAGAG<br>GAGGAAGATGGCTGACAAAATCCTCCCTCAAAGGATTCGG<br>GAGCTGGTCCCCGAGTCCCAGGCTTACATGGACCTCTTGG<br>CATTTGAGAGGAAACTGGATCAAACCATCATGCGGAAGCG<br>GGTGGACATCCAGGAGGCTCTGAAGAGGCCCATGAAGCAA<br>AAGCGGAAGCTGCGACTCTATATCTCCAACACTTTTAACC<br>CTGCGAAGCCTGATGCTGAGGATTCCGACGGCAGCATTGC<br>CTCCTGGGAGCTACGGGTGGAGGGGAAGCTCCTGGATGAT<br>CCCAGCAAACAGAAGCGGAAGTTCTCTTCTTTCTTCAAGA<br>GTTTGGTCATCGAGCTGGACAAAGATCTTTATGGCCCTGA<br>CAACCACCTCGTTGAGTGGCATCGGACACCCACGACCCAG<br>GAGACGGACGGCTTCCAGGTGAAACGGCCTGGGGACCTGA<br>GTGTGCGCTGCACGCTGCTCCTCATGCTGGACTACCAGCC<br>TCCCCAGTTCAAACTGGATCCCCGCCTAGCCCGGCTGCTG<br>GGGCTGCACACACAGAGCCGCTCAGCCATTGTCCAGGCCC<br>TGTGGCAGTATGTGAAGACCAACAGGCTGCAGGACTCCCA<br>TGACAAGGAATACATCAATGGGGACAAGTATTTCCAGCAG<br>ATTTTTGATTGTCCCCGGCTGAAGTTTTCTGAGATTCCCC<br>AGCGCCTCACAGCCCTGCTATTGCCCCTGACCCAATTGT<br>CATCAACCATGTCATCAGCGTGGACCCTTCAGACCAGAAG<br>AAGACGGCGTGCTATGACATTGACGTGGAGGTGGAGGAGC<br>CATTAAAGGGGCAGATGAGCAGCTTCCTCCTATCCACGGC<br>CAACCAGCAGGAGATCAGTGCTCTGGACAGTAAGATCCAT<br>GAGACGATTGAGTCCATAAACCAGCTCAAGATCCAGAGGG<br>ACTTCATGCTAAGCTTCTCCAGAGACCCCAAAGGCTATGT<br>CCAAGACCTGCTCCGCTCCCAGAGCCGGGACCTCAAGGTG<br>ATGACAGATGTAGCCGGCAACCCTGAAGAGGAGCGCCGGG<br>CTGAGTTCTACCACCAGCCCTGGTCCCAGGAGGCCGTCAG<br>TCGCTACTTCTACTGCAAGATCCAGCAGCGCAGGCAGGAG<br>CTGGAGCAGTCGCTGGTTGTGCGCAACACCTAGGAGCCCA<br>AAAATAAGCAGCACGACGGAACTTTCAGCCGTGTCCCGGG<br>CCCCAGCATTTTGCCCCGGGCTCCAGCATCACTCCTCTGC<br>CACCTTGGGGTGTGGGGCTGGATTAAAAGTCATTCATCTG<br>ACAAAAAAAAAAAAAAAAA | 37 |
| SPATA7 | NM_001040428.3 | ACAATAGCGACTCACTGGACCCAGCCCTTAGCAACGGCCT<br>GGCGACGGTTTCCCTGCTGCTGCAGCCCCCGTCGGCTCCT<br>CTTTTCCAGTCCTCCACTGCCGGGGCTGGGCCCGGCCGCG<br>GGAAGGACCGAAGGGGATACAGCCGTGTCCCTGCGGCGGCT | 38 |

TABLE 1-continued

GEP-NEN Biomarker/Houskeeper Sequence Information

| Gene Name | RefSeq Accession | Sequence | SEQ ID NO: |
|---|---|---|---|
| | | GCAAGAGGACTAAGCATGGATGGCAGCCGGAGAGTCAGAG<br>CAACCTCTGTCCTTCCCAGATATGGTCCACCGTGCCTATT<br>TAAAGGACACTTGAGCACCAAAAGTAATGCTGCAGTAGAC<br>TGCTCGGTTCCAGTAAGCGTGAGTACCAGCATAAAGTATG<br>CAGACCAACAACGAAGAGAGAAACTCAAAAAGGAATTAGC<br>ACAATGTGAAAAGAGTTCAAATTAACTAAAACTGCAATG<br>CGAGCCAATTATAAAAATAATTCCAAGTCACTTTTTAATA<br>CCTTACAAAAGCCCTCAGGCGAACCGCAAATTGAGGATGA<br>CATGTTAAAAGAAGAAATGAATGGATTTTCATCCTTTGCA<br>AGGTCACTAGTACCCTCTTCAGAGAGACTACACCTAAGTC<br>TACATAAATCCAGTAAAGTCATCACAAATGGTCCTGAGAA<br>GAACTCCAGTTCCTCCCCGTCCAGTGTGGATTATGCAGCC<br>TCCGGGCCCCGGAAACTGAGCTCTGGAGCCCTGTATGGCA<br>GAAGGCCCAGAAGCACATTCCCAATTCCCACCGGTTTCA<br>GTTAGTCATTTCGAAAGCACCCAGTGGGGATCTTTTGGAT<br>AAACATTCTGAACTCTTTTCTAACAAACAATTGCCATTCA<br>CTCCTCGCACTTTAAAAACAGAAGCAAAATCTTTCCTGTC<br>ACAGTATCGCTATTATACACCTGCCAAAAGAAAAAAGGAT<br>TTTACAGATCAACGGATAGAAGCTGAAACCCAGACTGAAT<br>TAAGCTTTAAATCTGAGTTGGGGACAGCTGAGACTAAAAA<br>CATGACAGATTCAGAAATGAACATAAAGCAGGCATCTAAT<br>TGTGTGACATATGATGCCAAAGAAAAAATAGCTCCTTTAC<br>CTTTAGAAGGGCATGACTCAACATGGGATGAGATTAAGGA<br>TGATGCTCTTCAGCATTCCTCACCAAGGGCAATGTGTCAG<br>TATTCCCTGAAGCCCCCTTCAACTCGTAAAATCTACTCTG<br>ATGAAGAAGAACTGTTGTATCTGAGTTTCATTGAAGATGT<br>AACAGATGAAATTTTGAAACTTGGTTTATTTTCAAACAGG<br>TTTTTAGAACGACTGTTCGAGCGACATATAAAACAAATA<br>AACATTTGGAGGAGGAAAAAATGCGCCACCTGCTGCATGT<br>CCTGAAAGTAGACTTAGGCTGCACATCGGAGGAAAACTCG<br>GTAAAGCAAAATGATGTTGATATGTTGAATGTATTTGATT<br>TTGAAAAGGCTGGGAATTCAGAACCAAATGAATTAAAAAA<br>TGAAAGTGAAGTAACAATTCAGCAGGAACGTCAACAATAC<br>CAAAAGGCTTTGGATATGTTATTGTCGGCACCAAAGGATG<br>AGAACGAGATATTCCCTTCACCAACTGAATTTTTCATGCC<br>TATTTATAAATCAAAGCATTCAGAAGGGGTTATAATTCAA<br>CAGGTGAATGATGAAACAAATCTTGAAACTTCAACTTTGG<br>ATGAAAATCATCCAAGTATTTCAGACAGTTTAACAGATCG<br>GGAAACTTCTGTGAATGTCATTGAAGGTGATAGTGACCCT<br>GAAAAGGTTGAGATTTCAAATGGATTATGTGGTCTTAACA<br>CATCACCCTCCCAATCTGTTCAGTTCTCCAGTGTCAAAGG<br>CGACAATAATCATGACATGGAGTTATCAACTCTTAAAATC<br>ATGGAAATGAGCATTGAGGACTGCCCTTTGGATGTTTAAT<br>CTTCATTAATAAATACCTCAAATGGCCAGTAACTCAAAAA<br>AAAAAAAAAAAAAA | |
| SST1 | NM_001049.2 | TGGTCATCGCACGGCGGCAGCTCCTCACCTGGATTTAGAA<br>GAGCTGGCGTCCCCGCCCGCCCAAGCCTTTAAACTCTCGT<br>CTGCCAGAACCCGCCAACTCTCCAGGCTTAGGGCCAGTTT<br>CCGCGATTCTAAGAGTAATTGCGTGGGCACCTGTGCTGGG<br>GCCAGGCGCAAAGAAGGGAGTTGGTCTGCGCGAAGATCGT<br>CAACCTGCTAACAGACCGCACATGCACTTTGCACCGACCA<br>TCTACGTCTCAGTCTGGAGGTTGCGCACTTTGGCTGCTGA<br>CGCGCTGGTGGTGCCTATTAATCATTTACCAGTCCAGAGC<br>CGCGCCAGTTAATGGCTGTGCCGTGCGGTGCTCCCACATC<br>CTGGCCTCTCCTCTCCACGGTCGCCTGTGCCCGGGCACCC<br>CGGAGCTGCAAACTGCAGAGCCCAGGCAACCGCTGGGCTG<br>TGCGCCCCGCCGGCGCCGGTAGGAGCCGCGCTCCCCGCAG<br>CGGTTGCGCTCTACCCGGAGGCGCTGGGCGGCTGTGGGCT<br>GCAGGCAAGCGGTCGGTGGGAGGGAGGGCGCAGGCGGC<br>GGGTGCGCGAGGAGAAAGCCCCAGCCCTGGCAGCCCCACT<br>GGCCCCCCTCAGCTGGGATGTTCCCCAATGGCACCGCCTC<br>CTCTCCTTCCTCCTCCTAGCCCCAGCCCGGGCAGCTGC<br>GGCGAAGGCGGCGGCAGCAGGGGCCCCGGGGCCGGCGCTG<br>CGGACGGCATGGAGGAGCCAGGGCGAAATGCGTCCCAGAA<br>CGGGACCTTGAGCGAGGGCCAGGGCAGCGCCATCCTGATC<br>TCTTTCATCTACTCCGTGGTGTGCCTGGTGGGGCTGTGTG<br>GGAACTCTATGGTCATCTACGTGATCCTGCGCTATGCCAA<br>GATGAAGACGGCCACCAACATCTACATCCTAAATCTGGCC<br>ATTGCTGATGAGCTGCTCATGCTGAGCGTGCCCTTCCTAG<br>TCACCTCCACGTTGTTGCGCCACTGGCCCTTCGGTGCGCT<br>GCTCTGCCGCCTCGTGCTCAGCGTGGACGCGGTCAACATG<br>TTCACCAGCATCTACTGTCTGACTGTGCTCAGCGTGGACC<br>GCTACGTGGCCGTGGTGCATCCCATCAAGGCGGCCCGCTA<br>CCGCCGGCCCACCGTGGCCAAGGTAGTAAACCTGGGCGTG | 39 |

TABLE 1-continued

GEP-NEN Biomarker/Houskeeper Sequence Information

| Gene Name | RefSeq Accession | Sequence | SEQ ID NO: |
|---|---|---|---|
| | | TGGGTGCTATCGCTGCTCGTCATCCTGCCCATCGTGGTCT<br>TCTCTCGCACCGCGGCCAACAGCGACGGCACGGTGGCTTG<br>CAACATGCTCATGCCAGAGCCCGCTCAACGCTGGCTGGTG<br>GGCTTCGTGTTGTACACATTTCTCATGGGCTTCCTGCTGC<br>CCGTGGGGGCTATCTGCCTGTGCTACGTGCTCATCATTGC<br>TAAGATGCGCATGGTGGCCCTCAAGGCCGGCTGGCAGCAG<br>CGCAAGCGCTCGGAGCGCAAGATCACCTTAATGGTGATGA<br>TGGTGGTGATGGTGTTTGTCATCTGCTGGATGCCTTTCTA<br>CGTGGTGCAGCTGGTCAACGTGTTTGCTGAGCAGGACGAC<br>GCCACGGTGAGTCAGCTGTCGGTCATCCTCGGCTATGCCA<br>ACAGCTGCGCCAACCCCATCCTCTATGGCTTTCTCTCAGA<br>CAACTTCAAGCGCTCTTTCCAACGCATCCTATGCCTCAGC<br>TGGATGGACAACGCCGCGGAGGAGCCGGTTGACTATTACG<br>CCACCGCGCTCAAGAGCCGTGCCTACAGTGTGGAAGACTT<br>CCAACCTGAGAACCTGGAGTCCGGCGGCGTCTTCCGTAAT<br>GGCACCTGCACGTCCCGGATCACGACGCTCTGAGCCCGGG<br>CCACGCAGGGGCTCTGAGCCCGGGCCACGCAGGGGCCCTG<br>AGCCAAAAGAGGGGGAGAATGAGAAGGGAAGGCCGGGTGC<br>GAAAGGGACGGTATCCAGGGCGCCAGGGTGCTGTCGGGAT<br>AACGTGGGGCTAGGACACTGACAGCCTTTGATGGGAGGAAC<br>CCAAGAAAGGCGCGCGACAATGGTAGAAGTGAGAGCTTTG<br>CTTATAAACTGGGAAGGCTTTCAGGCTACCTTTTTCTGGG<br>TCTCCCACTTTCTGTTCCTTCCTCCACTGCGCTTACTCCT<br>CTGACCCTCCTTCTATTTTCCCTACCCTGCAACTTCTATC<br>CTTTCTTCCGCACCGTCCCGCCAGTGCAGATCACGAACTC<br>ATTAACAACTCATTCTGATCCTCAGCCCCTCCAGTCGTTA<br>TTTCTGTTTGTTTAAGCTGAGCCACGGATACCGCCACGGG<br>TTTCCCTCGGCGTTAGTCCCTAGCCGCGCGGGGCCGCTGT<br>CCAGGTTCTGTCTGGTGCCCCTACTGGAGTCCCGGGAATG<br>ACCGCTCTCCCTTTGCGCAGCCCTACCTTAAGGAAAGTTG<br>GACTTGAGAAAGATCTAAGCAGCTGGTCTTTTCTCCTACT<br>CTTGGGTGAAGGTGCATCTTTCCCTGCCCTCCCCTGTCCC<br>CCTCTCGCCGCCCGCCCGCCACCACCACTCTCACTCCACC<br>CAGAGTAGAGCCAGGTGCTTAGTAAAATAGGTCCCGCGCT<br>TCGAACTCCAGGCTTTCTGGAGTTCCCACCCAAGCCCTCC<br>TTTGGAGCAAAGAAGGAGCTGAGAACAAGCCGAATGAGGA<br>GTTTTTATAAGATTGCGGGGTCGGAGTGTGGGCGCGTAAT<br>AGGAATCACCCTCCTACTGCGCGTTTTCAAAGACCAAGCG<br>CTGGGCGCTCCCGGGCCGCGCGTCTGCGTTAGGCAGGGCA<br>GGGTAGTGCAGGGCACACCTTCCCCGGGGTTCGGGGTTCG<br>GGGTTCGGTTGCAGGGCTGCAGCCCGCCTTGGCTTTCTCC<br>CTCACCCAAGTTTCCGGAGGAGCCGACCTAAAAGTAACAA<br>TAGATAAGGTTTCCTGCTCCAGTGTATCTCAAAAGACCGG<br>GCGCCAGGGGCGGGGACCTAGGGCGACGTCTTCAGAGTC<br>CGCCAGTGTTGGCGGTGTCGCCGCAACCTGCAGGCTCCCG<br>AGTGGGGCCTGCCTGGTCTCTAGAGGGTTGCTGCCTTTCA<br>AGCGGTGCCTAAGAAGTTATTTTCTTGTTTAACATATATA<br>TTTATTAATTTATTTGTCGTGTTGGAAAATGTGTCTCTGC<br>TTTCCTTTTCTCTGCTTGCCTAGCCCCAGGTCTTTTCTTT<br>GGGACCCTGGGGGCGGGCATGGAAGTGGAAGTAGGGGCAA<br>GCTCTTGCCCCACTCCCTGGCCATCTCAACGCCTCTCCTC<br>AATGCTGGGCCCTCTTATCTCATCCTTTCCTCTAGCTTTT<br>CTATTTTTGATTGTGTTGAGTGAAGTTTGGAGATTTTTCA<br>TACTTTTCTTACTATAGTCTCTTGTTTGTCTTATTAGGAT<br>AATACATAAATGATAATGTGGGTTATCCTCCTCCCATGC<br>ACAGTGGAAAGTCCTGAACTCCTGGCTTTCCAGGAGACAT<br>ATATAGGGAACATCACCCTATATATAATTTGAGTGTATA<br>TATATTTATATATATGATGTGGACATATGTATACTTATCT<br>TGCTCCATTGTCATGAGTCCATGAGTCTAAGTATAGCCAC<br>TGATGGTGACAGGTGTGAGTCTGGCTGGAACACTTTCAGT<br>TTCAGGAGTGCAAGCAGCACTCAAACCTGGAGCTGAGGAA<br>TCTAATTCAGACAGAGACTTTAATCACTGCTGAAGATGCC<br>CCTGCTCCCTCTGGGTTCCAGCAGAGGTGATTCTTACATA<br>TGATCCAGTTAACATCATCACTTTTTTTGAGGACATTGAA<br>AGTGAAATAATTTGTGTCTGTGTTTAATATTACCAACTAC<br>ATTGGAAGCCTGAGCAGGGCGAGGACCAATAATTTTAATT<br>ATTTATATTTCCTGTATTGCTTTAGTATGCTGGCTTGTAC<br>ATAGTAGGCACTAAATACATGTTTGTTGGTTGATTGTTTA<br>AGCCAGAGTGTATTACAACAATCTGGAGATACTAAATCTG<br>GGGTTCTCAGGTTCACTCATTGACATGATATACAATGGTT<br>AAAATCACTATTGAAAAATACGTTTTGTGTATATTTGCTT<br>CAACAACTTTGTGCTTTCCTGAAAGCAGTAACCAAGAGTT<br>AAGATATCCCTAATGTTTTGCTTAAACTAATGAACAAATA<br>TGCTTTGGGTCATAAATCAGAAAGTTTAGATCTGTCCCTT<br>AATAAAAATATATATTACTACTCCTTTGGAAAATAGATTT | |

TABLE 1-continued

GEP-NEN Biomarker/Houskeeper Sequence Information

| Gene Name | RefSeq Accession | Sequence | SEQ ID NO: |
|---|---|---|---|
| | | TTAATGGTTAAGAACTGTGAAATTTACAAATCAAAATCTT<br>AATCATTATCCTTCTAAGAGGATACAAATTTAGTGCTCTT<br>AACTTGTTACCATTGTAATATTAACTAAATAAACAGATGT<br>ATTATGCTGTTAAAAAAAAAAAAAAAAAAAAAAAAAAAA<br>AAAAAAAAAAAAAAAAAAAAAA | |
| SST3 | NM_001051.4 | CTGCATCTCTCCCTCTCACCCGTGTCTCCTCTCCTCTCTT<br>TCCTTCTCGTCTTCTCCCTGTCACGCATCTCTCATCACTC<br>CCCCTCATTCTGCCTTTCCTCCTACTCACGGTCTCCTCTC<br>CCTCTCCCTCTCTCTCTCCCCCTCCCTCTTTCTCTCTC<br>TCTCTCTTTCTCCACCTCCTCCCGACCCCCTTTCCCCTCT<br>ATTTCTATTGGCTTCTGTGTCCCTTGCTCCCCTCTTCTCT<br>TCCTCACCCTGGGAAGCTTCTCCCCCCTATCCTTGCCCCT<br>GCCCCCCCAGGATGTGTCCTGGAGATGGGGGGTGACGTAC<br>CAGGCTCTGGTTGGGAAGTCAGGGCCGGAGACCAGATGGG<br>AGAGGCTCTGTGGACAGCCGTGGCCGAGGGCCTGGGAGGG<br>AACCTGAGCCCGCAAGCGGTCTAGAAGTGGGTGCCTTGTG<br>GGGACCCTAGTTAGGAGTGCCCTGGGGGCACCTGGGGACT<br>GGGCAGGGAGAGGGGACAGCAGAATGATAACCAGCCTGGC<br>GGCAAGGAGGGAAGCCCTCACCCCATGGGCAGGCAAATAG<br>CTGACTGCTGACCACCCTCCCCTCAGCCATGGACATGCTT<br>CATCCATCATCGGTGTCCACGACCTCAGAACCTGAGAATG<br>CCTCCTCGGCCTGGCCCCAGATGCCACCCTGGGCA<u>A</u>CGT<br>GTCGGCGGGCCCAAGCCCGGCAGGGCTGGCCGTCAGTGGC<br>GTTCTGATCCCCCTGGTCTACCTGGTGGTGTGCGTGGTGG<br>GCCTGCTGGGTAACTCGCTGGTCATCTATGTGGTCCTGCG<br>GCACACGGCCAGCCCTTCAGTCACCAACGTCTACATCCTC<br>AACCTGGCGCTGGCCGACGAGCTCTTCATGCTGGGGCTGC<br>CCTTCCTGGCCGCCCAGAACGCCCTGTCCTACTGGCCCTT<br>CGGCTCCCTCATGTGCCGCCTGGTCATGGCGGTGGATGGC<br>ATCAACCAGTTCACCAGCATATTCTGCCTGACTGTCATGA<br>GCGTGGACCGCTACCTGGCCGTGGTACATCCCACCCGCTC<br>GGCCCGCTGGCGCACAGCTCCGGTGGCCCGCACGGTCAGC<br>GCGGCTGTGTGGGTGGCCTCAGCCGTGGTGGTGCTGCCCG<br>TGGTGGTCTTCTCGGGAGTGCCCCGCGGCATGAGCACCTG<br>CCACATGCAGTGGCCCGAGCCGGCGGCGGCCTGGCGAGCC<br>GGCTTCATCATCTACACGGCCGCACTGGGCTTCTTCGGGC<br>CGCTGCTGGTCATCTGCCTCTGCTACCTGCTCATCGTGGT<br>GAAGGTGCGCTCAGCTGGGCGCCGGGTGTGGGCACCCTCG<br>TGCCAGCGGCGGCGGCGCTCCGAACGCAGGGTCACGCGCA<br>TGGTGGTGGCCGTGGTGGCGCTCTTCGTGCTCTGCTGGAT<br>GCCCTTCTACGTGCTCAACATCGTCAACGTGGTGTGCCCA<br>CTGCCCGAGGAGCCTGCCTTCTTTGGGCTCTACTTCCTGG<br>TGGTGGCGCTGCCCTATGCCAACAGCTGTGCCAACCCCAT<br>CCTTTATGGCTTCCTCTCCTACCGCTTCAAGCAGGGCTTC<br>CGCAGGGTCCTGCTGCGGCCCTCCCGCCGTGTGCGCAGCC<br>AGGAGCCCACTGTGGGGCCCCGGAGAAGACTGAGGAGGA<br>GGATGAGGAGGAGGAGGATGGGGAGGAGAGCAGGGAGGGG<br>GGCAAGGGGAAGGAGATGAACGGCCGGGTCAGCCAGATCA<br>CGCAGCCTGGCACCAGCGGGCAGGAGCGGCCGCCCAGCAG<br>AGTGGCCAGCAAGGAGCAGCAGCTCCTACCCCAAGAGGCT<br>TCCACTGGGGAGAAGTCCAGCACGATGCGCATCAGCTACC<br>TGTAGGGGCCTGGGGAAAGCCAGGATGGCCCGAGGAAGAG<br>GCAGAAGCCGTGGGTGTGCCTAGGGCCTACTTCCCAAGGT<br>GCCACAGGCCCATGATGGGATGTTGAGGGGCCTGGACTTT<br>GATGCTATTGCTGCCAGGTCTTGCTGTGTGACCTTGGGTA<br>GGTTGCTTCTACTCTCTGGGCCTTGTTTTCTCCTCTGTGA<br>CTCAGGGATAGGAGTCATCAGCCTGGATGAGCTATGTCAG<br>ATGAGAGGTTTGGAGGGCACTGTTGCTGGGCTGACCTGGC<br>TGAGCAGGCAAAAGGTGGGTGCAGACTGGCCTCCCCCCAG<br>GGATGGAGTGTCTTGGGGCATCAACTAGAATCTTGGCCCT<br>CAGAGGGATAAACCAAGGCCAGGATTTCTTGGGCTCAGAG<br>TCAGGAACACAGGAGCTGCTGGGGGCTGGGCTGGAAACCT<br>AAACAGAAGAAAGCCTAACCCGGTGGGAGGAGTGGGGCAG<br>AAATGGTCAGGCCCCAGATCAGCTCCCTCCCCTCGACTGT<br>GAGGGCCTTGGACCAGCTCTGCTCCTCTCTAGGCCTCAGGC<br>TTCACCTGGGTAAAACCCAACAACCTCTACACCCTTTTGG<br>CCCAGGCAGTCAATGCTGGAGGTCCTGTGCTCCTGGACGG<br>GAAGAGCAGGTGAATTCCTGCTCATGGAAGCGAATGAAG<br>TCCAGCTTCAGGGTCTCACTGCCTGGGCTTTTGCAAGG<br>CCCTGCATCTACTTTTGTACTTGTCATTTTGTATTCGTTT<br>TCTTAAAGAGGGACCTCGAACTGCATAAGCTTAGGCCACC<br>CAAAGCCTGGCTCTGCCCCTGCTGAGGTCAGCCACCCAAT<br>CCCCAAGGAAGCTCATGTTGGGTCTTATGGCTGGAGTAGG<br>GGCCCCCGGGGGTTCCCAGGTCTTTTGAGGGCTTCCAGGC | 40 |

TABLE 1-continued

GEP-NEN Biomarker/Houskeeper Sequence Information

| Gene Name | RefSeq Accession | Sequence | SEQ ID NO: |
|---|---|---|---|
| | | ACCTCCTTGTAGGAAGGGCCATCCCTGTTCCTCTCCTTGT<br>GACCCATATTCTCCCTTCCTGGAGACCGAGACAGGGACCC<br>AGCCCATGAGGACTGGCATGGAAAGGCAGAGTGTCTGAAG<br>AGCGCTGTGAGGAGAAGGAAGAGGAAGGGAGAAGAGGAAG<br>AGGAAGGAGAAGGAAGAGGAAGACAAGGGGGAAAGGGGAG<br>GATGAGGAGGGGAAGGAGAAGTACAGATCTGTTTCCTGG<br>AGCCGTCTTTGGCCCCCCTGGGCTGAGCTCAGTGGTAGCA<br>TCTGTGAACCTGAGTTGCCGACAACAGCCCCACCCAACCA<br>GTACTGAGGGAAGGACACGATCAGGGTGGAACAGCCAGGG<br>TGCAATGGCAAATGCACAGAGTACAGACAGGCACAGGGCC<br>TGCGTCCCTGAGGGGCCTCAGAGTGCTGCCAAGAGGGCTC<br>AGGGCCTTAATAAAGCCCTAGGGTGGAGCTGGCTACCAGGG<br>ACATTGGGAGGACTGGGGAGCTCCCTCCCCATGCTCTATC<br>ATCCTGGAGACTACAGGTCGGGAGGCCCAGGGAAGACAAG<br>AAGAGGCTGAAGTGGGACTGTGGAGGGGGACCATGGGGAG<br>CAGCCACCATCCAAGGCTGGGCCTAGACTCCCTCCCAGAG<br>ATGGTCCCTCAGAGCTGTGGTGAGGCTGGCCCTGGGAGGG<br>TGAGACCCCGGTGAAATCCTTCCGCTTCCCCACCCCTTG<br>CAGAGGGCAGGGTCCTCAGGGAAAGCACAGGAACCAGAC<br>TTTTGGAGACTTGGATCTTCAGCACACCTCAGGGTCCTGG<br>GCTGGCATTGGCCTTCCGGGCCTCAATTTCCCCATCAACA<br>AATGGAGATGAATCCCAGCTTGGCTGCCTCCTGGGATCTA<br>ACGAGAAAATGAGTCATGTGAGGTAACTTCCAGGCTCACT<br>GCAATGGGTACGGTGGGGTGTATCAGATTATAAAGTGGGG<br>GTGCCCTCCTCACCCCCAGGCTTGGCCTATACCCCCCTCT<br>CCATCAAGTGGCCTCTCTGTGTCTGTCCTTTGGGGTGAGG<br>ACACTGTAGGCCATGAGAAATGGGCAGTTGGGGGGTCAGA<br>GGCCAAGGGTTAGGGAGGCAGGGCTTGGGGAGAGTGTGGG<br>ACCATCAGAAGAGAAGGAAGTTTACAAAACCACATTTTGT<br>GTGGAGATGGAGGCTGGAGGCCCGGCCCTGGGACTTGGTC<br>TGGGGTTTCTTGAGGAAGATCTGAGGGTCCAAGGGAGGAA<br>GGATGCCCTGGCCTTCTGGCCTTCTCTGGCTGATCCTGCC<br>TTCTTGCTGCCTAGGACAGGAGAGTAATGTCCTAGAATGG<br>TCCCTGGGAGGCCAGTTAGGAAACCCTTTGCTGCTTCTGT<br>CTCTAGCTCTTGTCAATAAAGACGGTGACACCTGAAAAAA<br>AAAAAAAAAA | |
| SST4 | NM_001052.2 | CCGAGCTCTCTGGCGCAGCGCTAGCTCCGCCGCGCTCAGC<br>TGCCCTGCGCCGGCACCCCTGGTCATGAGCGCCCCCTCGA<br>CGCTGCCCCCGGGGGCGAGGAAGGGCTGGGACGGCCTG<br>GCCCTCTGCAGCCAATGCCAGTAGCGCTCCGGCGGAGGCG<br>GAGGAGGCGGTGGCGGGGCCCGGGGACGCGCGGGCGGCGG<br>GCATGGTCGCTATCCAGTGCATCTACGCGCTGGTGTGCCT<br>GGTGGGGCTGGTGGGCAACGCCCTGGTCATCTTCGTGATC<br>CTTCGCTACGCCAAGATGAAGACGGCTACCAACATCTACC<br>TGCTCAACCTGGCCGTAGCCGACGAGCTCTTCATGCTGAG<br>CGTGCCCTTCGTGGCCTCGTCGGCCGCCCTGCGCCACTGG<br>CCCTTCGGCTCCGTGCTGTGCCGCGCGGTGCTCAGCGTCG<br>ACGGCCTCAACATGTTCACCAGCGTCTTCTGTCTCACCGT<br>GCTCAGCGTGGACCGCTACGTGGCCGTGGTGCACCCTCTG<br>CGCGCGGCGACCTACCGGCGGCCCAGCGTGGCCAAGCTCA<br>TCAACCTGGGCGTGTGGCTGGCATCCCTGTTGGTCACTCT<br>CCCCATCGCCATCTTCGCAGACACCAGACCGGCTCGCGGC<br>GGCCAGGCCGTGGCCTGCAACCTGCAGTGGCCACACCCGG<br>CCTGGTCGGCAGTCTTCGTGGTCTACACTTTCCTGCTGGG<br>CTTCCTGCTGCCCGTGCTGGCCATTGGCCTGTGCTACCTG<br>CTCATCGTGGGCAAGATGCGCGCCGTGGCCCTGCGCGCTG<br>GCTGGCAGCAGCGCAGGCGCTCGGAGAAGAAAATCACCAG<br>GCTGGTGCTGATGGTCGTGGTCGTCTTTGTGCTCTGCTGG<br>ATGCCTTTCTACGTGGTGCAGCTGCTGAACCTCTTCGTGA<br>CCAGCCTTGATGCCACCGTCAACCACGTGTCCCTTATCCT<br>TAGCTATGCCAACAGCTGCGCCAACCCCATTCTCTATGGC<br>TTCCTCTCCGACAACTTCCGCCGATTCTTCCAGCGGGTTC<br>TCTGCCTGCGCTGCTGCCTCCTGGAAGGTGCTGGAGGTGC<br>TGAGGAGGAGCCCCTGGACTACTATGCCACTGCTCTCAAG<br>AGCAAAGGTGGGGCAGGGTGCATGTGCCCCCCACTCCCT<br>GCCAGCAGGAAGCCCTGCAACCAGAACCCGGCCGCAAGCG<br>CATCCCCCTCACCAGGACCACCACCTTCTGAGGAGCCCTT<br>CCCCTACCCACCCTGCGT | 41 |
| SST5 | NM_001053.3 | ATGCCTGCATGTGCTGGTTCAGGGACTCACCACCCTGGCG<br>TCCTCCCTTCTTCTCTTGCAGAGCCTGACGCACCCCAGGG<br>CTGCCGCCATGGAGCCCCTGTTCCCAGCCTCCACGCCCAG<br>CTGGAACGCCTCCTCCCCGGGGCTGCCTCTGGAGGCGGT<br>GACAACAGGACGCTGGTGGGGCCGGCGCCCTCGGCAGGGG | 42 |

TABLE 1-continued

GEP-NEN Biomarker/Houskeeper Sequence Information

| Gene Name | RefSeq Accession | Sequence | SEQ ID NO: |
|---|---|---|---|
| | | CCCGGGCGGTGCTGGTGCCCGTGCTGTACCTGCTGGTGTG<br>TGCGGCCGGGCTGGGCGGGAACACGCTGGTCATCTACGTG<br>GTGCTGCGCTTCGCCAAGATGAAGACCGTCACCAACATCT<br>ACATTCTCAACCTGGCAGTGGCCGACGTCCTGTACATGCT<br>GGGGCTGCCTTTCCTGGCCACGCAGAACGCCGCGTCCTTC<br>TGGCCCTTCGGCCCCGTCCTGTGCCGCCTGGTCATGACGC<br>TGGACGGCGTCAACCAGTTCACCAGTGTCTTCTGCCTGAC<br>AGTCATGAGCGTGGACCGCTACCTGGCAGTGGTGCACCCG<br>CTGAGCTCGGCCCGCTGGCGCCGCCCGCGTGTGGCCAAGC<br>TGGCGAGCGCCGCGGCCTGGGTCCTGTCTCTGTGCATGTC<br>GCTGCCGCTCCTGGTGTTCGCGGACGTGCAGGAGGGCGGT<br>ACCTGCAACGCCAGCTGGCCGGAGCCCGTGGGGCTGTGGG<br>GCGCCGTCTTCATCATCTACACGGCCGTGCTGGGCTTCTT<br>CGCGCCGCTGCTGGTCATCTGCCTGTGCTACCTGCTCATC<br>GTGGTGAAGGTGAGGGCGGCGGGCGTGCGCGTGGGCTGCG<br>TGCCGGCGGCGCTCGGAGCGGAAGGTGACGCGCATGGTGTT<br>GGTGGTGGTGCTGGTGTTTGCGGGATGTTGGCTGCCCTTC<br>TTCACCGTCAACATCGTCAACCTGGCCGTGGCGCTGCCCC<br>AGGAGCCCGCCTCCGCCGGCCTCTACTTCTTCGTGGTCAT<br>CCTCTCCTACGCCAACAGCTGTGCCAACCCCGTCCTCTAC<br>GGCTTCCTCTCTGACAACTTCCGCCAGAGCTTCCAGAAGG<br>TTCTGTGCCTCCGCAAGGGCTCTGGTGCCAAGGACGCTGA<br>CGCCACGGAGCCGCGTCCAGACAGGATCCGGCAGCAGCAG<br>GAGGCCACGCCACCCGCGCACCGCGCCGCAGCCAACGGGC<br>TTATGCAGACCAGCAAGCTGTGAGAGTGCAGGCGGGGGGT<br>GGGCGGCCCCGTGTCACCCCCAGGAGCGGAGGTTGCACTG<br>CGGTGACCCCCACCCATGACCTGCCAGTCAGGATGCTCCC<br>CGGCGGTGGTGTGAGGACAGAGCTGGCTGAAGCCAGGCTG<br>GGGTAGACACAGGGCAGTAGGTTCCCCACCGTGACCGACC<br>ATCCCCTCTAACCGTCTGCCACACAGCGGGGGCTCCCGGG<br>AGGTAGGGGAGGTGGCCAGACCGGTGGGGGGGCTCCGCCAT<br>GCCGTGCAAGTGCTCAGGGCCGCCTCACCCTCCATCTGGC<br>CCCAGCCCATGCCGGCCTTCCCTCTGGGGAGCGACTTTTC<br>CAGAAGGCCGGCCAGGCGAGAGGGTCTTCCTGACGGCGGA<br>GCTGACCTGCCCGGCCCACCAGCTGCATGTCAGCTCCGAG<br>CCACCGGGTCCCCGTCCAAGGCTGCTCTGCTAAGTTAAAG<br>ACACCCGAAAGCGCTTGACTCAGGTCCCCGGAGTCCCTGG<br>CCAGGGCCCCAGCCCCTCGCTTGCCCTGCACTGTGTGGAC<br>TCTGGGGATGCAGGTGTAAGGGGAGTGTGGCTGGGCAGCC<br>CCTGGTCAGCCAGGGTCACGCCTGTCCTGGGGGCCCCACC<br>CTGCTGCCCGACACCCCCATGGGAGGCTGCGGGCGGCAG<br>TTGCTGTCTCAGAGAGGGGAGTGTGGGGGCTTGGGCGCTG<br>GCCTAGCCAGGGGCGAGGTGGGGAGGCGGCTGGTGCAGAG<br>GAGAGCTGGGGGCTGAGGTTGGGGTGAAGGCTGCAGCCCT<br>CCAGGCTGCTGGGGGTGCAGATGGCTGTGCCGTGCTGAGA<br>TTGGCTCTGTCTGGAGGGGTCCAGTGTGGGGTGCCTGAGG<br>GCACTAGGGAGAGGTGCTCCTGCTGCAGGAGGACCTGAGG<br>GTCAGGGCTTGGAGAGGACAGGGAACCTGCGGCCGTCTCT<br>TCTGCTTTGGGGCAGGGCTCTGGCCCGGGAGAGGGAACG<br>GGGACAGGAGCAGAGGACGGTCATCCAGGCGCAGCGGGGA<br>GCTGCTCCCCAGGCCACAGCAGACAGCACTGCTGAGAGGC<br>AGCGGCCGCGCGGGTGACGCAAATGGCAGGCCCTGGGAAT<br>CCCGCCGCCTCCCACCTAGAATTGTCCTACCTCCCCCACC<br>CCAAACACCAGCTTTTCCTGGCGCCCCAGGCCCAGAACGT<br>GGGCCCAGAGAGCCTTGCTGGGGTCTCTGGGGCACCTTGG<br>CCTTGCTCTGAGGCTGGAAGGAGAAGGACCAGGGTGCGGC<br>ATCACTCGGCCTCAGGGACCCCTCTGCCCTGCCCAGCACT<br>GGCCCCGACCCGTGCTCCCGCCGTCTGCCCAGAGCAGGAC<br>CTCAACCTCCTGGAGGGCACAGGGAGCGGCTGAGTGGGCA<br>CAAATCCTGGCAGGAGAAAGGCCCAGGCTGAGGCCAGGCC<br>TGGGAAACATCCAAGCAGTGAGGACACGCGTGTTTGACAA<br>CTGCTCCCCTGAATAAATGCGAGGATAAATGTTT | |
| TECPR2 | NM_001172631.1 | CCCCCGGCGGAGCCAGCTGCTGCTCTTCGGTGCTGGCCCC<br>GGTGCCGGCCCCGTTGCCCAGGGAACAGGCTCCCGGCAGC<br>CCCCGCGGCCCGGAGTCCATCCCGCCTCCTCCGGCCCGGC<br>GGGGCCGACGAGTCCGGAGGGGCTGCCGCGGGAGCCCCCA<br>GGTTTCCCTAGATGACAAATAAACATTCCTTTTCCTGCGT<br>GAAGATAGTCTGTGGAAACCTTGGCCATGGCATCGATATC<br>AGAGCCTGTTACATTCAGAGAGTTCTGCCCGTTGTACTAT<br>CTCCTCAATGCCATTCCGACAAAGATCCAGAAGGGTTTCC<br>GCTCTATCGTGGTCTATCTCACGGCCCTCGACACCAACGG<br>GGACTACATCGCGGTGGGCAGCAGCATCGGCATGCTCTAT<br>CTGTACTGCCGGCACCTCAACCAGATGAGGAAGTACAACT<br>TTGAGGGGAAGACCGGAATCTATCACTGTGGTGAAGCTGCT | 43 |

TABLE 1-continued

GEP-NEN Biomarker/Houskeeper Sequence Information

| Gene Name | RefSeq Accession | Sequence | SEQ ID NO: |
|---|---|---|---|
| | | GAGCTGCTTTGATGACCTGGTGGCAGCAGGCACAGCCTCT | |
| | | GGCAGGGTTGCAGTTTTTCAACTTGTATCTTCATTGCCAG | |
| | | GGAGAAATAAACAGCTTCGGAGATTTGATGTCACTGGTAT | |
| | | TCACAAAAATAGCATTACAGCTCTGGCTTGGAGCCCCAAT | |
| | | GGAATGAAATTGTTCTCTGGAGATGACAAAGGCAAAATTG | |
| | | TTTATTCTTCTCTGGATCTAGACCAGGGGCTCTGTAACTC | |
| | | CCAGCTGGTGTTGGAGGAGCCATCTTCCATTGTGCAGCTG | |
| | | GATTATAGCCAGAAAGTGCTGCTGGTCTCTACTCTGCAAA | |
| | | GAAGTCTGCTCTTTTACACTGAAGAAAAGTCTGTAAGGCA | |
| | | AATTGGAACACAACCAAGGAAAAGTACTGGGAAATTTGGT | |
| | | GCTTGTTTTATACCAGGACTCTGTAAGCAAAGTGATCTAA | |
| | | CCTTGTATGCGTCACGGCCCGGGCTCCGGCTATGGAAGGC | |
| | | TGATGTCCACGGGACTGTTCAAGCCACGTTTATCTTAAAA | |
| | | GATGCTTTTGCCGGGGGAGTCAAGCCTTTTGAACTGCACC | |
| | | CGCGTCTGGAATCCCCCAACAGTGGAAGTTGCAGCTTACC | |
| | | TGAGAGGCACCTGGGGCTTGTTTCATGTTTCTTTCAAGAA | |
| | | GGCTGGGTGCTGAGTTGGAATGAATATAGTATCTATCTCC | |
| | | TAGACACAGTCAACCAGGCCACAGTTGCTGGTTTGGAAGG | |
| | | ATCCGGTGATATTGTGTCTGTTTCGTGCACAGAAAATGAA | |
| | | ATATTTTTCTTGAAAGGAGATAGGAACATTATAAGAATTT | |
| | | CAAGCAGGCCTGAAGGATTAACATCAACAGTGAGAGATGG | |
| | | TCTGGAGATGTCTGGATGCTCAGAGCGTGTCCACGTGCAG | |
| | | CAAGCGGAGAAGCTGCCAGGGGCACAGTTTCTGAGACGA | |
| | | GGCTCAGAGGCTCTTCCATGGCCAGCTCCGTGGCCAGCGA | |
| | | GCCAAGGAGCAGGAGCAGCTCGCTCAACTCCACCGACAGC | |
| | | GGCTCCGGGCTCCTGCCCCTGGGCTCCAGGCCACCCCTG | |
| | | AGCTGGGCAAGGGCAGCCAGCCCCTGTCACAGAGATTCAA | |
| | | CGCCATCAGCTCAGAGGACTTTGACCAGGAGCTTGTCGTG | |
| | | AAGCCTATCAAAGTGAAAAGGAAGAAGAAGAAGAAGAAGA | |
| | | CAGAAGGTGGAAGCAGGAGCACCTGTCACAGCTCCCTGGA | |
| | | ATCGACACCCTGCTCCGAATTTCCTGGGACAGTCCCCAG | |
| | | TCCTTGAACACAGACTTGCTGTCGATGACCTCAAGTGTCC | |
| | | TGGGCAGTAGCGTGGATCAGTTAAGTGCAGAGTCTCCAGA | |
| | | CCAGGAAAGCAGCTTCAATGGTGAAGTGAACGGTGTCCCA | |
| | | CAGGAAAATACTGACCCCGAAACGTTTAATGTCCTGGAGG | |
| | | TGTCAGGATCAATGCCTGATTCTCTGGCTGAGGAAGATGA | |
| | | CATTAGAACTGAAATGCCACACTGTCACCATGCACATGGG | |
| | | CGGGAGCTGCTCAATGGAGCGAGGGAAGATGTGGGAGGCA | |
| | | GTGATGTCACGGGACTCGGAGATGAGCCGTGTCCTGCAGA | |
| | | TGATGGACCAAATAGCACACAGTTACCCTTCCAAGAACAG | |
| | | GACAGCTCTCCTGGGGCGCATGATGGGGAAGACATCCAAC | |
| | | CCATTGGCCCCCAAAGCACTTTTTGTGAAGTCCCCCTCCT | |
| | | GAACTCACTCACTGTGCCTTCCAGCCTCAGCTGGGCCCCA | |
| | | AGTGCTGAACAGTGGCTGCCTGGGACCAGAGCTGATGAAG | |
| | | GCAGCCCCGTGGAGCCCAGCCAAGAGCAGGACATCCTAAC | |
| | | CAGCATGGAGGCCTCTGGCCACCTCAGCACAAATCTCTGG | |
| | | CATGCTGTCACTGATGATGACACAGGTCAGAAAGAAATAC | |
| | | CCATTTCTGAACGTGTCTTGGGGAGTGTGGGAGGACAGCT | |
| | | GACTCCGGTCTCTGCCTTGGCAGCCAGCACTCACAAGCCC | |
| | | TGGCTTGAGCAGCCTCCACGGGATCAGACATTGACGTCCA | |
| | | GCGATGAGGAGGACATCTATGCCCACGGGCTTCCTTCTTC | |
| | | ATCCTCAGAGACGAGTGTGACAGAGCTCGGACCTAGTTGC | |
| | | TCCCAGCAGGACCTGAGCCGGCTGGGTGCAGAGGACGCCG | |
| | | GGCTGCTCAAGCCAGATCAGTTTGCAGAAAGCTGGATGGG | |
| | | CTACTCGGGTCCCGGCTATGGCATCCTCAGCTTGGTGGTC | |
| | | TCCGAGAAGTATATCTGGTGCCTGGACTACAAAGGCGGCC | |
| | | TGTTCTGCAGCGCGTTGCCGGGCGCCGGGCTGCGCTGGCA | |
| | | GAAGTTTGAAGATGCTGTCCAGCAGGTGGCAGTCTCGCCC | |
| | | TCAGGAGCCCTTCTCTGGAAGATTGAACAGAAATCTAACC | |
| | | GGGCTTTTGCTTGTGGGAAAGTCACCATCAAGGGGAAGCG | |
| | | GCACTGGTACGAAGCCCTGCCCCAGGCAGTGTTTGTGGCC | |
| | | CTGAGCGATGACACGGCCTGGATCATCAGGACCAGTGGGG | |
| | | ACCTATACTTGCAGACAGGTCTGAGCGTGGATCGCCCTTG | |
| | | TGCCAGAGCCGTAAAGGTGGACTGTCCCTACCCGCTGTCC | |
| | | CAGATCACAGCCCGGAACAATGTGGTGTGGGCGCTGACAG | |
| | | AGCAGAGGGCCCTCCTGTACCGGGAGGGCGTGAGCAGCTT | |
| | | CTGTCCGAAGGCGAGCAGTGGAAGTGTGACATTGTCAGC | |
| | | GAAAGGCAAGCTTTAGAACCCGTCTGCATAACGCTCGGCG | |
| | | ATCAGCAGACTCTCTGGGCCCTGGACATCCATGGGAACCT | |
| | | GTGGTTCAGAACTGGCATTATTTCCAAGAAGCCCCAAGGA | |
| | | GATGACGACCATTGGTGGCAAGTGAGCATCACGGACTATG | |
| | | TGGTGTTTGACCAGTGCAGCTTATTTCAGACGATAATCCA | |
| | | TGCCACTCACTCGGTGGCCACAGCAGCCCAAGCCCCCGTA | |
| | | GAAAAGGTGGCAGATAAGCTGCGCATGGCGTTTTGGTCCC | |
| | | AGCAGCTTCAGTGCCAGCCAAGCCTTCTCGGGGTCAATAA | |

TABLE 1-continued

GEP-NEN Biomarker/Houskeeper Sequence Information

| Gene Name | RefSeq Accession | Sequence | SEQ ID NO: |
|---|---|---|---|
| | | CAGCGGTGTCTGGATCTCCTCGGGCAAGAATGAATTCCAC GTCGCTAAGGGAAGTCTCATAGGCACCTACTGGAATCATG TGGTTCCCCGTGGGACAGCTTCTGCTACAAAATGGGCCTT TGTGTTGGCTTCTGCAGCTCCCACGAAGGAAGGAAGCTTC CTGTGGCTGTGCCAGAGCAGCAAGGACCTGTGCAGCGTCA GCGCCCAGAGCGCACAGTCGCGGCCCTCCACGGTGCAGCT GCCTCCCGAAGCCGAGATGCGCGCCTATGCCGCCTGCCAG GATGCGCTGTGGGCGCTGGACAGCCTCGGCCAGGTGTTCA TCAGGACGCTCTCCAAGAGCTGCCCCACGGGCATGCACTG GACCAGGCTGGACCTCTCCCAGCTAGGAGCTGTAAAATTG ACAAGCTTGGCATGTGGAAATCAGCACATCTGGGCCTGTG ATTCCAGGGGTGGAGTTTACTTCCGTGTAGGGACTCAGCC TCTCAATCCCAGTCTCATGCTTCCAGCCTGGATAATGATT GAGCCACCTGTCCAGGTAAGCAGAAGTTAGCTGGTGGAAC TCACTCTTCAGTAAGACAGAAACTGTGAGGATGCTGGTAC TGGGAAAAAGGATCTGCACAGCCTCTAGAGGCCTCCCAGC AAATGCGGGGAGCCATGCCCCCAGGGTCTACACACTCTCG TTCATCAACATCACAACTGGAATTCGGGATTTGTGAAGTT TAGAGCTGAACAGACTGTTACAGATTATGAGTCAACACGT ATATTTTCTCTTTCAAAATAATAATATTTCGTTTTTGACT TTTTACTAAGTGAATATTATTTTTTAAATCTGCCTATATA TTGGAACCTCTATTTTATAATAATAATGATAATAAATCAG TACCCAGAAGTATAAAGAAGGTAAAAGTTACTTTGAAAAA AAAAAAAAAAAAAAAAAAAAAAAAAAA | |
| TPH1 | NM_004179.2 | TTTTAGAGAATTACTCCAAATTCATCATGATTGAAGACAA TAAGGAGAACAAAGACCATTCCTTAGAAAGGGGAAGAGCA AGTCTCATTTTTTCCTTAAAGAATGAAGTTGGAGGACTTA TAAAAGCCCTGAAAATCTTTCAGGAGAAGCATGTGAATCT GTTACATATCGAGTCCCGAAAATCAAAAAGAAGAAACTCA GAATTTGAGATTTTTGTTGACTGTGACATCAACAGAGAAC AATTGAATGATATTTTTCATCTGCTGAAGTCTCATACCAA TGTTCTCTCTGTGAATCTACCAGATAATTTTACTTTGAAG GAAGATGGTATGGAAACTGTTCCTTGGTTTCCAAAGAAGA TTTCTGACCTGGACCATTGTGCCAACAGAGTTCTGATGTA TGGATCTGAACTAGATGCAGACCATCCTGGCTTCAAAGAC AATGTCTACCGTAAACGTCGAAAGTATTTTGCGGACTTGG CTATGAACTATAAACATGGAGACCCCATTCCAAAGGTTGA ATTCACTGAAGAGGAGATTAAGACCTGGGGAACCGTATTC CAAGAGCTCAACAAACTCTACCCAACCCATGCTTGCAGAG AGTATCTCAAAAACTTACCTTTGCTTTCTAAATATTGTGG ATATCGGGAGGATAATATCCCACAATTGGAAGATGTCTCC AACTTTTTAAAAGAGCGTACAGGTTTTTCCATCCGTCCTG TGGCTGGTTACTTATCACCAAGAGATTTCTTATCAGGTTT AGCCTTTCGAGTTTTTCACTGCACTCAATATGTGAGACAC AGTTCAGATCCCTTCTATACCCCAGAGCCAGATACCTGCC ATGAACTCTTAGGTCATGTCCCGCTTTTGGCTGAACCTAG TTTTTGCCCAATTCTCCCAAGAAATTGGCTTGGCTTCTCTT GGCGCTTCAGAGGAGGCTGTTCAAAAACTGGCAACGTGCT ACTTTTTCACTGTGGAGTTTGGTCTATGTAAACAAGATGG ACAGCTAAGAGTCTTTGGTGCTGGCTTACTTTCTTCTATC AGTGAACTCAAACATGCACTTTCTGGACATGCCAAAGTAA AGCCCTTTGATCCCAAGATTACCTGCAAACAGGAATGTCT TATCACAACTTTTCAAGATGTCTACTTTGTATCTGAAAGT TTTGAAGATGCAAAGGAGAAGATGAGAGAATTTACCAAAA CAATTAAGCGTCCATTTGGAGTGAAGTATAATCCATATAC ACGGAGTATTCAGATCCTGAAAGACACCAAGAGCATAACC AGTGCCATGAATGAGCTGCAGCATGATCTCGATGTTGTCA GTGATGCCCTTGCTAAGGTCAGCAGGAAGCCGAGTATCTA ACAGTAGCCAGTCATCCAGGAACATTTGAGCATCAATTCG GAGGTCTGGGCCATCTCTTGCTTTCCTTGAACACCTGATC CTGGAGGGACAGCATCTTCTGGCCAAACAATATTATCGAA TTCCACTACTTAAGGAATCACTAGTCTTTGAAAATTTGTA CCTGGATATTCTATTTACCACTTATTTTTTGTTTAGTTT TATTTCTTTTTTTTTTGGTAGCAGCTTTAATGAGACAAT TTATATACCATACAAGCCACTGACCACCCATTTTTAATAG AGAAGTTGTTTGACCCAATAGATAGATCTAATCTCAGCCT AACTCTATTTTCCCCAATCCTCCTTGAGTAAATGACCCT TTAGGATCGCTTAGAATAACTTGAGGAGTATTATGGCGCT GACTCATATTGTTACCTAAGATCCCCTTATTTCTAAAGTA TCTGTTACTTATTGC | 44 |
| TRMT112 | NM_016404.2 | GGCCACCCGCAGAACAGAGCTTCCGGGACCCACGCCTCGT TTGCACTGGGTGCTGGACAGCCGACGCAACTACAAATGGG GCGGAGCTTTCGGCACTGGAGCAGCTAATTTGCATATAGG | 45 |

TABLE 1-continued

GEP-NEN Biomarker/Houskeeper Sequence Information

| Gene Name | RefSeq Accession | Sequence | SEQ ID NO: |
|---|---|---|---|
| | | AATGAGGTGCGGCTCGGCTTCCATGGGCCTAATTTACAGA<br>TAGGGCGGTATTTCTGCCCCTTAACCGAAAGTGGGATACA<br>GAGGACGACGGTGTTAGGCGCCTGTGTAGGAGTAAAATGT<br>GTTTATTTTGCATTCAACGAGAGCTCCTGCATTGCAGCTA<br>TTTTGCATATGATTTGCATCTTACGAAGAATTTGTGGCAA<br>AAAAAAGCTGGGCGTGCGCCGTAGGAACCTCCTGCTGAGA<br>CGCTTCCGGTAGCGGCGCGTGACCCGACAGGTCTTTCACC<br>TACCTACCTCAGCTCCCACAAACACGAGAAGTTCCAGCAA<br>GTTCGCCACTTCCGGTTCTCCTGGCTATCCAATAGCATCG<br>AGAGGAGCATCCCCGGAAGTGAGGCAGCGGAGGACGACCT<br>TTTTCCGGTTCCGGCCTGGCGAGAGTTTGTGCGGCGACAT<br>GAAACTGCTTACCCACAATCTGCTGAGCTCGCATGTGCGG<br>GGGGTGGGGTCCCGTGGCTTCCCCCTGCGCCTCCAGGCCA<br>CCGAGGTCCGTATCTGCCCTGTGGAATTCAACCCCAACTT<br>CGTGGCGCGTATGATACCTAAAGTGGAGTGGTCGGCGTTC<br>CTGGAGGCGGCCGATAACTTGCGTCTGATCCAGGTGCCGA<br>AAGGGCCGGTTGAGGGATATGAGGAGAATGAGGAGTTTCT<br>GAGGACCATGCACCACCTGCTGCTGGAGGTGGAAGTGATA<br>GAGGGCACCCTGCAGTGCCCGGAATCTGGACGTATGTTCC<br>CCATCAGCCGCGGGATCCCCAACATGCTGCTGAGTGAAGA<br>GGAAACTGAGAGTTGATTGTGCCAGGCGCCAGTTTTTCTT<br>GTTATGACTGTGTATTTTGTTGATCTATACCCTGTTTCC<br>GAATTCTGCCGTGTGTATCCCCAACCCTTGACCCAATGAC<br>ACCAAACACAGTGTTTTTGAGCTCGGTATTATATATTTTT<br>TTCTCATTAAAGGTTTAAAACCAAAAGCGGTTTCTCTTTG<br>CAGCAAATATACATTAAAATAGAGTCTCTGTACAGCCAAG<br>GGCTCTGGGCCCTGGCTTGCCCCATGTCCCTGCGCCTCCC<br>TGGCCAAACCCAAAAATAAATATAGTGTTATTGCTCTGCA<br>GGGCATAGAGGCAGTGCTCTCCTACCCCCTGAGGAGGCTC<br>GTTGGGAGCTGATGGGGAAGCCCTG | |
| VMAT1 | NM_003053.3 | CACACACACACATACACAGAATCCTCAGATAACAGGAGGC<br>AATAAATCCAACAGCACATCCACGTTCAGAGAACAGTGTC<br>CCTGCTGTCTTGCTAACAGCTGCCAATACCTCACTGAGTG<br>CCTCACACCAACATGGGCTCCAAGTGAGTTTCCTTCGTCT<br>GGGCAGACTCCCTCCCCTCTTCCATAAAGGCTGCAGGAGA<br>CCTGTAGCTGTCACAGGACCTTCCCTAAGAGCCCGCAGGG<br>GAAGACTGCCCCAGTCCGGCCATCACCATGCTCCGGACCA<br>TTCTGGATGCTCCCCAGCGGTTGCTGAAGGAGGGGAGAGC<br>GTCCCGGCAGCTGGTGCTGGTGGTGGTATTCGTCGCTTTG<br>CTCCTGGACAACATGCTGTTTACTGTGGTGGTGCCAATTG<br>TGCCCACCTTCCTATATGACATGGAGTTCAAAGAAGTCAA<br>CTCTTCTCTGCACCTCGGCCATGCCGGAAGTTCCCCACAT<br>GCCCTCGCCTCTCCTGCCTTTTCCACCATCTTCTCCTTCT<br>TCAACAACAACACCGTGGCTGTTGAAGAAAGCGTACCTAG<br>TGGAATAGCATGGATGAATGACACTGCCAGCACCATCCCA<br>CCTCCAGCCACTGAAGCCATCTCAGCTCATAAAAACAACT<br>GCTTGCAAGGCACAGGTTCTTGGAGGAAGAGATTACCCG<br>GGTCGGGGTTCTGTTTGCTTCAAAGGCTGTGATGCAACTT<br>CTGGTCAACCCATTCGTGGGCCCTCTCACCAACAGGATTG<br>GATATCATATCCCCATGTTTGCTGGCTTTGTTATCATGTT<br>TCTCTCCACAGTTATGTTTGCTTTTTCTGGGACCTATACT<br>CTACTCTTTGTGGCCCGAACCCTTCAAGGCATTGGATCTT<br>CATTTTCATCTGTTGCAGGTCTTGGAATGCTGGCCAGTGT<br>CTACACTGATGACCATGAGAGAGGACGAGCCATGGGAACT<br>GCTCTGGGGGCCTGGCCTTGGGGTTGCTGGTGGGAGCTC<br>CCTTTGGAAGTGTAATGTACGAGTTTGTTGGGAAGTCTGC<br>ACCCTTCCTCATCCTGGCCTTCCTGGCACTACTGGATGGA<br>GCACTCCAGCTTTGCATCCTACAGCCTTCCAAAGTCTCTC<br>CTGAGAGTGCCAAGGGGACTCCCCTCTTTATGCTTCTCAA<br>AGACCCTTACATCCTGGTGGCTGCAGGGTCCATCTGCTTT<br>GCCAACATGGGGTGGCCATCCTGGAGCCCACACTGCCCA<br>TCTGGATGATGCAGACCATGTGCTCCCCCAAGTGGCAGCT<br>GGGTCTAGCTTTCTTGCCTGCCAGTGTGTCCTACCTCATT<br>GGCACCAACCTCTTTGGTGTGTTGGCCAACAAGATGGGTC<br>GGTGGCTGTGTTCCCTAATCGGGATGCTGGTAGTAGGTAC<br>CAGCTTGCTCTGTGTTCCTCTGGCTCACAATATTTTTGGT<br>CTCATTGGCCCAATGCAGGGCTTGGCCTTGCCATAGGCA<br>TGGTGGATTCTTCTATGATGCCCATCATGGGGCACCTGGT<br>GGATCTACGCCACACCTCGGTGTATGGGAGTGTCTACGCC<br>ATCGCTGATGTGGCTTTTTGCATGGGCTTTGCTATAGGTC<br>CATCCACCGGTGGTGCCATTGTAAAGGCCATCGGTTTTCC<br>CTGGCTCATGGTCATCACTGGGGTCATCAACATCGTCTAT<br>GCTCCACTCTGCTACTACCTGCGGAGCCCCCCGGCAAAGG<br>AAGAGAAGCTTGCTATTCTGAGTCAGGACTGCCCCATGGA | 46 |

TABLE 1-continued

GEP-NEN Biomarker/Houskeeper Sequence Information

| Gene Name | RefSeq Accession | Sequence | SEQ ID NO: |
|---|---|---|---|
| | | GACCCGGATGTATGCAACCCAGAAGCCCACGAAGGAATTT CCTCTGGGGAGGACAGTGATGAGGAGCCTGACCATGAGG AGTAGCAGCAGAAGGTGCTCCTTGAATTCATGATGCCTCA GTGACCACCTCTTTCCCTGGGACCAGATCACCATGGCTGA GCCCACGGCTCAGTGGGCTTCACATACCTCTGCCTGGGAA TCTTCTTTCCTCCCCTCCCATGGACACTGTCCCTGATACT CTTCTCACCTGTGTAACTTGTAGCTCTTCCTCTATGCCTT GGTGCCGCAGTGGCCCATCTTTTATGGGAAGACAGAGTGA TGCACCTTCCCGCTGCTGTGAGGTTGATTAAACTTGAGCT GTGACGGGTTCTGCAAGGGGTGACTCATTGCATAGAGGTG GTAGTGAGTAATGTGCCCCTGAAACCAGTGGGGTGACTGA CAAGCCTCTTTAATCTGTTGCCTGATTTTCTCTGGCATAG TCCCAACAGATCGGAAGAGTGTTACCCTCTTTTCCTCAAC GTGTTCTTTCCCGGGTTTTCCCAGCCGAGTTGAGAAAATG TTCTCAGCATTGTCTTGCTGCCAAATGCCAGCTTGAAGAG TTTTGTTTTGTTTTTTTTCATTTATTTTTTTTTTTAATAA AGTGAGTGATTTTTCTGTGGCTAAATCTAGAGCTGCTAAA AGGGCTTTACCCTCAGTGAAAAGTGTCTTCTATTTTCATT ATCTTTCAGAAACAGGAGCCCATTTCTCTTCTGCTGGAGT TATTGACATTCTCCTGACCTCCCCTGTGTGTTCCTACCTT TTCTGAACCTCTTAGACTCTTAGAAATAAAAGTAGAAGAA AGACAGAAAAAATAACTGATTAGACCCAAGATTTCATGGG AAGAAGTTAAAAGAAACTGCCTTGAAATCCCTCCTGATTG TAGATTTCCTAACAGGAGGGGTGTAATGTGACATTGTTCA TACTTGCTAATAAATACATTATTGCCTAATTCAAAAAAAA AAAAAAAAA | |
| VMAT2 | NM_003054.4 | AGAGCCGGACGGGGTAAACTGAGCGGCGGCGGCGGGGCGC TGGGGCGGAGACTGCGACCCGGAGCCGCCCGGACTGACGG AGCCCACTGCGGTGCGGGCGTTGGCGCGGGCACGGAGGAC CCGGGCAGGCATCGCAAGCGACCCCGAGCGGAGCCCCGGA GCCATGGCCCTGAGCGAGCTGGCGCTGGTCCGCTGGCTGC AGGAGAGCCGCCGCTCGCGGAAGCTCATCCTGTTCATCGT GTTCCTGGCGCTGCTGCTGGACAACATGCTGCTCACTGTC GTGGTCCCCATCATCCCAAGTTATCTGTACAGCATTAAGC ATGAGAAGAATGCTACAGAAATCCAGACGGCCAGGCCAGT GCACACTGCCTCCATCTCAGACAGCTTCCAGAGCATCTTC TCCTATTATGATAACTCGACTATGGTCACCGGGAATGCTA CCAGAGACCTGACACTTCATCAGACCGCCACACAGCACAT GGTGACCAACGCGTCCGCTGTTCCTTCCGACTGTCCCAGT GAAGACAAAGACCTCCTGAATGAAAACGTGCAAGTTGGTC TGTTGTTTGCCTCGAAAGCCACCGTCCAGCTCATCACCAA CCCTTTCATAGGACTACTGACCAACAGAATTGGCTATCCA ATTCCCATATTTGCGGGATTCTGCATCATGTTTGTCTCAA CAATTATGTTTGCCTTCTCCAGCAGCTATGCCTTCCTGCT GATTGCCAGGTCGCTGCAGGGCATCGGCTCGTCCTGCTCC TCTGTGGCTGGGATGGGCATGCTTGCCAGTGTCTACACAG ATGATGAAGAGAGGCAACGTCATGGGAATCGCCTTGGG AGGCCTGGCCATGGGGGTCTTAGTGGGCCCCCCCTTCGGG AGTGTGCTCTATGAGTTTGTGGGGAAGACGGCTCCGTTCC TGGTGCTGGCCGCCCTGGTACTCTTGGATGGAGCTATTCA GCTCTTTGTGCTCCAGCCGTCCCGGGTGCAGCCAGAGAGT CAGAAGGGGACACCCCTAACCACGCTGCTGAAGGACCCGT ACATCCTCATTGCTGCAGGCTCCATCTGCTTTGCAAACAT GGGCATCGCCATGCTGGAGCCAGCCCTGCCCATCTGGATG ATGGAGACCATGTGTTCCCGAAAGTGGCAGCTGGGCGTTG CCTTCTTGCCAGCTAGTATCTCTTATCTCATTGGAACCAA TATTTTTGGGATACTTGCACACAAAATGGGGAGGTGGCTT TGTGCTCTTCTGGGAATGATAATTGTTGGAGTCAGCATTT TATGTATTCCATTTGCAAAAAACATTTATGGACTCATAGC TCCGAACTTTGGAGTTGGTTTTGCAATTGGAATGGTGGAT TCGTCAATGATGCCTATCATGGGCTACCTCGTAGACCTGC GGCACGTGTCCGTCTATGGGAGTGTGTACGCCATTGCGGA TGTGGCATTTTGTATGGGTATGCTATAGGTCCTTCTGCT GGTGGTGCTATTGCAAAGGCAATTGGATTTCCATGGCTCA TGACAATTATTGGGATAATTGATATTCTTTTTGCCCCTCT CTGCTTTTTTCTTCGAAGTCCACCTGCCAAAGAAGAAAAA ATGGCTATTCTCATGGATCACAACTGCCCTATTAAACAA AAATGTACACTCAGAATAATATCCAGTCATATCCGATAGG TGAAGATGAAGAATCTGAAAGTGACTGAGATGAGATCCTC AAAAATCATCAAAGTGTTTAATTGTATAAAACAGTGTTTC CAGTGACACAACTCATCCAGAACTGTCTTAGTCATACCAT CCATCCCTGGTGAAAGAGTAAAACCAAAGGTTATTATTTC CTTTCCATGGTTATGGTCGATTGCCAACAGCCTTATAAAG AAAAAGAAGCTTTTCTAGGGGTTTGTATAAATAGTGTTGA | 47 |

TABLE 1-continued

GEP-NEN Biomarker/Houskeeper Sequence Information

| Gene Name | RefSeq Accession | Sequence | SEQ ID NO: |
|---|---|---|---|
| | | AACTTTATTTTATGTATTTAATTTTATTAAATATCATACA<br>ATATATTTTGATGAAATAGGTATTGTGTAAATCTATAAAT<br>ATTTGAATCCAAACCAAATATAATTTTTTAACTTACATTA<br>ACAAACATTTGGGCAAAAATCATATTGGTAATGAGTGTTT<br>AAAATTAAAGCACACATTATCTCTGAGACTCTTCCAACAA<br>AGAGAAACTAGAATGAAGTCTGAAAAACAGAATCAAGTAA<br>GACAGCATGTTATATAGTGACACTGAATGTTATTTAACTT<br>GTAGTTACTATCAATATATTTATGCGTTAAACAGCTAGTT<br>CTCTCAAGTGTAGAGGACAAGAACTTGTGTCAGTTATCTT<br>TTGAATCCATAAATCTTAGCTGGCATTAGTTTTCTATGTA<br>ATCACCTACCTAGAGAGAGTTGTAAATTATATGTTAACAT<br>GTTATCTGGTTGGCAGCAAACACTAAAGCCAATAAAGGAA<br>AAACAGTAAATGTTCCGAAAGCAGAGAAAAGCAACCAAAC<br>ATATTGTTATGAACTAAAAGCTTTCCCTTTAAGATGCATA<br>CTTGTCTTACTGGATGAAGAAAATTGAGGGTACATGTACC<br>TTATACTGTCAAGGTTGTTTAAACATGATAAGGTTAATCG<br>CCATCTACTTCAAGTTTTAGAAAAGGAAACAAGAAGCTGA<br>AAACAGCTGCTCTGACTTTAATATCTGACTATATCTTTGA<br>TCTGTTTGCAGGTCATCCAAGTGTTTTCTAGGAATATATT<br>TATTTTAGGTTGTCTGAAACTACTATTTTTTAGACTCCTG<br>AAAGTTGTTCACATCAATGTGAAGACAAATTTTAAATGAA<br>AATGAAGAATGAAATTATGTCTTGAATCATATATTAAGAA<br>GTAAAAATAATAGTGATCAGGCAGAAAAGAAAAATGGAAC<br>ATCTAAAAATGTATGTGCTAACTATATCATCCAGTGTGCA<br>GTGTTGTGTATTTTTCTAAGCATGACAACATTGATGTGCC<br>TTTTCAGTGTAACAGCAAATACTGTTAGTGAACATTGTCA<br>ATTTATGTCATTTTGTTAAGAGATATGACTGGAGTGTGCA<br>GTGTGGAATGTCTCTAATACTACTTGTGAATCCTGCAGTT<br>CTATAATCATAAACAAAAATTACTTAGTTTCGTTAAGCTA<br>AGATTGTGTTTGTGTTAACTTCGACATCAAGGAGCAAAGA<br>ACTTTAGAACAGACTCCTCAATCTTGTGACTTTCTTATTC<br>TCTAGGAAAGTAACACTTCGTTTCATGAAGCTTTTCTGTG<br>GGGCTTCGATTATTTCAAGTCTGGTTTCTAAGTGCAGTGT<br>GTTTGAAGCAAACGAACTTCCAACTCACTTATTTGGCATT<br>GGGCAACTTGGCCAAGTCTGCCACTTTGGAAGATGGCTCT<br>GGAGGAAACTCTCATATGGCTAAAAAGGCAGGCTAGTTTC<br>TTACTTCTACAGGGGTAGAGCCTTAAAAAAGAACGTGCTA<br>CAAATTGGTTCTCTTTGAGGGTTTCTGGTTCTCCCTGCCC<br>CCAATACCATATACTTTATTGCAATTTTATTTTTGCCTTT<br>ACGGCTCTGTGTCTTTCTGCAAGAAGGCCTGGCAAAGGTA<br>TGCCTGCTGTTGGTCCCTCGGGATAAGATAAAATATAAAT<br>AAAACCTTCAGAACTGTTTTGGAGCAAAAGATAGCTTGTA<br>CTTGGGGAAAAAAATTCTAAGTTCTTTTATATGACTAATA<br>TTCTTGGTTAGCAAGACTGGAAAGAGGTGTTTTTTTAAAA<br>TGTACATACCAGAACAAAGAACATACAGCTCTCTGAACAT<br>TTATTTTTTGAACAGAGGTGGTTTTTATGTTTGGACCTGG<br>TAATACAGATACAAAAACTTTAATGAGGTAGCAATGAATA<br>TTCAACTGTTTGACTGCTAAGTGTATCTGTCCATATTTTA<br>GCAAGTTTACTTAATAAATCTTCTGAACCATGAAAAAAAA<br>AAAAA | |
| VPS13C | NM_001018088.2 | CCGGAGGGGCTGTCATTTGCAGCGCTGGTCGCAGCCCTCA<br>GCTGCGCCGGGCGGTTCCGGCTCCTCCCTCTCCTTGTGCC<br>TCAGCGCCACCATGGTGCTGGAGTCGGTGGTCGCGGACTT<br>GCTGAACCGCTTCCTGGGGGACTATGTGGAGAACCTGAAC<br>AAGTCCCAGCTGAAGCTGGGCATCTGGGGCGGAAATGTGG<br>CTTTAGATAATCTACAGATAAAAGAAAATGCCCTGAGTGA<br>ATTGGATGTTCCTTTTAAAGTCAAGGCTGGCCAAATTGAT<br>AAATTAACTTTGAAGATTCCTTGGAAGAACCTTTATGGAG<br>AAGCAGTTGTTGCGACCCTGGAAGGATTATACCTGCTTGT<br>TGTCCCTGGAGCAAGTATTAAGTATGATGCTGTAAAAGAA<br>GAAAAATCCTTGCAGGATGTTAAACAGAAAGAGCTATCCC<br>GAATTGAAGAAGCCCTTCAAAAAGCAGCAGAAAAAGGCAC<br>ACATTCAGGGGAGTTCATATATGGCTTGGAGAACTTTGTT<br>TACAAGGACATCAAGCCTGGACGTAAACGTAAAAAGCACA<br>AAAAACATTTTAAGAAACCTTTTAAAGGTCTTGATCGTTC<br>AAAAGATAAGCCAAAAGAAGCCAAAAAGGATACATTTGTG<br>GAAAAATTGCAACTCAAGTAATAAAAAATGTACAAGTAA<br>AAATCACAGATATTCACATTAAATATGAAGATGATGTCAC<br>TGATCCAAAGCGGCCTCTTTCATTTGGTGTCACACTGGGA<br>GAGCTTAGTCTACTGACTGCAAATGAACACTGGACTCCAT<br>GCATATTTAAATGAAGCAGACAAAATTATATACAAGCTTAT<br>ACGACTTGATAGTCTTAGCGCCTACTGGAATGTAAATTGC<br>AGCATGTCTTACCAGAGATCAAGGGAACAGATTTTGGATC<br>AGCTGAAAAATGAAATTCTTACAAGTGGAAATATACCCCC | 48 |

TABLE 1-continued

GEP-NEN Biomarker/Houskeeper Sequence Information

| Gene Name | RefSeq Accession | Sequence | SEQ ID NO: |
|---|---|---|---|
| | | AAATTATCAATACATTTTCCAGCCAATATCAGCCTCTGCA<br>AAACTCTACATGAATCCTTATGCAGAATCAGAGCTCAAAA<br>CGCCCAAACTGGATTGCAACATAGAAATACAAAATATTGC<br>CATTGAACTGACCAAACCTCAGTACTTAAGTATGATTGAC<br>CTTTTGGAGTCAGTGGATTATATGGTTAGGAATGCGCCTT<br>ATAGGAAATACAAGCCTTATTTACCACTTCATACCAATGG<br>TCGACGATGGTGGAAATATGCAATTGATTCTGTTCTTGAA<br>GTTCATATAAGAAGGTATACACAGATGTGGTCATGGAGTA<br>ACATAAAAAAGCACAGGCAGTTACTCAAGAGTTATAAAAT<br>TGCCTACAAAAACAAGTTAACACAGTCTAAAGTCTCAGAA<br>GAAATACAGAAAGAAATTCAGGACTTGGAGAAGACTCTAG<br>ATGTTTTTAACATAATTTTAGCAAGGCAACAAGCACAAGT<br>TGAGGTGATTCGGTCTGGGCAAAAATTAAGGAAAAAGTCT<br>GCTGACACAGGCGAGAAACGTGGAGGCTGGTTTAGTGGGT<br>TGTGGGGTAAGAAAGAGTCTAAGAAAAAGGACGAAGAATC<br>ATTGATTCCTGAAACTATTGATGACCTTATGACTCCAGAG<br>GAAAAAGATAAACTCTTCACTGCCATTGGTTATAGTGAGA<br>GTACCCACAACCTAACTTTACCTAAGCAGTATGTTGCCCA<br>TATTATGACCCTGAAGTTAGTAAGCACCTCTGTTACGATA<br>AGAGAAAACAAGAATATTCCAGAAATACTAAAAATTCAGA<br>TAATTGGCCTGGGCACTCAAGTATCTCAGCGACCAGGAGC<br>ACAAGCACTTAAGGTAGAAGCGAAATTAGAACACTGGTAT<br>ATAACAGGTTTGAGACAGCAGGATATTGTGCCATCACTTG<br>TGGCTTCAATTGGTGACACTACATCATCCTTGCTTAAAAT<br>TAAATTTGAAACCAATCCGGAGGATAGTCCTGCTGACCAG<br>ACTCTGATTGTTCAGTCCCAGCCTGTGGAGGTCATCTATG<br>ATGCTAAAACTGTCAATGCAGTGGTTGAATTCTTTCAATC<br>AAATAAGGGATTGGATCTTGAGCAAATAACATCAGCAACA<br>TTGATGAAGCTGGAAGAAATTAAGGAGAGAACAGCTACAG<br>GACTTACACATATTATTGAAACTCGAAAAGTCCTTGATTT<br>AAGGATAAATCTGAAGCCTTCTTATCTAGTAGTTCCACAG<br>ACGGGTTTCCACCATGAAAAGTCAGATCTTCTGATTTTAG<br>ATTTTGGTACATTTCAGCTCAACAGTAAAGATCAAGGTTT<br>ACAGAAGACTACTAATTCATCTCTGGAAGAAATAATGGAT<br>AAGGCATATGACAAGTTTGATGTTGAAATAAAAAATGTAC<br>AACTACTTTTTGCAAGAGCAGAGGAAACCTGGAAAAAGTG<br>TCGATTTCAGCATCCATCAACTATGCATATATTGCAACCC<br>ATGGATATTCATGTTGAGTTGGCTAAGGCCATGGTAGAAA<br>AAGACATTAGAATGGCCAGATTTAAAGTGTCAGGAGGACT<br>TCCTTTGATGCATGTGAGAATTTCTGACCAGAAGATGAAA<br>GATGTGCTATATTTGATGAACAGTATACCTTTGCCACAGA<br>AATCATCAGCCCAGTCTCCAGAGAGACAGGTATCCTCAAT<br>TCCTATTATTTCAGGTGGTACAAAAGGTCTACTTGGTACT<br>TCACTATTGCTAGACACTGTGGAATCAGAGTCTGATGATG<br>AGTATTTTGATGCTGAAGATGGAGAACCACAGACTTGTAA<br>AAGTATGAAAGGATCAGAACTTAAAAAAGCTGCAGAGGTC<br>CCAAATGAGGAGCTCATCAATCTTCTACTCAAGTTTGAAA<br>TTAAAGAAGTGATTTTGGAATTTACTAAACAGCAGAAAGA<br>AGAAGATACAATTCTAGTATTTAATGTTACTCAGTTAGGA<br>ACAGAGGCCACAATGAGAACATTTGACTTAACTGTGGTAT<br>CTTATTTAAAGAAAATCAGCTTGGATTATCATGAAATTGA<br>AGGATCCAAAAGGAAGCCCCTTCACTTGATTAGCTCTTCT<br>GACAAACCTGGATTAGATCTTTTGAAAGTGGAGTATATTA<br>AGGCTGATAAGAATGGACCTAGTTTTCAAACTGCTTTTGG<br>AAAAACTGAACAAACAGTTAAGGTGGCCTTTTCATCTTTA<br>AATCTGTTGCTGCAAACACAAGCTCTTGTCGCTTCTATTA<br>ATTACCTCACAACCATTATTCCATCTGATGATCAAAGCAT<br>AAGTGTTGCTAAGGAGGTACAAATTTCAACTGAAAAACAA<br>CAAAAAAATTCAACTCTGCCAAAAGCGATTGTATCCTCCA<br>GAGATAGTGACATTATTGATTTCAGGCTATTTGCCAAGTT<br>GAATGCTTTCTGTGTCATTGTTTGCAACGAAAAGAACAAT<br>ATCGCCGAAATCAAGATTCAAGGACTGGATTCCTCCCTTT<br>CTCTCCAGTCAAGAAAGCAGTCACTTTTTGCCCGACTAGA<br>AAATATTATTGTCACAGATGTTGATCCAAAGACAGTTCAT<br>AAGAAAGCTGTGTCAATAATGGGAAATGAAGTTTTCCGTT<br>TTAATTTGGATTTGTATCCAGATGCTACTGAGGGGGATTT<br>GTATACTGACATGTCCAAAGTGGATGGTGTGCTGTCTCTG<br>AATGTTGGCTGTATTCAGATTGTCTATCTTCATAAATTCC<br>TTATGTCACTTCTGAACTTCCTGAATAATTTCCAGACAGC<br>CAAAGAGTCTCTGAGTGCTGCCACTGCCCAGGCTGCAGAA<br>AGGGCTGCCACAAGTGTGAAAGATCTTGCCCAGAGGAGTT<br>TTCGTGTTTCCATCAATATTGATTTGAAAGCACCGGTTAT<br>AGTCATCCCACAGTCTTCTATTTCCACCAATGCAGTAGTG<br>GTAGATCTTGGGTTAATCAGAGTTCATAATCAGTTCAGTC<br>TGGTGTCTGATGAAGACTACTTAAATCCTCCAGTAATTGA | |

TABLE 1-continued

GEP-NEN Biomarker/Houskeeper Sequence Information

| Gene Name | RefSeq Accession | Sequence | SEQ ID NO: |
|---|---|---|---|
| | | TAGAATGGATGTGCAGCTAACAAAGCTTACACTTTATAGG<br>ACAGTGATCCAGCCAGGCATCTACCATCCTGATATTCAGC<br>TGTTGCACCCAATTAACTTGGAATTTCTTGTAAATCGGAA<br>TCTAGCTGCATCTTGGTACCACAAGGTGCCTGTTGTGGAA<br>ATTAAAGGACATCTTGATTCAATGAATGTTAGTCTAAATC<br>AAGAAGATCTTAATCTTTTATTTAGGATACTAACAGAAAA<br>TCTCTGTGAGGGTACTGAAGACTTGGATAAAGTGAAACCA<br>AGAGTACAAGAGACAGGTGAAATTAAAGAGCCCCTTGAAA<br>TCTCTATATCACAAGATGTACATGATTCAAAAAATACTTT<br>AACAACTGGAGTGGAAGAAATTAGGTCTGTAGACATCATT<br>AATATGCTGCTGAATTTTGAAATTAAAGAGGTTGTGGTTA<br>CTTTGATGAAAAAATCAGAAAAGAAAGGAAGGCCTTTACA<br>TGAGCTAAATGTCCTGCAACTTGGAATGGAAGCTAAAGTT<br>AAAACCTATGACATGACTGCTAAAGCTTATCTAAAAAAAA<br>TTAGTATGCAGTGCTTTGATTTCACTGACTCTAAAGGGGA<br>ACCTCTTCACATTATTAACTCTTCTAATGTGACTGACGAA<br>CCCCTTCTGAAAATGTTACTGACAAAGGCAGACAGTGATG<br>GACCAGAATTTAAAACTATTCATGACAGTACCAAACAGAG<br>ACTGAAGGTTTCATTTGCATCCTTAGACTTAGTACTTCAT<br>TTGGAAGCTTTACTTTCCTTCATGGATTTTTTATCATCTG<br>CTGCTCCATTCTCTGAGCCTTCCTCTTCTGAGAAGGAATC<br>CGAGCTGAAACCACTTGTGGGGGAGTCCAGAAGTATCGCT<br>GTCAAAGCTGTATCCAGCAACATTTCCCAAAAGGATGTGT<br>TTGATTTAAAGATCACAGCTGAATTAAATGCATTTAATGT<br>CTTTGTCTGTGATCAGAAGTGTAACATTGCAGATATTAAA<br>ATACATGGAATGGATGCCTCTATTTCTGTGAAGCCTAAGC<br>AGACTGATGTGTTTGCCAGACTTAAAGATATTATAGTTAT<br>GAATGTAGATTTGCAGTCCATTCACAAAAAGGCTGTCTCT<br>ATTTTGGGAGATGAAGTCTTTAGGTTCCAACTGACTCTTT<br>ATCCAGATGCCACAGAAGGAGAGGCCTATGCTGATATGTC<br>CAAAGTAGACGGCAAACTTAGTTTTAAAGTGGGTTGTATT<br>CAGATTGTTTATGTTCATAAATTCTTCATGTCTCTTTTGA<br>ACTTCCTCAACAATTTCCAAACTGCTAAAGAAGCTTTGAG<br>TACAGCCACAGTCCAGGCTGCAGAAAGAGCTGCTTCCAGC<br>ATGAAAGACTTGGCTCAAAAGAGTTTCCGCCTTTTGATGG<br>ATATTAATTTGAAAGCACCAGTTATTATTATTCCTCAGTC<br>TTCAGTATCACCTAATGCTGTTATAGCAGATCTGGGTTTA<br>ATCAGAGTTGAAAACAAGTTTAGCTTGGTTCCTATGGAAC<br>ATTATTCTCTTCCTCCAGTCATTGATAAAATGAACATCGA<br>ACTCACTCAGTTGAAGCTGTCAAGAACTATTTTGCAGGCT<br>AGCTTGCCACAAAATGACATTGAAATTTTAAAACCAGTCA<br>ACATGCTTTTGTCCATACAGCGAAACTTAGCAGCAGCATG<br>GTATGTGCAAATTCCAGGGATGGAGATAAAAGGAAAACTA<br>AAACCTATGCAGGTTGCTCTCAGTGAAGATGACTTGACAG<br>TTTTAATGAAAATTTTGCTAGAAAATCTTGGAGAAGCTTC<br>CTCACAACCAAGCCCTACACAGTCTGTGCAGGAGACTGTA<br>AGAGTGAGAAAAGTTGATGTTTCAAGTGTACCTGACCATC<br>TCAAAGAACAAGAAGATTGGACAGACTCAAAGCTCTCTAT<br>GAACCAGATTGTCAGTCTCCAATTTGACTTTCACTTTGAA<br>TCTCTTTCCATTATCCTTTATAACAATGATATCAACCAGG<br>AATCTGGAGTTGCATTTCATAATGACAGTTTCCAACTTGG<br>TGAACTCAGACTACATCTTATGGCCTCCTCAGGGAAGATG<br>TTTAAGGATGGCTCAATGAATGTCAGCGTTAAACTTAAGA<br>CATGCACCCTTGATGATCTCAGAGAAGGAATTGAGAGAGC<br>AACATCGAGAATGATTGACAGAAAGAATGACCAAGATAAC<br>AACAGTTCTATGATTGATATAAGTTACAAACAAGACAAAA<br>ATGGAAGTCAAATTGATGCTGTTCTTGACAAGCTGTATGT<br>ATGTGCCAGTGTGGAATTTCTGATGACTGTGGCAGATTTC<br>TTTATCAAAGCTGTGCCTCAGAGTCCAGAAAATGTGGCAA<br>AAGAAACACAGATTTTACCAAGACAGACTGCCACAGGGAA<br>GGTCAAGATAGAGAAAGATGACTCTGTTAGACCAAATATG<br>ACTTTAAAGGCCATGATCACAGATCCAGAAGTGGTATTTG<br>TTGCCAGCCTGACAAAGGCTGATGCTCCTGCTCTGACAGC<br>CTCGTTTCAGTGCAACCTTTCTCTGTCAACATCCAAACTC<br>GAACAGATGATGGAAGCTTCTGTGAGAGATCTGAAAGTGC<br>TCGCTTGCCCTTTTCTCAGAGAAAAGAGAGGGAAAAACAT<br>TACCACAGTCTTGCAGCCCTGTTCTTTATTTATGGAAAAA<br>TGTACGTGGGCTTCAGGAAAGCAAAATATAAATATTATGG<br>TTAAAGAATTTATAATTAAGATTTCACCCATAATTCTTAA<br>TACTGTGTTGACAATCATGGCTGCATTGTCTCCAAAAACA<br>AAAGAAGATGGATCCAAAGATACGTCTAAGGAAATGGAAA<br>ATCTTTGGGGTATCAAATCGATTAATGATTATAACACTTG<br>GTTTCTTGGTGTTGACACGGCAACAGAAATAACGGAAAGC<br>TTCAAAGGCATTGAACATTCACTGATAGAGGAAAATTGTG<br>GTGTTGTTGTAGAATCCATTCAAGTTACCTTAGAATGTGG | |

TABLE 1-continued

GEP-NEN Biomarker/Houskeeper Sequence Information

| Gene Name | RefSeq Accession | Sequence | SEQ ID NO: |
|---|---|---|---|
| | | CCTTGGACATCGAACTGTACCTTTATTATTGGCAGAGTCT | |
| | | AAGTTTTCAGGAAATATTAAAAATTGGACTTCTCTAATGG | |
| | | CTGCTGTTGCTGACGTGACACTACAGGTGCACTATTACAA | |
| | | TGAGATCCATGCTGTCTGGGAGCCACTGATTGAGAGAGTG | |
| | | GAGGGGAAGAGACAATGGAATTTAAGGCTTGATGTAAAGA | |
| | | AGAACCCAGTTCAGGATAAAAGTTTGCTGCCAGGAGATGA | |
| | | TTTTATTCCTGAGCCACAAATGGCAATTCATATTTCTTCA | |
| | | GGAAATACAATGAATATAACAATATCCAAAAGTTGTCTTA | |
| | | ATGTTTTCAACAATTTAGCAAAAGGTTTTTCAGAGGGCAC | |
| | | TGCTTCTACTTTTGACTACTCTTTAAAGGACAGAGCTCCT | |
| | | TTTACGGTAAAAAATGCTGTAGGTGTTCCCATTAAGGTGA | |
| | | AGCCCAATTGTAATCTCAGAGTAATGGGCTTCCCTGAGAA | |
| | | AAGTGATATTTTTGATGTTGATGCTGGCCAGAATTTGGAA | |
| | | CTGGAGTATGCCAGCATGGTACCTTCAAGTCAAGGGAACC | |
| | | TATCTATATTGAGCCGTCAAGAAAGCTCCTTCTTCACTCT | |
| | | GACCATTGTACCTCATGGATATACAGAAGTTGCAAATATC | |
| | | CCTGTGGCCAGACCTGGACGGCGATTGTATAATGTACGGA | |
| | | ATCCCAATGCCAGTCATTCTGACTCTGTCTTGGTACAAAT | |
| | | TGATGCAACTGAAGGGAATAAAGTAATTACCCTTCGCTCT | |
| | | CCTCTACAGATCAAAAACCATTTCTCCATTGCATTTATCA | |
| | | TCTATAAATTTGTTAAGAATGTTAAGCTATTGGAGCGCAT | |
| | | TGGGATAGCCAGACCTGAAGAGGAGTTCCATGTTCCTTTA | |
| | | GATTCATATAGATGTCAATTGTTTATCCAGCCAGCTGGAA | |
| | | TCTTAGAGCATCAGTACAAAGAATCTACCACTTATATTTC | |
| | | CTGGAAGGAAGAACTTCATAGGAGCAGGGAAGTCAGATGC | |
| | | ATGTTGCAGTGTCCATCAGTAGAAGTCAGCTTCTTACCTC | |
| | | TCATAGTGAATACAGTTGCTCTGCCTGATGAATTGAGCTA | |
| | | CATATGTACACATGGGAAGACTGGGATGTAGCTTACATT | |
| | | ATTCATCTTTATCCTTCTCTCACTTTGCGGAATCTTCTCC | |
| | | CATATTCCCTAAGATATTTACTTGAGGGAACAGCAGAAAC | |
| | | TCATGAGCTGGCAGAAGGCAGTACTGCTGATGTTCTGCAT | |
| | | TCGAGAATCAGTGGTGAAATAATGGAATTAGTCCTGGTGA | |
| | | AATACCAGGGCAAAAACTGGAATGGACATTTCCGCATACG | |
| | | TGATACACTACCAGAATTCTTTCCTGTGTGTTTTTCTTCT | |
| | | GACTCCACAGAAGTGACGACAGTCGACCTGTCAGTCCACG | |
| | | TCAGGAGAATTGGCAGCCGGATGGTGCTGTCTGTCTTTAG | |
| | | TCCCTATTGGTTAATCAACAAGACTACCCGGGTTCTCCAG | |
| | | TATCGTTCAGAAGATATTCATGTGAAACATCCAGCTGATT | |
| | | TCAGGGATATTATTTTATTTTCTTTCAAGAAGAAGAACAT | |
| | | TTTTACTAAAAATAAGGTACAATTAAAAATTTCAACCAGT | |
| | | GCCTGGTCCAGTAGTTTCTCATTGGATACAGTGGGAAGTT | |
| | | ATGGGTGTGTGAAGTGTCCTGCCAACAATATGGAGTACCT | |
| | | GGTTGGTGTTAGCATCAAAATGAGCAGTTTCAACCTTTCA | |
| | | CGAATAGTTACCCTGACTCCCTTTTGTACCATTGCAAACA | |
| | | AGTCATCATTAGAACTAGAAGTTGGCGAGATTGCATCTGA | |
| | | TGGCTCAATGCCAACTAATAAATGGAACTATATTGCTTCT | |
| | | TCAGAGTGCCTTCCATTTTGGCCAGAAAGTTTGTCAGGCA | |
| | | AACTTTGTGTGAGAGTGGTGGGCTGTGAAGGATCTTCCAA | |
| | | ACCATTCTTTTATAACCGACAGGATAATGGCACTTTATTG | |
| | | AGCTTAGAAGATCTGAATGGGGGTATCTTGGTGGATGTAA | |
| | | ACACTGCCGAACATTCAACTGTCATAACTTTTTCTGATTA | |
| | | CCATGAGGGATCTGCACCTGCCTTGATAATGAACCATACA | |
| | | CCATGGGACATCCTCACATACAAACAGAGTGGGTCACCAG | |
| | | AAGAAATGGTCTTGCTGCCAAGACAGGCTCGACTTTTTGC | |
| | | CTGGGCAGATCCTACTGGTACCAGAAAACTTACATGGACA | |
| | | TATGCAGCAAATGTTGGGGAACATGATCTGTTAAAGGATG | |
| | | GATGTGGACAGTTTCCATATGATGCAAACATCCAGATACA | |
| | | CTGGGTATCATTTCTGGATGGGCGCCAGAGAGTTTTGCTT | |
| | | TTCACCGATGATGTTGCCTTGGTTTCCAAAGCACTGCAGG | |
| | | CAGAAGAAATGGAACAGGCTGATTATGAAATAACCTTGTC | |
| | | TCTCCACAGTCTTGGGCTTTCACTGGTTAACAATGAAAGC | |
| | | AAGCAGGAAGTTTCCTATATTGGGATAACCAGTTCTGGTG | |
| | | TTGTTTGGGAGGTGAAACCAAAGCAGAAATGGAAGCCATT | |
| | | TAGTCAAAAGCAGATAATCTTATTGGAACAATCCTATCAG | |
| | | AAACATCAAATATCAAGAGACCATGGCTGGATTAAGCTAG | |
| | | ATAATAATTTTGAGGTCAATTTTGATAAAGATCCAATGGA | |
| | | AATGCGCCTCCCTATTCGTAGCCCTATTAAACGAGACTTT | |
| | | TTATCAGGAATTCAGATTGAATTTAAGCAGTCTTCTCACC | |
| | | AGAGAAGTTTAAGGGCCAGGTTGTACTGGCTTCAGGTTGA | |
| | | TAATCAGTTACCAGGTGCAATGTTCCCTGTTGTATTTCAT | |
| | | CCTGTTGCCCCTCCAAAATCTATTGCTTTAGATTCAGAGC | |
| | | CCAAGCCTTTCATTGATGTGAGTGTCATCACAAGATTTAA | |
| | | TGAGTACAGTAAAGTCTTACAGTTCAAGTATTTTATGGTC | |
| | | CTCATTCAGGAAATGGCCTTAAAAATTGATCAAGGGTTTC | |
| | | TAGGAGCTATTATTGCACTGTTTACCCCAACAACAGACCC | |

TABLE 1-continued

GEP-NEN Biomarker/Houskeeper Sequence Information

| Gene Name | RefSeq Accession | Sequence | SEQ ID NO: |
|---|---|---|---|
| | | TGAAGCTGAAAGAAGACGGACAAAGTTAATCCAACAAGAT<br>ATTGATGCTCTAAATGCAGAATTAATGGAGACTTCAATGA<br>CTGATATGTCAATTCTTAGTTTCTTTGAACATTTCCATAT<br>TTCTCCTGTGAAGTTGCATTTGAGTTTGTCTTTGGGTTCC<br>GGAGGTGAAGAATCAGACAAAGAAAAACAGGAAATGTTTG<br>CAGTTCATTCTGTCAACTTGCTGTTGAAAAGCATAGGTGC<br>TACTCTGACTGATGTGGATGACCTTATATTCAAACTTGCT<br>TATTATGAAATTCGATATCAGTTCTACAAGAGAGATCAGC<br>TTATATGGAGTGTTGTTAGGCATTACAGTGAACAGTTCTT<br>GAAACAGATGTATGTCCTTGTATTGGGGTTAGATGTACTT<br>GGAAACCCATTTGGATTAATTAGAGGTCTGTCTGAAGGAG<br>TTGAAGCTTTATTCTATGAACCCTTCCAGGGTGCTGTTCA<br>AGGCCCTGAAGAATTTGCAGAGGGGTTAGTGATTGGAGTG<br>AGAAGCCTCTTTGGACACACAGTAGGTGGTGCAGCAGGAG<br>TTGTATCTCGAATCACCGGTTCTGTTGGGAAAGGTTTGGC<br>AGCAATTACAATGGACAAGGAATATCAGCAAAAAAGAAGA<br>GAAGAGTTGAGTCGACAGCCCAGAGATTTTGGAGACAGCC<br>TGGCCAGAGGAGGAAAGGGCTTTCTGCGAGGAGTTGTTGG<br>TGGAGTGACTGGAATAATAACAAAACCTGTGGAAGGTGCC<br>AAAAAGGAAGGAGCTGCTGGATTCTTTAAAGGAATTGGAA<br>AAGGGCTTGTGGGTGCTGTGGCCCGTCCAACTGGTGGAAT<br>CGTAGATATGGCCAGTAGTACCTTCCAAGGCATTCAGAGG<br>GCAGCAGAATCAACTGAGGAAGTATCTAGCCTCCGTCCCC<br>CTCGCCTGATCCATGAAGATGGCATCATTCGTCCTTATGA<br>CAGACAGGAATCTGAGGGCTCTGACTTACTTGAGCAAGAA<br>CTGGAAATACAGGAATAAATGTTTCCTAAACTACTACTTG<br>ATTTCATCCTTAAAAATCAAAACAAACTGTGGTGTTAATT<br>GACTGTGTGTGAATTCCATTGTCAATTTTAATGAAATTTT<br>CTTTAAAACTCTCACCTCCATCTGAACTTTTCATAGTAGT<br>GGGATTGACTACAAATAAAAACTTGTGGTATTCCTGGTAA<br>TACTGTCCAGAAATAAGAGATTAGTATAAAATATTAAAGG<br>ATGCAGAGAATCAGCTCTCTTCTGCGTTTAATAGATGAAA<br>GCCTTTATTGAGCTCAGAAGCAGATACTGTTACTATCATT<br>TCGAAAATTTTATCTTATGGTGTTCATGTGCATTTCAGGT<br>AAAATTGAAAACAGGACAATTATTATGTCCAATTAATAT<br>GTTTATGTTTGTGAGTCTTGATGATGGAATTACATAGCTT<br>TCTGTTTCACAAATGGCTCTAAATTTGCTTAAGTTACGGG<br>ACTATTACCTGGAGCATCTGCTTTAATAATTGAATTGTCA<br>GTTGCTCTGAGCCTGCCCTTAGACCTCAAGTAATAAATAG<br>TTGGCACATGAATTTTGAGGATATGTTTCCTCTTCCCTCT<br>TTTTCCTATTTAACCCCTTGGTACTGTTGCTAAATAAATG<br>ATAGCCATTTTATAATTATGTTATATACATTTTCAGCCTT<br>TAGCATTTCTGCTTTTCAAAAATTGAATCTCCTTGTTGGT<br>TATGCTTATTTCATAATTATTAGTTTTAATTAATGTAGAT<br>AGAAGTTGAACATGTAATTAGGCAAATTGCTGTGTGGCAC<br>TTGAATACATAGATTTCTTTATTTTCAAAAACCAACCTTT<br>TGCTTTTAAATCCTTAGAGAGGGTTTATTATCTTAGAGAA<br>AAAATAATTATAATCATTATTTTTGAAATTAGTATCCTCT<br>TAATTCTCAACATAAGTTATGTTTCAATTTCTTTTTTTTG<br>TAATAAATGATGGAAATGTTTAACAATGTCTTATCTAGCA<br>ACTTTCATGCTTCTCCTCAGAAATGAAGCCAAAGTATAAA<br>CTTAGATTTAATGTGTTGTATATTTGAAGAGAATGAAACT<br>ATTAACATATAATTGTTCAGTTGGATTATGTATTTTAAGG<br>ATTGCAGTTATCAAAATAATAAATTGAATGTTTTATGTTT<br>AACCACTTTAAAGAAGAAAGACTGACATCCAAAAACCAGC<br>GTGTGCTAGATATACAAAGGAAATTACTTCTGTCCTTAAG<br>GGACCAAGTATAACAAAACATGTAACTGTTAAAAGTAGCT<br>GACAAACCTTTCTTGTGCCTAGATAATTTAGCATTGGCAA<br>AAATGTCACCACATGCAGTTTTCTAGGAGAGTCAAGCACA<br>AATAACTAATTCAAGATGCTGACTTAAATCATCTCCAATA<br>GTTACCCTTCCTGAGATTCTAAAGTAACAATTTTTAATTT<br>TACTGGTTATATTGCTGTTTTACTGAGACTTACTTTTAAG<br>AACCCCTGTAACTTAAGATTTTTTCTTAATTGTTTTGTTT<br>AGCTCTGTTATTAATTTTTTCCTTGTGATATCTTTTTATA<br>ACTCTCTGTCAAAAAGCACAAAACTTCAAGAAACTTTTAA<br>TTATTTTGTCTGAACATATAATCTTGTCTGATTTCTTAGT<br>TTTTATTAAGATATCAGACAACTTTTAAAACTTTAGTGCA<br>TTATTATAATTACTGGAAGAAAAAGAATGATTATACACTA<br>ATGAGAGGACTTGGTAGTTTTTGTCGTGGATGTCAAGTGT<br>GGGCATGGATAATTGAAATATTTAGGCTATTTCATTCTTT<br>GCCCATCTTGCTGTGATCAGTTAGTTGGGTAAAAATATTT<br>ATTGATTATTTAGACTGTACTGGATATACAAAAGAAGCCT<br>TCTGTCCTTAAGGGACCGAGTAAAACAAAACATGGAAATA<br>TTAAAGAGTATTAGAGTATAAAAGTATATCTTTTTAGCCC<br>TTTGTAATATGGCCAAATTCTAAATAATTTATTTGGGGAT | |

TABLE 1-continued

GEP-NEN Biomarker/Houskeeper Sequence Information

| Gene Name | RefSeq Accession | Sequence | SEQ ID NO: |
|---|---|---|---|
| | | CTTTTGATCCTCATGTTCCTTTTTCTCCTAAGTACTACTT<br>TGTATTCTTTAATATGCAGCTTTGAGAGTTACTGAATCAT<br>ATATTATATTTCCATGAGATGTACTATTCTACTTATCCTC<br>TAATCTTCATATATATATACACACACACATATATATACAC<br>ATACATATATACACACGTACATATATGTACACATACAGAT<br>ATACATACACACAAACACATATATACACACATACATATAC<br>ACACATATATATACACATACAAATATACACATATATACAC<br>ATACATATATATACACACATACAAATATACCCATATGTAC<br>ACATACATATATACACATACATATATACACACACATATAC<br>ACACATATATACGCAAACATACACATATTTACACATACAT<br>ATATACATACATTATATGTATGTATATATAGTCATTTAAT<br>ACTCATTTTGGTTCACATACTTATGATCATGCAACGTTTA<br>AAACAGCATTTCTTGCTTTTTAGTTTTAGTTATATTTTTC<br>CATGTTCTTAGAAATGCCTCATTAACATTTTTAATTCTTG<br>TATTGCCATCTATTGAGGTGACATTACATTGTGTTTTTAT<br>CTCGTCTTAATTCATGACATTAAATTATTCTACTAACAGT<br>AATAATGCTGTAATAAACATCATTATAGATTTTGCTTTTT<br>TATATCTTGTTTGCTTTTTCATATTTCCTTAGAATTTACT<br>TGAAAAAATTGAATTACTGGGTAAAGGGCTTTTGCAAAGT<br>ATTGTTAAATTCCTCGAGTTGCATTTTTGGAAAGGGGACG<br>TGAATATTTTATCAACTAATTTGGTCTCCCTGCTGCCATT<br>AGTGACTGAATATCTTAATCTGAATCTCAGAGTGTAGTGG<br>GTTTTTAGTAGTGCTGAAGACAAGTTTTCTAAAGTGTATT<br>ATGGTGATAAATTATATTTTAAAAACTGTCAATGGCTTGA<br>AGCACAATAGCCTAATAACTAACGAAAATACATACAAGAT<br>AGAAAGTGGGTAGTATTCTTGTACTTGCATTTCAGATCT<br>AAATATTTTAACATATTTAAATTTCAAGCTGCAGATAAAT<br>GCATTACATTATTAAATTCATTTCCCATTTTCTCTTTGAA<br>GAAATTAAGGCAAAAGTGTTAAAAGATTTTAACTAATTCG<br>CACAAGTGAATTGTGAAACAAGTAGCTATTGCTGTGAAAT<br>CTGCACTCCTCTCTGAGACTCATTCTGAAGATGAGATCCC<br>AGTTCTTTGTGGATTCCTCTTCCTTATTCATGGCTTTTTG<br>CAATTGTCAAGGAATGACTAGGTACCAAGCAACTTTAAAA<br>AATGTATATTTAAGCATTGAAATAATATCAAATGTGATTT<br>CTCTGCTTGTGGTTATATTGATTATATTATCCTTTTAATA<br>ATATTGGCATTATATTCTTGGTCGTAAAATGTCAAGGTCT<br>TATTTATTCAGTATATTTATGTTCTGTATTTTCATATATA<br>TTATCTATTTTCAGCCATGCATTATATATAATGTCAGTAA<br>TAGTATTTCATTAGCATTCATTATAAAAAAACTCGTTTTT<br>AATATTTGACTAATTCAAGTCACAGTACTTTTGAGATAGC<br>TGAAAAGGAAAATAAATGTGTTTTAATGTGCTACTAAAAA<br>AAAAAAA | |
| WDFY3 | NM_014991.4 | GCGGCCGCAGAATCGAGCTCGGGCCCCGGCCCCCGGCCCG<br>CGGCGCGGGGCTCCCGGGCCCCGCCGCGGACGTCGCGCCG<br>GTCGCCCCTTCCCCGTAGCCCGTGCGCCCTCGGCGCGGAG<br>CCCCGGCCCGCCGCGGTCCCGTCTCCTGGGCCTGTCCCGC<br>CCGCGCCCTCCGCCGGCCCTCAGGTATAATACTTCTCCAC<br>GTCTGCTTCAGGAAGAAAGTGCCTGCCATTCTTATCATTT<br>CTAAGCAGGTTCATGCCAGCCCAGAACAGAGAATCAGCTG<br>GAGCCCAGATTTCAAGTTTTGAGTAAAATACCTTCAAGCG<br>AATGGGCCCTATTGTGCTCACACATTCAGAACCTGTTACC<br>CAAGGAATTCCCTAAAGAATTAGAAGTGCGTCTCACCAAC<br>CAGCCAAGATGAACATGGTGAAGAGGATCATGGGGCGGCC<br>GAGGCAGGAGGAGTGCAGCCCACAAGACAACGCCTTAGGA<br>CTGATGCACCTCCGCCGGCTCTTCACGGAGTTGTGCCATC<br>CTCCCCGGCACATGACTCAGAAGGAACAAGAAGAGAAACT<br>GTATATGATGCTGCCAGTGTTTAACAGGGTTTTTGGAAAT<br>GCTCCGCCGAATACAATGACAGAAAAATTTTCTGATCTTC<br>TGCAGTTCACAACACAAGTCTCACGACTAATGGTGACAGA<br>AATTCGAAGGAGAGCATCAAACAAATCCACAGAGGCTGCA<br>AGTCGGGCCATAGTTCAGTTCCTAGAGATTAATCAGAGTG<br>AAGAAGCCAGTAGAGGCTGGATGCTTCTAACGACAATTAA<br>TTTGTTAGCTTCCTCTGGTCAGAAAACCGTGGACTGCATG<br>ACAACAATGTCAGTGCCTTCCACCCTGGTTAAATGTTTAT<br>AGGTGCACAGAATGAGCTACCTCTAGCAGAACGTCGAGGA<br>CTACTCCAGAAAGTTTTTGTACAGATCTTAGTGAAACTGT<br>GCAGTTTTGTTTCCCCTGCGGAGGAGCTGGCTCAGAAAGA<br>TGATCTCCAGCTTCTATTCAGTGCAATAACCTCTTGGTGC<br>CCTCCCTATAACCTGCCTTGGAGAAAGAGTGCTGGAGAAG<br>TCCTCATGACCATATCTCGTCATGGTCTTAGTGTCAATGT<br>AGTGAAGTATATTCATGAGAAAGAGTGTTTATCTACATGT<br>GTTCAGAATATGCAGCAATCAGATGACCTGTCTCCCCTAG<br>AAATTGTCGAAATGTTTGCTGGGCTTTCTTGTTTCCTCAA<br>AGATTCCAGCGATGTTTCCCAAACACTTCTGGATGATTTT | 49 |

TABLE 1-continued

GEP-NEN Biomarker/Houskeeper Sequence Information

| Gene Name | RefSeq Accession | Sequence | SEQ ID NO: |
|---|---|---|---|
| | | CGGATATGGCAAGGATATAATTTTCTTTGTGATCTCTTGC | |
| | | TTAGATTGGAACAAGCAAAAGAGGCAGAATCCAAAGATGC | |
| | | CTTGAAAGATCTGGTTAATCTGATAACTTCCCTAACAACA | |
| | | TATGGTGTCAGTGAACTAAAACCAGCTGGTATTACCACAG | |
| | | GGGCACCCTTTTTATTGCCTGGATTTGCAGTACCTCAGCC | |
| | | TGCAGGCAAAGGTCACAGTGTGAGAAACGTCCAGGCCTTT | |
| | | GCAGTTCTTCAGAATGCATTTTTAAAAGCAAAAACCAGCT | |
| | | TCCTTGCCCAAATCATCCTTGATGCTATCACAAATATTTA | |
| | | CATGGCTGACAATGCCAATTACTTCATCCTAGAGTCACAG | |
| | | CACACATTGTCACAGTTTGCAGAGAAGATTTCTAAACTCC | |
| | | CAGAAGTACAAAACAAATACTTTGAGATGCTGGAGTTTGT | |
| | | TGTTTTTAGCTTAAATTATATACCTTGTAAAGAACTTATT | |
| | | AGTGTCAGTATCCTCTTAAAATCTAGCTCTTCTTATCACT | |
| | | GTAGCATTATTGCAATGAAAACACTTCTTAAGTTTACAAG | |
| | | ACATGACTACATATTTAAAGACGTGTTCAGGGAGGTTGGC | |
| | | CTTTTGGAGGTCATGGTAAACCTTTTGCATAAATATGCTG | |
| | | CCCTGTTGAAGGATCCAACTCAGGCACTAAATGAACAAGG | |
| | | GGACTCAAGAAATAATAGTTCAGTTGAAGACCAAAAACAC | |
| | | CTGGCTTTATTGGTTATGGAGACCTTGACAGTGCTTCTTC | |
| | | AAGGATCAAACACAAATGCAGGAATTTTTCGAGAATTTGG | |
| | | AGGTGCAAGATGTGCACATAATATAGTAAAGTACCCTCAA | |
| | | TGCCGGCAGCATGCCTTGATGACTATCCAACAGCTGGTGC | |
| | | TCTCCCCAAATGGGGACGATGACATGGGCACTCTCCTGGG | |
| | | GCTAATGCATTCAGCCCCACCGACGGAATTGCAGTTGAAG | |
| | | ACTGATATTTTAAGGGCCCTCCTGTCGGTCCTTCGAGAAA | |
| | | GCCATCGTTCAAGAACAGTTTTTAGGAAAGTTGGAGGATT | |
| | | TGTGTACATTACATCCTTGCTCGTTGCTATGGAAAGATCT | |
| | | TTGAGCTGTCCACCCAAGAATGGCTGGGAGAAAGTGAACC | |
| | | AGAATCAAGTGTTTGAACTTCTTCACACTGTGTTCTGCAC | |
| | | GTTGACTGCAGCAATGCGCTATGAGCCAGCCAACTCTCAT | |
| | | TTCTTCAAAACAGAGATTCAGTATGAGAAGTTGGCAGATG | |
| | | CTGTTCGATTTCTTGGCTGCTTCTCAGACCTAAGAAAAAT | |
| | | AAGCGCCATGAATGTCTTCCCCTCAAATACACAGCCATTT | |
| | | CAAAGACTTTTAGAGGAAGATGTAATCTCAATAGAATCAG | |
| | | TGTCACCCACGTTACGGCACTGCAGTAAACTTTTTATTTA | |
| | | TCTTTACAAAGTAGCCACAGATTCTTTTGACAGTCGTGCA | |
| | | GAACAGATCCCTCCTTGCCTGACAAGTGAGTCTTCTCTCC | |
| | | CCTCTCCTTGGGGTACACCAGCTTTGTCCAGGAAAAGGCA | |
| | | TGCATATCATTCTGTTTCAACTCCCCCTGTTTACCCTCCT | |
| | | AAAAATGTTGCCGACCTGAAACTACATGTGACAACTTCAT | |
| | | CTCTGCAGAGTTCTGATGCAGTCATCATTCATCCTGGAGC | |
| | | CATGCTTGCCATGCTGGACCTACTGGCCTCTGTTGGGTCA | |
| | | GTGACACAGCCAGAACATGCTTTGGATCTTCAACTTGCCG | |
| | | TGGCAAATATTTTACAATCCCTGGTGCACACAGAAAGGAA | |
| | | CCAGCAAGTCATGTGTGAAGCTGGTCTTCATGCACGACTG | |
| | | CTGCAGAGGTGCAGTGCTGCATTGGCTGATGAGGACCACT | |
| | | CACTGCACCCGCCCCTGCAGCGGATGTTTGAACGATTAGC | |
| | | CTCTCAGGCTCTGGAACCCATGGTGTTGAGGGAGTTTTTA | |
| | | CGTTTGGCAAGTCCTTTAAATTGTGGTGCCTGGGACAAAA | |
| | | AACTGCTAAAACAATATAGGGTCCACAAACCAAGTTCACT | |
| | | GAGTTATGAACCAGAAATGAGAAGTAGTATGATCACATCT | |
| | | CTGGAAGGTCTGGGTACTGATAATGTTTTTAGCTTACATG | |
| | | AAGATAACCATTACCGGATAAGCAAGAGCCTGGTAAAATC | |
| | | TGCGGAAGGAAGTACTGTACCCCTGACCAGGGTGAAGTGT | |
| | | CTGGTCTCCATGACAACCCCACATGACATCAGACTTCATG | |
| | | GGTCATCAGTTACTCCAGCTTTTGTTGAATTTGACACATC | |
| | | ACTTGAAGGGTTTGGATGTCTTTTTTTGCCCAGTTTGGCC | |
| | | CCTCATAATGCTCCTACAAATAATACCGTCACAACAGGTC | |
| | | TTATTGATGGGCTGTGGTCAGTGGCATTGGTTCTGGTGA | |
| | | AAGATTCTTCCCTCCTCCCTCCGGCTTAAGTTACTCTAGC | |
| | | TGGTTTTGTATTGAACATTTTAGTTCTCCTCCAAATAACC | |
| | | ACCCTGTCAGACTTCTTACTGTTGTGCGCCGAGCAAATTC | |
| | | TTCTGAGCAACATTACGTGTGCCTTGCAATAGTTCTATCA | |
| | | GCAAAAGACCGATCTCTGATTGTTTCCACCAAAGAGGAAC | |
| | | TCCTCCAAAATTATGTTGATGATTTTAGTGAAGAGTCCTC | |
| | | ATTTTATGAAATTCTCCCATGCTGTGCTCGCTTTCGATGT | |
| | | GGAGAGCTTATCATTGAGGGACAGTGGCATCATTTGGTCC | |
| | | TGGTAATGAGCAAAGGCATGTTGAAAAACAGTACTGCAGC | |
| | | CCTTTATATTGATGGACAGCTTGTTAACACTGTAAAGCTT | |
| | | CATTATGTCCACAGTACTCCAGGGGGTTCAGGTTCGGCAA | |
| | | ATCCACCAGTGGTGAGCACGGTCTATGCCTACATTGGTAC | |
| | | TCCACCTGCCCAACGCCAAATTGCCTCATTGGTTTGGCGC | |
| | | CTGGGACCCACACATTTTCTAGAAGAAGTTTTACCTTCTT | |
| | | CAAATGTTACTACCATTTATGAACTTGGACCAAATTATGT | |
| | | TGGAAGCTTTCAGGCTGTATGTATGCCATGTAAAGATGCA | |

TABLE 1-continued

GEP-NEN Biomarker/Houskeeper Sequence Information

| Gene Name | RefSeq Accession | Sequence | SEQ ID NO: |
|---|---|---|---|
| | | AAATCCGAAGGGGTGGTGCCATCCCTGTGTCATTAGTAC | |
| | | CAGAGGAGAAAGTGTCATTTGGCCTCTATGCACTCTCTGT | |
| | | GTCGTCTCTAACAGTGGCAAGAATCCGGAAAGTGTATAAC | |
| | | AAATTGGATAGCAAAGCCATTGCTAAGCAGTTAGGCATTT | |
| | | CCTCACATGAGAATGCCACTCCTGTGAAGTTGATACACAA | |
| | | TTCAGCAGGACATCTTAATGGATCTGCACGGACAATTGGG | |
| | | GCCGCTCTGATTGGATACTTGGGAGTAAGAACATTTGTCC | |
| | | CTAAGCCTGTTGCCACTACTTTGCAGTACGTTGGTGGAGC | |
| | | TGCAGCCATCCTGGGCCTGGTGGCCATGGCCTCTGATGTG | |
| | | GAAGGGTTATATGCAGCAGTCAAGGCCCTGGTTTGTGTGG | |
| | | TCAAGAGTAACCCACTAGCCAGCAAAGAAATGGAAAGAAT | |
| | | CAAGGGCTACCAGTTGCTGGCAATGTTGCTTAAGAAGAAA | |
| | | CGTTCCCTTCTTAACAGCCACATCCTCCATCTAACTTTTT | |
| | | CTTTGGTGGGAACTGTTGATAGTGGACATGAGACCTCCAT | |
| | | TATTCCAAATTCAACTGCTTTCCAGGACCTCCTCTGTGAT | |
| | | TTTGAAGTCTGGCTCCATGCACCATATGAACTTCATCTTT | |
| | | CCTTATTTGAACACTTTATTGAACTGCTCACAGAGTCCAG | |
| | | TGAAGCCTCAAAGAATGCCAAATTAATGAGAGAATTCCAG | |
| | | TTAATCCCAAAGCTGCTCCTGACTCTTCGAGATATGTCTT | |
| | | TATCCCAGCCTACTATTGCTGCTATTAGTAATGTCCTGAG | |
| | | CTTCTTACTGCAAGGTTTTCCTAGCAGCAATGATCTGCTC | |
| | | AGATTTGGGCAGTTTATTTCTTCTACTTTGCCAACCTTTG | |
| | | CGGTTTGTGAGAAATTTGTAGTAATGGAAATAAATAATGA | |
| | | AGAGAAGCTTGACACTGGAACTGAAGAGGAGTTTGGAGGT | |
| | | CTTGTATCAGCTAATCTTATACTTTTGAGGAACAGACTTC | |
| | | TGGATATCTTGCTAAAACTAATTTATACATCTAAAGAAAA | |
| | | GACAAGCATTAATTTGCAAGCTTGTGAAGAACTGGTGAAG | |
| | | ACACTGGGTTTTGACTGGATCATGATGTTTATGGAGGAAC | |
| | | ACTTACATTCCACCACAGTTACAGCAGCCATGAGGATTCT | |
| | | TGTTGTCCTACTAAGTAATCAGTCTATTCTCATCAAGTTT | |
| | | AAAGAAGGACTCAGTGGTGGAGGATGGCTTGAACAGACAG | |
| | | ATTCTGTCTTAACTAATAAGATTGGAACTGTATTAGGATT | |
| | | CAACGTGGGCAGAAGTGCTGGTGGGAGATCGACGGTCAGG | |
| | | GAGATTAACCGAGATGCTTGTCATTTTCCTGGTTTTCCAG | |
| | | TCCTTCAGTCATTCCTTCCTAAACACACTAATGTCCCTGC | |
| | | CCTCTATTTTCTCCTCATGGCCTTGTTTCTGCAGCAGCCA | |
| | | GTTAGTGAGCTGCCTGAGAACCTGCAGGTCAGTGTGCCTG | |
| | | TCATCAGCTGCCGGAGTAAGCAGGGTTGCCAGTTTGATTT | |
| | | GGATTCCATTTGGACATTCATCTTTGGAGTTCCTGCCTCC | |
| | | AGCGGAACTGTGGTCTCTTCTATCCATAACGTATGCACAG | |
| | | AAGCTGTTTTTTATTATTGGGAATGCTCCGCAGCATGCT | |
| | | GACTTCACCTTGGCAATCAGAAGAAGAGGGATCTTGGCTC | |
| | | CGAGAATATCCTGTGACCCTGATGCAGTTCTTCAGATATT | |
| | | TGTATCACAACGTGCCAGACCTTGCCTCCATGTGGATGAG | |
| | | CCCTGACTTCCTGTGTGCATTAGCAGCCACCGTCTTCCCC | |
| | | TTCAATATTCGCCCTTACTCAGAGATGGTGACTGACCTTG | |
| | | ATGATGAAGTTGGATCTCCAGCAGAAGAGTTTAAAGCGTT | |
| | | TGCAGCAGACACAGGGATGAACAGGAGCCAATCAGAGTAC | |
| | | TGCAATGTGGGCACCAAGACATATCTGACCAATCACCCGG | |
| | | CTAAAAAGTTCGTTTTTGACTTCATGCGGGTCTTAATCAT | |
| | | AGACAACCTCTGTCTCACTCCTGCCAGCAAGCAAACTCCA | |
| | | CTAATTGATCTTTTGTTGGAGGCTTCCCCTGAAAGGTCTA | |
| | | CAAGAACTCAGCAAAAAGAATTTCAAACTTACATTTTGGA | |
| | | TAGCGTGATGGACCATTTGCTTGCAGCTGATGTGTTATTA | |
| | | GGGGAAGATGCATCTCTGCCTATTACCAGTGGAGGAAGCT | |
| | | ACCAGGTATTGGTGAACAATGTGTTTTATTTCACACAGCG | |
| | | TGTGGTGGACAAGCTTTGGCAAGGCATGTTCAACAAAGAA | |
| | | TCTAAACTTCTTATAGATTTTATAATTCAACTAATTGCAC | |
| | | AGTCAAAGAGAAGATCACAGGGATTGTCACTGGATGCAGT | |
| | | GTATCATTGCCTCAATAGGACCATCTTGTACCAGTTCTCA | |
| | | CGGGCACACAAAACCGTTCCTCAGCAAGTAGCTCTGCTTG | |
| | | ATTCACTCAGGGTCCTCACTGTAAACAGAAACTTGATCCT | |
| | | GGGACCTGGGAACCATGACCAAGAATTCATTAGCTGTCTG | |
| | | GCCCACTGCTTGATAAATCTACATGTTGGAAGCAACGTGG | |
| | | ATGGATTTGGACTGGAAGCAGAAGCCCGCATGACCACATG | |
| | | GCACATTATGATCCCTCGGACATTGAACCAGATGGTAGT | |
| | | TACAGCCAAGATATTAGTGAAGGGCGTCAGCTTCTCATAA | |
| | | AAGCTGTCAACAGAGTTTGGACTGAACTGATACATAGTAA | |
| | | GAAACAAGTCTTAGAGGAACTTTTCAAAGTAACTCTACCT | |
| | | GTGAATGAAAGGGGCCACGTGGACATAGCTACAGCAAGGC | |
| | | CACTCATTGAAGAAGCTGCCCTGAAGTGCTGGCAGAATCA | |
| | | TTTGGCCCATGAAAAGAAATGCATAAGTCGAGGAGAAGCT | |
| | | TTAGCGCCCACCACACAGTCCAAATTATCCCGTGTCAGCA | |
| | | GTGGCTTTGTCTTTCCAAGTTAACAGGATCAAGAAGGAA | |
| | | TCGAAAAGAAAGTGGTCTTAATAAACACAGTCTTTCCACC | |

TABLE 1-continued

GEP-NEN Biomarker/Houskeeper Sequence Information

| Gene Name | RefSeq Accession | Sequence | SEQ ID NO: |
|---|---|---|---|
| | | CAGGAGATTTCGCAGTGGATGTTTACTCACATTGCTGTTG<br>TTCGTGACTTAGTAGATACACAATATAAAGAATATCAGGA<br>GCGTCAGCAGAATGCCCTGAAGTACGTGACAGAAGAGTGG<br>TGTCAGATCGAGTGCGAGCTGTTGAGGGAGCGGGGGCTGT<br>GGGGCCCTCCCATCGGCTCCCACCTCGACAAGTGGATGCT<br>GGAGATGACAGAAGGGCCCTGCAGGATGAGGAAAAAGATG<br>GTGCGAAATGATATGTTTTATAACCATTACCCTTACGTGC<br>CAGAAACTGAGCAAGAGACAAATGTGGCGTCTGAGATCCC<br>AAGTAAACAGCCTGAGACACCCGATGATATTCCTCAAAAG<br>AAACCTGCTCGATATAGAAGAGCCGTAAGTTATGACAGTA<br>AAGAGTACTACATGCGACTGGCCTCTGGCAATCCCGCCAT<br>TGTCCAAGACGCCATTGTGGAGAGTTCAGAAGGTGAAGCT<br>GCTCAGCAAGAACCAGAGCATGGGGAAGACACTATTGCTA<br>AAGTCAAAGGTTTGGTCAAGCCTCCTCTAAAACGCTCCCG<br>ATCTGCACCTGATGGAGGAGATGAGGAGAACCAGGAGCAG<br>CTACAAGACCAGATTGCTGAGGGCAGCTCCATAGAAGAGG<br>AGGAGAAAACAGATAATGCTACCTTACTGCGCCTGTTAGA<br>GGAAGGAGAAAAGATCCAACACATGTACCGCTGTGCTCGA<br>GTCCAGGGCCTAGATACCAGTGAGGGGCTCCTTCTTTTTG<br>GTAAAGAGCATTTTTATGTGATTGATGGATTTACCATGAC<br>AGCAACCAGGGAAATAAGAGATATTGAAACCTTACCTCCA<br>AATATGCATGAGCCTATTATTCCTAGAGGAGCCAGGCAAG<br>GCCCTAGTCAACTCAAGAGAACATGCAGCATTTTTGCATA<br>TGAAGATATCAAGGAAGTTCATAAAAGGAGATATCTCCTG<br>CAGCCTATTGCTGTGGAAGTTTTCTCTGGAGATGGACGGA<br>ATTACCTCCTTGCTTTTCAGAAAGGAATCAGAAACAAAGT<br>CTATCAAAGGTTTTTGGCTGTAGTGCCATCTCTAACGGAC<br>AGTTCAGAATCTGTATCTGGGCAACGACCAAACACGAGTG<br>TGGAGCAGGGATCTGGGTTACTTAGCACTTTGGTTGGAGA<br>GAAGTCTGTGACTCAGAGATGGGAGAGAGGTGAAATCAGC<br>AACTTCCAATATTTGATGCATTTGAACACTTTGGCTGGCA<br>GATCATATAATGATCTCATGCAGTATCCTGTCTTCCCCTG<br>GATCCTTGCAGATTATGACTCAGAGGAGGTGGATCTTACT<br>AATCCCAAGACGTTTAGAAACCTGGCTAAGCCAATGGGAG<br>CACAAACAGATGAACGATTAGCTCAGTATAAGAAGCGGTA<br>TAAAGACTGGGAGGATCCTAATGGAGAAACTCCTGCATAC<br>CACTATGGGACCCACTATTCATCTGCAATGATTGTGGCCT<br>CATACCTTGTAAGGATGGAGCCTTTCACACAGATATTCTT<br>AAGGCTACAGGGTGGCCACTTTGACCTGGCTGACCGGATG<br>TTTCACAGTGTGCGCGAGGCCTGGTATTCAGCGTCAAAGC<br>ACAATATGGCAGATGTAAAAGAACTTATCCCAGAGTTCTT<br>TTATTTACCAGAATTCCTGTTCAATTCCAACAACTTTGAT<br>CTAGGCTGTAAACAAAATGGCACCAAGCTTGGAGATGTTA<br>TCCTTCCACCCTGGGCAAAAGGGGACCCACGAGAATTCAT<br>CAGAGTCCATCGTGAGGCTTTGGAGTGTGATTACGTGAGT<br>GCCCATCTACATGAGTGGATTGACTTAATCTTCGGTTATA<br>AACAGCAAGGCCCTGCTGCAGTAGAAGCTGTAAATGTCTT<br>CCATCATCTTTTTTATGAGGGTCAAGTGGATATCTACAAC<br>ATCAATGACCCACTAAAGGAGACAGCCACAATTGGGTTCA<br>TTAATAACTTCGGTCAGATCCCTAAACAGTTATTTAAAAA<br>ACCTCATCCACCAAAGCGAGTGAGAAGTCGACTCAATGGA<br>GACAATGCAGGAATCTCTGTCCTACCAGGATCTACAAGTG<br>ACAAGATCTTTTTTCATCATCTAGACAACTTGAGGCCTTC<br>TCTAACACCTGTAAAAGAACTCAAAGAACCTGTAGGACAA<br>ATCGTATGTACAGATAAAGGTATTCTTGCGGTGGAACAGA<br>ATAAGGTTCTTATCCCACCAACCTGGAATAAAACTTTTGC<br>TTGGGGCTATGCAGACCTCAGTTGCAGACTGGGAACCTAT<br>GAGTCAGACAAGGCCATGACTGTTTATGAATGCTTGTCTG<br>AGTGGGGCCAGATTCTCTGTGCAATCTGCCCCAACCCCAA<br>GCTGGTCATCACGGGTGGAACAAGCACGGTTGTGTGTGTG<br>TGGGAGATGGGCACCTCCAAAGAAAAGGCCAAGACCGTCA<br>CCCTCAAACAGGCCTTACTGGGCCACACTGATACCGTCAC<br>CTGCGCCACAGCATCATTAGCCTATCACATAATTGTCAGT<br>GGGTCCCGTGATCGAACCTGTATCATTTGGGATTTGAACA<br>AACTGTCATTTCTAACCCAGCTTCGAGGGCATCGAGCTCC<br>AGTTTCTGCTCTTTGTATCAATGAATTAACAGGGGACATT<br>GTGTCCTGCGCTGGCACATATATCCATGTGTGGAGCATCA<br>ATGGGAACCCTATCGTGAGTGTCAACACGTTCACAGGTAG<br>GAGCCAGCAGATCATCTGCTGCTGCATGTCGGAGATGAAC<br>GAATGGGACACGCAGAACGTCATAGTGACAGGACACTCAG<br>ATGGAGTGGTTCGGTTTTGGAGAATGGAATTTTTGCAAGT<br>TCCTGAAACACCAGCTCCTGAGCCTGCTGAAGTCCTAGAA<br>ATGCAGGAAGACTGTCCAGAAGCACAAATAGGGCAGGAAG<br>CCCAAGACGAGGACAGCAGTGATTCAGAAGCAGATGAGCA<br>GAGCATCAGCCAGGACCCTAAGGACACTCCAAGCCAACCC | |

TABLE 1-continued

GEP-NEN Biomarker/Houskeeper Sequence Information

| Gene Name | RefSeq Accession | Sequence | SEQ ID NO: |
|---|---|---|---|
| | | AGCAGCACCAGCCACAGGCCCCGGGCAGCCTCCTGCCGCG | |
| | | CAACAGCCGCCTGGTGTACTGACAGTGGCTCTGACGACTC | |
| | | CAGACGCTGGTCCGACCAGCTCAGTCTAGATGAGAAAGAC | |
| | | GGCTTCATATTTGTGAACTATTCAGAGGGCCAGACCAGAG | |
| | | CCCATCTGCAGGGCCCCCTTAGCCACCCCCACCCCAATCC | |
| | | CATTGAGGTGCGGAATTACAGCAGATTGAAACCTGGGTAC | |
| | | CGATGGGAACGGCAGCTGGTGTTCAGGAGTAAGCTGACTA | |
| | | TGCACACAGCCTTTGATCGAAAGGACAATGCACACCCAGC | |
| | | TGAGGTCACTGCCTTGGGCATCTCCAAGGATACACAGTAGG | |
| | | ATCCTCGTTGGTGACAGTCGAGGCCGAGTTTTCAGCTGGT | |
| | | CTGTGAGTGACCAGCCAGGCCGTTCTGCTGCTGATCACTG | |
| | | GGTGAAGGATGAAGGTGGTGACAGCTGCTCAGGCTGCTCG | |
| | | GTGAGGTTTTCACTCACAGAAAGACGACACCATTGCAGGA | |
| | | ACTGTGGTCAGCTCTTCTGCCAGAAGTGCAGTCGCTTTCA | |
| | | ATCTGAAATCAAACGCTTGAAAATCTCATCCCCGGTGCGT | |
| | | GTTTGTCAGAACTGTTATTATAACTTACAGCATGAGAGAG | |
| | | GTTCAGAAGATGGGCCTCGAAATTGTTGAAGATTCAACAA | |
| | | GCTGAGTGGAGACCATGGTCTGTAGACCCCTTCCCGATTC | |
| | | TCCTGTCCCAGCTTGGAAGGCATTGAAAACAGTCTCCGTT | |
| | | TACACATCTCTTCATACCACGTGTTTGAAGTGTTAAAATT | |
| | | CAAAGGGATCATTGAATAAAACGGGTGTAGAGTACAGGAA | |
| | | TGGGGCAGACGCGATTCAGGTGAACAGCACAAGAAGAATA | |
| | | TGAGGTGGTTCCTAGGAGCAACACTTTCGACCTCCAGTTC | |
| | | TCCCTGATGACAGTAGCTGTCTCCAAGAGAAAAATCCTCA | |
| | | CTTATTAACTCTCTTTTCTTGCATCTCATTTTTATAGAGC | |
| | | TACTCATCCTTATTTGGAAAAACCAACAACAAAAAAGGCT | |
| | | TTTAGAAAATGGTTGTAAATCTGACTTCTTTGCAAGTAAC | |
| | | TATGTATATTGTAAATAGATATAAAAGGCCTTTTTTCTAA | |
| | | ATAAGGACTTAACTGCCTGTAACATGAAACTTCAAACTAA | |
| | | ACCACTAACTCAATGAACTACTTATGGTTTGTCTGACATC | |
| | | CCTCACTTACCAATTAATTATAAATATGTTTTTTTAAATC | |
| | | CCCAAAGACATTATCTGTGGTCTTTTTTTCCTTTCAAGCT | |
| | | CAGCCTGTGTGCCTGATGTCATTTCTTTCAAGTTGCCCAC | |
| | | AGTATCTCCACTTAAACTAGGCTAGTAACCAAAATAATGT | |
| | | GGACCTTCTTTAGGAAACAGTGTGGGAGAATAGGAGTCCA | |
| | | GCCGTAAGATAAACTGGAAATATTTGGGCGTCTTGTACCT | |
| | | GGCTACGCACCACCTCAGTGTTGTTCCTACATAAACAGGG | |
| | | CCCCTTTTAAACTTGTATGTGGACTGCTGTTTGGTCAAAG | |
| | | AATACCTTCTTAGCATTGCAGAAAGGTGGTCAGATGACCA | |
| | | GTGTAGTGCAGGAAACAGCCCTGTCTCAACTAATGGAAAT | |
| | | ATATTTGCATGTAACCCAAAATTAGCTTATCTTGCATAGA | |
| | | ACATAATAAGTATGTGTCTTTGGTGACACTAATGTTCTAC | |
| | | TATAGCTTATTTTCAAACAAGGGGTAAAAAAAGGAAAGAA | |
| | | AGAAGTGTACAGAATTAACATATAAACTTTGTTGTAAAAC | |
| | | TGAATCATGTCAGAACTGCTTAAAATTAACCTTTACCATT | |
| | | TAATGTCATCTACCTGAAAACAGTGAGATTTATACTGTAT | |
| | | CAATGTCTATTTTTTTGTTTTGCTATGAATATAATTACA | |
| | | GTATTTTAATATTTAGTTATTTAATTTGTTCTACTAGTTG | |
| | | GATACAGAACACACAAATCCAGGGGGATTAAAGCTGGAAG | |
| | | GGGCTAAGAGATTAGTTTACAGAGAAAAGGCTTGGTGGTG | |
| | | GGATTTTTTTAAATGTGTGTTATGTACATATATATATATA | |
| | | TATAATATATATTAAAAATGAAACAATTAATCTAGATTTT | |
| | | AACATTTTCAGAAACTTAGTGATAACATTATGAACAATTC | |
| | | TAAAAGCCCTGTGATTTGAAAAATATAGAATCATTAATGG | |
| | | CCCAAGATAGGCCTTCACACCTTCACAGGTGCGAAAGGAA | |
| | | AGGCCTTCACACCCTCACAGAGGCATCATGCAAAGGACAG | |
| | | CGGCTTTGGCTTTTCCAATTTTCCATCTTTAGGCCCTGGT | |
| | | GAGAGGCACACTTATGCACTAAAATGCACATATATGCACA | |
| | | TGCATTCAAAAATAGGCATTTGGTACAATGGTGATCTTGT | |
| | | ACCTGATGGGCTGAAACCAGCTTAAGAACAAATTTGTTCT | |
| | | TCCTGATATGATAACTAGGTCTCCAAGAGAAAATAGAAAG | |
| | | GCTGCTTTAGTGCCTTACGCTTACTAAATTTAAATCTTTA | |
| | | TTTACCTGGGTTTGAGCCTACAGTCTATTTATGATTACAT | |
| | | ATCAAAATTGATTAAAACACTTCCATTTCTAAAAGTTCAA | |
| | | ATATACTTGTTAATAAAAGGATTATCGGCATTAATACTTT | |
| | | AATTTAAAGAAAAGTTGTGTTCTGTTTTCCTTTCTGTGTC | |
| | | TTACTCCCCCCACACTCTCCCTCCCCCATCACCATCTTCA | |
| | | ATTCTAATAAATAATGCTGATGTTCAACAGTTGCAGAAAT | |
| | | TGTGCTATTATGTAACTGTGGGCCTTGCCCCTGTCTGGCC | |
| | | CTCTAGATGATTTGTAGCAGTGTTATTCTACACTTTTAA | |
| | | AAGAAGCGTCCTCCTTTTGTCCATGAATCATGTTTACCCC | |
| | | ATACCCAGTGGCAGAGGTGTTCTTTAAAGACTTGAATATA | |
| | | TGAATGTGTGTGTAGTTACTTAAAGGTTATTCCTCTTT | |
| | | GTAATAGGAAACTATATGGGATGAACACTTTTAAACTTTC | |
| | | CGACACAACTTCCATTACTAACTTTCTAACAGAACTTCCA | |

TABLE 1-continued

GEP-NEN Biomarker/Houskeeper Sequence Information

| Gene Name | RefSeq Accession | Sequence | SEQ ID NO: |
|---|---|---|---|
| | | TAACTAGAAGGTGGAAACCAAAACCCTCATGGTAGTATTT<br>CCTCTGGCAGCTGGTGCTGTGGGCAACTGTTTTGTTCAAT<br>CGGGTTTCTTTTCTTTTTGCCTCTAATGCAGAAATCAACA<br>GAATCACTCACACATACAAGTACACTCACATACATAAACT<br>AATTATTTCTCTGGATATCTTTCTGTGTTCCATGTAAATT<br>TATTTACCAACATCTATTGTCAACATGTACATCTACCTTA<br>GTATGGTCTGCATTCTTTTTCTGAGAGTACCTCATAGGGC<br>TCCTGCCTGATCTTTGTAGTTTGTTCATTCATCCATCCAC<br>CTGTTCATTTGTTCATCCATGTATTCTAACATTTCTATGT<br>AGTGTGCAACTCTAATGTCATGCTTTTGAAGAAGAGAATA<br>GCTGCCCATAGCAGCCATCCGTCTGGATAATAGCAAAACA<br>CTCTAGATAAGTTATTTTGCACTTTCTTATGTATAAAGTT<br>GGTAGAAACTTATTTTTGCTTTGTATCATTTAAATACATT<br>TTGTTTTGGTAAATGAACTGTGTATAAAATATTTATGCCG<br>TTAAAACTGTTTTTAGAAAGTATTTTTAATTTCAGCAAGT<br>TTGGTTACTTGTTGCATGACTCTTAACACAGCTGACTTTT<br>TGTGTCAGTGCAATGTATATTTTTTGTCCTGTTATTAACT<br>TGTAAGCCCTAGTAATGGCCAATTATTTGTACAGCAACAG<br>AAGTAAATTGAAGATACTGGCTAAGACTGGATTGATTGTG<br>GACTTTTATACTATATTGCAGAAACCAATATCTGTTTCTT<br>GGTGGTTATGTAAAAGACCTGAAGAATTACTATCTAGTGT<br>GCAGTCTGTGATATCTGAATGTTCATTGTATATTTGTCTC<br>TGATGCAAAAAGGTAGAGTAACACAATTACAATACATGAT<br>TAAATGCAATAGTCCAGGTACTTAAGTAATTTTTTTTTCA<br>TTTCAAATAAATACCTATTTACCACCAAAAGAAAGAAAAA<br>AAAAAAAA | |
| ZFHX3 | NM_001164766.1 | CGCGGCCCGAGCGCCTCTTTTCGGGATTAAAAGCGCCGCC<br>AGCTCCCGCCGCCGCCGCCGTCGCCAGCAGCGCCGCTGCA<br>GCCGCCGCCGCCGGAGAAGCAACCGCTGGGCGGTGAGATC<br>CCCCTAGACATGCGGCTCGGGGGCGGGCAGCTGGTGTCAG<br>AGGAGCTGATGAACCTGGGCGAGAGCTTCATCCAGACCAA<br>CGACCCGTCGCTGAAGCTCTTCCAGTGCGCCGTCTGCAAC<br>AAGTTCACGACGGACAACCTGGACATGCTGGGCCTGCACA<br>TGAACGTGGAGCGCAGCCTGTCGGAGGACGAGTGGAAGGC<br>GGTGATGGGGGACTCATACCAGTGCAAGCTCTGCCGCTAC<br>AACACCCAGCTCAAGGCCAACTTCCAGCTGCACTGCAAGA<br>CAGACAAGCACGTGCAGAAGTACCAGCTGGTGGCCCACAT<br>CAAGGAGGGCGGCAAGGCCAACGAGTGGAGGCTCAAGTGT<br>GTGGCCATCGGCAACCCCGTGCACCTCAAGTGCAACGCCT<br>GTGACTACTACACCAACAGCCTGGAGAAGCTGCGGCTGCA<br>CACGGTCAACTCCAGGCACGAGGCCAGCCTGAAGTTGTAC<br>AAGCACCTGCAGCAGCATGAGAGTGGTGTAGAAGGTGAGA<br>GCTGCTACTACCACTGCGTTCTGTGCAACTACTCCACCAA<br>GGCCAAGCTCAACCTCATCCAGCATGTGCGCTCCATGAAG<br>CACCAGCGAAGCGAGAGCCTGCGAAAGCTGCAGCGGCTGC<br>AGAAGGGCCTTCCAGAGGAGGACGAGGACCTGGGGCAGAT<br>CTTCACCATCCGCAGGTGCCCCTCCACGGACCCAGAAGAA<br>GCCATTGAAGATGTTGAAGGACCCAGTGAAACAGCTGCTG<br>ATCCAGAGGAGCTTGCTAAGGACCAAGAGGGCGGAGCATC<br>GTCCAGCCAAGCAGAGAAGGAGCTGACAGATTCTCCTGCA<br>ACCTCCAAACGCATCTCCTTCCCAGGTAGCTCAGAGTCTC<br>CCCTCTCTTCGAAGCGACCAAAAACAGCTGAGGAGATCAA<br>ACCGGAGCAGATGTACCAGTGTCCCTACTGCAAGTACAGT<br>AATGCCGATGTCAACCGGCTCCGGGTGCATGCCATGACGC<br>AGCACTCGGTGCAACCCATGCTTCGCTGCCCCCTGTGCCA<br>GGACATGCTCAACAACAAGATCCACCTCCAGCTGCACCTC<br>ACCCACCTCCACAGCGTGGCACCTGACTGCGTGGAGAAGC<br>TCATTATGACGGTGACCACCCCTGAGATGGTGATGCCAAG<br>CAGCATGTTCCTCCCAGCAGCTGTTCCAGATCGAGATGGG<br>AATTCCAATTTGGAAGAGGCAGGAAAGCAGCCTGAAACCT<br>CAGAGGATCTGGGAAAGAACATCTTGCCATCCGCAAGCAC<br>AGAGCAAAGCGGAGATTTGAAACCATCCCCTGCTGACCCA<br>GGCTCTGTGAGAGAAGACTCAGGCTTCATCTGCTGGAAGA<br>AGGGGTGCAACCAGGTTTTCAAAACTTCTGCTGCCCTTCA<br>GACGCATTTTAATGAAGTGCATGCCAAGAGGCCTCAGCTG<br>CCGGTGTCAGATCGCCATGTGTACAAGTACCGCTGTAATC<br>AGTGTAGCCTGGCCTTCAAGACCATTGAAAAGTTGCAGCT<br>CCATTCTCAGTACCATGTGATCAGAGCTGCCACCATGTGC<br>TGTCTTTGTCAGCGCAGTTTCCGAACTTTCCAGGCTCTGA<br>AGAAGCACCTTGAGACAAGCCACCTGGAGCTGAGTGAGGC<br>TGACATCCAACAGCTTTATGGTGGCCTGCTGGCCAATGGG<br>GACCTCCTGGCAATGGGAGACCCCACTCTGGCAGAGGACC<br>ATACCATAATTGTTGAGGAAGACAAGGAGGAAGAGAGTGA<br>CTTGGAAGATAAACAGAGCCCAACGGGCAGTGACTCTGGG | 50 |

TABLE 1-continued

GEP-NEN Biomarker/Houskeeper Sequence Information

| Gene Name | RefSeq Accession | Sequence | SEQ ID NO: |
|---|---|---|---|
| | | TCAGTACAAGAAGACTCGGGCTCAGAGCCAAAGAGAGCTC | |
| | | TGCCTTTCAGAAAAGGTCCCAATTTTACTATGGAAAAGTT | |
| | | CCTAGACCCTTCTCGCCCTTACAAGTGTACCGTCTGCAAG | |
| | | GAATCTTTCACTCAAAAGAATATCCTGCTAGTACACTACA | |
| | | ATTCTGTCTCCCACCTGCATAAGTTAAAGAGAGCCCTTCA | |
| | | AGAATCAGCAACCGGTCAGCCAGAACCCACCAGCAGCCCA | |
| | | GACAACAAACCTTTTAAGTGTAACACTTGTAATGTGGCCT | |
| | | ACAGCCAGAGTTCCACTCTGGAGATCCATATGAGGTCTGT | |
| | | GTTACATCAAACCAAGGCCCGGGCAGCCAAGCTGGAGGCT | |
| | | GCAAGTGGCAGCAGCAATGGGACTGGGAACAGCAGCAGTA | |
| | | TTTCCTTGAGCTCCTCCACGCCAAGTCCTGTGAGCACCAG | |
| | | TGGCAGTAACACCTTTACCACCTCCAATCCAAGCAGTGCT | |
| | | GGCATTGCTCCAAGCTCTAACTTACTAAGCCAAGTGCCCA | |
| | | CTGAGAGTGTAGGGATGCCACCCCTGGGGAATCCTATTGG | |
| | | TGCCAACATTGCTTCCCCTTCAGAGCCCAAAGAGGCCAAT | |
| | | CGGAAGAAACTGGCAGATATGATTGCATCCAGGCAGCAGC | |
| | | AACAACAGCAGCAGCAACAGCAACAACAACAACAACAACA | |
| | | ACAACAACAAGCACAAACGCTGGCCCAGGCCCAGGCTCAA | |
| | | GTTCAAGCTCACCTGCAGCAGGAGCTGCAGCAACAGGCTG | |
| | | CCCTGATCCAGTCTCAGCTGTTTAACCCCACCCTCCTTCC | |
| | | TCACTTCCCCATGACAACTGAGACCCTGCTGCAACTACAG | |
| | | CAGCAGCAGCACCTCCTCTTCCCTTTCTACATCCCCAGTG | |
| | | CTGAGTTCCAGCTTAACCCCGAGGTGAGCTTGCCAGTGAC | |
| | | CAGTGGGGCACTGACACTGACTGGGACAGGCCCAGGCCTG | |
| | | CTGGAAGATCTGAAGGCTCAGGTTCAGGTCCCACAGCAGA | |
| | | GCCATCAGCAGATCTTGCCGCAGCAGCAGCAGAACCAACT | |
| | | CTCTATAGCCCAGAGTCACTCTGCCCTCCTTCAGCCAAGC | |
| | | CAGCACCCCGAAAAGAAGAACAAATTGGTCATCAAAGAAA | |
| | | AGGAAAAAGAAAGCCAGAGAGAGAGGGACAGCGCCGAGGG | |
| | | GGGAGAGGGCAACACCGGTCCGAAGGAAACACTGCCAGAT | |
| | | GCCTTGAAGGCCAAAGAGAAGAAAGAGTTGGCACCAGGGG | |
| | | GTGGTTCTGAGCCTTCCATGCTCCCTCCACGCATTGCTTC | |
| | | AGATGCCAGAGGGAACGCCACCAAGGCCCTGCTGGAGAAC | |
| | | TTTGGCTTTGAGTTGGTCATCCAGTATAATGAGAACAAGC | |
| | | AGAAGGTGCAGAAAAAGAATGGGAAGACTGACCAGGGAGA | |
| | | GAACCTGGAAAAGCTCGAGTGTGACTCCTGCGGCAAGTTG | |
| | | TTTTCCAACATCTTGATTTTAAAGAGTCATCAAGAGCACG | |
| | | TTCATCAGAATTACTTTCCTTTCAAACAGCTCGAGAGGTT | |
| | | TGCCAAACAGTACAGAGACCACTACGATAAACTGTACCCA | |
| | | CTGAGGCCCCAGACCCCAGAGCCACCACCACCTCCCCCTC | |
| | | CACCCCCTCCACCCCCACTTCCGGCAGCGCCGCCTCAGCC | |
| | | GGCGTCCACACCAGCCATCCCCGCATCAGCCCCACCCATC | |
| | | ACCTCACCTACAATTGCACCGGCCCAGCCATCAGTGCCGC | |
| | | TCACCCAGCTCTCCATGCCGATGGAGCTGCCCATCTTCTC | |
| | | GCCGCTGATGATGCAGACGATGCCGCTGCAGACCTTGCCG | |
| | | GCTCAGCTACCCCCGCAGCTGGGACCTGTGGAGCCTCTGC | |
| | | CTGCGGACCTGGCCCAACTCTACCAGCATCAGCTCAATCC | |
| | | AACCCTGCTCCAGCAGCAGAACAAGAGGCCTCGCACCAGG | |
| | | ATCACAGATGATCAGCTCCGAGTCTTGCGGCAATATTTTG | |
| | | ACATTAACAACTCCCCCAGTGAAGAGCAAATAAAAGAGAT | |
| | | GGCAGACAAGTCCGGGTTGCCCCAGAAAGTGATCAAGCAC | |
| | | TGGTTCAGGAACACTCTCTTCAAAGAGAGGCAGCGTAACA | |
| | | AGGACTCCCCTTACAACTTCAGTAATCCTCCTATCCACCAG | |
| | | CCTGGAGGAGCTCAAGATTGACTCCCGGCCCCCTTCGCCG | |
| | | GAACCTCCAAAGCAGGAGTACTGGGGAAGCAAGAGGTCTT | |
| | | CAAGAACAAGGTTTACGGACTACCAGCTGAGGGTCTTACA | |
| | | GGACTTCTTCGATGCCAATGCTTACCCAAAGGATGATGAA | |
| | | TTTGAGCAACTCTCTAATTTACTGAACCTTCCAACCCGAG | |
| | | TGATAGTGGTGTGGTTTCAGAATGCCCGACAGAAGGCCAG | |
| | | GAAGAATTATGAGAATCAGGGAGAGGGCAAAGATGGAGAG | |
| | | CGGCGTGAGCTTACAAATGATAGATACATTCGAACAAGCA | |
| | | ACTTGAACTACCAGTGCAAAAAATGTAGCCTGGTGTTTCA | |
| | | GCGCATCTTTGATCTCATCAAGCACCAGAAGAAGCTGTGT | |
| | | TACAAGGATGAGGATGAGGAGGGCAGGACGACAGCCAAA | |
| | | ATGAGGATTCCATGGATGCCATGGAAATCCTGACGCCTAC | |
| | | CAGCTCATCCTGCAGTACCCCGATGCCCTCACAGGCTTAC | |
| | | AGCGCCCCAGCACCATCAGCCAATAATACAGCTTCCTCCG | |
| | | CTTTCTTGCAGCTTACAGCGGAGGCTGAGGAACTGGCCAC | |
| | | CTTCAATTCAAAAACAGAGGCAGGCGATGAGAAACCAAAG | |
| | | CTGGCGGAAGCTCCCAGTGCACAGCCAAACCAAACCCAAG | |
| | | AAAAGCAAGGACAACCAAAGCCAGAGCTGCAGCAGCAAGA | |
| | | GCAGCCCGAGCAGAAGACCAACACTCCCCAGCAGAAGCTC | |
| | | CCCCAGCTGGTGTCCCTGCCTTCGTTGCCACAGCCTCCTC | |
| | | CACAAGCGCCCCCTCCACAGTGCCCCTTACCCCAGTCGAG | |
| | | CCCCAGTCCTTCCCAGCTCTCCCACCTGCCCCTCAAGCCC | |

TABLE 1-continued

GEP-NEN Biomarker/Houskeeper Sequence Information

| Gene Name | RefSeq Accession | Sequence | SEQ ID NO: |
|---|---|---|---|
| | | CTCCACACATCAACTCCTCAACAGCTCGCAAACCTACCTC | |
| | | CTCAGCTAATCCCCTACCAGTGTGACCAGTGTAAGTTGGC | |
| | | ATTTCCGTCATTTGAGCACTGGCAGGAGCATCAGCAGCTC | |
| | | CACTTCCTGAGCGCGCAGAACCAGTTCATCCACCCCCAGT | |
| | | TTTTGGACAGGTCCCTGGATATGCCTTTCATGCTCTTTGA | |
| | | TCCCAGTAACCCACTCCTGGCCAGCCAGCTGCTCTCTGGG | |
| | | GCCATACCTCAGATTCCAGCAAGCTCAGCCACTTCTCCTT | |
| | | CAACTCCAACCTCCACAATGAACACTCTCAAGAGGAAGCT | |
| | | GGAGGAAAAGGCCAGTGCAAGCCCTGGCGAAAACGACAGT | |
| | | GGGACAGGAGGAGAAGAGCCTCAGAGAGACAAGCGTTTGA | |
| | | GAACAACCATCACACCGGAACAACTAGAAATTCTCTACCA | |
| | | GAAGTATCTACTGGATTCCAATCCGACTCGAAAGATGTTG | |
| | | GATCACATTGCACACGAGGTGGGCTTGAAGAAACGTGTGG | |
| | | TACAAGTCTGGTTTCAGAACACCCGAGCTCGGGAAAGGAA | |
| | | AGGACAGTTCCGGGCTGTAGGCCCAGCGCAGGCCCACAGG | |
| | | AGATGCCCTTTTTGCAGAGCGCTCTTCAAAGCCAAGACTG | |
| | | CTCTTGAGGCTCATATCCGGTCCCGTCACTGGCATGAAGC | |
| | | CAAGAGAGCTGGCTACAACCTAACTCTGTCTGCGATGCTC | |
| | | TTAGACTGTGATGGGGGACTCCAGATGAAAGGAGATATTT | |
| | | TTGACGGAACTAGCTTTTCCCACCTACCCCCAAGCAGTAG | |
| | | TGATGGTCAGGGTGTCCCCCTCTCACCTGTGAGTAAAACC | |
| | | ATGGAATTGTCACCCAGAACTCTTCTAAGCCCTTCCTCCA | |
| | | TTAAGGTGGAAGGGATTGAAGACTTTGAAAGCCCCTCCAT | |
| | | GTCCTCAGTTAATCTAAACTTTGACCAAACTAAGCTGGAC | |
| | | AACGATGACTGTTCCTCTGTCAACACAGCAATCACAGATA | |
| | | CCACAACTGGAGACGAGGGCAACGCAGATAACGACAGTGC | |
| | | AACGGGAATAGCAACTGAAACCAAATCCTCTTCTGCACCC | |
| | | AACGAAGGGTTGACCAAAGCGGCCATGATGGCAATGTCTG | |
| | | AGTATGAAGATCGGTTGTCATCTGGTCTGGTCAGCCCGGC | |
| | | CCCGAGCTTTTATAGCAAGGAATATGACAATGAAGGTACA | |
| | | GTGGACTACAGTGAAACCTCAAGCCTTGCAGATCCCTGCT | |
| | | CCCCGAGTCCTGGTGCGAGTGGATCTGCAGGCAAATCTGG | |
| | | TGACAGCGGAGATCGGCCTGGGCAGAAACGTTTTCGCACT | |
| | | CAAATGACCAATCTGCAGCTGAAGGTCCTCAAGTCATGCT | |
| | | TTAATGACTACAGGACACCCACTATGCTAGAATGTGAGGT | |
| | | CCTGGGCAATGACATTGGACTGCCAAAGAGAGTCGTTCAG | |
| | | GTCTGGTTCCAGAATGCCCGGGCAAAAGAAAAGAAGTCCA | |
| | | AGTTAAGCATGGCCAAGCATTTTGGTATAAACCAAACGAG | |
| | | TTATGAGGGACCCAAAACAGAGTGCACTTTGTGTGGCATC | |
| | | AAGTACAGCGCTCGGCTGTCTGTACGTGACCATATCTTTT | |
| | | CCCAACAGCATATCTCCAAAGTTAAAGACACCATTGGAAG | |
| | | CCAGCTGGACAAGGAGAAAGAATACTTTGACCCAGCCACC | |
| | | GTACGTCAGTTGATGGCTCAACAAGAGTTGGACCGGATTA | |
| | | AAAAGGCCAACGAGGTCCTTGGACTGGCAGCTCAGCAGCA | |
| | | AGGGATGTTTGACAACACCCCTCTTCAGGCCCTTAACCTT | |
| | | CCTACAGCATATCCAGCGCTCCAGGGCATTCCTCCTGTGT | |
| | | TGCTCCCGGGCCTCAACAGCCCCTCCTTGCCAGGCTTTAC | |
| | | TCCATCCAACACAGCTTTAACGTCTCCTAAGCCGAACTTG | |
| | | ATGGGTCTGCCCAGCACAACTGTTCCTTCCCTGGCCTCC | |
| | | CCACTTCTGGATTACCAAATAAACCGTCCTCAGCGTCGCT | |
| | | GAGCTCCCAACCCCAGCACAAGCCACGATGGCGATGGGC | |
| | | CCTCAGCAACCCCCCAGCAGCAGCAGCAGCAGCAGCAAC | |
| | | CACAGGTGCAGCAGCCTCCCCCGCCGCCAGCAGCCCAGCC | |
| | | GCCACCCACACCACAGCTCCCACTGCAACAGCAGCAGCAA | |
| | | CGCAAGGACAAAGACAGTGAGAAAGTAAAGGAGAAGGAAA | |
| | | AGGCACACAAAGGGAAAGGGGAACCCCTGCCTGTCCCCAA | |
| | | GAAGGAGAAAGGAGAGGCCCCCACGGCAACTGCAGCCACG | |
| | | ATCTCAGCCCCGCTGCCCACCATGGAGTATGCGGTAGACC | |
| | | CTGCACAGCTGCAGGCCCTGCAGGCCGCGTTGACTTCGGA | |
| | | CCCCACAGCATTGCTCACAAGCCAGTTCCTTCCTTACTTT | |
| | | GTACCAGGCTTTTCTCCTTATTATGCTCCCCAGATCCCTG | |
| | | GCGCCCTGCAGAGCGGGTACCTGCAGCCTATGTATGGCAT | |
| | | GGAAGGCCTGTTCCCCTACAGCCCTGCACTGTCGCAGGCC | |
| | | CTGATGGGGCTGTCCCAGGCTCCCTACTGCAGCAGTACC | |
| | | AGCAATACCAGCAGAGTCTGCAGGAGGCAATTCAGCAGCA | |
| | | GCAGCAGCGGCAACTACAGCAGCAGCAGCAGCAAAAAGTG | |
| | | CAGCAGCAGCAGCCCAAAGCAAGCCAAACCCCAGTCCCCC | |
| | | CCGGGGCTCCTTCCCCAGACAAAGACCCTGCCAAAGAATC | |
| | | CCCCAAACCAGAAGAACAGAAAAACACCCCCGTGAGGTG | |
| | | TCCCCCCTCCTGCCGAAACTCCCTGAAGAGCCAGAAGCAG | |
| | | AAAGCAAAGTGCGGACTCCCTCTACGACCCCTTCATTGT | |
| | | TCCAAAGGTGCAGTACAAGTTGGTCTGCCGCAAGTGCCAG | |
| | | GCGGGCTTCAGCGACGAGGAGGCAGCGAGGAGCCACCTGA | |
| | | AGTCCCTCTGCTTCTTCGGCCAGTCTGTGGTGAACCTGCA | |
| | | AGAGATGGTGCTTCACGTCCCCACCGGCGGCGGCGGCGGT | |

TABLE 1-continued

GEP-NEN Biomarker/Houskeeper Sequence Information

| Gene Name | RefSeq Accession | Sequence | SEQ ID NO: |
|---|---|---|---|
| | | GGCAGTGGCGGCGGCGGCGGCGGTGGCGGCGGCGGCGGCG | |
| | | GCGGCGGCTCGTACCACTGCCTGGCGTGCGAGAGCGCGCT | |
| | | CTGTGGGGAGGAAGCTCTGAGTCAACATCTCGAGTCGGCC | |
| | | TTGCACAAACACAGAACAATCACGAGAGCAGCAAGAAACG | |
| | | CCAAAGAGCACCCTAGTTTATTACCTCACTCTGCCTGCTT | |
| | | CCCCGATCCTAGCACCGCATCTACCTCGCAGTCTGCCGCT | |
| | | CACTCAAACGACAGCCCCCCTCCCCCGTCGGCCGCCGCCC | |
| | | CCTCCTCCGCTTCCCCCCACGCCTCCAGGAAGTCTTGGCC | |
| | | GCAAGTGGTCTCCCGGGCTTCGGCAGCGAAGCCCCCTTCT | |
| | | TTTCCTCCTCTCTCCTCATCTTCAACGGTTACCTCAAGTT | |
| | | CATGCAGCACCTCAGGGGTTCAGCCCTCGATGCCAACAGA | |
| | | CGACTATTCGGAGGAGTCTGACACGGATCTCAGCCAAAAG | |
| | | TCCGACGGACCGGCGAGCCCGGTGGAGGGTCCCAAAGACC | |
| | | CCAGCTGCCCCAAGGACAGTGGTCTGACCAGTGTAGGAAC | |
| | | GGACACCTTCAGATTGTAAGCTTTGAAGATGAACAATACA | |
| | | AACAAATGAATTTAAATACAAAAATTAATAACAAACCAAT | |
| | | TTCAAAAATAGACTAACTGCAATTCCAAAGCTTCTAACCA | |
| | | AAAAACAAAAAAAAAAAAAAAGAAAAAAAGAAAAAGC | |
| | | GTGGGTTGTTTTCCCATATACCTATCTATGCCGGTGATTT | |
| | | TACATTCTTGTCTTTTTCTTTTCTTTTAATATTAAAAAAA | |
| | | AAAAAAAAGCCCTAACCCTGTTACATTGTGTCCTTTTGAA | |
| | | GGTACTATTGGTCTGGGAAACAGAAGTCCGCAGGGCCTCC | |
| | | CTAATGTCTTTGGAGCTTAAACCCCTTGTATATTTGCCCC | |
| | | TTTTCAATAAACGCCCCACGCTGATAGCACAGAGGAGCCC | |
| | | GGCATGCACTGTATGGGAAAGCAGTCCACCTTGTTACAGT | |
| | | TTTAAATTTCTTGCTATCTTAGCATTCAGATACCAATGGC | |
| | | TTGCTAAAAGAAAAAAGAAATGTAATGTCTTTTTATTCT | |
| | | CAGGTCAATCGCTCACACTTTGTTTTCAGAATCATTGTTT | |
| | | TATATATTATTGTTTTTTCAGTTTTTTTTTTTTTTTTGT | |
| | | TCCAGAAAAGATTTTTTGTTTTGTTAACTTAAAAATGGGC | |
| | | AGAAAGTATTCAAGAAAAACAATGTGAACTGCTTTAGCTT | |
| | | TCTGGGGATTTTTAAGGATAGCTTTTCTGCTGAAGCCAAT | |
| | | TTCAAGGGGAAAAGTTAAGCACTCCCACTTTCAAAAAAAA | |
| | | AAAAAAATAATAACCCACACACACAAAGAGTGTTGAGGAC | |
| | | TTGTAGCTTAAAAAAAATAAGTTTTAAAAACTGACTTTCT | |
| | | GTATTTATGATAGATATGACCATTTTTGGTGTTGAGTAGA | |
| | | TTGTTGCATTGGAAATGAACTGAAGCAGTATGGTAGATTT | |
| | | AAAAGGAAAAAAAAAAAAAAACCTTTTGTGTACATTTAGC | |
| | | TTTTTGTATGGTCCAGCTGACAGCTCCTCATTTGATGTTG | |
| | | TCTTGTTCATTCCTAGCAGATGATAGATTGCAATCCGTTG | |
| | | ATTCGCCTAAGCTTTTCTCCCCTTGTCCCTTAATTCCACT | |
| | | TTCTCTTTCTTGTCCCTTAATTCCACTTTCTCTTTCCTTC | |
| | | TCCCACCTCCCGTCCTATAATCTCCCACTTAAGGTAGCTG | |
| | | CCTTCATTTCTTAGAGGGAGCTGCAGAATTATTTTATAAA | |
| | | ACTAAAGAAAGAATTTCAAGGGATTCTAGGGGTCATTAGG | |
| | | ATCCTCACAGATTATTTTGGTTGGGGAGTTGAAACTTTT | |
| | | TAAAGGCATATAATTCTAGTTACCTGTGTCTGTTAGCTTT | |
| | | GTGCATTTATTTTTATTTATCCTTCTTTTGGCTTTTTTT | |
| | | TCTTTGTACCCCTTCTTTTCCTCCTTGTTTGGTAGGAGCT | |
| | | TCAAATATTCTTTTTTTTCTATACTAAAGGATTTGTTTC | |
| | | CATTTGTGTAATTGGCTGTGTACTTTTCTTTTCTAAAAAA | |
| | | AGTTTTTGGTTAGGGATTTGGTTTTTGGTTTTGTGTTTGT | |
| | | TTTTTCTTTCCTCTCTCAGAAAAAAAAATTTCATGCTTTA | |
| | | AATAAAATCCAAAGACACACCCTTTCACTGCTGATGCAGA | |
| | | AAAAAGGGAAAGGGTTCTTGTTACTTGAGAATTTGTTTCT | |
| | | GATTTAAACAAACAAGACTTAGTTTAATAAAAGAAAGAGA | |
| | | AAAACAAAAGATTCCCAGGTTGTTATGTGCTTCTTCTGCA | |
| | | AGCAGAGAGGCAAATGTTAATGACAATTCCATATACCAAA | |
| | | AGACACATTTTTTACTTCAAAGTTTTGTCCTTGTGTTAGG | |
| | | CAGTCTGAGCAGCGAGTGATCCAGAGCGCAGCCAACAAAG | |
| | | CAGCAGATAGCAGTGTACAGAAAGCAAAAAAGGAACTGTA | |
| | | TGTGAGGCACTTGTTTCTGTTAATATCCATATTCCTGTTA | |
| | | ACACACACCCTTTCTCATGTAAAAAGAAAAATAAATAAAT | |
| | | GGTCTGAACTTTGAAAACTTTGTGCTGCTAAAACATAGAT | |
| | | TTTGGAGACAAATAAATAGATGCTTTGCTGTTTCACTTTC | |
| | | ATAGCTAAACATCAACAGAAACCATCTCCCCTTGCCCCCA | |
| | | AAGTGTGAAATCCTTCTTCCCTTCGTTTTCTTCCTTATGT | |
| | | TTCAAAAGGGAACTTTGAAGACTGTGAATACAGGTTCCAT | |
| | | TGGTCACCTTTCGGGCTTCTTCCCCAGTGCTGAAGCCAC | |
| | | TCATCGACTTTGCAAAAGACTGGAGCATTCCAAGATCTGA | |
| | | AAATGATTTTTTTCTTTTTTCTTTTTTAGCCGGGACT | |
| | | ATTTTATTTTTATGAATTTGTTTTTAGTTTAATGAAATAG | |
| | | TAGATCCTGAAATGTTGTACATATTTCTAACTAGGCTGAT | |
| | | GCACAGTGCAAATTCCTTTTTAATTGTTTTTTTAAGTA | |
| | | GAAATACTAAAGAAAGAATACCATCTAACTATTCATACCA | |

TABLE 1-continued

GEP-NEN Biomarker/Houskeeper Sequence Information

| Gene Name | RefSeq Accession | Sequence | SEQ ID NO: |
|---|---|---|---|
| | | GTATCCAGTTGTAGCATAAGGTGTCAAAAGCAAGTACGCA<br>AAACATTTACTGTTTTAACAAGCTATTTCCTTTTAACAAG<br>AAATCTTGTATTTCTTCCTGTGTTTGAGATGAACATTTTT<br>AAATTTTAAAGTTGTACAGTTTTTTGTTTTCCATTATTTT<br>ATCTTGTTTGTAACTCTATGAAATATATATATATATATTT<br>TTTGCCATTTAACTGTTGTATGTTACTCTGTGTCTGTACC<br>ATATAGAAAAAAAATTGTTTTTGTTTTTGGTTCTCTATGT<br>GATATCAGTTAACAATGTAACACTAGCTTTACCTGTCAAA<br>TTCTGCTAGGTCTTCTCTGAAAACGTTGTTTTTAAAAATG<br>ATATTGCTTGGTAATAGTGCAATTTCTATCCTTTTCCCTC<br>CCCCCTCAACTTTTAAGTTCTTTTCTTTATAATTTTGCTG<br>CCCCCTCCCTGATGGTTTGGGTTTTTGTTTTTGTTTTTGT<br>TTTTTTTTTTCATGGAGCTACTATGCCATCCTCCCTCTGT<br>GAGGCAGAGTGACTGTCAGTGTTTTGTTATGCCATGCCTT<br>GAGCTGTGGGTGTTTGGCGACAATAAGGTGGTTGAATAGA<br>TTGGCTGAGCACACTTCCACCCACCTAGTGTTCTCAGAGG<br>GGTTATGTGATTGTTTCAACCTGGAGTGGGTTGCACCCTT<br>AATGCTTTCCTCTGCAACTAAACCGCCCACATATATGTTC<br>ATTGAAAAAAGTAAGAATAATTCTCAGCACTAACCCAGAA<br>GTAGCAAAGCAGTCAGTGATGGTGAACATTAGAGGTCAAA<br>CATGAGTTAGATGTTTGTGGGCTGACAGCCATCGTGGCTA<br>TGACCAGTACTATTTACAAAGCATGAATTCACTACAATGC<br>TCAACTGTTTGTTTAGCTTTATCTCACTTGGGGAATTTAT<br>TCCTGTCTGCTGCATTGTAGGTAGCTGGGTAGGATATATT<br>TCCACTTGCTTTTTAAATTAGTTCTTCACCTCCATTGACA<br>CTCGTTTTTTGGTTTTCTCCCTATAGTGTGGGTTGGTGCT<br>AGACACCAGTCTGACCCACAGAATGGGAGTTATTTCATCC<br>ATCTTTCCTCCATCCTTCCAAAAACCACATATCTACACAA<br>GGAAAAATTTAATACATCTAGGAATTTTTTTTTAATTAC<br>AAGCTATTTAAAGAGATGAATGTGGCCAAAGTTTTACACA<br>ATTGAAAATAAAGTAAAACAGACGGCATGTGTTTAAACCT<br>GAGTTTATCAGGCATGGCAGGAAGTTGCAGGAGAGAGAGG<br>CAGTGACCCAAGCCAGTGCACTTGATGTTCATGGACATAT<br>ATTTTTTTTAAATAATAAATTAAAACATTTTAAATAGAAG<br>CATAAATTGAGTTGTTTGTTGGCGCTGAGATACTGCCCAC<br>TGTGAAACAAAGCTTTGACTAGTTTTTGTTTGTTTACTT<br>TCTTCAGGGGGGAGGGGGCAAGTTTGGGTAGGAAAGAAA<br>GCATAAATGAACGTGACCCTGAGGTGAAGAGGTATATGAA<br>CAGCCTTTGCAATGTACAAAAGAAAAAAAAACAAAAAAC<br>AACAAAAAAATAGAGCAAGTGAAACCAAAAATGATGTTC<br>TTGGTGTTTTCTATAATGTAGTCTTGTTAGCTTTTTTGT<br>TACTGTAACAATGCTGATCTCGAACTGTACCAAAATACAT<br>GGAGACTAACAAACAGAACCACATGGAACTTTCAAACTGA<br>AAAAAAATTTGTCACAAAAACTTTGTTGTCATAGTTAAG<br>TTGATTGTAGATGGTAATTGAATATACTCCTTTGAAAATA<br>TTTCATCAAGTATGTTTCCTGCTCATTGTGATACATTAAA<br>AAAAAATATGAGCAAAA | |
| ZXDC | NM_001040653.3 | GGGCGCGGGCAGCTCTGCGTCCGAAGCTGCTCCGACGCCG<br>TCGCTGGGACCAAGATGGACCTCCCGGCGCTGCTCCCCGC<br>CCCGACTGCGCGCGGAGGGCAACATGGCGGCGGCCCCGGC<br>CCGCTCCGCCGAGCCCCAGCGCCGCTCGGCGCGAGCCCCG<br>CGCGCCGCCGCCTGCTACTGGTGCGGGGCCCTGAAGATGG<br>CGGGCCCGGGGCGCGGCCCGGGGAGGCCTCCGGGCCAAGC<br>CCGCCGCCCGCCGAGGACGACAGCGACGGCGACTCTTTCT<br>TGGTGCTGCTGGAAGTGCCGCACGGCGGCGCTGCCGCCGA<br>GGCTGCCGGATCACAGGAGGCCGAGCCTGGCTCCCGTGTC<br>AACCTGGCGAGCCGCCCCGAGCAGGGCCCCAGCGGCCCGG<br>CCGCCCCCCCGGCCCTGGCGTAGCCCCGGCGGGCGCCGT<br>CACCATCAGCAGCCAGGACCTGCTGGTGCGTCTCGACCGC<br>GGCGTCCTCGCGCTGTCTGCGCCGCCCGGCCCCGCAACCG<br>CGGGCGCCGCCGCTCCCCGCCGCGCGCCCCAGGCCTCCGG<br>CCCCAGCACGCCCGGCTACCGCTGCCCCGAGCCGCAGTGC<br>GCGCTGGCCTTCGCCAAGAAGCACCAGCTCAAGGTGCACC<br>TGCTCACGCACGGCGGCGGTCAGGGCCGGCGGCCCTTCAA<br>GTGCCCACTGGAGGGCTGTGGTTGGGCCTTCACAACGTCC<br>TACAAGCTCAAGCGGCACCTGCAGTCGCACGACAAGCTGC<br>GGCCCTTCGGCTGTCCAGTGGGCGGCTGTGGCAAGAAGTT<br>CACTACGGTCTATAACCTCAAGGCGCACATGAAGGGCCAC<br>GAGCAGGAGAGCCTGTTCAAGTGCGAGGTGTGCGCCGAGC<br>GCTTCCCCACGCACGCCAAGCTCAGCTCCCACCAGCGCAG<br>CCACTTCGAGCCCGAGCGCCCTTACAAGTGTGACTTTCCC<br>GGCTGTGAGAAGAC<u>ATTTATCACAGTGAGTGCCCTGTTTT<br>CCCATAACCGAGCCCACTTCAGGGAACAAGAGCTCTTTTC</u><br>CTGCTCCTTTCCTGGGTGCAGCAAGCAGTATGATAAAGCC | 51 |

TABLE 1-continued

GEP-NEN Biomarker/Houskeeper Sequence Information

| Gene Name | RefSeq Accession | Sequence | SEQ ID NO: |
|---|---|---|---|
| | | TGTCGGCTGAAAATTCACCTGCGGAGCCATACAGGTGAAA | |
| | | GACCATTTATTTGTGACTCTGACAGCTGTGGCTGGACCTT | |
| | | CACCAGCATGTCCAAACTTCTAAGGCACAGAAGGAAACAT | |
| | | GACGATGACCGGAGGTTTACCTGCCCTGTCGAGGGCTGTG | |
| | | GGAAATCATTCACCAGAGCAGAGCATCTGAAAGGCCACAG | |
| | | CATAACCCACCTAGGCACAAAGCCGTTCGAGTGTCCTGTG | |
| | | GAAGGATGTTGCGCGAGGTTCTCCGCTCGTAGCAGTCTGT | |
| | | ACATTCACTCTAAGAAACACGTGCAGGATGTGGGTGCTCC | |
| | | GAAAAGCCGTTGCCCAGTTTCTACCTGCAACAGACTCTTC | |
| | | ACCTCCAAGCACAGCATGAAGGCGCACATGGTCAGACAGC | |
| | | ACAGCCGGCGCCAAGATCTCTTACCTCAGCTAGAAGCTCC | |
| | | GAGTTCTCTTACTCCCAGCAGTGAACTCAGCAGCCCAGGC | |
| | | CAAAGTGAGCTCACTAACATGGATCTTGCTGCACTCTTCT | |
| | | CTGACACACCTGCCAATGCTAGTGGTTCTGCAGGTGGGTC | |
| | | GGATGAGGCTCTGAACTCCGGAATCCTGACTATTGACGTC | |
| | | ACTTCTGTGAGCTCCTCTCTGGGAGGGAACCTCCCTGCTA | |
| | | ATAATAGCTCCCTAGGGCCGATGGAACCCCTGGTCCTGGT | |
| | | GGCCCACAGTGATATTCCCCAAGCCTGGACAGCCCTCTG | |
| | | GTTCTCGGGACAGCAGCCACGGTTCTGCAGCAGGGCAGCT | |
| | | TCAGTGTGGATGACGTGCAGACTGTGAGTGCAGGAGCATT | |
| | | AGGCTGTCTGGTGGCTCTGCCCATGAAGAACTTGAGTGAC | |
| | | GACCCACTGGCTTTGACCTCCAATAGTAACTTAGCAGCAC | |
| | | ATATCACCACACCGACCTCTTCGAGCACCCCCCGAGAAAA | |
| | | TGCCAGTGTCCCGGAACTGCTGGCTCCAATCAAGGTGGAG | |
| | | CCGGACTCGCCTTCTCGCCCAGGAGCAGTTGGGCAGCAGG | |
| | | AAGGAAGCCATGGGCTGCCCCAGTCCACGTTGCCCAGTCC | |
| | | AGCAGAGCAGCACGGTGCCCAGGACACAGAGCTCAGTGCA | |
| | | GGCACTGGCAACTTCTATTTGGTATGAAGCACTCTATTCA | |
| | | GTCACCACCATATAGGTCACTTCTCTCATACTCGGTCTTG | |
| | | AGGATATTCTGGATTAATCCTTTCTATGCAGACGTTTCTG | |
| | | GTTTACAAAAGGACGCAGCCCTGGACTACAAGTCTGGAAC | |
| | | TGACAAGTTCTTATGACCTTGACAAATCACCTTAACCCAT | |
| | | CTGAGCCTTAAATTCTCATTTATTTCCTGCATAAGGAGAT | |
| | | TTGGCTAAATGCTTTCTGAGGTCCTTTGGAGTCCTGTGGC | |
| | | TCCATGGTAATGTGCTCCTTTCCTTGAAGATTGGGGGTTT | |
| | | TGTAATGTTGAGATACTTTGCCTCTATGCTTGTCAGCTCA | |
| | | TGACCAGTCCTAGAAGAGGAGTCGAGACATAAGCCACCTT | |
| | | CAGAGGTTCAATGGAAACTTTAAAACCATACCAAACTCTT | |
| | | TTTTAAAATTAGAATTAACAAGAAAAAAAAAAAGGGTGGG | |
| | | GTTTATGAGCCTTAGTTCTTGGAGGATTATAAGAGTACTT | |
| | | CCCCAGTTTTGAGGCTGGACAGTTAATATACTTTATATCA | |
| | | ATTATACATTTAATATAATTTAATTTAAAATAATTTAAAG | |
| | | ATTCTTAGGAGATAGTCTGACTTTCCTGACCTAGATGGGA | |
| | | ATGATCAGATAGGGATTTTTTTGTGGCACAGGCTAAATT | |
| | | TGATGGTGACATTTATATTGTTGAGAATGTTACATCTTAT | |
| | | TTTACCACAACTTTTAAAAAATGTTACATCTTTTGCAGTA | |
| | | GGATCAGTTGTGAGGCACATAGTAGCTGAGGCTCCATGGA | |
| | | GCCACCTTTCATTTCTTTCAGTCAGAGAGGAGGACAGTCT | |
| | | CTGTCTCTGCATTTCTGGTGTCTTGCTTGTCGGTGGCAGA | |
| | | GCCATGCTTGCCGGCATTTGCTTAGGCGGCCATAGTAGTT | |
| | | GCTAAGTGTACAGGTGACTGGGCAGGGATGGGAGGTGGCC | |
| | | ACAGGTCAGAGACAAGTGCTCAGTCAGTCCCTGGTGCCAG | |
| | | GACTGTGTGCCTCGGTGCCTTGGGAAATGGAAGCTCCCTG | |
| | | GTGCAGCTGCAGCTGTGGGTGGAGGTAGAGAAGCCAGCAA | |
| | | GACCTTGGTCTTAACCCCGTGTTCATTTTCTTGCTAGCTG | |
| | | TGTGACGTTGGGCTACCTCGCTTCTCTGAGTACAAATGGT | |
| | | GTGTGGTGAATGGGTCCCAGGTATGCTACGAGCTTTGAGG | |
| | | GCTGCTCTTTTTCTCTTCATAGCGATAAGTGTTAAACTGT | |
| | | CTTTCTTAGGAAACGTTCACAGACTTGCAACAGCTGATGT | |
| | | CCTCTGAGTACTGTCTGACTCCCTCAGGCAAGTTCCTGAA | |
| | | TTCAGTACCATCATTATTATTTTTGTGTAAGACTTTGACA | |
| | | AAGTATAGCCCCTGCCACCAGAGCAGCCTGTACAGTGGGT | |
| | | CTCTAAGGTGGGACCTGCCCCGGGCCTGCCATGCACGTGT | |
| | | GTGAAACAGCGTGAAAAGTGTCGCGGTAAGGTGACCCTGG | |
| | | GTTACCCAGGCAAGGCTCGGTGTTTGTTTCAGAAAGCAGA | |
| | | GAAGTATGTAATTGATTTTAAAAGTTTCTGTTTAAAATAT | |
| | | TTGGCTATGTTTTAGACTATGAAGGAATGAACTTTGCTTC | |
| | | TCTGGATAAGAAAGTCACATACATTGTTCCAGCTCCAAGT | |
| | | TTGTTCGGCCCTCGCCACAAGTGGATGTAGCGTTTGGCCC | |
| | | TTTGTGTGCCTTGCTGGTGACTCTGGTTTTGGGAGCTCGG | |
| | | ATATGTCCCAGAAGCAGGCTTATGGCACTTCTGTAGCTCC | |
| | | CTTGCTACCCTTCCTTTGTGTCTAGATAAGTGACTGACAT | |
| | | GCTTTTCTTTGGTCTCAGGAAAGTGGGGCTCAGCAAGAA | |
| | | CTGATTACCGAGCCATTCAACTAGCCAAGGAAAAAAAGCA | |
| | | GAGAGGAGCGGGGAGCAATGCAGGTGAGGCCGTGTGTGCT | |

TABLE 1-continued

GEP-NEN Biomarker/Houskeeper Sequence Information

| Gene Name | RefSeq Accession | Sequence | SEQ ID NO: |
|---|---|---|---|
| | | GCAGCCGGACGAGCAAGGGCCTGAGGGTTCTCTGTCACTG<br>TTACTGGCAGAAGAAACACAGCAGGTGTTTCTGTGCTCTT<br>GGTTTTACTTTTCTGTTCAGAATACCCTTTTATCAACTCC<br>TTAGTTTTATTTGAACTTAAGGGAAAAAATTAGTAACAAA<br>ATTCCCAGCATCAGTATGAACATATTTTATTTGCCTAAAC<br>AAGCTTTGTGAAAGTTAAGCGTTCAAACACCAGTGTCAGT<br>TACCTGGAAGGCTACTAAGGTAAATAAGCAAAGCAGGCCA<br>GTTGTCAGGAAAGCAGAGATTGTGCCTGGTGCTGAATGGC<br>CTTGGGGCCTGATCTTGGCATGGCAGAGACCTGGGGACTG<br>CCACTGTCCCCAGGTACGTGTACATGGAGCCAAACTGTGT<br>GTCCTGTGGCATTGTCAGAGTTATGTTGAAATCTTATTTG<br>AAAATGTTAGCAACTTACTTGCATTTTTAAAGACCAAACA<br>AGAGCTGGTAACCTATGGCCTCAAGCATCTGTCCTTCCTA<br>AAAATGGAATAGTGGGATGTAGTGCTTAATGGAAACTGCT<br>AAATCTTTTTCTAAAAACTAACAGTGGATTTTTAAAATAT<br>ATTGTTTTTTGTGTATTTCATTTGTCCTTTGTATTTATCT<br>AAAAGGGTTGATATGATTTTATATCTTGCTCTCTATTCCT<br>AATAGTATTATGACTTCTTATTTAAAATAAATAACAATTG<br>CCGGTTTTCTGTTAAAAAAAAAAAA | |
| ZZZ3 | NM_015534.4 | GTTGGCAGAGCAGTTGTCCTGGATGGCGGAGCCTTGGGTT<br>CCGGGGGCCTGGGACCTGCAACTCTTTCTACAAGATATCA<br>AGTTATTCTAGTACAACCATATAAATAAATAATACCTGAA<br>GTCTCAGTGTAACATGGACAATTAACAGTGATGACAGATA<br>AATACAGACGCATGGGGATCAAATACTAGGCAAAACGCTT<br>TTTAAAAGTGTATCAGGCTTTTAAGAAACACTGCAGGATC<br>CTGTCTATCTTAATGCTGATAGAGCTCAGCTAAAAATTTA<br>GGAGGTTCTAGTATTCTTCATGGCTGAAGCTGAGAGAGTC<br>TGAAACCCTGATGCTTAAGCTCCATTCTAGATCATAGCTC<br>CAACTCCTTCAGGATATAAGGAAAAGAGATTATATTTCCA<br>CAATGATAGATCTTTGGTTGTACAGGTTTCCCAATGAGTG<br>GATCATGATGACCGTATTGTAGGGACTTGCCATAGTATGG<br>CTGCTTCCCGATCTACTCGTGTTACAAGATCAACAGTGGG<br>GTTAAACGGCTTGGATGAATCTTTTTGTGGTAGAACTTTA<br>AGGAATCGTAGCATTGCGCATCCTGAAGAAATCTCTTCTA<br>ATTCTCAAGTACGATCAAGATCACCAAAGAAGAGACCAGA<br>GCCTGTGCCAATTCAGAAAGGAAATAATAATGGGAGAACC<br>ACTGATTTAAAACAGCAGAGTACCCGAGAATCATGGGTAA<br>GCCCTAGGAAAAGAGGACTTTCTTCTTCAGAAAAGGATAA<br>CATAGAAAGGCAGGCTATAGAAAATTGTGAGAGAAGGCAA<br>ACAGAACCTGTTTCACCAGTTTTAAAAAGAATTAAGCGTT<br>GTCTTAGATCTGAAGCACCAAACAGTTCAGAAGAAGATTC<br>TCCTATAAAATCAGACAAGGAGTCAGTAGAACAGAGGAGT<br>ACAGTAGTGGACAATGATGCAGATTTTCAAGGGACTAAAC<br>GAGCTTGTCGATGTCTTATACTGGATGATTGTGAGAAAAG<br>GGAAATTAAAAAGGTGAATGTCAGTGAGGAAGGGCCACTT<br>AATTCTGCAGTAGTTGAAGAAATCACAGGCTATTTGGCTG<br>TCAATGGTGTTGATGACAGTGATTCAGCTGTTATAAACTG<br>TGATGACTGTCAGCCTGATGGGAACACTAAACAAAATAGC<br>ATTGGTTCCTATGTGTTACAGGAAAAATCAGTAGCTGAAA<br>ATGGGGATACGGATACCCAAACTTCAATGTTCCTTGATAG<br>TAGGAAGGAGGACAGTTATATAGACCATAAGGTGCCTTGC<br>ACAGATTCACAAGTGCAGGTCAAGTTGGAGGACCACAAAA<br>TAGTAACTGCCTGCTTGCCTGTGGAACATGTTAATCAGCT<br>GACTACTGAGCCAGCTACAGGGCCCTTTTCTGAAACTCAG<br>TCATCTTTAAGGGATTCTGAGGAGGAAGTAGATGTGGTGG<br>GAGATAGCAGTGCCTCAAAAGAGCAGTGTAAAGAAAACAC<br>CAATAACGAACTGGACACAAGTCTTGAGAGTATGCCAGCC<br>TCCGGAGAACCTGAACCATCTCCTGTTCTAGACTGTGTTT<br>CAGCTCAAATGATGTCTTTATCAGAACCTCAAGAACATCG<br>TTATACTCTGAGAACCTCACCACGAAGGGCAGCCCCTACC<br>AGAGGTAGTCCCACTAAAAACAGTTCTCCTTACAGAGAAA<br>ATGGACAATTTGAGGAGAATAATCTTAGTCCTAATGAAAC<br>AAATGCAACTGTTAGTGATAATGTAAGTCAATCTCCTACA<br>AATCCTGGTGAAATTTCTCAAAATGAAAAGGGATATGTT<br>GTGACTCTCAAAATAATGGAAGTGAAGGAGTAAGTAAACC<br>ACCCTCAGAGGCAAGACTCAATATTGGACATTTGCCATCT<br>GCCAAAGAGAGTGCCAGTCAGCACATTACAGAAGAGGAAG<br>ATGATGATCCTGATGTTTATTACTTTGAATCAGATCATGT<br>GGCACTGAAACACAACAAAGATTACAGAGACTATTACAG<br>ACGATTGCTGTACTCGAGGCTCAGCGTTCTCAAGCAGTCC<br>AAGACCTTGAAAGTTTAGGCAGGCACCAGAGAGAAGCACT<br>GAAAAATCCCATTGGATTTGTGGAAAAACTCCAGAAGAAG<br>GCTGATATTGGGCTTCCATATCCACAGAGAGTTGTTCAAT<br>TGCCTGAGATCGTATGGGACCAATATACCCATAGCCTTGG | 52 |

TABLE 1-continued

GEP-NEN Biomarker/Houskeeper Sequence Information

| Gene Name | RefSeq Accession | Sequence | SEQ ID NO: |
|---|---|---|---|
| | | GAATTTTGAAAGAGAATTTAAAAATCGTAAAAGACATACT<br>AGAAGAGTTAAGCTAGTTTTTGATAAAGTAGGTTTACCTG<br>CTAGACCAAAAAGTCCTTTAGATCCTAAGAAGGATGGAGA<br>GTCCCTTTCATATTCTATGTTGCCTTTGAGTGATGGTCCA<br>GAAGGCTCAAGCAGTCGTCCTCAGATGATAAGAGGACGCT<br>TGTGTGATGATACCAAACCTGAAACATTTAACCAGTTGTG<br>GACTGTTGAAGAACAGAAAAAGCTGGAACAGCTACTCATC<br>AAATACCCTCCTGAAGAAGTAGAATCTCGACGCTGGCAGA<br>AGATAGCAGATGAATTGGGCAACAGGACAGCAAAACAGGT<br>TGCCAGCCGAGTACAGAAGTATTTCATAAAGCTAACTAAA<br>GCTGGCATTCCAGTACCAGGCAGAACACCAAACTTATATA<br>TATACTCCAAAAAGTCTTCAACAAGCAGACGACAGCACCC<br>TCTTAATAAGCATCTCTTTAAGCCTTCCACTTTCATGACT<br>TCACATGAACCGCCAGTGTATATGGATGAAGATGATGACC<br>GATCTTGTTTTCATAGCCACATGAACACTGCTGTTGAAGA<br>TGCATCAGATGACGAAAGTATTCCTATCATGTATAGGAAT<br>TTACCTGAATATAAAGAACTATTACAGTTTAAAAAGTTAA<br>AGAAGCAGAAACTTCAGCAAATGCAAGCTGAAAGTGGATT<br>TGTGCAACATGTGGGCTTTAAGTGTGATAACTGTGGCATA<br>GAACCCATCCAGGGTGTTCGGTGGCATTGCCAGGATTGTC<br>CTCCAGAAATGTCTTTGGATTTCTGTGATTCTTGTTCAGA<br>CTGTCTACATGAAACAGATATTCACAAGGAAGATCACCAA<br>TTAGAACCTATTTATAGGTCAGAGACATTCTTAGACAGAG<br>ACTACTGTGTGTCTCAGGGCACCAGTTACAATTACCTTGA<br>CCCAAACTACTTTCCAGCAAACAGATGACATGGAAGAGAA<br>CATCATTTACTAGTCCTCTTCAACACATAGCAATGGTATC<br>ATTGTTAATTATGTGCACAGTTTGGAAAGATTCTCTGCTT<br>TCCCAGAAATGACACTCACAGCATGAGAGCTTCCTGAGTG<br>TTCTCGTCAAGTACAGCTCTGCACCGTTGTGGCTCTAGAT<br>CACTGTTCAGCAGCTGAACATTCCTGGTGAGCAAAGGTTT<br>CCCTGGTGAATTTTTCACCACTGCGTTTTAGGTGGTGATC<br>TTAAATGGGTGAGATGGAACGAGAGCACACATTAAAGAGA<br>GAGTAAATTCCAAAGGTTTCAAAGAACTTGGTCATAAATA<br>TGATAATGAGAAGACAAAGTATTTATATTAAAACAGTTTA<br>GTAGCCTTCAGTTTTGTGAAAATAGTTTTCAGCACAGAAA<br>CTGACTTCTTTAGACAAAGTTTTAACCAATGATGGTGTTT<br>GCTTCTAGGATATACACTTTAAAAGAACTCACTGTCCCAG<br>TGGTGGTCATTGATGGCCTTTAGTAAATTGGAGCTGCTTA<br>ATCATATTGATATCTAATTTCTTTTAACCACAATGAATTG<br>TCCTTAATTACCAACAGTGAAGCACTACAGGAGGCAACTG<br>TGGCATTGCTTCCTTAACCAGCTCATGGTGTGTGAATGTT<br>ATAAAATTGTCACTCAGATATATTTTTTAAATGTAATGTT<br>ATATAAGATGATCATGTGATGTGTACAAACTATGGTGAAA<br>AGTGCCAGTGGTAGTAACTGTGTAAAGTTTCTAATTCACA<br>ACATTAATTCCTTTAAAATACACAGCCTTCTGCCTCTGTA<br>TTTGGAGTTGTCAGTACAACTCATCAAAGAAAACTGCCTA<br>ATATAAAAATCATATATATGGTAATAATTTCCCTCTTTTG<br>TAGTCTGCACAAGATCCATAAAAGATTGTATTTTTATTAC<br>TATTTAAACAAGTGATTAAATTTAGTCTGCACAGTGAGCA<br>AGGGTTCACATGCATTCTTTTATACTGCTGGATTTTGTTG<br>TGCATCATTTAAAACATTTTGTATGTTTCTTCTTATCTGT<br>GTATACAGTATGTTCTTGAATGATGTTCATTTGTCAGGAG<br>AACTGTGAGAAATAAACTATGTGGATACTGTCTGTTTATA<br>TTAAAAGAAAAAAAAAAAAAAAAA | |

The 51 GEP-NEN biomarkers include: AKAP8L (A kinase (PRKA) anchor protein 8-like), APLP2 (amyloid beta (A4) precursor-like protein 2), ARAF1 (v-raf murine sarcoma 3611 viral oncogene homolog), ATP6V1H (ATPase, H+ transporting, lysosomal 50/57 kDa, V1 subunit H), BNIP3L (BCL2/adenovirus E1B 19 kDa interacting protein 3-like), BRAF (v-raf murine sarcoma viral oncogene homolog B1), C21ORF7 (chromosome 21 open reading frame 7), CD59 (CD59 molecule, complement regulatory protein), COMMD9 (COMM domain containing 9), CTGF (connective tissue growth factor), ENPP4 (ectonucleotide pyrophosphatase/phosphodiesterase 4), FAM131A (family with sequence similarity 131, member A, transcript variant 2), FLJ 10357 (Rho guanine nucleotide exchange factor (GEF) 40 (ARHGEF40), FZD7 (frizzled homolog 7 (Drosophila)), GLT8D1 (glycosyltransferase 8 domain containing 1, transcript variant 3), HDAC9 (histone deacetylase 9, transcript variant 6), HSF2 (heat shock transcription factor 2, transcript variant 1), Ki-67 (antigen identified by monoclonal antibody Ki-67), KRAS (v-Ki-ras2 Kirsten rat sarcoma viral oncogene homolog), LEO1 (Pafl/RNA polymerase II complex component homolog (S. cerevisiae)), MORF4L2 (mortality factor 4 like 2, transcript variant 1), NAP1L1 (nucleosome assembly protein 1-like 1), NOL3 (nucleolar protein 3 (apoptosis repressor with CARD domain), transcript variant 3), NUDT3 (nudix (nucleoside diphosphate linked moiety X)-type motif 3), OAZ2 (ornithine decarboxylase antizyme 2), PANK2 (pantothenate kinase 2), PHF21A (PHD finger protein 21A, transcript variant 1), PKD1 (polycystic kidney disease 1 (autosomal dominant), transcript variant 2), PLD3 (phospholipase D family, member 3, transcript variant 1), PNMA2 (paraneoplastic antigen MA2), PQBP1 (polyglutamine binding protein 1, transcript variant 2), RAF1 (v-raf-1 murine leukemia viral oncogene homolog 1), RNF41 (ring finger protein 41, transcript variant 4), RSF1 (remodeling and spacing factor 1), RTN2 (reticulon 2, transcript variant 1), SMARCD3 (SWI/SNF related, matrix associated, actin dependent regulator of chromatin, subfamily d, member 3, transcript variant 3), SPATA7 (spermatogenesis associated 7, transcript variant 2), SST1 (somatostatin receptor 1), SST3 (somatostatin receptor 3), SST4 (somatostatin receptor 4), SST5 (somatostatin receptor 5, transcript variant 1), TECPR2 (tectonin beta-propeller repeat containing 2, transcript variant 2), TPH1 (tryptophan hydroxylase 1), TRMT112 (tRNA methyltransferase 11-2 homolog (*S. cerevisiae*)), VMAT1 (solute carrier family 18 (vesicular monoamine), member 1), VMAT 2 (solute carrier family 18 (vesicular monoamine), member 2), VPS13C (vacuolar protein sorting 13 homolog C (*S. cerevisiae*), transcript variant 2B), WDFY3 (WD repeat and FYVE domain containing 3), ZFHX3 (zinc finger homeobox 3, transcript variant B), ZXDC (zinc finger C, transcript variant 2), and ZZZ3 (zinc finger, ZZ-type containing 3), including gene products typically human gene products, including transcripts, mRNA, cDNA, coding sequences, proteins and polypeptides, as well as polynucleotides (nucleic acids) encoding the proteins and polypeptides, including naturally occurring variants, e.g., allelic variants, splice variants, transcript variants, and single nucleotide polymorphism (SNP) variants. For example, the biomarkers include polynucleotides, proteins, and polypeptides having the sequences disclosed herein, and naturally occurring variants thereof.

The housekeeping gene used to normalize expression of the 51 marker genes is the human ALG9 (asparagine-linked glycosylation 9, alpha-1,2-mannosyltransferase homolog).

Of these 51 differentially expressed biomarker genes, 38 biomarker genes are useful for the generation of mathematically-derived expression level scores for diagnosing, monitoring, and/or prognosticating the presence of GEP-NEN and/or different states of GEP-NENs. These 38 GEP-NEN biomarkers include: PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and GLT8D1.

Of the 38 biomarker genes useful for the generation of a mathematically-derived expression level score for diagnosing, monitoring, and/or prognosticating the presence of GEP-NENs, at least 22 biomarker genes may be needed to generate an adequate classifier. These at least 22 biomarker genes include PNMA2, NAP1L1, FZD7, SLC18A2, NOL3, SSTR5, TPH1, RAF1, RSF1, SSTR3, SSTR1, CD59, ARAF, APLP2, KRAS, MORF4L2, TRMT112, MKI67, SSTR4, CTGF, SPATA7, and ZFHX3.

The ALG9 biomarkers/housekeeping genes include human ALG9 gene products, including natural variants, e.g., allelic variants, and homologs and analogs thereof. In one example, the ALG9 biomarker/housekeeping gene is a polynucleotide having the nucleotide sequence set forth in SEQ ID NO: 1 (referenced at NM_024740.2), or containing a protein-coding portion thereof, a natural variant thereof, or a protein encoded by such a polynucleotide.

The AKAP8L biomarkers include human AKAP8L gene products, including natural variants, e.g., allelic variants, and homologs and analogs thereof. In one example, the AKAP8L biomarker is a polynucleotide having the nucleotide sequence set forth in SEQ ID NO: 2 (referenced at NM_014371.3), or containing a protein-coding portion thereof, a natural variant thereof, or a protein encoded by such a polynucleotide.

The APLP2 biomarkers include human APLP2 gene products, including natural variants, e.g., allelic variants, and homologs and analogs thereof. In one example, the APLP2 biomarker is a polynucleotide having the nucleotide sequence set forth in SEQ ID NO: 3 (referenced at NM_001142276.1) or containing a protein-coding portion thereof, a natural variant thereof, or a protein encoded by such a polynucleotide.

The ARAF1 biomarkers include human ARAF1 gene products, including natural variants, e.g., allelic variants, and homologs and analogs thereof. In one example, the ARAF1 biomarker is a polynucleotide having the nucleotide sequence set forth in SEQ ID NO: 4 (referenced at NM_001654.4), or containing a protein-coding portion thereof, a natural variant thereof, or a protein encoded by such a polynucleotide.

The ATP6V1H biomarkers include human ATP6V1H gene products, including natural variants, e.g., allelic variants, and homologs and analogs thereof. In one example, the ATP6V1H biomarker is a polynucleotide having the nucleotide sequence set forth in SEQ ID NO: 5 (referenced at NM_015941.3), or containing a protein-coding portion thereof, a natural variant thereof, or a protein encoded by such a polynucleotide.

The BNIP3L biomarkers include human BNIP3L gene products, including natural variants, e.g., allelic variants, and homologs and analogs thereof. In one example, the BNIP3L biomarker is a polynucleotide having the nucleotide sequence set forth in SEQ ID NO: 6 (referenced at NM_004331.2), or containing a protein-coding portion thereof, a natural variant thereof, or a protein encoded by such a polynucleotide.

The BRAF biomarkers include BRAF gene products, including natural variants, e.g., allelic variants, and homologs and analogs thereof. In one example, the BRAF biomarker is a polynucleotide having the nucleotide sequence set forth in SEQ ID NO: 7 (referenced at NM_004333.4), or containing a protein-coding portion thereof, a natural variant thereof, or a protein encoded by such a polynucleotide.

The C21ORF7 biomarkers include C21ORF7 gene products, including natural variants, e.g., allelic variants, and homologs and analogs thereof. In one example, the C21ORF7 biomarker is a polynucleotide having the nucleotide sequence set forth in SEQ ID NO: 8 (referenced at NM_020152.3), or containing a protein-coding portion thereof, a natural variant thereof, or a protein encoded by such a polynucleotide.

The CD59 biomarkers include CD59 gene products, including natural variants, e.g., allelic variants, and homologs and analogs thereof. In one example, the CD59 biomarker is a polynucleotide having the nucleotide sequence set forth in SEQ ID NO: 9 (referenced at NM_203331.2), or containing a protein-coding portion thereof, a natural variant thereof, or a protein encoded by such a polynucleotide.

The COMMD9 biomarkers include COMMD9 gene products, including natural variants, e.g., allelic variants, and homologs and analogs thereof. In one example, the COMMD9 biomarker is a polynucleotide having the nucleotide sequence set forth in SEQ ID NO: 10 (referenced at NM_001101653.1), or containing a protein-coding portion thereof, a natural variant thereof, or a protein encoded by such a polynucleotide.

The CTGF biomarkers include CTGF gene products, including natural variants, e.g., allelic variants, and homologs and analogs thereof. In one example, the CTGF biomarker is a polynucleotide having the nucleotide sequence set forth in SEQ ID NO: 11 (referenced at NM_001901.2), or containing a protein-coding portion thereof, a natural variant thereof, or a protein encoded by such a polynucleotide.

The ENPP4 biomarkers include ENPP4 gene products, including natural variants, e.g., allelic variants, and homologs and analogs thereof. In one example, the ENPP4 biomarker is a polynucleotide having the nucleotide sequence set forth in SEQ ID NO. 12 (referenced at NM_014936.4), or containing a protein-coding portion thereof, a natural variant thereof, or a protein encoded by such a polynucleotide.

The FAM131A biomarkers include FAM131A gene products, including natural variants, e.g., allelic variants, and homologs and analogs thereof. In one example, the FAM131A biomarker is a polynucleotide having the nucleotide sequence set forth in SEQ ID NO: 13 (referenced at NM_001171093.1), or containing a protein-coding portion thereof, a natural variant thereof, or a protein encoded by such a polynucleotide.

The FLJ1035 biomarkers include FLJ1035 gene products, including natural variants, e.g., allelic variants, and homologs and analogs thereof. In one example, the FLJ1035 biomarker is a polynucleotide having the nucleotide sequence set forth in SEQ ID NO: 14 (referenced at NM_018071.4), or containing a protein-coding portion thereof, a natural variant thereof, or a protein encoded by such a polynucleotide.

The FZD7 biomarkers include FZD7 gene products, including natural variants, e.g., allelic variants, and homologs and analogs thereof. In one example, the FZD7 biomarker is a polynucleotide having the nucleotide sequence set forth in SEQ ID NO: 15 (referenced at NM_003507.1), or containing a protein-coding portion thereof, a natural variant thereof, or a protein encoded by such a polynucleotide.

The GLT8D1 biomarkers include GLT8D1 gene products, including natural variants, e.g., allelic variants, and homologs and analogs thereof. In one example, the GLT8D1 biomarker is a polynucleotide having the nucleotide sequence set forth in SEQ ID NO: 16 (referenced at NM_001010983.2), or containing a protein-coding portion thereof, a natural variant thereof, or a protein encoded by such a polynucleotide.

The HDAC9 biomarkers include HDAC9 gene products, including natural variants, e.g., allelic variants, and homologs and analogs thereof. In one example, the HDAC9 biomarker is a polynucleotide having the nucleotide sequence set forth in SEQ ID NO: 17 (referenced at NM_001204144.1), or containing a protein-coding portion thereof, a natural variant thereof, or a protein encoded by such a polynucleotide.

The HSF2 biomarkers include HSF2 gene products, including natural variants, e.g., allelic variants, and homologs and analogs thereof. In one example, the HSF2 biomarker is a polynucleotide having the nucleotide sequence set forth in SEQ ID NO: 18 (referenced at NM_004506.3), or containing a protein-coding portion thereof, a natural variant thereof, or a protein encoded by such a polynucleotide.

The Ki-67 biomarkers include Ki-67 gene products, including natural variants, e.g., allelic variants, and homologs and analogs thereof. In one example, the Ki-67 biomarker is a polynucleotide having the nucleotide sequence set forth in SEQ ID NO: 19 (referenced at NM_001145966.1), or containing a protein-coding portion thereof, a natural variant thereof, or a protein encoded by such a polynucleotide.

The KRAS biomarkers include KRAS gene products, including natural variants, e.g., allelic variants, and homologs and analogs thereof. In one example, the KRAS biomarker is a polynucleotide having the nucleotide sequence set forth in SEQ ID NO: 20 (referenced at NM_004985.4), or containing a protein-coding portion thereof, a natural variant thereof, or a protein encoded by such a polynucleotide.

The LEO1 biomarkers include LEO gene products, including natural variants, e.g., allelic variants, and homologs and analogs thereof. In one example, the LEO1 biomarker is a polynucleotide having the nucleotide sequence set forth in SEQ ID NO: 21 (referenced at NM_138792.3), or containing a protein-coding portion thereof, a natural variant thereof, or a protein encoded by such a polynucleotide.

The MORF4L2 biomarkers include MORF4L2 gene products, including natural variants, e.g., allelic variants, and homologs and analogs thereof. In one example, the MORF4L2 biomarker is a polynucleotide having the nucleotide sequence set forth in SEQ ID NO: 22 (referenced at NM_001142418.1), or containing a protein-coding portion thereof, a natural variant thereof, or a protein encoded by such a polynucleotide.

The NAP1L1 biomarkers include NAP1L1 gene products, including natural variants, e.g., allelic variants, and homologs and analogs thereof. In one example, the NAP1L1 biomarker is a polynucleotide having the nucleotide sequence set forth in SEQ ID NO: 23 (referenced at NM_139207.2), or containing a protein-coding portion thereof, a natural variant thereof, or a protein encoded by such a polynucleotide.

The NOL3 biomarkers include NOL3 gene products, including natural variants, e.g., allelic variants, and homologs and analogs thereof. In one example, the NOL3 biomarker is a polynucleotide having the nucleotide sequence set forth in SEQ ID NO. 24 (referenced at NM_001185057.2), or containing a protein-coding portion thereof, a natural variant thereof, or a protein encoded by such a polynucleotide.

The NUDT3 biomarkers include NUDT3 gene products, including natural variants, e.g., allelic variants, and homologs and analogs thereof. In one example, the NUDT3 biomarker is a polynucleotide having the nucleotide sequence set forth in SEQ ID NO: 25 (referenced at NM_006703.3), or containing a protein-coding portion thereof, a natural variant thereof, or a protein encoded by such a polynucleotide.

The OAZ2 biomarkers include OAZ2 gene products, including natural variants, e.g., allelic variants, and homologs and analogs thereof. In one example, the OAZ2 biomarker is a polynucleotide having the nucleotide sequence set forth in SEQ ID NO: 26 (referenced at NM_002537.3), or containing a protein-coding portion thereof, a natural variant thereof, or a protein encoded by such a polynucleotide.

The PANK2 biomarkers include PANK2 gene products, including natural variants, e.g., allelic variants, and homologs and analogs thereof. In one example, the PANK2 biomarker is a polynucleotide having the nucleotide sequence set forth in SEQ ID NO: 27 (referenced at NM_024960.4), or containing a protein-coding portion thereof, a natural variant thereof, or a protein encoded by such a polynucleotide.

The PHF21A biomarkers include PHF21A gene products, including natural variants, e.g., allelic variants, and homologs and analogs thereof. In one example, the PHF21A biomarker is a polynucleotide having the nucleotide sequence set forth in SEQ ID NO: 28 (referenced at NM_001101802.1), or containing a protein-coding portion thereof, a natural variant thereof, or a protein encoded by such a polynucleotide.

The PKD1 biomarkers include PKD1 gene products, including natural variants, e.g., allelic variants, and homologs and analogs thereof. In one example, the PKD1 biomarker is a polynucleotide having the nucleotide sequence set forth in SEQ ID NO: 29 (referenced at NM_000296.3), or containing a protein-coding portion thereof, a natural variant thereof, or a protein encoded by such a polynucleotide.

The PLD3 biomarkers include PLD3 gene products, including natural variants, e.g., allelic variants, and homologs and analogs thereof. In one example, the PLD3 biomarker is a polynucleotide having the nucleotide sequence set forth in SEQ ID NO. 30 (referenced at NM_001031696.3), or containing a protein-coding portion thereof, a natural variant thereof, or a protein encoded by such a polynucleotide.

The PNMA2 biomarkers include PNMA2 gene products, including natural variants, e.g., allelic variants, and homologs and analogs thereof. In one example, the PNMA2 biomarker is a polynucleotide having the nucleotide sequence set forth in SEQ ID NO: 31 (referenced at NM_007257.5), or containing a protein-coding portion thereof, a natural variant thereof, or a protein encoded by such a polynucleotide.

The PQBP1 biomarkers include PQBP1 gene products, including natural variants, e.g., allelic variants, and homologs and analogs thereof. In one example, the PQBP1 biomarker is a polynucleotide having the nucleotide sequence set forth in SEQ ID NO: 32 (referenced at NM_001032381.1), or containing a protein-coding portion thereof, a natural variant thereof, or a protein encoded by such a polynucleotide.

The RAF1 biomarkers include RAF1 gene products, including natural variants, e.g., allelic variants, and homologs and analogs thereof. In one example, the RAF1 biomarker is a polynucleotide having the nucleotide sequence set forth in SEQ ID NO: 33 (referenced at NM_002880.3), or containing a protein-coding portion thereof, a natural variant thereof, or a protein encoded by such a polynucleotide.

The RNF41 biomarkers include RNF41 gene products, including natural variants, e.g., allelic variants, and homologs and analogs thereof. In one example, the RNF41 biomarker is a polynucleotide having the nucleotide sequence set forth in SEQ ID NO: 34 (referenced at NM_001242826.1), or containing a protein-coding portion thereof, a natural variant thereof, or a protein encoded by such a polynucleotide.

The RSF1 biomarkers include RSF1 gene products, including natural variants, e.g., allelic variants, and homologs and analogs thereof. In one example, the RSF1 biomarker is a polynucleotide having the nucleotide sequence set forth in SEQ ID NO: 35 (referenced at NM_016578.3), or containing a protein-coding portion thereof, a natural variant thereof, or a protein encoded by such a polynucleotide.

The RTN2 biomarkers include RTN2 gene products, including natural variants, e.g., allelic variants, and homologs and analogs thereof. In one example, the RTN2 biomarker is a polynucleotide having the nucleotide sequence set forth in SEQ ID NO. 36 (referenced at NM_005619.4), or containing a protein-coding portion thereof, a natural variant thereof, or a protein encoded by such a polynucleotide.

The SMARCD3 biomarkers include SMARCD3 gene products, including natural variants, e.g., allelic variants, and homologs and analogs thereof. In one example, the SMARCD3 biomarker is a polynucleotide having the nucleotide sequence set forth in SEQ ID NO: 37 (referenced at NM_001003801.1), or containing a protein-coding portion thereof, a natural variant thereof, or a protein encoded by such a polynucleotide.

The SPATA7 biomarkers include SPATA7 gene products, including natural variants, e.g., allelic variants, and homologs and analogs thereof. In one example, the SPATA7 biomarker is a polynucleotide having the nucleotide sequence set forth in SEQ ID NO: 38 (referenced at NM_001040428.3), or containing a protein-coding portion thereof, a natural variant thereof, or a protein encoded by such a polynucleotide.

The SSTR1 biomarkers include SSTR1 gene products, including natural variants, e.g., allelic variants, and homologs and analogs thereof. In one example, the SSTR1 biomarker is a polynucleotide having the nucleotide sequence set forth in SEQ ID NO: 39 (referenced at NM_001049.2), or containing a protein-coding portion thereof, a natural variant thereof, or a protein encoded by such a polynucleotide.

The SSTR3 biomarkers include SSTR3 gene products, including natural variants, e.g., allelic variants, and homologs and analogs thereof. In one example, the SSTR3 biomarker is a polynucleotide having the nucleotide sequence set forth in SEQ ID NO: 40 (referenced at NM_001051.4), or containing a protein-coding portion thereof, a natural variant thereof, or a protein encoded by such a polynucleotide.

The SST4 biomarkers include SST4 gene products, including natural variants, e.g., allelic variants, and homologs and analogs thereof. In one example, the SST4 biomarker is a polynucleotide having the nucleotide sequence set forth in SEQ ID NO: 41 (referenced at NM_001052.2), or containing a protein-coding portion thereof, a natural variant thereof, or a protein encoded by such a polynucleotide.

The SST5 biomarkers include SST5 gene products, including natural variants, e.g., allelic variants, and homologs and analogs thereof. In one example, the SST5 biomarker is a polynucleotide having the nucleotide sequence set forth in SEQ ID NO: 42 (referenced at NM_001053.3), or containing a protein-coding portion thereof, a natural variant thereof, or a protein encoded by such a polynucleotide.

The TECPR2 biomarkers include TECPR2 gene products, including natural variants, e.g., allelic variants, and homologs and analogs thereof. In one example, the TECPR2 biomarker is a polynucleotide having the nucleotide sequence set forth in SEQ ID NO: 43 (referenced at NM_001172631.1), or containing a protein-coding portion thereof, a natural variant thereof, or a protein encoded by such a polynucleotide.

The TPH1 biomarkers include TPH1 gene products, including natural variants, e.g., allelic variants, and homologs and analogs thereof. In one example, the TPH1 biomarker is a polynucleotide having the nucleotide sequence set forth in SEQ ID NO: 44 (referenced at NM_004179.2), or containing a protein-coding portion thereof, a natural variant thereof, or a protein encoded by such a polynucleotide.

The TRMT112 biomarkers include TRMT112 gene products, including natural variants, e.g., allelic variants, and homologs and analogs thereof. In one example, the TRMT112 biomarker is a polynucleotide having the nucleotide sequence set forth in SEQ ID NO: 45 (referenced at NM_016404.2), or containing a protein-coding portion thereof, a natural variant thereof, or a protein encoded by such a polynucleotide.

The VMAT1 biomarkers include VMAT1 gene products, including natural variants, e.g., allelic variants, and homologs and analogs thereof. In one example, the VMAT1 biomarker is a polynucleotide having the nucleotide sequence set forth in SEQ ID NO: 46 (referenced at NM_003053.3), or containing a protein-coding portion thereof, a natural variant thereof, or a protein encoded by such a polynucleotide.

The VMAT2 biomarkers include VMAT2 gene products, including natural variants, e.g., allelic variants, and homologs and analogs thereof. In one example, the VMAT2 biomarker is a polynucleotide having the nucleotide sequence set forth in SEQ ID NO: 47 (referenced at NM_003054.4), or containing a protein-coding portion thereof, a natural variant thereof, or a protein encoded by such a polynucleotide.

The VPS13C biomarkers include VPS13C gene products, including natural variants, e.g., allelic variants, and homologs and analogs thereof. In one example, the VPS13C biomarker is a polynucleotide having the nucleotide sequence set forth in SEQ ID NO. 48 (referenced at NM_001018088.2), or containing a protein-coding portion thereof, a natural variant thereof, or a protein encoded by such a polynucleotide.

The WDFY3 biomarkers include WDFY3 gene products, including natural variants, e.g., allelic variants, and homologs and analogs thereof. In one example, the WDFY3 biomarker is a polynucleotide having the nucleotide sequence set forth in SEQ ID NO: 49 (referenced at NM_014991.4), or containing a protein-coding portion thereof, a natural variant thereof, or a protein encoded by such a polynucleotide.

The ZFHX3 biomarkers include ZFHX3 gene products, including natural variants, e.g., allelic variants, and homologs and analogs thereof. In one example, the ZFHX3 biomarker is a polynucleotide having the nucleotide sequence set forth in SEQ ID NO: 50 (referenced at NM_001164766.1), or containing a protein-coding portion thereof, a natural variant thereof, or a protein encoded by such a polynucleotide.

The ZXDC biomarkers include ZXDC gene products, including natural variants, e.g., allelic variants, and homologs and analogs thereof. In one example, the ZXDC biomarker is a polynucleotide having the nucleotide sequence set forth in SEQ ID NO: 51 (referenced at NM_001040653.3), or containing a protein-coding portion thereof, a natural variant thereof, or a protein encoded by such a polynucleotide.

The ZZZ3 biomarkers include ZZZ3 gene products, including natural variants, e.g., allelic variants, and homologs and analogs thereof. In one example, the ZZZ3 biomarker is a polynucleotide having the nucleotide sequence set forth in SEQ ID NO: 52 (referenced at NM_015534.4), or containing a protein-coding portion thereof, a natural variant thereof, or a protein encoded by such a polynucleotide.

In some embodiments, the panel of polynucleotides further includes one or more polynucleotide able to specifically hybridize to "housekeeping," or reference genes, for example, genes for which differences in expression is known or not expected to correlate with differences in the variables analyzed, for example, with the presence or absence of GEP-NEN or other neoplastic disease, differentiation of various GEP-NEN sub-types, metastasis, mucosal or other tissue types, prognostic indications, and/or other phenotype, prediction, or outcome. In some aspects, expression levels of such housekeeping genes are detected and used as an overall expression level standards, such as to normalize expression data obtained for GEP-NEN biomarkers across various samples.

Housekeeping genes are well known in the art. Typically, the housekeeping genes include one or more genes characterized as particularly appropriate for analyzing GEP-NEN samples, such as ALG9. See Kidd M, et al., "GeneChip, geNorm and Gastrointestinal tumors: novel reference genes for real-time PCR." Physiol Genomics 2007; 30:363-70. In the current application, ALG9 is the housekeeping gene of choice.

The present invention provides methods, compositions, and systems, for the detection of the GEP-NEN biomarkers and for identifying, isolating, and enriching tumors and cells that express the GEP-NEN biomarkers. For example, provided are agents, sets of agents, and systems for detecting the GEP-NEN biomarkers and methods for use of the same, including for diagnostic and prognostic uses.

In one embodiment, the agents are proteins, polynucleotides or other molecules which specifically bind to or specifically hybridize to the GEP-NEN biomarkers. The agents include polynucleotides, such as probes and primers, e.g. sense and antisense PCR primers, having identity or complementarity to the polynucleotide biomarkers, such as mRNA, or proteins, such as antibodies, which specifically bind to such biomarkers. Sets and kits containing the agents, such as agents specifically hybridizing to or binding the panel of biomarkers, also are provided.

Thus, the systems, e.g., microarrays, sets of polynucleotides, and kits, provided herein include those with nucleic acid molecules, typically DNA oligonucleotides, such as primers and probes, the length of which typically varies between 15 bases and several kilo bases, such as between 20 bases and 1 kilobase, between 40 and 100 bases, and between 50 and 80 nucleotides or between 20 and 80 nucleotides. In one aspect, most (i.e. at least 60% of) nucleic acid molecules of a nucleotide microarray, kit, or other system, are capable of hybridizing to GEP-NEN biomarkers.

In one example, systems containing polynucleotides that specifically hybridize to the biomarkers, e.g., nucleic acid microarrays, are provided to detect and measure changes in expression levels and determine expression profiles of the biomarkers according to the provided methods. Among such systems, e.g., microarrays, are those comprising polynucleotides able to hybridize to at least as at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following sets of biomarkers:

PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/ KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and GLT8D1 gene products;

In some aspects, at least 60%, or at least 70%, at least 80%, or more, of the nucleic acid molecules of the system, e.g., microarray, are able to hybridize to biomarkers in the panel of biomarkers. In one example, probes immobilized on such nucleotide microarrays comprise at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more nucleic acid molecules able to hybridize to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more of the biomarkers, where each of the nucleic acid molecules is capable of specifically hybridizing to a different one of the biomarkers, such that at least that many different biomarkers can be bound.

In one example, the remaining nucleic acid molecules, such as 40% or at most 40% of the nucleic acid molecules on the microarray or in the set of polynucleotides are able to hybridize to a set of reference genes or a set of normalization genes (such as housekeeping genes), for example, for normalization in order to reduce systemic bias. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment. To reduce systemic bias, the determined RNA levels are preferably corrected for background non-specific hybridization and normalized.

The use of such reference probes is advantageous but not mandatory. In one embodiment a set of polynucleotides or system, e.g., microarray, is provided wherein at least 90% of the nucleic acid sequences are able to hybridize to the GEP-NEN biomarkers; further embodiments include such systems and sets in which at least 95% or even 100% of the polynucleotides hybridize to the biomarkers.

Disclosed herein are exemplary suitable polynucleotides, such as PCR primers. Other nucleic acid probes and primers, able to hybridize to different regions of the biomarkers are of course also suitable for use in connection with the provided systems, kits and methods.

The present invention provides methods for detecting and quantifying the biomarkers, including detecting the presence, absence, amount or relative amount, such as expression levels or expression profile of the biomarkers. Typically, the methods are nucleic acid based methods, for example, measuring the presence, amount or expression levels of biomarker mRNA expression. Such methods typically are carried out by contacting polynucleotide agents to biological samples, such as test samples and normal and reference samples, for example, to quantify expression levels of nucleic acid biomarkers (e.g., mRNA) in the samples.

Detection and analysis of biomarkers according to the provided embodiments can be performed with any suitable method known in the art. For example, where the biomarkers are RNA biomarkers, RNA detection and quantification methods are used.

Exemplary methods for quantifying or detecting nucleic acid expression levels, e.g., mRNA expression, are well known, and include northern blotting and in situ hybridization (Parker and Barnes, Methods in Molecular Biology 106:247-283, 1999); RNAse protection assays (Hod, Biotechniques 13:852-854, 1992); and quantitative or semi-quantitative reverse transcription polymerase chain reaction (RT-PCR) (Weis et al., Trends in Genetics 8:263-264, 1992), representative methods for sequencing-based gene expression analysis include Serial Analysis of Gene Expression (SAGE), and gene expression analysis by massively parallel signature sequencing (MPSS).

Therefore, in one embodiment, expression of the biomarker or biomarker panel includes RNA expression; the methods include determining levels of RNA of the biomarkers, such as RNA obtained from and/or present in a sample of a patient, and performing analysis, diagnosis, or predictive determinations based upon the RNA expression levels determined for the biomarkers or panel of biomarkers.

RNA samples can be processed in numerous ways, as is known to those in the art. Several methods are well known for isolation of RNA from samples, including guanidinium thiocyanate-phenol-chloroform extraction, which may be carried out using the TRIZOL® reagent, a proprietary formulation (see Chomczynski P, Sacchi N (2006). "The single-step method of RNA isolation by acid guanidinium thiocyanate-phenol-chloroform extraction: twenty-something years on". Nat Protoc 1 (2): 581-5). In this method, TRIZOL® is used to extract RNA and DNA; chloroform and centrifugation are used to separate RNA from other nucleic acids, followed by a series of washes with ethanol for cleanup of the RNA sample.

The RNA samples can be freshly prepared from samples e.g., cells or tissues at the moment of harvesting; alternatively, they can be prepared from samples that stored at −70° C. until processed for sample preparation. Alternatively, tissues or cell samples can be stored under and/or subjected to other conditions known in the art to preserve the quality of the RNA, including fixation for example with formalin or similar agent; and incubation with RNase inhibitors such as RNASIN® (ribonuclease inhibitors) or RNASECURE™ (RNase inactivation reagents); aqueous solutions such as RNALATER® (RNA stabilization solutions), Hepes-Glutamic acid buffer mediated Organic solvent Protection Effect (HOPE®), and RCL2® (formalin-free tissue fixatives); and non-aqueous solutions such as Universal Molecular Fixative (Sakura Finetek USA Inc.). A chaotropic nucleic acid isolation lysis buffer (Boom method, Boom et al. J Clin Microbiol. 1990; 28:495-503) may also be used for RNA isolation.

In one embodiment, RNA is isolated from buffy coat by incubating samples with TRIZOL®, followed by RNA clean-up. RNA is dissolved in diethyl pyrocarbonate water and measured spectrophotometrically, and an aliquot analyzed on a Bioanalyzer (Agilent Technologies, Palo Alto, CA) to assess the quality of the RNA (Kidd M, et al. "The role of genetic markers—NAP 1L1, MAGE-D2, and MTA1—in defining small-intestinal carcinoid neoplasia," Ann Surg Oncol 2006; 13(2):253-62). In another embodiment, RNA is isolated from plasma using the QIAamp RNA Blood Mini Kit; in some cases, this method allows better detection by real-time PCR of significantly more housekeeping genes from plasma compared to the TRIZOL® approach. In another embodiment, RNA is isolated directly from whole blood, for example, using the QIAamp RNA Blood Mini Kit in a similar manner.

Methods for isolating RNA from fixed, paraffin-embedded tissues as the RNA source are well-known and generally include mRNA isolation, purification, primer extension and amplification (for example: T. E. Godfrey et al, Molec. Diagnostics 2: 84-91 [2000]; K. Specht et al., Am. J. Pathol. 158: 419-29 [2001]). In one example, RNA is extracted from a sample such as a blood sample using the QIAamp RNA Blood Mini Kit RNA. Typically, RNA is extracted from tissue, followed by removal of protein and DNA and analysis of RNA concentration. An RNA repair and/or amplification step may be included, such as a step for reverse transcription of RNA for RT-PCR.

Expression levels or amounts of the RNA biomarkers may be determined or quantified by any method known in the art, for example, by quantifying RNA expression relative to housekeeping gene or with relation to RNA levels of other genes measured at the same time. Methods to determine RNA levels of genes are known to a skilled person and include, but are not limited to, Northern blotting, (quantitative) PCR, and microarray analysis.

RNA biomarkers can be reverse transcribed to produce cDNA and the methods of the present invention can include detecting and quantifying that produced cDNA. In some embodiments, the cDNA is detected by forming a complex with a labeled probe. In some embodiments, the RNA biomarkers are directed detected by forming a complex with a labeled probe or primer.

Northern blotting may be performed for quantification of RNA of a specific biomarker gene or gene product, by hybridizing a labeled probe that specifically interacts with the RNA, following separation of RNA by gel electrophoresis. Probes are for example labeled with radioactive isotopes or chemiluminescent substrates. Quantification of the labeled probe that has interacted with said nucleic acid expression product serves as a measure for determining the level of expression. The determined level of expression can be normalized for differences in the total amounts of nucleic acid expression products between two separate samples with for instance an internal or external calibrator by comparing the level of expression of a gene that is known not to differ in expression level between samples or by adding a known quantity of RNA before determining the expression levels.

For RT-PCR, biomarker RNA is reverse transcribed into cDNA. Reverse transcriptase polymerase chain reaction (RT-PCR) is, for example, performed using specific primers that hybridize to an RNA sequence of interest and a reverse transcriptase enzyme. Furthermore, RT-PCR can be performed with random primers, such as for instance random hexamers or decamers which hybridize randomly along the RNA, or oligo d(T) which hybridizes to the poly(A) tail of mRNA, and reverse transcriptase enzyme.

In some embodiments, RNA expression levels of the biomarkers in a sample, such as one from a patient suffering from or suspected of suffering from GEP-NEN or associated symptom or syndrome, are determined using quantitative methods such as by real-time rt-PCR (qPCR) or microarray analysis. In some embodiments, quantitative Polymerase Chain Reaction (QPCR) is used to quantify the level of expression of nucleic acids. In one aspect, detection and determining expression levels of the biomarkers is carried out using RT-PCR, GeneChip analysis, quantitative real-time PCR (Q RT-PCR), or carcinoid tissue microarray (TMA) immunostaining/quantitation, for example, to compare biomarker RNA, e.g., mRNA, or other expression product, levels in different sample populations, characterize patterns of gene expression, to discriminate between closely related mRNAs, and to analyze RNA structure.

In one example, QPCR is performed using real-time PCR (RTPCR), where the amount of product is monitored during the amplification reaction, or by end-point measurements, in which the amount of a final product is determined. As is known to a skilled person, rtPCR is for instance performed by the use of a nucleic acid intercalator, such as for example ethidium bromide or SYBR® Green I dye, which interacts which all generated double stranded products resulting in an increase in fluorescence during amplification, or for instance by the use of labeled probes that react specifically with the generated double stranded product of the gene of interest. Alternative detection methods that can be used are provided by amongst other things dendrimer signal amplification, hybridization signal amplification, and molecular beacons.

In one embodiment, reverse transcription on total RNA is carried out using the High Capacity cDNA Archive Kit (Applied Biosystems (ABI), Foster City, CA) following the manufacturer's suggested protocol (briefly, using 2 micrograms of total RNA in 50 microliters water, mixing with 50 uL of 2×RT mix containing Reverse Transcription Buffer, deoxynucleotide triphosphate solution, random primers, and Multiscribe Reverse Transcriptase). RT reaction conditions are well known. In one example, the RT reaction is performed using the following thermal cycler conditions: 10 mins, 25° C.; 120 min., 37° C. {see Kidd M, et al., "The role of genetic markers—NAP 1 LI, MAGE-D2, and MTA1—in defining small-intestinal carcinoid neoplasia," Ann Surg Oncol 2006; 13(2):253-62).

For measurement of individual transcript levels, in one embodiment, Assays-on-Demand™ products are used with the ABI 7900 Sequence Detection System according to the manufacturer's suggestions (see Kidd M, Eick G, Shapiro M D, et al. Microsatellite instability and gene mutations in transforming growth factor-beta type II receptor are absent in small bowel carcinoid tumors. Cancer 2005; 103(2):229-36). In one example, cycling is performed under standard conditions, using the TaqMan® Universal PCR Master Mix Protocol, by mixing cDNA in 7.2 uL water, 0.8 uL 20 ASSAYS-ON-DEMAND™ (gene expression products) primer and probe mix and 8 uL of 2× TaqMan Universal Master mix, in a 384-well optical reaction plate, under the following conditions: 50° C., 2 min.; 95° C.; 10 min.; 50 cycles at 95° C. for 15 min., 60° for 1 min (see Kidd M, et al, "The role of genetic markers—NAP 1 LI, MAGE-D2, and MTA1—in defining small-intestinal carcinoid neoplasia," Ann Surg Oncol 2006; 13(2):253-62).

Typically, results from real-time PCR are normalized, using internal standards and/or by comparison to expression levels for housekeeping genes. For example, in one embodiment, Raw $AC_T$(delta $C_T$=change in cycle time as a function of amplification) data from QPCR as described above is normalized using well-known methods, such as geNorm {see Vandesompele J, De Preter K, Pattyn F, et al. Accurate normalization of real-time quantitative RT-PCR data by geometric averaging of multiple internal control genes. Genome Biol 2002; 3(7):RESEARCH0034). Normalization by house-keeping gene expression levels is also well-known. See Kidd M, et al., "GeneChip, geNorm, and gastrointestinal tumors: novel reference genes for real-time PCR," Physiol Genomics 2007; 30(3):363-70.

Microarray analysis involves the use of selected nucleic acid molecules that are immobilized on a surface. These nucleic acid molecules, termed probes, are able to hybridize to nucleic acid expression products. In a preferred embodiment the probes are exposed to labeled sample nucleic acid, hybridized, washed and the (relative) amount of nucleic acid expression products in the sample that are complementary to a probe is determined. Microarray analysis allows simultaneous determination of nucleic acid expression levels of a large number of genes. In a method according to the invention it is preferred that at least 5 genes according to the invention are measured simultaneously.

Background correction can be performed for instance according to the "offset" method that avoids negative intensity values after background subtraction. Furthermore, normalization can be performed in order to make the two channels on each single array comparable for instance using global loess normalization, and scale normalization which ensures that the log-ratios are scaled to have the same median-absolute-deviation (MAD) across arrays.

Protein levels may, for example, be measured using antibody-based binding assays. Enzyme labeled, radioactively labeled or fluorescently labeled antibodies may be used for detection of protein. Exemplary assays include enzyme-linked immunosorbent assays (ELISA), radio-immuno assays (RIA), Western Blot assays and immunohistochemical staining assays. Alternatively, in order to determine the expression level of multiple proteins simultaneously protein arrays such as antibody-arrays are used.

Typically, the biomarkers and housekeeping markers are detected in a biological sample, such as a tissue or fluid sample, such as a blood, such as whole blood, plasma, serum, stool, urine, saliva, tears, serum or semen sample, or a sample prepared from such a tissue or fluid, such as a cell preparation, including of cells from blood, saliva, or tissue, such as intestinal mucosa, tumor tissue, and tissues containing and/or suspected of containing GEP-NEN metastases or shed tumor cells, such as liver, bone, and blood. In one embodiment, a specific cell preparation is obtained by fluorescence-activated cell sorting (FACS) of cell suspensions or fluid from tissue or fluid, such as mucosa, e.g., intestinal mucosa, blood or buffy coat samples.

In some embodiments, the sample is taken from a GEP-NEN patient, a patient suspected of having GEP-NEN, a patient having and/or suspected of having cancer generally, a patient exhibiting one or more GEP-NEN symptoms or syndromes or determined to be at-risk for GEP-NEN, or a GEP-NEN patient undergoing treatment or having completed treatment, including patients whose disease is and/or is thought to be in remission.

In other embodiments, the sample is taken from a human without GEP-NEN disease, such as a healthy individual or an individual with a different type of cancer, such as an adenocarcinoma, for example, a gastrointestinal adenocarcinoma or one of the breast, prostate, or pancreas, or a gastric or hepatic cancer, such as esophageal, pancreatic, gallbladder, colon, or rectal cancer.

In some embodiments, the sample is taken from the GEP-NEN tumor or metastasis. In other embodiments, the sample is taken from the GEP-NEN patient, but from a tissue or fluid not expected to contain GEP-NEN or GEP-NEN cells; such samples may be used as reference or normal samples. Alternatively, the normal or reference sample may be a tissue or fluid or other biological sample from a patient without GEP-NEN disease, such as a corresponding tissue, fluid or other sample, such as a normal blood sample, a normal small intestinal (SI) mucosa sample, a normal enterochromaffin (EC) cell preparation.

In some embodiments, the sample is a whole blood sample. As neuroendocrine tumors metastasize, they typically shed cells into the blood. Accordingly, detection of the panels of GEP-NEN biomarkers provided herein in plasma and blood samples may be used for identification of GEP-NENs at an early time point and for predicting the presence of tumor metastases, e.g., even if anatomic localization studies are negative. Accordingly, the provided agents and methods are useful for early diagnosis.

Thus, in some embodiments, the methods can identify a GEP-NEN molecular signature or expression profile in 1 mL or about 1 mL of whole blood. In some aspects, the molecular signature or expression profile is stable for up to four hours (for example, when samples are refrigerated 4-8° C. following phlebotomy) prior to freezing. In one aspect, the approach able to diagnose, prognosticate or predict a given GEP-NEN-associated outcome using a sample obtained from tumor tissue is also able to make the same diagnosis, prognosis, or prediction using a blood sample.

A number of existing detection and diagnostic methodologies require 7 to 10 days to produce a possible positive result, and can be costly. Thus, in one aspect, the provided methods and compositions are useful in improving simplicity and reducing costs associated with GEP-NEN diagnosis, and make early-stage diagnosis feasible.

Thus in one example, the biomarkers are detected in circulation, for example by detection in a blood sample, such as a serum, plasma, cells, e.g., peripheral blood mononuclear cells (PBMCs), obtained from buffy coat, or whole blood sample.

Tumor-specific transcripts have been detected in whole blood in some cancers. See Sieuwerts A M, et al., "Molecular characterization of circulating tumor cells in large quantities of contaminating leukocytes by a multiplex real-time PCR," Breast Cancer Res Treat 2009; 118(3):455-68 and Mimori K, et al, "A large-scale study of MT1-MMP as a marker for isolated tumor cells in peripheral blood and bone marrow in gastric cancer cases," Ann Surg Oncol 2008; 15(10):2934-42.

The CELLSEARCH® CTC Test (circulating tumor cell kits) (described by Kahan L., "Medical devices; immunology and microbiology devices; classification of the immunomagnetic circulating cancer cell selection and enumeration system. Final rule," Fed Regist 2004; 69:26036-8) uses magnetic beads coated with EpCAM-specific antibodies that detects epithelial cells (CK—Aug. 18, 2019) and leukocytes (CD45), as described by Sieuwerts A M, Kraan J, Bolt-de Vries J, et al., "Molecular characterization of circulating tumor cells in large quantities of contaminating leukocytes by a multiplex real-time PCR," Breast Cancer Res Treat 2009; 118(3):455-68. This method has been used to detect circulating tumor cells (CTCs), and monitoring disease progression and therapy efficacy in metastatic prostate (Danila D C, Heller G, Gignac G A, et al. Circulating tumor cell number and prognosis in progressive castration-resistant prostate cancer. Clin Cancer Res 2007; 13(23):7053-8), colorectal (Cohen S J, Alpaugh R K, Gross S, et al.).

Isolation and characterization of circulating tumor cells in patients with metastatic colorectal cancer. Clin Colorectal Cancer 2006; 6(2). 125-32. and breast (Cristofanilli M, Budd G T, Ellis M J, et al., Circulating tumor cells, disease progression, and survival in metastatic breast cancer. N Engl J Med 2004; 351(8):781-91).

This and other existing approaches have not been entirely satisfactory for detection of GEP-NEN cells, which can exhibit variable expression and/or not express cytokeratin (See Van Eeden S, et al, Classification of low-grade neuroendocrine tumors of midgut and unknown origin," Hum Pathol 2002; 33(11): 1126-32; Cai Y C, et al., "Cytokeratin 7 and 20 and thyroid transcription factor 1 can help distinguish pulmonary from gastrointestinal carcinoid and pancreatic endocrine tumors," Hum Pathol 2001; 32(10): 1087-93, and studies described herein, detecting EpCAM transcript expression in two of twenty-nine GEP-NEN samples).

Factors to consider in the available detection methods for circulating tumor cells are relatively low numbers of the cells in peripheral blood, typically about 1 per $10^6$ peripheral blood mononuclear cells (PBMCs) (see Ross A A, et al. "Detection and viability of tumor cells in peripheral blood stem cell collections from breast cancer patients using immunocytochemical and clonogenic assay techniques," Blood 1993; 82(9):2605-10), and the potential for leukocyte contamination. See Sieuwerts A M, et al. "Molecular characterization of circulating tumor cells in large quantities of contaminating leukocytes by a multiplex real-time PCR," Breast Cancer Res Treat 2009; 118(3):455-68; Mimori K, et al) and technical complexity of available approaches. These factors can render available methods not entirely satisfactory for use in the clinical laboratory.

In some embodiments, Neuroendocrine cells are FACS-sorted to heterogeneity, using known methods, following acridine orange (AO) staining and uptake, as described Kidd M, et al., "Isolation, Purification and Functional Characterization of the Mastomys EC cell," Am J Physiol 2006; 291:G778-91; Modlin E V I, et al., "The functional characterization of normal and neoplastic human enterochromaffin cells," Clin Endocrinol Metab 2006; 91(6):2340-8.

In some embodiments, the provided detection methods are used to detect, isolate, or enrich for the GEP-NEN cells and/or biomarkers in two to three mL of blood or less. The methods are performed using standard laboratory apparatuses and thus are easily performed in the clinical laboratory setting. In one example, a readout is obtained within 12 hours, at an average cost of approximately 20-30 per sample.

The present invention provides diagnostic, prognostic, and predictive uses for the agents and detection methods provided herein, such as for the diagnosis, prognosis, and prediction of GEP-NEN, associated outcomes, and treatment responsiveness. For example, available GEP-NEN classification methods are limited, in part due to incorrect classifications and that individual lesions or tumors can evolve into different GEP-NEN sub-types or patterns, and/or contain more than one GEP-NEN sub-type. Known classification frameworks are limited, for example, in the ability to predict response to treatment or discriminate accurately between tumors with similar histopathologic features that may vary substantially in clinical course and treatment response, and to predict treatment responsiveness.

There is therefore a need for molecular or gene-based classification schemes. The provided methods and systems, including GEP-NEN-specific predictive gene-based models, address these issues, and may be used in identifying and analyzing molecular parameters that are predictive of biologic behavior and prediction based on such parameters.

Among the provided diagnostic, prognostic, and predictive methods are those which employ statistical analysis and biomathematical algorithms and predictive models to analyze the detected information about expression of GEP-NEN biomarkers and other markers such as housekeeping genes. In some embodiments, expression levels, detected binding or other information is normalized and assessed against reference value(s), such as expression levels in normal samples or standards. Provided embodiments include methods and systems for classification and prediction of GEP-NENs using the detected and measured information about the expression of the GEP-NEN biomarkers, for example, in classification, staging, prognosis, treatment design, evaluation of treatment options, and prediction of GEP-NEN disease outcomes, e.g., predicting development of metastases.

In some embodiments, the methods are used to establish GEP-NEN diagnosis, such as diagnosis or detection of early-stage disease or metastasis, define or predict the extent of disease, identify early spread or metastasis, predict outcome or prognosis, predict progression, classify disease activity, monitor treatment responsiveness, detect or monitor for recurrence, and to facilitate early therapeutic intervention. For example, among the provided methods and algorithms are those for use in classification, staging, prognosis, treatment design, evaluation of treatment options, and prediction of GEP-NEN disease outcomes, e.g., predicting development of metastases.

In one embodiment, the methods, algorithms and models are useful for diagnostic surveillance, such as routine surveillance and patient follow-up. In some embodiments, the methods, algorithms and models provide for early diagnosis; in one aspect, the methods are capable of detection of low-volume tumors, and detection of circulating tumor cells, including at early stages of disease, such as detection of as few as at or about 3 circulating GEP-NEN cells per milliliter of blood. In some embodiments, early evidence of disease allows early therapeutic intervention, at a time when therapies are more effective, which can improve survival rates and disease outcomes.

For example, in one embodiment, the methods useful for early detection of the recurrence and/or metastasis of GEP-NEN, such as after treatment for example following surgical or chemical intervention. In some aspect, the methods are performed weekly or monthly following therapeutic intervention, for example, on human blood samples. In some aspects, the methods are capable of detecting micrometastases that are too small to be detected by conventional means, such as by imaging methods. For example, in one aspect the methods are capable of detecting metastases less than one centimeter (cm), such as at or about 1 cm, 0.9 cm, 0.8 cm, 0.7 cm, 0.6 cm, 0.5 cm, 0.4 cm, 0.3 cm, 0.2 cm, or 0.1 cm metastases, such as in the liver.

For example, among the provided methods and systems are those that determine the presence or absence (or both) of a GEP-NEN in a subject or sample with a correct call rate of between 56 and 92%, such as at least or at least about a 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% correct call rate. In some cases, the methods are useful for diagnosis with a specificity or sensitivity of at least or at least about 70%, 7%5, 80%, 81%, 82%, 83%, 84%, 85%, 86%, 87%, 88%, 89%, 90%, 91%, 92%, 93%, 94%, 95%, 96%, 97%, 98%, 99%, or 100%.

In other aspects, the methods are capable of detecting the recurrence, metastasis, or spread of GEP-NEN following treatment or during initial disease progression at an earlier stage as compared with other diagnostic methods, such as imaging and detection of available biomarkers. In some aspects, the detected expression levels and/or expression signature of the biomarkers correlate significantly with the progression of disease, disease severity or aggressiveness, lack of responsiveness of treatment, reduction in treatment efficacy, GEP-NEN-associated events, risk, prognosis, type or class of GEP-NEN or disease stage.

Among the provided embodiments are methods that use the provided biomarkers and detection thereof in treatment development, strategy, and monitoring, including evaluation of response to treatment and patient-specific or individualized treatment strategies that take into consideration the likely natural history of the tumor and general health of the patient.

GEP-NEN management strategies include surgery—for cure (rarely achieved) or cytoreduction—radiological intervention—for example, by chemoembolization or radiofrequency ablation—chemotherapy, cryoablation, and treatment with somatostatin and somatostatin analogues (such as SANDOSTATIN® LAR (Octreotide acetate injection)) to control symptoms caused by released peptides and neuroamines. Biological agents, including interferon, and hormone therapy, and somatostatin-tagged radionucleotides are under investigation.

In one example, Cryoablation liberates GEP-NEN tissue for entry into the blood, which in turn induces symptoms, as described by Mazzaglia P J, et ah, "Laparoscopic radiofrequency ablation of neuroendocrine liver metastases: a 10-year experience evaluating predictors of survival," Surgery 2007; 142(1): 10-9. Chemo therapeutic agents, e.g., systemic cytotoxic chemotherapeutic agents, include etoposide, cisplatin, 5-fluorouracil, streptozotocin, doxorubicin; vascular endothelial growth factor inhibitors, receptor tyrosine kinase inhibitors (e.g., Sunitinib, Sorafenib, and Vatalanib), and mammalian target of rapamycin (mTOR) inhibitors (e.g., Temsirolimus and Everolimus), and combinations thereof, for example to treat disseminated and/or poorly differentiated/aggressive disease. Other treatment approaches are well known.

In some embodiments, the detection and diagnostic methods are used in conjunction with treatment, for example, by performing the methods weekly or monthly before and/or after treatment. In some aspects, the expression levels and profiles correlate with the progression of disease, ineffectiveness or effectiveness of treatment, and/or the recurrence or lack thereof of disease. In some aspects, the expression information indicates that a different treatment strategy is preferable. Thus, provided herein are therapeutic methods, in which the GEP-NEN biomarker detection methods are performed prior to treatment, and then used to monitor therapeutic effects.

At various points in time after initiating or resuming treatment, significant changes in expression levels or expression profiles of the biomarkers (e.g., as compared to expression or expression profiles before treatment, or at some other point after treatment, and/or in a normal or reference sample) indicates that a therapeutic strategy is or is not successful, that disease is recurring, or that a different therapeutic approach should be used. In some embodiments, the therapeutic strategy is changed following performing of the detection methods, such as by adding a different therapeutic intervention, either in addition to or in place of the current approach, by increasing or decreasing the aggressiveness or frequency of the current approach, or stopping or reinstituting the treatment regimen.

In another aspect, the detected expression levels or expression profile of the biomarkers identifies the GEP-NEN disease for the first time or provides the first definitive diagnosis or classification of GEP-NEN disease. In some aspects of this embodiment, a treatment approach is designed based upon the expression levels or expression profiles, and/or the determined classification. The methods include iterative approaches, whereby the biomarker detection methods are followed by initiation or shift in therapeutic intervention, followed by continued periodic monitoring, reevaluation, and change, cessation, or addition of a new therapeutic approach, optionally with continued monitoring.

In some aspects, the methods and systems determine whether or not the assayed subject is responsive to treatment, such as a subject who is clinically categorized as in complete remission or exhibiting stable disease. In some aspects, the methods and systems determine whether or not the subject is untreated (or treatment-I, i.e., has not received treatment) or is non-responsive (i.e., clinically categorized as "progressive." For example, methods are provided for distinguishing treatment-responsive and non-responsive patients, and for distinguishing patients with stable disease or those in complete remission, and those with progressive disease. In various aspects, the methods and systems make such calls with at least at or about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% correct call rate (i.e., accuracy), specificity, or sensitivity.

In some aspects, the sensitivity or correct call rate for the diagnostic or predictive or prognostic outcome is greater than, e.g., significantly greater than, that obtained using a known diagnosis or prognostic method, such as detection and measurement of circulating CgA or other single protein.

Typically, the diagnostic, prognostic, and predictive methods, often in an initial step, select a subset of biomarkers based on their ability to build a classifier that may accurately predict and classify GEP-NEN and/or different stages of GEP-NEN.

Any of a number of well-known methods for evaluating differences in gene expression may be used to select the subset of biomarkers. For example, an accurate classifier may be based on topographic, pattern-recognition based protocols e.g., support vector machines (SVM) (Noble W S. What is a support vector machine? Nat Biotechnol. 2006; 24(12): 1565-7). Machine-learning based techniques are typically desirable for developing sophisticated, automatic, and/or objective algorithms for analyzing high-dimensional and multimodal biomedical data. In some examples, SVM—a variant of the supervised learning algorithm—is used in connection with the provided methods and systems. SVMs have been used to predict the grading of astrocytomas with a >90 accuracy, and prostatic carcinomas with an accuracy of 74-80% (Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11; Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11).

Other algorithms for building an accurate classifier include linear discriminant analysis (LDA), naive Bayes (NB), and K-nearest neighbor (KNN) protocols. Such approaches are useful for identifying individual or multivariable alterations in neoplastic conditions (Drozdov I, Tsoka S, Ouzounis C A, Shah A M. Genome-wide expression patterns in physiological cardiac hypertrophy. BMC Genomics. 2010; 11: 55; Freeman T C, Goldovsky L, Brosch M, et al. Construction, visualization, and clustering of transcription networks from microarray expression data. PLoS Comput Biol 2007; 3(10): 2032-42; Zampetaki A, Kiechl S, Drozdov I, et al. Plasma microRNA profiling reveals loss of endothelial miR-126 and other microRNAs in type 2 diabetes. Circ Res. 2010; 107(6): 810-7. Epub 2010 Jul. 22; Dhawan M, Selvaraja S, Duan Z H. Application of committee kNN classifiers for gene expression profile classification. Int J Bioinform Res Appl. 2010; 6(4): 344-52; Kawarazaki S, Taniguchi K, Shirahata M, et al. Conversion of a molecular classifier obtained by gene expression profiling into a classifier based on real-time PCR: a prognosis predictor for gliomas. BMC Med Genomics. 2010; 3: 52; Vandebriel R J, Van Loveren H, Meredith C. Altered cytokine (receptor) mRNA expression as a tool in immunotoxicology. Toxicology. 1998; 130(1): 43-67; Urgard E, Vooder T, Vosa U, et al. Metagenes associated with survival in non-small cell lung cancer. Cancer Inform. 2011; 10: 175-83. Epub 2011 Jun. 2; Pimentel M, Amichai M, Chua K, Braham L. Validating a New Genomic Test for Irritable Bowel Syndrome Gastroenterology 2011; 140 (Suppl 1): S-798; Lawlor G, Rosenberg L, Ahmed A, et al. Increased Peripheral Blood GATA-3 Expression in Asymptomatic Patients With Active Ulcerative Colitis at Colonoscopy. Gastroenterology 2011; 140 (Suppl 1)).

In some embodiments, an accurate classifier for GEP-NEN and/or different stages of GEP-NEN is based on a combination of the SVM, LDA, NB, and KNN protocols. This is termed the Multi-Analyte-Algorithm Risk Classifier for NETs (MAARC-NET).

Methods using the predictive algorithms and models use statistical analysis and data compression methods, such as those well known in the art. For example, expression data may be transformed, e.g., ln-transformed, and imported into a statistical analysis program, such as PARTEK® GENOMICS SUITE® (genomic data analysis software) or similar program, for example. Data are compressed and analyzed for comparison.

Whether differences in expression level score or values are deemed significant may be determined by well-known statistical approaches, and typically is done by designating a threshold for a particular statistical parameter, such as a threshold p-value (e.g., p<0.05), threshold S-value (e.g., +0.4, with S<−0.4 or S>0.4), or other value, at which differences are deemed significant, for example, where expression of a biomarker is considered significantly down- or up-regulated, respectively, among two different samples, for example, representing two different GEP-NEN subtypes, tumors, stages, localizations, aggressiveness, or other aspect of GEP-NEN or normal or reference sample.

In one aspect, the algorithms, predictive models, and methods are based on biomarkers expressed from genes associated with regulatory gene clusters (i.e., SSTRome, Proliferome. Signalome. Metabolome, Secretome, Secretome, Plurome, EpiGenome, and Apoptome) underlying various GEP-NEN subtypes.

In one aspect, the methods apply the mathematical formulations, algorithms or models identify specific cutoff points, for example, pre-determined expression level scores, which distinguish between normal and GEP-NEN samples, between GEP-NEN and other cancers, and between various sub-types, stages, and other aspects of disease or disease outcome. In another aspect, the methods are used for prediction, classification, prognosis, and treatment monitoring and design. In one aspect, the predictive embodiments are useful for identifying molecular parameters predictive of biologic behavior, and prediction of various GEP-NEN-associated outcomes using the parameters. In one aspect of these embodiments, machine learning approaches are used, e.g., to develop sophisticated, automatic and objective algorithms for the analysis of high-dimensional and multimodal biomedical data.

A "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a subset or panel of GEP-NEN biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a subset or panel of GEP-NEN has an AUC in the range of about 0.75 to 1.0. In certain of these embodiments, the AUC is in the range of about 0.50 to 0.85, 0.85 to 0.9, 0.9 to 0.95, or 0.95 to 1.0.

For the comparison of expression level scores or other values, and to identify expression profiles (expression signatures) or regulatory signatures based on GEP-NEN biomarker expression, data are compressed. Compression typically is by Principal Component Analysis (PCA) or similar technique for describing and visualizing the structure of high-dimensional data. PCA allows the visualization and comparison of GEP-NEN biomarker expression and determining and comparing expression profiles (expression signatures, expression patterns) among different samples, such as between normal or reference and test samples and among different tumor types.

In some embodiments, expression level data are acquired, e.g., by real-time PCR, and reduced or compressed, for example, to principal components.

PCA is used to reduce dimensionality of the data (e.g., measured expression values) into uncorrelated principal components (PCs) that explain or represent a majority of the variance in the data, such as about 50%, 60%, 70%, 75%, 80%, 85%, 90%, 95%, or 99% of the variance.

In one example, the PCA is 3-component PCA, in which three PCs are used that collectively represent most of the variance, for example, about 75%, 80%, 85%, 90/0, or more variance in the data (Jolliffe I T, "Principle Component Analysis," Springer, 1986).

PCA mapping, e.g., 3-component PCA mapping is used to map data to a three dimensional space for visualization, such as by assigning first ($1^{st}$), second ($2^{nd}$) and third ($3^{rd}$) PCs to the X-, Y-, and Z-axes, respectively.

PCA may be used to determine expression profiles for the biomarkers in various samples. For example, reduced expression data for individual sample types (e.g., each tumor type, sub-type or grade, or normal sample type) are localized in a PCA coordinate system and localized data used to determine individual transcript expression profiles or signatures.

In one aspect, the expression profile is determined for each sample by plotting or defining a centroid (center of mass; average expression), corresponding to or representing the sample's individual transcript expression profile (regulatory signature), as given by the principal component vector, as determined by PCA for the panel of biomarkers.

Generally, two centroids or points of localization separated by a relatively large distance in this coordinate system represent two relatively distinct transcript expression profiles. Likewise, relatively close centroids represent relatively similar profiles. In this representation, the distance between centroids is inversely equivalent to the similarity measure (greater distance=less similarity) for the different samples, such that large distances or separation between centroids indicates samples having distinct transcript expression signatures. Proximity of centroids indicates similarity between samples. For example, the relative distance between centroids for different GEP-NEN tumor samples represents the relative similarity of their regulatory signatures or transcript expression profiles.

In one aspect, the statistical and comparative analysis includes determining the inverse correlation between expression levels or values for two biomarkers. In one example, this correlation and the cosine of the angle between individual expression vectors (greater angle=less similarity), is used to identify related gene expression clusters (Gabriel K R, "The biplot graphic display of matrices with application to principal component analysis," Biometrika 1971; 58(3):453).

In some embodiments, there is a linear correlation between expression levels of two or more biomarkers, and/or the presence or absence of GEP-NEN, sub-type, stage, or other outcome. In one aspect, there is an expression-dependent correlation between the provided GEP-NEN biomarkers and characteristics of the biological samples, such as between biomarkers (and expression levels thereof) and various GEP-NEN sub-types (e.g., benign versus active disease).

Pearson's Correlation (PC) coefficients ($R^2$) may be used to assess linear relationships (correlations) between pairs of values, such as between expression levels of a biomarker for different biological samples (e.g., tumor sub-types) and between pairs of biomarkers. This analysis may be used to linearly separate distribution in expression patterns, by calculating PC coefficients for individual pairs of the biomarkers (plotted on x- and y-axes of individual Similarity Matrices). Thresholds may be set for varying degrees of linear correlation, such as a threshold for highly linear correlation of (R>0.50, or 0.40). Linear classifiers can be applied to the datasets. In one example, the correlation coefficient is 1.0.

In one embodiment, regulatory clusters are determined by constructing networks of correlations using statistical analyses, for example, to identify regulatory clusters composed of subsets of the panel of biomarkers. In one example, PC correlation coefficients are determined and used to construct such networks of correlations. In one example, the networks are identified by drawing edges between transcript pairs having R above the pre-defined threshold. Degree of correlation can provide information on reproducibility and robustness.

Also provided herein are objective algorithms, predictive models, and topographic analytical methods, and methods using the same, to analyze high-dimensional and multimodal biomedical data, such as the data obtained using the provided methods for detecting expression of the GEP-NEN biomarker panels. As discussed above, the objective algorithms, models, and analytical methods include mathematical analyses based on topographic, pattern-recognition based protocols e.g., support vector machines (SVM) (Noble W S. What is a support vector machine? Nat Biotechnol. 2006; 24(12): 1565-7), linear discriminant analysis (LDA), naive Bayes (NB), and K-nearest neighbor (KNN) protocols, as well as other supervised learning algorithms and models, such as Decision Tree, Perceptron, and regularized discriminant analysis (RDA), and similar models and algorithms well-known in the art (Gallant S I, "Perceptron-based learning algorithms," Perceptron-based learning algorithms 1990; 1(2): 179-91).

In some embodiments, Feature Selection (FS) is applied to remove the most redundant features from a dataset, such as a GEP-NEN biomarker expression dataset, and generate a relevant subset of GEP-NEN biomarkers. FS enhances the generalization capability, accelerates the learning process, and improves model interpretability. In one aspect, FS is employed using a "greedy forward" selection approach, selecting the most relevant subset of features for the robust learning models. (Peng H, Long F, Ding C, "Feature selection based on mutual information: criteria of max-dependency, max-relevance, and min-redundancy," IEEE Transactions on Pattern Analysis and Machine Intelligence, 2005; 27(8): 1226-38).

In some embodiments, Support Vector Machines (SVM) algorithms are used for classification of data by increasing the margin between the n data sets (Cristianini N, Shawe-Taylor J. An Introduction to Support Vector Machines and other kernel-based learning methods. Cambridge: Cambridge University Press, 2000).

In some embodiments, the predictive models include Decision Tree, which maps observations about an item to a conclusion about its target value (Zhang H, Singer B. "Recursive Partitioning in the Health Sciences," (Statistics for Biology and Health). Springer, 1999). The leaves of the tree represent classifications and branches represent conjunctions of features that devolve into the individual classifications. It has been used effectively (70-90%) to predict prognosis of metastatic breast cancer (Yu L et al "TGF-beta receptor-activated p38 MAP kinase mediates Smad-independent TGF-beta responses," Embo J 2002; 21(14):3749-59), as well as colon cancer (Zhang H et al "Recursive partitioning for tumor classification with gene expression microarray data," Proc Natl Acad Sci USA 2001; 98(12): 6730-5), to predict the grading of astrocytomas (Glotsos D et al "Automated diagnosis of brain tumours astrocytomas using probabilistic neural network clustering and support vector machines," Int J Neural Syst 2005; 15(1-2): 1-11) with a >90% accuracy, and prostatic carcinomas with an accuracy of 74-80% (Mattfeldt T et al. "Classification of prostatic carcinoma with artificial neural networks using comparative genomic hybridization and quantitative stereological data," Pathol Res Pract 2003; 199(12):773-84). The efficiency of this technique has been measured by 10-fold cross-validation (Pirooznia M et al "A comparative study of different machine learning methods on microarray gene expression data," BMC Genomics 2008; 9 Suppl 1:S13).

The predictive models and algorithms further include Perceptron, a linear classifier that forms a feed forward neural network and maps an input variable to a binary classifier (Gallant S I. "Perceptron-based learning algorithms," Perceptron-based learning algorithms 1990; 1(2): 179-91). It has been used to predict malignancy of breast cancer (Markey M K et al. "Perceptron error surface analysis: a case study in breast cancer diagnosis," Comput Biol Med 2002; 32(2):99-109). In this model, the learning rate is a constant that regulates the speed of learning. A lower learning rate improves the classification model, while increasing the time to process the variable (Markey M K et al. "Perceptron error surface analysis: a case study in breast cancer diagnosis," Comput Biol Med 2002; 32(2):99-109). In one example, a learning rate of 0.05 is used. In one aspect, a Perceptron algorithm is used to distinguish between localized or primary tumors and corresponding metastatic tumors. In one aspect, three data scans are used to generate decision boundaries that explicitly separate data into classes.

The predictive models and algorithms further include Regularized Discriminant Analysis (RDA), which can be used as a flexible alternative to other data mining techniques, including Linear and Quadratic Discriminant Analysis (LDA, QDA) (Lilien R H, Farid H, Donald B R. "Probabilistic disease classification of expression-dependent proteomic data from mass spectrometry of human serum," J Comput Biol 2003; 10(6):925-46; Cappellen D, Luong-Nguyen N H, Bongiovanni S, et al. "Transcriptional program of mouse osteoclast differentiation governed by the macrophage colony-stimulating factor and the ligand for the receptor activator of NFkappa B." J Biol Chem 2002; 277(24):21971-82). RDA's regularization parameters, $\gamma$ and $\lambda$, are used to design an intermediate classifier between LDA and QDA. QDA is performed when $\gamma=0$ and $\lambda^{\wedge}0$ while LDA is performed when $\gamma=0$ and $\lambda=1$ (Picon A, Gold L I, Wang J, Cohen A, Friedman E. A subset of metastatic human colon cancers expresses elevated levels of transforming growth factor beta 1. Cancer Epidemiol. Biomarkers Prev. 1998; 7(6):497-504).

To reduce over-fitting, RDA parameters are selected to minimize cross-validation error while not being equal 0.0001, thus forcing RDA to produce a classifier between LDA, QDA, and L2 (Pima I, Aladjem M., "Regularized discriminant analysis for face recognition," Pattern Recognition 2003; 37(9): 1945-48). Finally, regularization itself has been used widely to overcome over-fitting in machine learning (Evgeniou T, Pontil M, Poggio T. "Regularization Networks and Support Vector Machines," Advances in Computational Math 2000; 13(1): 1-50; Ji S, Ye J. Kernel "Uncorrelated and Regularized Discriminant Analysis: A Theoretical and Computational Study," IEEE Transactions on Knowledge and Data Engineering 2000; 20(10): 1311-21).

In one example, regularization parameters are defined as $\gamma=0.002$ and $\lambda=0$. In one example, for each class pair, S-values are assigned to all transcripts which are then arranged by a decreasing S-value. RDA is performed, e.g., 21 times, such that the $N^{th}$ iteration consists of top N scoring transcripts. Error estimation can be carried out by a 10-fold cross-validation of the RDA classifier. This can be done by partitioning the tissue data set into complementary subsets, performing the analysis on one subset (called the training set), and validating the analysis on the other subset (called the validation set or testing set).

In one example, misclassification error is averaged to reduce variability in the overall predictive assessment, which can provide a more accurate approach to error estimation compared to other approaches, including bootstrapping and leave-one-out cross-validation (Kohavi R. "A study of cross-validation and bootstrap for accuracy estimation and model selection," Proceedings of the Fourteenth International Joint Conference on Artificial Intelligence, 1995; 2(12): 1137-43).

In one example, selection for tissue classification is performed, for example, by computing the rank score (S) for each gene and for each class pair as:

$$S = \frac{|\mu_{c2} - \mu_{c1}|}{\sigma_{c1} + \sigma_{c2}}$$

where $\mu c_1$ and $\mu c_2$ represent means of first and second class respectively and $\sigma c_1$ and $\sigma c_2$ are inter-class standard deviations. A large S value is indicative of a substantial differential expression ("Fold Change") and a low standard deviation ("transcript stability") within each class. Genes may be sorted by a decreasing S-value and used as inputs for the regularized discriminant analysis algorithm (RDA).

The algorithms and models may be evaluated, validated and cross-validated, for example, to validate the predictive and classification abilities of the models, and to evaluate specificity and sensitivity. In one example, radial basis function is used as a kernel, and a 10-fold cross-validation used to measure the sensitivity of classification (Cristianini N, Shawe-Taylor J. "An Introduction to Support Vector Machines and other kernel-based learning methods," Cambridge: Cambridge University Press, 2000). Various classification models and algorithms may be compared by the provided methods, for example, using training and cross-validation, as provided herein, to compare performance of the predictive models for predicting particular outcomes.

Embodiments of the provided methods, systems, and predictive models are reproducible, with high dynamic range, can detect small changes in data, and are performed using simple methods, at low cost, e.g., for implementation in a clinical laboratory.

Kits and other articles of manufacture are provided for use in the diagnostic, prognostic, predictive, and therapeutic applications described herein. In some embodiments, the kits include a carrier, package, or packaging, compartmentalized to receive one or more containers such as vials, tubes, plates, and wells, in which each of the containers includes one of the separate elements for use in the methods provided herein, and in some aspects further include a label or insert with instructions for use, such as the uses described herein. In one example, the individual containers include individual agents for detection of the GEP-NEN biomarkers as provided herein; in some examples, individual containers include agents for detection of housekeeping genes and/or normalization.

For example, the container(s) can comprise an agent, such as a probe or primer, which is or can be detectably labeled. Where the method utilizes nucleic acid hybridization for detection, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody.

The kits will typically comprise the container(s) described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapeutic or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as GEP-NEN.

In another embodiment, an article(s) of manufacture containing compositions, such as amino acid sequence(s), small molecule(s), nucleic acid sequence(s), and/or antibody(s), e.g., materials useful for the diagnosis, prognosis, or therapy of GEP-NEN is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of GEP-NEN biomarkers in biological samples, e.g., blood or cells and tissues, or for relevant laboratory, prognostic, diagnostic, prophylactic and therapeutic purposes; indications and/or directions for such uses can be included on or with such container, as can reagents and other compositions or tools used for these purposes.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Differential Expression of NET Marker GENESIN Primary NETs—An exon-level screen of localized small intestinal NETs using Affymetrix Human Exon 1.0 ST arrays was performed to define alternative splicing events in neuroendocrine tumor tissue in comparison to a control (normal intestinal mucosa). Exon expression analysis identified 1287 differentially expressed genes between normal intestinal mucosa and NET tumor tissues. Five hundred and twenty nine genes were upregulated and 758 were downregulated. As an example, a subset of NET marker genes was focused on, in particular CgA, Tph1, VMAT2, SCG5, and PTPRN2. The RMA-normalized exon expression of the NET marker genes in this subset is shown in FIGS. 1A-1E in normal (green) and tumor (red) samples. Of these genes, Tph1 was the only gene where all exons were differentially expressed in tumor (FC>1.5, p<0.05), while CgA was the only gene where all exon expressions remained constant between tumor and normal samples.

Two of 17 differentially expressed exons were identified in VMAT2 and eight of 9 in SCG5. In PTPRN2 six of 30 exons were differentially expressed. These results demonstrate that specific primer/probe sets are required to maximize differences between neoplasia and normal gene expression.

Validating Alternative Splicing in NET Marker Genes by RT-PCR—With reference to FIGS. 2A-2E, the findings of differential exon transcript levels was validated using reverse transcriptase polymerase chain reaction (RT-PCR). All marker gene exons, including $Tph1_{1-2}$, $VMAT2_{9-10}$, $SCG5_{2-3}$, and $PTPRN2_{12-13}$, were confirmed to be differentially expressed in tumor samples versus normal mucosa, with the exception of $CgA_{4-5}$.

Genomic and RT-PCR data from FIGS. 1A-1E and 2A-2E, respectively, identify that differential splicing occurs in NETs and that candidate biomarkers, e.g., VMAT2, require the use of specific primer/probe sets to effectively capture differences in expression of target transcripts.

To evaluate the relevance in blood, a microarray analysis of peripheral NET blood samples was performed. Up-regulated genes (n=1,397) included GO-Fat terms such as "RNA splicing", "Vesicle-mediated transport", and "Chromatin modification" which is consistent with known roles for these processes in NET pathobiology. Comparisons of the blood transcriptome with GEP-NET transcriptomes identified 236 up-regulated genes, 72 of which were examined for utility as biomarkers. A preliminary screen identified 51 genes as upregulated in tumor blood samples compared to controls. Forty-two genes (83%) were transcribed from multiple exons. A minimum of two primer/probe sets were tested for these genes in blood to define the most relevant combinations for target amplification. The housekeeping gene and 51 validated targets and exons of interest for primer/probe sets are described in TABLE 2. The amplicon positions identified for each GEN-NEN biomarker in Table 2 are the identified as underlined sequences in Table 1.

TABLE 2

Primer Details

| GEP-NEN Biomarker | | NCBI Chromosome location | UniGene ID | RefSeq | Amplicon Size Length | Exon Boundary | Position |
|---|---|---|---|---|---|---|---|
| Symbol | Name | | | | | | |
| ALG9 | asparagine-linked glycosylation 9, alpha-1,2-mannosyl transferase homolog | Chr. 11-111652919-111742305 | Hs.503850 | NM_024740.2 | 68 | 4-5 | 541-600 |
| AKAP8L | A kinase (PRKA) anchor protein 8-like | Chr.19: 15490859-15529833 | Hs.399800 | NM_014371.3 | 75 | 12-13 | 1596-1670 |
| APLP2 | amyloid beta (A4) precursor-like protein 2 | Chr. 11-129939716-130014706 | Hs.370247 | NM_001142276.1 | 102 | 14-15 | 2029-2132 |
| ARAF1 | v-raf murine sarcoma 3611 viral oncogene homolog | Chr. X-47420578-47431320 | Hs.446641 | NM_001654.4 | 74 | 10-11 | 1410-1475 |

TABLE 2-continued

Primer Details

| GEP-NEN Biomarker | | NCBI Chromosome location | UniGene ID | RefSeq | Amplicon Size Length | Exon Boundary | Position |
|---|---|---|---|---|---|---|---|
| Symbol | Name | | | | | | |
| ATP6V1H | ATPase, H + transporting, lysosomal 50/57 kDa, V1, Subunit H | Chr.8: 54628115-54755850 | Hs.491737 | NM_015941.3 | 102 | 13-14 | 1631-1732 |
| BNIP3L | BCL2/adenovirus E1B 19 kDa interacting protein 3-like | Chr.8: 26240523-26270644 | Hs.131226 | NM_004331.2 | 69 | 2-3 | 374-342 |
| BRAF | v-raf murine sarcoma viral oncogene homolog B1 | Chr. 7-140433812-140624564 | Hs.550061 | NM_004333.4 | 77 | 1-2 | 165-233 |
| C21ORF7 | chromosome 21 open reading frame 7 | Chr.21: 30452873-30548204 | Hs.222802 | NM_020152.3 | 76 | — | 611-686 |
| CD59 | CD59 molecule, complement regulatory protein | Chr. 11-33724556-33758025 | Hs.278573 | NM_203331.2 | 70 | 3-4 | 193-264 |
| COMMD9 | COMM domain containing 9 | Chr.11: 36293842-36310999 | Hs.279836 | NM_001101653.1 | 85 | 2-3 | 191-275 |
| CTGF | connective tissue growth factor | Chr. 6-132269316-132272518 | Hs.410037 | NM_001901.2 | 60 | 4-5 | 929-990 |
| ENPP4 | ectonucleotide pyrophosphatase/phosphodiesterase 4 | Chr.6: 46097701-46114436 | Hs.643497 | NM_014936.4 | 82 | 3-4 | 1221-1303 |
| FAM131A | family with sequence similarity 131, member A, transcript variant 2 | Chr.3: 184053717-184064063 | Hs.591307 | NM_001171093.1 | 64 | 4-5 | 498-561 |
| FLJ10357 | Rho guanine nucleotide exchange factor (GEF) 40 (ARHGEF40) | Chr.14: 21538527-21558036 | Hs.35125 | NM_018071.4 | 102 | 16-17 | 3557-3658 |
| FZD7 | frizzled homolog 7 (Drosophila) | Chr. 2-202899310-202903160 | Hs.173859 | NM_003507.1 | 70 | 1-1 | 1-70 |
| GLT8D1 | glycosyltransferase 8 domain containing 1, transcript variant 3 | Chr.3: 52728504-52740048 | Hs.297304 | NM_001010983.2 | 87 | 4-5 | 924-1010 |
| HDAC9 | histone deacetylase 9, transcript variant 6 | Chr.7: 18535369-19036993 | Hs.196054 | NM_001204144.1 | 69 | 11-12 | 1777-1845 |
| HSF2 | heat shock transcription factor 2, transcript variant 1 | Chr.6: 122720696-122754264 | Hs.158195 | NM_004506.3 | 82 | 10-11 | 1324-1405 |
| Ki-67 | antigen identified by monoclonal antibody Ki-67 | Chr. 10-129894923-129924655 | Hs.689823 | NM_001145966.1 | 78 | 6-7 | 556-635 |
| KRAS | v-Ki-ras2 Kirsten rat sarcoma viral oncogene homolog | Chr. 12-25358180-25403854 | Hs.505033 | NM_004985.4 | 130 | 4-5 | 571-692 |
| LEO1 | Leo1, Paf1/RNA polymerase II complex component homolog (S. cerevisiae) | Chr.15: 52230222-52263958 | Hs.567662 | NM_138792.3 | 122 | 10-11 | 1753-1874 |
| MORF4L2 | mortality factor 4 like 2, transcript variant 1 | Chr.X: 102930426-102943086 | Hs.326387 | NM_001142418.1 | 153 | 5-5 | 1294-1447 |
| NAP1L1 | nucleosome assembly protein 1-like 1 | Chr. 12-76438672-76478738 | Hs.524599 | NM_139207.2 | 139 | 16-16 | 1625-1764 |
| NOL3 | nucleolar protein 3 (apoptosis repressor with CARD domain), transcript variant 3 | Chr.16: 67204405-67209643 | Hs.513667 | NM_001185057.2 | 118 | 1-2 | 131-248 |
| NUDT3 | nudix (nucleoside diphosphate linked moiety X)-type motif 3 | Chr.6: 34255997-34360441 | Hs.188882 | NM_006703.3 | 62 | 2-3 | 500-561 |
| OAZ2 | ornithine decarboxylase antizyme 2 | Chr.15: 64979773-64995462 | Hs.713816 | NM_002537.3 | 96 | 1-2 | 189-284 |

TABLE 2-continued

Primer Details

| GEP-NEN Biomarker | | NCBI Chromosome location | UniGene ID | RefSeq | Amplicon Size Length | Exon Boundary | Position |
|---|---|---|---|---|---|---|---|
| Symbol | Name | | | | | | |
| PANK2 | pantothenate kinase 2 | Chr.20: 3869486-3904502 | Hs.516859 | NM_024960.4 | 126 | 4-5 | 785-910 |
| PHF21A | PHD finger protein 21A, transcript variant 1 | Chr.11: 45950870-46142985 | Hs.502458 | NM_001101802.1 | 127 | 16-17 | 2241-2367 |
| PKD1 | polycystic kidney disease 1 (autosomal dominant), transcript variant 2 | Chr.16: 2138711-2185899 | Hs.75813 | NM_000296.3 | 110 | 16-17 | 7224-7333 |
| PLD3 | phospholipase D family, member 3, transcript variant 1 | Chr.19: 40854332-40884390 | Hs.257008 | NM_001031696.3 | 104 | 6-7 | 780-883 |
| PNMA2 | paraneoplastic antigen MA2 | Chr. 8- 26362196-26371483 | Hs.591838 | NM_007257.5 | 60 | 3-3 | 283-343 |
| PQBP1 | polyglutamine binding protein 1, transcript variant 2 | Chr.X: 48755195-48760422 | Hs.534384 | NM_001032381.1 | 68 | 2-3 | 157-224 |
| RAF1 | v-raf-1 murine leukemia viral oncogene homolog 1 | Chr. 3- 12625100-12705700 | Hs.159130 | NM_002880.3 | 90 | 7-8 | 1186-1277 |
| RNF41 | ring finger protein 41, transcript variant 4 | Chr.12: 56598285-56615735 | Hs.524502 | NM_001242826 | 72 | 2-3 | 265-336 |
| RSF1 | remodeling and spacing factor 1 | Chr.11: 77377274-77531880 | Hs.420229 | NM_016578.3 | 60 | 7-8 | 2804-2863 |
| RTN2 | reticulon 2, transcript variant 1 | Chr.19: 45988550-46000313 | Hs.47517 | NM_005619.4 | 87 | 9-10 | 1681-1766 |
| SMARCD3 | SWI/SNF related, matrix associated, actin dependent regulator of chromatin, subfamily d, member 3, transcript variant 3 | Chr.7: 150936059-150974231 | Hs.647067 | NM_001003801.1 | 109 | 8-9 | 986-1094 |
| SPATA7 | spermato genesis associated 7, transcript variant 2 | Chr.14: 88851988-88904804 | Hs.525518 | NM_001040428.3 | 81 | 1-2 | 160-241 |
| SST1 | somatostatin receptor 1 | Chr.14: 38677204-38682268 | Hs.248160 | NM_001049.2 | 85 | 3-3 | 724-808 |
| SST3 | somatostatin receptor 3 | Chr.22: 37602245-37608353 | Hs.225995 | NM_001051.4 | 84 | 2-2 | 637-720 |
| SST4 | somatostatin receptor 4 | Chr.20: 23016057-23017314 | Hs.673846 | NM_001052.2 | 104 | 1-1 | 91-194 |
| SST5 | somatostatin receptor 5, transcript variant 1 | Chr.16: 1122756-1131454 | Hs.449840 | NM_001053.3 | 157 | 1-1 | 1501-1657 |
| TECPR2 | tectonin beta-propeller repeat containing 2, transcript variant 2 | Chr.14: 102829300-102968818 | Hs.195667 | NM_001172631.1 | 61 | 12-13 | 3130-3191 |
| TPH1 | tryptophan hydroxylase 1 | Chr. 11- 18042538-18062309 | Hs.591999 | NM_004179.2 | 145 | 1-2 | 73-219 |
| TRMT112 | tRNA methyltransferase 11-2 homolog (S. cerevisiae) | Chr.11: 64084163-64085033 | Hs.333579 | NM_016404.2 | 91 | 1-2 | 45-135 |
| VMAT1 | solute carrier family 18 (vesicular monoamine), member 1 | Chr. 8- 20002366-20040717 | Hs.158322 | NM_003053.3 | 102 | 1-2 | 93-196 |
| VMAT2 | solute carrier family 18 (vesicular monoamine), member 2 | Chr. 10- 119000716-119037095 | Hs.596992 | NM_003054.4 | 60 | 9-10 | 896-957 |
| VPS13C | vacuolar protein sorting 13 homolog C (S. cerevisiae), transcript variant 2B | Chr.15: 62144588-62352647 | Hs.511668 | NM_001018088.2 | 65 | 69-70 | 9685-9749 |

TABLE 2-continued

Primer Details

| GEP-NEN Biomarker Symbol | Name | NCBI Chromosome location | UniGene ID | RefSeq | Amplicon Size Length | Exon Boundary | Position |
|---|---|---|---|---|---|---|---|
| WDFY3 | WD repeat and FYVE domain containing 3 | Chr.4: 85590690-85887544 | Hs.480116 | NM_014991.4 | 81 | 64-65 | 10190-10270 |
| ZFHX3 | zinc finger homeobox3, transcript variant B | Chr.16: 72816784-73092534 | Hs.598297 | NM_001164766.1 | 68 | 5-6 | 886-953 |
| ZXDC | zinc finger C, transcript variant 2 | Chr.3: 126156444-126194762 | Hs.440049 | NM_001040653.3 | 61 | 1-2 | 936-1001 |
| ZZZ3 | zinc finger, ZZ-type containing 3 | Chr.1: 78030190-78148343 | Hs.480506 | NM_015534.4 | 62 | 13-14 | 2909-2971 |

Figure 3:
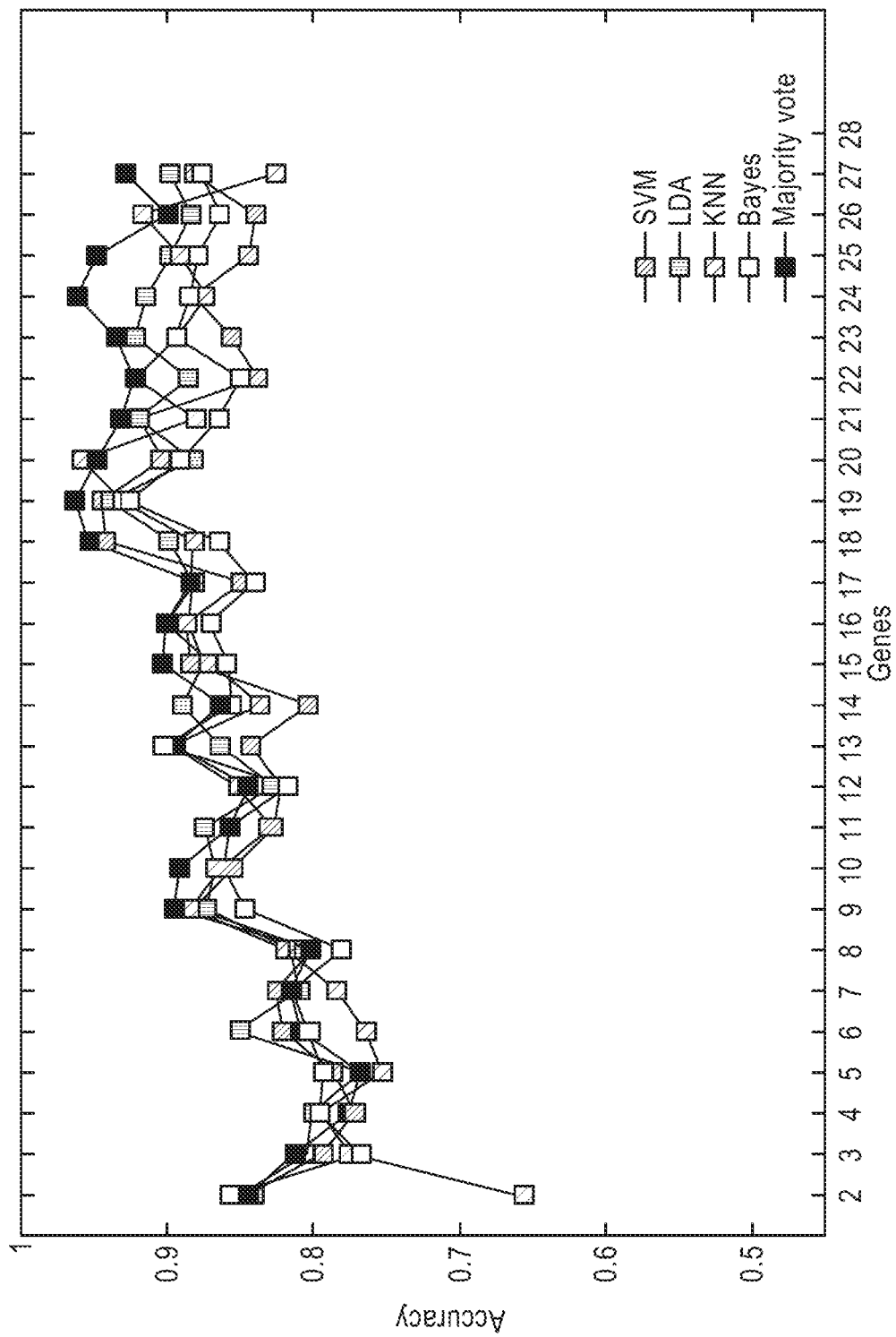
FIG. 3 is a line graph showing the prediction accuracy of four classification algorithms (SVM, LDA, KNN, and Bayes) using sequential addition of up to 22 significantly up-regulated genes (p<0.05) in GEP-NET samples obtained using the results of 10-fold cross validation.

Delineation of Minimum Gene Set for Mathematically-Derived (MAARC-NET) Scoring System—Four classification algorithms (SVM, LDA, KNN, and Bayes) and a 10-fold cross-validation design were used to build a classifier for the identification of GEP-NETs in blood. See Modlin I, Drozdov I, Kidd M: The Identification of gut neuroendocrine tumor disease by multiple synchronous transcript analysis in blood. *Plos One* 2013, e63364. These classifiers were built on a training set and significantly up-regulated features between control and tumor cases were calculated by t-test. With reference to FIG. 3, an examination of the 51 genes featured in TABLE 2 identified that inclusion of at least 22 genes was sufficient to build an accurate (>0.85) classifier. FIG. 3 shows the prediction accuracy of each classifier algorithm using sequential addition of up to 27 significantly up-regulated genes (p<0.05) in the GEP-NET samples obtained using results of the 10-fold cross validation. The average accuracy of the SVM, LDA, KNN, and Bayes algorithms to distinguish GEP-NET from control blood samples using the sequentially added 27 genes was comparable—0.89 (0.85-1.0), 0.89 (0.86-0.93), 0.88 (0.85-0.93), and 0.86 (0.85-0.93) respectively. The "majority voting" combination of the four classifiers achieved an accuracy of 0.88. The at least 22 genes sufficient to build an accurate classifier were used to develop the MAARC-NET scoring system, and are featured in TABLE 3.

TABLE 3

Twenty Two Genes Included in the Mathematically-Derived MAARC-NET Scoring System

| | Fold Change | p-value | Adjusted p-value |
|---|---|---|---|
| PNMA2 | 0.819515 | 6.74E-21 | 3.43E-19 |
| NAP1L1 | 0.662434 | 4.9E-18 | 1.25E-16 |
| FZD7 | 0.799858 | 3.82E-15 | 6.5E-14 |
| SLC18A2 | 0.524046 | 1.08E-12 | 1.37E-11 |
| NOL3 | 0.809571 | 7.22E-10 | 7.36E-09 |
| SSTR5 | 0.877322 | 1.64E-09 | 1.4E-08 |
| TPH1 | 0.459185 | 1.75E-07 | 1.27E-06 |
| RAF1 | 0.316509 | 1.54E-06 | 7.86E-06 |
| RSF1 | 0.530054 | 1.74E-06 | 8.07E-06 |
| SSTR3 | 0.555269 | 3.82E-06 | 1.62E-05 |
| SSTR1 | 0.493052 | 1.73E-05 | 6.81E-05 |
| CD59 | 0.26257 | 2.7E-05 | 9.82E-05 |
| ARAF | 0.228332 | 4.07E-05 | 0.000138 |
| APLP2 | 0.228153 | 4.42E-05 | 0.000141 |
| KRAS | 0.205822 | 9.92E-05 | 0.000298 |
| MORF4L2 | 0.319826 | 0.000169 | 0.000453 |
| TRMT112 | 0.269618 | 0.001125 | 0.002524 |
| MKI67 | 0.191245 | 0.003468 | 0.007074 |
| SSTR4 | 0.313807 | 0.003734 | 0.007324 |
| CTGF | 0.196845 | 0.007665 | 0.01303 |
| SPATA7 | 0.288625 | 0.01467 | 0.02338 |
| ZFHX3 | 0.13248 | 0.031354 | 0.045687 |

Figure 4C:
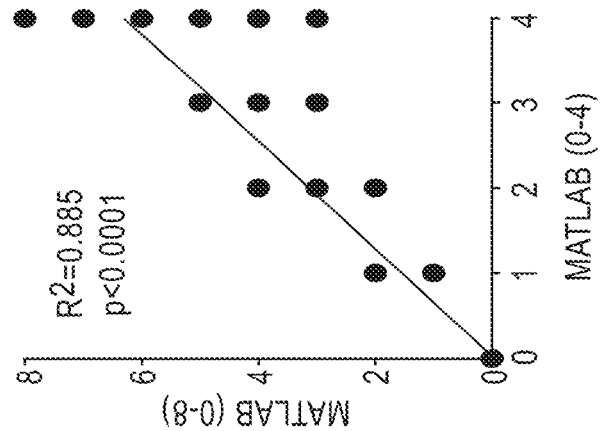
FIGS. 4A-4C are graphs showing mathematically-derived MAARC-NET scores in the test set.
Figure 4B:
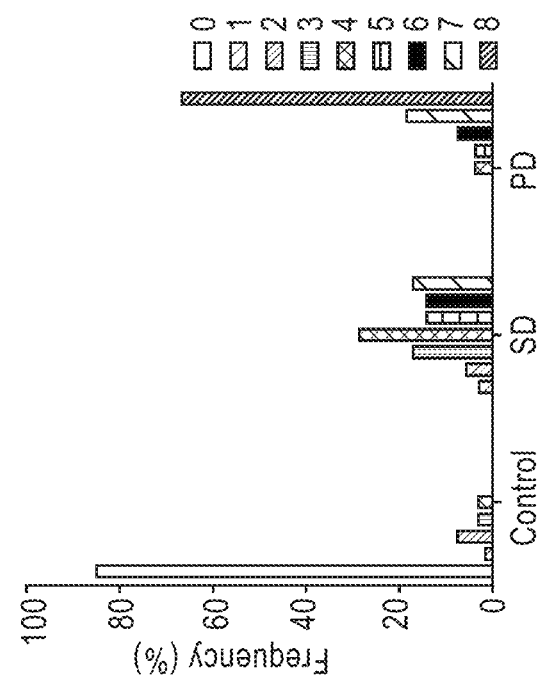
Figure 4A:
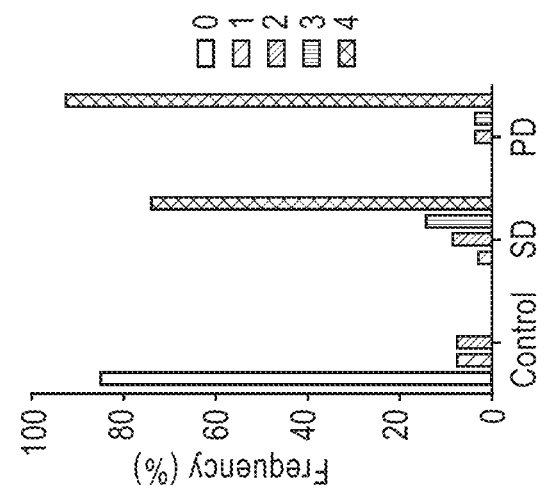

Refinement of Mathematically-Derived MAARC-NET Scoring System—Individual PCR-based gene expressions are included in a score. See Modlin I, Drozdov I, Kidd M, *Plos One* 2013. The score is based on a "majority vote" strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naïve Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN. With reference to FIG. 4A, an audit of samples identified that 85% of controls exhibited a score of "0." No tumors scored "0." ROC analyses identified that a score of 2 was the cut-off for normal samples (controls) versus tumors (score≥2). This approach exhibited correct call rates of 91-97% with sensitivities and specificities of 85-98% and 93-97% for the identification of GEP-NETs in two independent sets. See Modlin I, Drozdov I, Kidd M, *Plos One* 2013.

These data were initially derived from a test data set of 130 samples (n=67 controls, n=63 NETs). Inherent in the test set are two classes of NETs—clinically defined as treated, stable disease (SD: n=35) and untreated, progressive disease (PD: n=28). The classification algorithm also segregated the tumor call into two units "treated" and "untreated." The 0-4 binary classification was therefore amended to represent 3 possible calls for each particular sample: "normal", "tumor (treated)" and "tumor (untreated)".

A number of rules were implemented to generate an amended majority vote strategy. A call of "normal" was assigned a value of 0; a call of tumor "treated" was assigned a value of 1; a call of tumor "untreated" was assigned a value of 2. By way of example, if a sample results in four calls of "normal," a value of 0 was assigned for each call, thereby totaling a score of 0. If a sample results in four calls of tumor "treated," a value of 1 was assigned for call, thereby totaling a score of 4. If a sample results in four calls of tumor "untreated," a "2" is assigned for each, thereby totaling a score of 8. Scores in the amended majority vote strategy can therefore range between 0 and 8.

Examination of the test dataset (n=130) was used to establish whether the amended majority vote-derived score could serve as a measure of "treatment" responses. Similarly to the published 0-4 score shown in FIG. 4A, the majority of NET patients exhibited an amended majority vote score>2 as shown in FIG. 4B. With reference to FIG. 4C, majority vote and amended majority vote scores were significantly related ($R^2$=0.89, p<0.0001).

Figure 5A:
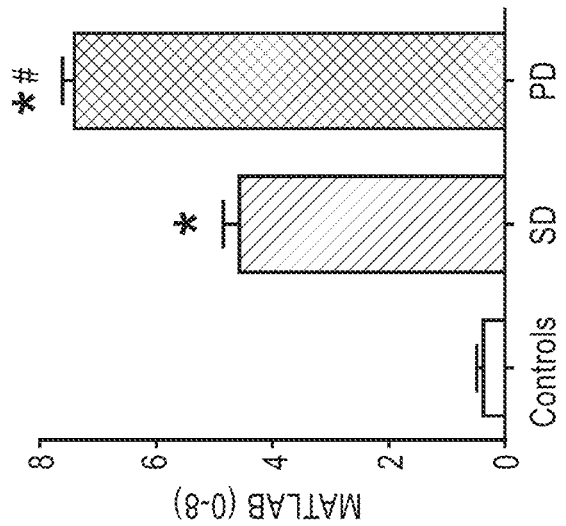
FIGS. 5A-5B are graphs showing MAARC-NET scores in the test set and a Receiver Operating Characteristics (ROC) analysis.

With reference to FIG. 5A, analysis of the data in the test set identified that an amended mathematically-derived score (0-8) was significantly elevated in tumors compared to controls and was highest in PD relative to SD.

Figure 5B:
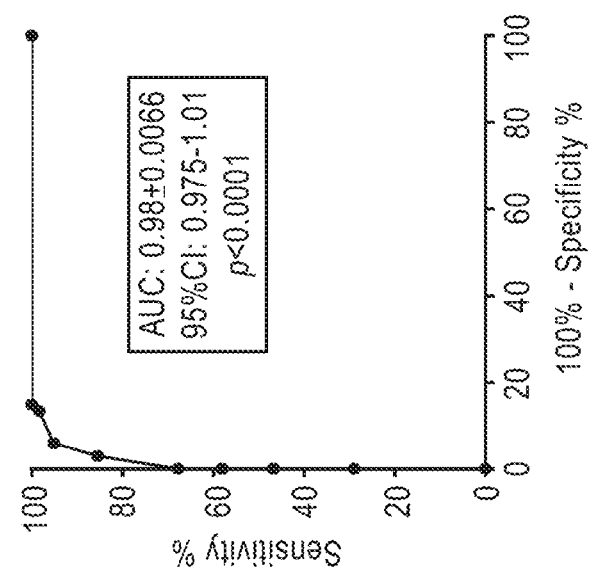

With reference to FIG. 5B, a receiver operating characteristic (ROC) curve was generated of controls versus GEP-NETs (SD and PD combined). A ROC curve is a generalization of the set of potential combinations of sensitivity and specificity possible for predictors. A ROC curve is a plot of the true positive rate (sensitivity) against the false positive rate (1-specificity) for the different possible cut-points of a diagnostic test. FIG. 5B is a graphical representation of the functional relationship between the distribution of the sensitivity and specificity values in the test set and in a cohort of control samples. The area under the curve (AUC) is an overall indication of the diagnostic accuracy of (1) the amended mathematically-derived scores and (2) a receiver operating characteristic (ROC) curve. AUC may be determined by the "trapezoidal rule." For a given ROC curve, the data points are connected by straight line segments, perpendiculars are erected from the abscissa to each data point, and the sum of the areas of the triangles and trapezoids so constructed is computed.

The ROC curve in FIG. 5B identifies that the amended mathematically-derived score may be utilized to differentiate between controls and GEP-NETs—exhibiting an AUC of >0.98, and a p<0.0001; *p<0.05 vs. controls; #p<0.05 vs. SD (2-tailed Mann-Whitney U-test).

Amended mathematically-derived scores were subsequently examined in an independent set (SD: n=111, PD: n=48). With reference to FIG. 6A, the scores were significantly elevated in the independent set, exhibiting a p<0.0001. With reference to FIG. 6B, a frequency distribution plot of amended mathematically-derived scores in SD and PD patients confirmed that PD samples exhibited higher scores, with #p<0.0001 vs. SD (2-tailed Mann-Whitney U-test).

Figure 7B:
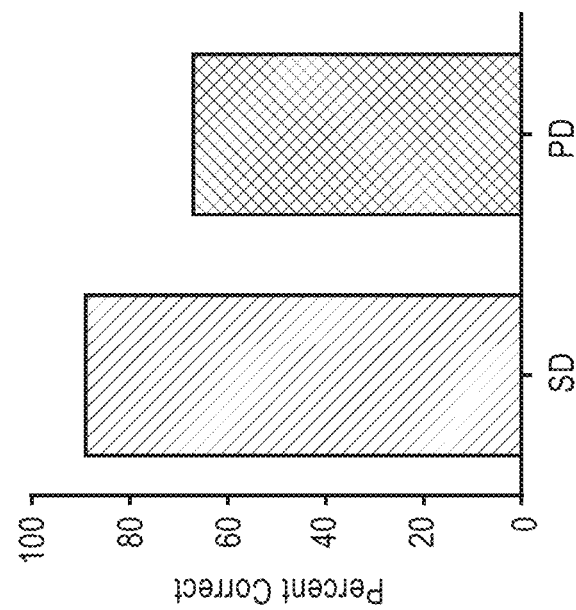
FIGS. 7A-7B are (FIG. 7A) a graph of ROC of SD versus PD NETs with an AUC of >0.93, p<0.0001 and (FIG. 7B) a graph of the percentage of SD and PD NETs correctly called using a cut-off score of ≥7.
Figure 7A:
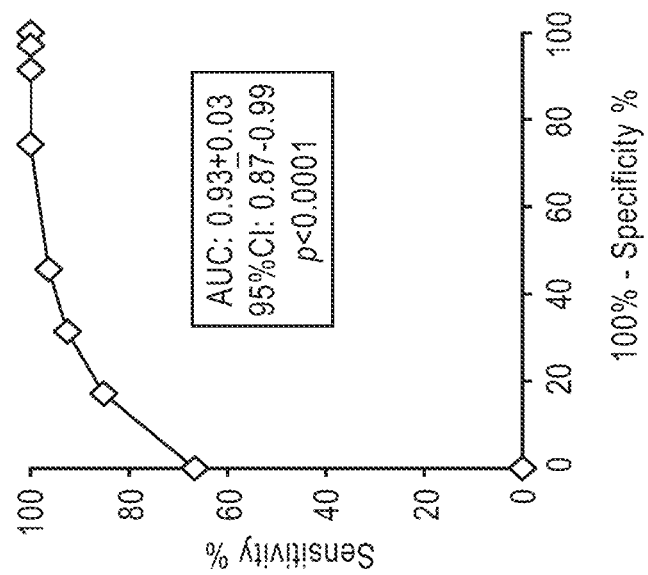

With reference to FIG. 7A, a second ROC curve was generated to determine whether the amended mathematically-derived score could be utilized to differentiate SD from PD. In the test set (SD: n=35, PD: n=28), the ROC analysis identified that the score could be used to differentiate PD from SD tumors with an AUC of 0.93. A score cutoff of >6.5 (i.e. a score of ≥7) had a sensitivity of 85% and 83% specificity for detecting PDs (Likelihood ratio: 4.97).

With reference to FIG. 7B, the utility of the amended mathematically-derived scoring system to differentiate between SD and PD in the independent set (n=111 SD, n=48 PD) was assessed. The percentage correctly called ranged between 70-90% using a cut-off of ≥7. For SD, 89% of NETs were correctly predicted using the cut-off of ≥7 while 67% of PD were correctly predicted. The performance metrics were: sensitivity=67%, specificity=89%, PPV=73% and NPV=86%. Accordingly, the data indicate that a mathematically-derived MAARC-NET score ranging from 0-8 has utility for discriminating between controls and GEP-NETs.

Application of Scoring System and Developing a Nomogram for "NETEST 1"—To differentiate between controls and NETs, a cut-off of ≥3 has a sensitivity of 95% and 94% specificity. The sensitivity can be improved to 98% using a cut-off of ≥2. To differentiate between SD and PD, a cut-off of ≥7 can be used (sensitivity of 85% and 83% specificity). The sensitivity can be improved to 96% using a cut-off of ≥5.

The mathematically-derived MAARC-NET scores therefore range from 0-2 (control); 2-5 (SD); and 5-8 (PD). These scores can be converted to a percentage as displayed in TABLE 4.

TABLE 4

Mathematically-Derived Scores Percentage

| | Mathematically-derived Score | | | |
|---|---|---|---|---|
| | 0-2 | 2-5 | 5-7 | 7-8 |
| Disease Nomogram Score | 0 | 0-55% | 55-75% | 75-100% |
| | | Low | Moderate | High |

Figure 8:
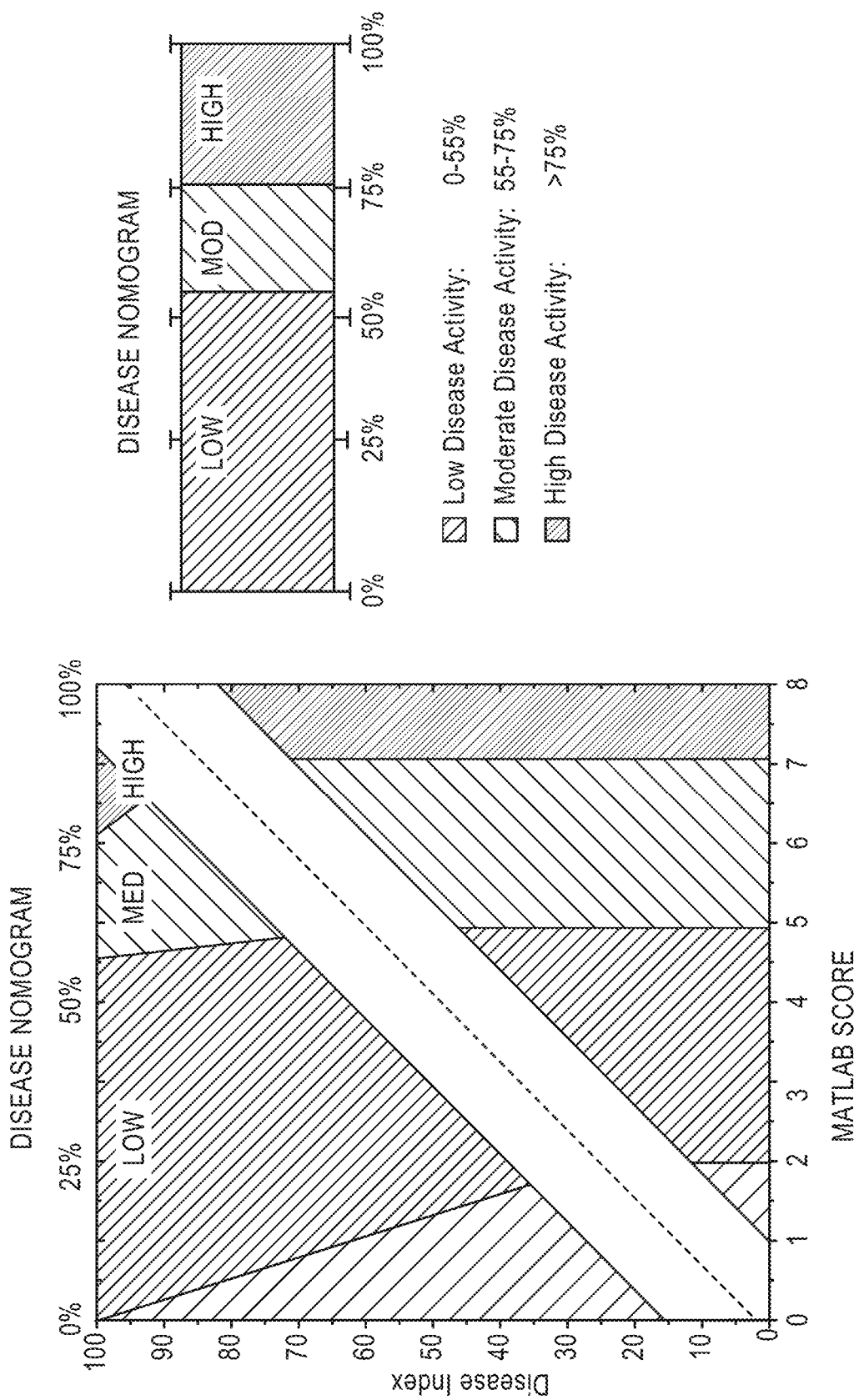
FIG. 8 is a nomogram for NETest 1 demonstrating how the score is achieved and categorizing patients into different disease classes.

With reference to FIG. 8, the score percentages from TABLE 4 can be displayed within a nomogram representing "NETest 1." The NETest 1 nomogram demonstrates how the amended mathematically-derived score is achieved and how it categorizes patients into different classes of GEP-NEN (no disease, stable disease, or progressive disease).

Figure 9:
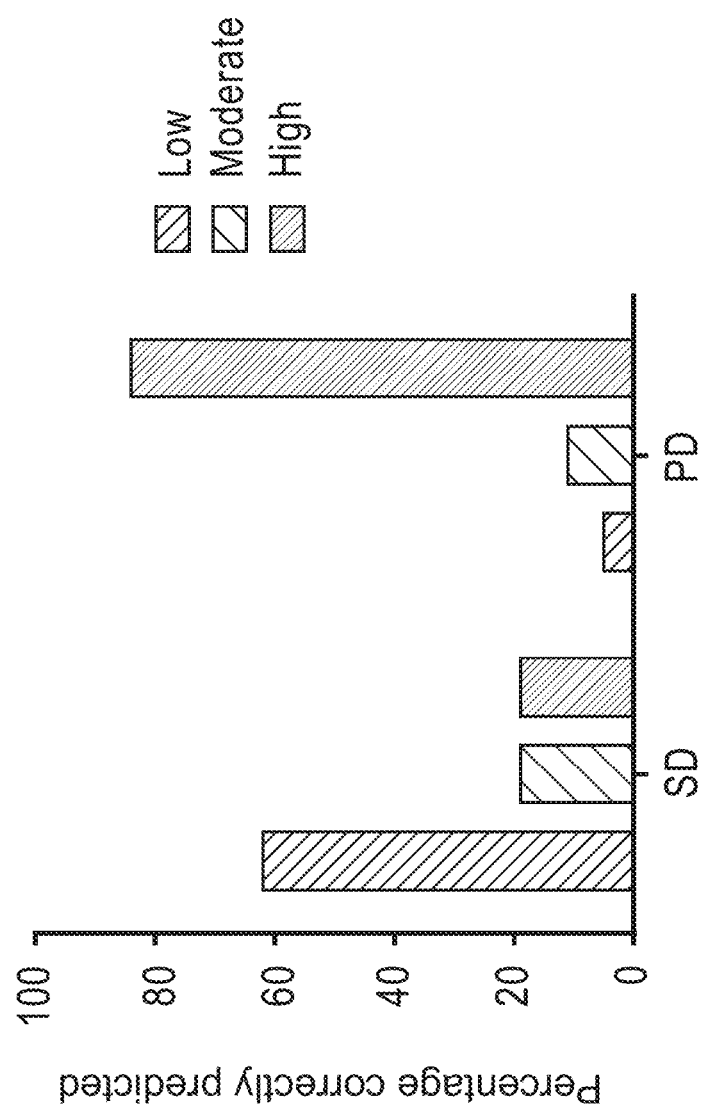
FIG. 9 is a graph of the utility of the nomogram of FIG. 8. The percentages of correctly predicted SD and PD NETs, including the level of disease activity, using the nomogram of FIG. 8 are shown.

With reference to FIG. 9, the utility of the NETest 1 nomogram was assessed. Values for the correct predictions of SD and PD using the NETest 1 nomogram of FIG. 8 are shown. Overall, the NETest 1 nomogram identified 80% of SD patients as exhibiting low or moderate disease activity and 84% of PD patients as exhibiting high disease activity.

Figure 10B:
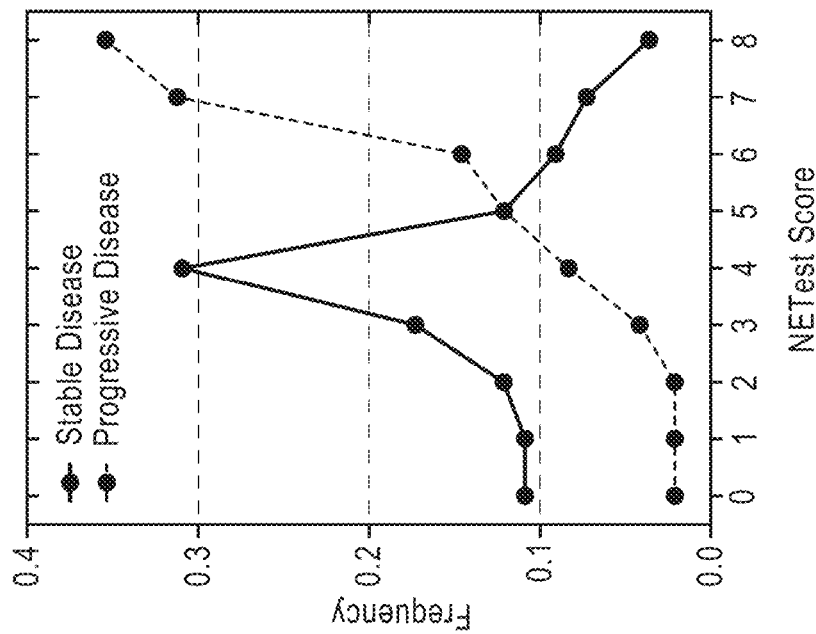
FIGS. 10A-10B are graphs each showing the frequency distribution for the 0-8 score in SD and PD NET tumors in (FIG. 10A) the test set and (FIG. 10B) the independent set.
Figure 10A:
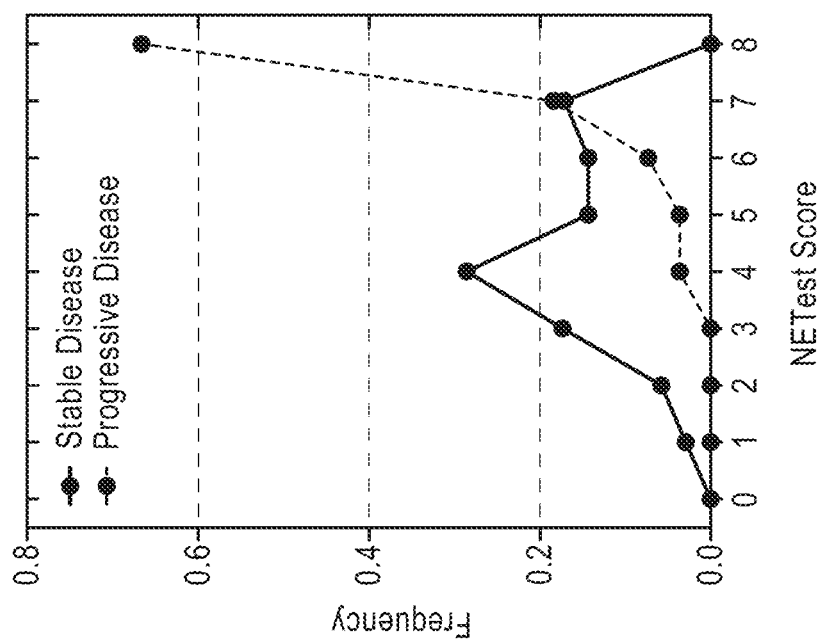

Application of Scoring System and Developing a Nomogram for "NETEST 2"—MAARC-NET-derivedNETest Scores (0-8) in patients clinically defined as either stable or progressive disease (best clinical judgment and/or imaging data) were examined. The frequency distribution of scores for each subtype in both the test set (FIG. 10A) or the independent set (FIG. 10B) demonstrate that SD patients have a median NETest value of 4 and PD patients range from 7-8. However, SD patients can exhibit MAARC-NET-derived scores>4 while PD can exhibit scores<7.

Figure 11B:
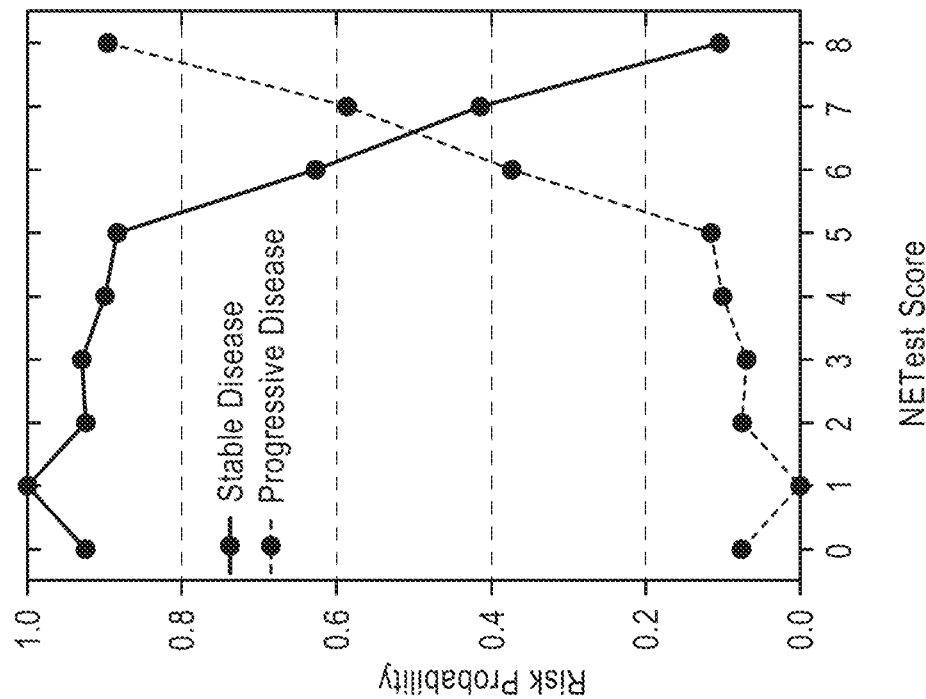
FIGS. 11A-11B are graphs of (FIG. 11A) the frequency distribution for the 0-8 score in SD and PD in the combined sets and (FIG. 11B) the risk probability for a score being either SD or PD vs. NETest Score.
Figure 11A:
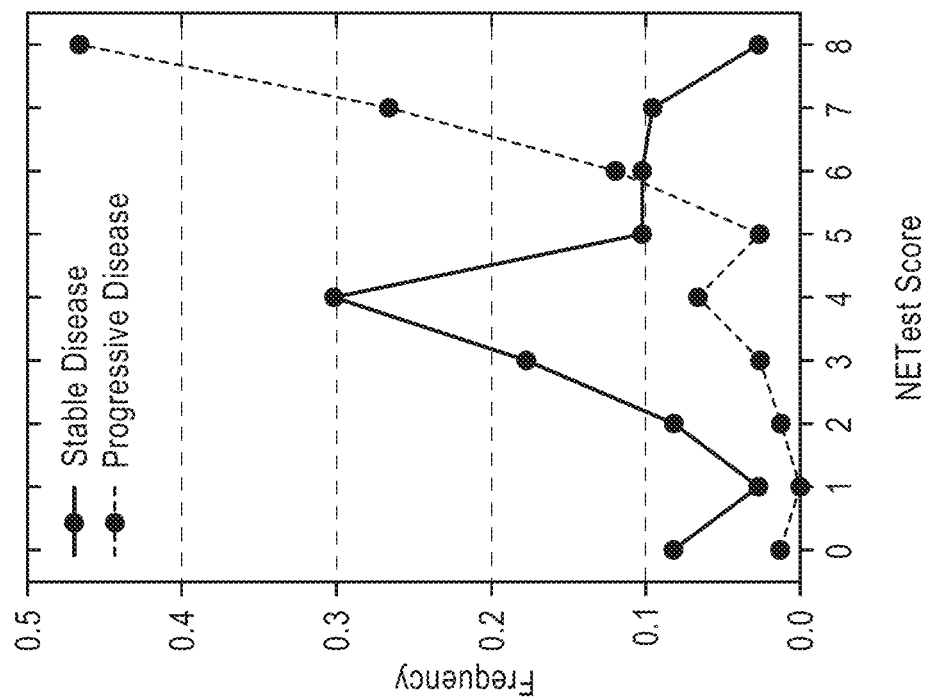

An assessment of the complete patient group (test set+ independent set) demonstrated that the highest frequency SD score was 4 (30% —FIG. 11A), while 46% of PD had a score of 8 (FIG. 11A). A risk probability assessment identified that NETest scores ranging between 0-5 were associated with SD with a ≥90% certainty (FIG. 11B). A score of 8 was most likely PD (>90%). However, scores of 6 and 7 could not accurately differentiate SD versus PD.

Based on these results from FIGS. 11A and 11B, the NETest 1 nomogram from FIG. 8 can be updated to include risk values. The NETest 2a nomogram of FIG. 12 includes the NETest with the inclusion of score and risk categorizations.

To upgrade the risk assessment NETest 2a nomogram, individual gene expression in SD and PD samples may be evaluated. The genes that were most differentially expressed in SD and PD samples were identified and used in decision trees to generate the rules for defining whether a NETest score was SD or PD. This approach provides the basis for NETest 2.

Figure 12:
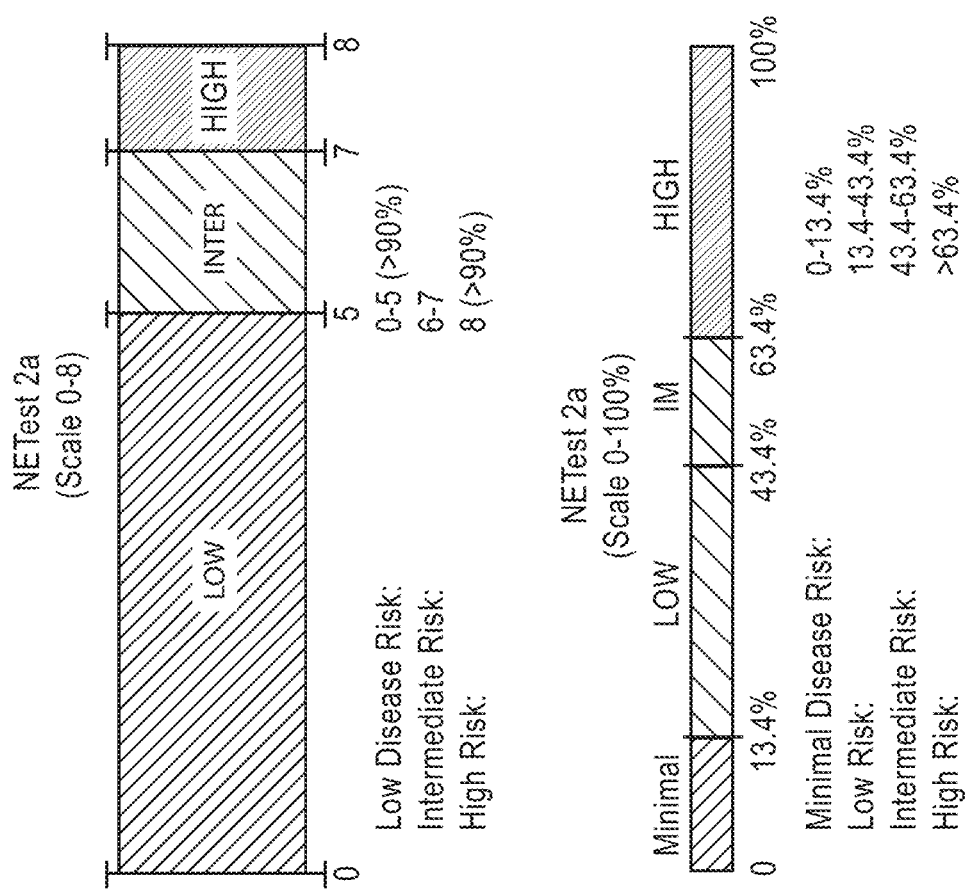
FIG. 12 is a nomogram of NETest 2a with the inclusion of score and risk categorizations. Top figure includes MAARC-NET as 0-8 scores; bottom figure is the 0-100% scaled version.

A NETest score of 5 has a >90% chance of identifying an SD sample (as shown in FIGS. 11A-11B and 12). Comparisons of the individual 51 gene expression profiles between patients scored as 5 (SD versus PD) identified expression of SMARCD3 and TPH1 as candidate differentiation markers. Using the rule:

If SMARCD3≤0.13 and TPH1<4 then call PD.

This allowed for 100% accuracy in defining progressive disease.

A NETest score of 6 has a ~50% chance of differentiating SD from PD samples. Gene expression profile analysis identified VMAT1 and PHF21A as candidates. A ROC analysis defined the AUCs for each to differentiate PD from SD to be:

VMAT1: ROC=0.835

PHF21A: ROC=0.733

Using the rule:

If VMAT1≥0 and PHF21A<1.2 then SD

If VMAT1≥0 and PHF21A≥1.2 then PD

This allowed for 100% accuracy in defining progressive disease and 90% accuracy in defining SD. The overall accuracy was 93%.

A NETest score of 7 has a ~50% chance of differentiating SD from PD samples. As for NETest scores of 6, gene expression profile analysis identified both VMAT1 and PHF21A as candidates. A ROC analysis defined the AUCs for each to differentiate PD from SD to be:

VMAT1: ROC=0.835

PHF21A: ROC=0.733

Using the rule:

If VMAT1≥0 and PHF21A>1 then SD

If VMAT1≥0 and PHF21A≤1 then PD

This allowed for a 100% accuracy for defining progressive disease and 95% accuracy for SD. The overall accuracy was 97.5%.

A NETest score of 8 has a ≥90% chance of identifying a sample as PD. Expression of ZZZ3 was identified as a candidate. A ROC analysis defined the AUC for this gene to be 1.0.

Using the rule:

If ZZZ3≤14 then PD

This allowed for a 100% accuracy for defining progressive disease and differentiating from SD.

Figure 13:
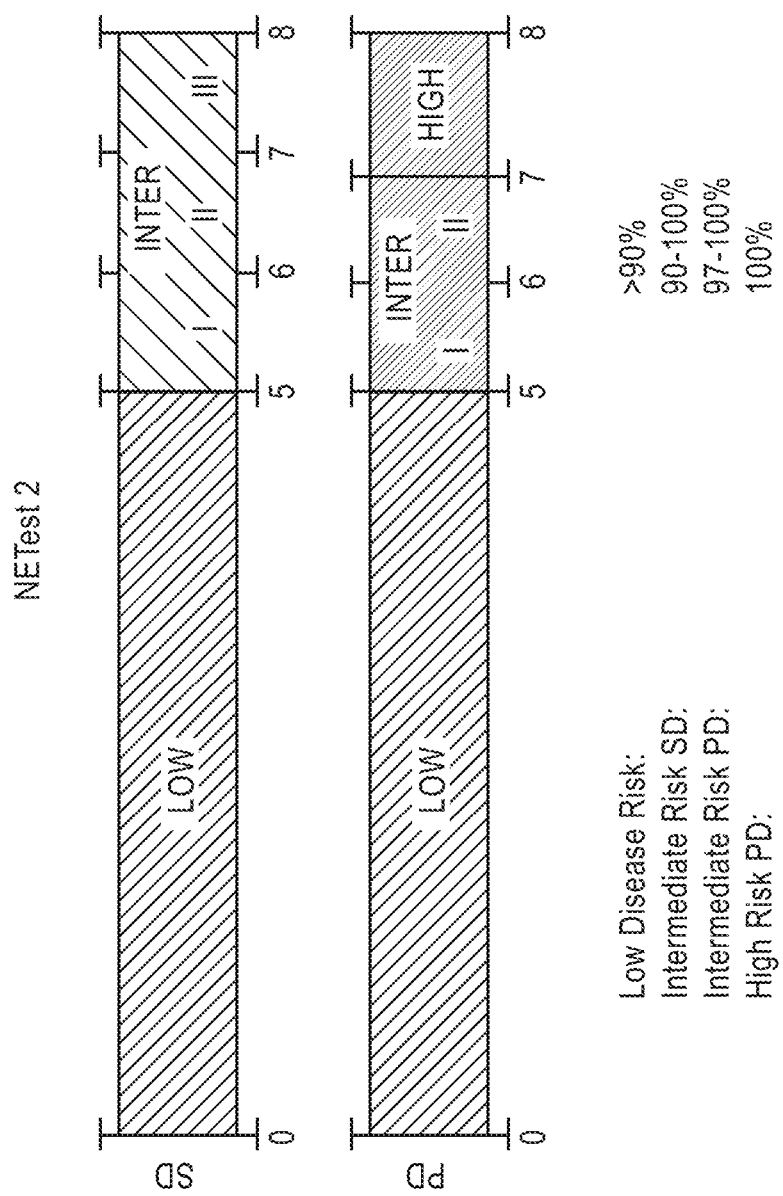
FIG. 13 is a nomogram of NETest 2 with the inclusion of risk category delineation.

With reference to FIG. 13, this individual gene expression information was used to finalize the "NETest 2" nomogram, which provides an accurate disease categorization profile for the patient. The combination of NETest scores and individual gene expression information used in the NETest 2 nomogram of FIG. 13 is further detailed in TABLE 5.

TABLE 5

NETEST 2 Nomogram Information

| | | Accuracy |
|---|---|---|
| Low risk stable disease | NETest score 0-5 | 90-100% |
| Intermediate risk stable disease (I) | NETest score 6 (low PHF21A) | 90-100% |
| Intermediate risk stable disease (II) | NETest score 7 (high PHF21A) | 95-100% |
| Intermediate risk stable disease (III) | NETest score 8 (high ZZZ3) | 100% |
| Intermediate risk progressive disease (I) | NETest score 6 (high PHF21A) | 100% |
| Intermediate risk progressive disease (II) | NETest score 7 (low PHF21A) | 97.5-100% |
| High risk progressive disease | NETest score 8 (low ZZZ3) | 100% |

Defining Clinically Relevant Genes—To further refine the scoring system, gene cluster expression was examined and algorithms were developed to capture the information. Individual gene clusters incorporate biological information that may augment the mathematically-derived MAARC-NET scoring systems. One focus may be given to literature-curated gene clusters which are included in TABLE 6.

TABLE 6

Genes included in each Cluster

| Cluster Name | Genes |
|---|---|
| Proliferome | Ki67, NAP1L1, NOL3, TECPR2 |
| Growth Factor Signalome | ARAF1, BRAF, KRAS, RAF1 |
| Metabolome | ATP6V1H, OAZ2, PANK2, PLD3 |
| Secretome I (General) | PNMA2, VMAT2 |
| Secretome II (Progressive) | PQBP1, TPH1 |
| Epigenome | MORF4L2, NAP1L1, PQBP1, RNF41, RSF1, SMARCD3, ZFHX3 |
| Apoptome | BNIP3L, WDFY3 |
| Plurome | COMMD9 |
| SSTRome | SSTR1, SSTR3, SSTR4, SSTR5 |

Figures 14A, 14B:
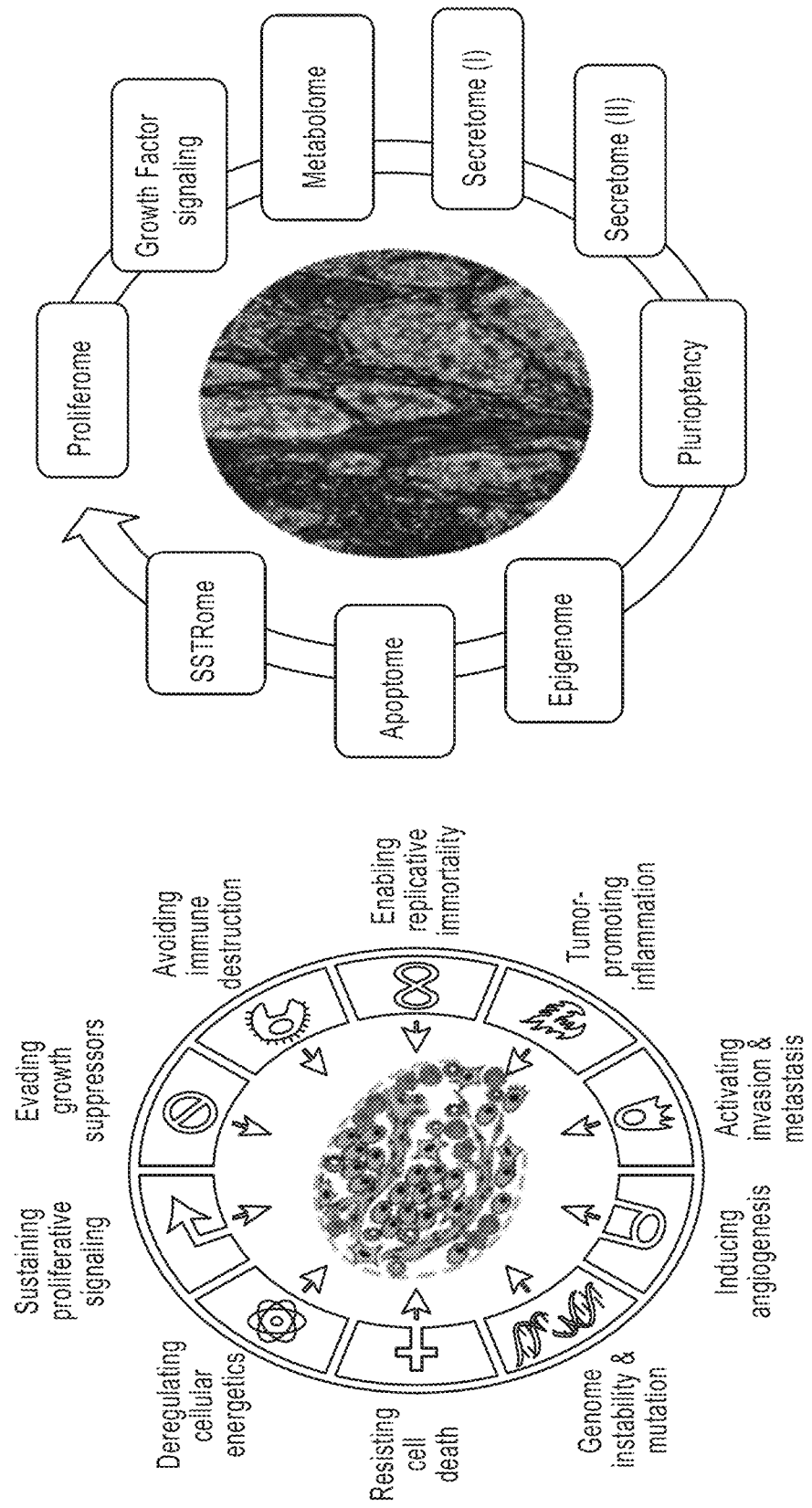
FIGS. 14A-14B are illustrations representing the Hallmarks of Neoplasia refocused on NETs.

With reference to FIG. 14A, the Hallmarks of Neoplasia are illustrated, including the delineation of tumor (adenocarcinoma)-derived hallmarks. With reference to FIG. 14B, the NET hallmarks based on the Hanahan and Weinberg classifications are illustrated.

Values for the nine clusters represented in FIGS. 14A-14B were derived from gene addition. In addition to the gene clusters, two algorithms were also assessed:

1) the "PDA" algorithm, which included a summation of the proliferome, signalome, secretome II, plurome and epigenome (the PDA algorithm is also referred to as Progressive Diagnostic I);

2) the "NDA" algorithm, which included expression of 15 genes associated with disease: these included ARAF1, BRAF, KRAS, RAF1, Ki67, NAP1L1, NOL3, GLT8D1, PLD3, PNMA2, VMAT2, TPH1, FZD7, MORF4L2 and ZFHX3 (the NDA algorithm is also referred to as Progressive Diagnostic II). Genes were summated and an averaged value was derived.

Figures 15A, 15B:
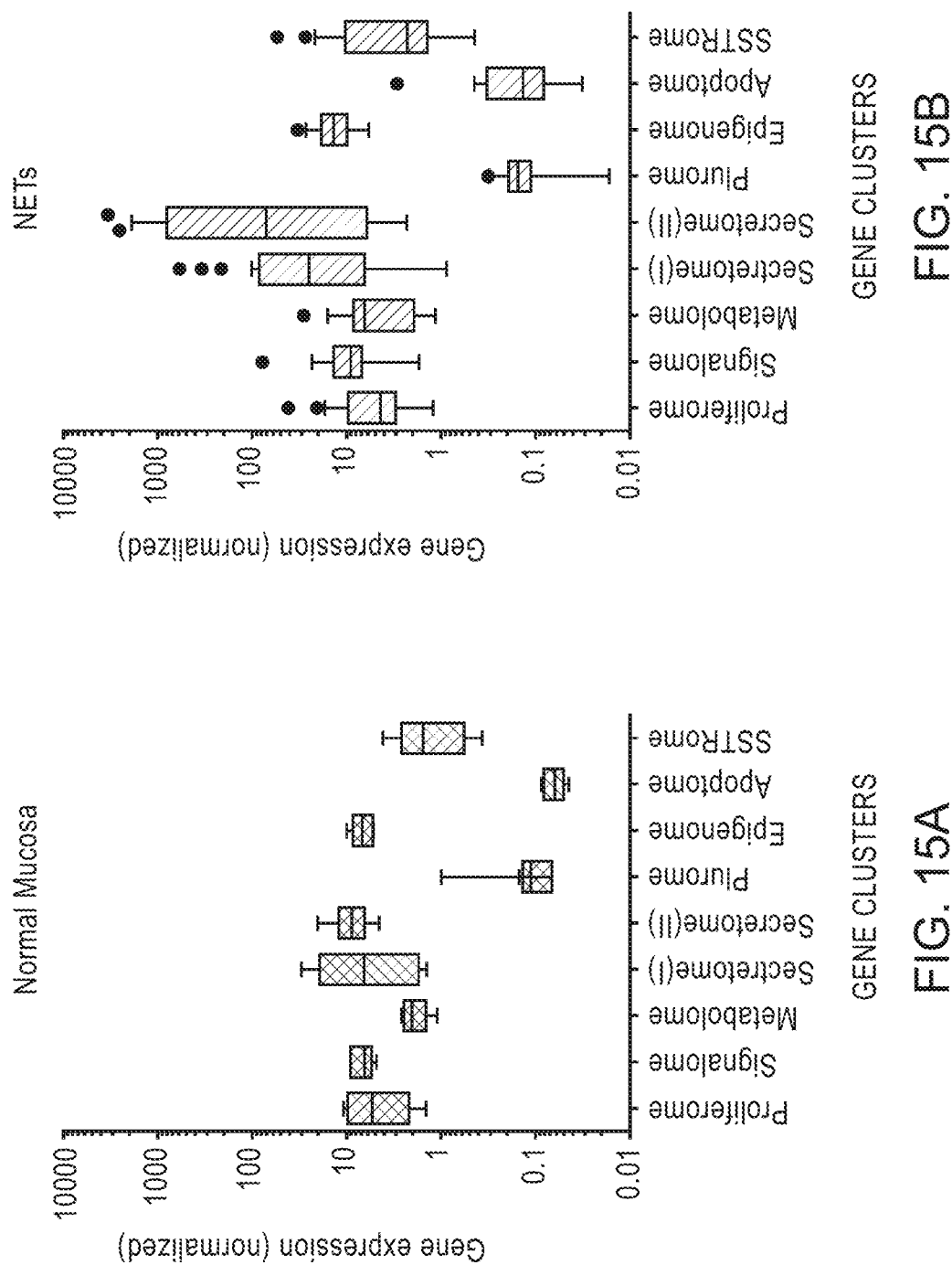
FIGS. 15A-15B are graphs showing normalized gene expression of gene clusters in (FIG. 15A) normal mucosa and (FIG. 15B) NETs.
Figure 16:
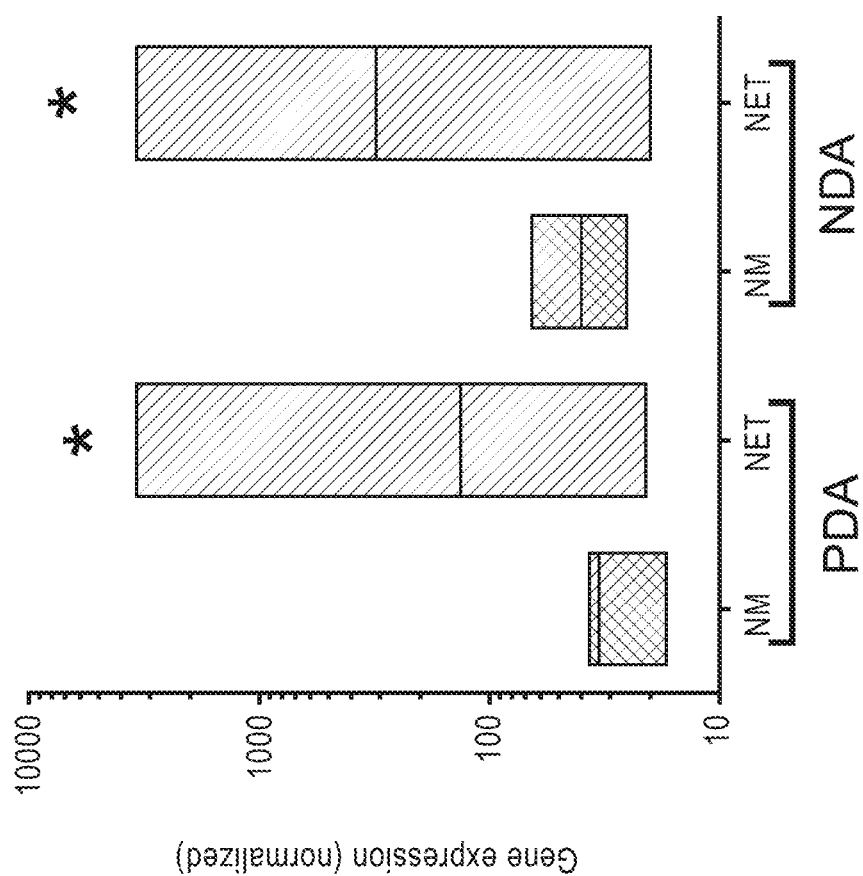
FIG. 16 is a graph of normalized gene expression as evaluated by the PDA and NDA algorithms in normal mucosa (NM) and NET.

Prior to assessing the value of the nine gene clusters and two algorithms in blood samples, their expression in NET tumor tissue was assessed to confirm that these were NET-relevant. With reference to FIGS. 15B and 15A, respectively, expression in 22 NETs may be compared to expression in normal mucosa (n=10). Assessment identified that seven of the nine clusters were specific to NETs (in comparison to normal mucosa). In particular, expression of the signalome, metabolome, secretome (I) and (II), epigenome, apoptome and SSTRome were elevated in NETs (p<0.05). Genes in the apoptome were decreased in NETs, while the proliferome was not different between NETs and normal mucosa. With respect to the algorithms, FIG. 16 shows that each of the PDA and NDA were significantly increased (p<0.05) in NET tumor tissue compared to normal mucosa.

Figures 17A, 17B, 17C:
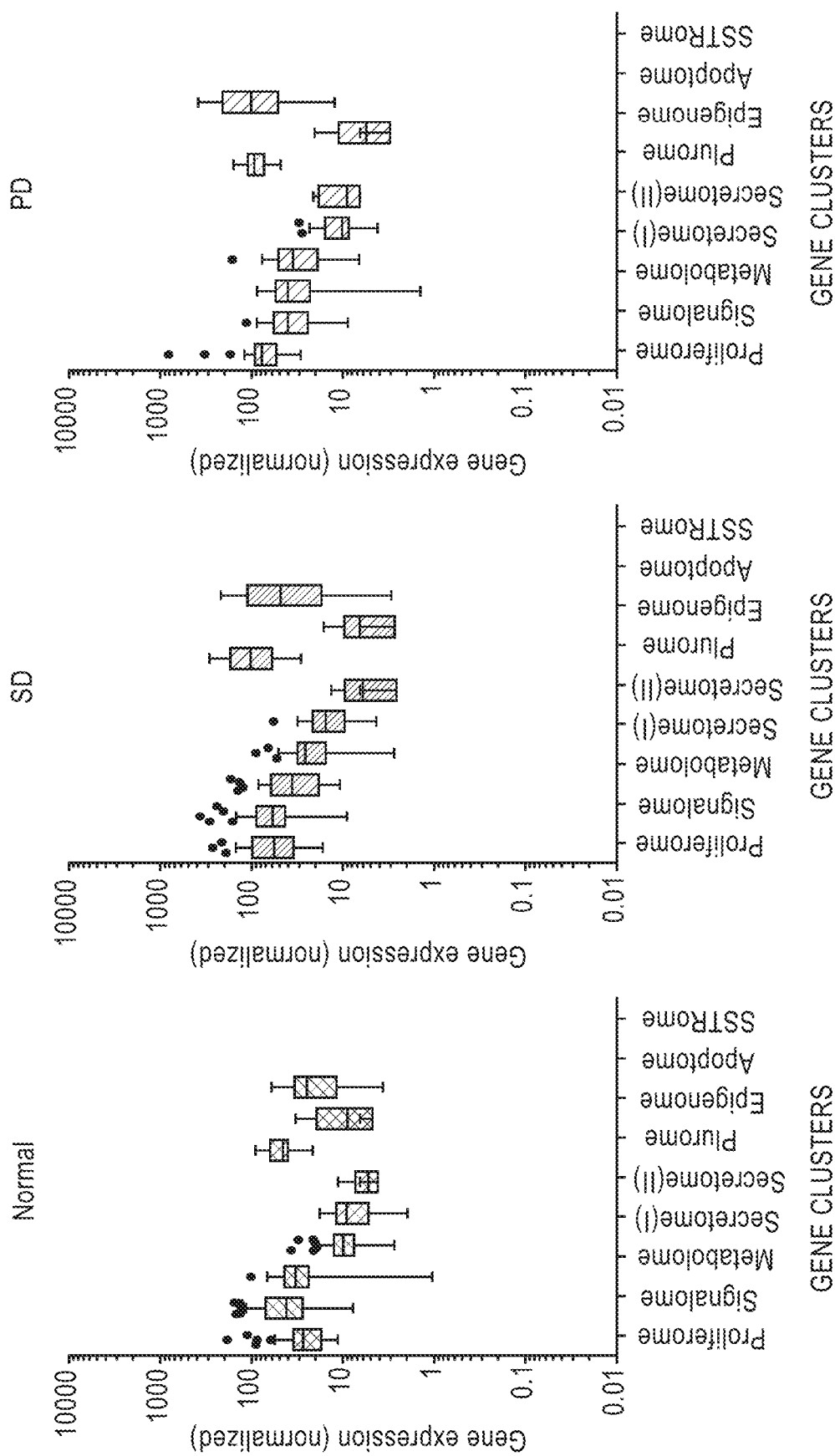
FIGS. 17A-17C are graphs of normalized gene expression in (FIG. 17A) normal mucosa, (FIG. 17B) a SD related gene cluster, and (FIG. 17C) a PD related gene cluster.

Thereafter, the expression of each of the clusters was assessed in blood samples. We examined the test (n=130) set and evaluated whether expression they were related to SD or PD. Significant differences were noted in gene expression between controls and SD/PD, as shown in FIGS. 17A-17C and TABLE 7.

TABLE 7

Gene Clusters and Clinical Outcome

| Cluster Name | Con vs SD | Con vs PD | SD vs PD |
|---|---|---|---|
| Proliferome | p < 0.05 | p < 0.05 | ns |
| Growth Factor Signalome | p < 0.05 | ns | p < 0.05 |
| Metabolome | ns | p < 0.05 | ns |
| Secretome I (General) | p < 0.05 | p < 0.05 | p < 0.05 |
| Secretome II (Progressive) | p < 0.05 | p < 0.05 | p < 0.05 |
| Epigenome | ns | p < 0.05 | p < 0.05 |
| Apoptome | p < 0.05 | p < 0.05 | ns |
| Plurome | p < 0.05 | p < 0.05 | ns |
| SSTRome | p < 0.05 | p < 0.05 | p < 0.05 | ns = not significant
Two-tailed Mann-Whitney U-test

These data demonstrate that gene clusters can be used to differentiate SD and PD from controls as well as identify differences between SD and PD.

Figure 18:
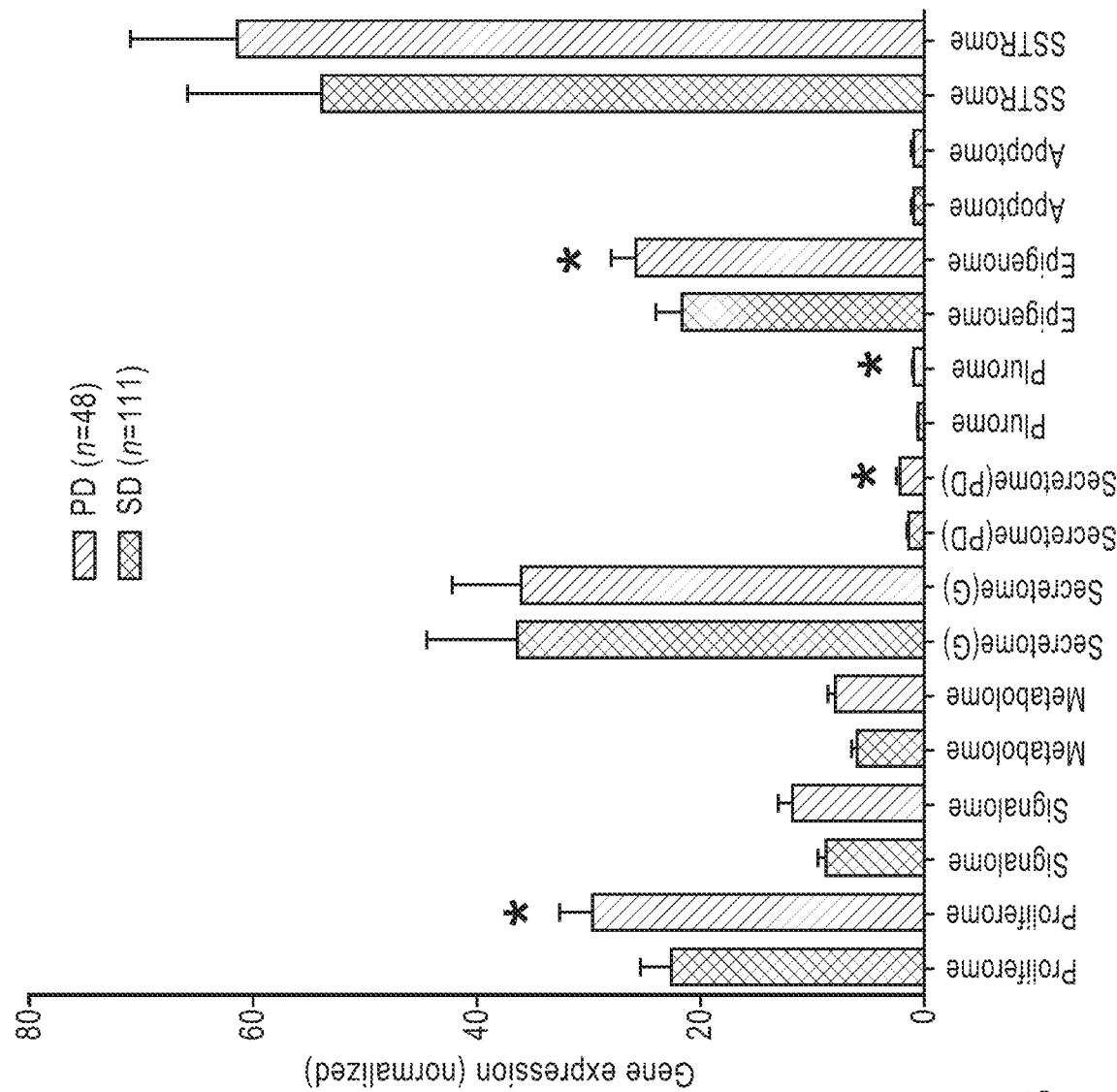
FIG. 18 is a graph of normalized gene expression in an independent test set, where the genes in PD and SD tumors were evaluated.

With reference to FIG. 18, gene cluster results were examined in the independent set (n=159), evaluating each of the clusters in SD vs PD. In the independent set, the proliferome, secretome (II), plurome and epigenome were significantly increased.

Figure 19B:
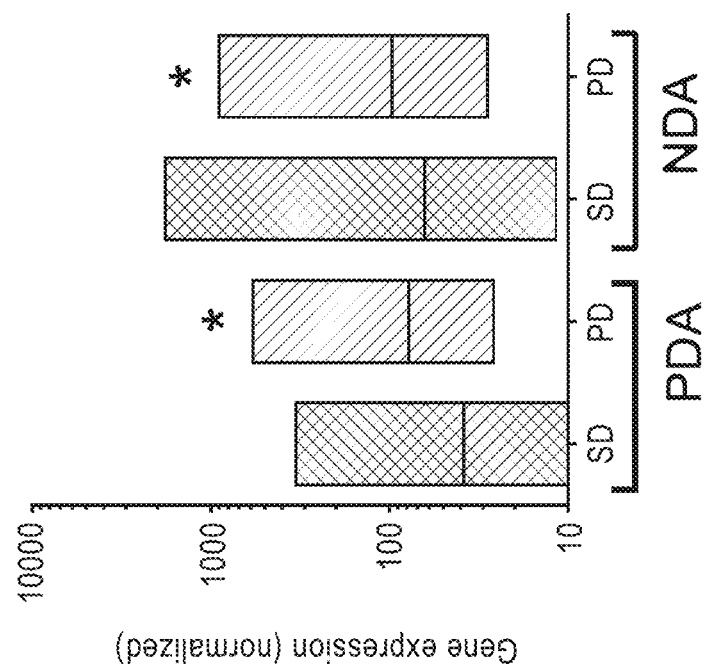
FIGS. 19A-19B are graphs showing normalized gene expression of PDA and NDA gene cluster algorithms in (FIG. 19A) the test set and (FIG. 19B) the independent set.
Figure 19A:
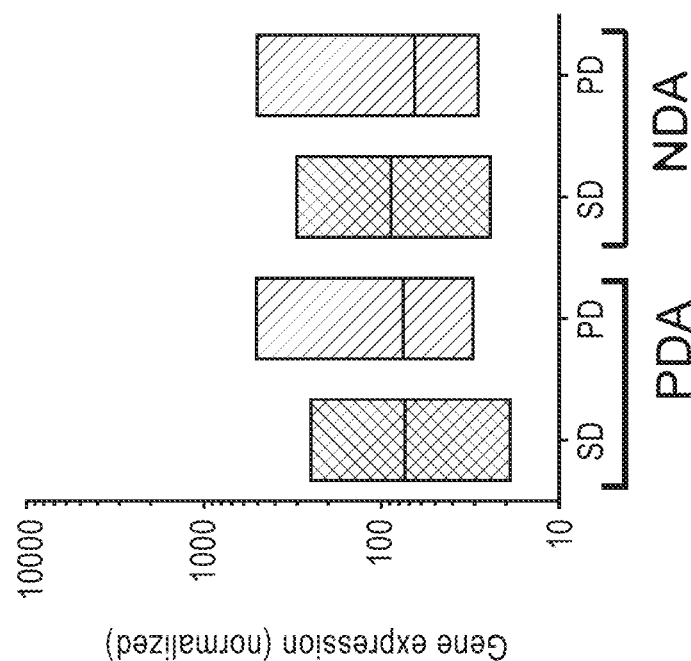

Next the PDA and NDA were evaluated in each of the two datasets (independent and test sets). With reference to FIG. 19A, no significant differences were identified between SD and PD for either of the two algorithms in the test set. With reference to FIG. 19B, each of the PDA and NDA were elevated in the independent set.

Next each of the algorithms were included in a combined set (test+independent: n=222) and their utility to predict SD versus PD was evaluated. With reference to FIG. 20A, both PDA and NDA were elevated in PD compared to SD in the combined sets. With reference to FIG. 20B, a ROC analysis identified the following parameters for PDA and NDA listed in TABLE 8.

TABLE 8

ROC Analysis Parameters, PDA and NDA in Combined Set

| | PDA | NDA |
|---|---|---|
| AUC | 0.72 ± 0.034 | 0.6 ± 0.038 |
| 95% CI | 0.652-0.785 | 0.525-0.675 |
| p-value | <0.0001 | 0.014 |
| ROC cut-off | 58 | 74 |

Two additional algorithms based on gene cluster expression differences in the test (TDA) and independent (IDA) set were evaluated. TDA included a summation of gene clusters significantly different between SD and PD in the test set.

These included TDA: Secretome (I), Plurome and SSTRome (the TDA algorithm is also referred to as Progressive Diagnostic III); and IDA: Proliferome, secretome (II), plurome and epigenome (the IDA algorithm is also referred to as Progressive Diagnostic IV).

Figure 21B:
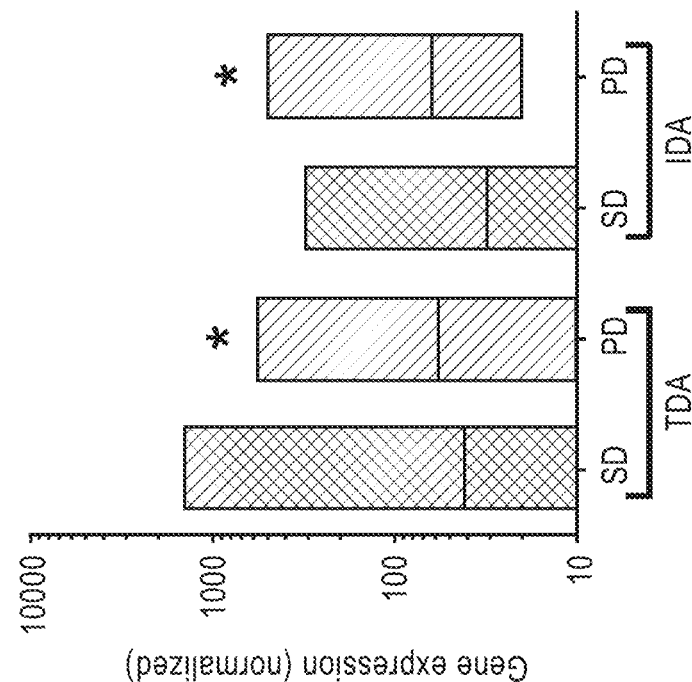
FIGS. 21A-21B are graphs showing normalized gene expression as evaluated by TDA and IDA gene cluster algorithms in (FIG. 21A) the test set, and (FIG. 21B) the independent set.
Figure 21A:
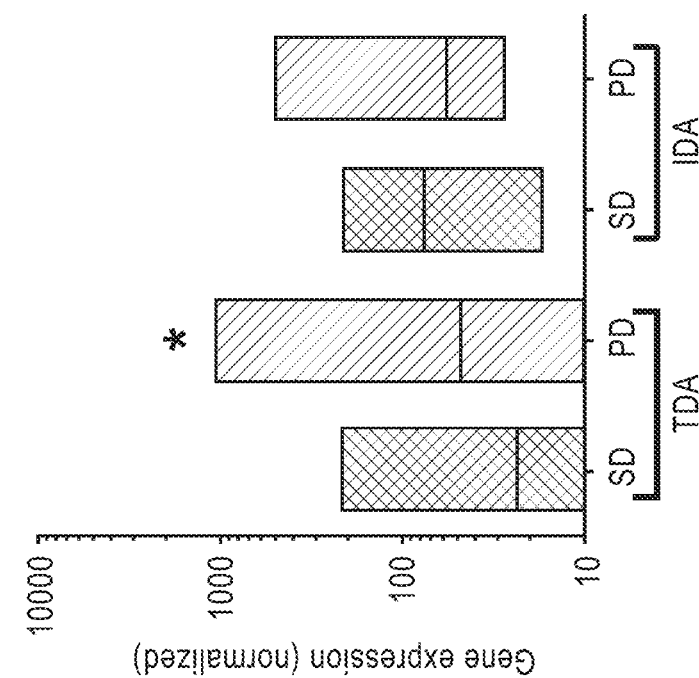

Each of the algorithms in the test set and independent set were evaluated. With reference to FIG. 21A, TDA was significantly elevated in PD compared to SD in the test set. With reference to FIG. 21B, both TDA and IDA algorithms were significantly elevated in the independent set.

Next, a ROC analyses with both algorithms in the combined dataset was performed. The ROC analysis identified the following parameters for TDA and IDA listed in TABLE 9.

TABLE 9

ROC Analysis Parameters, TDA and IDA in Combined Set

| | TDA | IDA |
|---|---|---|
| AUC | 0.62 ± 0.04 | 0.70 ± 0.034 |
| 95% CI | 0.542-0.698 | 0.637-0.770 |
| p-value | 0.003 | <0.001 |
| ROC-cut-off | >43 | >46 |

Figure 22B:
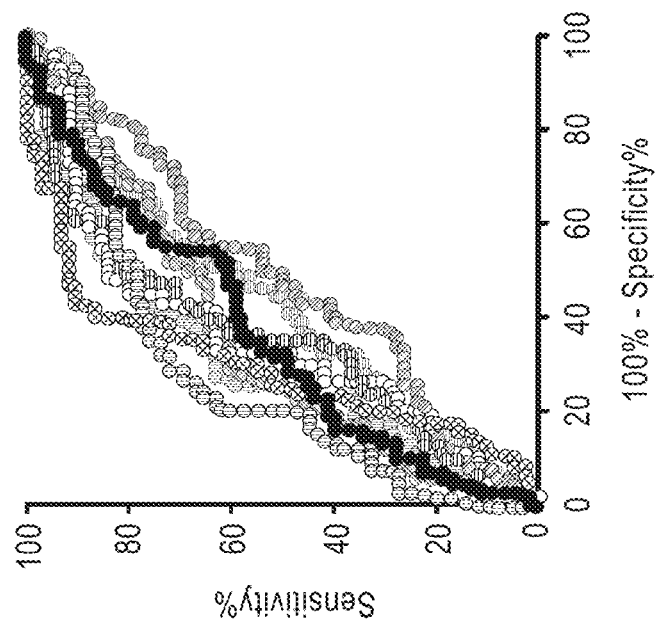
FIGS. 22A-22B are graphs showing a ROC analysis of (FIG. 22A) TDA and IDA for differentiating SD from PD, and (FIG. 22B) for each of the individual gene clusters.
Figure 22A:
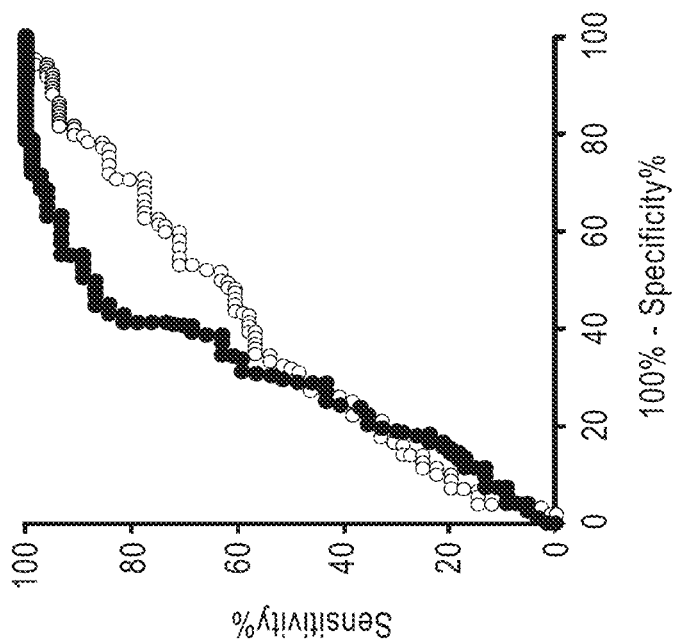

Algorithm-generated ROC curves of TDA and IDA for differentiating between SD and PD are shown in FIG. 22A. Algorithm-generated ROC curves for each of the clusters for differentiating between SD and PD are shown in FIG. 22B. The ROC curves in FIGS. 22A and 22B demonstrate that AUCs range from 0.51 (GF signalome) to 0.72 (plurome) for the differentiation of SD and PD.

Accordingly, individual gene cluster expression and algorithms that capture this information contain biologically relevant information that correlates with clinical observations. These provide the basis for defining clinically relevant MAARC-NET scoring systems.

Demonstration of Clinical Utility of NETEST Genes—
The clinical utility of NETest scores, as well as the scores from pertinent gene clusters and algorithms, will now be defined. An examination of how surgical removal of a NET altered the circulating gene signature was performed to demonstrate how the test will have utility as a measure of the completeness of surgical therapy.

Figure 23B:
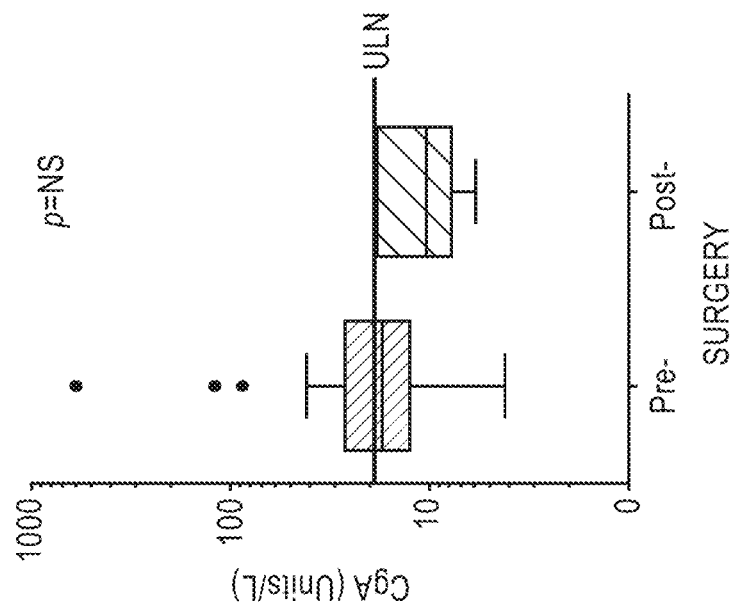
FIGS. 23A-23B are graphs showing the alternation in (FIG. 23A) NETest Score in Pre- and Post-Surgery conditions and (FIG. 23B) circulating Chromogranin A (CgA) levels in Pre- and Post-Surgery conditions.
Figure 23A:
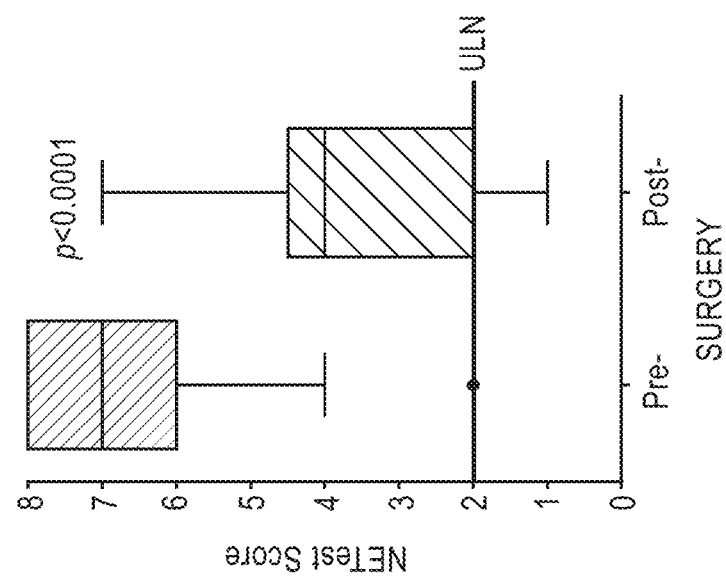

Parameters in 29 surgically treated patients prior to surgery and >1 month post-surgery was examined. As a group, MAARC-NET scores were significantly decreased (p<0.0001) from a mean of 6.58 f 1.48 to 3.65 f 1.6, as shown in in FIG. 23A. Chromogranin A (CgA), a gene used in a prior known single biomarker assay for NETs, was not significantly decreased (58.5±137.9 ng/ml vs. 55.25±154.8), as shown in FIG. 23B.

Figures 24A, 24B:
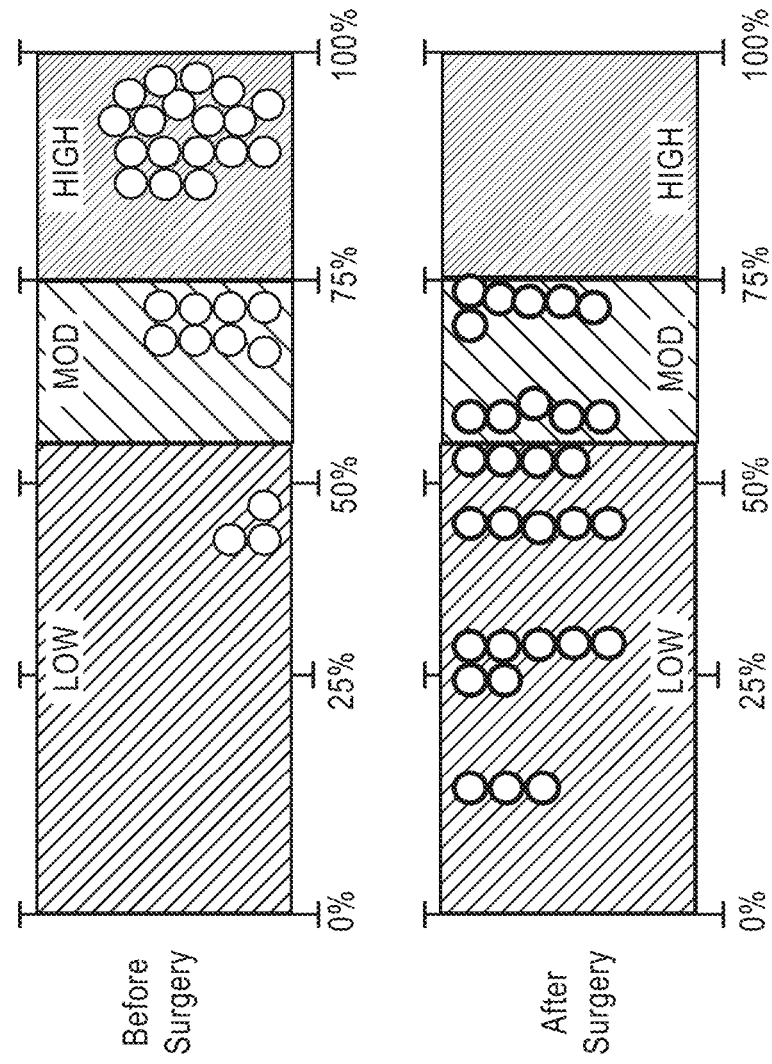
FIGS. 24A-24B are illustrations showing differences in the NETest nomogram in (FIG. 24A) pre-surgical therapy conditions and (FIG. 24B) post-surgical therapy conditions.

An examination of how NETest 1 performed, i.e. changes in NETest score pre- and post-surgical therapy, is included in FIGS. 24A-24B. Prior to surgery, 62% of patients were included in the high disease category; after surgery this was 0% ($\chi^2$=24, p=5×10$^{-8}$).

An alternative assessment of how surgery affected disease status is provided by the percentage changes in surgical approaches—no evidence of residual disease (R0) versus evidence of residual disease including metastases. With reference to FIG. 25A, levels for the MAARC-NET score were significantly decreased (p<0.003) in the R0 group (complete resection) compared to the R1/R2 group (incomplete resection).

Figure 26A:
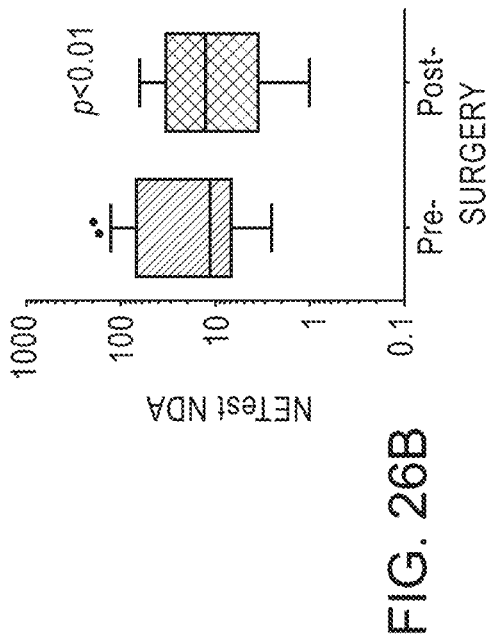
FIGS. 26A-26D are graphs showing the difference in NETest score for gene-derived algorithms, (FIG. 26A) PDA, (FIG. 26B) NDA, (FIG. 26C) TDA, and (FIG. 26D) IDA, in pre- and post-surgery conditions.
Figure 26B:
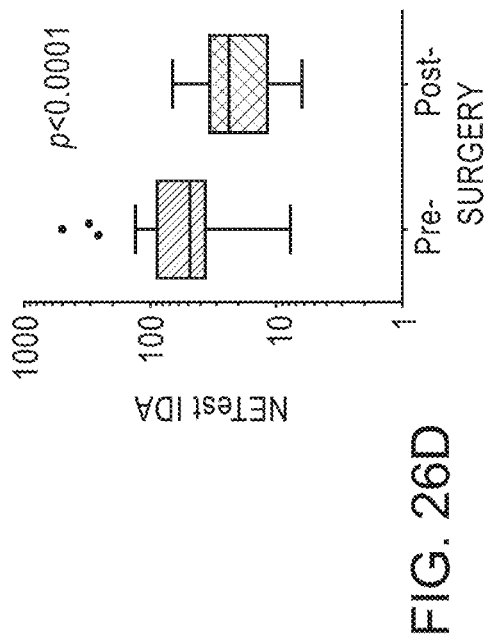
Figure 26C:
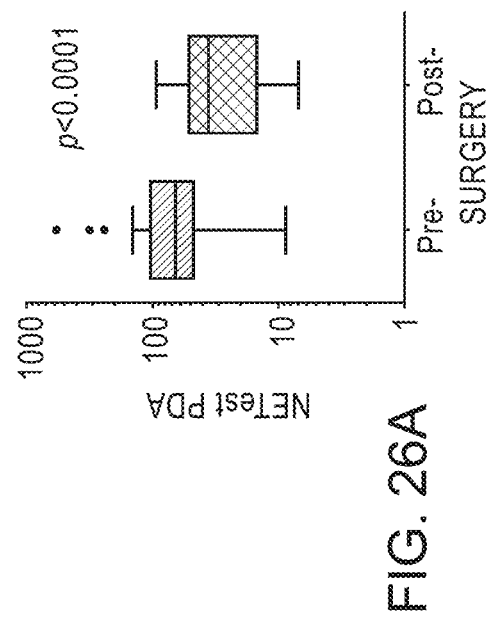
Figure 26D:
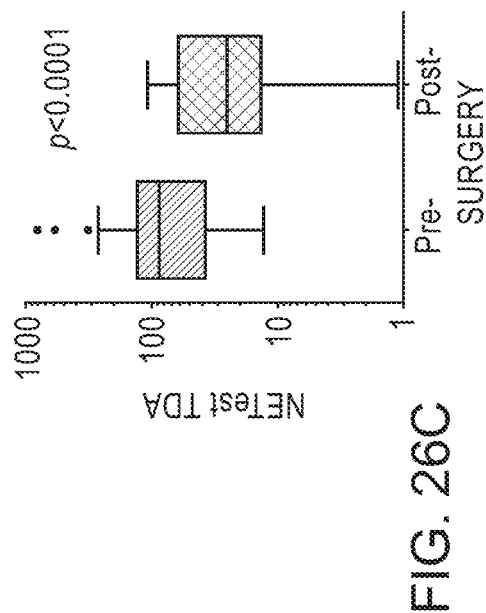

To better define the role of surgery each of the four algorithms were examined. Significant decreases were identified (post-surgery) in PDA (99.3±21 vs. 41.1±7.5, p<0.0001; FIG. 26A), NDA (45.8±10.3 vs. 29.6±7.8, p<0.01; FIG. 26B), TDA (133.3±32.3 vs. 43.8±9.3, p<0.0001; FIG. 26C) and IDA (86.1±19.3 vs. 34.1±7.2, p<0.0001; FIG. 26D).

With reference to FIGS. 27A-27I, an examination of individual clusters identified significant decreases in the SSTRome, proliferome, GF signalome, metabolome, secretome I/II and the epigenome pre- and post-surgery.

With reference to TABLE 10, surgical removal of the tumor tissue was associated with decreases in circulating gene expression to levels not different to or below ROC cut-off values for SD for each of the four algorithms and for 6 of the 9 gene clusters.

TABLE 10

Relationship Between Surgical Excision, Gene Clusters and Each of the Algorithms

| Algorithm/Cluster | p-value | Change | Pre-surgery | Post-surgery | ROC for SD |
|---|---|---|---|---|---|
| NDA | 0.009 | ↓ | 45 | 30 | <74 |
| PDA | <0.0001 | ↓ | 99 | 41 | <58 |
| TDA | <0.0001 | ↓ | 133 | 44 | <74 |
| IDA | <0.0001 | ↓ | 86 | 34 | <46 |
| SSTRome | <0.0001 | ↓ | 93 | 23 | <25.5 |
| Proliferome | <0.0001 | ↓ | 34 | 15 | <20 |
| GF Signalome | 0.009 | ↓ | 14.8 | 8 | <9 |
| Metabolome | 0.004 | ↓ | 8.2 | 6.8 | <6.5 |
| Secretome (I) | 0.004 | ↓ | 39.2 | 19.5 | <11 |
| Secretome (II) | 0.04 | ↓ | 2.4 | 0.85 | <1.6 |
| Plurome | NS | ↔ | 0.8 | 0.8 | <0.9 |
| Epigenome | 0.005 | ↓ | 48.7 | 17.7 | <2.3 |
| Apoptome | NS | ↔ | 0.72 | 0.84 | >0.5 |

All patients who had surgery can be considered as exhibiting progressive/active disease. Following surgery, the scores or algorithms were indicative of progressive disease in 3-7 of the twenty-nine patients (10-24%) depending on the algorithm used.

Surgery significantly reduced the circulating tumor signature and can provide evidence for the degree both of tumor removal as well as for evidence of residual active disease.

The clinical utility of the test therefore is defined by the examination of scores, algorithms and clusters and evaluation in comparison to pre-surgical bloods. Evidence of elevated expression of e.g., PDA or proliferome in post-surgical samples is indicative of residual progressive (highly active disease).

Figure 28:
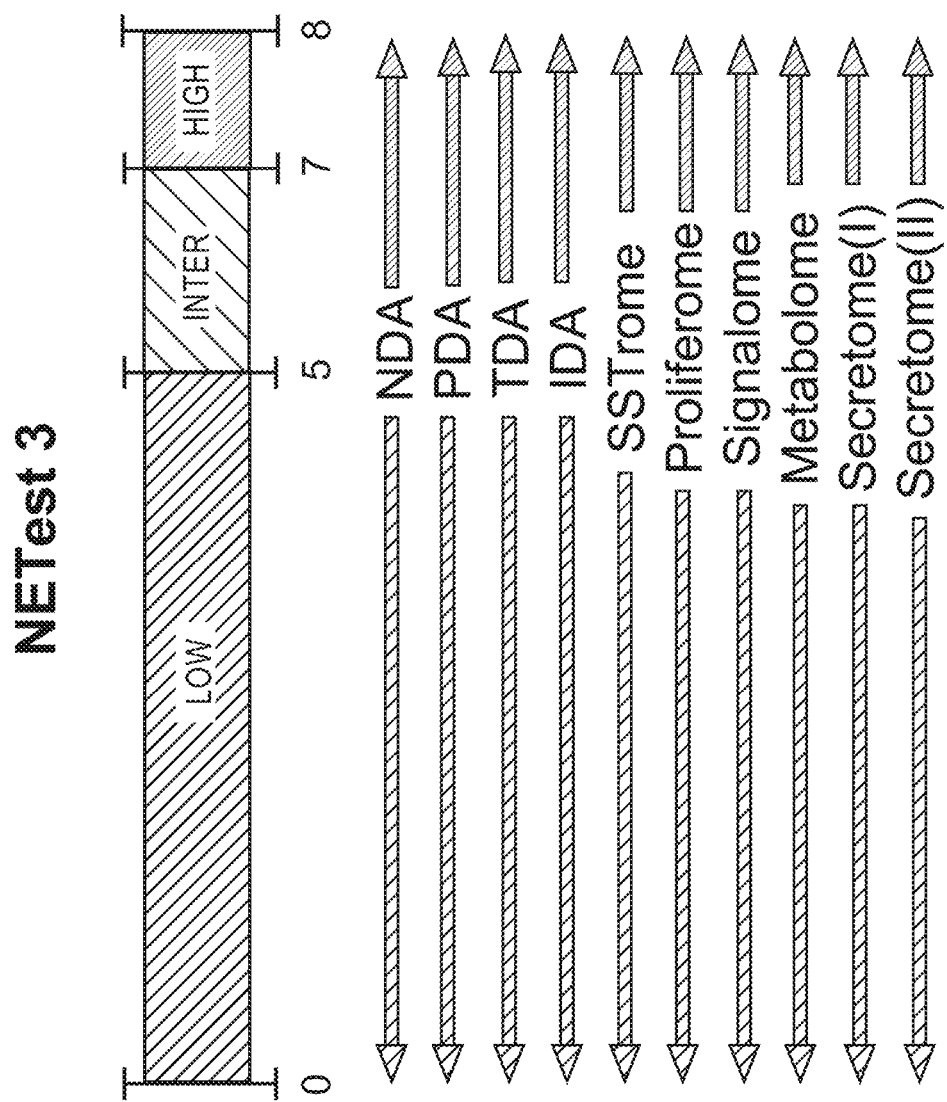
FIG. 28 is a nomogram of NETest 3 with the inclusion of surgically-relevant algorithms and gene clusters.

With reference to FIG. 28, a NETest 3 nomogram is illustrated with the inclusion of surgically-relevant algorithms and gene clusters. A combination score, as well as alterations in gene clusters e.g., a significant increase in the proliferome, will be indicative of disease regrowth following surgery. Of note, is that while post-operative imaging identified disease in n=1 (10%) of the R0 patients, elevated gene scores were evident in 6 (60%) at 1 month. Subsequently, two R0 individuals developed positive imaging at 6 months.

Effect of Standard Drug Therapies on Circulating NET Signature—The efficacy of a standard pharmacological therapy for NETs, somatostatin (used to treat>80% of patients), was evaluated on the circulating NET signature. Signatures were evaluated in patients treated with a somatostatin analog who were considered as either SD (n=63) or PD (n=26) by imaging and best clinical judgment. Those patients who were SD on somatostatin analogs were considered to be stable-treated patients, while those patients who were PD on somatostatin analogs were considered to be failing therapy.

Figure 29B:
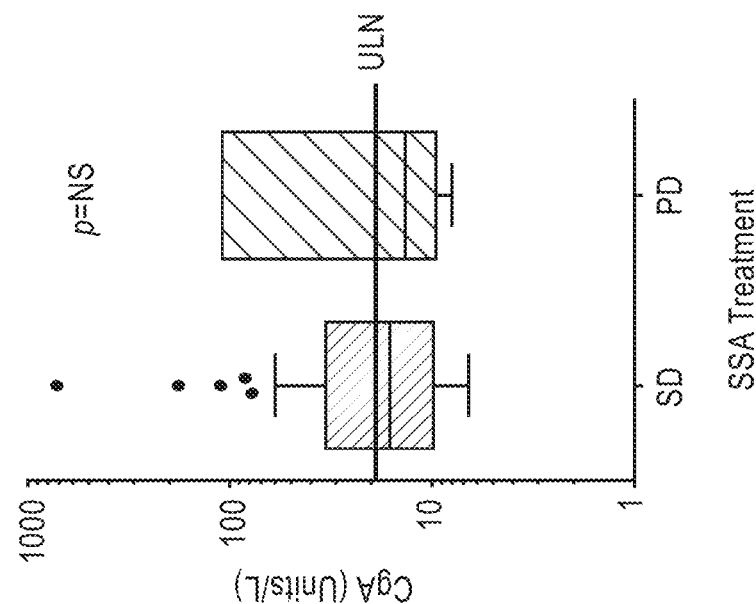
FIGS. 29A-29B are graphs showing the differences in (FIG. 29A) NETest score and (FIG. 29B) circulating CgA levels, each in in stable disease (SD) conditions and somatostatin analog (SSA) treatment failure (equivalent of PD conditions).
Figure 29A:
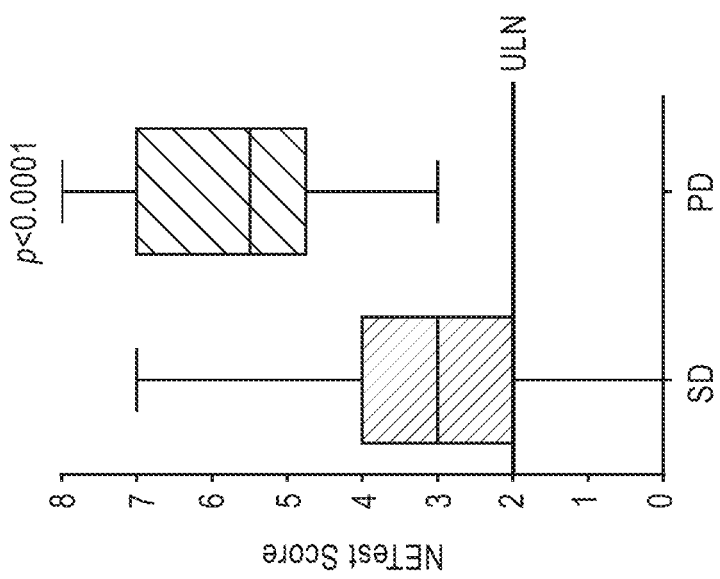

With reference to FIG. 29A, MAARC-NET scores were significantly lower in the SD group than those failing therapy: 3.33±0.21 vs 5.77±0.3 (p<0.001). With reference to FIG. 29B, Chromogranin A was not significantly different in the two groups (44.7±17.2 ng/ml vs. 102.4±58.7).

An assessment of the algorithms demonstrated significant differences in each of them in SD compared to PD. Specifically, PDA (62.8±11.4 vs. 153.9±36.2, p<0.002; FIG. 30A), NDA (6±0.6 vs. 13.5±3, p<0.03; FIG. 30B), TDA (56.8±7.4 vs. 154±37.2, p<0.02; FIG. 30C) and IDA (51.7±11.1 vs. 140.5±36, p<0.0005; FIG. 30D).

With reference to FIGS. 31A-31I, examination of individual clusters identified that the SSTRome, proliferome, secretome II, plurome and the epigenome were significantly lower in the SD group relative to the PD group.

These data demonstrate that patients who exhibit progressive disease despite somatostatin analog (SSA) therapy exhibit increases in the MAARC-NET score, as well as each of the four algorithms and specific gene clusters including an increase in proliferation, as well as the epigenome. One mechanism to evaluate whether the SSA treatment is effective therefore is to evaluate whether scores for these parameters alter. However, given the overlap in each of these parameters between the SD and PD groups, it would be helpful to better define the PD group. To do this, the expression may be compared of the circulating signature in those failing therapy to that in controls. The hypothesis behind this approach was that an effective therapy (i.e. SD) would normalize the signatures. The corollary is that PD will be significantly different to normal. To establish this, ROC analyses were used to examine normal circulating transcripts and compared to PD. All four algorithms were examined as well as the gene clusters.

Figures 32A, 32B:
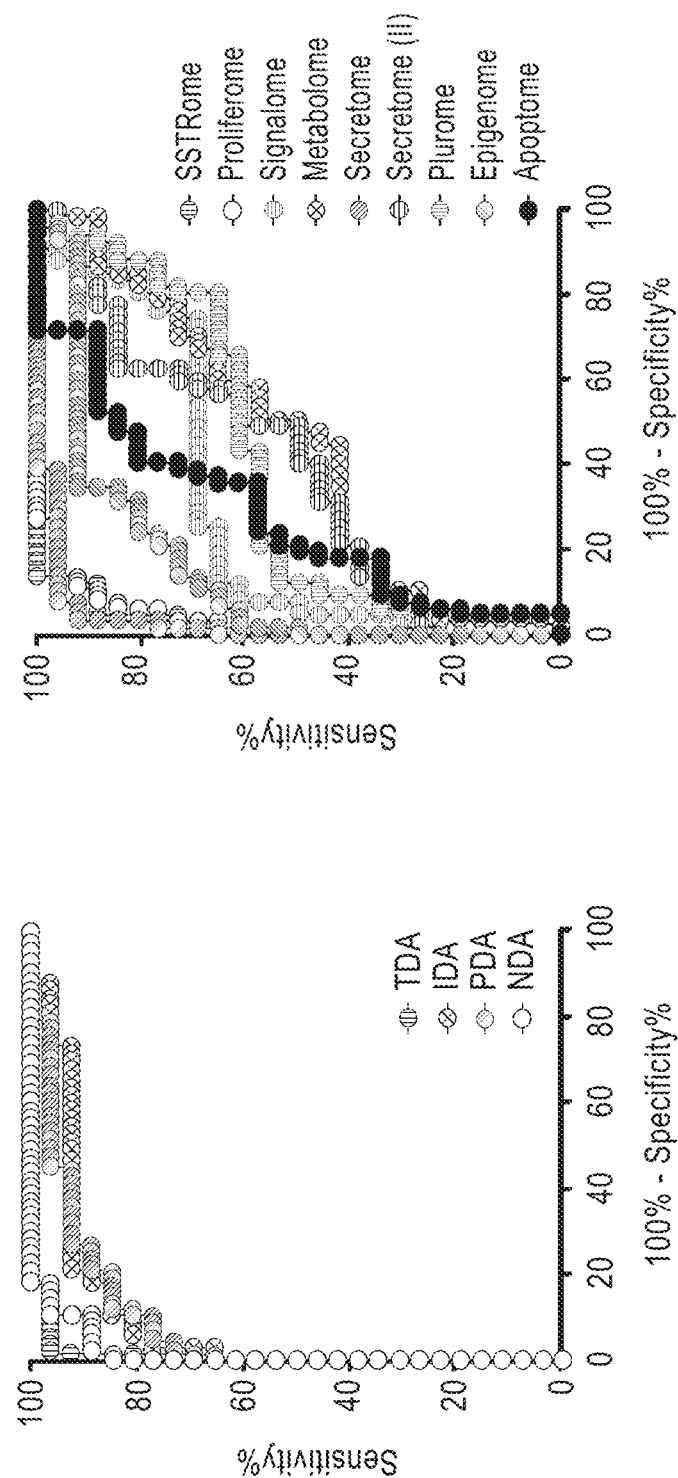
FIGS. 32A-32B are graphs showing a ROC analysis according to (FIG. 32A) gene-derived cluster algorithms and (FIG. 32B) gene clusters for differentiating treatment failure (equivalent of PD conditions) from controls.

With reference to FIGS. 32A-32B, analysis of the data identified that algorithms (FIG. 32A) and selected clusters (FIG. 32B) differentiated controls from PD treated with SSAs. Data for the individual clusters are included in TABLE 11.

TABLE 11

Relationship between Gene Clusters and each of the Algorithms for those Failing SSA Therapy and Controls

| Algorithm/Cluster | AUC | 95% CI | p-value | ROC for PD |
|---|---|---|---|---|
| NDA | 0.98 ± 0.01 | 0.965-1.00 | <0.0001 | >3 |
| PDA | 0.92 ± 0.04 | 0.851-0.994 | <0.0001 | >40 |
| TDA | 0.99 ± 0.01 | 0.975-1.01 | <0.0001 | >29 |
| IDA | 0.91 ± 0.04 | 0.828-0.998 | <0.0001 | >31 |
| SSTRome | 0.98 ± 0.01 | 0.95-1 | <0.0001 | >22 |
| Proliferome | 0.97 ± 0.02 | 0.94-1 | <0.0001 | >14 |
| GF Signalome | 0.71 ± 0.07 | 0.564-0.855 | <0.002 | >5 |
| Metabolome | 0.56 ± 0.07 | 0.41-0.7 | NS | <8 |
| Secretome (I) | 0.98 ± 0.02 | 0.944-1 | <0.0001 | >4 |
| Secretome (II) | 0.62 ± 0.07 | 0.486-0.759 | NS | >1.6 |
| Plurome | 0.61 ± 0.08 | 0.454-0.763 | NS | <0.7 |
| Epigenome | 0.86 ± 0.05 | 0.756-0.962 | <0.0001 | >16 |
| Apoptome | 0.73 ± 0.06 | 0.618-0.834 | <0.001 | <0.95 |

Based on the data in TABLE 11, NDA and TDA were examined as well as the SSTRome, Proliferome, and Secretome (I) in the SD cases to evaluate whether these parameters correlated with clinical assessments of therapeutic efficacy.

Figure 33B:
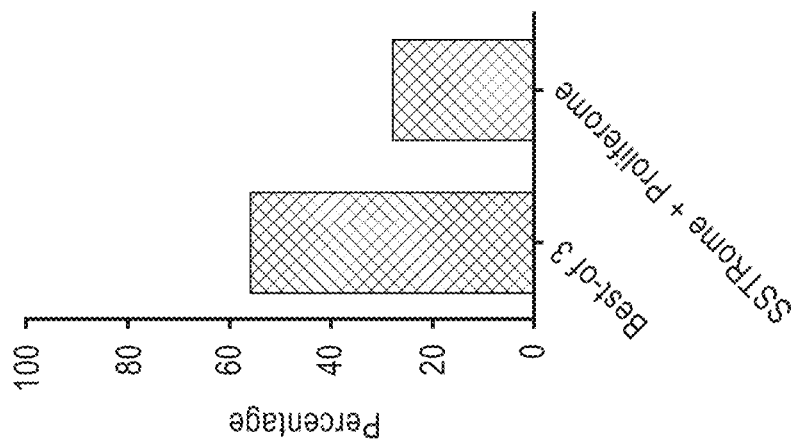
FIGS. 33A-33B are graphs showing the percentage of correct calls for each of (FIG. 33A) the gene-derived cluster algorithms and clusters for defining treatment failure in patients categorized as SD and (FIG. 33B) a Best-of-3 outperformed by a combination of SSTRome and Proliferome.
Figure 33A:
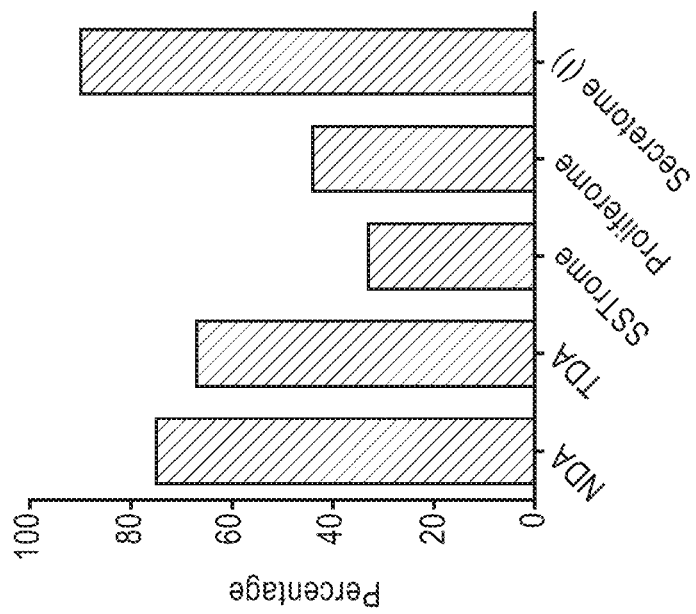
Figure 34:
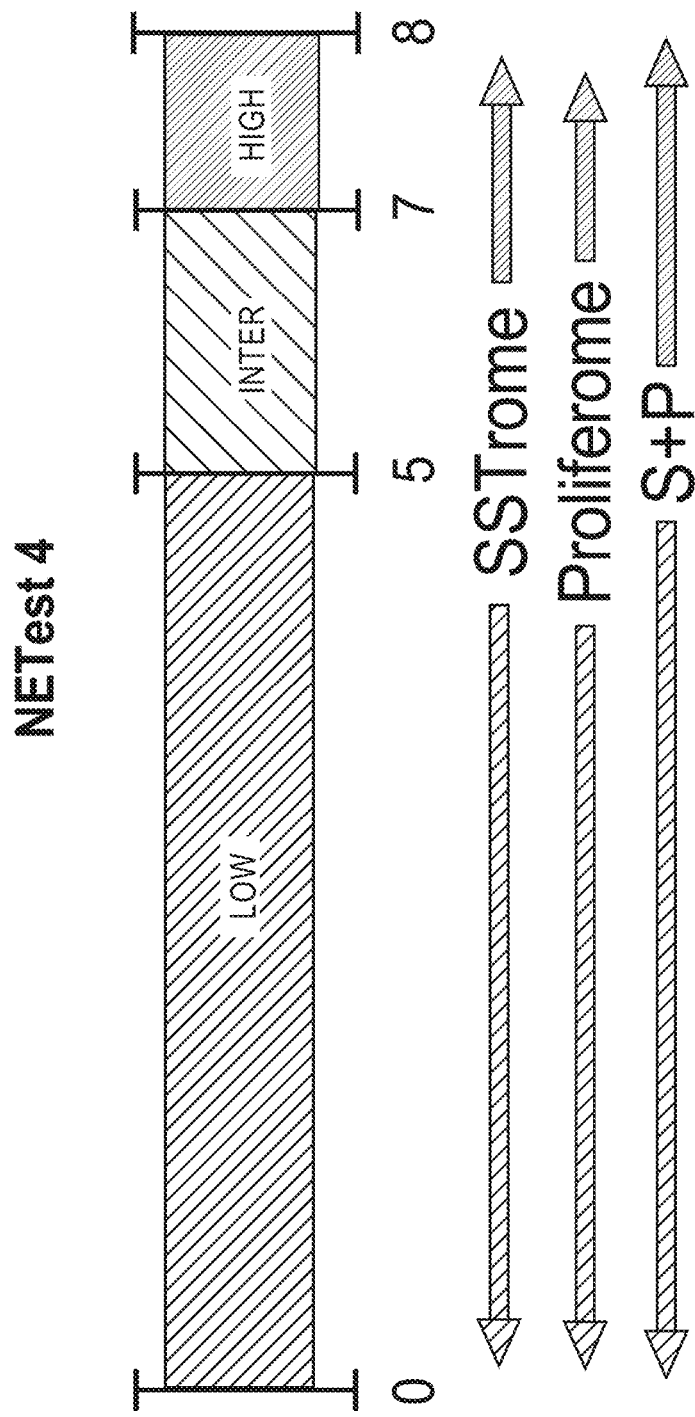
FIG. 34 is a nomogram for somatostatin analog treated patients including the mathematically-derived score as well as the SSTRome, Proliferome, and their combination.

An assessment of individual algorithms or gene clusters identified that samples would be categorized as exhibiting disease in 33-75% of cases (FIG. 33A). In comparison to a best of 3 score (56%) a combination of elevations in the SSTRome and Proliferome resulted in the lowest number of cases (28%) predicted as exhibiting progressive disease (FIG. 33B). With reference to FIG. 34, the nomogram for somatostatin analog treated patients, named "NETest 4," therefore includes the MAARC-NET score as well as the SSTRome, proliferome and their combination.

Utility of NETEST and Gene Expression for the Prediction of Somatostatin Analog Efficacy—To evaluate the utility of the NETest in therapy, the relationship between SSAs and clinically defined outcomes (per RECIST criteria) were evaluated. Samples were collected both pre-therapy as well as monthly in twenty-eight patients. Imaging was available to stage and categorize disease patterns pre- and during therapy (up to 12 months follow-up). In this prospective sample set, SSA resulted in a significant reduction in the number of patients with progressive disease (FIG. 35A).

Scores were also determined in blood samples collected prior to as well as monthly during SSA treatment to evaluate whether early alterations were predictive of outcome, i.e., response to therapy.

Figure 35B:
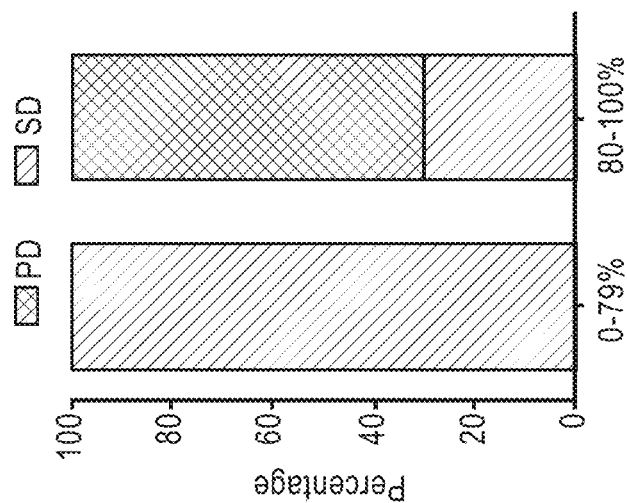
FIGS. 35A-35B are graphs that demonstrate therapeutic efficacy of SSAs and the proportion of patients with low/high NETest scores that developed disease recurrence.
Figure 35A:
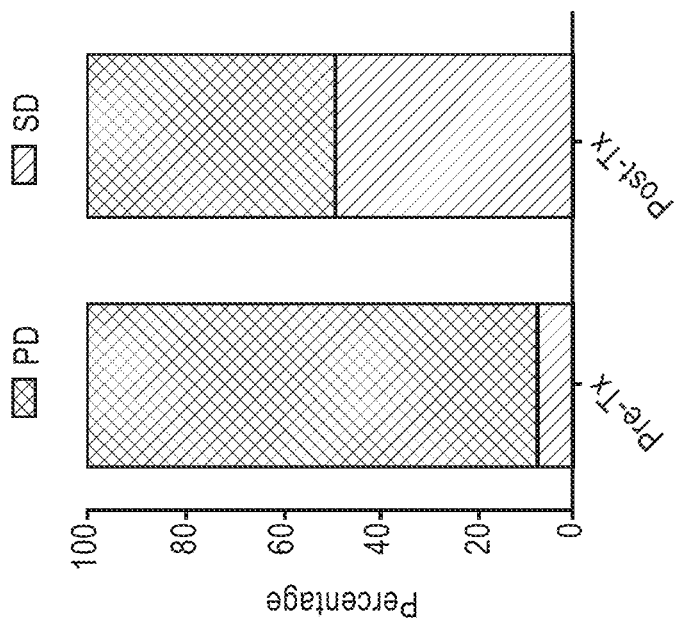

With reference to FIG. 35B, the results identify that elevated NETest scores (80-100% activity) measured at any time point during therapy were predictive of therapeutic responsiveness. With reference to FIG. 36A, a significant rise in the NETest (80-100%) occurred from 48-252 days (mean=105 days) prior to the detection of clinically significant disease (PD). The mean time for CgA was 70 days (range: 0-196 days). The NETest was more informative, occurring at an earlier time (p=0.04), and in more patients (high activity was noted in 100%) than CgA (57% exhibited>25% elevation, p=0.016).

Figure 36B:
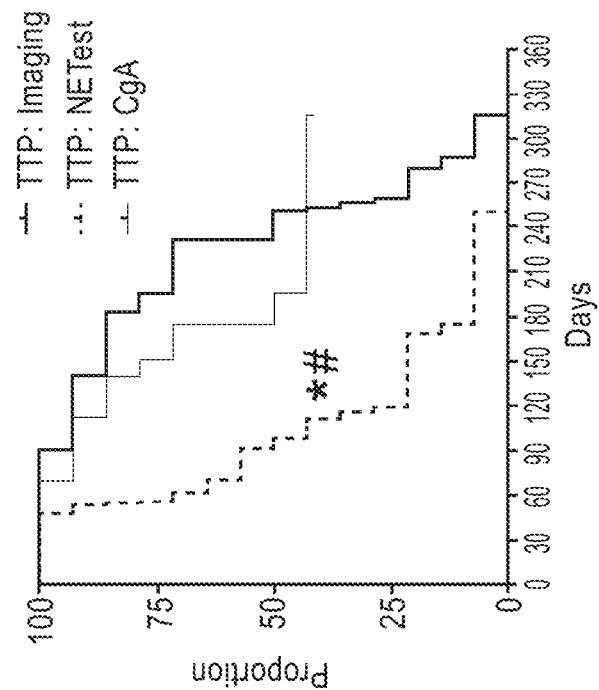
FIGS. 36A-36B are graphs that demonstrate the time point when either the NETest was elevated (>80%) or CgA was abnormal prior to the development of image positive disease recurrence as well as the times that these events occurred prior to image-positive disease recurrence.
Figure 36A:
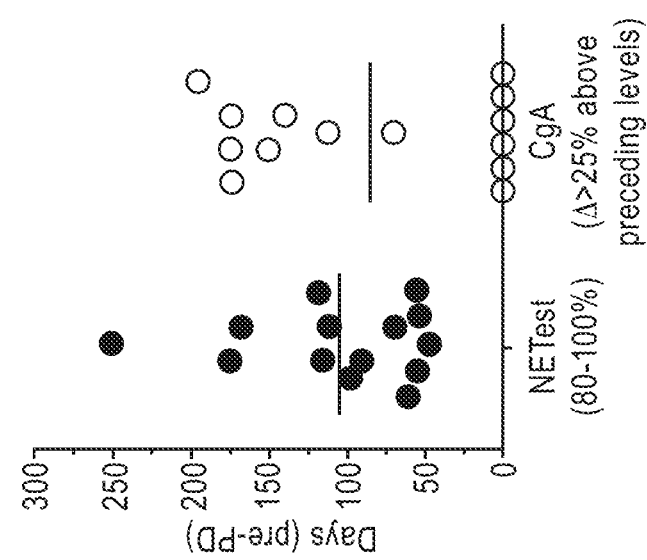

With reference to FIG. 36B, the elevation in NETest (80-100% score) occurred at a significantly earlier time (94.5 days) than image-identifiable disease progression (241 days) in the 14 patients (*p<0.0001, Chi$^2$=19). A similar analysis for CgA identified that this was not different to image-based assessment (FIG. 36B, 185.5 days vs. 241 days). CgA alterations occurred significantly later than the NETest (p=0.002, Chi$^2$=13.6).

Utility of NETEST and Gene Expression for the Prediction of Disease Recurrence—Utility of NETEST To evaluate the utility of the NETest disease recurrence, the relationship between the NETest and clinically defined outcomes (per RECIST criteria) was evaluated in a long-term prospective study. Samples were collected both pre-therapy as well as at intervals up to five years in thirty four patients. Imaging was available to stage and categorize disease patterns pre- and during therapy (up to 65 months follow-up).

Figure 37B:
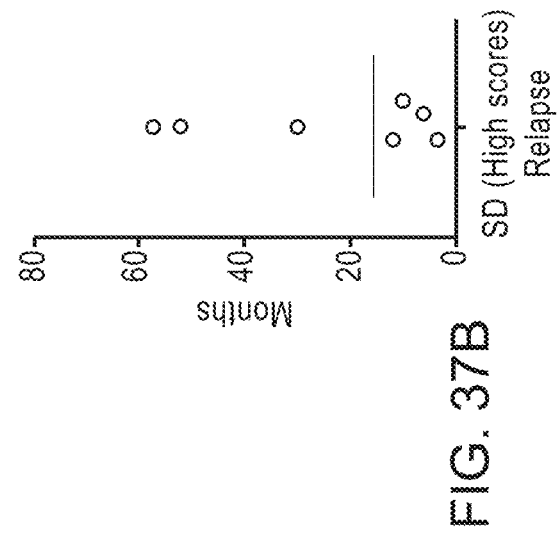
FIGS. 37A-37D are graphs that demonstrate the NETest scores prior to long-term follow up (FIG. 37A), and the times to relapse in patients with elevated scores (FIGS. 37B, 37D) or disease-free time (FIG. 37C).
Figure 37D:
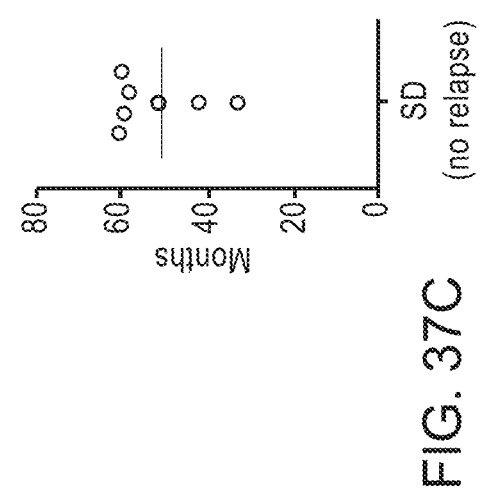
Figure 37A:
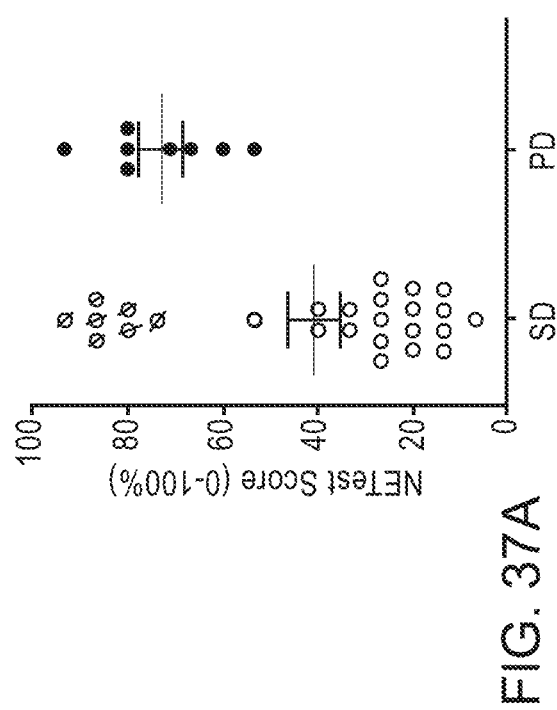
Figure 37C:
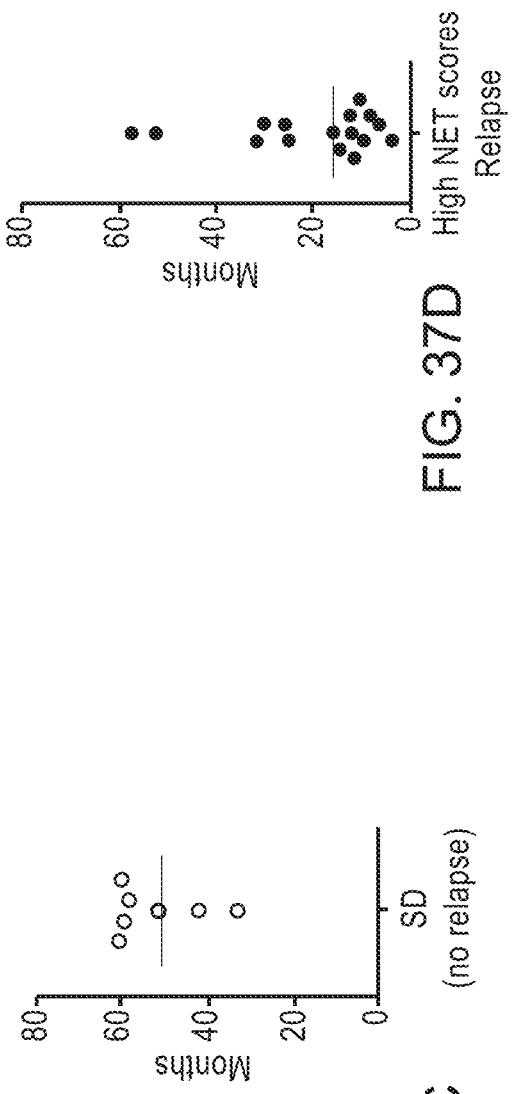

In this prospective sample set, the initial NETest scores were significantly elevated in the PD patients (median: 75%, range 53-94%) compared to the SD patients (median: 26%, range 7-94%; p=0.01) (FIG. 37A). Eight SD patients had levels>40%. Of these 7 developed disease recurrence in a median of 12.2 months (range 3.6-57.7; FIG. 37B). With reference to FIG. 37C, seven of the initial SD patients (with low NETest scores) did not develop recurrent disease. The median follow-up time was 58 months (range: 32-64).

Sixteen events of progressive disease were identified over the time course. Each was associated with elevated NETest (scores>80%). With reference to FIG. 37D, the median time to progression for patients with elevated scores was 13.4 months (range: 3.6-57).

Overall, 23/24 events where the NETest was elevated was associated with development of disease recurrence in median ~13 months. Seven of seven with consistently low scores were disease free (up to 5 years). The accuracy of the test was 97%.

Utility of NET Genes as Surrogate Measure of Tumor Proliferation and Imaging—The utility of NETest genes as well as clusters of genes to function as surrogate markers of histopathological and imaging parameters was evaluated. A particular focus was placed on the Ki-67 index (a marker of tumor proliferation) and on somatostatin-based imaging e.g., $^{68}$Ga-PET. This was undertaken to demonstrate that the NETest and elements thereof could have clinical utility as adjuncts for standard clinical measures. As an example, Ki-67 measurements are tissue based and therefore are invasive. Demonstrating a blood-derived correlate would provide a real-time measure of tumor growth without the need for a biopsy.

These analyses were conducted in two separate datasets: Dataset 1 (n=28) and Dataset 2 (n=22). Dataset 1 included patients who were collected for therapeutic intervention, namely peptide receptor radionucleotide therapy (PRRT). Dataset 2 included patients who exhibited stable disease and were undergoing routine follow-up.

Figure 38A:
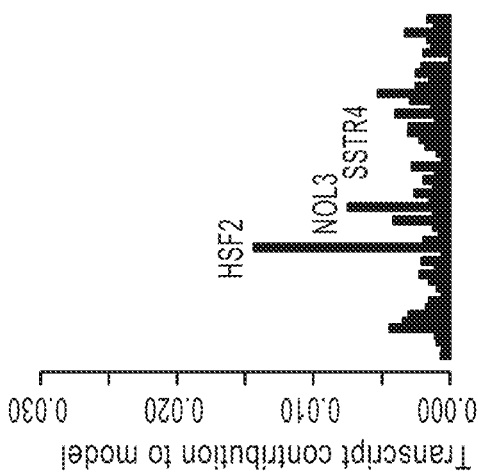
FIGS. 38A-38F are graphs including predicted Ki67 index versus Ki67 index in (FIGS. 38A-38B) SSTRome, (FIGS. 38C-38E) All genes, and (FIGS. 38D-38F) high relevant genes (KRAS, SSTR4, and VPS13C).
Figure 38B:
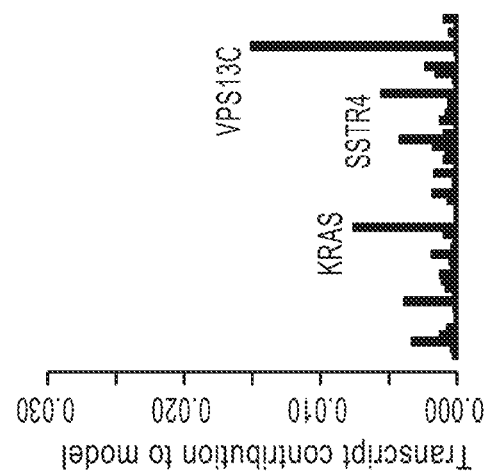

A Surrogate for the Ki-67 Index: Multivariate regression analysis did not identify any significant correlation between individual gene expression and the Ki-67 index (a marker of tumor proliferation) in either of the two groups. With reference to FIGS. 38A and 38B, examination of somatostatin receptor expression identified significant correlations (R=0.9, p=2×10$^{-8}$) with Ki67 in each of the tumor groups.

Figure 38C:
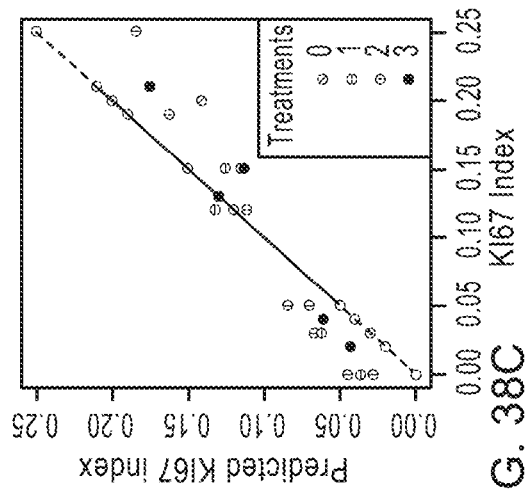
Figure 38E:
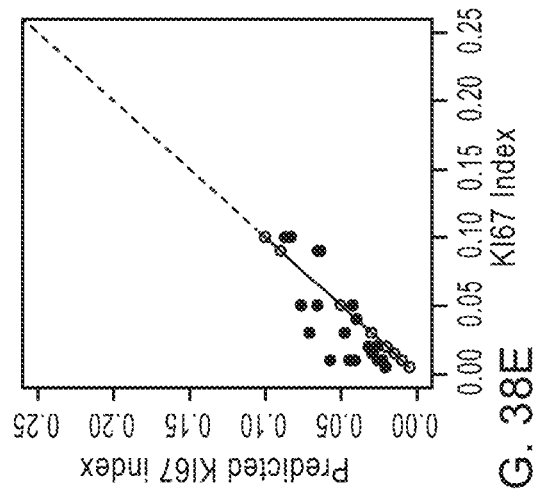
Figure 38D:
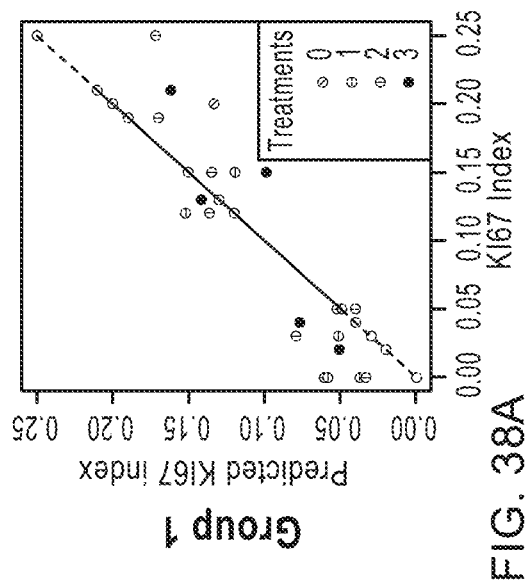
Figure 38F:
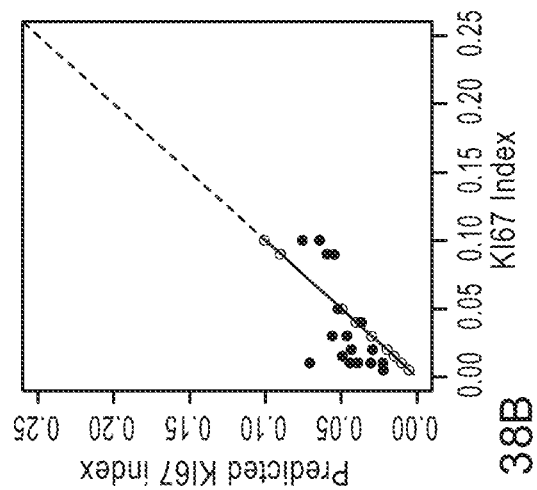

An examination of all genes in the NETest identified significantly higher correlations with Ki-67 (R=0.93-98, p=10$^{-9}$–10$^{-13}$, FIGS. 38C-38E). The single most informative gene was SSTR4 (FIG. 38D-38F). These data demonstrate firstly, that the NETest as a whole can be used as a liquid biopsy to determine the proliferative index of the tumor i.e., provides a surrogate marker for a tissue-based histopathological measurement. Secondly, expression of circulating somatostatin receptor genes can also be used as a measure of tumor proliferation.

Proliferome+SSTRome algorithm is also referred to as Progressive Diagnostic V; the highly relevant genes (KRAS, SSTR4, and VPS13C) algorithm is also referred to as Progressive Diagnostic VI; the highly relevant genes+SSTRome algorithm is also referred to as Progressive Diagnostic VII.

With reference to FIGS. 39A-39F, correlations (linear regression) between gene clusters (SSTRome and proliferome) or each of the algorithms and the Ki-67 index, are shown. Examination of individual gene clusters confirmed that the SSTRome and Proliferome correlated with the Ki-67 index (R=0.16-0.25, p<0.05, FIGS. 39A, 39C). Analysis of the algorithms identified that the NDA and TDA algorithms were highly correlated with the Ki-67 index (R=0.34-0.42, p<0.002, FIGS. 39B, 39F) while the PDA and IDA were less well-correlated (R=0.14-0.17, p=0.06, FIGS. 39D, 39E). These results demonstrate that gene clusters and algorithms including biologically relevant tumor information e.g., SSTRome can be utilized as a measure of tumor tissue proliferation.

Figure 40A:
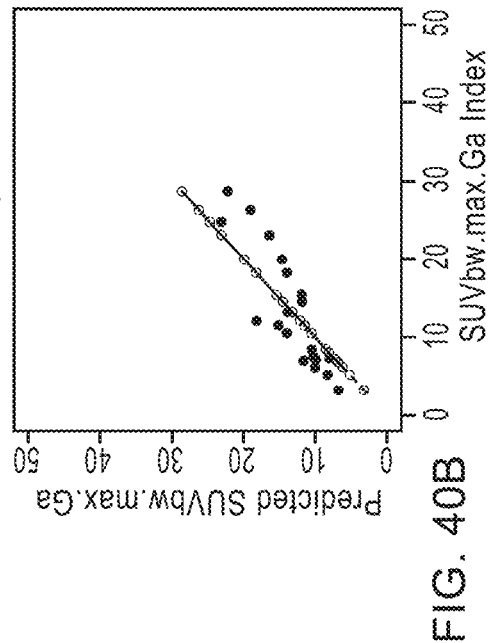
FIGS. 40A-40D are graphs modeling predicted SUVmax (tumor uptake–a measure of receptor density/target availability) for SSTRome (Group I.
Figure 40B:
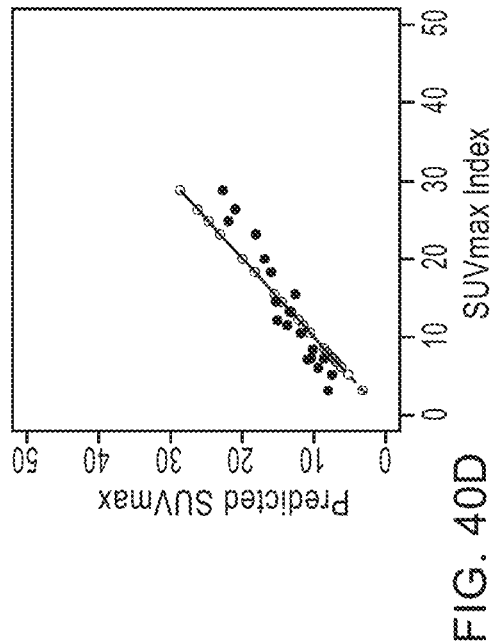
Figure 40C:
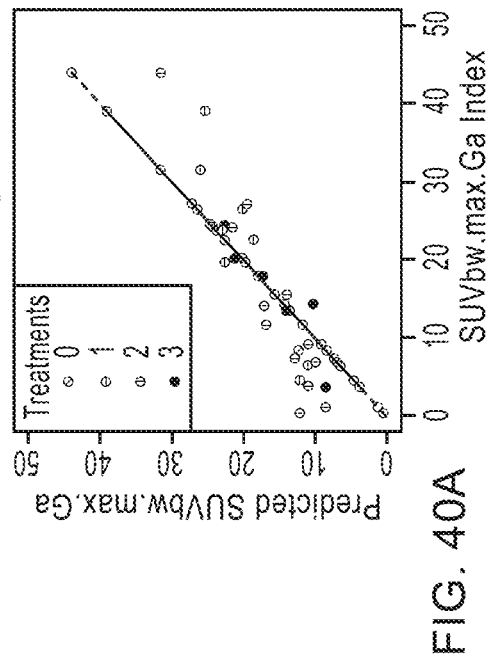
Figure 40D:
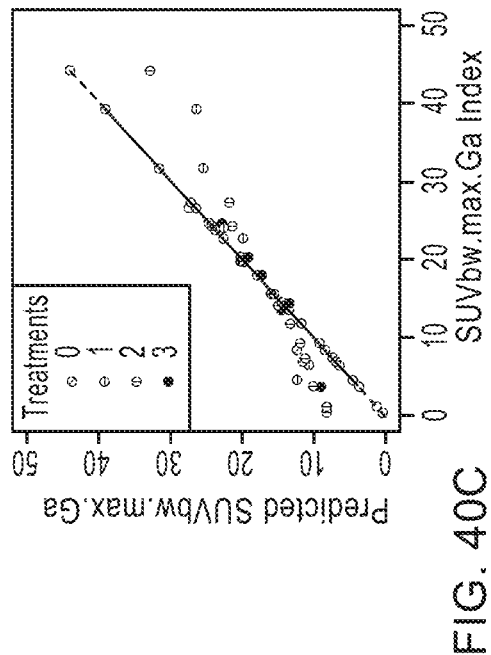

Relationship with Somatostatin-Based Imaging: Next was examined whether genes in the test correlated with two variables from somatostatin-based imaging, the SUVbmax (tumor uptake–a measure of receptor density/target availability) and the MTV (molecular tumor volume–a measure of the tumor burden). Multivariate regression analysis did not identify any single gene to correlate with the SUVmax. However, both the SSTRome as well as the NETest genes as a group were well correlated with the SUVmax. Correlations in both groups ranged between R=0.88-0.94 (p<$10^{-7}$) for the SSTRome (FIGS. 40A-40B) and R=0.97-0.98, p<$10^{-13}$ for the NET gene set (FIGS. 40C-40D).

Multivariate regression analysis identified ZFHX3 as a marker of MTV in Group 1 (R=0.98, FIG. 41A) while TPH1 was correlated with MTV in Group 2 (R=0.76, FIG. 41B).

Similarly to the SUVmax, both the SSTRome as well as the NETest genes as a group were well correlated with the MTV. Correlations in both groups ranged between R=0.72-0.77 (p<$10^{-4}$) for the SSTRome (FIGS. 41C-41E) and R=0.91-0.95, p<$10^{-12}$ for the NET gene set (FIGS. 41D-41F).

These data demonstrate that genes in the NETest correlate and can be used to estimate both the target availability for somatostatin analog-based therapies as well as provide a measure of the tumor burden. Both these aspects are critical for directing therapy as well as measuring the efficacy of therapy.

ZFHX3 as a Marker for Disease Assessment: The identification of ZFHX3 as the best marker for MTV, as shown in FIG. 41A, suggests that expression of this gene may have clinical utility as a measure of tumor burden and changes thereof. ZFHX3 is a zinc finger protein involved in the regulation of neuronal differentiation through the control of cell cycle arrest. Loss of ZFHX3 expression with a subsequent loss of cell cycle arrest therefore is related to tumor proliferation and the development of new lesions and/or progression of disease.

It was examined whether measurements of ZFHX3 may provide a marker of new growth/progression in NETs and if that alteration in ZFHX3 may reflect response to therapy or therapy failure (progression). Expression of this gene was initially assessed in patients who had evidence of new lesions.

Figure 42C:
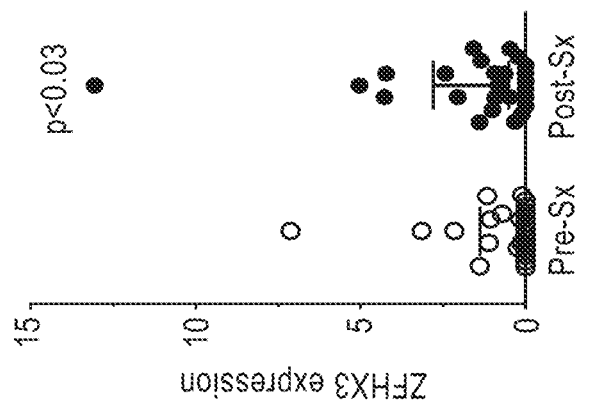
FIGS. 42A-42C are graphs showing ZFHX3 expression in patients identified with (FIG. 42A) new lesions by imaging, with (FIG. 42B) progressive disease by RECIST, and (FIG. 42C) following surgery.
Figure 42B:
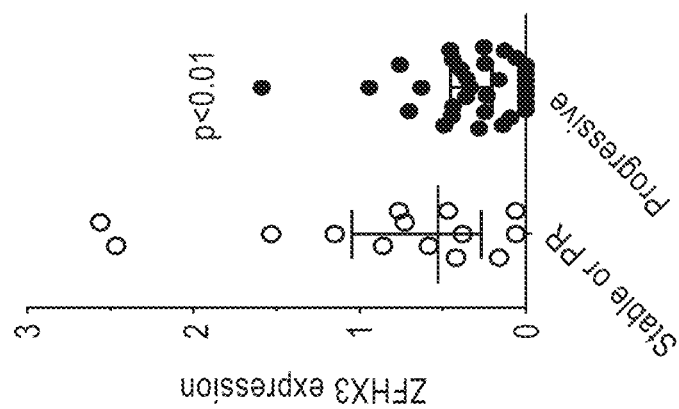
Figure 42A:
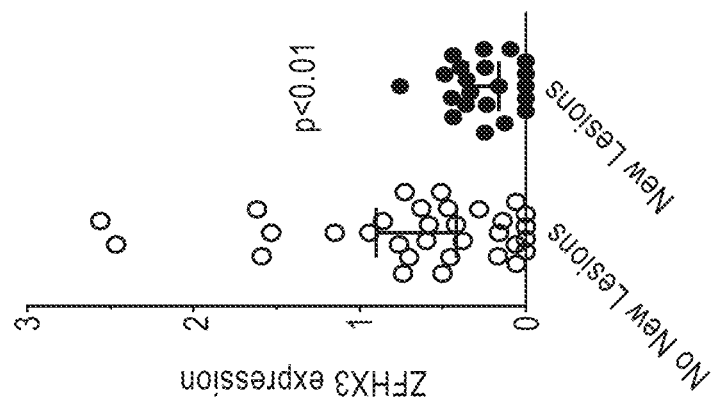

With reference to FIG. 42A, patients who had developed new lesions (identified by imaging) expressed significantly decreased ZFHX3. With reference to FIG. 42B, those patients that were determined as SD also have significantly higher levels than those who were progressive. Moreover, with reference to FIG. 42C, expression of the gene was increased following surgery.

Figure 43A:
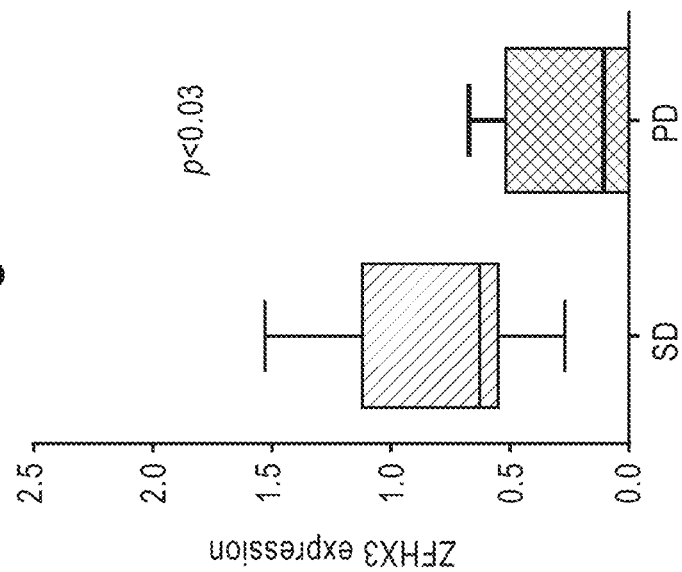
FIGS. 43A-43B are graphs showing ZFHX3 expression in (FIG. 43A) patients who remain in a stable disease state of GEP-NEN versus (FIG. 43B) those who develop a progressive disease state of GEP-NEN.
Figure 43B:
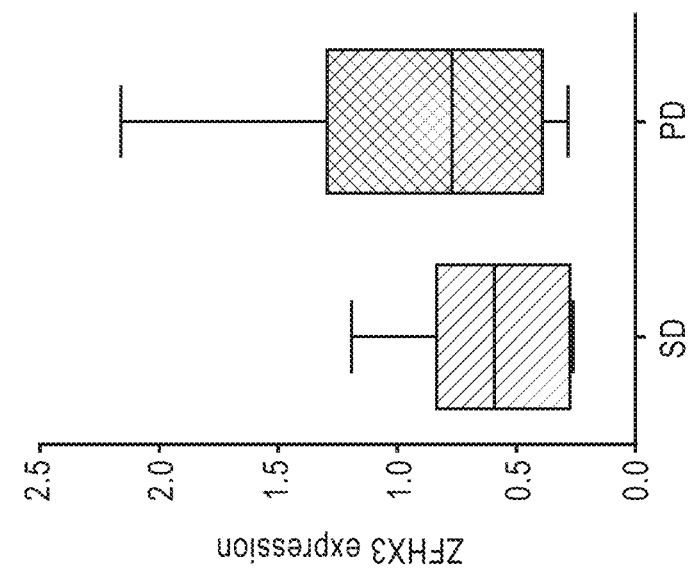

With reference to FIGS. 43A-43B, long-term follow-up (>3 years) in a group identified that patients who remained stable exhibited no changes in ZFHX3 expression over this time period, while patients who developed progressive disease had significantly lower expression levels.

These data demonstrate that ZFHX3 expression correlates with the development of new lesions and a decrease in expression can be used to define disease progression.

Utility of NETEST and Gene Expression for the Prediction of Therapeutic Efficacy—To further evaluate the utility of the NETest in therapy, the relationship between PRRT and clinically defined (per RECIST criteria) outcomes were evaluated. Samples were collected both pre-therapy as well as at follow-up in fifty-four patients. Imaging was available to stage and categorize disease patterns pre- and post-therapy (at 3 and 6 month follow-up).

Figure 44A:
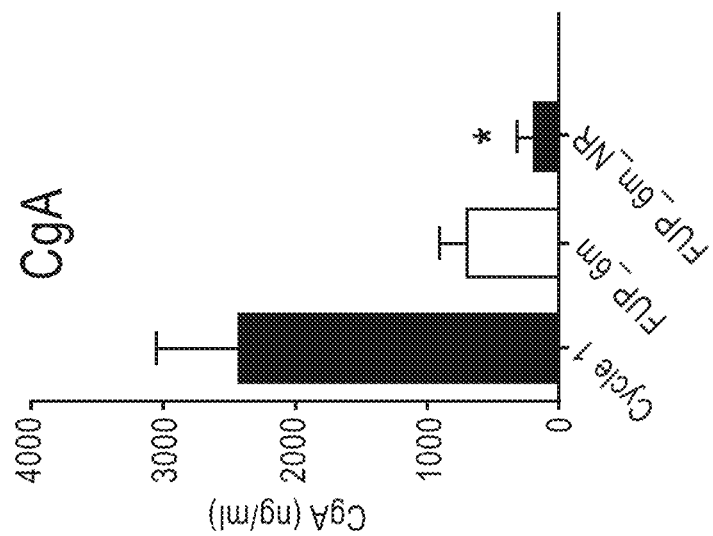
FIGS. 44A-44C are graphs representing (FIG. 44A) the effectiveness of peptide receptor radionucleotide therapy (PRRT), (FIG. 44B) changes in NETest Score versus clinical status at 6M Follow-up (FuP) in responders (R) and non-responders (NR)
Figure 44B:
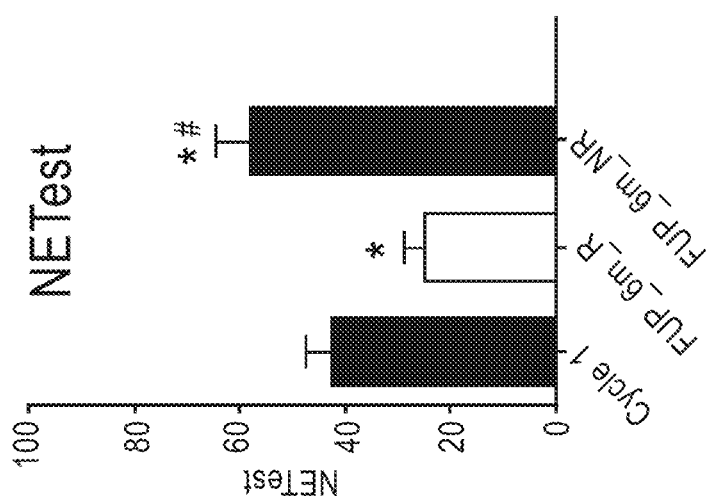
Figure 44C:
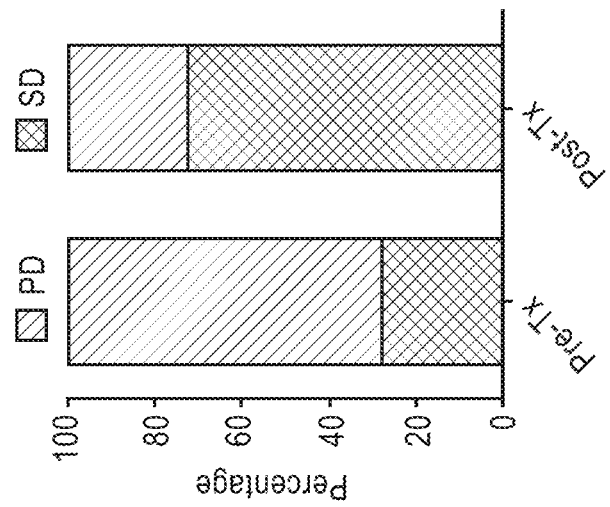
Figure 45:
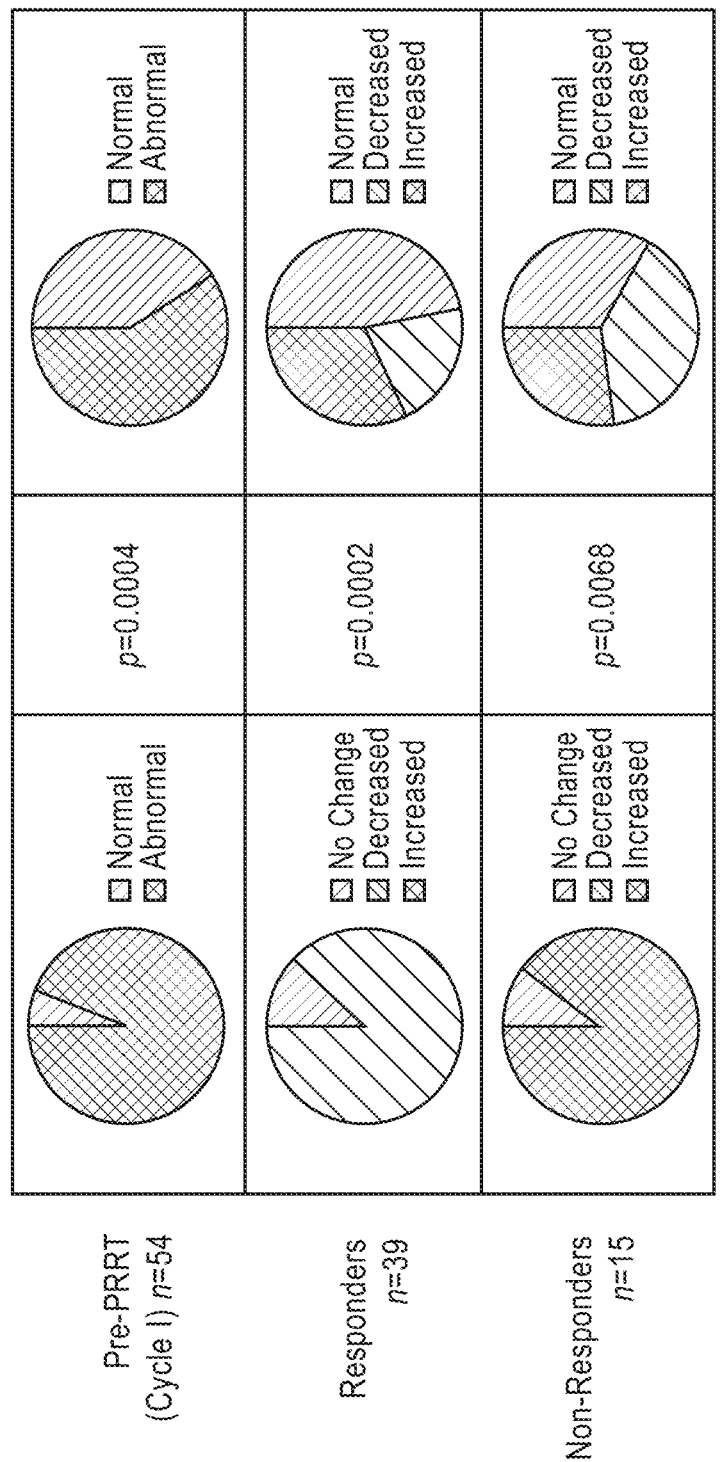
FIG. 45 are graphs showing concordance between the NETest in responders and non-responders prior to and after therapy and in addition the comparison to CgA.
Figure 46A:
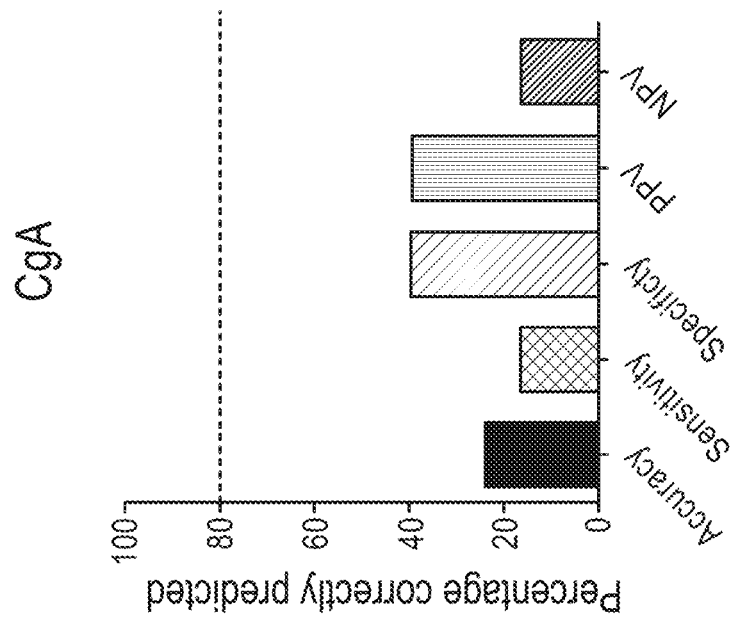
FIGS. 46A-46B shows the accuracy of the NETest Score versus CgA for treatment responses.
Figure 46B:
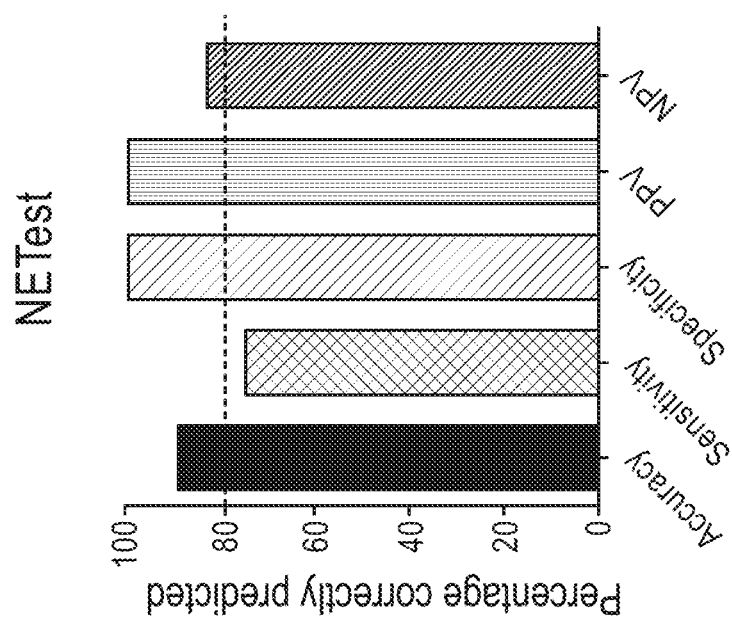

In this prospective sample set, radiotherapy significantly resulted in a reduction in the number of patients with progressive disease (FIG. 44A). Patients who did not respond to therapy i.e., categorized as progressive disease at the 6 month follow-up period exhibited an increase in the NETest score. The score was significantly reduced in patients with SD at this time point (FIG. 44B). No significant alterations were noted for CgA (FIG. 44C). Alterations in NETest paralleled changes in therapeutic responses (FIG. 45). The metrics for biomarkers and outcome identified that the NETest had an accuracy of 89%, sensitivity 75%, specificity 100%, PPV 100% and NPV 83% (FIG. 46A). With reference to FIG. 46B, CgA had an accuracy of 24%, sensitivity 17%, specificity 40%, PPV 40% and NPV 17%. The NETest significantly outperformed CgA (Chi-square=27.4; p=1.2×$10^{-7}$).

Pre-treatment NETest scores as well as grading were available and used to identify whether a combination of gene expression and clinical parameters were predictive of outcome, i.e., response to therapy.

Figure 47A:
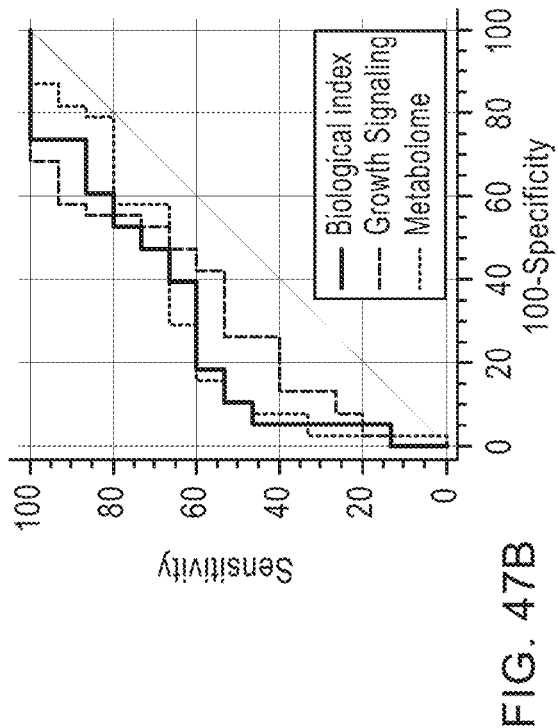
FIG. 47A-47D shows expression of two subsets of NETest genes, the signalome and metabolome in blood samples prior to therapy and the differences between responders (R) and non-responders (NR), the predictive utility of each as well as when combined into a biological index (FIG. 47B), the utility for predicting treatment response alone (Quotient) or as a combination with grade (Combination) (FIG. 47C) and the metrics of the combination for predicting the outcome of PRRT therapy (FIG. 47D).
Figure 47B:
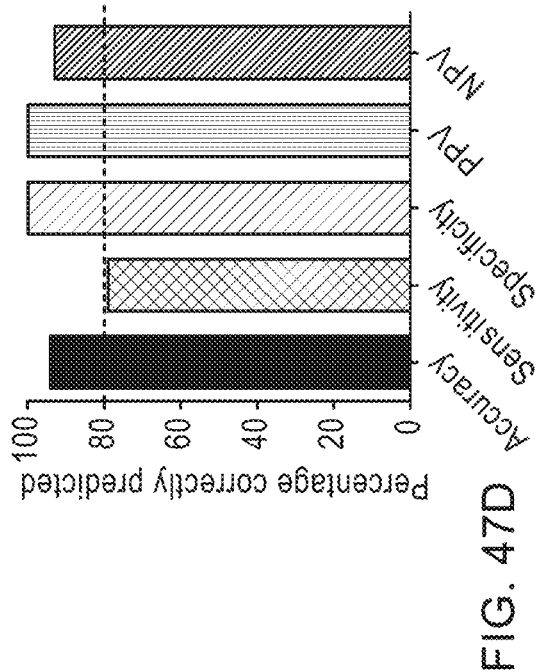

With reference to FIG. 47A, a subset of NETest gene expression levels were significantly different between responders and non-responders prior to therapy. These included genes linked to growth factor signaling (GF signalome: ARAF1, BRAF, KRAS and RAF1) as well as genes linked to metabolism (including ATP6V1H, OAZ2, PANK2, PLD3). Specifically, PRRT-responders exhibited significantly elevated growth factor signaling (9.4±1.3 vs. 5.3±0.7, p=0.05) and significantly elevated metabolomic gene expression (4.37 vs. 2.3±0.6, p=0.03) prior to PRRT. An integration of the two "clusters" (GF signalome+metabolome) into a "Biological Index" through summation of gene expression enabled prediction of future PRRT-responders from non-responders. A cut-off of 5.9 (normalized gene expression) exhibited>85% specificity for predicting response (>5.9 predicted PRRT responders) and resulted in an AUC of 0.74±0.08 (z-statistic=2.915, p=0.0036) (FIG. 47B).

Figure 47C:
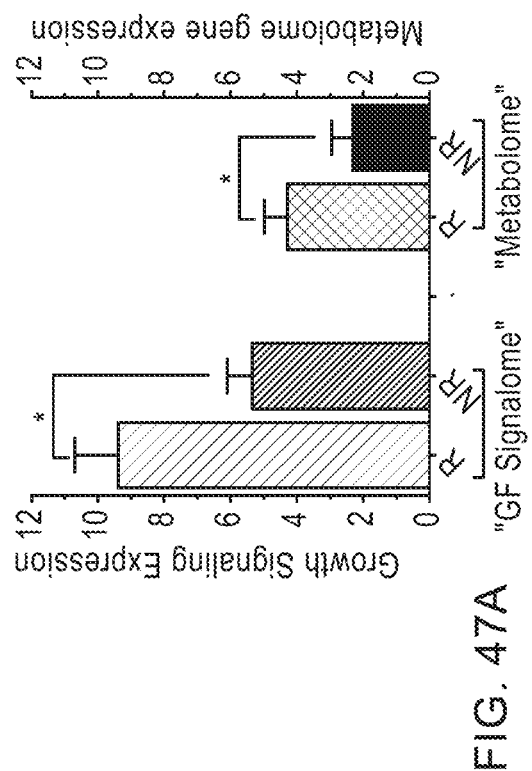

No clinical parameters were predictive of PRRT response except tumor grade. Low grade tumors responded (77%) to therapy while ~50% of high grade lesions were associated with responses. Grading alone was only 65% accurate (p=0.1). In contrast a "Prediction Quotient" which comprised the combination of the Biological Index ("GF signalome"+"metabolome") and the tumor grade was significantly (92%) more accurate. The Prediction Quotient had a significantly better AUC (0.90±0.07) than histological grade alone for predicting treatment response (AUC=0.66, difference between areas 0.23, z-statistic 2.25, p=0.024) (FIG. 47C).

Figure 47D:
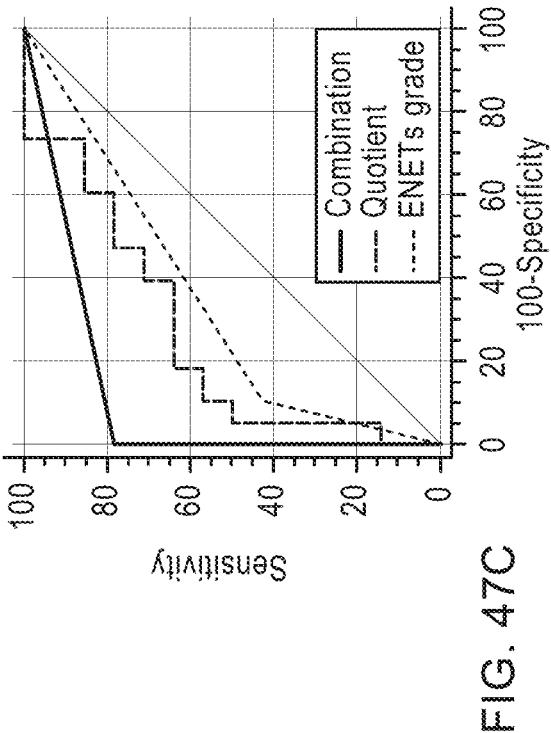

The Prediction Quotient was also clinically useful. Patients could be segregated into Low Grade/High Ome and High Grade/Low Ome groups. The latter had a significantly lower PFS (17 months) than the low grade/high Ome group (PFS not reached, Log-rank: 26.8; p<0.0001: FIG. 47D). The Hazard Ratio was 53.3.

These results demonstrate that alterations in score correlate with treatment responses and that circulating NET transcript measurements prior to therapy are predictive of outcome to PRRT.

The invention claimed is:

1. A method for treating a progressive gastroenteropancreatic neuroendocrine neoplasm (GEP-NEN) in a human subject in need thereof, the method comprising: determining the expression levels of at least 23 biomarkers from a test sample from the human subject by performing reverse transcription polymerase chain reaction (RT-PCR) with a plurality of probes or primers specific to detect the expression of the at least 23 biomarkers, wherein the at least 23 biomarkers comprise APLP2, ARAF, CD59, CTGF, FZD7, KRAS, MKI67/KI67, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, ZFHX3, and ALG9, wherein the test sample is blood, serum, plasma, or neoplastic tissue;

normalizing the expression levels of APLP2, ARAF, CD59, CTGF, FZD7, KRAS, MKI67/KI67, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, and ZFHX3 to the expression level of ALG9 to obtain normalized expression levels;

classifying the test sample with respect to the presence or development of a GEP-NEN using the normalized expression levels in a classification system, wherein the classification system is a machine learning system that comprises four different algorithms: Support Vector Machine, Linear Discrimination Analysis, K-Nearest Neighbor, and Naïve Bayes;

assigning a score based on a result of each of the four different algorithms;

comparing the score with a predetermined cutoff value;

determining the presence of a progressive GEP-NEN in the subject, wherein determining the presence of a progressive GEP-NEN in the subject comprises determining that the score is equal to or greater than the predetermined cutoff value, wherein the predetermined cutoff value is 5 on a MAARC-NET scoring system scale of 0-8;

administering a treatment to the subject identified as having a progressive GEP-NEN, wherein the treatment comprises surgery or drug therapy.

2. The method of claim 1, wherein determining the presence of a progressive GEP-NEN in the subject further comprises determining that the score is equal to or greater than a predetermined cutoff value of 5 and less than a predetermined cutoff value of 6;

determining the expression level of SMARCD3 from the test sample;

normalizing the expression level of SMARCD3 to the expression level of ALG9 to obtain a normalized expression level;

comparing the normalized expression level of SMARCD3 and TPH1 in the test sample with a first and a second predetermined cutoff value, respectively;

determining the presence of progressive GEP-NEN in the subject by determining that the normalized expression level of SMARCD3 is equal to or less than the first predetermined cutoff value and the expression level of TPH1 is less than the second predetermined cutoff value.

3. The method of claim 1, wherein determining the presence of a progressive GEP-NEN in the subject further comprises determining that the score is equal to or greater than a predetermined cutoff value of 6 and less than a predetermined cutoff value of 7;

determining the expression levels of VMAT1 and PHF21A from the test sample;

normalizing the expression levels of VMAT1 and PHF21A to the expression level of ALG9;

comparing the normalized expression level of VMAT1 and PHF21A with a first and a second predetermined cutoff value, respectively; and determining the presence of progressive GEP-NEN in the subject by determining that the normalized expression level of VMAT1 is equal to or greater than the first predetermined cutoff value and the expression level of PHF21A is equal to or greater than the second predetermined cutoff value.

4. The method of claim 1, wherein determining the presence of a progressive GEP-NEN in the subject further comprises determining that the score is equal to or greater than a predetermined cutoff value of 7 and less than a predetermined cutoff value of 8;

determining the expression levels of VMAT1 and PHF21A from the test sample, normalizing the expression levels of VMAT1 and PHF21A to the expression level of ALG9;

comparing the normalized expression level of VMAT1 and PHF21A with a first and a second predetermined cutoff value, respectively; and determining the presence of progressive GEP-NEN in the subject by determining that the normalized expression level of VMAT1 is equal to or greater than the first predetermined cutoff value and the expression level of PHF21A is equal to or less than the second predetermined cutoff value.

5. The method of claim 1, wherein determining the presence of a progressive GEP-NEN in the subject further comprises determining that the score is equal to a predetermined cutoff value of 8;

determining the expression level of ZZZ3 from the test sample;

normalizing the expression level of ZZZ3 to the expression level of ALG9;

comparing the normalized expression level of ZZZ3 with a predetermined cutoff value; and determining the presence of progressive GEP-NEN in the subject by determining that the normalized expression level of ZZZ3 is equal to or less than the predetermined cutoff value.

6. The method of claim 1, wherein the biomarker is RNA or cDNA.

7. The method of claim 6, wherein when the biomarker is RNA, the RNA is reverse transcribed to produce cDNA, and the produced cDNA expression level is detected.

8. The method of claim 1, wherein the expression level of the biomarker is detected by forming a complex between the biomarker and a labeled probe or primer.

9. The method of claim 6, wherein when the biomarker is RNA or cDNA, the RNA or cDNA detected by forming a complex between the RNA or cDNA and a labeled nucleic acid probe or primer.

10. The method of claim 9, wherein when the label is a fluorescent label.

11. The method of claim 9, wherein the complex between the RNA or cDNA and the labeled nucleic acid probe or primer is a hybridization complex.

12. The method of claim 1, wherein a subject in need thereof is a subject diagnosed with a GEP-NEN, a subject having at least one GEP-NEN symptom or a subject having a predisposition or familial history for developing a GEP-NEN.

13. The method of claim 1, wherein the drug therapy comprises somatostatin analog treatment, peptide receptor radionuclide therapy (PRRT) or any combination thereof.

14. The method of claim 1, wherein the drug therapy comprises somatostatin analog treatment.

15. The method of claim 1, wherein the drug therapy comprises peptide receptor radionuclide therapy (PRRT).

* * * * *

SEQUENCE LISTING

<160> NUMBER OF SEQ ID NOS: 52

<210> SEQ ID NO 1
<211> LENGTH: 6158
<212> TYPE: DNA
<213> ORGANISM: Homo sapiens

<400> SEQUENCE: 1

| | | | | | |
|---|---|---|---|---|---|
| gtcttttgtc | cctcggcgga | caccgtttgc | cagccaaagc | tatgtctgcg | cgctcaccga | 60 |
| cttcataggg | tgccgaattc | ttttttcccc | aggcttgcca | tggctagtcg | agggctcgg | 120 |
| cagcgcctga | agggcagcgg | ggccagcagt | ggggatacgg | ccccggctgc | ggacaagctg | 180 |
| cgggagctgc | tggcagccg | agaggcgggc | ggcgcggagc | accggaccga | gttatctggg | 240 |
| aacaaagcag | acaagtctg | ggcacctgaa | ggatctactg | ctttcaagtg | tctgctttca | 300 |
| gcaaggttat | gtgctgctct | cctgagcaac | atctctgact | gtgatgaaac | attcaactac | 360 |
| tgggagccaa | cacactacct | catctatggg | aagggtttc | agacttggga | atattcccca | 420 |
| gcatatgcca | ttcgctccta | tgcttacctg | ttgcttcatg | cctggccagc | tgcatttcat | 480 |
| gcaagaattc | tacaaactaa | taagattctt | gtgttttact | ttttgcgatg | tcttctggct | 540 |
| tttgtgagct | gtatttgtga | actttacttt | tacaaggctg | tgtgcaagaa | gtttgggttg | 600 |
| cacgtgagtc | gaatgatgct | agccttcttg | gttctcagca | ctggcatgtt | ttgctcatca | 660 |
| tcagcattcc | ttcctagtag | cttctgtatg | tacactacgt | tgatagccat | gactggatgg | 720 |
| tatatggaca | agacttccat | tgctgtgctg | ggagtagcag | ctggggctat | cttaggctgg | 780 |
| ccattcagtg | cagctcttgg | tttacccatt | gcctttgatt | tgctggtcat | gaaacacagg | 840 |
| tggaagagtt | tctttcattg | gtcgctgatg | cccctcatac | tatttctggt | gcctgtggtg | 900 |
| gtcattgaca | gctactatta | tgggaagttg | gtgattgcac | cactcaacat | tgttttgtat | 960 |
| aatgtcttta | ctcctcatgg | acctgatctt | tatggtacag | aaccctggta | tttctattta | 1020 |
| attaatggat | ttctgaattt | caatgtagcc | tttgctttgg | ctctcctagt | cctaccactg | 1080 |
| acttctctta | tggaatacct | gctgcagaga | tttcatgttc | agaatttagg | ccacccgtat | 1140 |
| tggcttacct | tggctccaat | gtatatttgg | tttataattt | tcttcatcca | gcctcacaaa | 1200 |
| gaggagagat | ttcttttccc | tgtgtatcca | cttatatgtc | tctgtggcgc | tgtggctctc | 1260 |
| tctgcacttc | agcacagttt | tctgtacttc | cagaaatgtt | accactttgt | gtttcaacga | 1320 |
| tatcgcctgg | agcactatac | tgtgacatcg | aattggctgg | cattaggaac | tgtcttcctg | 1380 |
| tttgggctct | tgtcattttc | tcgctctgtg | gcactgttca | gaggatatca | cgggcccctt | 1440 |
| gatttgtatc | cagaatttta | ccgaattgct | acagacccaa | ccatccacac | tgtcccagaa | 1500 |
| ggcagacctg | tgaatgtctg | tgtgggaaaa | gagtggtatc | gatttcccag | cagcttcctt | 1560 |
| cttcctgaca | attggcagct | tcagttcatt | ccatcagagt | tcagaggtca | gttaccaaaa | 1620 |
| ccttttgcag | aaggacctct | ggccacccgg | attgttccta | ctgacatgaa | tgaccagaat | 1680 |
| ctagaagagc | catccagata | tattgatatc | agtaaatgcc | attatttagt | ggatttggac | 1740 |
| accatgagag | aaacaccccg | ggagccaaaa | tattcatcca | ataaagaaga | atggatcagc | 1800 |
| ttggcctata | gaccattcct | tgatgcttct | agatcttcaa | agctgctgcg | ggcattctat | 1860 |
| gtcccttcc | tgtcagatca | gtatacagtg | tacgtaaact | acaccatcct | caaacccgg | 1920 |
| aaagcaaagc | aaatcaggaa | gaaaagtgga | ggttagcaac | acacctgtgg | ccccaaagga | 1980 |
| caaccatctt | gttaactatt | gattccagtg | acctgactcc | ctgcaagtca | tcgcctgtaa | 2040 |
| catttgtaat | aaaggtcttc | tgacatgaat | actggaatct | gggtgctctg | gctagtcaa | 2100 |

```
agtctatttc aaagtctaat caaagtcaca tttgctccct gtgtgtgtct ctgttctgca    2160
tgtaaacttt ttgcagctag gcagagaaag gccctaaagc acagatagat atattgctcc    2220
acatctcatt gttttcctc tgttcaatta tttactagac cggagaagag cagaaccaac     2280
ttacaggaag aattgaaaat cctggtactg gatggctgtg ataagctgtt ctccacactc    2340
tggcctggca tctgagaact agcaagcctc tcttaggcca tatgggcttc tccaccaaag    2400
ctgtttggca gctcctagca gaccttctta ttgaaatcct catgctgaaa atgaacacag    2460
cctagttgcc aacccacatg tccttttcac ctccagcaag actaagcttc tttaaagcac    2520
ttcacaggac taggaccctg tcctggagct atctcaggaa aaaggtgacc atttgaggaa    2580
ctgtgaccta atttattat aatgatgcct ctaattttca tttcctttac aaccaactgt     2640
aactataagg ttgtattgct tttttgttca gttttagcat gctattttt gaattctaga     2700
ctcctccatg tgaagatatc aacagacaaa actacaactg tataggacat atttggagaa    2760
aattctatca attgatacat ttggatgaca tcacattttt aagtaatgta atctgaggcc    2820
attgctgagg aaattaagaa ttttccttt tttttaacca cccccagtga aaaggatcag     2880
tgtatattta tagcacctat tttttagttc tgtctgttgt gaggcacatc ctgcatgggg    2940
cacttctagt caaataggca atgataagga cctaattaaa atgtgataag tgtatactat    3000
tactttaaaa gccttacag tcagtacttc agtttacaag gcactttcac agcatctcgt     3060
ttgatcctca cagtcacaac atgtggtaga caaggcaggt gatttttatc cccatttac     3120
agataaggaa acaggctgcg ggtggggagt gaggggaggg aaagatagtt agttgcctaa    3180
ggtcacacag ccagtaagta atagagctgg gactggaacc caggtttcct tactctcatc    3240
tattgctcct ccatattcct cactcaacca tgaaaacatt acttgaaagg actgatgagg    3300
ttaaccagag acctaactga tattgtaact ttctattta aggaagaatt gtgtctgtat     3360
ttgagttctt tggagcctcc agtctgcctg tgtgttagac cagcacagca gtgctgtgtg    3420
atgcagcctg acctgtggca ggaaagtagt gcttctgttt ggaagtcatg ttcttttgca    3480
gccacacagg atccaaatat cagtactatt cctgtagtca atctggggtc acattatagg    3540
tgccttattt ccctaagggt aactgatctg aatatctgca aataggatga atctattttt    3600
cagaagttcc atctttcatt tttctttttt tttttgagac agagtctcat tctgtcgccc    3660
atgctggagt gcagtggcgc gatctcggct cgctgcaacc tctgcctccc aggttgaagc    3720
aattctcatg cctcagccac ccgagtagct gggattacag gcatgcgcca tcatgcccag    3780
ctaatttatg tattttagt agagttggag tttcaccatg ttggccaggc tggtcttgga     3840
ctcctgacct caggtcatcc acccgcctca gcctcccaaa gtgctggtat acaggcgtg     3900
agccaccgca cccagcccca tctttcattt tcaaagagaa gggcattcta ataggaactg    3960
gtgccaagag agaagaaaag aagtgataac agaagaaatg gctagttaca atattaaaaa    4020
gctcctcttt gagatctcct ctgcaggaat atcagacg gagttgaagc gctggagagg      4080
taataggtct agacagtaca gaacaataac tggggagtgt gtgaggatag actgggctcc    4140
cccttgcttg aaagatctct ggcatttaat tctcaattct tgattactat ttccagtgt     4200
aaaactagca catatgatct gactacagga cagagaattt taagtgaaac atttgcctta    4260
cttgcagtaa taatgtgctg ttcttcacag tagctaaggc cctctatgtt tcccagaggt    4320
aaataagaat ccaggaatgg aggtccatct gtgatgaatg gctttttct aatcaaagta     4380
gtataatgct gttttatctg ttttgtcatc ttgttttttt ttttttttaa aaaacaaaa    4440
```

```
ccttaattat aatatagcgc aaagaaaggc caggactgat gcaggggattc cttggaaata    4500 tcagttccta tcacttttaa aacctgattt tggatctctc tgttctatgt atgtctttag    4560
tgagagcaca atacatggca gaacgctgtg ccaaatgtta taggtaagga atatagaaat    4620
gaatgttttt tgttgtgaag gtgttttcat gtgatatttt ataaacacat tttaaaaaat    4680
ctccatcact ttttagtata ggaaggatag ctttgcctgg gaaaaacagt ttcaacacac    4740
ctgctcagag tagcagttct ccctcaaaaa agcagtgttc agcctgcact gactgttctg    4800
cttgccaaaa ggaggaagca tgcaagatac ttatttctcc atagattgtg gagtatagag    4860
ggatgtggga ctacagatta ttatttttt tccccgagac agagtcttgc tctgtcgccc     4920
aggttggaac acaatggcac gacctcagct cactgcaacc tctgtctccc gggttcaagc    4980
aattctcctg cttcagcctc ctgagtagct gggattacag gcacacacca ccaccgcact    5040
cagctaattt ttgtatttt agtagaggtg gggttttacc atgttggcca ggctggtctt     5100
aaactcctga ccttgtaatc atcccgcctc ggcctcctaa agtgctagga ttacaggcat    5160
gagccaccgc acccggccca gataattttt aatagccttt gatcatgggg tgagtgaggg    5220
agtaggtata cttggcaaat gcatggttct ctgatttcta gctctaaagc agccttatct    5280
gaatccccaa atcttgtgat gctgagtacc attactgaac cagtctgcac ggtaggcatc    5340
tgctaccaaa atttacctcc tacctggtag gtgtcatctg ataagaaaga agacaggtta    5400
ttttaatttt tgagataat cacagaaaat tgcagcccat actctttatt accgaattca     5460
agtttggaaa tagaccctt gttttaaatc atgatgggtc tttatcccaa tcatttatct     5520
gggtcatttt tccaactttg gagttctagg aaagaacctt gaaaacctga tatgattctg    5580
cagcatgagg tctacggtga ccatttgggc aaagctccag tggcaatcat ttattgtgtt    5640
ttgcatttcc tgggatttat tgaaataaga attcactgtg attatgtagt cttctggcta    5700
gtatcaggca gctctgcttt taatttggtt aatttattt tctctgaaga gggagaagag     5760
gtacaattta atcttggcct ccacaagcat attaaagctc acgtgttaat cagtgcattc    5820
ttatgctcct acattaaatg ccttgggtaa atggataaat ggacatgtgc ccagctttaa    5880 tttttttgc aacagaaaga tcagacttcc gtatggcatc gttggatttc agaggctttc     5940
tggtgtatct gtaaatctga atgttgcctt ctgccagtct gtataaccag gtgattcatg    6000
ctgcaaatga aatcaggaag cagtaaagtg ttaaagcaag agtattgtcc aattcacttg    6060
tcttcctgat ccttgtactt tatttcacgt gtcggtgttt acattacata cttatatttc    6120
ctgtgaaaga aagagttaaa taaattgtag cagtttga                            6158

<210> SEQ ID NO 2
<211> LENGTH: 2231
<212> TYPE: DNA
<213> ORGANISM: Homo sapiens

<400> SEQUENCE: 2
actgatatga ggaggcatag agatagacag cggttccttc caatagacgt gaagccgagg      60
ccggtatgag ccaatgcggt cgggaggcgg ggctcgggtg tgtgtggagg ggaccctgtg    120
gttagcagca gctatcgcag cgtcggatgt tcagagcagc agaagccggc gtcgtcggat    180
gttgtgttgc ccgccaccat gagctacaca ggctttgtcc agggatctga aaccactttg    240
cagtcgacat actcggatac cagcgctcag cccacctgtg attatggata tggaacttgg    300
aactctggga caaatagagg ctacgagggc tatggctatg ctatggctta ggccaggat     360 aacaccacca actatgggta tggtatggcc acttcacact cttgggaaat gcctagctct    420
```

| | | |
|---|---|---|
| gacacaaatg caaacactag tgcctcgggt agcgccagtg ccgattccgt tttatccaga | 480 |
| attaaccagc gcttagatat ggtgccgcat ttggagacag acatgatgca aggaggcgtg | 540 |
| tacggctcag gtggagaaag gtatgactct tatgagtcct gcgactcgag ggccgtcctg | 600 |
| agtgagcgcg acctgtaccg gtcaggctat gactacagcg agcttgaccc tgagatggaa | 660 |
| atggcctatg agggccaata cgatgcctac cgcgaccagt tccgcatgcg tggcaacgac | 720 |
| accttcggtc ccagggcaca gggctgggcc cggatgccc ggagcggccg ccaatggcc | 780 |
| tcaggctatg ggcgcatgtg ggaagacccc atggggccc ggggccagtg catgtctggt | 840 |
| gcctctcggc tgccctccct cttctcccag aacatcatcc ccgagtacgg catgttccag | 900 |
| ggcatgcgag gtggggcgc cttcccgggc ggctcccgct ttggtttcgg gtttggcaat | 960 |
| ggcatgaagc agatgaggcg gacctggaag acctggacca cagccgactt ccgaaccaag | 1020 |
| aagaagaaga gaaagcaggg cggcagtcct gatgagccag atagcaaagc cacccgcacg | 1080 |
| gactgctcgg acaacagcga ctcagacaat gatgagggca ccgaggggga agccacagag | 1140 |
| ggccttgaag gcaccgaggc tgtggagaag ggctccagag tggacggaga ggatgaggag | 1200 |
| ggaaaagagg atgggagaga agaaggcaaa gaggatccag agaaggggc cctaaccacc | 1260 |
| caggatgaaa atggccagac caagcgcaag ttgcaggcag gcaagaagag tcaggacaag | 1320 |
| cagaaaaagc ggcagcgaga ccgcatggtg gaaaggatcc agtttgtgtg ttctctgtgc | 1380 |
| aaataccgga ccttctatga ggacgagatg gccagccatc ttgacagcaa gttccacaag | 1440 |
| gaacacttta gtacgtagg caccaagctc cctaagcaga cggctgactt tctgcaggag | 1500 |
| tacgtcacta acaagaccaa gaagacagag gagctccgaa aaaccgtgga ggaccttgat | 1560 |
| ggcctcatcc agcaaatcta cagagaccag gatctgaccc aggaaattgc catggagcat | 1620 |
| tttgtgaaga aggtggaggc agcccattgt gcagcctgcg acctcttcat tcccatgcag | 1680 |
| tttgggatca tccagaagca tctgaagacc atggatcaca accggaaccg caggctcatg | 1740 |
| atggagcagt ccaagaagtc ctccctcatg gtggcccgca gtattctcaa caacaagctc | 1800 |
| atcagcaaga agctggagcg ctacctgaag ggcgagaacc ctttcaccga cagccccgag | 1860 |
| gaggagaagg agcaggagga ggctgagggc ggtgccctgg acgaggggc gcagggcgaa | 1920 |
| gcggcaggga tctcggaggg cgcagagggc gtgccggcgc agcctcccgt gcccccagag | 1980 |
| ccagcccccg ggccgtgtc gccgccaccg ccgccgccc cagaggagga ggaggagggc | 2040 |
| gccgtgccct tgctgggagg ggcgctgcaa cgccagatcc gcggcatccc gggcctcgac | 2100 |
| gtggaggacg acgaggaggg cggcggggc gccccgtgac ccgagctcgg ggcgggcgga | 2160 |
| gcccgcgtgg ccgaagctgg aaaccaaacc taataaagtt ttcccatccc accaaaaaaa | 2220 |
| aaaaaaaaaa a | 2231 |

<210> SEQ ID NO 3
<211> LENGTH: 3791
<212> TYPE: DNA
<213> ORGANISM: Homo sapiens

<400> SEQUENCE: 3

| | | |
|---|---|---|
| agaaggaggg cgtggtaata tgaagtcagt tccggttggt gtaaaccccc gggcggcg | 60 |
| gcgaactggc tttagatgct tctgggtcgc ggtgtgctaa gcgaggagtc cgagtgtgtg | 120 |
| agcttgagag ccgcgcgcta gagcgacccg gcgagggatg gcggccaccg gaccgcggc | 180 |
| cgccgcagcc acgggcaggc tcctgcttct gctgctggtg gggctcacgg cgcctgcctt | 240 |

-continued

```
ggcgctggcc ggctacatcg aggctcttgc agccaatgcc ggaacaggat ttgctgttgc      300
tgagcctcaa atcgcaatgt tttgtgggaa gttaaatatg catgtgaaca ttcagactgg      360
gaaatgggaa cctgatccaa caggcaccaa gagctgcttt gaaacaaaag aagaagttct      420
tcagtactgt caggagatgt atccagagct acagatcaca aatgtgatgg aggcaaacca      480
gcgggttagt attgacaact ggtgccggag ggacaaaaag caatgcaaga gtcgctttgt      540
tacacctttc aagtgtctcg tgggtgaatt tgtaagtgat gtcctgctag ttccagaaaa      600
gtgccagttt ttccacaaag agcggatgga ggtgtgtgag aatcaccagc actggcacac      660
ggtagtcaaa gaggcatgtc tgactcaggg aatgacctta tatagctacg gcatgctgct      720
cccatgtggg gtagaccagt tccatggcac tgaatatgtg tgctgccctc agacaaagat      780
tattggatct gtgtcaaaag aagaggaaga ggaagatgaa gaggaagagg aagaggaaga      840
tgaagaggaa gactatgatg tttataaaag tgaatttcct actgaagcag atctggaaga      900
cttcacagaa gcagctgtgg atgaggatga tgaggatgag gaagaagggg aggaagtggt      960
ggaggaccga gattactact atgacacctt caaaggagat gactacaatg aggagaatcc     1020
tactgaaccc ggcagcgacg gcaccatgtc agacaaggaa attactcatg atgtcaaagc     1080
tgtctgctcc caggaggcga tgacgggcc ctgccgggcc gtgatgcctc gttggtactt     1140
cgacctctcc aagggaaagt gcgtgcgctt tatatatggt ggctgcggcg gcaacaggaa     1200
caattttgag tctgaggatt attgtatggc tgtgtgtaaa gcgatgattc ctccaactcc     1260
tctgccaacc aatgatgttg atgtgtattt cgagacctct gcagatgata atgagcatgc     1320
tcgcttccag aaggctaagg agcagctgga gattcggcac cgcaaccgaa tggacagggt     1380
aaagaaggaa tgggaagagg cagagcttca agctaagaac ctccccaaag cagagaggca     1440
gactctgatt cagcacttcc aagccatggt taaagcttta gagaaggaag cagccagtga     1500
gaagcagcag ctggtggaga cccacctggc ccgagtggaa gctatgctga atgaccgccg     1560
tcggatggct ctgagaaact acctggctgc cttgcagtct gacccgccac ggcctcatcg     1620
cattctccag gccttacggc gttatgtccg tgctgagaac aaagatcgct acataccat      1680 ccgtcattac cagcatgtgt tggctgttga cccagaaaag gcggcccaga tgaaatccca     1740
ggtgatgaca catctccacg tgattgaaga aaggaggaac caaagcctct ctctgctcta     1800
caaagtacct tatgtagccc aagaaattca agaggaaatt gatgagctcc ttcaggagca     1860
gcgtgcagat atggaccagt tcactgcctc aatctcagag accctgtgg acgtccgggt      1920 gagctctgag gagagtgagg agatccacc gttccacccc ttccaccct tcccagccct     1980 acctgagaac gaaggatctg gagtgggaga gcaggatggg ggactgatcg gtgccgaaga     2040
gaaagtgatt aacagtaaga ataaagtgga tgaaaacatg gtcattgacg agactctgga     2100
tgttaaggaa atgattttca atgccgagag agttggaggc ctcgaggaag agcgggaatc     2160
cgtgggccca ctgcgggagg acttcagtct gagtagcagt gctctcattg gcctgctggt     2220
catcgcagtg gccattgcca cggtcatcgt catcagcctg gtgatgctga ggaagaggca     2280
gtatggcacc atcagccacg ggatcgtgga ggttgatcca atgctcaccc cagaagagcg     2340
tcacctgaac aagatgcaga accatggcta tgagaacccc acctacaaat acctggagca     2400
gatgcagatt taggtggcag ggagcgcggc agccctggcg gagggatgca ggtgggccgg     2460
aagatcccac gattccgatc gactgccaag cagcagccgc tgccagggc tgcgtctgac      2520 atcctgacct cctggactgt aggactatat aaagtactac tgtagaactg caatttccat     2580 tctttttaaat gggtgaaaaa tggtaatata acaatatatg atatataaac cttaaatgaa     2640
```

```
aaaaatgatc tattgcagat atttgatgta gttttctttt ttaaattaat cagaaacccc    2700
acttccattg tattgtctga cacatgctct caatatataa taaatgggaa atgtcgattt    2760
tcaataatag acttatatgc aggctgtcgt tccggttatg ttgtgtaagt caactcttca    2820
gcctcattca ctgtcctggc tttatttaa agaaaaaaaa ggcagtattc ccttttaaa      2880
tgagctttca ggaagttgct gagaaatggg gtggaatagg gaactgtaat ggccactgaa    2940
gcacgtgaga gaccctcgca aaatgatgtg aaaggaccag tttcttgaag tccagtgttt    3000
ccacggctgg atacctgtgt gtctccataa aagtcctgtc accaaggacg ttaaaggcat    3060
tttattccag cgtcttctag agagcttagt gtatacagat gagggtgtcc gctgctgctt    3120
tccttcggaa tccagtgctt ccacagagat tagcctgtag cttatatttg acattcttca    3180
ctgtctgttg tttacctacc gtagcttttt accgttcact tccccttcca actatgtcca    3240
gatgtgcagg ctcctcctct ctggactttc tccaaaggca ctgaccctcg gcctctactt    3300
tgtcccctca cctccacccc ctcctgtcac cggccttgtg acattcactc agagaagacc    3360
acaccaagga ggcggccgct ggcccaggag agaacacggg gaggtttgtt tgtgtgaaag    3420
gaaagtagtc caggctgtcc ctgaaaactga gtctgtggac actgtggaaa gctttgaaca    3480
attgtgtttt cgtcacagga gtctttgtaa tgcttgtaca gttgatgtcg atgctcactg    3540
cttctgcttt ttcttcttt ttattttaaa tctgaaggtt ctggtaacct gtggtgtatt    3600
tttattttcc tgtgactgtt tttgttttgt ttttttcctt tttcctcccc tttgaccta    3660
ttcatgtctc tacccactat gcacagatta aacttcacct acaaactcct taatatgatc    3720
tgtggagaat gtacacagtt taaacacatc aataaatact ttaacttcca ccgagaaaaa    3780
aaaaaaaaa a                                                         3791
```

<210> SEQ ID NO 4
<211> LENGTH: 2562
<212> TYPE: DNA
<213> ORGANISM: Homo sapiens

<400> SEQUENCE: 4

```
cttgacagac gtgaccctga cccaataagg gtggaaggct gagtcccgca gagccaataa      60
cgagagtccg agaggcgacg gaggcggact ctgtgaggaa acaagaagag aggcccaaga    120
tggagacggc ggcggctgta gcggcgtgac aggagcccca tggcacctgc ccagccccac    180
ctcagcccat cttgacaaaa tctaaggctc catggagcca ccacggggcc cccctgccaa    240
tggggccgag ccatcccggg cagtgggcac cgtcaaagta tacctgccca acaagcaacg    300
cacggtggtg actgtccggg atggcatgag tgtctacgac tctctagaca aggccctgaa    360
ggtgcgggt ctaaatcagg actgctgtgt ggtctaccga ctcatcaagg gacgaaagac    420
ggtcactgcc tgggacacag ccattgctcc cctggatggc gaggagctca ttgtcgaggt    480
ccttgaagat gtcccgctga ccatgcacaa ttttgtacgg aagaccttct tcagcctggc    540
gttctgtgac ttctgcctta agtttctgtt ccatggcttc cgttgccaaa cctgtggcta    600
caagttccac cagcattgtt cctccaaggt ccccacagtc tgtgttgaca tgagtaccaa    660
ccgccaacag ttctaccaca gtgtccagga tttgtccgga ggctccagac agcatgaggc    720
tccctcgaac cgcccctga atgagttgct aaccccccag ggtccagcc cccgcacca      780
gcactgtgac ccggagcact tccccttccc tgccccagcc aatgccccc tacagcgcat    840
ccgctccacg tccactccca acgtccatat ggtcagcacc acggccccca tggactccaa    900
```

| | | |
|---|---|---|
| cctcatccag ctcactggcc agagtttcag cactgatgct gccggtagta gaggaggtag | 960 | |
| tgatggaacc ccccggggga gccccagccc agccagcgtg tcctcgggga ggaagtcccc | 1020 | |
| acattccaag tcaccagcag agcagcgcga gcggaagtcc ttggccgatg acaagaagaa | 1080 | |
| agtgaagaac ctggggtacc gggactcagg ctattactgg gaggtaccac ccagtgaggt | 1140 | |
| gcagctgctg aagaggatcg ggacgggctc gtttggcacc gtgtttcgag ggcggtggca | 1200 | |
| tggcgatgtg gccgtgaagg tgctcaaggt gtcccagccc acagctgagc aggcccaggc | 1260 | |
| tttcaagaat gagatgcagg tgctcaggaa gacgcgacat gtcaacatct tgctgtttat | 1320 | |
| gggcttcatg acccggccgg gatttgccat catcacacag tggtgtgagg gctccagcct | 1380 | |
| ctaccatcac ctgcatgtgg ccgacacacg cttcgacatg gtccagctca tcgacgtggc | 1440 | |
| ccggcagact gcccagggca tggactacct ccatgccaag aacatcatcc accgagatct | 1500 | |
| caagtctaac aacatcttcc tacatgaggg gctcacggtg aagatcggtg actttggctt | 1560 | |
| ggccacagtg aagactcgat ggagcggggc ccagcccttg gagcagccct caggatctgt | 1620 | |
| gctgtggatg gcagctgagg tgatccgtat gcaggacccg aacccctaca gcttccagtc | 1680 | |
| agacgtctat gcctacgggg ttgtgctcta cgagcttatg actggctcac tgccttacag | 1740 | |
| ccacattggc tgccgtgacc agattatctt tatggtgggc cgtggctatc tgtccccgga | 1800 | |
| cctcagcaaa atctccagca actgccccaa ggccatgcgg cgcctgctgt ctgactgcct | 1860 | |
| caagttccag cgggaggagc ggcccctctt ccccagatc ctggccacaa ttgagctgct | 1920 | |
| gcaacggtca ctccccaaga ttgagcggag tgcctcggaa ccctccttgc accgcaccca | 1980 | |
| ggccgatgag ttgcctgcct gcctactcag cgcagcccgc cttgtgcctt aggccccgcc | 2040 | |
| caagccacca gggagccaat ctcagccctc cacgccaagg agccttgccc accagccaat | 2100 | |
| caatgttcgt ctctgccctg atgctgcctc aggatccccc attccccacc ctgggagatg | 2160 | |
| aggggtccc catgtgcttt tccagttctt ctggaattgg gggaccccg ccaaagactg | 2220 | |
| agcccctgt ctcctccatc atttggtttc ctcttggctt tggggatact tctaaatttt | 2280 | |
| gggagctcct ccatctccaa tggctgggat tgtgtggcagg gattccactc agaacctctc | 2340 | |
| tggaattgtg tgcctgatgtg ccttccactg gattttgggg ttcccagcac cccatgtgga | 2400 | |
| ttttgggggg tccctttgt gtctccccg ccattcaagg actcctctct ttcttcacca | 2460 | |
| agaagcacag aattctgctg ggcctttgct tgtttaaaaa aaaaaaaaaa aaaaaaaaa | 2520 | |
| aaaaaaaaa aaaaaaaaaa aaaaaaaaa aaaaaaaaa aa | 2562 | |

<210> SEQ ID NO 5
<211> LENGTH: 2186
<212> TYPE: DNA
<213> ORGANISM: Homo sapiens

<400> SEQUENCE: 5

| | | |
|---|---|---|
| agcagtcacg tgcctccgat cacgtgaccg gcgcctctgt cattctactg cggccgccct | 60 | |
| ggcttccttc tacctgtgcg gccctcaacg tctccttggt gcgggacccg cttcactttc | 120 | |
| ggctcccgga gtctccctcc actgctcaga cctctggacc tgacaggaga cgcctacttg | 180 | |
| gctctgacgc ggcgccccag cccggctgtg tccccggcgc cccggaccac cctccctgcc | 240 | |
| ggctttgggt gcgttgtggg gtcccgagga ttcgcgagat tgttgaaag acattcaaga | 300 | |
| ttacgaagtt tagatgacca aaatggatat ccgaggtgct gtggatgctg ctgtccccac | 360 | |
| caatattatt gctgccaagg ctgcagaagt tcgtgcaaac aaagtcaact ggcaatccta | 420 | |
| tcttcaggga cagatgattt ctgctgaaga ttgtgagttt attcagaggt ttgaaatgaa | 480 | |

| | | |
|---|---|---|
| acgaagccct gaagagaagc aagagatgct tcaaactgaa ggcagccagt gtgctaaaac | 540 | |
| atttataaat ctgatgactc atatctgcaa agaacagacc gttcagtata tactaactat | 600 | |
| ggtggatgat atgctgcagg aaaatcatca gcgtgttagc attttctttg actatgcaag | 660 | |
| atgtagcaag aacactgcgt ggccctactt tctgccaatg ttgaatcgcc aggatccctt | 720 | |
| cactgttcat atggcagcaa gaattattgc caagttagca gcttggggaa agaactgat | 780 | |
| ggaaggcagt gacttaaatt actatttcaa ttggataaaa actcagctga gttcacagaa | 840 | |
| actgcgtggt agcggtgttg ctgttgaaac aggaacagtc tcttcaagtg atagttcgca | 900 | |
| gtatgtgcag tgcgtggccg ggtgtttgca gctgatgctc cgggtcaatg agtaccgctt | 960 | |
| tgcttgggtg aagcagatg gggtaaattg cataatggga gtgttgagta caagtgtgg | 1020 | |
| ctttcagctc cagtatcaaa tgattttttc aatatggctc ctggcattca gtcctcaaat | 1080 | |
| gtgtgaacac ctgcggcgct ataatatcat tccagttctg tctgatatcc ttcaggagtc | 1140 | |
| tgtcaaagag aaagtaacaa gaatcattct tgcagcattt cgtaactttt tagaaaaatc | 1200 | |
| aactgaaaga gaaactcgcc aagaatatgc cctggctatg attcagtgca agttctgaa | 1260 | |
| acagttggag aacttggaac agcagaagta cgatgatgaa gatatcagcg aagatatcaa | 1320 | |
| atttcttttg gaaaaacttg gagagagtgt ccaggacctt agttcatttg atgaatacag | 1380 | |
| ttcagaactt aaatctggaa ggttggaatg gagtcctgtg cacaaatctg agaaattttg | 1440 | |
| gagagagaat gctgtgaggt taaatgagaa gaattatgaa ctcttgaaaa tcttgacaaa | 1500 | |
| acttttggaa gtgtcagatg atccccaagt cttagctgtt gctgctcacg atgttggaga | 1560 | |
| atatgtgcgg cattatccac gaggcaaacg ggtcatcgag cagctcggtg ggaagcagct | 1620 | |
| ggtcatgaac cacatgcatc atgaagacca gcaggtccgc tataatgctc tgctggccgt | 1680 | |
| gcagaagctc atggtgcaca actgggaata ccttggcaag cagctccagt ccgagcagcc | 1740 | |
| ccagaccgct gccgcccgaa gctaagcctg cctctggcct tcccctccgc tcaatgcag | 1800 | |
| aaccagtagt gggagcactg tgtttagagt taagagtgaa cactgtttga ttttacttgg | 1860 | |
| aatttcctct gttatatagc ttttcccaat gctaatttcc aaacaacaac aacaaaataa | 1920 | |
| catgtttgcc tgttaagttg tataaaagta ggtgattctg tatttaaaga aaatattact | 1980 | |
| gttacatata ctgcttgcaa tttctgtatt tattgttctc tggaaataaa tatagttatt | 2040 | |
| aaaggattct cactccaaac atggcctctc tctttacttg gactttgaac aaaagtcaac | 2100 | |
| tgttgtctct tttcaaacca aattgggaga attgttgcaa agtagtgaat ggcaaataaa | 2160 | |
| tgttttaaaa tctatcgctc tatcaa | 2186 | |

```
<210> SEQ ID NO 6
<211> LENGTH: 3505
<212> TYPE: DNA
<213> ORGANISM: Homo sapiens

<400> SEQUENCE: 6
```

| | | |
|---|---|---|
| cgtcagggc aggggaggga cggcgcaggc gcagaaaagg gggcggcgga ctcggcttgt | 60 | |
| tgtgttgctg cctgagtgcc ggagacggtc ctgctgctgc cgcagtcctg ccagctgtcc | 120 | |
| gacaatgtcg tcccacctag tcgagccgcc gccgcccctg cacaacaaca acaacaactg | 180 | |
| cgaggaaaat gagcagtctc tgccccgcc ggccggcctc aacagttcct gggtggagct | 240 | |
| acccatgaac agcagcaatg gcaatgataa tggcaatggg aaaaatgggg gctggaaca | 300 | |
| cgtaccatcc tcatcctcca tccacaatgg agacatggag aagattcttt tggatgcaca | 360 | |

```
acatgaatca ggacagagta gttccagagg cagttctcac tgtgacagcc cttcgccaca    420
agaagatggg cagatcatgt ttgatgtgga aatgcacacc agcagggacc atagctctca    480
gtcagaagaa gaagttgtag aaggagagaa ggaagtcgag gctttgaaga aaagtgcgga    540
ctgggtatca gactggtcca gtagacccga aaacattcca cccaaggagt tccacttcag    600
acaccctaaa cgttctgtgt ctttaagcat gaggaaaagt ggagccatga agaaggggg     660 tattttctcc gcagaatttc tgaaggtgtt cattccatct ctcttccttt ctcatgtttt    720
ggctttgggg ctaggcatct atattggaaa gcgactgagc acaccctctg ccagcaccta    780
ctgagggaaa ggaaaagccc ctggaaatgc gtgtgacctg tgaagtggtg tattgtcaca    840
gtagcttatt tgaacttgag accattgtaa gcatgaccca acctaccacc ctgtttttac    900
atatccaatt ccagtaactc tcaaattcaa tattttattc aaactctgtt gaggcatttt    960
actaacctta taccctttt ggcctgaaga cattttagaa tttcctaaca gagtttactg   1020
ttgtttagaa atttgcaagg gcttctttt cgcaaatgcc accagcagat tataattttg     1080
tcagcaatgc tattatctct aattagtgcc accagactag acctgtatca ttcatggtat   1140 aaatttact cttgcaacat aactaccatc tctctcttaa aacgagatca ggttagcaaa    1200
tgatgtaaaa gaagctttat tgtctagttg ttttttttcc cccaagacaa aggcaagttt   1260
ccctaagttt gagttgatag ttattaaaaa gaaacaaaa caaaaaaaaa aggcaaggca    1320
caacaaaaaa atatcctggg caataaaaaa aatattttaa accagctttg gagccacttt   1380
tttgtctaag cctcctaata gcgtctttta atttatagga ggcaaactgt ataaatgata   1440
ggtatgaaat agaataagaa gtaaaataca tcagcagatt ttcatactag tatgttgtaa   1500
tgctgtcttt tctatggtgt agaatctttc tttctgataa ggaacgtctc aggcttagaa   1560
atatatgaaa ttgcttttg agattttgc gtgtgtgttt gatatttttt acgataatta    1620
gctgcatgtg aattttcat gaccttcttt acattttta tttttatt ctttatttt         1680 ttttctctaa gaagaggctt tggaatgagt tccaatttgt gatgttaata caggcttctt   1740
gttttaggaa gcatcaccta tactctgaag cctttaaaact ctgaagagaa ttgtttcaga   1800
gttattccaa gcacttgtgc aacttggaaa aacagacttg ggttgtggga acagttgaca   1860
gcgttctgaa aagatgccat ttgtttcctt ctgatctctc actgaataat gtttactgta   1920
cagtcttccc aaggtgattc ctgcgactgc aggcactggt catttctca tgtagctgtc    1980 ttttcagtta tggtaaactc ttaaagttca gaacactcaa cagattcctt cagtgatata   2040
cttgttcgtt catttctaaa atgtgaagct ttaggaccaa attgttagaa agcatcagga   2100
tgaccagtta tctcgagtag atttctcttgg atttcagaac atctagcatg actctgaagg   2160
ataccacatg ttttatatat aaataattac tgtttatgat atagacattg atattgacta   2220
tttagagaac cgttgttaat tttaaaacta gcaatctata aagtgcacca ggtcaacttg   2280
aataaaaaca ctatgacaga caggtttgcc agtttgcaga aactaactct tttctcacat    2340
caacatttgt aaaattgatg tgttatagtg gaaaataaca tatagattaa acaaaatttt   2400 tatcttttt caagaatata gctggctatc tttaagaaag atgatatatc ctagttttga    2460
aagtaatttt ctttttctt tctagcattt gatgtctaaa taattttgga catctttttc    2520
ctagaccatg tttctgtctt actcttaaac ctggtaacac ttgatttgcc ttctataacc   2580
tatttatttc aagtgttcat atttgaattt ctttgggaag aaagtaaatc tgatggctca   2640 ctgattttg aaaagcctga ataaaattgg aaagactgga aagttaggag aactgactag     2700
ctaaactgct acagtatgca atttctatta caattggtat tacagggggg aaaagtaaaa   2760
```

| | |
|---|---|
| ttacacttta cctgaaagtg acttcttaca gctagtgcat tgtgctcttt ccaagttcag | 2820 |
| cagcagttct atcagtggtg ccactgaaac tgggtatatt tatgatttct ttcagcgtta | 2880 |
| aaaagaaaca tagtgttgcc cttttctta aagcatcagt gaaattatgg aaaattactt | 2940 |
| aaaacgtgaa tacatcatca cagtagaatt tattatgaga gcatgtagta tgtatctgta | 3000 |
| gccctaacac atgggatgaa cgttttactg ctacacccag atttgtgttg aacgaaaaca | 3060 |
| ttgtggtttg gaaaggagaa ttcaacaatt aatagttgaa attgtgaggt taatgtttaa | 3120 |
| aaagctttac acctgtttac aatttgggga caaaaaggca ggcttcattt ttcatatgtt | 3180 |
| tgatgaaaac tggctcaaga tgtttgtaaa tagaatcaag agcaaaactg cacaaacttg | 3240 |
| cacattggaa agtgcaacaa gttcccgtga ttgcagtaaa aatatttact attctaaaaa | 3300 |
| aatgagaatt gaagacttag ccagtcagat aagttttttc atgaacccgt tgtgaaaatt | 3360 |
| attggaatta actgagccaa agtgattatg cattcttcat ctattttagt tagcactttg | 3420 |
| tatcgttata tacagtttac aatacatgta taacttgtag ctataaacat tttgtgccat | 3480 |
| taaagctctc acaaaacttt aaaaa | 3505 |

<210> SEQ ID NO 7
<211> LENGTH: 2949
<212> TYPE: DNA
<213> ORGANISM: Homo sapiens

<400> SEQUENCE: 7

| | |
|---|---|
| cgcctccctt cccctcccc gcccgacagc ggccgctcgg gccccggctc tcggttataa | 60 |
| gatggcggcg ctgagcggtg gcggtggtgg cggcgcggag ccgggccagg ctctgttcaa | 120 |
| cggggacatg gagcccgagg ccggcgccgg cgccggcgcc gcggcctctt cggctgcgga | 180 |
| ccctgccatt ccggaggagg tgtggaatat caaacaaatg attaagttga cacaggaaca | 240 |
| tatagaggcc ctattggaca aatttggtgg ggagcataat ccaccatcaa tatatctgga | 300 |
| ggcctatgaa gaatacacca gcaagctaga tgcactccaa caaagagaac aacagttatt | 360 |
| ggaatctctg gggaacggaa ctgattttc tgtttctagc tctgcatcaa tggataccgt | 420 |
| tacatcttct tcctcttcta gcctttcagt gctaccttca tctctttcag ttttttcaaaa | 480 |
| tcccacagat gtggcacgga gcaaccccaa gtcaccacaa aaacctatcg ttagagtctt | 540 |
| cctgcccaac aaacagagga cagtggtacc tgcaaggtgt ggagttacag tccgagacag | 600 |
| tctaaagaaa gcactgatga tgagaggtct aatcccagag tgctgtgctg tttacagaat | 660 |
| tcaggatgga gagaagaaac caattggttg ggacactgat atttcctggc ttactggaga | 720 |
| agaattgcat gtggaagtgt tggagaatgt tccacttaca acacacaact ttgtacgaaa | 780 |
| aacgttttc accttagcat tttgtgactt ttgtcgaaag ctgcttttcc agggtttccg | 840 |
| ctgtcaaaca tgtggttata aatttcacca gcgttgtagt acagaagttc cactgatgtg | 900 |
| tgttaattat gaccaacttg atttgctgtt tgtctccaag ttcttgaac cacccaat | 960 |
| accacaggaa gaggcgtcct tagcagagac tgccctaaca tctggatcat cccttccgc | 1020 |
| acccgcctcg gactctattg gccccaaat tctcaccagt ccgtctcctt caaaatccat | 1080 |
| tccaattcca cagcccttcc gaccagcaga tgaagatcat cgaaatcaat ttgggcaacg | 1140 |
| agaccgatcc tcatcagctc ccaatgtgca tataaacaca atagaacctg tcaatattga | 1200 |
| tgacttgatt agagaccaag gatttcgtgg tgatggagga tcaaccacag gtttgtctgc | 1260 |
| tacccccct gcctcattac ctggctcact aactaacgtg aaagccttac agaaatctcc | 1320 |

```
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctctttt    2460 ttttaaggtg aaccaaagaa cacttgtgtg gttaaagact agatataatt tttcccccaaa    2520 ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttttta    2880 taacaatttg gaaaatgtgg atgtcttta tttccttgaa gcaataaact aagtttcttt    2940
ttataaaaa                                                          2949

<210> SEQ ID NO 8
<211> LENGTH: 2260
<212> TYPE: DNA
<213> ORGANISM: Homo sapiens

<400> SEQUENCE: 8
cgcagccccg gttcctgccc gcacctctcc ctccacacct ccccgcaagc tgagggagcc      60
ggctccggcc tcggccagcc caggaaggcg ctcccacagc gcagtggtgg gctgaagggc     120
tcctcaagtg ccgccaaagt gggagcccag gcagaggagg cgccgagagc gagggagggc     180
tgtgaggact gccagcacgc tgtcacctct caatagcagc ccaaacagat taagacatgg     240
gagatgtaca agggcagccg tggggctggc aacagcttcg taatcctggc ttcctgcttt     300
ctgggtcaaa gccctggtgg tgtgttcttg atatcggtcc atctagtggc gttgtttgat     360
tcctcccacc ttgctgatca ttcgtagtgt agccccaag gtgtggaata accccttaagc     420 ccttaccggg gtccttctgg actgagaatt gttgtaaagt aatactgctc aggtgaaaga     480
```

| | | | | |
|---|---|---|---|---|
| caacttgagt | ggttaaatta | ctgtcatgca | aagcgactag atggttcagc tgattgcacc | 540 |
| tttagaagtt | atgtggaacg | aggcagcaga | tcttaagccc cttgctctgt cacgcaggct | 600 |
| ggaatgcagt | ggtggaatca | tggctcacta | cagccctgac ctcctgggcc cagagatgga | 660 |
| gtctcgctat | tttgcccagg | ttggtcttga | acacctggct tcaagcagtc ctcctgcttt | 720 |
| tggcttcttg | aagtgcttgg | attacagtat | ttcagtttta tgctctgcaa caagtttggc | 780 |
| catgttggag | gacaatccaa | aggtcagcaa | gttggctact ggcgattgga tgctcactct | 840 |
| gaagccaaag | tctattactg | tgcccgtgga | aatccccagc tcccctctgg atgatacacc | 900 |
| ccctgaagac | tccattcctt | tggtctttcc | agaattagac cagcagctac agcccctgcc | 960 |
| gccttgtcat | gactccgagg | aatccatgga | ggtgttcaaa cagcactgcc aaatagcaga | 1020 |
| agaataccat | gaggtcaaaa | aggaaatcac | cctgcttgag caaggaaga aggagctcat | 1080 |
| tgccaagtta | gatcaggcag | aaaaggagaa | ggtggatgct gctgagctgg ttcgggaatt | 1140 |
| cgaggctctg | acggaggaga | tcggacgtt | gaggttggcc cagtctcaat gtgtggaaca | 1200 |
| actggagaaa | cttcgaatac | agtatcagaa | gaggcagggc tcgtcctaac tttaaatttt | 1260 |
| tcagtgtgag | catacgaggc | tgatgactgc | cctgtgctgg ccaaaagatt tttattttaa | 1320 |
| atgaatagtg | agtcagatct | attgcttctc | tgtattaccc acatgacaac tgtctataat | 1380 |
| gagtttactg | cttgccagct | tctagcttga | gagaagggat attttaaatg agatcattaa | 1440 |
| cgtgaaacta | ttactagtat | atgttttttgg | agatcagaat tcttttccaa agatatatgt | 1500 |
| tttttttcttt | tttaggaaga | tatgatcatg | ctgtacaaca gggtagaaaa tgataaaaat | 1560 |
| agactattga | ctgacccagc | taagaatcgt | gggctgagca gagttaaacc atgggacaaa | 1620 |
| cccataacat | gttcaccata | gtttcacgta | tgtgtatttt taaatttcat gcctttaata | 1680 |
| tttcaaatat | gctcaaattt | aaactgtcag | aaacttctgt gcatgtattt atatttgcca | 1740 |
| gagtataaac | ttttatactc | tgattttat | ccttcaatga ttgattatac taagaataaa | 1800 |
| tggtcacata | tcctaaaagc | ttcttcatga | aattattagc agaaaccatg tttgtaacca | 1860 |
| aagcacattt | gccaatgcta | actggctgtt | gtaataataa acagataagg ctgcatttgc | 1920 |
| ttcatgccat | gtgacctcac | agtaaacatc | tctgcctttg cctgtgtgtg ttctggggga | 1980 |
| gggggacat | ggaaaatat | tgtttggaca | ttacttgggt gagtgcccat gaaaacatca | 2040 |
| gtgaacttgt | aactattgtt | ttgttttgga | tttaaggaga tgttttagat cagtaacagc | 2100 |
| taataggaat | atgcgagtaa | attcagaatt | gaaacaattt ctccttgttc tacctatcac | 2160 |
| cacattttct | caaattgaac | tctttgttat | atgtccattt ctattcatgt aacttcttt | 2220 |
| tcattaaaca | tggatcaaaa | ctgacaaaaa | aaaaaaaaa | 2260 |

<210> SEQ ID NO 9
<211> LENGTH: 7680
<212> TYPE: DNA
<213> ORGANISM: Homo sapiens

<400> SEQUENCE: 9

| | | | | |
|---|---|---|---|---|
| ggggccgggg | ggcggagcct | tgcgggctgg | agcgaaagaa tgcggggct gagcgcagaa | 60 |
| gcggctcgag | gctggaagag | gatcttgggc | gccgccagtc tttagcacca gttggtgtag | 120 |
| gagttgagac | ctacttcaca | gtagttctgt | ggacaatcac aatgggaatc caaggagggt | 180 |
| ctgtcctgtt | cgggctgctg | ctcgtcctgg | ctgtcttctg ccattcaggt catagcctgc | 240 |
| agtgctacaa | ctgtcctaac | ccaactgctg | actgcaaaac agccgtcaat tgttcatctg | 300 |

```
atttttgatgc gtgtctcatt accaaagctg ggttacaagt gtataacaag tgttggaagt    360
ttgagcattg caatttcaac gacgtcacaa cccgcttgag ggaaaatgag ctaacgtact    420
actgctgcaa gaaggacctg tgtaacttta acgaacagct tgaaaatggt gggacatcct    480
tatcagagaa aacagttctt ctgctggtga ctccatttct ggcagcagcc tggagccttc    540
atccctaagt caacaccagg agagcttctc ccaaactccc cgttcctgcg tagtccgctt    600
tctcttgctg ccacattcta aaggcttgat attttccaaa tggatcctgt tgggaaagaa    660
taaaattagc ttgagcaacc tggctaagat agagggctc tgggagactt tgaagaccag     720
tcctgtttgc agggaagccc cacttgaagg aagaagtcta agagtgaagt aggtgtgact    780
tgaactagat tgcatgcttc ctcctttgct cttgggaaga ccagctttgc agtgacagct    840
tgagtgggtt ctctgcagcc ctcagattat ttttcctctg gctccttgga tgtagtcagt    900
tagcatcatt agtacatctt tggagggtgg ggcaggagta tatgagcatc ctctctcaca    960
tggaacgctt tcataaactt cagggatccc gtgttgccat ggaggcatgc caaatgttcc   1020
atatgtgggt gtcagtcagg gacaacaaga tccttaatgc agagctagag gacttctggc   1080
agggaagtgg ggaagtgttc cagatagcag ggcatgaaaa cttagagagg tacaagtggc   1140
tgaaaatcga gttttttcctc tgtctttaaa ttttatatgg gctttgttat cttccactgg   1200
aaaagtgtaa tagcatacat caatggtgtg ttaaagctat ttccttgcct ttttttttatt   1260
ggaatggtag gatatcttgg ctttgccaca cacagttaca gagtgaacac tctactacat   1320
gtgactggca gtattaagtg tgcttatttt aaatgttact ggtagaaagg cagttcaggt   1380
atgtgtgtat atagtatgaa tgcagtgggg acaccctttg tggttacagt ttgagacttc   1440
caaaggtcat ccttaataac aacagatctg caggggtatg ttttaccatc tgcatccagc   1500
ctcctgctaa ctcctagctg actcagcata gattgtataa ataccctttg taacggctct   1560
tagcacactc acagatgttt gaggctttca gaagctcttc taaaaaatga tacacacctt   1620
tcacaagggc aaacttttttc cttttcccctg tgtattctag tgaatgaatc tcaagattca   1680
gtagacctaa tgacatttgt atttatgat cttggctgta tttaatggca taggctgact    1740
tttgcagatg gaggaattttc ttgattaatg ttgaaaaaaa acccttgatt atactctgtt   1800
ggacaaaccg agtgcaatga atgatgcttt tctgaaaatg aaatataaca agtgggtgaa   1860
tgtggttatg gccgaaaagg atatgcagta tgcttaatgg tagcaactga agaagacat    1920
cctgagcagt gccagctttc ttctgttgat gccgttccct gaacatagga aaatagaaac    1980
ttgcttatca aaacttagca ttaccttggt gctctgtgtt ctctgttagc tcagtgtctt   2040
tccttacatc aataggtttt ttttttttttt tttggcctga ggaagtactg accatgccca    2100
cagccaccgg ctgagcaaag aagctcattt catgtgagtt ctaaggaatg agaaacaatt   2160
ttgatgaatt taagcagaaa atgaatttct gggaactttt ttggggggcgg gggggtgggg   2220
aattcagcca cactccagaa agccaggagt cgacagtttt ggaagcctct ctcaggattg   2280
agattctagg atgagattgg cttactgcta tcttgtgtca tgtacccact ttttggccag   2340
actacactgg gaagaaggta gtcctctaaa gcaaatctg agtgccacta aatggggaga    2400
tggggctgtt aagctgtcca aatcaacaag ggtcatataa atggccttaa actttgggt    2460
tgctttctgc aaaaagttgc tgtgactcat gccatagaca aggttgagtg cctggaccca   2520
aaggcaatac tgtaatgtaa agacatttat agtactaggc aaacagcacc ccaggtactc   2580
caggccctcc tggctggaga gggctgtggc aatagaaaat tagtgccaac tgcagtgagt   2640
cagcctaggt taaatagaga gtgtaagagt gctggacagg aacctccacc ctcatgtcac   2700
```

```
atttcttcaa tgtgaccctt ctggcccctc tcctcctgac agcggaacaa tgactgcccc    2760
gataggtgag gctggaggaa gaatcagtcc tgtccttggc aagctcttca ctatgacagt    2820
aaaggctctc tgcctgctgc caaggcctgt gactttctaa cctggcctca cgctgggtaa    2880
gcttaaggta gaggtgcagg attagcaagc ccacctggct accaggccga cagctacatc    2940
ctccaactga ccctgatcaa cgaagaggga ttcatgtgtc tgtctcagtt ggttccaaat    3000
gaaaccaggg agcaggggag ttaggaatcg aacaccagtc atgcctactg gctctctgct    3060
cgagagccaa taccctgtgc cctccactca tctggattta caggaactgt catagtgttc    3120
agtattgggt ggtgataagc ccattggatt gtccccttgg ggggatgagc taggggtgca    3180
aggaacacct gatgagtaga taagtggagc tcatggtatt tcctgaaaga tgctaatcta    3240
tttgccaaac ttggtcttga atgtactggg ggcttcaagg tatgggtata tttttcttgt    3300
gtccttgcag ttagcccccca tgtcttatgt gtgtcctgaa aaaataagag cctgcccaag    3360
actttgggcc tcttgacaga attaaccact tttatacatc tgagttctct tggtaagttc    3420
tttagcagtg ttcaaagtct actagctcgc attagtttct gttgctgcca acagatctga    3480
actaatgcta acagatcccc ctgagggatt cttgatgggc tgagcagctg gctgagcta    3540 gtactgactg acattcattg tgatgagggc agctttctgg tacaggattc taagctctat    3600
gttttatata cattttcatc tgtacttgca cctcacttta cacaagagga aactatgcaa    3660
agttagctgg atcgctcaag gtcacttagg taagttggca agtccatgct tcccactcag    3720
ctcctcaggt cagcaagtct acttctctgc ctattttgta tactctcttt aatatgtgcc    3780
tagctttgga aagtctagaa tgggtccctg gtgccttttt actttgaaga aatcagtttc    3840
tgcctctttt tggaaaagaa acaaagtgc aattgttttt tactggaaag ttacccaata    3900
gcatgaggtg aacaggacgt agttaggcct tcctgtaaac agaaaatcat atcaaaacac    3960
tatcttccca tctgtttctc aatgcctgct acttcttgta gatatttcat ttcaggagag    4020
cagcagttaa acccgtggat tttgtagtta ggaacctggg ttcaaaccct cttccactaa    4080
ttggctatgt ctctggacaa gttttttttt tttttttttt ttaaacccctt tctgaacttt    4140 cactttctat gtctacctca aagaattgtt gtgaggcttg agataatgca tttgtaaagg    4200
gtctgccaga taggaagatg ctagttatgg atttacaagg ttgttaaggc tgtaagagtc    4260
taaaacctac agtgaatcac aatgcattta cccccactga cttggacata agtgaaaact    4320
agccagaagt ctctttttca aattacttac aggttattca atataaaatt tttgtaatgg    4380
ataatcttat ttatctaaac taaagcttcc tgtttataca cactcctgtt attctgggat    4440
aagataaatg accacagtac cttaatttct aggtgggtgc ctgtgatggt tcattgtagg    4500
taaggacatt ttctctttt cagcagctgt gtaggtccag agcctctggg agaggagggg    4560
ggtagcatgc acccagcagg ggactgaact gggaaactca aggttctttt tactgtgggg    4620
tagtgagctg cctttctgtg atcggtttcc ctagggatgt tgctgttccc ctccttgcta    4680
ttcgcagcta catacaacgt ggccaacccc agtaggctga tcctatatat gatcagtgct    4740
ggtgctgact ctcaatagcc ccacccaagc tggctatagg tttacagata cattaattag    4800
gcaacctaaa atattgatgc tggtgttggt gtgacataat gctatggcca gaactgaaac    4860
ttagagttat aattcatgta ttagggttct ccagagggac agaattagta ggatatatgt    4920
atatatgaaa gggaggttat tagggagaac tggctcccac agttagaagg cgaagtcgca    4980
caataggccg tctgcaagct gggttagaga gaagccagta gtggctcagc ctgagttcaa    5040
```

```
aaacctcaaa actggggaag ctgacagtgc agccagcctt cagtctgtgg ccaaaggccc    5100
aagagcccct ggcaaccaac ccactggtgc aagtcctaga ttccaaaggc tgaagaacct    5160
ggagtctgat gtccaagagc aggaagagtg gaagaaagcc agaagactca gcaaacaagg    5220
tagacagtgt ctaccaccat agtggccata ccaaagaggc taccgattcc ttcctgctac    5280
ctggatccct gaagttgccc tggtctctgc accttctaaa cctagttctt aagagctttc    5340
cattacatga gctgtctcaa agccctccaa taaattctca gtgtaagctt ctgttgcttg    5400
tggacagaaa attctgacag acctaccctc taagtgttac tgtcaggata acatgagaac    5460
gcacaacagt aagtggtcac taagtgttag ctacggttat tttgcccaag gtagcatggc    5520
tagttgatgc cggttgatgg ggcttaaacc cagctccctc atcttccagg cctctgtact    5580
ccctattcca ctaaactacc tctcaggttt atttttttaa attcttactc tgcaagtaca    5640
taggaccaca tttacctggg aaaacaagaa taaaggctgc tctgcatttt ttagaaactt    5700
ttttgaaagg gagatgggaa tgcctgcacc cccaagtcca gaccaacaca atggttaatt    5760
gagatgaata ataaaggaaa gactgttctg ggcttcccag aatagcttgg tccttaaatt    5820
gtggcacaaa caacctcctg tcagagccag cctcctgcca ggaagagggg taggagacta    5880
gaggccgtgt gtgcagcctt gccctgaagg ctagggtgac aatttggagg ctgtccaaac    5940
accctggcct ctagagctgg cctgtctatt tgaaatgccg gctctgatgc taatcggcga    6000
ccctcaggca agttacttaa ccttacatgc ctcagttttc tcatctggaa aatgagaacc    6060
ctaggtttag ggttgttaga aaagttaaat gagttaagac aagtgcctgg gacacagtag    6120
cctcttgtgt gtgtttatca ttatgtcctc agcaggtcgt agaagcagct tctcaggtgt    6180
gaggctggcg cgattatctg gagtgggttg ggttttctag gatggacccc ctgctgcatt    6240
ttcctcattc atccaccagg gcttaatggg gaatcaagga atccatgtgt aactgtataa    6300
taactgtagc cacactccaa tgaccaccta ctagttgtcc ctggcactgc ttatacatat    6360
gtccatcaaa tcaatcctat gaagtagata ctgtcttcat tttatagatc agagacaatt    6420
ggggttcaga gagctgatgt gattttccca gggtcacaga gagtcccaga ttcaggcaca    6480
actcttgtat tccaagacac aaccactaca tgtccaaagg ctgcccagag ccaccgggca    6540
cggcaaattg tgacatatcc ctaaagaggc tgagcacctg gtcaggatct gatggctgac    6600
agtgtgtcca gatgcagagc tggagtgggg gaggggaagg ggggctcctt gggacagaga    6660
aggctttctg tgctttctct gaagggagca gtctgaggac caagggaacc cggcaaacag    6720
cacctcaggt actccaggcc ctcctggctg gagagggctg tggcaatgga aaattagtgc    6780
caactgcaat gagtcagcct cggttaaata gagagtgaag aatgctggac aggaacctcc    6840
accctcatgt cacatttctt cagtgtgacc cttctggccc ctctcctcct gacagcggaa    6900
caatgactgc cccgataggt gaggctggag gaagaatcag tcctgtcctt ggcaagctct    6960
tcactatgac agtaaaggct ctctgcctgc tgccaaggcc tgtgactttc taacctggcc    7020
tcacgctggg taagcttaag gtagaggtgc aggattagca agcccacctg gctaccaggc    7080
cgacagctac atctttcaac tgaccctgat caacgaagag ggacttgtgt ctctcagttg    7140
gttccaaatg aaaccaggga gcagggcgt taggaagctc caacaggatg gtacttaatg    7200
gggcatttga gtggagaggt aggtgacata gtgctttgga gcccagggag ggaaaggttc    7260
tgctgaagtt gaattcaaga ctgttctttc atcacaaact tgagtttcct ggacatttgt    7320
ttgcagaaac aaccgtaggg ttttgcctta acctcgtggg tttattatta cctcataggg    7380
actttgcctc ctgacagcag tttatgggtg ttcattgtgg cacttgagtt ttcttgcata    7440
```

```
cttgttagag aaaccaagtt tgtcatcaac ttcttattta accccctggc tataacttca    7500
tggattatgt tataattaag ccatccagag taaaatctgt ttagattatc ttggagtaag    7560
ggggaaaaaa tctgtaattt tttctcctca actagatata tacataaaaa atgattgtat    7620
tgcttcattt aaaaaatata acgcaaaatc tcttttcctt ctaaaaaaaa aaaaaaaaaa    7680

<210> SEQ ID NO 10
<211> LENGTH: 2880
<212> TYPE: DNA
<213> ORGANISM: Homo sapiens

<400> SEQUENCE: 10
gcttccctgg gtgccacggt catgtgactt cggcaagatg gctgccctga cagcggagca      60
ttttgcagca ctccagagcc tgctcaagct gctccaggct ctgcaccgcc tcactaggct     120
ggtggcattc cgtgacctgt cctctgccga ggcaattctg gctctctttc cagaaaattt     180
ccaccaaaac ctcaaaaacc tgctgacaaa gatcatccta gaacatgtgt ctacttggag     240
aaccgaagcc caggcaaatc agatctctct gccacgcctg gtcgatctgg actggagagt     300
ggatatcaaa acctcctcag acagcatcag ccgcatggcc gtccccacct gcctgctcca     360
gatgaagatc caagaagatc ccagcctatg cggagacaaa ccctccatct cagctgtcac     420
cgtggagctg agcaaagaaa cactggacac catgttagat ggcctgggcc gcatccgaga     480
ccaactctct gccgtggcca gtaaatgatc cagccagctg ccagggccac tgccatgacc     540
cagctgctca tgagtgataa atgtctcccc atatgcaggc tgcccttgca gctgcagctg     600
acaacaggca ggatggtggg gacagcaggg ggctactgcc atccagaagt tacagttgga     660 ttggaagaa gcagccagat cccccgctgt tctcactcat cttctttctc tttctgaagc     720
tggagagcag aagcccccat cttttgaaaag ctcctgagtg caacttaatt accaccatgg     780
cagggtgagg gaacatttgc atcgtcagct gcctctgcat agctgtttga gaaattcagg     840
cccaaatcat gcagcctatc caataagtaa gtttatttcc aacattagct ctaattagtt     900
catttccaat cccagaacac atggaggaa tcggacaggt gatgccagca gttcctgctc     960
ctctgtcagg gaagccaggc agagcccaca gagcatggtc catccagagt gttccctgag    1020 cccccctccac catactggaa cccctcttca gtgtaggaag tctgaaatgg gtgctaattc    1080
ccttcttcat gaaaccaggg ccctcttcct tcatctaatg cagccactcc taggtgaaga    1140
agtgggaata attggaaata acaacagtt ctaaaacttc catgattttt gtagcttctt    1200
ttgtccccaa gttgaagctt ttggccagta ccttctctag ttttttaaaga tgatcccaac    1260 ttcctaattc ccagctaagc ccttgaccca tggtgtgaca tgaaatcagg caattgaatc    1320
gcaccacttt ctgtgttttc acctgttacg tagaacaaaa ggaagcaagg tggccaggcg    1380
caatggctca cgcctgtaat cccagcactt tgggaggccg aggcaggcag atcatgaggt    1440
caggagatcg agaccatggt gaaacccat ctctactaaa aatacaaaaa attagctggg    1500
cgcggtggcg ggcatctgta gtcccagctc ctcgggaggc tgaggcagga aatggcgtg    1560 aacctgggag gcagagcttg cagtgagccg agatcgtgcc actgcactcc agtctgggtg    1620
acagagaagg actcgtctca aaaataaaa ataaataaaa aggaagcaag ctaatcatc    1680 agtatgtgct tgttacaaga gctatgatga aggcactcct tcgagtttaa ccaaatgaga    1740
tcatctctgt catgtgcctc acgcctcaca gggactccat gtgtgaagat tccccttca    1800 ctcaccagat catctccatg gcaacagctt gcagcctgct cttggagtgc tttgttttgg    1860
```

-continued

| | |
|---|---|
| cagcttctct gctagtttgt gtatggagtg aatggaggag gtaaatccac agattaagaa | 1920 |
| tatgctgtca ggagtcaggc agccaaggtc agaagccagc tctgcttctc agtggtaagg | 1980 |
| tgcttgactt ctacatctca attttcaccc actttgtact ttttcctaa attaaatgag | 2040 |
| tataatagta gtacctactt gataggactt ttgtgaaaat taaatgatat aatgcaccta | 2100 |
| aaaacagtac tgttacaact aataggaaag ctttgatta ttaatggatg agagtagaaa | 2160 |
| gcttggtgca tttattgtct catctactat aacagagttg gtgtgagaat tagtattatc | 2220 |
| atcctcccct tattgaccag gaaaccagct cattgagatt gagtcatctg ctggtaaatg | 2280 |
| gtctcattaa gaggtggacc catatttctc tagctttctc tttacaacac aggactttgc | 2340 |
| aaggaacata taattctgtg actagcgcca tttggaaaat gttgaaactg aagtagagat | 2400 |
| gagagatctt acgtctgcct acccagtgag atacgaggaa ggtcaaggga aaaaaaattc | 2460 |
| caagctcttc tttatctgct ataggaaatg aacattcaat tttttgcatg caacgacaag | 2520 |
| aggtcaagga ccccagaagc cagcccgcta cttccaagtt gagagcccct ggtcataccc | 2580 |
| tccagttgag ctcagatttg tcacaaattt acccctctcc tttccttcca ttccccatga | 2640 |
| cctgcagaga gagatgtcag ataccttcct cttggcctcc catgggcatc cataagaaac | 2700 |
| ttacttgaag caagaagccc agtataggtg tctgggcagt tggacatttc ctctagccag | 2760 |
| atctgtccga atagagccat ctgggtacat gacgcagagg gcatttgata aataactgga | 2820 |
| aaagtcaata atctttgct acccttcaaa aaaaaaaaaa aaaaaaaaaa aaaaaaaaaa | 2880 |

<210> SEQ ID NO 11
<211> LENGTH: 2358
<212> TYPE: DNA
<213> ORGANISM: Homo sapiens

<400> SEQUENCE: 11

| | |
|---|---|
| aaactcacac aacaactctt ccccgctgag aggagacagc cagtgcgact ccaccctcca | 60 |
| gctcgacggc agccgccccg gccgacagcc ccgagacgac agcccggcgc gtccggtcc | 120 |
| ccacctccga ccaccgccag cgctccaggc cccgccgctc cccgctcgcc gccaccgcgc | 180 |
| cctccgctcc gcccgcagtg ccaaccatga ccgccgccag tatgggcccc gtccgcgtcg | 240 |
| ccttcgtggt cctcctcgcc ctctgcagcc ggccggccgt cggccagaac tgcagcgggc | 300 |
| cgtgccggtg cccggacgag ccggcgccgc gctgcccggc gggcgtgagc ctcgtgctgg | 360 |
| acggctgcgg ctgctgccgc gtctgcgcca agcagctggg cgagctgtgc accgagcgcg | 420 |
| accccctgcg acccgcacaag ggcctcttct gtgacttcgg ctccccggcc aaccgcaaga | 480 |
| tcggcgtgtg caccgccaaa gatggtgctc cctgcatctt cggtggtacg gtgtaccgca | 540 |
| gcggagagtc cttccagagc agctgcaagt accagtgcac gtgcctggac ggggcggtgg | 600 |
| gctgcatgcc cctgtgcagc atggacgttc gtctgcccag ccctgactgc ccttcccga | 660 |
| ggagggtcaa gctgcccggg aaatgctgcg aggagtgggt gtgtgacgag cccaaggacc | 720 |
| aaaccgtggt tgggcctgcc ctcgcggctt accgactgga agacacgttt ggcccagacc | 780 |
| caactatgat tagagccaac tgcctggtcc agaccacaga gtggagcgcc tgttccaaga | 840 |
| cctgtgggat gggcatctcc acccgggtta ccaatgacaa cgcctcctgc aggctagaga | 900 |
| agcagagccg cctgtgcatg gtcaggcctt gcgaagctga cctggaagag aacattaaga | 960 |
| agggcaaaaa gtgcatccgt actcccaaaa tctccaagcc tatcaagttt gagctttctg | 1020 |
| gctgcaccag catgaagaca taccgagcta aattctgtgg agtatgtacc gacggccgat | 1080 |
| gctgcacccc ccacagaacc accaccctgc cggtggagtt caagtgccct gacggcgagg | 1140 |

```
tcatgaagaa gaacatgatg ttcatcaaga cctgtgcctg ccattacaac tgtcccggag    1200
acaatgacat ctttgaatcg ctgtactaca ggaagatgta cggagacatg gcatgaagcc    1260
agagagtgag agacattaac tcattagact ggaacttgaa ctgattcaca tctcattttt    1320
ccgtaaaaat gatttcagta gcacaagtta tttaaatctg tttttctaac tgggggaaaa    1380
gattcccacc caattcaaaa cattgtgcca tgtcaaacaa atagtctatc aaccccagac    1440
actggtttga agaatgttaa gacttgacag tggaactaca ttagtacaca gcaccagaat    1500
gtatattaag gtgtggcttt aggagcagtg ggagggtacc agcagaaagg ttagtatcat    1560
cagatagcat cttatacgag taatatgcct gctatttgaa gtgtaattga aaggaaaat    1620 tttagcgtgc tcactgacct gcctgtagcc ccagtgacag ctaggatgtg cattctccag    1680
ccatcaagag actgagtcaa gttgttcctt aagtcagaac agcagactca gctctgacat    1740
tctgattcga atgacactgt tcaggaatcg gaatcctgtc gattagactg gacagcttgt    1800
ggcaagtgaa tttgcctgta acaagccaga tttttaaaa tttatattgt aaatattgtg    1860
tgtgtgtgtg tgtgtgtata tatatatata tgtacagtta tctaagttaa tttaaagttg    1920
tttgtgcctt tttatttttg tttttaatgc tttgatattt caatgttagc ctcaatttct    1980
gaacaccata ggtagaatgt aaagcttgtc tgatcgttca aagcatgaaa tggatactta    2040
tatgaaaatt ctgctcagat agaatgacag tccgtcaaaa cagattgttt gcaaagggga    2100
ggcatcagtg tccttggcag gctgatttct aggtaggaaa tgtggtagcc tcacttttaa    2160
tgaacaaatg gcctttatta aaaactgagt gactctatat agctgatcag ttttttcacc    2220
tggaagcatt tgtttctact ttgatatgac tgtttttcgg acagtttatt tgttgagagt    2280
gtgaccaaaa gttacatgtt tgcacctttc tagttgaaaa taaagtgtat attttttcta    2340
taaaaaaaaa aaaaaaaa                                                  2358

<210> SEQ ID NO 12
<211> LENGTH: 4697
<212> TYPE: DNA
<213> ORGANISM: Homo sapiens

<400> SEQUENCE: 12
agacgctcgc ctggcagctg cgcacactcg gagcgccccg agcggcgcag atagggacgt      60
tggggctgtg ccccgcggcg cggcgcctgc cactgcgcag gcgcctcagg aagagctcgg     120
catcgcccct cttcctccag gtccccctc cccgcaactt cccacgagtg ccaggtgccg     180
cgagcgccga gttccgcgca ttggaaagaa gcgaccgcgg cggctggaac cctgattgct     240
gtccttcaac gtgttcatta tgaagttatt agtaatactt tgttttctg gacttataac     300 tggttttaga agtgactctt cctctagttt gccacctaag ttactactag tatccttga     360 tggcttcaga gctgattatc tgaagaacta tgaatttcct catctccaga attttatcaa     420
agaaggtgtt ttggtagagc atgttaaaaa tgttttattc acaaaaacat ttccaaacca     480
ctacagtatt gtgacaggct tgtatgaaga aagccatggc attgtggcta attccatgta     540
tgatgcagtc acaaagaaac acttttctga ctctaatgac aaggatcctt tttggtggaa     600
tgaggcagta cctatttggg tgaccaatca gcttcaggaa aacagatcaa gtgctgctgc     660
tatgtggcct ggtactgatg tacccattca cgataccatc tcttcctatt ttatgaatta     720
caactcctca gtgtcatttg aggaaagact aaataataatt actatgtggc taaacaattc     780
gaacccacca gtcacctttg caacactata ttgggaagaa ccagatgcaa gtggccacaa     840
```

```
atacggacct gaagataaag aaaacatgag cagagtgttg aaaaaaatag atgatcttat    900
cggtgactta gtccaaagac tcaagatgtt agggctatgg gaaaatctta atgtgatcat    960
tacaagtgat catgggatga cccagtgttc tcaggacaga ctgataaacc tggattcctg   1020
catcgatcat tcatactaca ctcttataga tttgagccca gttgctgcaa tacttcccaa   1080
aataaataga acagaggttt ataacaaact gaaaaactgt agccctcata tgaatgttta   1140
tctcaaagaa gacattccta acagatttta ttaccaacat aatgatcgaa ttcagcccat   1200
tattttggtt gccgatgaag ctggacaatt tgtgctaaat gaatcatcac aaaaattagg   1260
tgaccatggt tatgataatt ctttgcctag tatgcatcca tttctagctg cccacggacc   1320
tgcatttcac aaaggctaca agcatagcac aattaacatt gtggatattt atccaatgat   1380
gtgccacatc ctgggattaa aaccacatcc caataatggg acctttggtc atactaagtg   1440
cttgttagtt gaccagtggt gcattaatct cccagaagcc atcgcgattg ttatcggttc   1500
actcttggtg ttaaccatgc taacatgcct cataataatc atgcagaata gactttctgt   1560
acctcgtcca ttttctcgac ttcagctaca agaagatgat gatgatcctt taattgggtg   1620
acatgtgcta gggcttatac aaagtgtctt tgattaatca caaaactaag aatacatcca   1680
aagaatagtg ttgtaactat gaaaaagaat actttgaaag acaagaact tagactaagc   1740
atgttaaaat tattactttg ttttccttgt gttttgtttc ggtgcatttg ctaataagat   1800
aacgctgacc atagtaaaat tgttagtaaa tcattaggta acatcttgtg gtaggaaatc   1860
attaggtaac atcaatccta actagaaata ctaaaaatgg cttttgagaa aaatacttcc   1920
tctgcttgta ttttgcgatg aagatgtgat acatctttaa atgaaaatat accaaaattt   1980
agtaggcatg tttttctaat aaatttatat atttgtaaag aaaacaacag aaatctttat   2040
gcaatttgtg aattttgtat attagggagg aaaagcttcc tatattttta tatttacctt   2100
taattagttt gtatctcaag taccctcttg aggtaggaaa tgctctgtga tggtaaataa   2160
aattggagca gacagaaaag atatagcaaa tgaagaaata ttttaaggaa acctatttga   2220
aaaaaaagc aaagaccatt tgataaaagc ctgagttgtc accattatgt cttaagctgt   2280
tagtcttaaa gattattgtt aaaaaattca gaagaaaaga gagacaagtg ctcttctctc   2340
tatctatgct taatgccttt atgtaagtta cttagttgtt tgcgtgtgcc tgtgcaagtg   2400
tgtttgtgtg tggttgtgtg gacattatgt gatttactat ataaggaggt cagagatgga   2460
ctgtggccag gcttccacat tcctgaagca cacagatctc aggaaaggtt attttttgcac   2520
ttcatatttg tttactttct cctaactcac aagttaaaat cataacttaa tttcattaac   2580
ttttatcatt taactctctc atgtttgttg taacctgagg tatccaaatg ctacagaaaa   2640
atttatgacc caaatacaaa tctcaatttg actgggacag aatgaggaat ggagattttt   2700
gtatttatct ttgggacttt atgccttact ttttaggcta tagaatagtt aagaaatttt   2760
aaacaaaatt tagtatcttt tggtctttca caccattcat atgttaagtg gcagaatagc   2820
cttagtgcta cctccacttt tttctccagt atttgcatca cagaaataat ccctctgttt   2880
aacatgtttg ttcagagcca agggtttatt gtgaagaact gtcatcctgc ctttgctagc   2940
tggtaccttc tagtaatcaa aattaatatg aagaaactag gttgtgacag actagattat   3000
atttagtagg ggaaaaattg ggctcaagaa ccattcatca gtacgtgaga caagcagtta   3060
atagtatgat ctttaaagtt ttgacaatat aaaataaact tggtaactgt tttacaaata   3120
taaaagtata ataaatatgc agcccagtta aatattgatt atctgtgatg gtaaagaaca   3180
acagtggtgc cagtcatcaa acatacagtg cgtcctattg agtcactgct aatttcttga   3240
```

```
gcctggtatt tgctgcctat tgtatttgtg gttgttgaga ggcattttca aaccctgtat    3300
aaataatcca tgctgttggt cataagttaa ctgtattaag aacagtaaaa taaataaaaa    3360
ccaatagtac taattttgct ttaaaaaaat ttctaatttt tttcacataa aacaattatc    3420
ctaaaggtta atagttgatc gaaacagaat aatagaaaaa ttctacttta atttccatta    3480
aaaagcaaat agcattgaca catttaaagc ttttcattta aagtagtgga tgttttgaa     3540 gtatctaaaa tagtagcaga atattttata cttggtcctt gcaatggtgt gagttttaat    3600
gattgcatta tcgtgattgg tggttatgag tttcagaaat ctatacttgg catccaactc    3660
atgagtggat tttatatagg atggaacagg aaggtatgtc ctgtcagtat cttaacccctt   3720 tcaacaagac atttacctat ttgtctttcc ttacgttctc aaaatattaa ctcgaattgt    3780
aaattaagca aaaatttaaa aagtatatgt tgatgggaca agaagaatag tatttattta    3840
ataaaacata tattatattg aactatgtgt taattcattt gtatctttta aaaaattatc    3900
actgttaaag ccattgactc ctttagtaca ctgagaaaaa tcttatagta aaactagcct    3960
ttcacattaa ggttttggtg tgtattttgt taaataacta acatgctgct ctattttctg    4020
ggtgtagaaa gtatttggct ctaggaaaca tttacttgtt tgtgaaaaca ataccccaag    4080
gtaataggaa aagtttgagt taagtgtttt taattcagtc agtgaattca gaataagtac    4140
attcatgtat aacataggga cagttctgct gctgttattt atatgcaatt cttctggtaa    4200
atagcaatag aataaaacat atttcaatgt ttgtgtatag gttttatatt attattccac    4260
taggaatggc ataagaattt atagataaat tcttgtaaca ttaaaggatt aaaatgtttt    4320
tacattgttt ttgggtgtct ccttcttgtg cccatatctg ataagcttta tggattattg    4380
catttaattc cttttatttg gagggtttta cttccttgtt aacatataaa gttataaatg    4440
aaggacaagg aggagatgga aaatgtgtat ttattgttaa ttcttaaaat agtgtgtaaa    4500
taaaataaca tcagtgtgct ttaaagaaat gtgtatgtag tgccttaatt taaattaaaa    4560 tattttttgac tgttacttga gttcagaatt aatgactttg ttcatgatttt ttaaaatgtg    4620 tgtgaataaa atctaccaaa aaattcttac tgtaattatt aaatataaag ttcagtgtca    4680
aaaaaaaaaa aaaaaaa                                                   4697
```

<210> SEQ ID NO 13
<211> LENGTH: 2448
<212> TYPE: DNA
<213> ORGANISM: Homo sapiens

<400> SEQUENCE: 13

```
accggcccgg ttccctctcc ggggagcggc ggcggacgcg cggctccac ccctcccctc     60 tcacgggctc tcccctcccc agtgtggccg cgacccctacc ctctgcaagg cgatggcccg   120
cgccccgagc gcaggctagc gtgcctgggt gcccggccat gggctgtatc ggctctcgga   180
gcccggcggg tcaggcattt ctggggacca acagctggcc gaggctcagg atagagacg    240 gctgctccag ctaaaggtga atgttggaga cacagtcgcg atgctgccca agtcccggcg   300
agccctaact atccaggaga tcgctgcgct ggccaggtcc tccctgcatg gtatttccca   360
ggtggtgaag gaccacgtga ccaagcctac cgccatggcc cagggccgag tggctcacct   420
cattgagtgg aagggctgga gcaagccgag tgactcacct gctgccctgg aatcagcctt   480
ttcctcctat tcagacctca gcgagggcga acaagaggc cgctttgcag caggagtggc   540
tgagcagttt gccatcgcgg aagccaagct ccgagcatgg tcttcggtgg atggcgagga   600
```

```
ctccactgat gactcctatg atgaggactt tgctggggga atggacacag acatggctgg    660
gcagctgccc ctggggccgc acctccagga cctgttcacc ggccaccggt tctcccggcc    720
tgtgcgccag ggctccgtgg agcctgagag cgactgctca cagaccgtgt ccccagacac    780
cctgtgctct agtctgtgca gcctggagga tgggttgttg ggctcccggg ccggctggc     840 ctcccagctg ctgggcgatg agctgcttct cgccaaactg cccccagcc gggaaagtgc     900 cttccgcagc ctgggccac tggaggccca ggactcactc tacaactcgc ccctcacaga     960
gtcctgcctt tccccgcgg aggaggagcc agcccctgc aaggactgcc agccactctg    1020
cccaccacta acgggcagct gggaacggca gcggcaagcc tctgacctgg cctcttctgg   1080
ggtggtgtcc ttagatgagg atgaggcaga gccagaggaa cagtgaccca catcatgcct   1140
ggcagtggca tgcatccccc ggctgctgcc aggggcagag cctctgtgcc caagtgtggg   1200
ctcaaggctc ccagcagagc tccacagcct agagggctcc tgggagcgct cgcttctccg   1260
ttgtgtgttt tgcatgaaag tgtttggaga ggaggcaggg gctgggctgg gggcgcatgt   1320
cctgccccca ctcccggggc ttgccggggg ttgcccgggg cctctggggc atggctacag   1380
ctgtggcaga cagtgatgtt catgttctta aaatgccaca cacacatttc ctcctcggat   1440
aatgtgaacc actaaggggg ttgtgactgg gctgtgtgag ggtggggtgg gaggggccc    1500 agcaaccccc caccctcccc atgcctctct cttctctgct tttcttctca cttccgagtc   1560
catgtgcagt gcttgataga atcacccccca cctggagggg ctggctcctg ccctcccgga  1620
gcctatgggt tgagccgtcc ctcaagggcc cctgcccagc tgggctcgtg ctgtgcttca   1680
ttcacctctc catcgtctct aaatcttcct cttttttcct aaagacagaa ggttttttggt 1740 ctgttttttc agtcggatct tctcttctct gggaggcttt ggaatgatga aagcatgtac   1800
cctccaccct tttcctggcc ccctaatggg gcctgggccc tttcccaacc cctcctagga   1860
tgtgcgggca gtgtgctggc gcctcacagc cagccgggct gcccattcac gcagagctct   1920
ctgagcggga ggtggaagaa aggatggctc tggttgccac agagctggga cttcatgttc   1980
ttctagagag ggccacaaga gggccacagg ggtggccggg agttgtcagc tgatgcctgc   2040
tgagaggcag gaattgtgcc agtgagtgac agtcatgagg gagtgtctct tcttggggag   2100
gaaagaaggt agagcctttc tgtctgaatg aaaggccaag gctacagtac agggccccac   2160
cccagccagg gtgttaatgc ccacgtagtg gaggcctctg gcagatcctg cattccaagg   2220
tcactggact gtacgttttt atggttgtgg aagggtggg tggctttaga attaagggcc    2280
ttgtaggctt tggcaggtaa gagggcccaa ggtaagaacg agagccaacg ggcacaagca   2340
ttctatatat aagtggctca ttaggtgttt attttgttct atttaagaat tgttttatt    2400 aaattaatat aaaaatcttt gtaaatctct aaaaaaaaaa aaaaaaaa              2448
```

<210> SEQ ID NO 14
<211> LENGTH: 5948
<212> TYPE: DNA
<213> ORGANISM: Homo sapiens

<400> SEQUENCE: 14

```
ggagcgggcc gagccgccac cgcggccgga gctgtcccct agccagaccc ggcgagacac     60
gagcggcggg agggaggcgg tggcgcgccc ggccccgccc gcccgaccaa gcgtcggacg    120
cggcccggcg ccgagccatg gagcctgagc cagtggagga ctgtgtgcag agcactctcg    180
ccgccctgta tccacccttt gaggcaacag ccccccaccct gttgggccag gtgttccagg    240
tggtggagag gacttatcgg gaggacgcac tgaggtacac gctggacttc ctggtaccag    300
```

-continued

```
ccaagcacct gcttgccaag gtccagcagg aagcctgtgc ccaatacagt ggattcctct    360
tcttccatga ggggtggccg ctctgcctgc atgaacaggt ggtggtgcag ctagcagccc    420
taccctggca actgctgcgc ccaggagact tctatctgca ggtggtgccc tcagctgccc    480
aagcaccccg actagcactc aagtgtctgg cccctggggg tgggcgggtg caggaggttc    540
ctgtgcccaa tgaggcttgt gcctacctat tcacacctga gtggctacaa ggcatcaaca    600
aggaccggcc aacaggtcgc ctcagtacct gcctactgtc tgcgccctct gggattcagc    660
ggctgccctg gctgagctc atctgtccac gatttgtgca caaagagggc ctcatggttg     720
gacatcagcc aagtacactg cccccagaac tgccctctgg acctccaggg cttcccagcc    780
ctccacttcc tgaggaggcg ctgggtaccc ggagtcctgg ggatgggcac aatgcccctg    840
tggaaggacc tgagggcgag tatgtggagc tgttagaggt gacgctgccc gtgaggggga    900
gcccaacaga tgctgaaggc tccccaggcc tctccagagt ccggacggta cccacccgca    960
agggcgctgg agggaagggc cgccaccgga gacaccgggc gtggatgcac cagaagggcc   1020
tggggcctcg gggccaggat ggagcacgcc caccggcga ggggagcagc accggagcct    1080
cccctgagtc tcccccagga gctgaggctg tcccagaggc agcagtcttg gaggtgtctg   1140
agccccagc agaggctgtg ggagaagcct ccggatcttg cccctgagg ccaggggagc     1200
ttagaggagg aggaggagga ggccaggggg ctgaaggacc acctggtacc cctcggagaa   1260
caggcaaagg aaacagaaga aagaagcgag ctgcaggtcg aggggctctt agccgaggag   1320
gggacagtgc cccactgagc cctggggaca aggaagatgc cagccaccaa gaagcccttg   1380
gcaatctgcc ctcaccaagt gagcacaagc ttccagaatg ccacctggtt aaggaggaat   1440
atgaaggctc agggaagcca gaatctgagc caaaagagct caaaacagca ggcgagaaag   1500
agcctcagct ctctgaagcc tgtgggccta cagaagaggg ggccggagag agagagctgg   1560
aggggccagg cctgctgtgt atggcaggac acacaggccc agaaggcccc ctgtctgaca   1620
ctccaacacc tccgctggag actgtgcagg aaggaaaagg ggacaacatt ccagaagagg   1680
cccttgcagt ctccgtctct gatcaccctg atgtagcttg ggacttgatg gcatctggat   1740
tcctcatcct gacgggaggg gtggaccaga gtgggcgagc tctgctgacc attaccccac   1800
cgtgccctcc tgaggagccc ccaccctccc gagacacgct gaacacaact cttcattacc   1860
tccactcact gctcaggcct gatctacaga cactgggggt gtccgtcctg ctggaccttc   1920
gtcaggcacc tccactgcct ccagcactca ttcctgcctt gagccaactt caggactcag   1980
gagatcctcc ccttgttcag cggctgctga ttctcattca tgatgacctt ccaactgaac   2040
tctgtggatt tcagggtgct gaggtgctgt cagagaatga tctgaaaaga gtggccaagc   2100
cagaggagct gcagtgggag ttaggaggtc acagggaccc ctctcccagt cactgggtag   2160
agatacacca ggaagtggta aggctatgtc gcctgtgcca aggtgtgctg ggctcggtac   2220
ggcaggccat tgaggagctg gagggagcag cagagccaga ggaagaggag gcagtgggaa   2280
tgcccaagcc actgcagaag gtgctggcag atccccggct gacggcactg cagagggatg   2340
ggggggccat cctgatgagg ctgcgctcca ctcccagcag caagctggag gccaaggcc    2400
cagctacact gtatcaggaa gtggacgagg ccattcacca gcttgtgcgc ctctccaacc   2460
tgcacgtgca gcagcaagag cagcggcagt gcctgcggcg actccagcag gtgttgcagt   2520
ggctctcggg cccaggggag gagcagctgg caagctttgc tatgcctggg gacaccttgt   2580
ctgccctgca ggagacagag ctgcgattcc gtgctttcag cgctgaggtc caggagcgcc   2640
```

```
tggcccaggc acggsaggcc ctggctctgg aggagaatgc cacctcccag aaggtgctgg    2700
atatctttga acagcggctg gagcaggttg agagtggcct ccatcgggcc ctgcggctac    2760
agcgcttctt ccagcaggca catgaatggg tggatgaggg cttgctcgg ctggcaggag     2820 ctgggccggg tcggaggct gtgctggctg cactggccct cgcggcggcc ccagagccca    2880
gtgccggcac cttccaggag atgcgggccc tggccctgga cctgggcagc ccagcagccc    2940
tgcgagaatg gggccgctgc caggcccgct gccaagagct agagaggagg atccagcaac    3000
acgtgggaga ggaggcgagc ccacggggct accgacgacg gcgggcagac ggtgccagca    3060 gtggagggc ccagtgggggg ccccgcagcc cctcgcccag cctcagctcc ttgctgctcc    3120
ccagcagccc tgggccacgg ccagccccat cccattgctc cctggcccca tgtggagagg    3180
actatgagga agagggccct gagctggctc cagaagcaga gggcaggccc caagagctg     3240 tgctgatccg aggcctggag gtcaccagca ctgaggtggt agacaggacg tgctcaccac    3300
gggaacacgt gctgctgggc cgggctaggg ggccagacgg accctgggga gtaggcaccc    3360
cccggatgga gcgcaagcga agcatcagtg cccagcagcg gctggtgtct gagctgattg    3420
cctgtgaaca agattacgtg gccaccttga gtgagccagt gccaccccct gggcctgagc    3480
tgacgcctga acttcggggc acctgggctg ctgccctgag tgcccgggaa aggcttcgca    3540
gcttccaccg gacacacttt ctgcgggagc ttcagggctg cgccacccac cccctacgca    3600 ttgggggcctg cttccttcgc cacggggacc agttcagcct ttatgcacag tacgtgaagc    3660
accgacacaa actggagaat ggtctggctg cgctcagtcc cttaagcaag ggctccatgg    3720
aggctggccc ttacctgccc cgagccctgc agcagcctct ggaacagctg actcggtatg    3780
ggcggctcct ggaggagctc ctgagggaag ctgggcctga gctcagttct gagtgccggg    3840
ccccttgggg tgctgtacag ctgctccggg aacaagaggc ccgtggcaga gacctgctgg    3900
ccgtggaggc ggtgcgtggc tgtgagatag atctgaagga gcagggacag ctcttgcatc    3960
gagacccctt cactgtcatc tgtggccgaa agaagtgcct tcgccatgtc tttctcttcg    4020
agcatctcct cctgttcagc aagctcaagg gccctgaagg ggggtcagag atgtttgttt    4080
acaagcaggc cttaagact gctgatatgg ggctgacaga aaacatcggg acagcggac      4140 tctgctttga gttgtggttt cggcggcggc gtgcacgaga ggcatacact ctgcaggcaa    4200
cctcaccaga gatcaaactc aagtggacaa gttctattgc ccagctgctg tggagacagg    4260
cagcccacaa caaggagctc cgagtgcagc agatggtgtc catgggcatt gggaataaac    4320
ccttcctgga catcaaagcc cttggggagc ggacgctgag tgccctgctc actggaagag    4380
ccgcccgcac ccgggcctcc gtggccgtgt catcctttga gcatgccggc ccctcccttc    4440
ccggcctttc gccgggagcc tgctccctgc ctgcccgcgt cgaggaggag gcctgggatc    4500
tggacgtcaa gcaaatttcc ctggcccag aaacacttga ctcttctgga gatgtgtccc     4560
caggaccaag aaacagcccc agcctgcaac ccccccaccc tgggagcagc actcccaccc    4620
tggccagtcg agggatctta ggctataccc gacagagtca tgctcgagcc ctgagtgacc    4680
ccaccacgcc tctgtgacct ggagaagatc cagaacttgc gtgcagcttc tcctctcagc    4740
acactttggg ctgggatggc agtggggcat aatggagccc tgggcgatcg ctgaatttct    4800
tccctctgct tcctggacac agaggaggtc taacgaccag agtattgccc tgccaccact    4860
atctctagtc tccctagctt ggtgccttct cctgcaggag tcagagcagc acattgcttt    4920
gccttcatac cctggaggtg gggaagttat ccctcttccg gtgctttccc atcctgggcc    4980
actgtatcca ggacatcact cccatgccag ccctccctgg cagcccatgt tctcctcttt    5040
```

```
tctcaccccc tgactttccc tgagaagaat catctctgcc aggtcaactg gagtccctgg      5100
tgactccatt ctgaggtgtc acaagcaatg aagctatgca acaataggaa gggtgtgaca      5160
ggggaaccgt agactttata tatgtaatta ctgttattat aatactattg ttatattaaa      5220
tgtatttact cacactttgc ctctaaggag ctagagtagt cctctggatt aaggtgataa      5280
ataacttgag cactttccct caaccagccc ttaactagaa cacagaaaat aaaaccaaga      5340
ctggaaggtc ccctctaccc ctcccaggcc cagagctagc tgactgtgta tgagcctggg      5400
agaatgtgtc tcctccacag tggctcccag aggttccaca cactctctga agctccttct      5460
cccacactgc acctactcct tgaggctgaa ctggtcacag acaaactggg atccagcaca      5520
gtccagcagt tctcaaaatg aggtcctcag gccacagtgc gtgagaactt gcttggctgt      5580
ttgttaaatg ctaattcttg gccccatca gagctactgc atcgaaacct gggggtaaaa       5640
cccaatattc tgcatttctt atcaaactct ttgggtgata actaagtgtc tgaagaggtg      5700
actatttcct gacagaagga cccaaagagg aagcaggac ataggtaggc agacagacac       5760
agggccctgt gcctcaagac acctgtttat tggggacacg actctgcaat agggatgaca      5820
ggaatcgtac caaaaatagc gacgtctaca ggggccctga tggggctaga agggtacagt      5880 gcccccacc ctcacccctt gtacaaaaat aaactctcac gcctatggac cagcaaaaaa        5940
aaaaaaaa                                                               5948

<210> SEQ ID NO 15
<211> LENGTH: 3851
<212> TYPE: DNA
<213> ORGANISM: Homo sapiens

<400> SEQUENCE: 15
ctctcccaac cgcctcgtcg cactcctcag gctgagagca ccgctgcact cgcggccggc        60
gatgcgggac cccggcgcgg ccgctccgct ttcgtccctg ggcctctgtg ccctggtgct       120
ggcgctgctg ggcgcactgt ccgcgggcgc cggggcgcag ccgtaccacg agagaaggg       180 catctccgtg ccggaccacg gcttctgcca gcccatctcc atcccgctgt gcacggacat      240
cgcctacaac cagaccatcc tgcccaacct gctgggccac acgaaccaag aggacgcggg      300
cctcgaggtg caccagttct acccgctggt gaaggtgcag tgttctcccg aactccgctt      360
tttcttatgc tccatgtatg cgcccgtgtg caccgtgctc gatcaggcca tcccgccgtg      420
tcgttctctg tgcgagcgcg cccgccaggg ctgcgaggcg ctcatgaaca agttcggctt      480
ccagtggccc gagcggctgc gctgcgagaa cttcccggtg cacggtgcgg gcgagatctg      540
cgtgggccag aacacgtcgg acggctccgg gggcccaggc ggcggcccca ctgcctaccc      600
taccgcgccc tacctgccgg acctgcccct caccgcgctg cccccggggg cctcagatgg      660
cagggggcgt cccgccttcc ccttctcatg ccccgtcag ctcaaggtgc cccgtacct        720 gggctaccgc ttcctggggt agcgcgattg tggcgcccg tgcgaaccgg gccgtgccaa       780
cggcctgatg tactttaagg aggaggagag gcgcttcgcc cgcctctggg tgggcgtgtg      840
gtccgtgctg tgctgcgcct cgacgctctt taccgttctc acctacctgg tggacatgcg      900
gcgcttcagc tacccagagc ggcccatcat cttcctgtcg ggctgctact tcatggtggc      960
cgtggcgcac gtggccggct tccttctaga ggaccgcgcc gtgtgcgtgg agcgcttctc     1020
ggacgatggc taccgcacgg tggcgcaggg caccaagaag gagggctgca ccatcctctt     1080
catggtgctc tacttcttcg gcatggccag ctccatctgg tgggtcattc tgtctctcac     1140
```

```
ttggttcctg gcggccggca tgaagtgggg ccacgaggcc atcgaggcca actcgcagta    1200
cttccacctg gccgcgtggg ccgtgcccgc cgtcaagacc atcactatcc tggccatggg    1260
ccaggtagac ggggacctgc tgagcggggt gtgctacgtt ggcctctcca gtgtggacgc    1320
gctgcgggc ttcgtgctgg cgcctctgtt cgtctacctc ttcataggca cgtccttctt    1380
gctggccggc ttcgtgtccc tcttccgtat ccgcaccatc atgaaacacg acggcaccaa    1440
gaccgagaag ctggagaagc tcatggtgcg catcggcgtc ttcagcgtgc tctacacagt    1500
gcccgccacc atcgtcctgg cctgctactt ctacgagcag gccttccgcg agcactggga    1560
gcgcacctgg ctcctgcaga cgtgcaagag ctatgccgtg ccctgcccgc ccggccactt    1620
cccgcccatg agccccgact tcaccgtctt catgatcaag tacctgatga ccatgatcgt    1680
cggcatcacc actggcttct ggatctggtc gggcaagacc ctgcagtcgt ggcgccgctt    1740
ctaccacaga cttagccaca gcagcaaggg ggagactgcg gtatgagccc cggcccctcc    1800
ccaccttttcc cacccccagcc ctcttgcaag aggagaggca cggtagggaa aagaactgct    1860
gggtggggc ctgtttctgt aactttctcc ccctctactg agaagtgacc tggaagtgag    1920
aagttctttg cagatttggg gcgaggggtg atttggaaaa aagacctgg gtggaaagcg    1980
gtttggatga aaagatttca ggcaaagact tgcaggaaga tgatgataac ggcgatgtga    2040
atcgtcaaag gtacgggcca gcttgtgcct aatagaaggt tgagaccagc agagactgct    2100
gtgagtttct cccggctccg aggctgaacg gggactgtga gcgatccccc tgctgcaggg    2160
cgagtggcct gtccagaccc ctgtgaggcc ccgggaaagg tacagccctg tctgcggtgg    2220
ctgctttgtt ggaagaggg agggcctcct gcggtgtgct tgtcaagcag tggtcaaacc    2280
ataatctctt ttcactgggg ccaaactgga gcccagatgg gttaatttcc agggtcagac    2340
attacggtct ctcctcccct gccccctccc gcctgttttt cctcccgtac tgctttcagg    2400
tcttgtaaaa taagcatttg gaagtcttgg gaggcctgcc tgctagaatc ctaatgtgag    2460
gatgcaaaag aaatgatgat aacatttga gataaggcca aggagacgtg gagtaggtat    2520
ttttgctact ttttcatttt ctggggaagg caggaggcag aaagacgggt gttttatttg    2580
gtctaatacc ctgaaaagaa gtgatgactt gttgctttc aaaacaggaa tgcattttc    2640
cccttgtctt tgttgtaaga gacaaaagag gaaacaaaag tgtctccctg tggaaaggca    2700
taactgtgac gaaagcaact tttataggca aagcagcgca aatctgaggt ttcccgttgg    2760
ttgttaattt ggttgagata acattcctt tttaaggaaa agtgaagagc agtgtgctgt    2820
cacacaccgt taagccagag gttctgactt cgctaaagga aatgtaagag gttttgttgt    2880
ctgtttttaaa taaatttaat tcggaacaca tgatccaaca gactatgtta aaatattcag    2940
ggaaatctct cccttcattt acttttctctt gctataagcc tatatttagg tttcttttct    3000
attttttct cccatttgga tcctttgagg taaaaaaaca taatgtcttc agcctcataa    3060
taaaggaaag ttaattaaaa aaaaaagca aagagccatt ttgtcctgtt ttcttggttc    3120
catcaatctg tttattaaac atcatccata tgctgaccct gtctctgtgt ggttgggttg    3180
ggaggcgatc agcagatacc atagtgaacg aagaggaagg tttgaaccat gggccccatc    3240
tttaaagaaa gtcattaaaa gaaggtaaac ttcaaagtga ttctggagtt ctttgaaatg    3300
tgctggaaga cttaaattta ttaatcttaa atcatgtact tttttttctgt aatagaactc    3360
ggattctttt gcatgatggg gtaaagctta gcagagaatc atgggagcta acctttatcc    3420
cacctttgac actaccctcc aatcttgcaa cactatcctg tttctcagaa cagttttaaa    3480
atgccaatca tagagggtac tgtaaagtgt acaagttact ttatatatgt aatgttcact    3540
```

```
tgagtggaac tgcttttac attaaagtta aaatcgatct tgtgtttctt caaccttcaa    3600
aactatctca tctgtcagat ttttaaaact ccaacacagg ttttggcatc ttttgtgctg    3660
tatctttaa gtgcatgtga aatttgtaaa atagagataa gtacagtatg tatattttgt    3720
aaatctccca tttttgtaag aaaatatata ttgtatttat acatttttac tttggatttt    3780
tgttttgttg gctttaaagg tctaccccac tttatcacat gtacagatca caaataaatt    3840
ttttaaata c                                                          3851

<210> SEQ ID NO 16
<211> LENGTH: 2394
<212> TYPE: DNA
<213> ORGANISM: Homo sapiens

<400> SEQUENCE: 16
gacgggccgg tacagcccgt gtccccgccc cgcgccatcg ctaggcgacg tgcgcttttg      60
ccgcgccgtg ctcccgcga gggcagctga ggtggtggtg gcggccgcct tgtcgaggca     120
tcgcgcgccc gtgaagtgtt cgccgtcagt gctgttgggt gcctggagcc gcgtcccccg     180
tcccgaaaac tgtccttgac agtacttgcg cggcccaacg gccgccggcg ccccgcgtc     240
tccatggcga cggcctttt ccctgcgagg accccggcgg cagggctgcc ccgcggcgcc     300
tgcttggcgc gacgctctag cggttaccgc tgcgggctgg ctgggcgtag tggggctgcg     360
cggctgccac ggagctagag ggcaagtgtg ctcggcccag cgtgcaggga acgcgggcgg     420
ccagacaacg ggctgggctc cggggcctgc ggcgcgggcg ctgagctggc agggcgggtc     480
ggggcgcggg ctgcatccgc atctcctcca tcgcctgcag taagggcggc cgcggcgagc     540
ctttgagggg aacgacttgt cggagcccta accaggggta tctctgagcc tggtgggatc     600
cccggagcgt cacatcactt tccgatcact tcaaagtaca gcagaccgag gacacggttg     660
ttaccaagac caggctgttg ccttggaaga gcccagagcg tgtcaaggga gacagccaca     720
tcacgccaga aatacatgac agctggatta gccctgggag agggaggccc agatgtggga     780
gctcagggga ggtgcagctc aacgtggagt ttggaggagg ctaccttgac ctttgaatgc     840
caagtgggag ccagccagat gaaagggtt aaaaactaat atttatatga cagaagaaaa     900
agatgtcatt ccgtaaagta aacatcatca tcttggtcct ggctgttgct ctcttcttac     960
tggttttgca ccataacttc ctcagcttga gcagtttgtt aaggaatgag gttacagatt    1020
caggaattgt agggcctcaa cctatagact ttgtcccaaa tgctctccga catgcagtag    1080
atgggagaca agaggagatt cctgtggtca tcgctgcatc tgaagacagg cttggggggg    1140
ccattgcagc tataaacagc attcagcaca acactcgctc caatgtgatt ttctacattg    1200
ttactctcaa caatacagca gaccatctcc ggtcctggct caacagtgat tccctgaaaa    1260
gcatcagata caaaattgtc aatttgacc ctaaactttt ggaaggaaaa gtaaaggagg    1320
atcctgacca gggggaatcc atgaaacctt aacctttgc aaggttctac ttgccaattc    1380
tggttcccag cgcaaagaag gccatataca tggatgatga tgtaattgtg caaggtgata    1440
ttcttgccct ttacaataca gcactgaagc caggacatgc agctgcattt tcagaagatt    1500
gtgattcagc tctactaaa gttgtcatcc gtggagcagg aaaccagtac aattacattg    1560
gctatcttga ctataaaaag gaaagaattc gtaagctttc catgaaagcc agcacttgct    1620
catttaatcc tggagttttt gttgcaaacc tgacggaatg gaaacgacag aatataacta    1680
accaactgga aaaatggatg aaactcaatg tagaagaggg actgtatagc agaaccctgg    1740
```

-continued

| | |
|---|---|
| ctggtagcat cacaacacct cctctgctta tcgtatttta tcaacagcac tctaccatcg | 1800 |
| atcctatgtg gaatgtccgc caccttggtt ccagtgctgg aaaacgatat tcacctcagt | 1860 |
| ttgtaaaggc tgccaagtta ctccattgga atggacattt gaagccatgg ggaaggactg | 1920 |
| cttcatatac tgatgtttgg gaaaaatggt atattccaga cccaacaggc aaattcaacc | 1980 |
| taatccgaag atataccgag atctcaaaca taaagtgaaa cagaatttga actgtaagca | 2040 |
| agcatttctc aggaagtcct ggaagatagc atgcgtggga agtaacagtt gctaggcttc | 2100 |
| aatgcctatc ggtagcaagc catggaaaaa gatgtgtcag ctaggtaaag atgacaaact | 2160 |
| gccctgtctg gcagtcagct cccagacag actatagact ataaatatgt ctccatctgc | 2220 |
| cttaccaagt gttttcttac tacaatgctg aatgactgga aagaagaact gatatggcta | 2280 |
| gttcagctag ctggtacaga taattcaaaa ctgctgttgg ttttaatttt gtaacctgtg | 2340 |
| gcctgatctg taaataaaac ttacattttt caataggtaa aaaaaaaaaa aaaa | 2394 |

<210> SEQ ID NO 17
<211> LENGTH: 4463
<212> TYPE: DNA
<213> ORGANISM: Homo sapiens

<400> SEQUENCE: 17

| | |
|---|---|
| gcagcgcgca ccgagccggc cgcgccgcgc ccgccgctct cgccgctttc gccgcggtct | 60 |
| cctcctctag cgcccgccgc ggccggtaaa tctcggctgg aggagcagcg gcggcccccg | 120 |
| agtcaacttt cattcccttt ttgcttctgc ctcaccattc tcttctcctc ctcgaaagat | 180 |
| ggctgtttgg agaaggggga gaagttaaga ggtcgccagc gcggagcgaa ggagggcgcg | 240 |
| atagcctcag caggagcggg cggaggtttc tcctctgcca accctcctg gaccattgtc | 300 |
| agcagttgaa cgacaaaggc tgtgaatctg catcctagtc ttagcagtcc ctctgattct | 360 |
| catgatgagc tcacctgcac agcctgacct catgtggaac cttgtaccat gggtgctatt | 420 |
| ctgtggctgt gtaggatct cccagatgg ggtggctgga cgagagcagc tcttggctca | 480 |
| gcaaagaatg cacagtatga tcagctcagt ggatgtgaag tcagaagttc ctgtgggcct | 540 |
| ggagcccatc tcacctttag acctaaggac agacctcagg atgatgatgc ccgtggtgga | 600 |
| ccctgttgtc cgtgagaagc aattgcagca ggaattactt cttatccagc agcagcaaca | 660 |
| aatccagaag cagcttctga tagcagagtt tcagaaacag catgagaact tgacacggca | 720 |
| gcaccaggct cagcttcagg agcatatcaa ggaacttcta gccataaaac agcaacaaga | 780 |
| actcctagaa aaggagcaga aactggagca gcagaggcaa gaacaggaag tagagaggca | 840 |
| tcgcagagaa cagcagcttc ctcctctcag aggcaaagat agaggacgag aaagggcagt | 900 |
| ggcaagtaca gaagtaaagc agaagcttca agagttccta ctgagtaaat cagcaacgaa | 960 |
| agacactcca actaatggaa aaaatcattc cgtgagccgc catcccaagc tctggtacac | 1020 |
| ggctgcccac cacacatcat tggatcaaag ctctccaccc cttagtgaa catctccatc | 1080 |
| ctacaagtac acattaccag gagcacaaga tgcaaaggat gatttccccc ttcgaaaaac | 1140 |
| tgaatcctca gtcagtagca gttctccagg ctctggtccc agttcaccaa acaatgggcc | 1200 |
| aactggaagt gttactgaaa atgagacttc ggttttgccc cctacccctc atgccgagca | 1260 |
| aatggtttca cagcaacgca ttctaattca tgaagattcc atgaacctgc taagtcttta | 1320 |
| tacctctcct tctttgccca acattacctt ggggcttccc gcagtgccat cccagctcaa | 1380 |
| tgcttcgaat tcactcaaag aaaagcagaa gtgtgagacg cagacgctta ggcaaggtgt | 1440 |
| tcctctgcct gggcagtatg gaggcagcat cccggcatct tccagccacc ctcatgttac | 1500 |

```
tttagaggga aagccaccca acagcagcca ccaggctctc ctgcagcatt tattattgaa   1560
agaacaaatg cgacagcaaa agcttcttgt agctggtgga gttcccttac atcctcagtc   1620
tcccttggca acaaaagaga gaatttcacc tggcattaga ggtacccaca aattgccccg   1680
tcacagaccc ctgaaccgaa cccagtctgc acctttgcct cagagcacgt tggctcagct   1740
ggtcattcaa cagcaacacc agcaattctt ggagaagcag aagcaatacc agcagcagat   1800
ccacatgaac aaactgcttt cgaaatctat tgaacaactg aagcaaccag gcagtcacct   1860
tgaggaagca gaggaagagc ttcaggggga ccaggcgatg caggaagaca gagcgccctc   1920
tagtggcaac agcactagga gcgacagcag tgcttgtgtg gatgacacac tgggacaagt   1980
tggggctgtg aaggtcaagg aggaaccagt ggacagtgat gaagatgctc agatccagga   2040
aatggaatct ggggagcagg ctgcttttat gcaacaggta ataggcaaag atttagctcc   2100
aggatttgta attaaagtca ttatctgaac atgaaatgca ttgcaggttt ggtaaatgga   2160
tatgatttcc tatcagtttta tatttctcta tgatttgagt tcagtgttta aggattctac   2220
ctaatgcaga tatatgtata tatctatata gaggtctttc tatatactga tctctatata   2280
gatatcaatt tttcattgaa aatccactgg taaggaaata cctgttatac taaaattatg   2340
atacataata tctgagcagt taataggctt taaatttatc ccaaagcctg ctacaccaat   2400
tacttctaaa gaaacaaat tcactgttat tttgagttta tgtgttgaga tcagtgactg   2460
ctggatagtc tcccagtctg atcaatgaag cattcgatta gttttttgatt ttttgcaaca   2520 tctagaattt aattttcaca tcactgtaca taatgtatca tactatagtc ttgaacactg   2580
ttaaaggtag tctgcccctt ccttcctctc tcttttttta gttaagtaga aatgttctgg   2640
tcaccatgcc agtagtccta ggttattgtg taggttgcaa ttgaacatat taggaataca   2700
ggtggtttta aatatataga tgcaaattgc agcactactt taaatattag attatgtctc   2760
acatagcact gctcatttta cttttatttt gtgtaatttg atgacactgt ctatcaaaaa   2820
agagcaaatg aagcagatgc aaatgttagt gagaagtaat gtgcagcatt atggtccaat   2880
cagatacaat attgtgtcta caattgcaaa aaacacagta acaggatgaa tattatctga   2940
tatcaagtca aaatcagttt gaaaagaagg tgtatcatat tttatattgt cactagaatc   3000
tcttaagtat aattccataa tgacatgggc atataccgta acattctggc aaataacaat   3060
tagaaaagat aggtttaaca aaaaaattta cttgtatata atgcaccttc aggaggacta   3120
tgtcctttga tgctataaaa tacaaacaac tttgaaggca acagaagaca ctgtttattc   3180
aagtcagttc tttgtcaggt tcctgctgtt ctcctacaga aaagtgattc tgtgagggtg   3240
aacaggaaat gccttgtgga aacaggaagt ccaagtgatt catgtactga ggaatgtagg   3300
aaaaaaaatc tgaggatagt gctttactct ttctgttttt aaagggcact ctatgaattg   3360
atttattgtc taagaaaata acaccacaag tagggaaatt gttacggaag cttttcactg   3420
gaacatttcc ttcatattcc cttttgatat gtttaccttg ttttataggt ttacttttgt   3480
taagctagtt aaaggttcgt tgtattaaga ccccctttaat atggataatc caaattgacc   3540
tagaatcttt gtgaggtttt ttctattaaa atatttatat ttctaaatcc gaggtatttc   3600
aaggtgtagt atcctatttc aaaggagata tagcagtttt gccaaatgta gacattgttc   3660
aactgtatgt tattggcacg tgttgtttac attttgctgt gacatttaaa atatttctt   3720 taaaaatgtt actgctaaag atacattatc cttttttaaa aagtctccat tcaaattaaa   3780
ttaacataac tagaagttag aaagtttaaa agttttccac ataatgaaag tccttctgat   3840
```

| | |
|---|---|
| aatttgacaa atagctataa taggaacact ccctatcacc aacatatttt ggttagtata | 3900 |
| ttccttcata ttaaaatgac ttttgtcag ttgttttgca ttaaaaatat ggcatgccta | 3960 |
| agataaaatt gtatattttt tccatctcat aaatattcat tttcttcaaa gtctttttc | 4020 |
| aatctcataa aaagggata gtgcatcttt taaaatacat tttatttggg gaggaacatg | 4080 |
| tggctgagca gacttttgta taatattact tcaaagatat gtaatcacaa acaaaaaaaa | 4140 |
| ctatttttta taatgtcatt tgagagagtt tcatcagtac agttggtgga cgttaattgt | 4200 |
| ttgaatttga tagtctttga atttaatcaa gaaactacct ggaaccagtg aaaaggaaag | 4260 |
| ctggacttaa ataatcttag aattaattga taaatgtctc ttttaaaatc tactgtattt | 4320 |
| attataattt acacccttga aggtgatctc ttgttttgtg ttgtaaatat attgtttgta | 4380 |
| tgtttccctt cttgccttct gttataagtc tcttcctttc tcaaataaag ttttttttaa | 4440 |
| aagaaaaaaa aaaaaaaaa aaa | 4463 |

<210> SEQ ID NO 18
<211> LENGTH: 2697
<212> TYPE: DNA
<213> ORGANISM: Homo sapiens

<400> SEQUENCE: 18

| | |
|---|---|
| acttgtccgt cacgtgcggc cgcccggcct ctcggccttg ccgcgcgcct ggcggggttg | 60 |
| gggggggcggg gaccaagatc tgctgcgcct gcgttgtggg cgttctcggg gagctgctgc | 120 |
| cgtagctgcc gccgccgcta ccaccgcgtt cgggtgtaga atttggaatc cctgcgccgc | 180 |
| gttaacaatg aagcagagtt cgaacgtgcc ggctttcctc agcaagctgt ggacgcttgt | 240 |
| ggaggaaacc cacactaacg agttcatcac ctggagccag aatggccaaa gttttctggt | 300 |
| cttggatgag caacgatttg caaaagaaat tcttcccaaa tatttcaagc acaataatat | 360 |
| ggcaagcttt gtgaggcaac tgaatatgta tggtttccgt aaagtagtac atatcgactc | 420 |
| tggaattgta aagcaagaaa gagatggtcc tgtagaattt cagcatcctt acttcaaaca | 480 |
| aggacaggat gacttgttgg agaacattaa aaggaaggtt tcatcttcaa aaccagaaga | 540 |
| aaataaaatt cgtcaggaag atttaacaaa aattataagt agtgctcaga aggttcagat | 600 |
| aaaacaggaa actattgagt ccaggctttc tgaattaaaa agtgagaatg agtccctttg | 660 |
| gaaggaggtg tcagaattac gagcaaagca tgcacaacag caacaagtta ttcgaaagat | 720 |
| tgtccagttt attgttacat tggttcaaaa taaccaactt gtgagtttaa aacgtaaaag | 780 |
| gcctctactt ctaaacacta atggagccca aaagaagaac ctgtttcagc acatagtcaa | 840 |
| agaaccaact gataatcatc atcataaagt tccacacagt aggactgaag gtttaaagcc | 900 |
| aagggagagg atttcagatg acatcattat ttatgatgtt actgatgata atgcagatga | 960 |
| agaaaatatc ccagttattc cagaaactaa tgaggatgtt atatctgatc cctccaactg | 1020 |
| tagccagtac cctgatattg tcatcgttga agatgacaat gaagatgagt atgcacctgt | 1080 |
| cattcagagt ggagagcaga tgaaccagc cagagaatcc ctaagttcag gcagtgatgg | 1140 |
| cagcagccct ctcatgtcta gtgctgtcca gctaaatggc tcatccagtc tgacctcaga | 1200 |
| agatccagtg accatgatgg attccatttt gaatgataac atcaatcttt tgggaaaggt | 1260 |
| tgagctgttg gattatcttg acagtattga ctgcagttta gaggacttcc aggccatgct | 1320 |
| atcaggaaga caatttagca tagacccaga tctcctggtt gatcttttca ctagttctgt | 1380 |
| gcagatgaat cccacagatt acatcaataa tacaaaatct gagaataaag gattagaaac | 1440 |
| taccaagaac aatgtagttc agccagtttc ggaagaggga agaaaatcta atccaaacc | 1500 |

```
agataagcag cttatccagt ataccgcctt tccacttctt gcattcctcg atgggaaccc    1560
tgcttcttct gttgaacagg cgagtacaac agcatcatca gaagttttgt cctctgtaga    1620
taaacccata gaagttgatg agcttctgga tagcagccta gacccagaac caacccaaag    1680
taagcttgtt cgcctggagc cattgactga agctgaagct agtgaagcta cactgtttta    1740
tttatgtgaa cttgctcctg cacctctgga tagtgatatg ccacttttag atagctaaat    1800
ccccaggaag tggactttac atgtatatat tcatcaaaat gatgaactat ttatttttaaa    1860 gtatcatttg gtacttttt tgtaaattgc tttgttttgt ttaatcagat actgtggaat    1920
aaaagcacct tttgcttttc tcactaacca cacactcttg cagagctttc aggtgttact    1980
cagctgcata gttacgcaga tgtaatgcac attattggcg tatctttaag ttggattcaa    2040
atggccattt ttctccaatt ttggtaaatt ggatatcttt ttttacaaa tacgaccatt    2100 aacctcagtt aaattttgt ttgttttcct gtttgatgct gtctatttgc attgagtgta    2160
agtcatttga actaatggta taactcctaa agctttctct gctccagtta tttttattaa    2220
atatttttca cttggcttat ttttaaaact gggaacataa agtgcctgta tcttgtaaaa    2280
cttcatttgt ttcttttggt tcagagaagt tcatttatgt tcaaagacgt ttattcatgt    2340
tcaacaggaa agacaaagtg tacgtgaatg ctcgctgtct gatagggttc cagctccata    2400
tatatagaaa gatcgggggt gggatgggat ggagtgagcc ccatccagtt agttggacta    2460
gttttaaata aaggttttcc ggtttgtgtt tttttgaacc atactgttta gtaaaataaa    2520
tacaatgaat gttgagtact agtgtctgtt atgtgtcttc tttagaggtg acactcacat    2580
gaaacaattt tttcttctca taggaagcag tagctttaaa ctgtctgtgg ttcattattc    2640
tcaatatgaa tcataccaag atatttgtgc ctcatctcga aaatatattg tatattg       2697

<210> SEQ ID NO 19
<211> LENGTH: 11427
<212> TYPE: DNA
<213> ORGANISM: Homo sapiens

<400> SEQUENCE: 19
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa     120
atttgcttct ggccttcccc tacgattat acctggcctt cccctacgga ttatactcaa     180
cttactgttt agaaaatgtg gcccacgaga cgcctggtta ctatcaaaag gagcggggtc     240
gacggtcccc actttcccct gagcctcagc acctgcttgt ttggaagggg tattgaatgt     300
gacatccgta tccagcttcc tgttgtgtca aaacaacatt gcaaaattga atccatgag     360 caggaggcaa tattacataa tttcagttcc acaaatccaa cacaagtaaa tgggtctgtt     420
attgatgagc ctgtacggct aaaacatgga gatgtaataa ctattattga tcgttccttc     480
aggtatgaaa atgaaagtct tcagaatgga aggaagtcaa ctgaatttcc aagaaaaata     540
cgtgaacagg agccagcacg tcgtgtctca agatctagct tctcttctga ccctgatgag     600
agtgagggaa tacctttgaa aagaaggcgt gtgtcctttg gtgggcacct aagacctgaa     660
ctatttgatg aaaacttgcc tcctaatacg cctctcaaaa ggggagaagc cccaaccaaa     720
agaaagtctc tggtaatgca cactccacct gtcctgaaga aaatcatcaa ggaacagcct     780
caaccatcag gaaacaaga gtcaggttca gaaatccatg tggaagtgaa ggcacaaagc     840
ttggttataa gccctccagc tcctagtcct aggaaaactc cagttgccag tgatcaacgc     900
```

-continued

```
cgtaggtcct gcaaaacagc ccctgcttcc agcagcaaat ctcagacaga ggttcctaag    960
agaggaggga gaaagagtgg caacctgcct tcaaagagag tgtctatcag ccgaagtcaa   1020
catgatattt tacagatgat atgttccaaa agaagaagtg gtgcttcgga agcaaatctg   1080
attgttgcaa aatcatgggc agatgtagta aaacttggtg caaaacaaac acaaactaaa   1140
gtcataaaac atggtcctca aaggtcaatg aacaaaaggc aaagaagacc tgctactcca   1200
aagaagcctg tgggcgaagt tcacagtcaa tttagtacag gccacgcaaa ctctccttgt   1260
accataataa tagggaaagc tcatactgaa aaagtacatg tgcctgctcg accctacaga   1320
gtgctcaaca acttcatttc caaccaaaaa atggacttta aggaagatct ttcaggaata   1380
gctgaaatgt tcaagacccc agtgaaggag caaccgcagt tgacaagcac atgtcacatc   1440
gctatttcaa attcagagaa tttgcttgga aaacagtttc aaggaactga ttcaggagaa   1500
gaacctctgc tccccacctc agagagtttt ggaggaaatg tgttcttcag tgcacagaat   1560
gcagcaaaac agccatctga taaatgctct gcaagccctc ccttaagacg gcagtgtatt   1620
agagaaaatg gaaacgtagc aaaaacgccc aggaacacct acaaaatgac ttctctggag   1680
acaaaaactt cagatactga gacagagcct tcaaaaacag tatccactgc aaacaggtca   1740
ggaaggtcta cagagttcag gaatatacag aagctacctg tggaaagtaa gagtgaagaa   1800
acaaatacag aaattgttga gtgcatccta aaaagaggtc agaaggcaac actactacaa   1860
caaaggagag aaggagagat gaaggaaata gaaagacctt ttgagacata taggaaaat    1920
attgaattaa agaaaacga tgaaaagatg aaagcaatga agagatcaag aacttggggg    1980
cagaaatgtg caccaatgtc tgacctgaca gacctcaaga gcttgcctga tacagaactc   2040
atgaaagaca cggcacgtgg ccagaatctc ctccaaaccc aagatcatgc caaggcacca   2100
aagagtgaga aaggcaaaat cactaaaatg ccctgccagt cattcaaacc agaaccaata   2160
aacaccccaa cacacacaaa acaacagttg aaggcatccc tggggaaagt aggtgtgaaa   2220
gaagagctcc tagcagtcgg caagttcaca cggacgtcag gggagaccac gcacacgcac   2280
agagagccag caggagatgg caagagcatc agaacgttta aggagtctcc aaagcagatc   2340
ctggacccag cagcccgtgt aactggaatg aagaagtggc caagaacgcc taaggaagag   2400
gcccagtcac tagaagacct ggctggcttc aaagagctct tccagacacc aggtccctct   2460
gaggaatcaa tgactgatga gaaaactacc aaaatagcct gcaaatctcc accaccagaa   2520
tcagtggaca ctccaacaag cacaaagcaa tggcctaaga gaagtctcag gaaagcagat   2580
gtagaggaag aattcttagc actcaggaaa ctaacaccat cagcagggaa agccatgctt   2640
acgcccaaac cagcaggagg tgatgagaaa gacattaaag catttatggg aactccagtg   2700
cagaaactgg acctggcagg aacttttacct ggcagcaaaa gacagctaca gactcctaag   2760
gaaaaggccc aggctctaga agacctggct ggctttaaag agctcttcca gactcctggt   2820
cacaccgagg aattagtggc tgctggtaaa accactaaaa taccctgcga ctctccacag   2880
tcagacccag tggacacccc aacaagcaca aagcaacgac ccaagagaag tatcaggaaa   2940
gcagatgtag agggagaact cttagcgtgc aggaatctaa tgccatcagc aggcaaagcc   3000
atgcacacgc ctaaaccatc agtaggtgaa gagaaagaca tcatcatatt tgtgggaact   3060
ccagtgcaga aactggacct gacagagaac ttaaccggca gcaagagacg gccacaaact   3120
cctaaggaag aggcccaggc tctggaagac ctgactggct ttaaagagct cttccagacc   3180
cctggtcata ctgaagaagc agtggctgct ggcaaaacta ctaaaatgcc ctgcgaatct   3240
tctccaccag aatcagcaga caccccaaca agcacaagaa ggcagcccaa gacacctttg   3300
```

```
gagaaaaggg acgtacagaa ggagctctca gccctgaaga agctcacaca gacatcaggg    3360
gaaaccacac acacagataa agtaccagga ggtgaggata aaagcatcaa cgcgtttagg    3420
gaaactgcaa aacagaaact ggacccagca gcaagtgtaa ctggtagcaa gaggcaccca    3480
aaaactaagg aaaaggccca acccctagaa gacctggctg gcttgaaaga gctcttccag    3540
acaccagtat gcactgacaa gcccacgact cacgagaaaa ctaccaaaat agcctgcaga    3600
tcacaaccag acccagtgga cacaccaaca agctccaagc cacagtccaa gagaagtctc    3660
aggaaagtgg acgtagaaga agaattcttc gcactcagga aacgaacacc atcagcaggc    3720
aaagccatgc acacacccaa accagcagta agtggtgaga aaaacatcta cgcatttatg    3780
ggaactccag tgcagaaact ggacctgaca gagaacttaa ctggcagcaa gagacggcta    3840
caaactccta aggaaaaggc ccaggctcta gaagacctgg ctggctttaa agagctcttc    3900
cagacacgag gtcacactga ggaatcaatg actaacgata aaactgccaa agtagcctgc    3960
aaatcttcac aaccagaccc agacaaaaac ccagcaagct ccaagcgacg gctcaagaca    4020
tccctgggga agtgggcgt gaaagaagag ctcctagcag ttggcaagct cacacagaca    4080
tcaggagaga ctacacacac acacacagag ccaacaggag atggtaagag catgaaagca    4140
tttatggagt ctccaaagca gatcttagac tcagcagcaa gtctaactgg cagcaagagg    4200
cagctgagaa ctcctaaggg aaagtctgaa gtccctgaag acctggccgg cttcatcgag    4260
ctcttccaga caccaagtca cactaaggaa tcaatgacta acgaaaaaac taccaaagta    4320
tcctacagag cttcacagcc agacctagtg gacaccccaa caagctccaa gccacagccc    4380
aagagaagtc tcaggaaagc agacactgaa gaagaatttt tagcatttag gaaacaaacg    4440
ccatcagcag gcaaagccat gcacacaccc aaaccagcag taggtgaaga gaaagacatc    4500
aacacgtttt tgggaactcc agtgcagaaa ctggaccagc caggaaattt acctggcagc    4560
aatagacggc tacaaactcg taaggaaaag gcccaggctc tagaagaact gactggcttc    4620
agagagcttt tccagacacc atgcactgat aaccccacga ctgatgagaa aactaccaaa    4680
aaaatactct gcaaatctcc gcaatcagac ccagcggaca ccccaacaaa cacaaagcaa    4740
cggcccaaga gaagcctcaa gaaagcagac gtagaggaag aattttttagc attcaggaaa    4800
ctaacaccat cagcaggcaa agccatgcac acgcctaaag cagcagtagg tgaagagaaa    4860
gacatcaaca catttgtggg gactccagtg agaaactgg acctgctagg aaatttacct    4920
ggcagcaaga cacggccaca aactcctaaa gaaaaggcca aggctctaga agatctggct    4980
ggcttcaaag agctcttcca gacaccaggt cacactgagg aatcaatgac cgatgacaaa    5040
atcacagaag tatcctgcaa atctccacaa ccagacccag tcaaaacccc aacaagctcc    5100
aagcaacgac tcaagatatc cttggggaaa gtaggtgtga aagaagaggt cctaccagtc    5160
ggcaagctca cacagacgtc agggaagacc acacagacac acagagagac agcaggagat    5220
ggaaagagca tcaaagcgtt taaggaatct gcaaagcaga tgctggaccc agcaaactat    5280
ggaactggga tggagaggtg gccaagaaca cctaaggaag aggcccaatc actagaagac    5340
ctggccggct tcaaagagct cttccagaca ccagaccaca ctgaggaatc aacaactgat    5400
gacaaaacta ccaaaatagc ctgcaaatct ccaccaccag aatcaatgga cactccaaca    5460
agcacaagga ggcggcccaa aacaccttg gggaaaaggg atatagtgga agagctctca    5520
gccctgaagc agctcacaca gaccacacac agacaaaag taccaggaga tgaggataaa    5580
ggcatcaacg tgttcaggga aactgcaaaa cagaaactgg acccagcagc aagtgtaact    5640
```

-continued

```
ggtagcaaga ggcagccaag aactcctaag ggaaaagccc aaccccctaga agacttggct    5700
ggcttgaaag agctcttcca gacaccaata tgcactgaca agcccacgac tcatgagaaa    5760
actaccaaaa tagcctgcag atctccacaa ccagacccag tgggtacccc aacaatcttc    5820
aagccacagt ccaagagaag tctcaggaaa gcagacgtag aggaagaatc cttagcactc    5880
aggaaacgaa caccatcagt agggaaagct atggacacac ccaaaccagc aggaggtgat    5940
gagaaagaca tgaaagcatt tatgggaact ccagtgcaga aattggacct gccaggaaat    6000
ttacctggca gcaaaagatg gccacaaact cctaaggaaa aggcccaggc tctagaagac    6060
ctggctggct tcaaagagct cttccagaca ccaggcactg acaagcccac gactgatgag    6120
aaaactacca aaatagcctg caaatctcca caaccagacc cagtggacac cccagcaagc    6180
acaaagcaac ggcccaagag aaacctcagg aaagcagacg tagaggaaga atttttagca    6240
ctcaggaaac gaacaccatc agcaggcaaa gccatggaca caccaaaacc agcagtaagt    6300
gatgagaaaa atatcaacac atttgtggaa actccagtgc agaaactgga cctgctagga    6360
aatttacctg gcagcaagag acagccacag actcctaagg aaaaggctga ggctctagag    6420
gacctggttg gcttcaaaga actcttccag acaccaggtc acactgagga atcaatgact    6480
gatgacaaaa tcacagaagt atcctgtaaa tctccacagc cagagtcatt caaaacctca    6540
agaagctcca agcaaaggct caagataccc ctggtgaaag tggacatgaa agaagagccc    6600
ctagcagtca gcaagctcac acggacatca ggggagacta cgcaaacaca cacagagcca    6660
acaggagata gtaagagcat caaagcgttt aaggagtctc caaagcagat cctggaccca    6720
gcagcaagtg taactggtag caggaggcag ctgagaactc gtaaggaaaa ggcccgtgct    6780
ctagaagacc tggttgactt caaagagctc ttctcagcac caggtcacac tgaagagtca    6840
atgactattg acaaaaacac aaaaattccc tgcaaatctc ccccaccaga actaacagac    6900
actgccacga gcacaaagag atgccccaag acacgtccca ggaaagaagt aaaagaggag    6960
ctctcagcag ttgagaggct cacgcaaaca tcagggcaaa gcacacacac acacaaagaa    7020
ccagcaagcg gtgatgaggg catcaaagta ttgaagcaac gtgcaaagaa gaaaccaaac    7080
ccagtagaag aggaacccag caggagaagg ccaagagcac ctaaggaaaa ggcccaaccc    7140
ctggaagacc tggccggctt cacagagctc tctgaaacat caggtcacac tcaggaatca    7200
ctgactgctg gcaaagccac taaaataccc tgcgaatctc ccccactaga agtggtagac    7260
accacagcaa gcacaaagag gcatctcagg acacgtgtgc agaaggtaca agtaaaagaa    7320
gagccttcag cagtcaagtt cacacaaaca tcaggggaaa ccacggatgc agacaaagaa    7380
ccagcaggtg aagataaagg catcaaagca ttgaaggaat ctgcaaaaca gacaccggct    7440
ccagcagcaa gtgtaactgg cagcaggaga cggccaagag cacccaggga aagtgcccaa    7500
gccatagaag acctagctgg cttcaaagac ccagcagcag gtcacactga gaatcaatg    7560
actgatgaca aaaccactaa aataccctgc aaatcatcac cagaactaga agacaccgca    7620
acaagctcaa agagacggcc caggacacgt gcccagaaag tagaagtgaa ggaggagctg    7680
ttagcagttg gcaagctcac acaaacctca ggggagacca cgcacaccga caagagccg     7740
gtaggtgagg gcaaaggcac gaaagcattt aagcaacctg caaagcggaa gctgacgca     7800
gaagatgtaa ttggcagcag gagacagcca agagcaccta aggaaaaggc ccaacccctg    7860
gaagatctgg ccagcttcca agagctctct caaacaccag gccacactga ggaactggca    7920
aatggtgctc tgatagcttt acaagcgct ccaaagcaaa cacctgacag tggaaaaacct     7980
ctaaaaatat ccagaagagt tcttcgggcc cctaaagtag aacccgtggg agacgtggta    8040
```

```
agcaccagag accctgtaaa atcacaaagc aaaagcaaca cttccctgcc cccactgccc    8100
ttcaagaggg gaggtggcaa agatggaagc gtcacgggaa ccaagaggct gcgctgcatg    8160
ccagcaccag aggaaattgt ggaggagctg ccagccagca agaagcagag ggttgctccc    8220
agggcaagag gcaaatcatc cgaacccgtg gtcatcatga agagaagttt gaggacttct    8280
gcaaaaagaa ttgaacctgc ggaagagctg aacagcaacg acatgaaaac caacaaagag    8340
gaacacaaat tacaagactc ggtccctgaa aataagggaa tatccctgcg ctccagacgc    8400
caaaataaga ctgaggcaga acagcaaata actgaggtct ttgtattagc agaaagaata    8460
gaaataaaca gaaatgaaaa gaagcccatg aagacctccc cagagatgga cattcagaat    8520
ccagatgatg gagcccggaa acccatacct agagacaaag tcactgagaa caaaaggtgc    8580
ttgaggtctg ctagacagaa tgagagctcc cagcctaagg tggcagagga gagcggaggg    8640
cagaagagtg cgaaggttct catgcagaat cagaaaggga aaggagaagc aggaaattca    8700
gactccatgt gcctgagatc aagaaagaca aaaagccagc ctgcagcaag cactttggag    8760
agcaaatctg tgcagagagt aacgcggagt gtcaagaggt gtgcagaaaa tccaaagaag    8820
gctgaggaca atgtgtgtgt caagaaaata agaaccagaa gtcataggga cagtgaagat    8880
atttgacaga aaaatcgaac tgggaaaaat ataataaagt tagttttgtg ataagttcta    8940
gtgcagttt tgtcataaat tacaagtgaa ttctgtaagt aaggctgtca gtctgcttaa    9000
gggaagaaaa ctttggattt gctgggtctg aatcggcttc ataaactcca ctgggagcac    9060
tgctgggctc ctggactgag aatagttgaa caccgggggc tttgtgaagg agtctgggcc    9120
aaggtttgcc ctcagctttg cagaatgaag ccttgaggtc tgtcaccacc cacagccacc    9180
ctacagcagc cttaactgtg acacttgcca cactgtgtcg tcgtttgttt gcctatgtcc    9240
tccagggcac ggtggcagga acaactatcc tcgtctgtcc caacactgag caggcactcg    9300
gtaaacacga atgaatggat gagcgcacgg atgaatggag cttacaagat ctgtctttcc    9360
aatggccggg ggcatttggt ccccaaatta aggctattgg acatctgcac aggacagtcc    9420
tatttttgat gtccttttcct ttctgaaaat aaagttttgt gctttggaga atgactcgtg    9480
agcacatctt tagggaccaa gagtgacttt ctgtaaggag tgactcgtgg cttgccttgg    9540
tctcttggga atacttttct aactagggtt gctctcacct gagacattct ccacccgcgg    9600
aatctcaggg tcccaggctg tgggccatca cgacctcaaa ctggctccta atctccagct    9660
ttcctgtcat tgaaagcttc ggaagtttac tggctctgct cccgcctgtt ttctttctga    9720
ctctatctgg cagcccgatg ccacccagta caggaagtga caccagtact ctgtaaagca    9780
tcatcatcct tggagagact gagcactcag caccttcagc cacgatttca ggatcgcttc    9840
cttgtgagcc gctgcctccg aaatctcctt tgaagcccag acatctttct ccagcttcag    9900
acttgtagat ataactcgtt catcttcatt tactttccac tttgccccct gtcctctctg    9960
tgttccccaa atcagagaat agcccgccat cccccaggtc acctgtctgg attcctcccc   10020
attcacccac cttgccaggt gcaggtgagg atggtgcacc agacagggta gctgtccccc   10080
aaaatgtgcc ctgtgcgggc agtgccctgt ctccacgttt gtttcccag tgtctggcgg   10140
ggagccaggt gacatcataa atacttgctg aatgaatgca gaaatcagcg gtactgactt   10200
gtactatatt ggctgccatg ataggggttct cacagcgtca tccatgatcg taagggagaa   10260
tgacattctg cttgagggag ggaatagaaa gggcagggga ggggacatct gagggcttca   10320
cagggctgca aagggtacag ggattgcacc agggcagaac aggggagggt gttcaaggaa   10380
```

```
gagtggctct tagcagaggc actttggaag gtgtgaggca taaatgcttc cttctacgta     10440
ggccaacctc aaaactttca gtaggaatgt tgctatgatc aagttgttct aacactttag     10500
acttagtagt aattatgaac ctcacataga aaaatttcat ccagccatat gcctgtggag     10560
tggaatattc tgtttagtag aaaaatcctt tagagttcag ctctaaccag aaatcttgct     10620
gaagtatgtc agcaccttt ctcaccctgg taagtacagt atttcaagag cacgctaagg      10680
gtggttttca ttttacaggg ctgttgatga tgggttaaaa atgttcattt aagggctacc     10740
cccgtgttta atagatgaac accacttcta cacaaccctc cttggtactg ggggagggag     10800
agatctgaca aatactgccc attccctag gctgactgga tttgagaaca aatacccacc       10860
catttccacc atggtatggt aacttctctg agcttcagtt tccaagtgaa tttccatgta     10920
ataggacatt cccattaaat acaagctgtt tttactttt cgcctcccag ggcctgtggg      10980
atctggtccc ccagcctctc ttgggctttc ttacactaac tctgtaccta ccatctcctg     11040
cctcccttag gcaggcacct ccaaccacca cacactccct gctgttttcc ctgcctggaa     11100
ctttccctcc tgccccacca agatcatttc atccagtcct gagctcagct taagggaggc     11160
ttcttgcctg tgggttccct caccccatg cctgtcctcc aggctggggc aggttcttag      11220
tttgcctgga attgttctgt acctcttgt agcacgtagt gttgtggaaa ctaagccact      11280
aattgagttt ctggctcccc tcctggggtt gtaagttttg ttcattcatg agggccgact     11340
gcatttcctg gttactctat cccagtgacc agccacagga gatgtccaat aaagtatgtg     11400
atgaaatggt cttaaaaaaa aaaaaaa                                          11427

<210> SEQ ID NO 20
<211> LENGTH: 5765
<212> TYPE: DNA
<213> ORGANISM: Homo sapiens

<400> SEQUENCE: 20
tcctaggcgg cggccgcggc ggcggaggca gcagcggcgg cggcagtggc ggcggcgaag        60
gtggcggcgg ctcggccagt actcccggcc cccgccattt cggactggga gcgagcgcgg      120
cgcaggcact gaaggcggcg gcggggccag aggctcagcg gctcccaggt gcgggagaga      180
ggcctgctga aaatgactga atataaactt gtggtagttg gagctggtgg cgtaggcaag      240
agtgccttga cgatacagct aattcagaat cattttgtgg acgaatatga tccaacaata      300
gaggattcct acaggaagca agtagtaatt gatggagaaa cctgtctctt ggatattctc      360
gacacagcag gtcaagagga gtacagtgca atgagggacc agtacatgag gactggggag      420
ggctttcttt gtgtatttgc cataaataat actaaatcat ttgaagatat tcaccattat      480
agagaacaaa ttaaaagagt taaggactct gaagatgtac ctatggtcct agtaggaaat      540
aaatgtgatt tgccttctag aacagtagac acaaaacagg ctcaggactt agcaagaagt      600
tatggaattc cttttattga acatcagca agacaagac agggtgttga tgatgccttc       660
tatacattag ttcgagaaat tcgaaaacat aaagaaaaga tgagcaaaga tggtaaaaag      720
aagaaaaaga agtcaaagac aaagtgtgta attatgtaaa tacaatttgt actttttct       780 taaggcatac tagtacaagt ggtaatttt gtacattaca ctaaattatt agcatttgtt      840
ttagcattac ctaatttttt tcctgctcca tgcagactgt tagcttttac cttaaatgct      900 tatttaaaa tgcacagtgga agtttttt tcctctaagt gccagtattc ccagagtttt     960 ggttttgaa ctagcaatgc ctgtgaaaaa gaaactgaat acctaagatt tctgtcttgg     1020 ggttttgt gcatgcagtt gattacttct tatttttctt accaattgtg aatgttggtg      1080
```

```
tgaaacaaat taatgaagct tttgaatcat ccctattctg tgttttatct agtcacataa    1140
atggattaat tactaatttc agttgagacc ttctaattgg ttttttactga aacattgagg    1200 gaacacaaat ttatgggctt cctgatgatg attcttctag gcatcatgtc ctatagtttg    1260
tcatccctga tgaatgtaaa gttacactgt tcacaaaggt tttgtctcct ttccactgct    1320
attagtcatg gtcactctcc ccaaaatatt atatttttc tataaaaga aaaaatgga      1380 aaaaaattac aaggcaatgg aaactattat aaggccattt ccttttcaca ttagataaat    1440
tactataaag actcctaata gcttttcctg ttaaggcaga cccagtatga atggggatt    1500 attatagcaa ccattttggg gctatatttta catgctacta aattttttata ataattgaaa    1560 agattttaac aagtataaaa aattctcata ggaattaaat gtagtctccc tgtgtcagac    1620
tgctctttca tagtataact ttaaatcttt tcttcaactt gagtctttga agatagtttt    1680
aattctgctt gtgacattaa aagattattt gggccagtta tagcttatta ggtgttgaag    1740
agaccaaggt tgcaaggcca ggccctgtgt gaacctttga gctttcatag agagtttcac    1800
agcatggact gtgtccccac ggtcatccag tgttgtcatg cattggttag tcaaaatggg    1860
gagggactag ggcagtttgg atagctcaac aagatacaat ctcactctgt ggtggtcctg    1920
ctgacaaatc aagagcattg cttttgtttc ttaagaaaac aaactctttt ttaaaaatta    1980
cttttaaata ttaactcaaa agttgagatt ttggggtggt ggtgtgccaa gacattaatt    2040 tttttttaa acaatgaagt gaaaaagttt tacaatctct aggtttggct agttctctta    2100
acactggtta aattaacatt gcataaacac ttttcaagtc tgatccatat ttaataatgc    2160
tttaaaataa aaataaaaac aatccttttg ataaatttaa aatgttactt atttttaaaat    2220 aaatgaagtg agatggcatg gtgaggtgaa agtatcactg gactaggaag aaggtgactt    2280
aggttctaga taggtgtctt ttaggactct gattttgagg acatcactta ctatccattt    2340
cttcatgtta aaagaagtca tctcaaactc ttagttttttt tttttttacaa ctatgtaatt    2400 tatattccat ttacataagg atacacttat ttgtcaagct cagcacaatc tgtaaatttt    2460
taacctatgt tacaccatct tcagtgccag tcttgggcaa aattgtgcaa gaggtgaagt    2520
ttatatttga atatccattc tcgttttagg actcttcttc catattagtg tcatcttgcc    2580
tccctacctt ccacatgccc catgacttga tgcagtttta atacttgtaa ttcccctaac    2640
cataagattt actgctgctg tggatatctc catgaagttt tcccactgag tcacatcaga    2700
aatgccctac atcttatttc ctcagggctc aagagaatct gacagatacc ataaagggat    2760
ttgacctaat cactaattttt caggtggtgg ctgatgcttt gaacatctct ttgctgccca    2820
atccattagc gacagtagga tttttcaaac ctggtatgaa tagacagaac cctatccagt    2880
ggaaggagaa tttaataaag atagtgctga aagaattcct taggtaatct ataactagga    2940
ctactcctgg taacagtaat acattccatt gttttagtaa ccagaaatct tcatgcaatg    3000
aaaaatactt taattcatga agcttacttt tttttttttgg tgtcagagtc tcgctcttgt    3060
cacccaggct ggaatgcagt ggcgccatct cagctcactg caacctccat ctcccaggtt    3120
caagcgattc tcgtgcctcg gcctcctgag tagctgggat tacaggcgtg tgccactaca    3180
ctcaactaat ttttgtattt ttaggagaga cggggtttca ccctgttggc caggctggtc    3240
tcgaactcct gacctcaagt gattcaccca ccttggcctc ataaacctgt tttgcagaac    3300
tcatttattc agcaaatatt tattgagtgc ctaccagatg ccagtcaccg cacaaggcac    3360
tgggtatatg gtatccccaa acaagagaca taatcccggt ccttaggtag tgctagtgtg    3420
```

```
gtctgtaata tcttactaag gcctttggta tacgacccag agataacacg atgcgtattt    3480
tagttttgca aagaaggggt ttggtctctg tgccagctct ataattgttt tgctacgatt    3540
ccactgaaac tcttcgatca agctacttta tgtaaatcac ttcattgttt taaaggaata    3600
aacttgatta tattgttttt ttatttggca taactgtgat tcttttagga caattactgt    3660
acacattaag gtgtatgtca gatattcata ttgacccaaa tgtgtaatat tccagttttc    3720
tctgcataag taattaaaat atacttaaaa attaatagtt ttatctgggt acaaataaac    3780
aggtgcctga actagttcac agacaaggaa acttctatgt aaaaatcact atgatttctg    3840
aattgctatg tgaaactaca gatctttgga acactgttta ggtagggtgt taagacttac    3900
acagtacctc gtttctacac agagaaagaa atggccatac ttcaggaact gcagtgctta    3960 tgagggata tttaggcctc ttgaattttt gatgtagatg ggcatttttt taaggtagtg    4020
gttaattacc tttatgtgaa cttgaatgg tttaacaaaa gatttgtttt tgtagagatt    4080
ttaaaggggg agaattctag aaataaatgt tacctaatta ttacagcctt aaagacaaaa    4140
atccttgttg aagttttttt aaaaaaagct aaattacata gacttaggca ttaacatgtt    4200
tgtggaagaa tatagcagac gtatattgta tcatttgagt gaatgttccc aagtaggcat    4260
tctaggctct atttaactga gtcacactgc ataggaattt agaacctaac ttttataggt    4320
tatcaaaact gttgtcacca ttgcacaatt ttgtcctaat atatacatag aaactttgtg    4380
gggcatgtta agtacagtt tgcacaagtt catctcattt gtattccatt gattttttt     4440 ttcttctaaa cattttttct tcaaacagta tataactttt tttaggggat ttttttttag   4500
acagcaaaaa ctatctgaag atttccattt gtcaaaagt aatgatttct tgataattgt    4560
gtagtaatgt tttttagaac ccagcagtta ccttaaagct gaatttatat ttagtaactt   4620
ctgtgttaat actggatagc atgaattctg cattgagaaa ctgaatagct gtcataaaat   4680
gaaactttct ttctaaagaa agatactcac atgagttctt gaagaatagt cataactaga   4740
ttaagatctg tgttttagtt taatagtttg aagtgcctgt ttgggataat gataggtaat   4800
ttagatgaat ttaggggaaa aaaaagttat ctgcagatat gttgagggcc catctctccc   4860
cccacacccc cacagagcta actgggttac agtgttttat ccgaaagttt ccaattccac   4920
tgtcttgtgt tttcatgttg aaaatacttt tgcattttc ctttgagtgc caatttctta    4980
ctagtactat ttcttaatgt aacatgttta cctggaatgt attttaacta ttttttgtata 5040 gtgtaaactg aaacatgcac attttgtaca ttgtgctttc ttttgtggga catatgcagt   5100
gtgatccagt tgttttccat catttggttg cgctgaccta ggaatgttgg tcatatcaaa   5160
cattaaaaat gaccactctt ttaattgaaa ttaacttta aatgtttata ggagtatgtg     5220
ctgtgaagtg atctaaaatt tgtaatattt ttgtcatgaa ctgtactact cctaattatt    5280
gtaatgtaat aaaaatagtt acagtgacta tgagtgtgta tttattcatg aaatttgaac   5340
tgtttgcccc gaaatggata tggaatactt tataagccat agacactata gtataccagt    5400
gaatctttta tgcagcttgt tagaagtatc ctttatttct aaaaggtgct gtggatatta   5460
tgtaaaggcg tgtttgctta aacttaaaac catatttaga agtagatgca aaacaaatct   5520
gcctttatga caaaaaaata ggataacatt atttatttat ttccttttat caagaaggt    5580 aattgataca caacaggtga cttggtttta ggcccaaagg tagcagcagc aacattaata   5640
atggaaataa ttgaatagtt agttatgtat gttaatgcca gtcaccagca ggctatttca   5700
aggtcagaag taatgactcc atacatatta tttatttcta taactacatt taaatcatta   5760
ccagg                                                                5765
```

<210> SEQ ID NO 21
<211> LENGTH: 2202
<212> TYPE: DNA
<213> ORGANISM: Homo sapiens

<400> SEQUENCE: 21

| | | | | | |
|---|---|---|---|---|---|
| cgtaaagaga | ggccgggagc | tgcccctaac | cgaggcagca | gcggacgtga | gcgataatgg | 60 |
| cggatatgga | ggatctcttc | gggagcgacg | ccgacagcga | agctgagcgt | aaagattctg | 120 |
| attctggatc | tgactcagat | tctgatcaag | agaatgctgc | ctctggcagt | aatgcctctg | 180 |
| gaagtgaaag | tgatcaggat | gaaagaggtg | attcaggaca | accaagtaat | aaggaactgt | 240 |
| ttggagatga | cagtgaggac | gagggagctt | cacatcatag | tggtagtgat | aatcactctg | 300 |
| aaagatcaga | caatagatca | gaagcttctg | agcgttctga | ccatgaggac | aatgaccect | 360 |
| cagatgtaga | tcagcacagt | ggatcagaag | cccctaatga | tgatgaagac | gaaggtcata | 420 |
| gatcggatgg | agggagccat | cattcagaag | cagaaggttc | tgaaaaagca | cattcagatg | 480 |
| atgaaaaatg | gggcagagaa | gataaaagtg | accagtcaga | tgatgaaaag | atacaaaatt | 540 |
| ctgatgatga | ggagagggca | caaggatctg | atgaagataa | gctgcagaat | tctgacgatg | 600 |
| atgagaaaat | gcagaacaca | gatgatgagg | agaggcctca | gctttccgat | gatgagagac | 660 |
| aacagctatc | tgaggaggaa | aaggctaatt | ctgatgatga | acggccggta | gcttctgata | 720 |
| atgatgatga | gaaacagaat | tctgatgatg | aagaacaacc | acagctgtct | gatgaagaga | 780 |
| aaatgcaaaa | ttctgatgat | gaaaggccac | aggcctcaga | tgaagaacac | aggcattcag | 840 |
| atgatgaaga | ggaacaggat | cataaatcag | aatctgcaag | aggcagtgat | agtgaagatg | 900 |
| aagttttacg | aatgaaacgc | aagaatgcga | ttgcatctga | ttcagaagcg | atagtgaca | 960 |
| ctgaggtgcc | aaaagataat | agtggaacca | tggatttatt | tggaggtgca | gatgatatct | 1020 |
| cttcagggag | tgatggagaa | gacaaaccac | ctactccagg | acagcctgtt | gatgaaaatg | 1080 |
| gattgcctca | ggatcaacag | gaagaggagc | caattcctga | gaccagaata | gaagtagaaa | 1140 |
| tacccaaagt | aaaacactgat | ttaggaaacg | acttatatttt | tgttaaactg | cccaactttc | 1200 |
| tcagtgtaga | gcccagacct | tttgatcctc | agtattatga | agatgaattt | gaagatgaag | 1260 |
| aaatgctgga | tgaagaaggt | agaaccaggt | taaaattaaa | ggtagaaaat | actataagat | 1320 |
| ggaggatacg | ccgagatgaa | gaaggaaatg | aaattaaaga | aagcaatgct | cggatagtca | 1380 |
| agtggtcaga | tggaagcatg | tccctgcatt | taggcaatga | agtgtttgat | gtgtacaaag | 1440 |
| ccccactgca | gggcgaccac | aatcatcttt | ttataagaca | aggtactggt | ctacagggac | 1500 |
| aagcagtctt | taaaacgaaa | ctcaccttca | gacctcactc | tacgacagt | gccacacata | 1560 |
| gaaagatgac | tctgtcactt | gcagataggt | gttcaaagac | acagaagatt | agaatcttgc | 1620 |
| caatggctgg | tcgtgatcct | gaatgccaac | gcacagaaat | gattaagaaa | gaagaagaac | 1680 |
| gtttgagggc | ttccatacgt | agggaatctc | agcagcgccg | aatgagagag | aaacagcacc | 1740 |
| agcgggggct | gagcgccagt | tacctggaac | ctgatcgata | cgatgaggag | gaggaaggcg | 1800 |
| aggagtccat | cagcttggct | gccattaaaa | accgatataa | aggggcatt | cgagaggaac | 1860 |
| gagccagaat | ctattcatca | gacagtgatg | agggatcaga | agaagataaa | gctcaaagat | 1920 |
| tactcaaagc | aaagaaactt | accagtgatg | aggaaggtga | accttccgga | aagagaaaag | 1980 |
| cagaagatga | tgataaagca | aataaaaagc | ataagaagta | tgtgatcagc | gatgaagagg | 2040 |
| aagaagatga | tgattgaagt | atgaaatatg | aaacatttt | atatatttta | ttgtacagtt | 2100 |

| ataaatatgt aaacatgagt tattttgatt gaaatgaatc gatttgcttt tgtgtaattt | 2160 |
| taattgtaat aaaacaattt aaaagcaaaa aaaaaaaaaa aa | 2202 |

<210> SEQ ID NO 22
<211> LENGTH: 2047
<212> TYPE: DNA
<213> ORGANISM: Homo sapiens

<400> SEQUENCE: 22

| ttgattatgg aacattctaa aacttagaca agacgattgt gattggctga agggcatacg | 60 |
| ccctcctcca gggtgacgtg tctgcctatg gatatcagtt gccagagaaa cctggcttta | 120 |
| ctatggcggt tggaggaacg gcagtgatca cacgtcggct gctgggaaga tctggattct | 180 |
| cgtttcaggt caccatcaga aaagctaagt ttgctgtata gtgaggatca ggagatctga | 240 |
| tcctgattgc agaaccttcc ctgattacag aatcttggga ttgttgagag gattacatgt | 300 |
| aaagtaccag gacagtgcat ggcacatatg atttcacaaa agttcatctt cattgcagat | 360 |
| acctgccttt ctttctaggt tgtatctccc acttcacccct tctagaccat cccagaagat | 420 |
| ctataagatt tcatctggga aatcactagg agttcttgga agggaaagaa ggaagattgt | 480 |
| tggttggaat aaaaacaggg ttgaatgagt tccagaaagc agggttctca acctcgtgga | 540 |
| cagcaatctg cagaagaaga gaacttcaaa aaaccaacta aagcaacat gcagagaagt | 600 |
| aaaatgagag gggcctcctc aggaaagaag acagctggtc cacagcagaa aaatcttgaa | 660 |
| ccagctctcc caggaagatg gggtggtcgc tctgcagaga accccccttc aggatccgtg | 720 |
| aggaagacca gaaagaacaa gcagaagact cctggaaacg gagatggtgg cagtaccagc | 780 |
| gaagcacctc agccccctcg gaagaaaagg gcccgggcag accccactgt tgaaagtgag | 840 |
| gaggcgttta agaatagaat ggaggttaaa gtgaagattc ctgaagaatt aaaaccatgg | 900 |
| cttgttgagg actgggactt agttaccagg cagaagcagc tgtttcaact ccctgccaag | 960 |
| aaaaatgtag atgcaattct ggaggagtat gcaaattgca agaaatcgca gggaaatgtt | 1020 |
| gataataagg aatatgcggt taatgaagtt gtggcaggaa taaaagaata tttcaatgtg | 1080 |
| atgtttgggca ctcagctgct ctacaaattt gagaggcccc agtatgctga aatcctcttg | 1140 |
| gctcaccctg atgctccaat gtcccaggtt tatggagcac cacacctact gagattattt | 1200 |
| gtaagaattg gagcaatgtt ggcctatacg ccccttgatg agaaaagcct tgcattattg | 1260 |
| ttgggctatt tgcatgattt cctaaaatat ctggcaaaga attctgcatc tctctttact | 1320 |
| gccagtgatt acaaagtggc ttctgctgag taccaccgca aagccctgtg agcgtctaca | 1380 |
| gacagctcac cattttttgtc ctgtatctgt aaacactttt tgttcttagt cttttttcttg | 1440 |
| taaaattgat gttctttaaa atcgttaatg tataacaggg cttatgtttc agtttgtttt | 1500 |
| ccgttctgtt ttaaacagaa aataaaagga gtgtaagctc cttttctcat ttcaaagttg | 1560 |
| ctaccagtgt atgcagtaat tagaacaaag aagaaacatt cagtagaaca ttttattgcc | 1620 |
| tagttgacaa cattgcttga atgctggtgg ttcctatccc tttgacacta cacaatttttc | 1680 |
| taatatgtgt taatgctatg tgacaaaacg ccctgattcc tagtgccaaa ggttcaactt | 1740 |
| aatgtatata cctgaaaacc catgcatttg tgctctttt ttttttttat ggtgcttgaa | 1800 |
| gtaaaacagc ccatcctctg caagtccatc tatgttgttc ttaggcattc tatctttgct | 1860 |
| caaattgttg aaggatggtg atttgtttca tggttttttgt atttgagtct aatgcacgtt | 1920 |
| ctaacatgat agaggcaatg cattattgtg tagccacggt tttctggaaa agttgatatt | 1980 |
| ttaggaattg tatttcagat cttaaataaa atttgtttct aaatttcaaa gcaaaaaaaa | 2040 | aaaaaaa 2047

<210> SEQ ID NO 23
<211> LENGTH: 4451
<212> TYPE: DNA
<213> ORGANISM: Homo sapiens

<400> SEQUENCE: 23

| | | | | | |
|---|---|---|---|---|---|
| aaaagatatg | gtggggtgct | taacagagga | ggttagacac | cggcgggaac | cagaggagcc | 60 |
| caagcgcggc | gcctgggcct | cggggctgca | ggagtcctcg | gtgggggtat | ggaggtcgcc | 120 |
| ggggaaggag | gacggttcag | ttgctaggca | acccggcctg | gacccgcctc | tcgctcgcgt | 180 |
| tgctgggaga | ctacaaggcc | gggaggaggg | cggcgaaagg | gccctacgtg | ctgacgctaa | 240 |
| ttgtatatga | gcgcgagcgg | cgggctcttg | ggtctttttt | agcgccatct | gctcgcggcg | 300 |
| ccgcctcctg | ctcctcccgc | tgctgctgcc | gctgccgccc | tgagtcactg | cctgcgcagc | 360 |
| tccggccgcc | tggctcccca | tactagtcgc | cgatatttgg | agttcttaca | acatggcaga | 420 |
| cattgacaac | aaagaacagt | ctgaacttga | tcaagatttg | gatgatgttg | aagaagtaga | 480 |
| agaagaggaa | actggtgaag | aaacaaaact | caaagcacgt | cagctaactg | ttcagatgat | 540 |
| gcaaaatcct | cagattcttg | cagcccttca | agaaagactt | gatggtctgg | tagaaacacc | 600 |
| aacaggatac | attgaaagcc | tgcctagggt | agttaaaaga | cgagtgaatg | ctctcaaaaa | 660 |
| cctgcaagtt | aaatgtgcac | agatagaagc | caaattctat | gaggaagttc | acgatcttga | 720 |
| aaggaagtat | gctgttctct | atcagcctct | atttgataag | cgatttgaaa | ttattaatgc | 780 |
| aatttatgaa | cctacggaag | aagaatgtga | atggaaacca | gatgaagaag | atgagatttc | 840 |
| ggaggaattg | aaagaaaagg | ccaagattga | agatgagaaa | aaagatgaag | aaaaagaaga | 900 |
| ccccaaagga | attcctgaat | tttggttaac | tgttttttaag | aatgttgact | tgctcagtga | 960 |
| tatggttcag | gaacacgatg | aacctattct | gaagcacttg | aaagatatta | agtgaagtt | 1020 |
| ctcagatgct | ggccagccta | tgagttttgt | cttagaattt | cactttgaac | ccaatgaata | 1080 |
| ttttacaaat | gaagtgctga | caaagacata | caggatgagg | tcagaaccag | atgattctga | 1140 |
| tcccttttct | tttgatggac | cagaaattat | gggttgtaca | gggtgccaga | tagattggaa | 1200 |
| aaaaggaaag | aatgtcactt | tgaaaactat | taagaagaag | cagaaacaca | agggacgtgg | 1260 |
| gacagttcgt | actgtgacta | aaacagtttc | caatgactct | ttctttaact | ttttttgcccc | 1320 |
| tcctgaagtt | cctgagagtg | gagatctgga | tgatgatgct | gaagctatcc | ttgctgcaga | 1380 |
| cttcgaaaatt | ggtcactttt | tacgtgagcg | tataatccca | agatcagtgt | tatattttac | 1440 |
| tggagaagct | attgaagatg | atgatgatga | ttatgatgaa | gaaggtgaag | agcggatga | 1500 |
| ggaaggggaa | gaagaaggag | atgaggaaaa | tgatccagac | tatgacccaa | agaaggatca | 1560 |
| aaacccagca | gagtgcaagc | agcagtgaag | caggatgtat | gtggccttga | ggataacctg | 1620 |
| cactggtcta | ccttctgctt | ccctggaaag | gatgaattta | catcatttga | caagcctatt | 1680 |
| ttcaagttat | ttgttgtttg | tttgcttgtt | tttgttttg | cagctaaaat | aaaaatttca | 1740 |
| aatacaattt | tagttcttac | aagataatgt | cttaattttg | taccaattca | ggtagaagta | 1800 |
| gaggcctacc | ttgaattaag | ggttatactc | agttttaac | acattgttga | agaaaaggta | 1860 |
| ccagctttgg | aacgagatgc | tatactaata | agcaagtgta | aaaaaaaaa | aaaagagga | 1920 |
| agaaaatctt | aagtgattga | tgctgttttc | ttttaaaaaa | aaaaaaaaa | attcattttc | 1980 |
| tttgggttag | agctagagag | aaggccccaa | gcttctatgg | tttcttctaa | ttcttattgc | 2040 |

```
ttaaagtatg agtatgtcac ttacccgtgc ttctgtttac tgtgtaatta aaatgggtag    2100
tactgtttac ctaactacct catggatgtg ttaaggcata ttgagttaaa tctcatataa    2160
tgtttctcaa tcttgttaaa agctcaaaat tttgggccta tttgtaatgc cagtgtgaca    2220
ctaagcattt tgttcacacc acgctttgat aactaaactg gaaaacaaag gtgttaagta    2280
cctctgttct ggatctgggc agtcagcact cttttagat ctttgtgtgg ctcctatttt     2340
tatagaagtg gagggatgca ctatttcaca aggtccaaga tttgttttca gatattttg     2400 atgactgtat tgtaaatact acagggatag cactatagta ttgtagtcat gagacttaaa    2460
gtggaaataa gactattttt gacaaaagat gccattaaat ttcagactgt agagccacat    2520
ttacaatacc tcaggctaat tactgttaat tttggggttg aacttttttt tgacagtgag    2580
ggtggattat tggattgtca ttagaggaag gtctagattt cctgctctta ataaaattac    2640
attgaattga tttttagagg taatgaaaac ttcctttctg agaagttagt gttaaggtct    2700
tggaatgtga acacattgtt tgtagtgcta tccattcctc tcctgagatt ttaacttact    2760
actggaaatc cttaaccaat tataatagct tttttctt attttcaaaa tgatttcctt      2820
tgctttgatt agacactatg tgcttttttt ttttaaccat agttcatcga aatgcagctt    2880
tttctgaact tcaaagatag aatcccattt ttaatgaact gaagtagcaa aatcatcttt    2940
ttcattcttt aggaaatagc tattgccaaa gtgaaggtgt agataatacc tagtcttgtt    3000
acataaaggg gatgtggttt gcagaagaat tttctttata aaattgaagt tttaagggac    3060
gtcagtgttt atgccatttt tccagttcca aaatgattcc attccattct agaaatttga    3120
agtatgtaac ctgaaatcct taataaaatt tggatttaat tttataaaat gtactggtga    3180
tattttgggt gttttttttt aaatgaatgt atatactttt tttttgaaga gtggagagta    3240
gtgatgtcta gagggagcta ttttgtgctg aggccactat gttctgtaaa tatataattt    3300
taagagcaac ctcacaatcc ctgctaagtg gagtttatta tttgaagact aaaatggaat    3360
tccatagttc ctgataggtt atattctggg ttattattct gagttatcta caaacatttt    3420
tgagatttgt ctttacactc tgattgtagt ttccagcagc ccatgcacac tgccaagtaa    3480
gtctcatttt ttcctgttag aaatggtgaa atatcatata atcacttata aagaaaactg    3540
atatgaaaaa attttagagt tgtttgcttt atggtcactc aagtagggta agtgttccac    3600
aaattccaca agttgatagt ttaacatgga tgtctgaaag ccacatatat aatttcttag    3660
gattcttaaa ttagtaaatc tagcttactg aagcagtatt agcatcacta ttttagattg    3720
caaaaatacc ttaattgtgt ggaactggct tgtagagtgg tacttaagaa aaatgggatt    3780
ctacctctat ttctgtttta gcacacttaa tcaggaaagg atatattaac tttcataaaa    3840 atattttgt tgtgtgaata ggttaatgat atggtaaggc ccctaaaata actgaattaa      3900
ttgtttattg taattgtagg ccattcccat tattaaaaat aaagacaaaa cttgaagtaa    3960
ctgaaaatct tatcgtgcta tgtagaaata ttgaactaat attcaaatat ttgaatgctt    4020
tggtttcagg gattggttta aaattggagt ccttttttat gggttagtct tacaaaaatt    4080
taagccttta tatttttgac tttaaatcaa aacaaatgtt attttaaatg tacagaatag    4140
attggtagtg cagaagagtg taagttcttc ataggagctt tagaaaagag aaatatgtgc    4200
taattcagtt ttttttttaat ctgcactgta catatatact tggtaattat gagcttgatt   4260 ttgttttttgg aaatatgtgt tcataattta ggtaatttgc tacttaaagc actaagtctc   4320
tgatacctga aaagtacatg taaatggtga tggtgaaata atactgcagt taacttaata    4380
gatgtatact ggtgattttt gtatgctgga ttaaaactcc agatattaaa ataaacctg     4440
```

| | |
|---|---|
| gataaaaagc c | 4451 |

<210> SEQ ID NO 24
<211> LENGTH: 1530
<212> TYPE: DNA
<213> ORGANISM: Homo sapiens

<400> SEQUENCE: 24

| | |
|---|---|
| ggcattcaga gagtagatgc cagtcctggg aaaggcaggg gaggagagga gagccacggc | 60 |
| tgacgcttgg ggacagaagg aggagcctga ggaggagaca ggacagagcg tctggagagg | 120 |
| caggaggaca ccgagttccc cgtgttggcc tccaggtcct gtgcttgcgg agccgtccgg | 180 |
| cggctgggat cgagccccga caatgggcaa cgcgcaggag cggccgtcag agactatcga | 240 |
| ccgcgagcgg aaacgcctgg tcgagacgct gcaggcggac tcgggactgc tgttggacgc | 300 |
| gctgctggcg cggggcgtgc tcaccgggcc agagtacgag gcattggatg cactgcctga | 360 |
| tgccgagcgc agggtgcgcc gcctactgct gctggtgcag ggcaagggcg aggccgcctg | 420 |
| ccaggagctg ctacgctgtg cccagcgtac cgcgggcgcg ccggaccccg cttgggactg | 480 |
| gcagcacgct accgggaccg cagctatgac cctccatgcc caggccactg gacgccggag | 540 |
| gcacccggct cggggaccac atgccccggg ttgcccagag cttcagaccc tgacgaggcc | 600 |
| gggggccctg agggctccga ggcggtgcaa tccgggaccc cggaggagcc agagccagag | 660 |
| ctggaagctg aggcctctaa agaggctgaa ccggagccgg agccagagcc agagctggaa | 720 |
| cccgaggctg aagcagaacc agagccgaa ctggagccag aaccggaccc agagcccgag | 780 |
| cccgacttcg aggaaaggga cgagtccgaa gattcctgaa ggccagagct ctgacaggcg | 840 |
| gtgccccgcc catgctggat aggacctggg atgctgctgg agctgaatcg gatgccacca | 900 |
| aggctcggtc cagcccagta ccgctggaag tgaataaact ccggagggtc ggacgggacc | 960 |
| tgggctctct ccacgattct ggctgtttgc ccaggaactt agggtgggta cctctgagtc | 1020 |
| ccagggacct gggcaggccc aagcccacca cgagcatcat ccagtcctca gccctaatct | 1080 |
| gcccttagga gtccaggctg caccctggag atcccaaacc tagcccccta gtgggacaag | 1140 |
| gacctgaccc tcctgcccgc atacacaacc catttcccct ggtgagccac ttggcagcat | 1200 |
| atgtaggtac cagctcaacc ccacgcaagt tcctgagctg aacatggagc aaggggaggg | 1260 |
| tgacttctct ccacataggg agggcttaga gctcacagcc ttgggaagtg agactagaag | 1320 |
| aggggagcag aaagggacct tgagtagaca aaggccacac acatcattgt cattactgtt | 1380 |
| ttaattgtct ggcttctctc tggactggga gctcagtgag gattctgacc agtgacttac | 1440 |
| acaaaggcg ctctatacat attataatat attcgcttac taaatgaata aggactttcc | 1500 |
| aaaaaaaaa aaaaaaaaa aaaaaaaaa | 1530 |

<210> SEQ ID NO 25
<211> LENGTH: 2410
<212> TYPE: DNA
<213> ORGANISM: Homo sapiens

<400> SEQUENCE: 25

| | |
|---|---|
| ggtgcagcct tacgccgctg acgcatcgcg cccaagatgg cggcgcggtc gtcgtcgggg | 60 |
| gtggcggcgg cagaggggc ggcggccctg gcggcagcgg agacggcagc cgtgacggtg | 120 |
| gcagcggcgg cgcggacct gggctgggg gaatgaggcg gccgcggcgg gccagcggcg | 180 |
| gagccgtgta gcggagaagc tcccctccc tgcttccctt ggccgagccg ggggcgcgcg | 240 |

```
cgcacgcggc cgtccagagc gggctcccca cccctcgact cctgcgaccc gcaccgcacc      300
cccacccggg cccggaggat gatgaagctc aagtcgaacc agacccgcac ctacgacggc      360
gacggctaca agaagcgggc cgcatgcctg tgtttccgca gcgagagcga ggaggaggtg      420
ctactcgtga gcagtagtcg ccatccagac agatggattg tccctggagg aggcatggag      480
cccgaggagg agccaagtgt ggcagcagtt cgtgaagtct gtgaggaggc tggagtaaaa      540
gggacattgg gaagattagt tggaattttt gagaaccagg agaggaagca caggacgtat      600
gtctatgtgc tcattgtcac tgaagtgctg gaagactggg aagattcagt taacattgga      660
aggaagaggg aatggtttaa aatagaagac gccataaaag tgctgcagta tcacaaaccc      720
gtgcaggcat catattttga aacattgagg caaggctact cagccaacaa tggcacccca      780
gtcgtggcca ccacatactc ggtttctgct cagagctcga tgtcaggcat cagatgactg      840
aagacttcct gtaagagaaa tggaaattgg aaactagact gaagtgcaaa tcttccctct      900 cacccctggct ctttccactt ctcacaggcc tcctctttca ataaggcat ggtgggcagc      960 aaagaaaggg tgtattgata atgttgctgt ttggtgttaa gtgatgggc ttttcttct     1020 gtttttattg agggtggggg ttgggtgtgt aatttgtaag tacttttgtg catgatctgt     1080
ccctccctct tcccacccct gcagtcctct gaagagaggc caacagcctt cccctgcctt     1140
ggattctgaa gtgttcctgt ttgtcttatc ctggccctgg ccagacgttt tctttgattt     1200 ttaattttt tttttattta aaagatacca gtatgagatg aaaacttcca ataatttgtc     1260
ctataatgtg ctgtacagtt cagtagagtg gtcactttca ctgcagtata catttatcta     1320
cacattatat atcggacata taatatgtaa ataaatgact tctagaaaga gaaatttgtt     1380 taattttca aggttttttt ctcttttaat ttgggcattt ctagaattga gagcctcaca     1440
attaacatac ctttttgttt tcgatgctag tggctgggca ggttgccctg tccttttctct     1500 atttcccagt cattgactgt agatatggga agagtttagc taccttcata gtgctcccag     1560
gactcatggc ctttccttct ttaagctgta tttccctgcc cagaaagaaa caggaagaaa     1620 cctttttta tttttttatt tttttttaac caagcaagga gcaaatggcc tcagcccaga     1680
tctgtaaaaa caatgataga aattgaattc tgccccacat gttgacagta gagttggaac     1740
tggattcttg ggattactta tctaaaaaac tggagcatca ggtccatttc tgttctgctg     1800
gtttggaatc ttttccgtaa tgctatttat tgccaacaat ggcctctctt tgtgtccata     1860
tatgccttac accgtgctga cctgggtatc atccatgtgc tctgaagcat ccaactttac     1920
tttgcaggtg catcaatgta gtcctgtccc tgaactgagt aaccgtgttc ctgaaaagta     1980
cactagggaa attcacctgc ttgcttgtct ttgtattggc atggcacttg tgattgcacc     2040
atggagcatg ctcagagcta ttaaattggt ctcccatctc ccaccaggat atgaaaggtc     2100
catatgggag gccacgtaat cacttattac agtggttaca taatacactg gctcactgca     2160
gactctcttg ttttttgata cagtttcgtg ctggcttcat ttgccaattg tgttgtttag     2220
ttcggaagta agagggtctt gagattgagg ggtagggagg gctacactga ctgatccgtg     2280
gcttaagaca ggagattatc tctgtactcc agtggcatct ccttagccaa gatgtgaaat     2340
taaaatcata gttcgcctca tttaaaaatt ctaataaagc actcaaactt tgaaaaaaaa     2400
aaaaaaaaa                                                            2410

<210> SEQ ID NO 26
<211> LENGTH: 1947
<212> TYPE: DNA
<213> ORGANISM: Homo sapiens
```

<400> SEQUENCE: 26

```
atgcagatga ggcactcggg ggcggggcgg cggcggcggc ggcggcggtg gcggccgggg    60
agggtcagtt ggaggcaggc gctcgctgag gcaaaaggag gcgctcggcc cgcggcctga   120
cagggactta gcccgcagag atcgaccccg cgcgcgtgac cccacaccca cccactcatc   180
catctatcca ctccctgcgc cgcctcctcc caccctgagc agagccgccg aggatgataa   240
acacccagga cagtagtatt ttgcctttga gtaactgtcc ccagctccag tgctgcaggc   300
acattgttcc agggcctctg tggtgctcct gatgcccctc acccactgtc gaagatcccc   360
ggtgggcgag gggcggcag ggatccttct ctctcagctc taatatataa ggacgagaag   420
ctcactgtga cccaggacct ccctgtgaat gatggaaaac ctcacatcgt ccacttccag   480
tatgaggtca ccgaggtgaa ggtctcttct tgggatgcag tcctgtccag ccagagcctg   540
tttgtagaaa tcccagatgg attattagct gatgggagca agaaggatt gttagcactg   600
ctagagtttg ctgaagagaa gatgaaagtg aactatgtct tcatctgctt caggaagggc   660
cgagaagaca gagctccact cctgaagacc ttcagcttct gggctttga gattgtacgt   720
ccaggccatc cctgtgtccc ctctcggcca gatgtgatgt tcatggttta tcccctggac   780
cagaacttgt ccgatgagga ctaatagtca tagaggatgc tttacccaag agccacagtg   840
ggggaagagg ggaagttagg cagccctggg acagacgaga gggctcctcg ctgtctaggg   900
aaggacactg aggggctcag ggtgagggtt gcctattgtg ttctcggagt tgactcgttg   960
aaattgtttt ccataaagaa cagtataaac atattattca catgtaatca ccaatagtaa  1020
atgaagatgt ttatgaactg gcattagaag ctttctaaac tgcgctgtgt gatgtgttct  1080
atctagccta ggggaggaca ttgcctagag ggggagggac tgtctgggtt caggggcatg  1140
gcctggaggg ctggtgggca gcactgtcag gctcaggttt ccctgctgtt ggctttctgt  1200
tttggttatt aagacttgtg tattttcttt ctttgcttcc tgtcacccca ggggctcctg  1260
agtataggct tttcagtccc tgggcagtgt ccttgagttg ttttttgaca ctcttacctg  1320
ggcttctctg tgtgcatttg cgtctggcct ggagtaagca ggtccgaccc ctccttcttt  1380
acagcttagt gttattctgg catttggtta agctggctta atctgtttaa tgttatcagt  1440
acattttaaa tagggcatt gaaatttact cccaccacca gggcttttt ggggatgcc   1500
tgggccttta aaacactagc caaactctaa ttaattctca aatcactgcc aggagttctt  1560
gctcctggct gcaggcccag gcccaaggt ctccttcttg gggtcacaaa cagcagtaag  1620
gaagaggaat atatagcaac tcagggcctg ggaattgtgg ggcaatccgt tcttagggac  1680
tggatacttc tggctggctg agtatagtac tagctgcctc cccaccaggt tccgagtagt  1740
gtctgagact ctgctctgca gggcctaggg tagcgctggg agtgtagaag tggcctgccc  1800
ttaactgttt tcactaaaca gcttttctct aggggagagc aaggggagag atctagatt   1860
gggtgagggg gacgggatg tcaggaggc aagtgtgttg tgttactgtg tcaataaact  1920
gatttaaagt tgtgaaaaaa aaaaaaa                                      1947
```

<210> SEQ ID NO 27
<211> LENGTH: 1712
<212> TYPE: DNA
<213> ORGANISM: Homo sapiens

<400> SEQUENCE: 27

```
atgctggggg aggggctggc ggcctcgacg gcagctgcgg aactaggccg agggacaaag    60
```

```
gctaagtttt tccatggttt ggactggata tcggtggaac tctggtcaag ctggtatatt    120
ttgaacccaa agacatcact gctgaagaag aagaggaaga agtggaaagt cttaaaagca    180
ttcggaagta cctgacctcc aatgtggctt atgggtctac aggcattcgg gacgtgcacc    240
tcgagctgaa ggacctgact ctgtgtggac gcaaaggcaa tctgcacttt atacgctttc    300
ccactcatga catgcctgct tttattcaaa tgggcagaga taaaaacttc tcgagtctcc    360
acactgtctt ttgtgccact ggaggtggag cgtacaaatt tgagcaggat tttctcacaa    420
taggtgatct tcagctttgc aaactggatg aactagattg cttgatcaaa ggaattttat    480
acattgactc agtcggattc aatggacggt cacagtgcta ttactttgaa aaccctgctg    540
attctgaaaa gtgtcagaag ttaccatttg atttgaaaaa tccgtatcct ctgcttctgg    600
tgaacattgg ctcaggggtt agcatcttag cagtatattc caaagataat tacaaacggg    660
tcacaggtac tagtcttgga ggaggaactt ttttggtct ctgctgtctt cttactggct    720
gtaccacttt tgaagaagct cttgaaatgg catctcgtgg agatagcacc aaagtggata    780
aactagtacg agatatttat ggagggact atgagaggtt tggactgcca ggctgggctg    840
tggcttcaag ctttggaaac atgatgagca aggagaagcg agaggctgtc agtaaagagg    900
acctggccag agcgactttg atcaccatca ccaacaacat tggctcaata gcaagaatgt    960
gtgcccttaa tgaaaacatt aaccaggtgg tatttgttgg aaatttcttg agaattaata   1020
cgatcgccat gcggcttttg gcatatgctt tggattattg gtccaagggg cagttgaaag   1080
cacttttttc ggaacacgag ggttattttg gagctgttgg agcactcctt gagctgttga   1140
agatcccgtg atcattacct ggggagggt tcctgaaacc ttccacaatg ggatctgtgg   1200
actttcattt ttttaagaga cttactcaat ttcatgactg tactacctga aacaaagtga   1260
gaaaggacag gtgtattttt ctaagtcatc aagataaatc cttaagaatt cagtctaaat   1320
tagcaaccag gaaggaaaaa tatattaaaa acaacaaaaa agtggcacat gtccaggcag   1380
tgtgaggatt tgctgtatat aagttgcctg ctttgtattt ttgaaatctc tgcatcactc   1440
attggaagtg cttctgaaga gagctgctct gtgttcagtt gactggtttt gtgtcctgtt   1500
tgaacttgct gaatgtaagg caggctacta tgcgttataa tctaatcaca atttgtcaat   1560
atggtcttgg caatcatctg tgcattactc tggtttgcat taagcctgtg tgtgaactta   1620
ctgtaaaaca tgttttattt caaggttctg caaaattaat tgggcaggtt aattgtgtac   1680
ctgaaactta acaagcagtt tttggaaggg ca                                  1712

<210> SEQ ID NO 28
<211> LENGTH: 7332
<212> TYPE: DNA
<213> ORGANISM: Homo sapiens

<400> SEQUENCE: 28
ggtgaatggg ctggtggtgc tcgctgctgc tgctgagagg aggaggagga tgaagagttg     60
ggcttgtttg tctcctacag tttctctcct gctgctctga ttccccctc ccgattccgg    120 cccgggggcct gtgtgtgtcc ctcctggagg aggaggagga tccagttcct cccccccaacc   180 ccctcctccc cacccccct tgcctgggga agagagagga agaaacagcc cagagagaga    240
gagagagaga gagtgagtga gagagagagg agaggagagg aggaggagga ggagggagaa    300
gggaacaacc taccatctta acacactaat atctaaaaag tgcgagaggc ccagagcagc    360
agcagaagca gcagcagcag ctccagcttc ttccctccct cccatgaag aagagttccc    420 tcctcctcct cctcctgctt ctcctgctca gagttcctgc ctccagctgc cagggggac    480
```

-continued

| | |
|---|---|
| agccagccag cagcaggagg ggggctagag agctgaagga gagccagttt ccccaaaatt | 540 |
| gctgcagtga aagaggagt ttgttacttt aaacagaggc tgaagaaact atagaattag | 600 |
| cagagaaagt ggagaaggta gaggatggag ttgcagactc tacaggaggc tcttaaagtg | 660 |
| gaaattcagg ttcaccagaa actggttgct caaatgaagc aggatccaca gaatgctgac | 720 |
| ttaaagaaac agcttcatga actccaagcc aaaatcacag ctttgagtga gaaacagaaa | 780 |
| agagtagttg aacagctacg gaagaacctg atagtaaagc aagaacaacc ggacaagttc | 840 |
| caaatacagc cattgccaca atctgaaaac aaactacaaa cagcacagca gcaaccacta | 900 |
| cagcaactac aacaacagca gcagtaccac caccaccacg cccagcagtc agctgcagcc | 960 |
| tctcccaacc tgactgcttc acagaagact gtaactacag cttctatgat taccacaaag | 1020 |
| acactacctc tcgtcttgaa agcagcaact gcgaccatgc ctgcctctgt ggtgggccag | 1080 |
| agacctacca ttgctatggt gaccgccatc aacagtcaga aggctgtgct cagcactgat | 1140 |
| gtgcagaaca caccagtcaa cctccagacg tctagtaagg tcactgggcc tggggcagag | 1200 |
| gctgtccaaa ttgtggcaaa aaacacagtc actctggttc aggcaacacc tcctcagccc | 1260 |
| atcaaagtac cacagtttat cccccctcct agactcactc cacgtccaaa ctttcttcca | 1320 |
| caggttcgac ccaagcctgt ggcccagaat aacattccta ttgccccagc accacctccc | 1380 |
| atgctcgcag ctcctcagct tatccagagg cccgtcatgc tgaccaagtt caccccaca | 1440 |
| acccttccca catcccagaa ttccatccac cccgtccgtg tcgtcaatgg gcagactgca | 1500 |
| accatagcca aaacgttccc catggcccag ctcaccagca ttgtgatagc tactccaggg | 1560 |
| accagactcg ctggacctca aactgtacag cttagcaagc caagtcttga aaacagaca | 1620 |
| gttaaatctc acacagaaac agatgagaaa caaacagaga gccgcaccat caccccacct | 1680 |
| gctgcaccca accaaaacg ggaggagaac cctcagaaac ttgccttcat ggtgtctcta | 1740 |
| gggttggtaa cacatgacca tctagaagaa atccaaagca agaggcaaga gcgaaaaaga | 1800 |
| agaacaacag caaatccggt ctacagtgga gcagtctttg agccagagcg taagaagagt | 1860 |
| gcagtgacat acctaaacag cacaatgcac cctgggaccc ggaagagagg tcgtcctcca | 1920 |
| aaatacaatg cagtgctggg gtttggagcc cttaccccaa catcccccca atccagtcat | 1980 |
| cctgactccc ctgaaaatga aaagacagag accacattca ctttccctgc acctgttcag | 2040 |
| cctgtgtccc tgcccagccc cacctccaca gacggtgata ttcatgagga ttttgcagc | 2100 |
| gtttgcagaa aaagtggcca gttactgatg tgcgacacat gttccgtgt atatcatttg | 2160 |
| gactgcttag acccccctct gaaaacaatt cccaagggca tgtggatctg tcccagatgt | 2220 |
| caggaccaga tgctgaagaa ggaagaagca attccatggc ctggaacttt agcaattgtt | 2280 |
| cattcctata ttgcctacaa agcagcaaaa gaagaagaga acagaagtt acttaaatgg | 2340 |
| agttcagatt taaaacaaga acgagaacaa ctagagcaaa aggtgaaaca gctcagcaat | 2400 |
| tccataagta aatgcatgga aatgaagaac accatcctgg cccggcagaa ggagatgcac | 2460 |
| agctccctgg agaaggtaaa acagctgatt cgcctcatcc acggcatcga cctctccaaa | 2520 |
| cctgtagact ctgaggccac tgtgggggcc atctccaatg gcccggactg caccccccct | 2580 |
| gccaatgccg ccacctccac gccggcccct tcccctcct cccagagctg cacagcgaac | 2640 |
| tgtaaccagg ggaagagac taaataacag agcccctcta ggagaagcca cgggatcccg | 2700 |
| gcggcaagga gaacagaaca ctgaagactc tagaaaagca aagccggatt tctgaaagt | 2760 |
| gcagaattct tttggttctt tggttccaga gagagagaag atgcttgtgc caggtggcac | 2820 |

```
cagagtttgc caattgatcc ttcttattct gtgtgtacat gcaaagattg gaccatgtta   2880
catgaaatag tgccagctgg aggttctttg ccagcaccat gccaagtgaa ataatatatt   2940
tactctctct attatacacc agtgtgtgcc tgcagcagcc tccacagcca cgatgggttt   3000
gtttctgttt tcttgggtgg ggagcaggga cgggcgagg gaggagagca ggtttcagat    3060
ccttacttgc cgagccgttt gtttaggtag agaagacaag tccaaagagt gtgtgggctt   3120
tcctgtttct aaactttcgc tactataaaa ccaaaaaaag gaattgagat ttcaccaacc   3180
ccagtgccca gaagagggaa ggggagtggc tggagggagc aggggtggg acagtgtatc    3240
aaataagcag tatttaatca cctctggcgg gggcctcgtg caaggggaga ctgacaccaa   3300
gaacagccag taggttcttc tcccctgcac tctgctccct gcgcggtaac cccaccactc   3360
ctgaagcctg cccagtctcc ttccttccct gcttggtgag tcgcgcatct ccgtggttat   3420
cccgctgtct cctctccaag aacaagcaga gcccgggcca ctggcccttg cccaaggcag   3480
ggaagaagga tgtgtgtgtc caggaaggaa aaaaaggtgg atcagtgatt ttacttgaaa   3540
acaagctcca tccttttct atatttataa gaagagaaga tcttgagtga agcagcacgc    3600
gacccaggtg tgtgtgaatt gaatggagac gtttcttttc tctttcttta attttgttt    3660
ttgttctttt tttcttaag gaaagttta ttttactgtt cattttactt tcttggtaac     3720
aaaaactaaa ataaggaata gaaaagctgt ttttcaggct gacagtccaa ttaagggtag   3780
ccaagaccctt gcatggtaga gtaggaatca tagtgtcagt gaggtcccgt gagtctttgt  3840
gagtccttgt gtcatcgttc gggcactgtt tttttatgca agggcaaaaa tctttgtatc   3900
tggggaaaaa aaacttttttt ttaaattaaa aaggaaaata aagatattg aggtcttcct   3960
agtgttactt aaattaagat caaggtaaga acattgtaa aaaaaaatta caaaagtgct    4020
atttgtttcc taaaaacagt gatttctatt aaaaaggtgt cagaactgga gaaaatgccg   4080
tgtagttata attttttagc acagaccctg ctgatcacga tgacattttg ccgtgtgtgt   4140
gtctctagac tggtgggcca gtctccttga aggacagagg cggagctccc cacccttctc   4200
tctcctcaga aaagaccgtg ctctcttctt ggtgcaggga tcttgtctcc tgttgtgaag   4260
cccaaatgga agcgtggatg gtatcagggc cctacccgtg gtcttctcag attctgctag   4320
agcaaaaggc tggtgcctaa ataagatccc ttcctttggt gctgcttttg gtctttcagc   4380
caccagcatt atgagtgcct gggggacacc tccgagggaa ctggccagcg gagctctgtg   4440
gtgcgcacgc accctggccg tgacaggagg gtgcgggagt acaggctggc tgcatcagcc   4500
cttggtgctt agaacagagg aggagtgaca tgttttgagg gtacgtctct gagacagagc   4560
cccagcgtgg ccttcgctct gtcttgcctt tggggagagg tctgaagctc ccactccttt   4620
ctctgcctgt tggctccagg caccagaaat ttactccact ccacccaccc acaagcctcc   4680
tgggtgaccc tgggctagaa ttgctgcgct tgcctcggct tggccggttg tggcctctcc   4740
ttgagaaaac cagggttgtg aaagactcag accattctct catcttgcct tgtcagaagt   4800
aaattgtgtc agatttgtgc tctcgctgga gacctttgcc ccttgcgtgc ccctggccga   4860
tgggagggcg gtggaggctc tgtaccctgg ccctgctgga gcatctcccc caagcccact   4920
ccaggccctg gaatggcca gagtctagga gaggtagaaa cgatcctatc agcttctctc    4980
ccacccaatt aggcccagag agacaaagac agatctgaaa gcaaatgcaa cagagaagag   5040
acacttctta gagtaaaatg tgtctcatct ctatcagcca tcgcctttca tcttcccagg   5100
ggcctcagaa gaaggaatta agttaggctg aacaggcctc agagttaggc cctggctgct   5160
tgattggctg agggggaaag agttcccttt tctcattcag aaaccaaggt gctgtgtcta   5220
```

```
gtcagggagc cttggagatg cctggactag ttgaggaat cgttggcaga ggatcagaga    5280
ccagcagcag gctgtctgcc ctgtctagag ctcttcccct caacttgtct gggcccatct   5340
gggggttgcc acacaacacc taacttacct tttcctgaaa aagttggga aaccatcatc    5400 actagaggcc tttgctcaga gaggagctgc cttaggagtc ttgggtcgga ggacggggct   5460
aggaattgac cagggctttg cctgccgccc tcagcagtgt cgggtacatt ctgacctcgc   5520
ctgcagctgg gctgtggatt cttcctgaca ttcagatgtg agctgttttg ggagtcagct   5580
agtatggagt acgagatgca acccagcccc caaacctaca ttctgcactc aaattccaaa   5640
acactgcttt actgtaaaga agaggcccct ggcacccaat ctccctgtcc ttcactgtcc   5700
cctcagacct gggcggggag ggggggggc ctgtgaccac ctgagacata cgctcgtgac     5760
actgccccac cccagccacc tccacttgct tcctcctcct tccctccgct gctctttccc   5820
cacggcccag aatttagctg ctctgacagc cacttttgag accagctggc tttgtagtca   5880
cttcagagag ctggagcggc tgcccactgg gccctgactg ggagtcccct gccagctcct   5940
gatcaggcgc tgcgccctgg tggcagtgat gactgggagt cccctgccag ctcctgtcca   6000
ggcgctgcat cctggtaaca gtgaggccat gttgctgtca tctccacctc tgcattcttg   6060
ctgcctgtgg gtcctttttc tttcatggag cctgctgggt cttgtctcac ctgtgctgag   6120
ctcctctggg gttttgattt cttccttcct tatcaggccc tttggggtaa gcctgctggt   6180
tgtacctgac atagggaggc agttaggggc agtccctggt ggggccgccc tggcagcctc   6240
cagctggcac catcgtgtgc ctggtttccc tgcaacacct gcctctctgt ccctgctgct   6300
gcttggctca ggcccaacag gcagcgtgca tggaggtggt tacacacagc tgtttccgtg   6360
agggtgaccg tgtctgcagc acgcttccgt ctccgcatgc acggctgcct ctccagccac   6420
ctctgatact tctctcttgg ggccatcaga gcctcccttg ggctgtcacc tcccagctca   6480
cacacactct tcagtggttt cctctcttca ttctcttata gggcgtggtc cttcttattt   6540
atctaaaggg ctgaatttag gagacttttt acccagggc aaaaggctct tagggtaatg    6600
agatggatgg tggcccaggt gcattttcca gggcctgggt tctccagatc ccgtggcttc   6660
tgttgagtgg aggcaacttt gctctgtgtg aacctcgccc ctgtccctct gccgggcacc   6720
cctggcagga agcaggactc ccatcctcac cctgacttag actgtcctct gagtcagctc   6780
ctctccaaga caggagtggg cagccctggg cagtcttctg gccccttgct aaagtgaggg   6840
gcaggaagct ggggctgccc tccagaaagc cggggtagga actctgaaaa atacctcctc   6900
taaacggaag cagggctctc cagttccact tggcgccccc tcccacaagg cccttcctcc   6960
ctgaggaccc caccccccta cccccttccc agcagccttt ggaccctcac ctctctccgg   7020
tgtccgtggg tcctcagccc agggtgagct gcagtcaggc gggatgggac gggcaggcca   7080
gaggtcagcc agctcctagc agagaagagc cagccagacc ccaaccctgt ctcttgtcca   7140 tgcccttgt gatttcagtc ttggtagact tgtatttgga gttttgtgct tcaaagtttt    7200
tgtttttgtt tgtttggttt ttgttttgag ggggtggggg gggatacaga gcagctgatc   7260
aatttgtatt tatttatttt aacattttac taaataaagc caaataaagc ctctcaaaaa   7320 aaaaaaaaa aa                                                        7332

<210> SEQ ID NO 29
<211> LENGTH: 14135
<212> TYPE: DNA
<213> ORGANISM: Homo sapiens
```

<400> SEQUENCE: 29

```
gcactgcagc gccagcgtcc gagcgggcgg ccgagctccc ggagcggcct ggccccgagc      60
cccgagcggg cgtcgctcag cagcaggtcg cggccgcagc cccatccagc cccgcgcccg     120
ccatgccgtc cgcgggcccc gcctgagctg cggcctccgc gcgcgggcgg gcctggggac     180
ggcggggcca tgcgcgcgct gccctaacga tgccgcccgc cgcgcccgcc cgcctggcgc     240
tggccctggg cctgggcctg tggctcgggg cgctggcggg gggccccggg cgcggctgcg     300
ggccctgcga gcccccctgc ctctgcggcc cagcgcccgg cgccgcctgc cgcgtcaact     360
gctcgggccg cgggctgcgg acgctcggtc ccgcgctgcg catccccgcg gacgccacag     420
cgctagacgt ctcccacaac ctgctccggg cgctggacgt tgggctcctg gcgaacctct     480
cggcgctggc agagctggat ataagcaaca caagatttc tacgttagaa aaggaatat      540
ttgctaattt atttaattta agtgaaataa acctgagtgg gaacccgttt gagtgtgact     600
gtggcctggc gtggctgccg cgatgggcgg aggagcagca ggtgcgggtg gtgcagcccg     660
aggcagccac gtgtgctggg cctggctccc tggctggcca gcctctgctt ggcatccccct    720
tgctggacag tggctgtggt gaggagtatg tcgcctgcct ccctgacaac agctcaggca     780
ccgtggcagc agtgtccttt tcagctgccc acgaaggcct gcttcagcca gaggcctgca     840
gcgccttctg cttctccacc ggccagggcc tcgcagccct ctcggagcag ggctggtgcc     900
tgtgtgggc ggcccagccc tccagtgcct cctttgcctg cctgtccctc tgctccggcc     960
ccccgccacc tcctgccccc acctgtaggg gccccaccct cctccagcac gtcttccctg    1020
cctcccagg ggccacctg gtggggcccc acggacctct ggcctctggc cagctagcag    1080
ccttccacat cgctgccccg ctccctgtca ctgccacacg ctgggacttc ggagacggct    1140
ccgccgaggt ggatgccgct gggccggctg cctcgcatcg ctatgtgctg cctgggcgct    1200
atcacgtgac ggccgtgctg gccctgggg ccggctcagc cctgctgggg acagacgtgc    1260
aggtggaagc ggcacctgcc gccctggagc tcgtgtgccc gtcctcggtg cagagtgacg    1320
agagccttga cctcagcatc cagaaccgcg gtggttcagg cctggaggcc gcctacagca    1380
tcgtggccct gggcgaggag ccggcccgag cggtgcaccc gctctgcccc tcggacacgg    1440
agatcttccc tggcaacggg cactgctacc gcctggtggt ggagaaggcg gcctggctgc    1500
aggcgcagga gcagtgtcag gcctgggccg gggccgccct ggcaatggtg gacagtcccg    1560
ccgtgcagcg cttcctggtc tcccgggtca ccaggagcct agacgtgtgg atcggcttct    1620
cgactgtgca ggggtggag gtgggccag cgccgcaggg cgaggccttc agcctggaga    1680
gctgccagaa ctggctgccc ggggagccac acccagccac agccgagcac tgcgtccggc    1740
tcgggcccac cggtggtgt aacaccgacc tgtgctcagc gccgcacagc tacgtctgcg    1800
agctgcagcc cggaggccca gtgcaggatg ccgagaacct cctcgtggga gcgcccagtg    1860
gggacctgca gggacccctg acgcctctgg cacagcagga cggcctctca gccccgcacg    1920
agcccgtgga ggtcatggta ttcccgggcc tgcgtctgag ccgtgaagcc ttcctcacca    1980
cggccgaatt tgggacccag gagctccggc ggcccgccca gctgcggctg caggtgtacc    2040
ggctcctcag cacagcaggg accccggaga acggcagcga gcctgagagc aggtccccgg    2100
acaacaggac ccagctggcc cccgcgtgca tgccaggggg acgctggtgc cctggagcca    2160
acatctgctt gccgctggac gcctcctgcc accccaggc ctgcgccaat ggctgcacgt    2220
cagggccagg gctacccggg gcccctatg cgctatggaa agagttcctc ttctccgttc    2280
ccgcggggcc cccgcgcag tactcggtca ccctccacgg ccaggatgtc ctcatgctcc    2340
```

```
ctggtgacct cgttggcttg cagcacgacg ctggccctgg cgccctcctg cactgctcgc    2400
cggctcccgg ccaccctggt ccccaggccc cgtacctctc cgccaacgcc tcgtcatggc    2460
tgccccactt gccagcccag ctggagggca cttgggcctg ccctgcctgt gccctgcggc    2520
tgcttgcagc cacggaacag ctcaccgtgc tgctgggctt gaggcccaac cctggactgc    2580
ggctgcctgg gcgctatgag gtccgggcag aggtgggcaa tggcgtgtcc aggcacaacc    2640
tctcctgcag ctttgacgtg gtctcccag tggctgggct gcgggtcatc taccctgccc    2700
cccgcgacgg ccgcctctac gtgcccacca acggctcagc cttggtgctc caggtggact    2760
ctggtgccaa cgccacggcc acggctcgct ggcctggggg cagtgtcagc gcccgctttg    2820
agaatgtctg ccctgccctg gtggccacct tcgtgcccgg ctgcccctgg gagaccaacg    2880 atacctgtt tcagtggta gcactgccgt ggctcagtga gggggagcac gtggtggacg    2940
tggtggtgga aaacagcgcc agccgggcca acctcagcct gcgggtgacg gcggaggagc    3000
ccatctgtgg cctccgcgcc acgcccagcc ccgaggcccg tgtactgcag ggagtcctag    3060
tgaggtacag ccccgtggtg gaggccggct cggacatggt cttccggtgg accatcaacg    3120
acaagcagtc cctgaccttc cagaacgtgg tcttcaatgt catttatcag agcgcggcgg    3180
tcttcaagct ctcactgacg gcctccaacc acgtgagcaa cgtcaccgtg aactacaacg    3240
taaccgtgga gcggatgaac aggatgcagg gtctgcaggt ctccacagtg ccggccgtgc    3300 tgtccccaa tgccacgcta gcactgacgg cgggcgtgct ggtggactcg gccgtggagg    3360
tggccttcct gtggaccttt ggggatgggg agcaggccct ccaccagttc cagcctccgt    3420
acaacgagtc cttcccggtt ccagacccct cggtggccca ggtgctggtg gagcacaatg    3480
tcatgcacac ctacgctgcc ccaggtgagt acctcctgac cgtgctggca tctaatgcct    3540
tcgagaacct gacgcagcag gtgcctgtga gcgtgcgcgc ctccctgccc tccgtggctg    3600
tgggtgtgag tgacgcgtc ctggtggccg gccggcccgt caccttctac ccgcacccgc    3660
tgccctcgcc tgggggtgtt cttacacgt gggacttcgg ggacggctcc cctgtcctga    3720
cccagagcca gccggctgcc aaccacacct atgcctcgag gggcacctac cacgtgcgcc    3780
tggaggtcaa caacacggtg agcggtgcgg cggcccaggc ggatgtgcgc gtctttgagg    3840
agctccgcgg actcagcgtg gacatgagcc tggccgtgga gcagggcgcc cccgtggtgg    3900
tcagcgccgc ggtgcagacg ggcgacaaca tcacgtggac cttcgacatg ggggacggca    3960
ccgtgctgtc gggcccggag gcaacagtgg agcatgtgta cctgcgggca cagaactgca    4020
cagtgaccgt gggtgcggcc agcccgcgcg gccacctggc ccggagcctg cacgtgctgg    4080
tcttcgtcct ggaggtgctg cgcgttgaac ccgccgcctg catccccacg cagcctgacg    4140
cgcggctcac ggcctacgtc accgggaacc cggcccacta cctcttcgac tggaccttcg    4200
gggatggctc ctccaacacg accgtgcggg ggtgcccgac ggtgacacac aacttcacgc    4260
ggagcggcac gttccccctg gcgctggtgc tgtccagccg cgtgaacagg cgcattact    4320 tcaccagcat ctgcgtggag ccagaggtgg gcaacgtcac cctgcagcca gagaggcagt    4380
ttgtgcagct cggggacgag gcctggctgg tggcatgtgc ctggccccg ttcccctacc    4440 gctacacctg ggactttggc accgaggaag ccgcccccac ccgtgccagg ggccctgagg    4500
tgacgttcat ctaccgagac ccaggctcct atcttgtgac agtcaccgcg tccaacaaca    4560
tctctgctgc caatgactca gccctggtgg aggtgcagga gcccgtgctg gtcaccagca    4620
tcaaggtcaa tggctccctt gggctggagc tgcagcagcc gtacctgttc tctgctgtgg    4680
```

```
gccgtgggcg ccccgccagc tacctgtggg atctggggga cggtgggtgg ctcgagggtc   4740
cggaggtcac ccacgcttac aacagcacag gtgacttcac cgttagggtg gccggctgga   4800
atgaggtgag ccgcagcgag gcctggctca atgtgacggt gaagcggcgc gtgcggggggc  4860
tcgtcgtcaa tgcaagccgc acggtggtgc ccctgaatgg gagcgtgagc ttcagcacgt   4920
cgctggaggc cggcagtgat gtgcgctatt cctgggtgct ctgtgaccgc tgcacgccca   4980
tccctgggg tcctaccatc tcttacacct tccgctccgt gggcaccttc aatatcatcg    5040
tcacggctga gaacgaggtg ggctccgccc aggacagcat cttcgtctat gtcctgcagc   5100
tcatagaggg gctgcaggtg gtgggcggtg ccgctacttc ccccaccaac cacacggtac   5160
agctgcaggc cgtggttagg gatggcacca acgtctccta cagctggact gcctggaggg   5220
acaggggccc ggcccctggcc ggcagcggca aaggcttctc gctcaccgtg ctcgaggccg   5280
gcacctacca tgtgcagctg cgggccacca acatgctggg cagcgcctgg gccgactgca   5340
ccatggactt cgtggagcct gtggggtggc tgatggtggc cgcctccccg aacccagctg   5400
ccgtcaacac aagcgtcacc ctcagtgccg agctggctgg tggcagtggt gtcgtataca   5460
cttggtcctt ggaggagggg ctgagctggg agacctccga gccatttacc acccatagct   5520
tccccacacc cggcctgcac ttggtcacca tgacggcagg gaacccgctg gctcagcca    5580
acgccaccgt ggaagtggat gtgcaggtgc ctgtgagtgg cctcagcatc agggccagcg   5640
agcccggagg cagcttcgtg gcggccgggt cctctgtgcc cttttggggg cagctggcca   5700
cgggcaccaa tgtgagctgg tgctgggctg tgcccggcgg cagcagcaag cgtggccctc   5760
atgtcaccat ggtcttcccg gatgctggca ccttctccat ccggctcaat gcctccaacg   5820
cagtcagctg ggtctcagcc acgtacaacc tcacggcgga ggagcccatc gtgggcctgg   5880
tgctgtgggc cagcagcaag gtggtggcgc ccgggcagct ggtccatttt cagatcctgc   5940
tggctgccgg ctcagctgtc accttccgcc tgcaggtcgg cggggccaac cccgaggtgc   6000
tccccgggcc ccgtttctcc cacagcttcc ccgcgtcgg agaccacgtg gtgagcgtgc    6060
ggggcaaaaa ccacgtgagc tgggcccagg cgcaggtgcg catcgtggtg ctggaggccg   6120
tgagtgggct gcaggtgccc aactgctgcg agcctggcat cgccacgggc actgagagga   6180
acttcacagc ccgcgtgcag cgcggctctc gggtcgccta cgcctggtac ttctcgctgc   6240
agaaggtcca gggcgactcg ctggtcatcc tgtcgggccg cgacgtcacc tacacgcccg   6300
tggccgcggg gctgttggag atccaggtgc gcgccttcaa cgccctgggc agtgagaacc   6360
gcacgctggt gctggaggtt caggacgccg tccagtatgt ggccctgcag agcggccccct  6420
gcttcaccaa ccgctcggcg cagtttgagg ccgccaccag ccccagcccc cggcgtgtgg   6480
cctaccactg ggactttggg gatgggtcgc cagggcagga cacagatgag cccagggccg   6540
agcactccta cctgaggcct ggggactacc gcgtgcaggt gaacgcctcc aacctggtga   6600
gcttcttcgt ggcgcaggcc acggtgaccg tccaggtgct ggcctgccgg gagccggagg   6660
tggacgtggt cctgccccctg caggtgctga tgcggcgatc acagcgcaac tacttggagg   6720
cccacgttga cctgcgcgac tgcgtcacct accagactga gtaccgctgg gaggtgtatc   6780
gcaccgccag ctgccagcgg ccggggcgcc cagcgcgtgt ggccctgccc ggcgtggacg   6840
tgagccggcc tcggctggtg ctgccgcggc tggcgctgcc tgtggggcac tactgctttg   6900
tgtttgtcgt gtcatttggg gacacgccac tgacacagag catccaggcc aatgtgacgg   6960
tggccccga gcgcctggtg cccatcattg agggtggctc ataccgcgtg tggtcagaca   7020
cacgggacct ggtgctggat gggagcgagt cctacgaccc caacctggag gacggcgacc   7080
```

```
agacgccgct cagtttccac tgggcctgtg tggcttcgac acagaggag gctggcgggt    7140
gtgcgctgaa ctttgggccc cgcgggagca gcacggtcac cattccacgg gagcggctgg   7200
cggctggcgt ggagtacacc ttcagcctga ccgtgtggaa ggccggccgc aaggaggagg   7260
ccaccaacca gacggtgctg atccggagtg gccgggtgcc cattgtgtcc ttggagtgtg   7320
tgtcctgcaa ggcacaggcc gtgtacgaag tgagccgcag ctcctacgtg tacttggagg   7380
gccgctgcct caattgcagc agcggctcca agcgagggcg gtgggctgca cgtacgttca   7440
gcaacaagac gctggtgctg gatgagacca ccacatccac gggcagtgca ggcatgcgac   7500
tggtgctgcg gcggggcgtg ctgcgggacg gcgagggata caccttcacg ctcacggtgc   7560
tgggccgctc tggcgaggag gagggctgcg cctccatccg cctgtcccc aaccgcccgc    7620
cgctgggggg ctcttgccgc ctcttcccac tgggcgctgt gcacgccctc accaccaagg   7680
tgcacttcga atgcacgggc tggcatgacg cggaggatgc tggcgccccg ctggtgtacg   7740
ccctgctgct gcggcgctgt cgccaggccc actgcgagga gttctgtgtc tacaagggca   7800
gcctctccag ctacggagcc gtgctgcccc cgggtttcag gccacacttc gaggtgggcc   7860
tggccgtggt ggtgcaggac cagctgggag ccgctgtggt cgccctcaac aggtctttgg   7920
ccatcaccct cccagagccc aacggcagcg caacggggct cacagtctgg ctgcacgggc   7980
tcaccgctag tgtgctccca gggctgctgc ggcaggccga tccccagcac gtcatcgagt   8040
actcgttggc cctggtcacc gtgctgaacg agtacgagcg ggccctggac gtggcggcag   8100
agcccaagca cgagcggcag caccgagccc agatacgcaa gaacatcacg gagactctgg   8160
tgtccctgag ggtccacact gtggatgaca tccagcagat cgctgctgcg ctggcccagt   8220
gcatggggcc cagcagggag ctcgtatgcc gctcgtgcct gaagcagacg ctgcacaagc   8280
tggaggccat gatgctcatc ctgcaggcag agaccaccgc gggcaccgtg acgcccaccg   8340
ccatcggaga cagcatcctc aacatcacag gagacctcat ccacctggcc agctcggacg   8400
tgcgggcacc acagccctca gagctgggag ccgagtcacc atctcggatg gtggcgtccc   8460
aggcctacaa cctgacctct gccctcatgc gcatcctcat gcgctcccgc gtgctcaacg   8520
aggagcccct gacgctggcg ggcgaggaga tcgtggccca gggcaagcgc tcggacccgc   8580
ggagcctgct gtgctatggc ggcgccccag ggcctggctg ccacttctcc atccccgagg   8640
ctttcagcgg ggccctggcc aacctcagtg acgtggtgca gctcatcttt ctggtggact   8700
ccaatccctt tcccttggc tatatcagca actacaccgt ctccaccaag gtggcctcga    8760
tgcattcca gacacaggcc ggcgcccaga tccccatcga gcggctggcc tcagagcgcg    8820
ccatcaccgt gaaggtgccc aacaactcgg actgggctgc ccggggccac cgcagctccg   8880
ccaactccgc caactccgtt gtggtccagc cccaggcctc cgtcggtgct gtggtcaccc   8940
tggacagcag caaccctgcg gccgggctgc atctgcagct caactatacg ctgctggacg   9000
gccactacct gtctgaggaa cctgagccct acctggcagt ctacctacac tcggagcccc   9060
ggcccaatga gcacaactgc tcggctagca ggaggatccg cccagagtca ctccagggtg   9120
ctgaccaccg gccctacacc ttcttcattt ccccggggag cagagaccca gcggggagtt   9180
accatctgaa cctctccagc cacttccgct ggtcggcgct gcaggtgtcc gtgggcctgt   9240
acacgtccct gtgccagtac ttcagcgagg aggacatggt gtggcggaca gaggggctgc   9300
tgcccctgga ggagcctcg ccccgccagg ccgtctgcct cacccgccac ctcaccgcct    9360
tcggcgccag cctcttcgtg cccccaagcc atgtccgctt tgtgtttcct gagccgacag   9420
```

```
cggatgtaaa ctacatcgtc atgctgacat gtgctgtgtg cctggtgacc tacatggtca    9480
tggccgccat cctgcacaag ctggaccagt tggatgccag ccggggccgc gccatccctt    9540
tctgtgggca gcggggccgc ttcaagtacg agatcctcgt caagacaggc tggggccggg    9600
gctcaggtac cacggcccac gtgggcatca tgctgtatgg ggtggacagc cggagcggcc    9660
accggcacct ggacggcgac agagccttcc accgcaacag cctggacatc ttccggatcg    9720 ccacccccgca cagcctgggt agcgtgtgga agatccgagt gtggcacgac aacaaagggc    9780
tcagccctgc ctggttcctg cagcacgtca tcgtcaggga cctgcagacg gcacgcagcg    9840
ccttcttcct ggtcaatgac tggctttcgg tggagacgga ggccaacggg ggcctggtgg    9900
agaaggaggt gctggccgcg agcgacgcag ccctttttgcg cttccggcgc ctgctggtgg    9960
ctgagctgca gcgtggcttc tttgacaagc acatctggct ctccatatgg gaccggccgc    10020
ctcgtagccg tttcactcgc atccagaggg ccacctgctg cgttctcctc atctgcctct    10080
tcctgggcgc caacgccgtg tggtacgggg ctgttggcga ctctgcctac agcacggggc    10140
atgtgtccag gctgagcccg ctgagcgtcg acacagtcgc tgttggcctg tgtccagcg    10200 tggttgtcta tcccgtctac ctggccatcc tttttctctt ccggatgtcc cggagcaagg    10260 tggctggagag cccgagcccc acacctgccg ggcagcaggt gctggacatc gacagctgcc    10320
tggactcgtc cgtgctggac agctccttcc tcacgttctc aggcctccac gctgaggcct    10380
ttgttggaca gatgaagagt gacttgtttc tggatgattc taagagtctg gtgtgctggc    10440
cctccggcga gggaacgctc agttggccgg acctgctcag tgacccgtcc attgtgggta    10500
gcaatctgcg gcagctggca cggggccagg cgggccatgg gctgggccca gaggaggacg    10560
gcttctccct ggccagcccc tactcgcctg ccaaatcctt ctcagcatca gatgaagacc    10620
tgatccagca ggtccttgcc gagggggtca gcagcccagc ccctacccaa gacacccaca    10680
tggaaacgga cctgctcagc agcctgtcca gcactcctgg ggagaagaca gagacgctgg    10740
cgctgcagag gctgggggag ctgggccac ccagcccagg cctgaactgg gaacagcccc    10800
aggcagcgag gctgtccagg acaggactgg tggagggtct gcggaagcgc ctgctgccgg    10860
cctggtgtgc ctccctggcc cacggcctca gcctgctcct ggtggctgtg gctgtggctg    10920
tctcagggtg ggtgggtgcg agcttccccc cgggcgtgag tgttgcgtgg ctcctgtcca    10980
gcagcgccag cttcctggcc tcattcctcg gctgggagcc actgaaggtc ttgctggaag    11040
ccctgtactt ctcactggtg gccaagcggc tgcacccgga tgaagatgac accctggtag    11100
agagcccggc tgtgacgcct gtgagcgcac gtgtgccccg cgtacggcca ccccacggct    11160
ttgcactctt cctggccaag gaagaagccc gcaaggtcaa gaggctacat ggcatgctgc    11220
ggagcctcct ggtgtacatg cttttttctgc tggtgaccct gctggccagc tatgggggatg    11280 cctcatgcca tgggcacgcc taccgtctgc aaagcgccat caagcaggag ctgcacagcc    11340
gggccttcct ggccatcacg cggtctgagg agctctggcc atggatggcc cacgtgctgc    11400
tgccctacgt ccacgggaac cagtccagcc cagagctggg gccccacgg ctgcggcagg    11460 tgcggctgca ggaagcactc tacccagacc ctcccggccc cagggtccac acgtgctcgg    11520
ccgcaggagg cttcagcacc agcgattacg acgttggctg ggagagtcct cacaatggct    11580
cggggacgtg ggcctattca gcgccggatc tgctgggggc atggtcctgg ggctcctgtg    11640
ccgtgtatga cagcggggc tacgtgcagg agctgggcct gagcctggag gagagccgcg    11700
accggctgcg cttcctgcag ctgcacaact ggctggacaa caggagccgc gctgtgttcc    11760
tggagctcac gcgctacagc ccggccgtgg ggctgcacgc cgccgtcacg ctgcgcctcg    11820
```

```
agttcccggc ggccggccgc gccctggccg ccctcagcgt ccgcccctttt gcgctgcgcc    11880
gcctcagcgc gggcctctcg ctgcctctgc tcacctcggt gtgcctgctg ctgttcgccg    11940
tgcacttcgc cgtggccgag gcccgtactt ggcacaggga agggcgctgg cgcgtgctgc    12000
ggctcggagc ctgggcgcgg tggctgctgg tggcgctgac ggcggccacg gcactggtac    12060
gcctcgccca gctgggtgcc gctgaccgcc agtggacccg tttcgtgcgc ggccgcccgc    12120
gccgcttcac tagcttcgac caggtggcgc agctgagctc cgcagccgt ggcctggcgg    12180
cctcgctgct cttcctgctt ttggtcaagg ctgcccagca gctacgcttc gtgcgccagt    12240
ggtccgtctt tggcaagaca ttatgccgag ctctgccaga gctcctgggg gtcaccttgg    12300
gcctggtggt gctcggggta gcctacgccc agctggccat cctgctcgtg tcttcctgtg    12360
tggactccct ctggagcgtg gcccaggccc tgttggtgct gtgccctggg actgggctct    12420
ctaccctgtg tcctgccgag tcctggcacc tgtcacccct gctgtgtgtg gggctctggg    12480
cactgcggct gtggggcgcc ctacggctgg gggctgttat tctccgctgg cgctaccacg    12540
ccttgcgtgg agagctgtac cggccggcct gggagcccca ggactacgag atggtggagt    12600
tgttcctgcg caggctgcgc ctctggatgg gcctcagcaa ggtcaaggag ttccgccaca    12660
aagtccgctt tgaagggatg gagccgctgc cctctcgctc ctccaggggc tccaaggtat    12720
ccccggatgt gcccccaccc agcgctggct ccgatgcctc gcacccctcc acctcctcca    12780
gccagctgga tgggctgagc gtgagcctgg gccggctggg gacaaggtgt gagcctgagc    12840
cctcccgcct ccaagccgtg ttcgaggccc tgctcaccca gttggaccga ctcaaccagg    12900
ccacagagga cgtctaccag ctggagcagc agctgcacag cctgcaaggc cgcaggagca    12960
gccgggcgcc cgccggatct tcccgtggcc catccccggg cctgcggcca gcactgccca    13020
gccgccttgc ccgggccagt cggggtgtgg acctggccac tggccccagc aggacacccc    13080
ttcgggccaa gaacaaggtc cacccccagca gcacttagtc ctccttcctg gcggggtgg    13140
gccgtggagt cggagtggac accgctcagt attactttct gccgctgtca aggccgaggg    13200
ccaggcagaa tggctgcacg taggttcccc agagagcagg cagggcatc tgtctgtctg    13260
tgggcttcag cactttaaag aggctgtgtg gccaaccagg acccagggtc ccctccccag    13320
ctcccttggg aaggacacag cagtattgga cggtttctag cctctgagat gctaatttat    13380
ttccccgagt cctcaggtac agcgggctgt gcccggcccc acccctggg cagatgtccc    13440
ccactgctaa ggctgctggc ttcagggagg gttagcctgc accgccgcca ccctgcccct    13500
aagttattac ctctccagtt cctaccgtac tccctgcacc gtctcactgt gtgtctcgtg    13560
tcagtaattt atatggtgtt aaaatgtgta tattttgta tgtcactatt ttcactaggg    13620
ctgaggggcc tgcgcccaga gctggcctcc cccaacacct gctgcgcttg gtaggtgtgg    13680
tggcgttatg gcagcccggc tgctgcttgg atgcgagctt ggccttgggc cggtgctggg    13740
ggcacagctg tctgccaggc actctcatca ccccagaggc cttgtcatcc tcccttgccc    13800
caggccaggt agcaagagag cagcgcccag gcctgctggc atcaggtctg ggcaagtagc    13860
aggactaggc atgtcagagg accccagggt ggttagagga aaagactcct cctgggggct    13920
ggctcccagg gtggaggaag gtgactgtgt gtgtgtgtgt gtgcgcgcgc gcacgcgcga    13980
gtgtgctgta tggcccaggc agcctcaagg ccctcggagc tggctgtgcc tgcttctgtg    14040
taccacttct gtgggcatgg ccgcttctag agcctcgaca cccccccaac ccccgcacca    14100
agcagacaaa gtcaataaaa gagctgtctg actgc                               14135
```

<210> SEQ ID NO 30
<211> LENGTH: 2207
<212> TYPE: DNA
<213> ORGANISM: Homo sapiens

<400> SEQUENCE: 30

| | | | | | |
|---|---|---|---|---|---|
| gcatcctctc | accgccggaa | gctgaactga | ctcgtccgcg | gccgctctac | cccaacaggc | 60 |
| cgccaccagc | gagagtgcgg | ccataaccat | cacgtgaccg | cccaccgaca | ccagcgagag | 120 |
| tgcagtcgta | accgtcacgt | gaccgcccac | cgtcggcccg | gcgctcccct | ccgcccgaag | 180 |
| ctagcaagcg | gcgcggccaa | tgagaaaggc | gcatgcctgg | ccccgccgg | cctgcagtct | 240 |
| agccgtagtg | cgcctgcgcg | cggctaggag | gggccgtcag | gcgggatac | agcctggaag | 300 |
| gtaatgcatg | tccatggtac | acaaattcac | aagtttggag | accctgacac | acccaccttc | 360 |
| tcacctgggc | tctgcgtatc | cccagcctt | gagggaagat | gaagcctaaa | ctgatgtacc | 420 |
| aggagctgaa | ggtgcctgca | gaggagcccg | ccaatgagct | gcccatgaat | gagattgagg | 480 |
| cgtggaaggc | tgcggaaaag | aaagcccgct | gggtcctgct | ggtcctcatt | ctggcggttg | 540 |
| tgggcttcgg | agccctgatg | actcagctgt | ttctatggga | atacggcgac | ttgcatctct | 600 |
| ttgggcccaa | ccagcgccca | gcccctgct | atgacccttg | cgaagcagtg | ctggtggaaa | 660 |
| gcattcctga | gggcctggac | ttccccaatg | cctccacggg | gaacccttcc | accagccagg | 720 |
| cctggctggg | cctgctcgcc | ggtgcgcaca | gcagcctgga | catcgcctcc | ttctactgga | 780 |
| ccctcaccaa | caatgacacc | cacacgcagg | agccctctgc | ccagcagggt | gaggaggtcc | 840 |
| tccggcagct | gcagacccctg | gcaccaaagg | gcgtgaacgt | ccgcatcgct | gtgagcaagc | 900 |
| ccagcgggcc | ccagccacag | gcggacctgc | aggctctgct | gcagagcggt | gcccaggtcc | 960 |
| gcatggtgga | catgcagaag | ctgacccatg | gcgtcctgca | taccaagttc | tgggtggtgg | 1020 |
| accagaccca | cttctacctg | ggcagtgcca | acatggactg | gcgttcactg | acccaggtca | 1080 |
| aggagctggg | cgtggtcatg | tacaactgca | gctgcctggc | tcgagacctg | accaagatct | 1140 |
| ttgaggccta | ctggttcctg | ggccaggcag | gcagctccat | cccatcaact | tggccccggt | 1200 |
| tctatgacac | ccgctacaac | caagagacac | caatggagat | ctgcctcaat | ggaaccctg | 1260 |
| ctctggccta | cctggcgagt | gcgccccac | ccctgtgtcc | aagtggccgc | actccagacc | 1320 |
| tgaaggctct | actcaacgtg | gtggacaatg | cccggagttt | catctacgtc | gctgtcatga | 1380 |
| actacctgcc | cactctggag | ttctcccacc | ctcacaggtt | ctggcctgcc | attgacgatg | 1440 |
| ggctgcggcg | ggccacctac | gagcgtggcg | tcaaggtgcg | cctgctcatc | agctgctggg | 1500 |
| gacactcgga | gccatccatg | cgggccttcc | tgctctctct | ggctgccctg | cgtgacaacc | 1560 |
| atacccactc | tgacatccag | gtgaaactct | ttgtggtccc | cgcggatgag | gcccaggctc | 1620 |
| gaatcccata | tgcccgtgtc | aaccacaaca | agtacatggt | gactgaacgc | gccacctaca | 1680 |
| tcggaacctc | caactggtct | ggcaactact | tcacggagac | ggcgggcacc | tcgctgctgg | 1740 |
| tgacgcagaa | tgggaggggc | ggcctgcgga | gccagctgga | ggccattttc | ctgagggact | 1800 |
| gggactcccc | ttacagccat | gaccttgaca | cctcagctga | cagcgtgggc | aacgcctgcc | 1860 |
| gcctgctctg | aggcccgatc | cagtgggcag | gccaaggcct | gctgggcccc | gcggaccca | 1920 |
| ggtgctctgg | gtcacggtcc | ctgtcccgc | gccccgctt | ctgtctgccc | cattgtggct | 1980 |
| cctcaggctc | tctcccctgc | tctcccacct | ctacctccac | ccccaccggc | ctgacgctgt | 2040 |
| ggccccggga | cccagcagag | ctgggggagg | gatcagcccc | caaagaaatg | ggggtgcatg | 2100 |
| ctgggcctgg | cccctggcc | caccccact | ttccagggca | aaagggccc | aggttataa | 2160 |

```
taagtaaata acttgtctgt acagcctgaa aaaaaaaaaa aaaaaaa                   2207
```

<210> SEQ ID NO 31
<211> LENGTH: 4846
<212> TYPE: DNA
<213> ORGANISM: Homo sapiens

<400> SEQUENCE: 31

```
gagcggtgct caggggaggg ctggagggga gggaaggaga gagagagggg agggcggcac       60
cgcccctagc cccgcgctcc ggaagtgaag cggccagacc accagctaat ggatgcggag      120
cggagggccc gctgaccgct ctccgcgcct ggagcagctt ggcttggctg gagctaagag      180
ccagacacac cactgtgtgg aggtgggtga tgtcttcctg tgctaaaagg tgaataaata      240
agctcctcac ctctcgcgga acactcggga acacatcaac aggggtccaa gccgccctgc      300
tgggaggctt ctcttcaaga gttctgggtc ccagagtgga aggcattttc ccatcaactg      360
gagagagacg aaacatcaga gaccaggagg ctgtggagaa agcagctgtc ccaggtgcct      420
caactatcag agaagggtca gcgtcacgtg gctgccagca tctttgagaa aatcactggc      480
aatcggactt cagagctgcg ggcacaggtg tggttagaac tgagatacga cctgcccacc      540
tgggtcaggc ctaaagacaa gaagtcctga gttcttgcca ctgagtaggc cagggtcatt      600
tgtccagaaa actttgtgac tgtctttgag tgacctagtc tgggacccat tcattggtgg      660
gttctaaggt tagaagctca tccaggatat tttcaatatt aagtcagtgc atagctgcac      720
cactaacaaa ttggtgcctg tagagtcaga gtgggtcaat tcttaggaca atggcgctgg      780
cactgttaga ggactggtgc aggataatga gtgtggatga gcagaagtca ctgatggtta      840
cggggatacc ggcggacttt gaggaggctg agattcagga ggtccttcag gagactttaa      900
agtctctggg caggtataga ctgcttggca agatattccg gaagcaggag aatgccaatg      960
ctgtcttact agagcttctg gaagatactg atgtctcggc cattcccagt gaggtccagg     1020
gaaaggggg tgtctggaag gtgatcttta agacccctaa tcaggacact gagtttcttg     1080
aaagattgaa cctgtttcta gaaaagagg ggcagacggt ctcgggtatg tttcgagccc     1140
tgggcagga gggcgtgtct ccagccacag tgccctgcat ctcaccagaa ttactggccc     1200
atttgttggg acaggcaatg gcacatgcgc ctcagcccct gctacccatg agataccgga     1260
aactgcgagt attctcaggg agtgctgtcc cagccccaga ggaagagtcc tttgaggtct     1320
ggttggaaca ggccacggag atagtcaaag agtggccagt aacagaggca gaaaagaaaa     1380
ggtggctggc ggaaagcctg cggggccctg ccctggacct catgcacata gtgcaggcag     1440
acaacccgtc catcagtgta gaagagtgtt tggaggcctt taagcaagtg tttgggagcc     1500
tagagagccg caggacagcc caggtgaggt atctgaagac ctatcaggag aaggagaga     1560
aggtctcagc ctatgtgtta cggctagaaa ccctgctccg gagagcggtg gagaaacgcg     1620
ccatccctcg gcgtattgcg gaccaggtcc gcctggagca ggtcatggct ggggccactc     1680
ttaaccagat gctgtggtgc cggcttaggg agctgaagga tcagggcccg ccccccagct     1740
tccttgagct aatgaaggta atacgggaag aagaggagga agaggcctcc tttgagaatg     1800
agagtatcga gagccagag gaacgagatg gctatggccg ctggaatcat gagggagacg     1860
actgaaaacc acctggggc aggacccaca gccagtgggc taagaccttt aaaaatttt     1920
tttcttaat gtatgggact gaaatcaaac catgaaagcc aattattgac cttccttcct     1980
tccttccttc cctcccttcc tccttctctc cttctctcct cctctctcct ctcctctcct     2040
```

```
ctctttcctt ccttccttcc ttttttcttt ttctctttct tctttatttc ttgggtctca    2100
ctctcatcac ccaggctaga gtgcagtggc acaaaaatct cggctcactg cagccttgac    2160
ttcccaggct caggctcagg tgatcctcac accttagcct cccaagtacc tgggactaca    2220
ggcacgcacc accatgccta gctattcttt tgtattttg gtagagacag ggttttgctg     2280
tgttgctcag gctggtctgg aacccctagg ctcaaatgat gtgcccaact cggcctccca    2340
aagtgctggg attacaggca tgaaccgcca tgcctggccc ttgattttc ttttaagaa      2400
aaaaatatct aggagtttct tagaccctat gtagattatt aatgaacaaa agattaaact    2460
ccaaatatta aatagtaagc ctgaaggaat ctgaaacact tgtacttcca attttcttta    2520
aataatccca aatagaccag aattggccca taccatagaa gaaagaattg gcagtcaaaa    2580
aaaaaaatac cttttgtaat gtttgaaaaa taaagctgtt tgacttgtca ggtgttttcc    2640
tttctcaaat cagcaaattc tctctgagtg cctggctttg tgagacactg tacaaggagt    2700
tacaagacta cagctataac ctgcagttga gcagttataa acctacaaaa tgggccctgc    2760
cctcagagag gttccagtct agatgaggag ctgatctaga caggtaaaag gctaactaac    2820
cctttgtgta aataagttca tcacccagt aaaagtgtca tcacccagtg aataggacca     2880
cctctgcctg cagattttg ttgttgttgt tgtcattgtt ttgttgtt taacctggga       2940
agtgttcttc ctgcctttct gctaggtgtc agatagatgg tcccagagct aggtgctgtg    3000
tcaggccctg aagacacaga tgactcaacc taagctttac tttccagagg tccacagcct    3060
gagaggtgtc cccaaagaaa ggggacatg aggggactgc atgcttgaga gcagggttgt     3120
ttagggcagg tttggattta gtgagcaggc tggtttgctt agagaaggct tttagtggca    3180
acaaaggatg aagaggagag aaaaggaact cacatttatt gagggcctac tgtgtgcaaa    3240
gtgtttcatg tatatctcat tgaatgtata cagccaccct gttgtggtat aattttgctc    3300
tttataaaga gaaagaccga agctcagatg agttaagtgg tctcctcaac accaaaatgc    3360
caagaagtga tggagcctag acagaagccc agaactttct gactcacact agtccatcct    3420
ctaccatcac gatgactttc aaattgtgct ctgcagttct gcagattttc tagcagtgcc    3480
atctccaaaa tgtgttttaa actctttatt tttttaatta ttattagtat tattttgaga    3540
ctgagtcttg ctctatcacc caggctggag tgcagtggtg caatctcagc tcactgcaac    3600
ctccgcctcc caggttcaag cgatttcgtg cctcagcctc ccgagtagct gggattacag    3660
gcacccacca ccacgcccag ctaattttg tatttttagt agaaatgggg tttcaccatg     3720
ttggccaggc tggtctcgaa ctcctgacct caagtgatcc actcacctcg gcctcccaaa    3780
gtgctgggat tacaggtgtg agccaccatg cctgggctaa actcttaag tctctagtaa     3840
atgcagctag attcaaatgg gctgataacc aaattttaac acatcagcat tcaccaccag    3900
gtttactttt attttcagat tggctcattt tgtgcagacc ttagagcaaa gtttccttta    3960
tggtatctgt gtacgtatcc aaacttcttt taattgttca cagatttaa aagcggtagc     4020
accacatggt tgtgtagatc agacctgtgt atttagatca gacctgtgta tcacgtaagt    4080
gtgtgagtgc agtgcagatg agcaccattt agttatatgt gctaggcaaa tctccaacac    4140
agttgatgtg tagtcttgtg gtagatttgt gcatactgta agcaaattgc ttagcttctc    4200
tagacatcag tttccacatc tgaaaaataa gaagatgaga gtacacggtt gttatgaaca    4260
aatgacttaa tgcttttaa gcacgttgca tgacatctgg aacacagaaa gccctcaata     4320
cattgaagct cttaggattt tcacgatgtt cctgtctgct caatgcatgc tttctttatt    4380
gttctgacag ttgtgtggta acaagctaat atgcttccag ttgacttcca gtctaccctg    4440
```

```
gtgttagaaa ccgtttcatc tcttattgta aatttgagtg cttgttgttt tttatatttg    4500
tgatgactct tccagcagtt gttgacaatt gttagaggtt tgacttttaa ataattactt    4560 atttttctg attgtggttc agtttaactg aagaatatcc tgagattgta agaaaagcat     4620
tttttaaaag gtatcacttg tgatcattta tctttctaaa ttctattttt aatactgttc    4680
caccaaagtg atgcagtggt taccatgaca ccctaatttc atgtgttttt gtatttatga    4740
aaatagtttc attgtcattt attggcggta tacaaagtaa aatgttataa atgtgaagtt    4800
ataaaataaa tatatgctaa taaaatcctg agttttctg tttcct                    4846
```

<210> SEQ ID NO 32
<211> LENGTH: 1014
<212> TYPE: DNA
<213> ORGANISM: Homo sapiens

<400> SEQUENCE: 32

```
tgcctcctga gcgtagtcca gttactttca ggctcgggga gtgaaggcct cgttgagaga      60
aggtctcatt cggtgttttg ggaagagagt cgtgtgggcc caggtctgtc tgctatcagc    120
tatgccgctg cccgttgcgc tgcagacccg cttggccaag agaggcatcc tcaaacatct    180
ggagcctgaa ccagaggaag agatcattgc cgaggactat gacgatgatc ctgtggacta    240
cgaggccacc aggttggagg cctaccacc aagctggtac aaggtgttcg acccttcctg      300
cgggctccct tactactgga atgcagacac agaccttgta tcctggctct ccccacatga    360
ccccaactcc gtggttacca aatcggccaa gaagctcaga agcagtaatg cagatgctga    420
agaaaagttg gaccggagcc atgacaagtc ggacagggc catgacaagt cggaccgcag     480
ccatgagaaa ctagacaggg gccacgacaa gtcagaccgg ggccacgaca agtctgacag    540
ggatcgagag cgtggctatg acaaggtaga cagagagaga gagcgagaca gggaacggga    600
tcgggaccgc gggtatgaca aggcagaccg ggaagagggc aaagaacggc gccaccatcg    660
ccgggaggag ctggctccct atcccaagag caagaaggca gtaagccgaa aggatgaaga    720
gttagacccc atggaccta gctcatactc agacgcccc cggggcacgt ggtcaacagg       780
actccccaag cggaatgagg ccaagactgg cgctgacacc acagcagctg ggcccctctt    840
ccagcagcgg ccgtatccat ccccaggggc tgtgctccgg gccaatgcag aggcctcccg    900
aaccaagcag caggattgaa gcttcggcct ccctggccct gggttaaaat aaaagctttc    960
tggtgatcct gcccaccaaa aaaaaaaaaa aaaaaaaaa aaaaaaaaaa aaaa          1014
```

<210> SEQ ID NO 33
<211> LENGTH: 3291
<212> TYPE: DNA
<213> ORGANISM: Homo sapiens

<400> SEQUENCE: 33

```
agaatcggag agccggtggc gtcgcaggtc gggaggacga gcaccgagtc gagggctcgc      60
tcgtctgggc cgcccgagag tcttaatcgc gggcgcttgg gccgccatct tagatggcgg    120
gagtaagagg aaaacgattg tgaggcggga acggctttct gctgcctttt ttgggccccg    180
aaaagggtca gctggccggg ctttggggcg cgtgccctga ggcgcggagc gcgtttgcta    240
cgatgcgggg gctgctcggg gctccgtccc ctgggctggg gacgcgccga atgtgaccgc    300
ctcccgctcc ctcacccgcc gcggggagga ggagcgggcg agaagctgcc gccgaacgac    360
aggacgttgg ggcggcctgg ctccctcagg tttaagaatt gtttaagctg catcaatgga    420
```

-continued

```
gcacatacag ggagcttgga agacgatcag caatggtttt ggattcaaag atgccgtgtt    480
tgatggctcc agctgcatct ctcctacaat agttcagcag tttggctatc agcgccgggc    540
atcagatgat ggcaaactca cagatccttc taagacaagc aacactatcc gtgttttctt    600
gccgaacaag caaagaacag tggtcaatgt gcgaaatgga atgagcttgc atgactgcct    660
tatgaaagca ctcaaggtga ggggcctgca accagagtgc tgtgcagtgt tcagacttct    720
ccacgaacac aaaggtaaaa aagcacgctt agattggaat actgatgctg cgtctttgat    780
tggagaagaa cttcaagtag atttcctgga tcatgttccc ctcacaacac acaactttgc    840
tcggaagacg ttcctgaagc ttgccttctg tgacatctgt cagaaattcc tgctcaatgg    900
atttcgatgt cagacttgtg gctacaaatt tcatgagcac tgtagcacca aagtacctac    960
tatgtgtgtg gactggagta acatcagaca actcttattg tttccaaatt ccactattgg   1020
tgatagtgga gtcccagcac taccttcttt gactatgcgc cgtatgcgag agtctgtttc   1080
caggatgcct gttagttctc agcacagata ttctacacct cacgccttca cctttaacac   1140
ctccagtccc tcatctgaag gttccctctc ccagaggcag aggtcgacat ccacacctaa   1200
tgtccacatg gtcagcacca ccctgcctgt ggacagcagg atgattgagg atgcaattcg   1260
aagtcacagc gaatcagcct cacctteage cctgtccagt agcccaaca atctgagccc   1320 aacaggctgg tcacagccga aaaccccgt gccagcacaa agagagcggg caccagtatc   1380
tgggacccag gagaaaaaca aaattaggcc tcgtggacag agagattcaa gctattattg   1440
ggaaatagaa gccagtgaag tgatgctgtc cactcggatt gggtcaggct cttttggaac   1500
tgtttataag ggtaaatggc acggagatgt tgcagtaaag atcctaaagg ttgtcgaccc   1560 aacccccagag caattccagg ccttcaggaa tgaggtggct gttctgcgca aaacacggca   1620
tgtgaacatt ctgcttttca tggggtacat gacaaaggac aacctggcaa ttgtgaccca   1680
gtggtgcgag ggcagcagcc tctacaaaca cctgcatgtc caggagacca gtttcagat   1740 gttccagcta attgacattg cccggcagac ggctcaggga atggactatt tgcatgcaaa   1800
gaacatcatc catagagaca tgaaatccaa caatatattt ctccatgaag gcttaacagt   1860
gaaaattgga gattttggtt tggcaacagt aaagtcacgc tggagtggtt ctcagcaggt   1920
tgaacaacct actggctctg tcctctggat ggccccagag gtgatccgaa tgcaggataa   1980
caacccattc agtttccagt cggatgtcta ctcctatggc atcgtattgt atgaactgat   2040
gacgggggag cttccttatt ctcacatcaa caaccgagat cagatcatct tcatggtggg   2100
ccgaggatat gcctccccag atcttagtaa gctatataag aactgcccca agcaatgaa   2160 gaggctggta gctgactgtg tgaagaaagt aaaggaagag aggcctcttt ttccccagat   2220
cctgtcttcc attgagctgc tccaacactc tctaccgaag atcaaccgga gcgcttccga   2280
gccatccttg catcgggcag cccacactga ggatatcaat gcttgcacgc tgaccacgtc   2340
cccgaggctg cctgtcttct agttgacttt gcacctgtct tcaggctgcc aggggaggag   2400
gagaagccag caggcaccac ttttctgctc cctttctcca gaggcagaac acatgttttc   2460
agagaagctg ctgctaagga ccttctagac tgctcacagg gccttaactt catgttgcct   2520
tcttttctat cccctttggc cctggggaaa ggaagccatt tgcagtgctg gtgtgtcctg   2580
ctccctcccc acattcccca tgctcaaggc ccagccttct gtagatgcgc aagtggatgt   2640
tgatggtagt acaaaaagca ggggcccagc cccagctgtt ggctacatga gtatttagag   2700
gaagtaaggt agcaggcagt ccagccctga tgtggagaca catgggattt tggaaatcag   2760
cttctggagg aatgcatgtc acaggcggga ctttcttcag agagtggtgc agcgccagac   2820
```

| | | | | |
|---|---|---|---|---|
| attttgcaca | taaggcacca | aacagcccag | gactgccgag | actctggccg | cccgaaggag | 2880 |
| cctgctttgg | tactatggaa | cttttcttag | gggacacgtc | ctcctttcac | agcttctaag | 2940 |
| gtgtccagtg | cattgggatg | gttttccagg | caaggcactc | ggccaatccg | catctcagcc | 3000 |
| ctctcaggga | gcagtcttcc | atcatgctga | attttgtctt | ccaggagctg | ccctatggg | 3060 |
| gcggggccgc | agggccagcc | ttgtttctct | aacaaacaaa | caaacaaaca | gccttgtttc | 3120 |
| tctagtcaca | tcatgtgtat | acaaggaagc | caggaataca | ggttttcttg | atgatttggg | 3180 |
| ttttaatttt | gtttttattg | cacctgacaa | atacagttta | tctgatggtc | cctcaattat | 3240 |
| gttattttaa | taaataaat | taaatttagg | tgtaaaaaaa | aaaaaaaaa | a | 3291 |

<210> SEQ ID NO 34
<211> LENGTH: 5216
<212> TYPE: DNA
<213> ORGANISM: Homo sapiens

<400> SEQUENCE: 34

| | | | | | |
|---|---|---|---|---|---|---|
| gatgtcccag | gggtattggg | gcgggggtt | gaaataactg | gggttcagga | ggagggatgg | 60 |
| tggtagagat | aaaaatgtga | gaagggagca | gcactggcga | ggagtcggga | gagtactcct | 120 |
| gattgtgaca | tcacattcat | ccctgggcg | atggagcttg | tcactgggaa | ggaatactca | 180 |
| gtcggagaat | agccaacaag | atgggttact | gggagaatct | cttcagtggc | actgagtgga | 240 |
| ggcatcaggg | ggttggagcc | ttgtgaacag | ggaacctgcc | ccccaacact | tggaaggacc | 300 |
| tgggtttcag | tgatgagaca | tggggtatga | tgtaacccgt | ttccagggg | atgttgacga | 360 |
| agatcttatc | tgccctattt | gcagtggagt | cttggaggag | ccagtacagg | cacctcattg | 420 |
| tgaacatgct | ttctgcaacg | cctgcatcac | ccagtggttc | tctcagcaac | agacatgtcc | 480 |
| agtggaccgt | agtgttgtga | cggtcgccca | tctgcgccca | gtacctcgga | tcatgcggaa | 540 |
| catgttgtca | aagctgcaga | ttgcctgtga | caacgctgtg | ttcggctgta | gtgccgttgt | 600 |
| ccggcttgac | aacctcatgt | ctcacctcag | cgactgtgag | cacaacccga | agcggcctgt | 660 |
| gacctgtgaa | cagggctgtg | gcctggagat | gcccaaagat | gagctgccca | accataactg | 720 |
| cattaagcac | ctgcgctcag | tggtacagca | gcagcagaca | cgcatcgcag | agctggagaa | 780 |
| gacgtcagct | gaacacaaac | accagctggc | ggagcagaag | cgagacatcc | agctgctaaa | 840 |
| ggcatacatg | cgtgcaatcc | gcagtgtcaa | ccccaacctt | cagaacctgg | aggagacaat | 900 |
| tgaatacaac | gagatcctag | agtgggtgaa | ctcccttcag | ccagcaagag | tgacccgctg | 960 |
| gggagggatg | atctcgactc | ctgatgctgt | gctccaggct | gtaatcaagc | gctccctggt | 1020 |
| ggagagtggc | tgtcctgctt | ctattgtcaa | cgagctgatt | gaaaatgccc | acgagcgtag | 1080 |
| ctggcccag | gtctggcca | cactagagac | tagacagatg | aaccgacgct | actatgagaa | 1140 |
| ctacgtggcc | aagcgcatcc | tggcaagca | ggctgttgtc | gtgatggcct | gtgagaacca | 1200 |
| gcacatgggg | gatgacatgg | tgcaagagcc | aggccttgtc | atgatatttg | cgcatggcgt | 1260 |
| ggaagagata | taagagaact | cgactggcta | tcaggaagag | atggaaatca | gaaaatccca | 1320 |
| tcactccagc | agctgggacc | tgagtcctac | ccaccattct | taatactgtg | gcttatacct | 1380 |
| gagccacaca | tctccctgcc | cttctggcac | tgaagggcct | tggggtagtt | tgctcagcct | 1440 |
| ttcaggtggg | aaacccagat | ttcctcccctt | tgccatattc | ccctaaaatg | tctataaatt | 1500 |
| atcagtctgg | gtgggaaagc | ccccacctcc | atccattttc | ctgcttaggg | tccctggttc | 1560 |
| cagttatttt | cagaaagcac | aaagagattc | aatttccctg | gaggatcagg | acagaggaag | 1620 |

```
gaatctctaa tcgtccctct cctccaaaac cagggaatca gagcagtcag gcctgttgac   1680
tctaagcagc agacatcctg aagaaatggt aagggtggag ccaaatctct agaaataagt   1740
agtgaggccg ttaattggcc atcactgatg gcccttaggg aaagactgga cctctgtgcc   1800
aagcagtatc cctgttcagc ccaccttaaa ggtgtaggca cccactgggt ctaccagtat   1860
gcaggttggg atactgaaaa tttccagatg agctcttctt tcctacaagt tttcataatt   1920
agggaatgcc agggtttagg gtaggggtta atctgttggg ggttgatgtg tttagcaaga   1980
agctactcct agcttttgct aaaatatggt tggcactgcc tcttgtggca caggccataa   2040
ttgttccata gaccctctc tagccctgtg actgtagtta gttactttga taattttctt     2100
tggccattgt ttgtttatat ttcacaaact ccacctactg ccccccccc tcttttttttt    2160 aagaatggcc tgatcatggc tatctcagcc acattgttgg caatttaatt tatttacttc   2220
cttttttttt tttaagaaa ggaaaaaga aaaaaaatc aaacttgaaa cttttctttt       2280
gatgttccta ttgtgggggt tctggatagg gtgggacagg gatgggggtg tgttttatat   2340 ttttccttt tcagcacaac ctttggcttt aatataggaa gagccaaggg agtcctcggc    2400
tgaacttacg atatctgccc caaacctctg taacccaac tgaaatgagg agcttcctct    2460
cttcctgtga aggatatgac agtccagcat cgatgcctgt gccctctgga aaaatttcct   2520 cctagcccctt ccagggcctt atcataaaac tctggattta gagtattcat tttgaaggca  2580
actccccctt ccccaagttt cctggagct gtatagctgg gttctaagct tcaccatgca    2640
aatcagaaat tttatctcta agtacaggct gtgccgtgtc tcacccacac cccctgggg    2700 acttcagttc catttcaggt tacctggggt ataccttgat ccctagagtg actggcagag   2760
taagagaagg ggagagataa taggtgtgat tattttaata tggaggtggg agtgtggttg   2820
gagatagaaa ggctcctccc caccatgtaa tggcttcctc tcagaatttt attccaggct   2880
agcttgctgc aggtctgggt agttggatca tggctccact gggattgggg tggaaagctt   2940
gaggggagta gggttccagc tctgggacat tgtgctcagg aatttgaaaa cgctgctata   3000
cttactctgg ttactacatt tcttccactc ccctttcccc tacctgcctt aaccaaggct   3060
catactgtcc tgtccttacc ctcagatgga gccaggaagc tcagtgaaag gcttccctac   3120
cctttgcact agtgtctctg caggttgctg gttgtgttgt atgtgctgtt ccatggtgtt   3180
gactgcacta ataataaacc ttttactcaa ctctctaaat tcttcagcat tactcccttt   3240
cttgagaagg tttcccctct gcttttgcct ttctctcacc ttaattccct ttcttcctta   3300
ctttgttacc taccttatc ttagtgctaa ctttctcttc aggaggatgt ctgggagtag    3360
tgtgcacttc acagctgctt tcccatgtac cctcctgcat tcttccctcc tatctcctgt   3420
tctgtagcag ccaaagctct ctagtgatct gaactgtgtg cttcccaggg tctgcccttta  3480 tcctaaattc catgtcttcc ctgagtggtc ctgagttttt gggataattt ctacagaaga   3540
tatgtatata tcttttcct ttgtcccaca agcaactttg ctttagaatc tagaattcct    3600
ttgcaggcag agaagtctct acctcccagt gttcctagc taagaacgta aatgtgagga    3660
gggaaatgta cttgcagagg tttcataatt atttacttat aaaaatagtc ttcatagccg   3720
ggcgcggtgg ctcacgcctg taatcccagc actttgggag gccgaggtgg gtggatcaca   3780
aggtcaggag ttcgagacca tcctggctaa cacagtgaaa cccgtctctc actaaaaata   3840
caaaaaatta gccgggcgtg gtggcaggca cctgtagtcc cagctactta ggaggctgag   3900
gcaggagaat ggcgtgaacc cgggaggcag agcttgcagt gagcagagat tgggccactg   3960
cattccagcc tgggcgacag agcaaggctc cgtctaaaaa aaaaaaaaa aaaaaagtc    4020
```

```
ttcataggcc gggcacggtg gctcacgtct gtaatcccag cactttggga ggccaaggtg   4080
ggtggatcac aacgtcagga gatcgagacc atcctggcta acatggtgaa accctgtctc   4140
tactaaaaat ataaataaat tagccggaca ggcgcctgtc ctcccagcta ctcaggaggc   4200
tgaggcagga gaatggtgtg aacctgggag gcggagcttg cagtgagctg agatcacgcc   4260
actgcactcc agcctgggca acagagcaag actccgtctc aaaaaaaaaa aaaaaaaaac   4320
cagtcttcat aagtatttgc tgctaccttt ccctgtcata agaaaaggta tagccagaca   4380
tggtgggacg ccactatgat cccagctcct tggaaggcta aggcacaaga atcgcttgaa   4440
cctgggaggt ggaggttgca gtgagctgag atcatgccac tgcactccag cctggtgaca   4500
gagcaagagc ctgtctcaaa aaaaaaaag aaagaaaag aaaagggat atctttcct      4560 cctcccagaa gtttgtttta aatttgagca tttatcatgc acctgatgta aacctaatag   4620
tactcttgat actctagtgg cttgaaaaaa aaaaaaaagg catttctgtg ctgagtctgc   4680
gcttctatgc acacaaggta tgtttataaa atactgataa gcatgtcaca gtatagagca   4740
taagaggcaa tgtatgtatc ctagtgacat tagcagtgct tttccccct taaactcctt    4800 taaaattact tttagaactt gctgctcatt cttgtgaatg ttatgaatgg tgtcatattg   4860
tccttttaca gaagatacga tttttagaaa caaatattca ttgaatgtct gccctgtgag   4920
atactcacta gagtgaacat gaggaggctt atgtagcaaa atggcaccta cctgcaaaga   4980
acttagtccc taatggagat gaatatataa taagggatca taaatgtgct aagtggattt   5040
actagtaata tgtgagccaa ggacgataaa gctcctgatt ctgatgggta tcaggaaagg   5100
cttttcagga agtgttactt gttataggtc agaggtcagc aaactacagg ttacaacccc   5160
actgcctgct tttgtaaaaa actttattgg aatacagtta tgcccacttg tttata        5216
```

<210> SEQ ID NO 35
<211> LENGTH: 5138
<212> TYPE: DNA
<213> ORGANISM: Homo sapiens

<400> SEQUENCE: 35

```
gatccgcaga ggagcccact tgagagcgcc tcctgtcgtc tgtaaggttg ccttgccatc     60
cctcggcacc ccaacttccc ccgccccccc atcgcctcct cctccatcct ccagttcaaa    120
atggcgacgg cggcggcagc ggcggcggtg atggctcctc cgggctgccc gggttcgtgc    180
cccaacttcg ccgtagtctg ctccttcttg gagcgctacg ggccgctgct agacctgcct    240
gagttgccgt tccctgagct ggagcgggtg ctgcaggcgc cgccgccgga cgtcggcaac    300
ggagaagtac caaaagaatt ggtggagctc catttgaagc tgatgaggaa aattggcaaa    360
tctgttactg cagacagatg ggaaaaatat ttgatcaaga tatgccaaga gtttaacagt    420
acctgggcat gggagatgga aagaagggc tatcttgaaa tgagtgttga atgcaaacta    480
gcactcttaa agtacctctg tgagtgtcag tttgatgaca atctcaaatt caagaatatt   540
attaatgagg aggatgccga tactatgcgt ctccagccaa ttggtcgaga caaagatggc   600
ctcatgtact ggtaccaatt ggatcaagat cacaatgtca gaatgtacat agaagaacaa   660
gatgatcaag atggctcttc atggaaatgc attgtcagaa atcgaacgga gttggctgag   720
actcttgcac tcctgaaagc acaaattgat cctgtactat tgaaaaactc tagccaacaa   780
gacaactctt ctcgggaaag tcccagctta gaggatgagg agactaaaaa agaggaagaa   840
acacctaaac aagaggaaca gaaagaaagt gaaaagatga aaagtgagga gcagcctatg   900
```

-continued

```
gatttagaaa accgttctac agccaatgtt ctagaagaga ctactgtgaa aaagaaaaa      960 gaagatgaaa aggaacttgt gaaactgcca gtcatagtga agctagaaaa acctttgcca    1020
gaaaatgaag aaaaaaagat tatcaaagaa gaaagtgatt ccttcaagga aaatgtcaaa    1080
cccattaaag ttgaggtgaa ggaatgtaga gcagatccta agataccaa aagtagcatg    1140 gagaagccag tggcacagga gcctgaaagg atcgaatttg gtggcaatat taaatcttct   1200
cacgaaatta ctgagaaatc tactgaagaa actgagaaac ttaaaaatga ccagcaggcc   1260
aagataccac taaaaaaacg agaaattaaa ctgagtgatg attttgacag tccagtcaag   1320
ggacctttgt gtaaatcagt tactccaaca aaagagtttt tgaaagatga aataaaacaa   1380
gaggaagaga cttgtaaaag gatctctaca atcactgctt gggtcatga agggaaacag    1440 ctggtaaatg gagaagttag tgatgaaagg gtagctccaa atttaagac agaaccaata    1500 gagacaaagt tttatgagac aaaggaagag agctatagcc cctctaagga cagaaatatc   1560
atcacggagg gaaatggaac agagtcctta aattctgtca taacaagtat gaaaacaggt   1620
gagcttgaga agaaacagc cccttttgagg aaagatgcag atagttcaat atcagtctta   1680
gagatccata gtcaaaaagc acaaatagag gaacccgatc ctccagaaat ggaaacttct   1740
cttgattctt ctgagatggc aaaagatctc tcttcaaaaa ctgctttatc ttccaccgag   1800
tcgtgtacca tgaaaggtga agagaagtct cccaaaacta agaaggataa gcgcccacca   1860
atcctagaat gtcttgaaaa gttagagaag tccaaaaaga cttttcttga taggacgca    1920 caaagattga gtccaatacc agaagaagtt ccaaagagta ctctagagtc agaaaagcct   1980
ggctctcctg aggcagctga aacttctcca ccatctaata tcattgacca ctgtgagaaa   2040
ctagcctcag aaaaagaagt ggtagaatgc cagagtacaa gtactgttgg tggccagtct   2100
gtgaaaaaag tagacctaga aaccctaaaa gaggattctg agttcacaaa ggtagaaatg   2160
gataatctgg acaatgccca gacctctggc atagaggagc cttctgagac aaagggttct   2220
atgcaaaaaa gcaaattcaa atataagttg gttcctgaag aagaaaccac tgcctcagaa   2280
aatacagaga taacctctga aaggcagaaa gagggcatca aattaacaat caggatatca   2340
agtcggaaaa agaagcccga ttctcccccc aaagttctag aaccagaaaa caagcaagag   2400
aagacagaaa aggaagagga gaaaacaaat gtgggtcgta cttttaagaag atctccaaga   2460 atatctagac ccactgcaaa agtggctgag atcagagatc agaaagctga taaaaaaaga   2520
ggggaaggag aagatgaggt ggaagaagag tcaacagctt tgcaaaaaac tgacaaaaag   2580
gaaattttga aaaatcaga gaaagataca aattctaaag taagcaaggt aaaacccaaa    2640
ggcaaagttc gatggactgg ttctcggaca cgtggcagat ggaaatattc cagcaatgat   2700
gaaagtgaag ggtctggcag tgaaaaatca tctgcagctt cagaagagga ggaagaaaag   2760
gaaagtgaag aagccatcct agcagatgat gatgaaccat gcaaaaaatg tggccttcca   2820
aaccatcctg agctaattct tctgtgtgac tcttgcgata gtggatacca tactgcctgc   2880
cttcgccctc ctctgatgat catcccagat ggagaatggt tctgcccacc ttgccaacat   2940
aaactgctct gtgaaaaatt agaggaacag ttgcaggatt tggatgttgc cttaaagaag   3000
aaagagcgtg ccgaacgaag aaaagaacgc ttggtgtatg ttggtatcag tattgaaaac   3060
atcattcctc cacaagagcc agactttct gaagatcaag aagaaagaa aaagattca     3120 aaaaaatcca agcaaacctt gcttgaaagg aggtcaacaa gaacaaggaa atgtataagc   3180
tacagatttg atgagtttga tgaagcaatt gatgaagcta ttgaagatga catcaaagaa   3240
gccgatggag gaggagttgg ccgaggaaaa gatatctcca ccatcacagg tcatcgtggg   3300
```

```
aaagacatct ctactatttt ggatgaagaa agaaaagaaa ataaacgacc ccagagggca    3360
gctgctgctc gaaggaagaa acgccggcga ttaaatgatc tggacagtga tagcaacctg    3420
gatgaagaag agagcgagga tgaattcaag atcagtgatg gatctcaaga tgagtttgtt    3480
gtgtctgatg aaaacccaga tgaaagtgaa gaagatccgc catctaatga tgacagtgac    3540
actgactttt gtagccgtag actgaggcga cacccctctc ggccaatgag gcagagcagg    3600
cgtttgcgaa gaaagacccc aaagaaaaaa tattccgatg atgatgaaga ggaggaatct    3660
gaggagaata gtagagactc tgaaagtgac ttcagtgatg attttagtga tgattttgta    3720
gaaactcggc gaaggcggtc aaggagaaat cagaaaagac aaattaacta caaagaagac    3780
tcagaaagtg acggttccca gaagagtttg cgacgtggta agaaataag gcgagtacac    3840 aagcgaagac tttccagctc agagagtgaa gagagctatt tgtccaagaa ctctgaagat    3900
gatgagctag ctaaagaatc aaagcggtca gttcgaaagc ggggccgaag cacagacgag    3960
tattcagaag cagatgagga ggaggaggaa gaggaaggca aaccatcccg caaacggcta    4020
caccggattg agacggatga ggaggagagt tgtgacaatg ctcatggaga tgcaaatcag    4080
cctgcccgtg acagccagcc tagggtcctg ccctcagaac aagagagcac caagaagccc    4140
taccggatag aaagtgatga ggaagaggac tttgaaaatg taggcaaagt ggggagccca    4200
ttggactata gcttagtgga cttaccttca accaatggac agagccctgg caaagccatt    4260
gagaacttga ttggcaagcc tactgagaag tctcagaccc ccaaggacaa cagcacagcc    4320
agtgcaagcc tagcctccaa tgggacaagt ggtgggcagg aggcaggagc accagaagag    4380
gaggaagatg agcttttgag agtgactgac cttgttgatt atgtctgtaa cagtgaacag    4440
ttataagact ttttttccat ttttgtgcta atttattcca cggtagctct cacaccagcg    4500
ggccagttat taaaagctgt ttaattttc ctagaaaact ccactacaga atgactttta    4560
gaagaaaaat ttcaacaaat cctgaagtct ttctgtgaag tgaccagttc tgaactttga    4620
agataaataa ttgctgtaaa ttccttttga ttttcttttt ccaggttcat ggtccttggt    4680
aatttcattc atggaaaaaa atcttattat aataacaaca aagatttgta tattttgac    4740 tttatatttc ctgagctctc ctgactttgt gaaaagggt ggatgaaaat gcattccgaa    4800
tctgtgaggg cccaaaacag aatttagggg tgggtgaaag cacttgtgct ttagcttttt    4860
catattaaat atatattata tttaaacatt catggcatag atgatgattt acagacaatt    4920
taaaagttca gtctgtact gttacagttt gagaattgta gataacatca tacataagtc    4980
atttagtaac agcctttgtg aaatgaactt gtttactatt ggagataacc acacttaata    5040
aagaagagac agtgaaagta ccatcataat taacctaaat ttttgttata gcagagtttc    5100
ttgtttaaaa aaaataaaa tcatctgaaa agcaaaaa                            5138
```

<210> SEQ ID NO 36
<211> LENGTH: 2288
<212> TYPE: DNA
<213> ORGANISM: Homo sapiens

<400> SEQUENCE: 36

```
cgcgcgctgc agtgccttcc ccacctcggc cccgcccgcc ccgccgagc cgagcaccag      60 ggcggcggcg gcggcggcgg cggcggcggc ggctggagca gcccgggagg aggaggcggc    120
gagaatggca gcgcgtcgt gggcgcggcg gagatgagcg cccgcgaccc cgggcccagg    180
gcggcacagc cggagtgggc gggggtcccg atgcaggccc gagggggggcc atggggcagg    240
```

-continued

```
tcctgccggt cttcgcccac tgcaaagaag ctccgtctac agcctcctca actcctgatt    300
ccacagaagg agggaacgac gactctgatt ttcgagagct gcacacagcc cgggaattct    360
cagaggagga cgaggaggag accacgtcgc aggactgggg cacccccgg gagctgacct     420 tctcctacat cgcctttgat ggtgtagtgg gctccggggg ccgcagggat tcaactgccc    480 gccgccccg ccccagggc cgctcagtct cggaaccacg agaccagcac cctcagccca     540
gcctgggcga cagcttggag agcatcccca gcctgagcca atccccggag cctggacgac    600
ggggtgatcc tgacaccgcg cctccatccg agcgccctct ggaagacctg aggcttcggt    660
tggaccatct gggctgggtg gcccggggaa cgggatccgg ggaggactct tccaccagca    720
gctccacccc gctggaagac gaagaacccc aagaacccaa cagattggag acaggagaag    780
ctggggaaga actggaccta cgactccgac ttgctcagcc ctcatcgccc gaggtcttga    840
ctccccagct cagtccgggc tctgggacac cccaggccgg tactccgtcc ccatcccgat    900
cgcgagattc gaactctggg cccgaagagc cattgctgga agaggaagaa aagcagtggg    960
ggccactgga gcgagagcca gtaaggggac agtgcctcga tagcacggac caattagaat    1020
tcacggtgga gccacgcctt ctaggaacag ctatggaatg gttaaagaca tcattgcttt    1080
tggctgttta caagacggtt ccaattttgg aattgtcccc acctctgtgg acagccattg    1140
gctgggtcca aggggcccc accccccta ctcctgtcct ccgggttcta ctgaagtggg      1200
caaaatcccc gagaagcagc ggtgtccca gcctctcact cggagccgat atggggagta    1260
aagtggcgga cctgctgtac tggaaggaca cgaggacgtc aggagtggtc ttcacaggcc    1320
tgatggtctc cctcctctgc ctcctgcact ttagcatcgt gtccgtggcc gcgcacttgg    1380
ctctgttgct gctctgcggc accatctctc tcagggttta ccgcaaagtg ctgcaggccg    1440
tgcaccgggg ggatggagcc aacctttcc aggcctacct ggatgtggac ctcaccctga    1500
ctcgggagca gacggaacgt ttgtcccacc agatcacctc ccgcgtggtc tcggcggcca    1560
cgcagctgcg gcacttcttc ctggtagaag acctcgtgga ttccctcaag ctggccctcc    1620
tcttctacat cttgaccttc gtgggtgcca tcttcaatgg tttgactctt ctcattctgg    1680
gagtgattgg tctattcacc atcccctgc tgtaccggca gcaccaggct cagatcgacc    1740
aatatgtggg gttggtgacc aatcagttga gccacatcaa agctaagatc cgagctaaaa    1800
tcccagggac cggagccctg gcctctgcag cagccgcagt ctccggatcc aaagccaaag    1860
ccgaatgaga acgtgtctc tgcccgcagg acgcctgccc ccagccccg cagccctctg      1920 gccccctcca tctcttgtcc gttcccaccc accccctcc tcggcccgag cctttccccg     1980
gtgggtgtca ggatcactcc cactagggac tctgcgctaa ttacctgagc gaccaggact    2040
acatttccca agaggctctg ctccaggagt ccaggaaaga cgaggcacct tggccgcggg    2100
gcctgctggg acttgtagtt gcctagacag ggcaccaccc tgcacttccg gacccgccgc    2160
tggaggcgcc gtgaggcgtt ggtgtctcct ggatgctact agcccaacg ccggggcttt     2220 gcatggggcc caggggaggc ctgagcttgg atttacactg taataaagac tcctgtggaa    2280
aacccgag                                                            2288
```

<210> SEQ ID NO 37
<211> LENGTH: 1700
<212> TYPE: DNA
<213> ORGANISM: Homo sapiens

<400> SEQUENCE: 37

```
agcaggactc agagggagaa gttggaggaa aaaaaaaggc agaaaaggga aagaaagagg    60
```

```
aagagagaga gagagtgaga ggagccgctg agcccacccc gatggccgcg gacgaagttg      120 ccggagggc gcgcaaagcc acgaaaagca aactttttga gtttctggtc catggggtgc       180
gccccgggat gccgtctgga gcccggatgc cccaccaggg ggcgcccatg gccccccgg       240 gctcccgta catgggcagc cccgccgtgc gacccggcct ggccccgcg ggcatggagc        300 ccgcccgcaa gcgagcagcg ccccgcccg ggcagagcca ggcacagagc cagggccagc      360
cggtgcccac cgccccgcg cggagccgca gtgccaagag gaggaagatg ctgacaaaa        420 tcctccctca aaggattcgg gagctggtcc ccgagtccca ggcttacatg gacctcttgg      480
catttgagag gaaactggat caaaccatca tgcggaagcg ggtggacatc caggaggctc      540
tgaagaggcc catgaagcaa aagcggaagc tgcgactcta tatctccaac actttaacc      600 ctgcgaagcc tgatgctgag gattccgacg gcagcattgc ctcctgggag ctacgggtgg     660
aggggaagct cctggatgat cccagcaaac agaagcggaa gttctcttct ttcttcaaga     720
gtttggtcat cgagctggac aaagatcttt atggccctga caaccacctc gttgagtggc     780
atcggacacc cacgacccag gagacggacg gcttccaggt gaaacggcct ggggacctga     840
gtgtgcgctg cacgctgctc ctcatgctgg actaccagcc tccccagttc aaactggatc     900
cccgcctagc ccggctgctg gggctgcaca cacagagccg ctcagccatt gtccaggccc     960
tgtggcagta tgtgaagacc aacaggctgc aggactccca tgacaaggaa tacatcaatg    1020
gggacaagta tttccagcag atttttgatt gtccccggct gaagttttct gagattcccc    1080
agcgcctcac agccctgcta ttgccccctg acccaattgt catcaaccat gtcatcagcg    1140
tggacccttc agaccagaag aagacggcgt gctatgacat tgacgtggag gtggaggagc    1200
cattaaaggg gcagatgagc agcttcctcc tatccacggc caaccagcag gagatcagtg    1260
ctctggacag taagatccat gagacgattg agtccataaa ccagctcaag atccagaggg    1320
acttcatgct aagcttctcc agagacccca aaggctatgt ccaagacctg ctccgctccc    1380
agagccggga cctcaaggtg atgacagatg tagccggcaa ccctgaagag gagcgccggg    1440
ctgagttcta ccaccagccc tggtcccagg aggccgtcag tcgctacttc tactgcaaga    1500
tccagcagcg caggcaggag ctggagcagt cgctggttgt gcgcaacacc taggagccca    1560
aaaataagca gcacgacgga actttcagcc gtgtcccggg ccccagcatt ttgccccggg    1620
ctccagcatc actcctctgc caccttgggg tgtgggctg gattaaaagt cattcatctg      1680
acaaaaaaaa aaaaaaaaaa                                                  1700

<210> SEQ ID NO 38
<211> LENGTH: 1935
<212> TYPE: DNA
<213> ORGANISM: Homo sapiens

<400> SEQUENCE: 38
acaatagcga ctcactggac ccagcccta gcaacggcct ggcgacggtt tccctgctgc       60
tgcagccccc gtcggctcct cttttccagt cctccactgc cggggctggg cccggccgcg     120
ggaaggaccg aagggatac agcgtgtccc tgcggcggct gcaagaggac taagcatgga     180
tggcagccgg agagtcagag caacctctgt ccttcccaga tatggtccac cgtgcctatt      240
taaaggacac ttgagcacca aaagtaatgc tgcagtagac tgctcggttc cagtaagcgt      300
gagtaccagc ataaagtatg cagaccaaca acgaagagag aaactcaaaa aggaattagc     360
acaatgtgaa aaagagttca aattaactaa aactgcaatg cgagccaatt ataaaaataa     420
```

```
ttccaagtca cttttttaata ccttacaaaa gccctcaggc gaaccgcaaa ttgaggatga      480
catgttaaaa gaagaaatga atggattttc atcctttgca aggtcactag taccctcttc      540
agagagacta cacctaagtc tacataaatc cagtaaagtc atcacaaatg gtcctgagaa      600
gaactccagt tcctccccgt ccagtgtgga ttatgcagcc tccggccccc ggaaactgag      660
ctctggagcc ctgtatggca gaaggcccag aagcacattc ccaaattccc accggtttca      720
gttagtcatt tcgaaagcac ccagtgggga tcttttggat aaacattctg aactcttttc      780
taacaaacaa ttgccattca ctcctcgcac tttaaaaaca gaagcaaaat ctttcctgtc      840
acagtatcgc tattatacac ctgccaaaag aaaaaaggat tttacagatc aacggataga      900
agctgaaacc cagactgaat taagctttaa atctgagttg gggacagctg agactaaaaa      960
catgacagat tcagaaatga acataaagca ggcatctaat tgtgtgacat atgatgccaa     1020
agaaaaaata gctcctttac ctttagaagg gcatgactca acatgggatg agattaagga     1080
tgatgctctt cagcattcct caccaagggc aatgtgtcag tattccctga gccccctttc     1140
aactcgtaaa atctactctg atgaagaaga actgttgtat ctgagtttca ttgaagatgt     1200
aacagatgaa attttgaaac ttggtttatt ttcaaacagg ttttttagaac gactgttcga     1260 gcgacatata aaacaaaata acatttggga ggaggaaaaa atgcgccacc tgctgcatgt     1320
cctgaaagta gacttaggct gcacatcgga ggaaaactcg gtaaagcaaa atgatgttga     1380
tatgttgaat gtatttgatt ttgaaaaggc tgggaattca gaaccaaatg aattaaaaaa     1440
tgaaagtgaa gtaacaattc agcaggaacg tcaacaatac caaaaggctt tggatatgtt     1500
attgtcggca ccaaaggatg agaacgagat attcccttca ccaactgaat tttcatgcc     1560 tattttataaa tcaaagcatt cagaaggggt tataattcaa caggtgaatg atgaaacaaa     1620
tcttgaaact tcaactttgg atgaaaatca tccaagtatt tcagacagtt taacagatcg     1680
ggaaacttct gtgaatgtca ttgaaggtga tagtgaccct gaaaaggttg agatttcaaa     1740
tggattatgt ggtcttaaca catcaccctc ccaatctgtt cagttctcca gtgtcaaagg     1800
cgacaataat catgacatgg agttatcaac tcttaaaatc atggaaatga gcattgagga     1860
ctgccctttg gatgtttaat cttcattaat aaatacctca aatggccagt aactcaaaaa     1920
aaaaaaaaaa aaaaa                                                      1935

<210> SEQ ID NO 39
<211> LENGTH: 4343
<212> TYPE: DNA
<213> ORGANISM: Homo sapiens

<400> SEQUENCE: 39
tggtcatcgc acggcggcag ctcctcacct ggatttagaa gagctggcgt ccccgcccgc       60
ccaagccttt aaactctcgt ctgccagaac ccgccaactc tccaggctta gggccagttt      120
ccgcgattct aagagtaatt gcgtgggcac ctgtgctggg gccaggcgca agaagggag       180 ttggtctgcg cgaagatcgt caacctgcta acagaccgca catgcacttt gcaccgacca      240
tctacgtctc agtctggagg ttgcgcactt ggctgctga cgcgctggtg gtgcctatta      300
atcatttacc agtccagagc cgcgccagtt aatggctgtg ccgtgcggtg ctcccacatc      360
ctggcctctc ctctccacgg tcgcctgtgc ccgggcaccc cggagctgca aactgcagag      420
cccaggcaac cgctgggctg tgcgccccgc cggcgccggt aggagccgcg ctcccgcag       480 cggttgcgct ctacccggag cgctgggcg gctgtgggct gcaggcaagc ggtcgggtgg       540
ggagggaggg cgcaggcggc gggtgcgcga ggagaaagcc ccagccctgg cagccccact       600
```

-continued

```
ggcccccctc agctgggatg ttccccaatg gcaccgcctc ctctccttcc tcctctccta    660
gccccagccc gggcagctgc ggcgaaggcg gcggcagcag gggccccggg gccggcgctg    720
cggacggcat ggaggagcca gggcgaaatg cgtcccagaa cgggaccttg agcgagggcc    780
agggcagcgc catcctgatc tctttcatct actccgtggt gtgcctggtg gggctgtgtg    840
ggaactctat ggtcatctac gtgatcctgc gctatgccaa gatgaagacg gccaccaaca    900
tctacatcct aaatctggcc attgctgatg agctgctcat gctcagcgtg cccttcctag    960
tcacctccac gttgttgcgc cactggccct cggtgcgct gctctgccgc ctcgtgctca     1020
gcgtggacgc ggtcaacatg ttcaccagca tctactgtct gactgtgctc agcgtggacc    1080
gctacgtggc cgtggtgcat cccatcaagg cggcccgcta ccgccggccc accgtggcca    1140
aggtagtaaa cctgggcgtg tgggtgctat cgctgctcgt catcctgccc atcgtggtct    1200
tctctcgcac cgcggccaac agcgacggca cggtggcttg caacatgctc atgccagagc    1260
ccgctcaacg ctggctggtg ggcttcgtgt tgtacacatt tctcatgggc ttcctgctgc    1320
ccgtgggggc tatctgcctg tgctacgtgc tcatcattgc taagatgcgc atggtggccc    1380
tcaaggccgg ctggcagcag cgcaagcgct cggagcgcaa gatcacctta atggtgatga    1440
tggtggtgat ggtgtttgtc atctgctgga tgccttttcta cgtggtgcag ctggtcaacg    1500
tgtttgctga gcaggacgac gccacggtga gtcagctgtc ggtcatcctc ggctatgcca    1560
acagctgcgc caaccccatc ctctatggct ttctctcaga caacttcaag cgctcttttcc    1620 aacgcatcct atgcctcagc tggatggaca acgccgcgga ggagccggtt gactattacg    1680
ccaccgcgct caagagccgt gcctacagtg tggaagactt ccaacctgag aacctggagt    1740
ccggcggcgt cttccgtaat ggcacctgca cgtcccggat cacgacgctc tgagcccggg    1800
ccacgcaggg gctctgagcc cgggccacgc agggggccctg agccaaaaga gggggagaat    1860
gagaagggaa ggccgggtgc gaaagggacg gtatccaggg cgccagggtg ctgtcgggat    1920
aacgtggggc taggacactg acagcctttg atggaggaac ccaagaaagg cgcgcgacaa    1980
tggtagaagt gagagctttg cttataaact gggaaggctt tcaggctacc ttttctgggg    2040
tctcccactt tctgttcctt cctccactgc gcttactcct ctgaccctcc ttctattttc     2100
cctaccctgc aacttctatc ctttcttccg caccgtcccg ccagtgcaga tcacgaactc    2160
attaacaact cattctgatc ctcagcccct ccagtcgtta tttctgtttg tttaagctga    2220
gccacggata ccgccacggg tttccctcgg cgttagtccc tagccgcgcg gggccgctgt    2280
ccaggttctg tctggtgccc ctactggagt cccgggaatg accgctctcc ctttgcgcag    2340
ccctacctta aggaaagttg gacttgagaa agatctaagc agctggtctt ttctcctact    2400
cttgggtgaa ggtgcatctt tccctgccct cccctgtccc cctctcgccg cccgcccgcc    2460
accaccactc tcactccacc cagagtagag ccaggtgctt agtaaaatag gtcccgcgct    2520
tcgaactcca ggctttctgg agttcccacc caagccctcc tttggagcaa agaaggagct    2580
gagaacaagc cgaatgagga gttttttataa gattgcgggg tcggagtgtg ggcgcgtaat    2640
aggaatcacc ctcctactgc gcgttttcaa agaccaagcg ctgggcgctc ccgggccgcg    2700
cgtctgcgtt aggcagggca gggtagtgca gggcacacct tccccggggt tcggggttcg    2760
gggttcggtt gcagggctgc agcccgcctt ggctttctcc ctcacccaag tttccggagg    2820
agccgaccta aaagtaacaa tagataaggt ttcctgctcc agtgtatctc aaaagaccgg    2880
gcgcaggggg cggggggacct agggcgacgt cttcagagtc cgccagtgtt ggcggtgtcg    2940
```

| | |
|---|---:|
| ccgcaacctg caggctcccg agtggggcct gcctggtctc tagagggttg ctgcctttca | 3000 |
| agcggtgcct aagaagttat tttcttgttt aacatatata tttattaatt tatttgtcgt | 3060 |
| gttggaaaat gtgtctctgc tttccttttc tctgcttgcc tagccccagg tcttttcttt | 3120 |
| gggaccctgg gggcgggcat ggaagtggaa gtaggggcaa gctcttgccc cactccctgg | 3180 |
| ccatctcaac gcctctcctc aatgctgggc cctcttatct catcctttcc tctagctttt | 3240 |
| ctattttga ttgtgttgag tgaagtttgg agattttca tacttttctt actatagtct | 3300 |
| cttgtttgtc ttattaggat aatacataaa tgataatgtg ggttatcctc ctctccatgc | 3360 |
| acagtggaaa gtcctgaact cctggctttc caggagacat ataggggaa acatcaccct | 3420 |
| atataatt tgagtgtata tatatttata tatatgatgt ggacatatgt atacttatct | 3480 |
| tgctccattg tcatgagtcc atgagtctaa gtatagccac tgatggtgac aggtgtgagt | 3540 |
| ctggctggaa cactttcagt ttcaggagtg caagcagcac tcaaacctgg agctgaggaa | 3600 |
| tctaattcag acagagactt taatcactgc tgaagatgcc cctgctccct ctgggttcca | 3660 |
| gcagaggtga ttcttacata tgatccagtt aacatcatca ctttttttga ggacattgaa | 3720 |
| agtgaaataa tttgtgtctg tgtttaatat taccaactac attggaagcc tgagcagggc | 3780 |
| gaggaccaat aattttaatt atttatattt cctgtattgc tttagtatgc tggcttgtac | 3840 |
| atagtaggca ctaaatacat gtttgttggt tgattgttta agccagagtg tattacaaca | 3900 |
| atctggagat actaaatctg gggttctcag gttcactcat tgacatgata tacaatggtt | 3960 |
| aaaatcacta ttgaaaaata cgttttgtgt atatttgctt caacaacttt gtgctttcct | 4020 |
| gaaagcagta accaagagtt aagatatccc taatgttttg cttaaactaa tgaacaaata | 4080 |
| tgctttgggt cataaatcag aaagtttaga tctgtccctt aataaaaata tatattacta | 4140 |
| ctcctttgga aaatagattt ttaatggtta agaactgtga aatttacaaa tcaaaatctt | 4200 |
| aatcattatc cttctaagag gatacaaatt tagtgctctt aacttgttac cattgtaata | 4260 |
| ttaactaaat aaacagatgt attatgctgt taaaaaaaaa aaaaaaaaaa aaaaaaaaa | 4320 |
| aaaaaaaaaa aaaaaaaaaa aaa | 4343 |

```
<210> SEQ ID NO 40
<211> LENGTH: 4171
<212> TYPE: DNA
<213> ORGANISM: Homo sapiens

<400> SEQUENCE: 40
```

| | |
|---|---:|
| ctgcatctct ccctctcacc cgtgtctcct ctcctctctt tccttctcgt ctttccctg | 60 |
| tcacgcatct ctcatcactc cccctcattc tgcctttcct cctactcacg gtctcctctc | 120 |
| cctctccctc tctctctctc cccctccctc tttctctctc tctctctttc tccacctcct | 180 |
| cccgaccccc tttcccctct atttctattg gcttctgtgt cccttgctcc cctcttctct | 240 |
| tcctcaccct gggaagcttc tccccctat ccttgcccct gcccccag gatgtgtcct | 300 |
| ggagatgggg ggtgacgtac caggctctgg ttgggaagtc agggccggag accagatggg | 360 |
| agaggctctg tggacagccg tggccgaggg cctgggaggg aacctgagcc cgcaagcggt | 420 |
| ctagaagtgg gtgccttgtg gggacccctag ttaggagtgc cctgggggca cctggggact | 480 |
| gggcagggag aggggacagc agaatgataa ccagcctggc ggcaaggagg gaagccctca | 540 |
| ccccatgggc aggcaaatag ctgactgctg accaccctcc cctcagccat ggacatgctt | 600 |
| catccatcat cggtgtccac gacctcagaa cctgagaatg cctcctcggc ctggcccca | 660 |
| gatgccaccc tgggcaacgt gtcggcgggc ccaagcccgg cagggctggc cgtcagtggc | 720 |

```
gttctgatcc ccctggtcta cctggtggtg tgcgtggtgg gcctgctggg taactcgctg      780
gtcatctatg tggtcctgcg gcacacggcc agcccttcag tcaccaacgt ctacatcctc      840
aacctggcgc tggccgacga gctcttcatg ctggggctgc ccttcctggc cgcccagaac      900
gccctgtcct actggccctt cggctccctc atgtgccgcc tggtcatggc ggtggatggc      960
atcaaccagt tcaccagcat attctgcctg actgtcatga gcgtggaccg ctacctggcc     1020
gtggtacatc ccacccgctc ggcccgctgg cgcacagctc cggtggcccg cacggtcagc     1080
gcggctgtgt gggtggcctc agccgtggtg gtgctgcccg tggtggtctt ctcgggagtg     1140
ccccgcggca tgagcacctg ccacatgcag tggcccgagc cggcggcggc ctggcgagcc     1200
ggcttcatca tctacacggc cgcactgggc ttcttcgggc cgctgctggt catctgcctc     1260
tgctacctgc tcatcgtggt gaaggtgcgc tcagctgggc gccgggtgtg ggcaccctcg     1320
tgccagcggc ggcggcgctc cgaacgcagg gtcacgcgca tggtggtggc cgtggtggcg     1380
ctcttcgtgc tctgctggat gcccttctac gtgctcaaca tcgtcaacgt ggtgtgccca     1440
ctgcccgagg agcctgcctt ctttgggctc tacttcctgg tggtggcgct gccctatgcc     1500
aacagctgtg ccaaccccat cctttatggc ttcctctcct accgcttcaa gcagggcttc     1560
cgcagggtcc tgctgcggcc ctcccgccgt gtgcgcagcc aggagcccac tgtggggccc     1620
ccggagaaga ctgaggagga ggatgaggag gaggaggatg gggaggagag cagggagggg     1680
ggcaagggga aggagatgaa cggccgggtc agccagatca cgcagcctgg caccagcggg     1740
caggagcggc cgcccagcag agtggccagc aaggagcagc agctcctacc ccaagaggct     1800
tccactgggg agaagtccag cacgatgcgc atcagctacc tgtagggggcc tggggaaagc     1860 caggatggcc cgaggaagag gcagaagccg tgggtgtgcc tagggcctac ttcccaaggt     1920
gccacaggcc catgatggga tgttgagggg cctggacttt gatgctattg ctgccaggtc     1980
ttgctgtgtg accttgggta ggttgcttct actctctggg ccttgttttc tcctctgtga     2040
ctcagggata ggagtcatca gcctggatga gctatgtcag atgagaggtt tggagggcac     2100
tgttgctggg ctgacctggc tgagcaggca aaaggtgggt gcagactggc ctcccccag      2160 ggatggagtg tcttggggca tcaactagaa tcttggccct cagagggata aaccaaggcc     2220
aggatttctt gggctcagag tcaggaacac aggagctgct gggggctggg ctggaaacct     2280
aaacagaaga aagcctaacc cggtgggagg agtggggcag aaatggtcag gccccagatc     2340
agctccctcc cctcgactgt gaggccttgg accagtctg ctcctctcta ggcctcaggc      2400
ttcacctggg taaaacccaa caacctctac accccttttgg cccaggcagt caatgctgga     2460
ggtcctgtgc tcctggacgg gaagagcagg tgaatttcct gctcatggaa gcgaatgaag     2520
tccagcttca gggtctctca ctgcctgggc ttttgcaagg ccctgcatct acttttgtac     2580
ttgtcatttt gtattcgttt tcttaaagag ggacctcgaa ctgcataagc ttaggccacc     2640
caaagcctgg ctctgcccct gctgaggtca gccacccaat ccccaaggaa gctcatgttg     2700
ggtcttatgg ctggagtagg ggccccgggg ggttcccagg tcttttgagg gcttccaggc     2760
acctccttgt aggaagggcc atccctgttc ctctccttgt gacccatatt ctcccttcct     2820
ggagaccgag acagggaccc agcccatgag gactggcatg gaaaggcaga gtgtctgaag     2880
agcgctgtga ggagaaggaa gaggaaggga gaagaggaag aggaaggaga aggaagagga     2940
agacaagggg gaaaggggag gatgaggagg gggaaggaga agtacagatc tgtttcctgg     3000
agccgtcttt ggcccccctg ggctgagctc agtggtagca tctgtgaacc tgagttgccg     3060
```

-continued

| | |
|---|---|
| acaacagccc cacccaacca gtactgaggg aaggacacga tcagggtgga acagccaggg | 3120 |
| tgcaatggca aatgcacaga gtacagacag gcacagggcc tgcgtccctg aggggcctca | 3180 |
| gagtgctgcc aagagggctc aggccttaat aaagccctag ggtggagctg gctaccaggg | 3240 |
| acattgggag gactggggag ctccctcccc atgctctatc atcctggaga ctacaggtcg | 3300 |
| ggaggcccag ggaagacaag aagaggctga agtgggactg tggaggggga ccatggggag | 3360 |
| cagccaccat ccaaggctgg gcctagactc cctcccagag atggtccctc agagctgtgg | 3420 |
| tgaggctggc cctgggaggg tgagaccccc ggtgaaatcc ttccgcttcc ccacccctgg | 3480 |
| cagagggcag gggtcctcag ggaaagcaca ggaaccagac ttttggagac ttggatcttc | 3540 |
| agcacacctc agggtcctgg gctggcattg gccttccggg cctcaatttc cccatcaaca | 3600 |
| aatggagatg aatcccagct tggctgcctc ctgggatcta acgagaaaat gagtcatgtg | 3660 |
| aggtaacttc caggctcact gcaatgggta cggtggggtg tatcagatta taaagtgggg | 3720 |
| gtgccctcct caccccagg cttggcctat acccccctct ccatcaagtg gcctctctgt | 3780 |
| gtctgtcctt tggggtgagg acactgtagg ccatgagaaa tgggcagttg ggggtcaga | 3840 |
| ggccaagggt tagggaggca gggcttgggg agagtgtggg accatcagaa gagaaggaag | 3900 |
| tttacaaaac cacattttgt gtggagatgg aggctggagg cccggccctg ggacttggtc | 3960 |
| tggggtttct tgaggaagat ctgagggtcc aagggaggaa ggatgccctg gccttctggc | 4020 |
| cttctctggc tgatcctgcc ttcttgctgc ctaggacagg agagtaatgt cctagaatgg | 4080 |
| tccctgggag gccagttagg aaacccttg ctgcttctgt ctctagctct tgtcaataaa | 4140 |
| gacggtgaca cctgaaaaaa aaaaaaaaaa a | 4171 |

<210> SEQ ID NO 41
<211> LENGTH: 1258
<212> TYPE: DNA
<213> ORGANISM: Homo sapiens

<400> SEQUENCE: 41

| | |
|---|---|
| ccgagctctc tggcgcagcg ctagctccgc cgcgctcagc tgccctgcgc cggcacccct | 60 |
| ggtcatgagc gcccccctcga cgctgccccc cgggggcgag gaaggggctgg ggacggcctg | 120 |
| gccctctgca gccaatgcca gtagcgctcc ggcggaggcg gaggaggcgg tggcggggcc | 180 |
| cggggacgcg cgggcggcgg gcatggtcgc tatccagtgc atctacgcgc tggtgtgcct | 240 |
| ggtggggctg gtgggcaacg ccctggtcat cttcgtgatc cttcgctacg ccaagatgaa | 300 |
| gacggctacc aacatctacc tgctcaacct ggccgtagcc gacgagctct tcatgctgag | 360 |
| cgtgcccttc gtggcctcgt cggccgccct gcgccactgg cccttcggct ccgtgctgtg | 420 |
| ccgcgcggtg ctcagcgtcg acggcctcaa catgttcacc agcgtcttct gtctcaccgt | 480 |
| gctcagcgtg gaccgctacg tggccgtggt gcaccctctg cgcgcggcga cctaccggcg | 540 |
| gcccagcgtg gccaagctca tcaacctggg cgtgtggctg gcatccctgt tggtcactct | 600 |
| ccccatcgcc atcttcgcag acaccagacc ggctcgcggc ggccaggccg tggcctgcaa | 660 |
| cctgcagtgg ccacacccgg cctggtcggc agtcttcgtg gtctacactt tcctgctggg | 720 |
| cttcctgctg cccgtgctgg ccattggcct gtgctacctg ctcatcgtgg caagatgcg | 780 |
| cgccgtggcc ctgcgcgctg gctggcagca gcgcaggcgc tcggagaaga aaatcaccag | 840 |
| gctggtgctg atggtcgtgg tcgtctttgt gctctgctgg atgcctttct acgtggtgca | 900 |
| gctgctgaac ctcttcgtga ccagccttga tgccaccgtc aaccgtgtgt cccttatcct | 960 |
| tagctatgcc aacagctgcg ccaaccccat tctctatggc ttcctctccg acaacttccg | 1020 |

| | |
|---|---|
| ccgattcttc cagcgggttc tctgcctgcg ctgctgcctc ctggaaggtg ctggaggtgc | 1080 |
| tgaggaggag ccctggact actatgccac tgctctcaag agcaaggtg gggcaggtg | 1140 |
| catgtgcccc ccactcccct gccagcagga agccctgcaa ccagaacccg gccgcaagcg | 1200 |
| catcccctc accaggacca ccaccttctg aggagccctt ccctaccca ccctgcgt | 1258 |

<210> SEQ ID NO 42
<211> LENGTH: 2674
<212> TYPE: DNA
<213> ORGANISM: Homo sapiens

<400> SEQUENCE: 42

| | |
|---|---|
| atgcctgcat gtgctggttc agggactcac caccctggcg tcctcccttc ttctcttgca | 60 |
| gagcctgacg caccccaggg ctgccgccat ggagcccctg ttcccagcct ccacgcccag | 120 |
| ctggaacgcc tcctccccgg gggctgcctc tggaggcggt gacaacagga cgctggtggg | 180 |
| gccggcgccc tcggcagggg cccggccggt gctggtgccc gtgctgtacc tgctggtgtg | 240 |
| tgcggccggg ctgggcggga acacgctggt catctacgtg gtgctgcgct cgccaagat | 300 |
| gaagaccgtc accaacatct acattctcaa cctggcagtg gccgacgtcc tgtacatgct | 360 |
| ggggctgcct ttcctggcca cgcagaacgc cgcgtccttc tggcccttcg ccccgtcct | 420 |
| gtgccgcctg gtcatgacgc tggacggcgt caaccagttc accagtgtct tctgcctgac | 480 |
| agtcatgagc gtggaccgct acctggcagt ggtgcacccg ctgagctcgg cccgctggcg | 540 |
| ccgcccgcgt gtggccaagc tggcgagcgc cgcggcctgg gtcctgtctc tgtgcatgtc | 600 |
| gctgccgctc ctggtgttcg cggacgtgca ggagggcggt acctgcaacg ccagctggcc | 660 |
| ggagcccgtg gggctgtggg gcgccgtctt catcatctac acggccgtgc tgggcttctt | 720 |
| cgcgccgctg ctggtcatct gcctgtgcta cctgctcatc gtggtgaagg tgagggcggc | 780 |
| gggcgtgcgc gtgggctgcg tgcggcggcg ctcggagcgg aaggtgacgc gcatggtgtt | 840 |
| ggtggtggtg ctggtgtttg cgggatgttg gctgcccttc ttcaccgtca acatcgtcaa | 900 |
| cctggccgtg gcgctgcccc aggagcccgc ctccgccggc ctctacttct tcgtggtcat | 960 |
| cctctcctac gccaacagct gtgccaaccc cgtcctctac ggcttcctct ctgacaactt | 1020 |
| ccgccagagc ttccagaagg ttctgtgcct ccgcaagggc tctggtgcca aggacgctga | 1080 |
| cgccacggag ccgcgtccag acaggatccg gcagcagcag gaggccacgc cacccgcgca | 1140 |
| ccgcgccgca gccaacgggc ttatgcagac cagcaagctg tgagagtgca ggcggggggt | 1200 |
| gggcggcccc gtgtcaccc caggagcgga ggttgcactg cggtgacccc cacccatgac | 1260 |
| ctgccagtca ggatgctccc cggcggtggt gtgaggacag agctggctga agccaggctg | 1320 |
| gggtagacac agggcagtag gttccccacc gtgaccgacc atcccctcta accgtctgcc | 1380 |
| acacagcggg ggctcccggg aggtagggga ggtggccaga ccggtggggg gctccgccat | 1440 |
| gccgtgcaag tgctcaggc cgcctcaccc tccatctggc cccagccat gccggccttc | 1500 |
| cctctgggga gcgactttc cagaaggccg gccaggcgag agggtcttcc tgacggcgga | 1560 |
| gctgaccctgc ccggcccacc agctgcatgt cagctccgag ccaccgggtc cccgtccaag | 1620 |
| gctgctctgc taagttaaag acacccgaaa gcgcttgact caggtccccg gagtccctgg | 1680 |
| ccagggcccc agcccctcgc ttgccctgca ctgtgtggac tctggggatg caggtgtaag | 1740 |
| gggagtgtgg ctgggcagcc cctggtcagc caggtcacg cctgtcctgg ggccccacc | 1800 |
| ctgctgcccg acacccccca tgggaggctg cgggcggcag ttgctgtctc agagagggga | 1860 |

| | |
|---|---|
| gtgtggggc ttgggcgctg gcctagccag gggcgaggtg gggaggcggc tggtgcagag | 1920 |
| gagagctggg ggctgaggtt ggggtgaagg ctgcagccct ccaggctgct gggggtgcag | 1980 |
| atggctgtgc cgtgctgaga ttggctctgt ctggaggggt ccagtgtggg gtgcctgagg | 2040 |
| gcactaggga gaggtgctcc tgctgcagga ggacctgagg gtcagggctt ggagaggaca | 2100 |
| gggaacctgc ggccgtctct tctgctttgg ggcaggggct ctggcccggg agagggaacg | 2160 |
| gggacaggag cagaggacgg tcatccaggc gcagcgggga gctgctcccc aggccacagc | 2220 |
| agacagcact gctgagaggc agcggccgcg cgggtgacgc aaatggcagg ccctgggaat | 2280 |
| cccgccgcct cccacctaga attgtcctac ctcccccacc ccaaacacca gcttttcctg | 2340 |
| gcgcccagg cccgaacgt gggcccagag agccttgctg gggtctctgg ggcaccttgg | 2400 |
| ccttgctctg aggctggaag gagaaggacc agggtgcggc atcactcggc ctcaggggacc | 2460 |
| cctctgccct gcccagcact ggccccgacc cgtgctcccg ccgtctgccc agagcaggac | 2520 |
| ctcaacctcc tggagggcac agggagcggc tgagtgggca caaatcctgg caggagaaag | 2580 |
| gcccaggctg aggccaggcc tgggaaacat ccaagcagtg aggacacgcg tgtttgacaa | 2640 |
| ctgctcccct gaataaatgc gaggataaat gttt | 2674 |

<210> SEQ ID NO 43
<211> LENGTH: 4427
<212> TYPE: DNA
<213> ORGANISM: Homo sapiens

<400> SEQUENCE: 43

| | |
|---|---|
| cccccggcgg agccagctgc tgctcttcgg tgctggcccc ggtgccggcc ccgttgccca | 60 |
| gggaacaggc tcccggcagc ccccgcggcc cggagtccat cccgcctcct ccggcccggc | 120 |
| ggggccgacg agtccggagg ggctgccgcg ggagccccca ggtttcccta gatgacaaat | 180 |
| aaacattcct tttcctgcgt gaagatagtc tgtggaaacc ttggccatgg catcgatatc | 240 |
| agagcctgtt acattcagag agttctgccc gttgtactat ctcctcaatg ccattccgac | 300 |
| aaagatccag aagggtttcc gctctatcgt ggtctatctc acggccctcg acaccaacgg | 360 |
| ggactacatc gcgtgtggca gcagcatcgg catgctctat ctgtactgcc ggcacctcaa | 420 |
| ccagatgagg aagtacaact ttgaggggaa gacggaatct atcactgtgg tgaagctgct | 480 |
| gagctgcttt gatgacctgg tggcagcagg cacagcctct ggcaggggttg cagttttttca | 540 |
| acttgtatct tcattgccag ggagaaataa acagcttcgg agatttgatg tcactggtat | 600 |
| tcacaaaaat agcattacag ctctggcttg gagcccaat ggaatgaaat tgttctctgg | 660 |
| agatgacaaa ggcaaaattg tttattcttc tctggatcta gaccaggggc tctgtaactc | 720 |
| ccagctggtg ttggaggagc catcttccat tgtgcagctg gattatagcc agaaagtgct | 780 |
| gctggtctct actctgcaaa gaagtctgct ctttacact gaagaaaagt ctgtaaggca | 840 |
| aattggaaca caaccaagga aaagtactgg gaaatttggt gcttgttta taccaggact | 900 |
| ctgtaagcaa agtgatctaa ccttgtatgc gtcacggccc gggctccggc tatggaaggc | 960 |
| tgatgtccac gggactgttc aagccacgtt tatcttaaaa gatgcttttg ccgggggagt | 1020 |
| caagcctttt gaactgcacc cgcgtctgga atccccaac agtggaagtt gcagcttacc | 1080 |
| tgagaggcac ctgggggcttg tttcatgttt ctttcaagaa ggctgggtgc tgagttggaa | 1140 |
| tgaatatagt atctatctcc tagacacagt caaccaggcc acagttgctg gtttggaagg | 1200 |
| atccggtgat attgtgtctg tttcgtgcac agaaaatgaa atattttttct tgaaaggaga | 1260 |
| taggaacatt ataagaattt caagcaggcc tgaaggatta acatcaacag tgagagatgg | 1320 |

```
tctggagatg tctggatgct cagagcgtgt ccacgtgcag caagcggaga agctgccagg    1380
ggccacagtt tctgagacga ggctcagagg ctcttccatg ccagctccg tggccagcga    1440
gccaaggagc aggagcagct cgctcaactc caccgacagc ggctccgggc tcctgccccc    1500
tgggctccag gccaccctg agctgggcaa gggcagccag ccctgtcac agagattcaa     1560
cgccatcagc tcagaggact ttgaccagga gcttgtcgtg aagcctatca aagtgaaaag    1620
gaagaagaag aagaagaaga cagaaggtgg aagcaggagc acctgtcaca gctccctgga    1680
atcgacaccc tgctccgaat tcctggggga cagtccccag tccttgaaca cagacttgct    1740
gtcgatgacc tcaagtgtcc tgggcagtag cgtggatcag ttaagtgcag agtctccaga    1800
ccaggaaagc agcttcaatg gtgaagtgaa cggtgtccca caggaaaata ctgaccccga    1860
aacgtttaat gtcctggagg tgtcaggatc aatgcctgat tctctggctg aggaagatga    1920
cattagaact gaaatgccac actgtcacca tgcacatggg cgggagctgc tcaatggagc    1980
gagggaagat gtgggaggca gtgatgtcac gggactcgga gatgagccgt gtcctgcaga    2040
tgatggacca aatagcacac agttaccctt ccaagaacag gacagctctc ctggggcgca    2100
tgatggggaa gacatccaac ccattggccc ccaaagcact ttttgtgaag tcccctcct    2160
gaactcactc actgtgcctt ccagcctcag ctgggcccca agtgctgaac agtggctgcc    2220
tgggaccaga gctgatgaag gcagcccgt ggagcccagc caagagcagg acatcctaac    2280
cagcatggag gcctctggcc acctcagcac aaatctctgg catgctgtca ctgatgatga    2340
cacaggtcag aaagaaatac ccatttctga acgtgtcttg gggagtgtgg gaggacagct    2400
gactccggtc tctgccttgg cagccagcac tcacaagccc tggcttgagc agcctccacg    2460
ggatcagaca ttgacgtcca gcgatgagga ggacatctat gcccacgggc ttccttcttc    2520
atcctcagag acgagtgtga cagagctcgg acctagttgc tcccagcagg acctgagccg    2580
gctgggtgca gaggacgccg ggctgctcaa gccagatcag tttgcagaaa gctggatggg    2640
ctactcgggt cccggctatg gcatcctcag cttggtggtc tccgagaagt atatctggtg    2700
cctggactac aaaggcggcc tgttctgcag cgcgttgccg ggcgccgggc tgcgctggca    2760
gaagtttgaa gatgctgtcc agcaggtggc agtctcgccc tcaggagccc ttctctggaa    2820
gattgaacag aaatctaacc gggcttttgc ttgtgggaaa gtcaccatca aggggaagcg    2880
gcactggtac gaagccctgc cccaggcagt gtttgtggcc ctgagcgatg acacggcctg    2940
gatcatcagg accagtgggg acctatactt gcagacaggt ctgagcgtgg atcgcccttg    3000
tgccagagcc gtaaaggtgg actgtcccta cccgctgtcc cagatcacag cccggaacaa    3060
tgtggtgtgg gcgctgacag agcagagggc cctcctgtac cgggagggcg tgagcagctt    3120
ctgtccggaa ggcgagcagt ggaagtgtga cattgtcagc gaaaggcaag ctttagaacc    3180
cgtctgcata acgctcgggg atcagcagac tctctgggcc ctggacatcc atgggaacct    3240
gtggttcaga actggcatta tttccaagaa gccccaagga gatgacgacc attggtggca    3300
agtgagcatc acggactatg tggtgtttga ccagtgcagc ttatttcaga cgataatcca    3360
tgccactcac tcggtggcca cagcagccca agccccgta gaaaaggtgg cagataagct    3420
gcgcatggcg ttttggtccc agcagcttca gtgccagcca agccttctcg ggtcaataa    3480
cagcggtgtc tggatctcct cgggcaagaa tgaattccac gtcgctaagg gaagtctcat    3540
aggcacctac tggaatcatg tggttccccg tgggacagct tctgctacaa aatgggcctt    3600
tgtgttggct tctgcagctc ccacgaagga aggaagcttc ctgtggctgt gccagagcag    3660
```

| | |
|---|---|
| caaggacctg tgcagcgtca gcgcccagag cgcacagtcg cggccctcca cggtgcagct | 3720 |
| gcctcccgaa gccgagatgc gcgcctatgc cgcctgccag gatgcgctgt gggcgctgga | 3780 |
| cagcctcggc caggtgttca tcaggacgct ctccaagagc tgccccacgg gcatgcactg | 3840 |
| gaccaggctg gacctctccc agctaggagc tgtaaaattg acaagcttgg catgtggaaa | 3900 |
| tcagcacatc tgggcctgtg attccagggg tggagtttac ttccgtgtag ggactcagcc | 3960 |
| tctcaatccc agtctcatgc ttccagcctg gataatgatt gagccacctg tccaggtaag | 4020 |
| cagaagttag ctggtggaac tcactcttca gtaagacaga aactgtgagg atgctggtac | 4080 |
| tgggaaaaag gatctgcaca gcctctagag gcctcccagc aaatgcgggg agccatgccc | 4140 |
| ccagggtcta cacactctcg ttcatcaaca tcacaactgg aattcgggat tgtgaagtt | 4200 |
| tagagctgaa cagactgtta cagattatga gtcaacacgt atattttctc tttcaaaata | 4260 |
| ataatatttc gtttttgact ttttactaag tgaatattat tttttaaatc tgcctatata | 4320 |
| ttggaacctc tattttataa taataatgat aataaatcag tacccagaag tataaagaag | 4380 |
| gtaaaagtta ctttgaaaaa aaaaaaaaaa aaaaaaaaaa aaaaaaa | 4427 |

<210> SEQ ID NO 44
<211> LENGTH: 1815
<212> TYPE: DNA
<213> ORGANISM: Homo sapiens

<400> SEQUENCE: 44

| | |
|---|---|
| ttttagagaa ttactccaaa ttcatcatga ttgaagacaa taaggagaac aaagaccatt | 60 |
| ccttagaaag gggaagagca agtctcattt tttccttaaa gaatgaagtt ggaggactta | 120 |
| taaaagccct gaaaatcttt caggagaagc atgtgaatct gttacatatc gagtcccgaa | 180 |
| aatcaaaaag aagaaactca gaatttgaga tttttgttga ctgtgacatc aacagagaac | 240 |
| aattgaatga tattttcat ctgctgaagt ctcataccaa tgttctctct gtgaatctac | 300 |
| cagataattt tactttgaag gaagatggta tggaaactgt tccttggttt ccaaagaaga | 360 |
| tttctgacct ggaccattgt gccaacagag ttctgatgta tggatctgaa ctagatgcag | 420 |
| accatcctgg cttcaaagac aatgtctacc gtaaacgtcg aaagtatttt gcggacttgg | 480 |
| ctatgaacta taaacatgga gaccccattc aaaggttga attcactgaa gaggagatta | 540 |
| agacctgggg aaccgtattc caagagctca caaaactcta cccaacccat gcttgcagag | 600 |
| agtatctcaa aaacttacct tgctttcta atattgtgg atatcgggag ataatatcc | 660 |
| cacaattgga agatgtctcc aactttttaa aagagcgtac aggttttcc atccgtcctg | 720 |
| tggctggtta cttatcacca agagatttct tatcaggttt agcctttcga gttttcact | 780 |
| gcactcaata tgtgagacac agttcagatc ccttctatac cccagagcca gatacctgcc | 840 |
| atgaactctt aggtcatgtc ccgcttttgg ctgaacctag ttttgcccaa ttctcccaag | 900 |
| aaattggctt ggcttctctt ggcgcttcag aggaggctgt tcaaaaactg caacgtgct | 960 |
| acttttcac tgtggagttt ggtctatgta acaagatgg acagctaaga gtctttggtg | 1020 |
| ctggcttact tcttctatc agtgaactca acatgcact ttctggacat gccaaagtaa | 1080 |
| agcccttga tcccaagatt acctgcaaac aggaatgtct tatcacaact tttcaagatg | 1140 |
| tctactttgt atctgaaagt tttgaagatg caaaggagaa gatgagagaa tttaccaaaa | 1200 |
| caattaagcg tccatttgga gtgaagtata atccatatac acggagtatt cagatcctga | 1260 |
| aagcaccaa gagcataacc agtgccatga atgagctgca gcatgatctc gatgttgtca | 1320 |
| gtgatgccct tgctaaggtc agcaggaagc cgagtatcta acagtagcca gtcatccagg | 1380 |

| | |
|---|---|
| aacatttgag catcaattcg gaggtctggg ccatctcttg ctttccttga acacctgatc | 1440 |
| ctggagggac agcatcttct ggccaaacaa tattatcgaa ttccactact taaggaatca | 1500 |
| ctagtctttg aaaatttgta cctggatatt ctatttacca cttatttttt tgtttagttt | 1560 |
| tatttctttt ttttttggt agcagcttta atgagacaat ttatatacca tacaagccac | 1620 |
| tgaccaccca tttttaatag agaagttgtt tgacccaata gatagatcta atctcagcct | 1680 |
| aactctattt tccccaatcc tccttgagta aaatgaccct ttaggatcgc ttagaataac | 1740 |
| ttgaggagta ttatggcgct gactcatatt gttacctaag atccccttat ttctaaagta | 1800 |
| tctgttactt attgc | 1815 |

<210> SEQ ID NO 45
<211> LENGTH: 1305
<212> TYPE: DNA
<213> ORGANISM: Homo sapiens

<400> SEQUENCE: 45

| | |
|---|---|
| ggccacccgc agaacagagc ttccgggacc cacgcctcgt ttgcactggg tgctggacag | 60 |
| ccgacgcaac tacaaatggg gcggagcttt cggcactgga gcagctaatt tgcatatagg | 120 |
| aatgaggtgc ggctcggctt ccatgggcct aatttacaga tagggcggta tttctgcccc | 180 |
| ttaaccgaaa gtgggataca gaggacgacg gtgttaggcg cctgtgtagg agtaaaatgt | 240 |
| gtttattttg cattcaacga gagctcctgc attgcagcta ttttgcatat gatttgcatc | 300 |
| ttacgaagaa tttgtggcaa aaaaaagctg ggcgtgcgcc gtaggaacct cctgctgaga | 360 |
| cgcttccggt agcggcgcgt gacccgacag gtctttcacc tacctacctc agctcccaca | 420 |
| aacacgagaa gttccagcaa gttcgccact tccggttctc ctggctatcc aatagcatcg | 480 |
| agaggagcat ccccggaagt gaggcagcgg aggacgacct ttttccggtt ccggcctggc | 540 |
| gagagtttgt gcggcgacat gaaactgctt acccacaatc tgctgagctc gcatgtgcgg | 600 |
| ggggtggggt cccgtggctt cccctgcgc ctccaggcca ccgaggtccg tatctgccct | 660 |
| gtggaattca acccccaactt cgtggcgcgt atgatacctta aagtggagtg gtcggcgttc | 720 |
| ctggaggcgg ccgataactt gcgtctgatc caggtgccga aagggccggt tgagggatat | 780 |
| gaggagaatg aggagtttct gaggaccatg caccacctgc tgctggaggt ggaagtgata | 840 |
| gagggcaccc tgcagtgccc ggaatctgga cgtatgttcc ccatcagccg cgggatcccc | 900 |
| aacatgctgc tgagtgaaga ggaaactgag agttgattgt gccaggcgcc agttttctt | 960 |
| gttatgactg tgtattttg ttgatctata ccctgtttcc gaattctgcc gtgtgtatcc | 1020 |
| ccaacccttg acccaatgac accaaacaca gtgtttttga gctcggtatt atatattttt | 1080 |
| ttctcattaa aggtttaaaa ccaaaagcgg tttctctttg cagcaaatat acattaaaat | 1140 |
| agagtctctg tacagccaag ggctctgggc cctggcttgc cccatgtccc tgcgcctccc | 1200 |
| tggccaaacc caaaaataaa tatagtgtta ttgctctgca gggcatagag gcagtgctct | 1260 |
| cctaccccct gaggaggctc gttgggagct gatggggaag ccctg | 1305 |

<210> SEQ ID NO 46
<211> LENGTH: 2770
<212> TYPE: DNA
<213> ORGANISM: Homo sapiens

<400> SEQUENCE: 46

| | |
|---|---|
| cacacacaca catacacaga atcctcagat aacaggaggc aataaatcca acagcacatc | 60 |

-continued

| | |
|---|---|
| cacgttcaga gaacagtgtc cctgctgtct tgctaacagc tgccaatacc tcactgagtg | 120 |
| cctcacacca acatgggctc caagtgagtt tccttcgtct gggcagactc cctcccctct | 180 |
| tccataaagg ctgcaggaga cctgtagctg tcacaggacc ttccctaaga gcccgcaggg | 240 |
| gaagactgcc ccagtccggc catcaccatg ctccggacca ttctggatgc tccccagcgg | 300 |
| ttgctgaagg aggggagagc gtcccggcag ctggtgctgg tggtggtatt cgtcgctttg | 360 |
| ctcctggaca acatgctgtt tactgtggtg gtgccaattg tgcccacctt cctatatgac | 420 |
| atggagttca agaagtcaa ctcttctctg cacctcggcc atgccggaag ttccccacat | 480 |
| gccctcgcct ctcctgcctt ttccaccatc ttctccttct tcaacaacaa caccgtggct | 540 |
| gttgaagaaa gcgtacctag tggaatagca tggatgaatg acactgccag caccatccca | 600 |
| cctccagcca ctgaagccat ctcagctcat aaaaacaact gcttgcaagg cacaggtttc | 660 |
| ttggaggaag agattacccg ggtcggggtt ctgtttgctt caaaggctgt gatgcaactt | 720 |
| ctggtcaacc cattcgtggg ccctctcacc aacaggattg gatatcatat ccccatgttt | 780 |
| gctggctttg ttatcatgtt tctctccaca gttatgtttg cttttctgg gacctatact | 840 |
| ctactctttg tggcccgaac ccttcaaggc attggatctt cattttcatc tgttgcaggt | 900 |
| cttggaatgc tggccagtgt ctacactgat gaccatgaga gaggacgagc catgggaact | 960 |
| gctctggggg gcctggcctt ggggttgctg gtgggagctc cctttggaag tgtaatgtac | 1020 |
| gagtttgttg ggaagtctgc acccttcctc atcctggcct tcctggcact actggatgga | 1080 |
| gcactccagc tttgcatcct acagccttcc aaagtctctc ctgagagtgc caaggggact | 1140 |
| cccctcttta tgcttctcaa agacccttac atcctggtgg ctgcagggtc catctgcttt | 1200 |
| gccaacatgg gggtggccat cctggagccc acactgccca tctggatgat gcagaccatg | 1260 |
| tgctccccca gtggcagct gggtctagct ttcttgcctg ccagtgtgtc ctacctcatt | 1320 |
| ggcaccaacc tctttggtgt gttggccaac aagatgggtc ggtggctgtg ttccctaatc | 1380 |
| gggatgctgg tagtaggtac cagcttgctc tgtgttcctc tggctcacaa tattttggt | 1440 |
| ctcattggcc ccaatgcagg gcttggcctt gccataggca tggtggattc ttctatgatg | 1500 |
| cccatcatgg ggcacctggt ggatctacgc cacacctcgg tgtatgggag tgtctacgcc | 1560 |
| atcgctgatg tggcttttg catgggcttt gctataggtc catccaccgg tggtgccatt | 1620 |
| gtaaaggcca tcggttttcc ctggctcatg gtcatcactg ggtcatcaa catcgtctat | 1680 |
| gctccactct gctactacct gcggagcccc ccggcaaagg aagagaagct tgctattctg | 1740 |
| agtcaggact gccccatgga gacccggatg tatgcaaccc agaagcccac gaaggaattt | 1800 |
| cctctggggg aggacagtga tgaggagcct gaccatgagg agtagcagca aaggtgctc | 1860 |
| cttgaattca tgatgcctca gtgaccacct ctttccctgg gaccagatca ccatggctga | 1920 |
| gcccacggct cagtgggctt cacataccts tgcctgggaa tcttcttttcc tcccctccca | 1980 |
| tggacactgt ccctgatact cttctcacct gtgtaacttg tagctcttcc tctatgcctt | 2040 |
| ggtgccgcag tggcccatct tttatgggaa gacagagtga tgcaccttcc cgctgctgtg | 2100 |
| aggttgatta aacttgagct gtgacgggtt ctgcaagggg tgactcattg catagaggtg | 2160 |
| gtagtgagta atgtgcccct gaaaccagtg gggtgactga caagcctctt taatctgttg | 2220 |
| cctgattttc tctggcatag tcccaacaga tcggaagagt gttaccctct tttcctcaac | 2280 |
| gtgttctttc ccgggttttc ccagccgagt tgagaaaatg ttctcagcat tgtcttgctg | 2340 |
| ccaaatgcca gcttgaagag ttttgttttg tttttttttca tttattttt tttttaataa | 2400 |
| agtgagtgat ttttctgtgg ctaaatctag agctgctaaa agggctttac cctcagtgaa | 2460 |

| | |
|---|---|
| aagtgtcttc tattttcatt atctttcaga aacaggagcc catttctctt ctgctggagt | 2520 |
| tattgacatt ctcctgacct cccctgtgtg ttcctacctt ttctgaacct cttagactct | 2580 |
| tagaaataaa agtagaagaa agacagaaaa aataactgat tagacccaag atttcatggg | 2640 |
| aagaagttaa aagaaactgc cttgaaatcc ctcctgattg tagatttcct aacaggaggg | 2700 |
| gtgtaatgtg acattgttca tacttgctaa taaatacatt attgcctaat tcaaaaaaaa | 2760 |
| aaaaaaaaaa | 2770 |

<210> SEQ ID NO 47
<211> LENGTH: 3885
<212> TYPE: DNA
<213> ORGANISM: Homo sapiens

<400> SEQUENCE: 47

| | |
|---|---|
| agagccggac ggggtaaaact gagcggcggc ggcggggcgc tggggcggag actgcgaccc | 60 |
| ggagccgccc ggactgacgg agcccactgc ggtgcgggcg ttggcgcggg cacggaggac | 120 |
| ccgggcaggc atcgcaagcg accccgagcg gagccccgga gccatggccc tgagcgagct | 180 |
| ggcgctggtc cgctggctgc aggagagccg ccgctcgcgg aagctcatcc tgttcatcgt | 240 |
| gttcctggcg ctgctgctgg acaacatgct gctcactgtc gtggtcccca tcatcccaag | 300 |
| ttatctgtac agcattaagc atgagaagaa tgctacagaa atccagacgg ccaggccagt | 360 |
| gcacactgcc tccatctcag acagcttcca gagcatcttc tcctattatg ataactcgac | 420 |
| tatggtcacc gggaatgcta ccagagacct gacacttcat cagaccgcca cacagcacat | 480 |
| ggtgaccaac gcgtccgctg ttccttccga ctgtcccagt gaagacaaag acctcctgaa | 540 |
| tgaaaacgtg caagttggtc tgttgtttgc ctcgaaagcc accgtccagc tcatcaccaa | 600 |
| cccctttcata ggactactga ccaacagaat tggctatcca attcccatat ttgcgggatt | 660 |
| ctgcatcatg tttgtctcaa caattatgtt tgccttctcc agcagctatg ccttcctgct | 720 |
| gattgccagg tcgctgcagg gcatcggctc gtcctgctcc tctgtggctg ggatgggcat | 780 |
| gcttgccagt gtctacacag atgatgaaga gagaggcaac gtcatgggaa tcgccttggg | 840 |
| aggcctggcc atgggggtct tagtgggccc ccccttcggg agtgtgctct atgagtttgt | 900 |
| ggggaagacg gctccgttcc tggtgctggc cgccctggta ctcttggatg gagctattca | 960 |
| gctctttgtg ctccagccgt cccggtgca gccagagagt cagaagggga caccccctaac | 1020 |
| cacgctgctg aaggacccgt acatcctcat tgctgcaggc tccatctgct ttgcaaacat | 1080 |
| gggcatcgcc atgctggagc cagccctgcc catctggatg atggagacca tgtgttcccg | 1140 |
| aaagtggcag ctgggcgttg ccttcttgcc agctagtatc tcttatctca ttggaaccaa | 1200 |
| tatttttggg atacttgcac acaaaaatggg gaggtggctt tgtgctcttc tgggaatgat | 1260 |
| aattgttgga gtcagcattt tatgtattcc atttgcaaaa aacatttatg gactcatagc | 1320 |
| tccgaacttt ggagttggtt ttgcaattgg aatggtggat tcgtcaatga tgcctatcat | 1380 |
| gggctacctc gtagacctgc ggcacgtgtc cgtctatggg agtgtgtacg ccattgcgga | 1440 |
| tgtggcattt tgtatggggt atgctatagg tccttctgct ggtggtgcta ttgcaaaggc | 1500 |
| aattggattt ccatggctca tgacaattat tgggataatt gatattcttt ttgcccctct | 1560 |
| ctgctttttt cttcgaagtc cacctgccaa agaagaaaaa atggctattc tcatggatca | 1620 |
| caactgccct attaaaacaa aaatgtacac tcagaataat atccagtcat atccgatagg | 1680 |
| tgaagatgaa gaatctgaaa gtgactgaga tgagatcctc aaaaatcatc aaagtgttta | 1740 |

```
attgtataaa acagtgtttc cagtgacaca actcatccag aactgtctta gtcataccat    1800
ccatccctgg tgaaagagta aaaccaaagg ttattatttc ctttccatgg ttatggtcga    1860
ttgccaacag ccttataaag aaaaagaagc ttttctaggg gtttgtataa atagtgttga    1920
aactttattt tatgtattta attttattaa atatcataca atatattttg atgaaatagg    1980
tattgtgtaa atctataaat atttgaatcc aaaccaaata taatttttta acttacatta    2040
acaaacattt gggcaaaaat catattggta atgagtgttt aaaattaaag cacacattat    2100
ctctgagact cttccaacaa agagaaacta gaatgaagtc tgaaaaacag aatcaagtaa    2160
gacagcatgt tatatagtga cactgaatgt tatttaactt gtagttacta tcaatatatt    2220
tatgcgttaa acagctagtt ctctcaagtg tagaggacaa gaacttgtgt cagttatctt    2280
ttgaatccat aaatcttagc tggcattagt tttctatgta atcacctacc tagagagagt    2340
tgtaaattat atgttaacat gttatctggt tggcagcaaa cactaaagcc aataaaggaa    2400
aaacagtaaa tgttccgaaa gcagagaaaa gcaaccaaac atattgttat gaactaaaag    2460 cttteccttt aagatgcata cttgtcttac tggatgaaga aaattgaggg tacatgtacc    2520
ttatactgtc aaggttgttt aaacatgata aggttaatcg ccatctactt caagttttag    2580
aaaaggaaac aagaagctga aaacagctgc tctgacttta atatctgact atatctttga    2640
tctgtttgca ggtcatccaa gtgttttcta ggaatatatt tattttaggt tgtctgaaac    2700
tactattttt tagactcctg aaagttgttc acatcaatgt gaagacaaat tttaaatgaa    2760
aatgaagaat gaaattatgt cttgaatcat atattaagaa gtaaaaataa tagtgatcag    2820
gcagaaaaga aaaatggaac atctaaaaat gtatgtgcta actatatcat ccagtgtgca    2880
gtgttgtgta ttttctaag catgacaaca ttgatgtgcc ttttcagtgt aacagcaaat    2940
actgttagtg aacattgtca atttatgtca ttttgttaag agatatgact ggagtgtgca    3000
gtgtggaatg tctctaatac tacttgtgaa tcctgcagtt ctataatcat aaacaaaaat    3060
tacttagttt cgttaagcta agattgtgtt tgtgttaact tcgacatcaa ggagcaaaga    3120
actttagaac agactcctca atcttgtgac tttcttattc tctaggaaag taacacttcg    3180
tttcatgaag cttttctgtg gggcttcgat tatttcaagt ctggtttcta agtgcagtgt    3240
gtttgaagca aacgaacttc caactcactt atttggcatt gggcaacttg ccaagtctg    3300 ccactttgga agatggctct ggaggaaact ctcatatggc taaaaaggca ggctagtttc    3360
ttacttctac aggggtagag ccttaaaaaa gaacgtgcta caaattggtt ctctttgagg    3420
gtttctggtt ctccctgccc ccaataccat atactttatt gcaattttat ttttgccttt    3480
acggctctgt gtcttctgc aagaaggcct ggcaaaggta tgcctgctgt tggtccctcg    3540
ggataagata aaatataaat aaaaccttca gaactgtttt ggagcaaaag atagcttgta    3600
cttggggaaa aaaattctaa gttctttat atgactaata ttcttggtta gcaagactgg    3660
aaagaggtgt ttttttaaaa tgtacatacc agaacaaaga acatacagct ctctgaacat    3720
ttattttttg aacagaggtg gttttatgt ttggacctgg taatacagat acaaaaactt    3780
taatgaggta gcaatgaata ttcaactgtt tgactgctaa gtgtatctgt ccatatttta    3840
gcaagtttac ttaataaatc ttctgaacca tgaaaaaaaa aaaaa                    3885
```

<210> SEQ ID NO 48
<211> LENGTH: 14607
<212> TYPE: DNA
<213> ORGANISM: Homo sapiens
<400> SEQUENCE: 48

```
ccggagggc tgtcatttgc agcgctggtc gcagccctca gctgcgccgg gcggttccgg    60
ctcctccctc tccttgtgcc tcagcgccac catggtgctg gagtcggtgg tcgcggactt   120
gctgaaccgc ttcctggggg actatgtgga gaacctgaac aagtcccagc tgaagctggg   180 catctgggc ggaaatgtgg ctttagataa tctacagata aaagaaaatg ccctgagtga   240
attggatgtt ccttttaaag tcaaggctgg ccaaattgat aaattaactt tgaagattcc   300
ttggaagaac ctttatggag aagcagttgt tgcgaccctg aaggattat acctgcttgt   360 tgtccctgga gcaagtatta agtatgatgc tgtaaaagaa gaaaaatcct gcaggatgt   420 taaacagaaa gagctatccc gaattgaaga agcccttcaa aaagcagcag aaaaaggcac   480
acattcaggg gagttcatat atggcttgga gaactttgtt tacaaggaca tcaagcctgg   540
acgtaaacgt aaaaagcaca aaaacattt taagaaacct tttaaaggtc ttgatcgttc   600
aaaagataag ccaaaagaag ccaaaaagga tacatttgtg gaaaaattgg caactcaagt   660
aataaaaaat gtacaagtaa aaatcacaga tattcacatt aaatatgaag atgatgtcac   720
tgatccaaag cggcctcttt catttggtgt cacactggga gagcttagtc tactgactgc   780
aaatgaacac tggactccat gcatattaaa tgaagcagac aaaattatat acaagcttat   840
acgacttgat agtcttagcg cctactggaa tgtaaattgc agcatgtctt accagagatc   900
aagggaacag atttttggatc agctgaaaaa tgaaattctt acaagtggaa atataccccc   960
aaattatcaa tacattttcc agccaatatc agcctctgca aaactctaca tgaatcctta  1020
tgcagaatca gagctcaaaa cgcccaaact ggattgcaac atagaaatac aaaatattgc  1080
cattgaactg accaaacctc agtacttaag tatgattgac cttttggagt cagtggatta  1140
tatggttagg aatgcgcctt ataggaaata caagccttat ttaccacttc ataccaatgg  1200
tcgacgatgg tggaaatatg caattgattc tgttcttgaa gttcatataa gaaggtatac  1260
acagatgtgg tcatggagta acataaaaaa gcacaggcag ttactcaaga gttataaaat  1320
tgcctacaaa aacaagttaa cacagtctaa agtctcagaa gaaatacaga agaaattca  1380 ggacttggag aagactctag atgttttaa cataatttta gcaaggcaac aagcacaagt  1440
tgaggtgatt cggtctgggc aaaaattaag gaaaagtct gctgacacag gcgagaaacg  1500
tggaggctgg tttagtgggt tgtggggtaa gaaagagtct aagaaaaagg acgaagaatc  1560
attgattcct gaaactattg atgacctat gactccagag gaaaaagata aactcttcac  1620
tgccattggt tatagtgaga gtacccacaa cctaacttta cctaagcagt atgttgccca  1680
tattatgacc ctgaagttag taagcaccctc tgttacgata agagaaaaca gaatattcc  1740 agaaatacta aaaattcaga taattggcct gggcactcaa gtatctcagc gaccaggagc  1800
acaagcactt aaggtagaag cgaaattaga acactggtat ataacaggtt tgagacagca  1860
ggatattgtg ccatcacttg tggcttcaat tggtgacact acatcatcct tgcttaaaat  1920
taaatttgaa accaatccgg aggatagtcc tgctgaccag actctgattg ttcagtccca  1980
gcctgtggag gtcatctatg atgctaaaac tgtcaatgca gtggttgaat ctttcaatc  2040 aaataaggga ttggatcttg agcaaataac atcagcaaca ttgatgaagc tggaagaaat  2100
taaggagaga acagctacag gacttacaca tattattgaa actcgaaaag tccttgattt  2160
aaggataaat ctgaagcctt cttatctagt agttccacag acgggtttcc accatgaaaa  2220
gtcagatctt ctgatttag attttggtac atttcagctc aacagtaaag atcaaggttt  2280
acagaagact actaattcat ctctggaaga aataatggat aaggcatatg acaagtttga  2340
```

```
tgttgaaata aaaaatgtac aactactttt tgcaagagca gaggaaacct ggaaaaagtg    2400
tcgatttcag catccatcaa ctatgcatat attgcaaccc atggatattc atgttgagtt    2460
ggctaaggcc atggtagaaa aagacattag aatggccaga tttaaagtgt caggaggact    2520
tcctttgatg catgtgagaa tttctgacca gaagatgaaa gatgtgctat atttgatgaa    2580
cagtatacct ttgccacaga atcatcagc ccagtctcca gagagacagg tatcctcaat     2640
tcctattatt tcaggtggta caaaaggtct acttggtact tcactattgc tagacactgt    2700
ggaatcagag tctgatgatg agtattttga tgctgaagat ggagaaccac agacttgtaa    2760
aagtatgaaa ggatcagaac ttaaaaaagc tgcagaggtc ccaaatgagg agctcatcaa    2820
tcttctactc aagtttgaaa ttaaagaagt gattttggaa tttactaaac agcagaaaga    2880
agaagataca attctagtat ttaatgttac tcagttagga acagaggcca caatgagaac    2940
atttgactta actgtggtat cttatttaaa gaaaatcagc ttggattatc atgaaattga    3000
aggatccaaa aggaagcccc ttcacttgat tagctcttct gacaaacctg gattagatct    3060
tttgaaagtg gagtatatta aggctgataa gaatggacct agttttcaaa ctgcttttgg    3120
aaaaactgaa caaacagtta aggtggcctt ttcatcttta aatctgttgc tgcaaacaca    3180
agctcttgtc gcttctatta attacctcac aaccattatt ccatctgatg atcaaagcat    3240
aagtgttgct aaggaggtac aaatttcaac tgaaaaacaa caaaaaaatt caactctgcc    3300
aaaagcgatt gtatcctcca gagatagtga cattattgat ttcaggctat ttgccaagtt    3360
gaatgctttc tgtgtcattg tttgcaacga aagaacaat atcgccgaaa tcaagattca     3420
aggactggat tcctcccttt ctctccagtc aagaaagcag tcacttttg cccgactaga     3480 aaatattatt gtcacagatg ttgatccaaa gacagttcat aagaaagctg tgtcaataat    3540
gggaaatgaa gttttccgtt ttaatttgga tttgtatcca gatgctactg aggggattt     3600 gtatactgac atgtccaaag tggatggtgt gctgtctctg aatgttggct gtattcagat    3660
tgtctatctt cataaattcc ttatgtcact tctgaacttc ctgaataatt ccagacagc     3720 caaagagtct ctgagtgctg ccactgccca ggctgcagaa agggctgcca caagtgtgaa    3780
agatcttgcc cagaggagtt tcgtgtttc catcaatatt gatttgaaag caccggttat    3840
agtcatccca cagtcttcta tttccaccaa tgcagtagtg gtagatcttg ggttaatcag    3900
agttcataat cagttcagtc tggtgtctga tgaagactac ttaaatcctc cagtaattga    3960
tagaatggat gtgcagctaa caaagcttac actttatagg acagtgatcc agccaggcat    4020
ctaccatcct gatattcagc tgttgcaccc aattaacttg gaatttcttg taaatcggaa    4080
tctagctgca tcttggtacc acaaggtgcc tgttgtggaa attaaaggac atcttgattc    4140
aatgaatgtt agtctaaatc aagaagatct taatctttta tttaggatac taacagaaaa    4200
tctctgtgag ggtactgaag acttggataa agtgaaacca agagtacaag agacaggtga    4260
aattaaagag cccccttgaaa tctctatatc acaagatgta catgattcaa aaaatacttt    4320
aacaactgga gtggaagaaa ttaggtctgt agacatcatt aatatgctgc tgaattttga    4380
aattaaagag gttgtggtta ctttgatgaa aaaatcagaa aagaaaggaa ggcctttaca    4440
tgagctaaat gtcctgcaac ttggaatgga agctaaagtt aaaacctatg acatgactgc    4500
taaagcttat ctaaaaaaaa ttagtatgca gtgctttgat ttcactgact ctaaagggga    4560
acctcttcac attattaact cttctaatgt gactgacgaa ccccttctga aaatgttact    4620
gacaaaggca gacagtgatg gaccagaatt taaaactatt catgacagta ccaaacagag    4680
actgaaggtt tcatttgcat ccttagactt agtacttcat ttggaagctt tactttcctt    4740
```

```
catggatttt ttatcatctg ctgctccatt ctctgagcct tcctcttctg agaaggaatc    4800
cgagctgaaa ccacttgtgg gggagtccag aagtatcgct gtcaaagctg tatccagcaa    4860
catttcccaa aaggatgtgt ttgatttaaa gatcacagct gaattaaatg catttaatgt    4920
ctttgtctgt gatcagaagt gtaacattgc agatattaaa atacatggaa tggatgcctc    4980
tatttctgtg aagcctaagc agactgatgt gtttgccaga cttaaagata ttatagttat    5040
gaatgtagat ttgcagtcca ttcacaaaaa ggctgtctct attttgggag atgaagtctt    5100
taggttccaa ctgactcttt atccagatgc cacagaagga gaggcctatg ctgatatgtc    5160
caaagtagac ggcaaactta gttttaaagt gggttgtatt cagattgttt atgttcataa    5220
attcttcatg tctcttttga acttcctcaa caatttccaa actgctaaag aagctttgag    5280
tacagccaca gtccaggctg cagaaagagc tgcttccagc atgaaaagact tggctcaaaa    5340 gagtttccgc cttttgatgg atattaattt gaaagcacca gttattatta ttcctcagtc    5400
ttcagtatca cctaatgctg ttatagcaga tctgggttta atcagagttg aaaacaagtt    5460
tagcttggtt cctatggaac attattctct tcctccagtc attgataaaa tgaacatcga    5520
actcactcag ttgaagctgt caagaactat tttgcaggct agcttgccac aaaatgacat    5580 tgaaattta aaaccagtca acatgctttt gtccatacag cgaaacttag cagcagcatg    5640
gtatgtgcaa attccaggga tggagataaa aggaaaacta aaacctatgc aggttgctct    5700
cagtgaagat gacttgacag ttttaatgaa aattttgcta gaaaatcttg agaagcttc    5760 ctcacaacca agcctacac agtctgtgca ggagactgta agagtgagaa aagttgatgt    5820
ttcaagtgta cctgaccatc tcaaagaaca agaagattgg acagactcaa agctctctat    5880
gaaccagatt gtcagtctcc aatttgactt tcactttgaa tctctttcca ttatcctta    5940 taacaatgat atcaaccagg aatctggagt tgcatttcat aatgacagtt tccaacttgg    6000
tgaactcaga ctacatctta tggcctcctc agggaagatg tttaaggatg gctcaatgaa    6060
tgtcagcgtt aaacttaaga catgcaccct tgatgatctc agagaaggaa ttgagagagc    6120
aacatcgaga atgattgaca gaaagaatga ccaagataac aacagttcta tgattgatat    6180
aagttacaaa caagacaaaa atggaagtca aattgatgct gttcttgaca gctgtatgt    6240 atgtgccagt gtggaatttc tgatgactgt ggcagatttc tttatcaaag ctgtgcctca    6300
gagtccagaa aatgtggcaa aagaaacaca gattttacca agacagactg ccacagggaa    6360
ggtcaagata gagaaagatg actctgttag accaaatatg actttaaagg ccatgatcac    6420
agatccagaa gtggtatttg ttgccagcct gacaaaggct gatgctcctg ctctgacagc    6480
ctcgtttcag tgcaaccttt ctctgtcaac atccaaactc gaacagatga tggaagcttc    6540
tgtgagagat ctgaaagtgc tcgcttgccc ttttctcaga gaaagagag ggaaaaacat    6600 taccacagtc ttgcagccct gttctttatt tatggaaaaa tgtacgtggg cttcaggaaa    6660
gcaaaatata aatattatgg ttaaagaatt tataattaag atttcaccca taattcttaa    6720
tactgtgttg acaatcatgg ctgcattgtc tccaaaaaca aagaagatg gatccaaaga    6780 tacgtctaag gaaatggaaa atctttgggg tatcaaatcg attaatgatt ataacacttg    6840
gtttcttggt gttgacacgg caacagaaat aacggaaagc ttcaaaggca ttgaacattc    6900
actgatagag gaaaattgtg gtgttgttgt agaatccatt caagttacct agaatgtgg    6960 ccttggacat cgaactgtac ctttattatt ggcagagtct aagttttcag gaaatattaa    7020
aaattggact tctctaatgg ctgctgttgc tgacgtgaca ctacaggtgc actattacaa    7080
```

```
tgagatccat gctgtctggg agccactgat tgagagagtg gaggggaaga gacaatggaa    7140
tttaaggctt gatgtaaaga agaacccagt tcaggataaa agtttgctgc caggagatga    7200
ttttattcct gagccacaaa tggcaattca tatttcttca ggaaatacaa tgaatataac    7260
aatatccaaa agttgtctta atgttttcaa caatttagca aaaggttttt cagagggcac    7320
tgcttctact tttgactact ctttaaagga cagagctcct tttacggtaa aaaatgctgt    7380
aggtgttccc attaaggtga agcccaattg taatctcaga gtaatgggct ccctgagaa     7440 aagtgatatt tttgatgttg atgctggcca gaatttggaa ctggagtatg ccagcatggt    7500
accttcaagt caagggaacc tatctatatt gagccgtcaa gaaagctcct tcttcactct    7560
gaccattgta cctcatggat atacagaagt tgcaaatatc cctgtggcca gacctggacg    7620
gcgattgtat aatgtacgga atcccaatgc cagtcattct gactctgtct tggtacaaat    7680
tgatgcaact gaagggaata agtaattac ccttcgctct cctctacaga tcaaaaacca     7740
tttctccatt gcatttatca tctataaatt tgttaagaat gttaagctat tggagcgcat    7800
tgggatagcc agacctgaag aggagttcca tgttcccttta gattcatata gatgtcaatt   7860
gtttatccag ccagctggaa tcttagagca tcagtacaaa gaatctacca cttatatttc    7920
ctggaaggaa gaacttcata ggagcaggga agtcagatgc atgttgcagt gtccatcagt    7980
agaagtcagc ttcttacctc tcatagtgaa tacagttgct ctgcctgatg aattgagcta    8040
catatgtaca catggggaag actggatgt  agcttacatt attcatcttt atccttctct    8100
cactttgcgg aatcttctcc catattccct aagatattta cttgagggaa cagcagaaac    8160
tcatgagctg gcagaaggca gtactgctga tgttctgcat tcgagaatca gtggtgaaat    8220
aatggaatta gtcctggtga ataccaggg  caaaaactgg aatggacatt ccgcatacg     8280 tgatacacta ccagaattct ttcctgtgtg tttttcttct gactccacag aagtgacgac    8340
agtcgacctg tcagtccacg tcaggagaat tggcagccgg atggtgctgt ctgtctttag    8400
tccctattgg ttaatcaaca agactacccg ggttctccag tatcgttcag aagatattca    8460
tgtgaaacat ccagctgatt tcagggatat tatttttattt tctttcaaga agaagaacat    8520
ttttactaaa aataaggtac aattaaaaat ttcaaccagt gcctggtcca gtagtttctc    8580
attggataca gtgggaagtt atgggtgtgt gaagtgtcct gccaacaata tggagtacct    8640
ggttggtgtt agcatcaaaa tgagcagttt caacctttca cgaatagtta ccctgactcc    8700
cttttgtacc attgcaaaca agtcatcatt agaactagaa gttggcgaga ttgcatctga    8760
tggctcaatg ccaactaata aatggaacta tattgcttct tcagagtgcc ttccattttg    8820
gccagaaagt ttgtcaggca aactttgtgt gagagtggtg ggctgtgaag gatcttccaa    8880
accattcttt tataaccgac aggataatgg cactttattg agcttagaag atctgaatgg    8940
gggtatcttg gtggatgtaa acactgccga acattcaact gtcataactt tttctgatta    9000
ccatgaggga tctgcacctg ccttgataat gaaccataca ccatgggaca tcctcacata    9060
caaacagagt gggtcaccag aagaaatggt cttgctgcca agacaggctc gactttttgc    9120
ctgggcagat cctactggta ccagaaaact tacatggaca tatgcagcaa atgttgggga    9180
acatgatctg ttaaaggatg gatgtggaca gtttccatat gatgcaaaca tccagataca    9240
ctgggtatca tttctggatg ggcgccagag agttttgctt ttcaccgatg atgttgcctt    9300
ggtttccaaa gcactgcagg cagaagaaat ggaacaggct gattatgaaa taaccttgtc    9360
tctccacagt cttgggcttt cactggttaa caatgaaagc aagcaggaag tttcctatat    9420
tgggataacc agttctggtg ttgtttggga ggtgaaacca aagcagaaat ggaagccatt    9480
```

-continued

```
tagtcaaaag cagataatct tattggaaca atcctatcag aaacatcaaa tatcaagaga   9540
ccatggctgg attaagctag ataataattt tgaggtcaat tttgataaag atccaatgga   9600
aatgcgcctc cctattcgta gccctattaa acgagacttt ttatcaggaa ttcagattga   9660
atttaagcag tcttctcacc agagaagttt aagggccagg ttgtactggc ttcaggttga   9720
taatcagtta ccaggtgcaa tgttccctgt tgtatttcat cctgttgccc ctccaaaatc   9780
tattgcttta gattcagagc ccaagccttt cattgatgtg agtgtcatca caagatttaa   9840
tgagtacagt aaagtcttac agttcaagta ttttatggtc tcattcagg aaatggcctt    9900
aaaaattgat caagggtttc taggagctat tattgcactg tttaccccaa caacagaccc   9960
tgaagctgaa agaagacgga caaagttaat ccaacaagat attgatgctc taaatgcaga  10020
attaatggag acttcaatga ctgatatgtc aattcttagt ttctttgaac atttccatat  10080
ttctcctgtg aagttgcatt tgagtttgtc tttgggttcc ggaggtgaag aatcagacaa  10140
agaaaaacag gaaatgtttg cagttcattc tgtcaacttg ctgttgaaaa gcataggtgc  10200
tactctgact gatgtggatg accttatatt caaacttgct tattatgaaa ttcgatatca  10260
gttctacaag agagatcagc ttatatggag tgttgttagg cattacagtg aacagttctt  10320
gaaacagatg tatgtccttg tattggggtt agatgtactt ggaaacccat ttggattaat  10380
tagaggtctg tctgaaggag ttgaagcttt attctatgaa cccttccagg gtgctgttca  10440
aggccctgaa gaatttgcag aggggttagt gattggagtg agaagcctct ttggacacac  10500
agtaggtggt gcagcaggag ttgtatctcg aatcaccggt tctgttggga aggtttggc    10560
agcaattaca atggacaagg aatatcagca aaaagaaga gaagagttga gtcgacagcc    10620
cagagatttt ggagacagcc tggccagagg aggaaagggc tttctgcgag agttgttgg    10680
tggagtgact ggaataataa caaaacctgt ggaaggtgcc aaaaaggaag gagctgctgg   10740
attcttaaa ggaattggaa aagggcttgt gggtgctgtg gcccgtccaa ctggtggaat    10800
cgtagatatg gccagtagta ccttccaagg cattcagagg gcagcagaat caactgagga   10860
agtatctagc ctccgtcccc ctcgcctgat ccatgaagat ggcatcattc gtccttatga   10920
cagacaggaa tctgagggct ctgacttact tgagcaagaa ctggaaatac aggaataaat   10980
gtttcctaaa ctactacttg atttcatcct taaaaatcaa aacaaactgt ggtgttaatt   11040
gactgtgtgt gaattccatt gtcaatttta atgaaatttt ctttaaaact ctcacctcca   11100
tctgaacttt tcatagtagt gggattgact acaaataaaa acttgtggta ttcctggtaa   11160
tactgtccag aaataagaga ttagtataaa atattaaagg atgcagagaa tcagctctct   11220
tctgcgttta atagatgaaa gcctttattg agctcagaag cagatactgt tactatcatt   11280
tcgaaaattt tatcttatgg tgttcatgtg catttcaggt aaaattgaaa aacaggacaa   11340
ttattatgtc caattaatat gtttatgttt gtgagtcttg atgatggaat tacatagctt   11400
tctgtttcac aaatggctct aaatttgctt aagttacggg actattacct ggagcatctg   11460
ctttaataat tgaattgtca gttgctctga gcctgcctt agacctcaag taataaatag    11520
ttggcacatg aattttgagg atatgttttcc tcttcccctct ttttcctatt taacccttg   11580
gtactgttgc taaataaatg atagccattt tataattatg ttatatacat tttcagcctt   11640
tagcatttct gcttttcaaa aattgaatct ccttgttggt tatgcttatt tcataattat   11700
tagttttaat taatgtagat agaagttgaa catgtaatta ggcaaattgc tgtgtggcac   11760
ttgaatacat agatttcttt attttcaaaa accaacctttt tgcttttaaa tccttagaga   11820
```

```
gggtttatta tcttagagaa aaaataatta taatcattat ttttgaaatt agtatcctct   11880
taattctcaa cataagttat gtttcaattt ctttttttg taataaatga tggaaatgtt    11940
taacaatgtc ttatctagca actttcatgc ttctcctcag aaatgaagcc aaagtataaa   12000
cttagattta atgtgttgta tatttgaaga gaatgaaact attaacatat aattgttcag   12060
ttggattatg tattttaagg attgcagtta tcaaataat aaattgaatg ttttatgttt    12120
aaccacttta aagaagaaag actgacatcc aaaaaccagc gtgtgctaga tatacaaagg   12180
aaattacttc tgtccttaag ggaccaagta taacaaaaca tgtaactgtt aaaagtagct   12240
gacaaacctt tcttgtgcct agataattta gcattggcaa aaatgtcacc acatgcagtt   12300
ttctaggaga gtcaagcaca aataactaat tcaagatgct gacttaaatc atctccaata   12360
gttacccttc ctgagattct aaagtaacaa ttttaatt tactggttat attgctgttt     12420
tactgagact tactttaag aacccctgta acttaagatt ttttcttaat tgttttgttt    12480
agctctgtta ttaattttt ccttgtgata tctttttata actctctgtc aaaaagcaca    12540
aaacttcaag aaacttttaa ttattttgtc tgaacatata atcttgtctg atttcttagt   12600
ttttattaag atatcagaca acttttaaaa ctttagtgca ttattataat tactggaaga   12660
aaaagaatga ttatacacta atgagaggac ttggtagttt ttgtcgtgga tgtcaagtgt   12720
gggcatggat aattgaaata tttaggctat ttcattcttt gcccatcttg ctgtgatcag   12780
ttagttgggt aaaaatattt attgattatt tagactgtac tggatataca aaagaagcct   12840
tctgtcctta agggaccgag taaaacaaaa catggaaata ttaaagagta ttagagtata   12900
aaagtatatc ttttagccc tttgtaatat ggccaaattc taaataattt atttggggat    12960
cttttgatcc tcatgttcct ttttctccta agtactactt tgtattcttt aatatgcagc   13020
tttgagagtt actgaatcat atattatatt tccatgagat gtactattct acttatcctc   13080
taatcttcat atatatatac acacacacat atatatacac atacatatat acacacgtac   13140
atatatgtac acatacagat atacatacac acaaacacat atatacacac atacatatac   13200
acacatatat atacacatac aaatatacac atatatacac atatatatat acacacacat   13260
acaaatatac ccatatgtac acatacatat atacacatac atatatacac acacatatac   13320
acacatatat acgcaaacat acacatattt acacatacat atatacatac attatatgta   13380
tgtatatata gtcatttaat actcattttg gttcacatac ttatgatcat gcaacgttta   13440
aaacagcatt tcttgctttt tagttttagt tatatttttc catgttctta gaaatgcctc   13500
attaacattt ttaattcttg tattgccatc tattgaggtg acattacatt gtgtttttat   13560
ctcgtcttaa ttcatgacat taaattattc tactaacagt aataatgctg taataaacat   13620
cattatagat tttgcttttt tatatcttgt ttgcttttc atatttcctt agaatttact    13680
tgaaaaaatt gaattactgg gtaaagggct tttgcaaagt attgttaaat tcctcgagtt   13740
gcatttttgg aaaggggacg tgaatatttt atcaactaat ttggtctccc tgctgccatt   13800
agtgactgaa tatcttaatc tgaatctcag agtgtagtgg gttttagta gtgctgaaga    13860 caagttttct aaagtgtatt atggtgataa attatatttt aaaaactgtc aatggcttga   13920
agcacaatag cctaataact aacgaaaata catacaagat agaaagtggg tagtatttct   13980
tgtacttgca tttcagatct aaatatttta acatatttaa atttcaagct gcagataaat   14040
gcattacatt attaaattca tttcccattt tctctttgaa gaaattaagg caaaagtgtt   14100 aaagatttt aactaattcg cacaagtgaa ttgtgaaaca gtagctatt gctgtgaaat     14160 ctgcactcct ctctgagact cattctgaag atgagatccc agttctttgt ggattcctct   14220
```

```
tccttattca tggcttttg caattgtcaa ggaatgacta ggtaccaagc aactttaaaa    14280
aatgtatatt taagcattga aataatatca aatgtgattt ctctgcttgt ggttatattg    14340
attatattat cctttaata atattggcat tatattcttg gtcgtaaaat gtcaaggtct    14400
tatttattca gtatatttat gttctgtatt ttcatatata ttatctattt tcagccatgc    14460
attatatata atgtcagtaa tagtatttca ttagcattca ttataaaaaa actcgttttt    14520
aatatttgac taattcaagt cacagtactt ttgagatagc tgaaaaggaa aataaatgtg    14580
ttttaatgtg ctactaaaaa aaaaaaa                                        14607
```

<210> SEQ ID NO 49
<211> LENGTH: 14329
<212> TYPE: DNA
<213> ORGANISM: Homo sapiens

<400> SEQUENCE: 49

```
gcggccgcag aatcgagctc gggccccggc cccggcccg cggcgcgggg ctcccgggcc       60
ccgccgcgga cgtcgcgccg gtcgcccctt ccccgtagcc cgtgcgccct cggcgcggag     120
ccccggcccg ccgcggtccc gtctcctggg cctgtcccgc ccgcgccctc cgccggccct     180
caggtataat acttctccac gtctgcttca ggaagaaagt gcctgccatt cttatcattt     240
ctaagcaggt tcatgccagc ccagaacaga gaatcagctg gagcccagat ttcaagtttt     300
gagtaaaata ccttcaagcg aatgggccct attgtgctca cacattcaga acctgttacc     360
caaggaattc cctaaagaat tagaagtgcg tctcaccaac cagccaagat gaacatggtg     420
aagaggatca tggggcggcc gaggcaggag gagtgcagcc cacaagacaa cgccttagga     480
ctgatgcacc tccgccggct cttcacggag ttgtgccatc ctccccggca catgactcag     540
aaggaacaag aagagaaact gtatatgatg ctgccagtgt ttaacagggt ttttggaaat     600
gctccgccga atacaatgac agaaaaattt tctgatcttc tgcagttcac aacacaagtc     660
tcacgactaa tggtgacaga aattcgaagg agagcatcaa acaaatccac agaggctgca     720
agtcgggcca tagttcagtt cctagagatt aatcagagtg aagaagccag tagaggctgg     780
atgcttctaa cgacaattaa tttgttagct tcctctggtc agaaaaccgt ggactgcatg     840
acaacaatgt cagtgccttc caccctggtt aaatgtttat atctgttttt tgaccttcca     900
catgtgcctg aggcagttgg aggtgcacag aatgagctac tctagcaga acgtcgagga     960 ctactccaga agttttttgt acagatctta gtgaaactgt gcagttttgt ttcccctgcg    1020
gaggagctgg ctcagaaaga tgatctccag cttctattca gtgcaataac ctcttggtgc    1080
cctccctata acctgccttg gagaaagagt gctggagaag tcctcatgac catatctcgt    1140
catggtctta gtgtcaatgt agtgaagtat attcatgaga aagagtgttt atctacatgt    1200
gttcagaata tgcagcaatc agatgacctg tctcccctag aaattgtcga aatgtttgct    1260
gggctttctt gttcctcaa agattccagc gatgtttccc aaacacttct ggatgatttt    1320
cggatatggc aaggatataa ttttctttgt gatctcttgc ttagattgga acaagcaaaa    1380
gaggcagaat ccaaagatgc cttgaaagat ctggttaatc tgataacttc cctaacaaca    1440
tatggtgtca gtgaactaaa accagctggt attaccacag gggcaccctt tttattgcct    1500
ggatttgcag tacctcagcc tgcaggcaaa ggtcacagtg tgagaaacgt ccaggccttt    1560
gcagttcttc agaatgcatt tttaaaagca aaaaccagct tccttgccca aatcatcctt    1620
gatgctatca caaatattta catggctgac aatgccaatt acttcatcct agagtcacag    1680
```

-continued

```
cacacattgt cacagtttgc agagaagatt tctaaactcc cagaagtaca aaacaaatac   1740
tttgagatgc tggagtttgt tgttttagc ttaaattata taccttgtaa agaacttatt    1800
agtgtcagta tcctcttaaa atctagctct tcttatcact gtagcattat tgcaatgaaa   1860
acacttctta agtttacaag acatgactac atatttaaag acgtgttcag ggaggttggc   1920
cttttggagg tcatggtaaa ccttttgcat aaatatgctg ccctgttgaa ggatccaact   1980
caggcactaa atgaacaagg ggactcaaga aataatagtt cagttgaaga ccaaaaacac   2040
ctggctttat tggttatgga gaccttgaca gtgcttcttc aaggatcaaa cacaaatgca   2100
ggaattttc gagaatttgg aggtgcaaga tgtgcacata atatagtaaa gtaccctcaa    2160
tgccggcagc atgccttgat gactatccaa cagctggtgc tctccccaaa tggggacgat   2220
gacatgggca ctctcctggg gctaatgcat tcagccccac cgacggaatt gcagttgaag   2280
actgatattt aagggcccct cctgtcggtc cttcgagaaa gccatcgttc aagaacagtt   2340
tttaggaaag ttggaggatt tgtgtacatt acatccttgc tcgttgctat ggaaagatct   2400
ttgagctgtc cacccaagaa tggctgggag aaagtgaacc agaatcaagt gtttgaactt   2460
cttcacactg tgttctgcac gttgactgca gcaatgcgct atgagccagc caactctcat   2520
ttcttcaaaa cagagattca gtatgagaag ttggcagatg ctgttcgatt tcttggctgc   2580
ttctcagacc taagaaaaat aagcgccatg aatgtcttcc cctcaaatac acagccattt   2640
caaagacttt tagaggaaga tgtaatctca atagaatcag tgtcacccac gttacggcac   2700
tgcagtaaac tttttattta tctttacaaa gtagccacag attctttga cagtcgtgca    2760
gaacagatcc ctccttgcct gacaagtgag tcttctctcc cctctccttg gggtacacca   2820
gctttgtcca ggaaaaggca tgcatatcat tctgtttcaa ctcccctgt ttaccctcct    2880
aaaaatgttg ccgacctgaa actacatgtg acaacttcat ctctgcagag ttctgatgca   2940
gtcatcattc atcctggagc catgcttgcc atgctggacc tactggcctc tgttgggtca   3000
gtgacacagc cagaacatgc tttggatctt caacttgccg tggcaaatat tttacaatcc   3060
ctggtgcaca cagaaaggaa ccagcaagtc atgtgtgaag ctggtcttca tgcacgactg   3120
ctgcagaggt gcagtgctgc attggctgat gaggaccact cactgcaccc gccctgcag    3180
cggatgtttg aacgattagc ctctcaggct ctggaaccca tggtgttgag ggagttttta   3240
cgttggcaa gtccttttaa ttgtggtgcc tgggacaaaa aactgctaaa acaatatagg    3300
gtccacaaac caagttcact gagttatgaa ccagaaatga gaagtagtat gatcacatct   3360
ctggaaggtc tgggtactga taatgttttt agcttacatg aagataacca ttaccggata   3420
agcaagagcc tggtaaaatc tgcggaagga agtactgtac ccctgaccag ggtgaagtgt   3480
ctggtctcca tgacaacccc acatgacatc agacttcatg ggtcatcagt tactccagct   3540
tttgttgaat ttgacacatc acttgaaggg tttggatgtc ttttttttgcc cagtttggcc   3600
cctcataatg ctcctacaaa taataccgtc acaacaggtc ttattgatgg ggctgtggtc   3660
agtggcattg gttctggtga aagattcttc cctcctccct ccggcttaag ttactctagc   3720
tggttttgta ttgaacattt tagttctcct ccaaataacc accctgtcag acttcttact   3780
gttgtgcgcc gagcaaattc ttctgagcaa cattacgtgt gccttgcaat agttctatca   3840
gcaaaagacc gatctctgat tgttccacc aaagaggaac tcctccaaaa ttatgttgat    3900
gattttagtg aagagtcctc atttatgaa attctcccat gctgtgctcg ctttcgatgt    3960
ggagagctta tcattgaggg acagtggcat catttggtcc tggtaatgag caaaggcatg   4020
ttgaaaaaca gtactgcagc ccttttatatt gatggacagc ttgttaacac tgtaaagctt   4080
```

```
cattatgtcc acagtactcc aggggggttca ggttcggcaa atccaccagt ggtgagcacg   4140
gtctatgcct acattggtac tccacctgcc aacgccaaa ttgcctcatt ggtttggcgc    4200
ctgggaccca cacattttct agaagaagtt ttaccttctt caaatgttac taccatttat   4260
gaacttggac caaattatgt tggaagcttt caggctgtat gtatgccatg taaagatgca   4320
aaatccgaag gggtggtgcc atcccctgtg tcattagtac cagaggagaa agtgtcattt   4380
ggcctctatg cactctctgt gtcgtctcta acagtggcaa gaatccggaa agtgtataac   4440
aaattggata gcaaagccat tgctaagcag ttaggcattt cctcacatga gaatgccact   4500
cctgtgaagt tgatacacaa ttcagcagga catcttaatg gatctgcacg gacaattggg   4560
gccgctctga ttggatactt gggagtaaga acatttgtcc ctaagcctgt tgccactact   4620
ttgcagtacg ttggtggagc tgcagccatc ctgggcctgg tggccatggc ctctgatgtg   4680
gaagggttat atgcagcagt caaggccctg gtttgtgtgg tcaagagtaa cccactagcc   4740
agcaaagaaa tggaaagaat caagggctac cagttgctgg caatgttgct taagaagaaa   4800
cgttcccttc ttaacagcca catcctccat ctaactttt ctttggtggg aactgttgat    4860
agtggacatg agacctccat tattccaaat tcaactgctt tccaggacct cctctgtgat   4920
tttgaagtct ggctccatgc accatatgaa cttcatcttt ccttatttga cactttatt    4980 gaactgctca cagagtccag tgaagcctca aagaatgcca aattaatgag agaattccag   5040
ttaatcccaa agctgctcct gactcttcga gatatgtctt tatcccagcc tactattgct   5100
gctattagta atgtcctgag cttcttactg caaggttttc ctagcagcaa tgatctgctc   5160
agatttgggc agtttatttc ttctactttg ccaacctttg cggtttgtga gaaatttgta   5220 gtaatgggaaa taaataatga agagaagctt gacactggaa ctgaagagga gtttggaggt   5280
cttgtatcag ctaatcttat acttttgagg aacagacttc tggatatctt gctaaaacta   5340
atttatacat ctaaagaaaa gacaagcatt aatttgcaag cttgtgaaga actggtgaag   5400
acactgggtt ttgactggat catgatgttt atggaggaac acttacattc caccacagtt   5460
acagcagcca tgaggattct tgttgtccta ctaagtaatc agtctattct catcaagttt   5520
aaagaaggac tcagtggtgg aggatggctt gaacagacag attctgtctt aactaataag   5580
attggaactg tattaggatt caacgtgggc agaagtgctg gtgggagatc gacggtcagg   5640
gagattaacc gagatgcttg tcattttcct ggttttccag tccttcagtc attccttcct   5700
aaacacacta atgtccctgc cctctatttt ctcctcatgg ccttgtttct gcagcagcca   5760
gttagtgagc tgcctgagaa cctgcaggtc agtgtgcctg tcatcagctg ccggagtaag   5820
cagggttgcc agtttgattt ggattccatt tggacattca tctttggagt tcctgcctcc   5880
agcggaactg tggtctcttc tatccataac gtatgcacga aagctgtttt tttattattg   5940
ggaatgctcc gcagcatgct gacttcacct tggcaatcag aagaagaggg atcttggctc   6000
cgagaatatc ctgtgaccct gatgcagttc ttcagatatt tgtatcacaa cgtgccagac   6060
cttgcctcca tgtggatgag ccctgacttc ctgtgtgcat tagcagccac cgtcttcccc   6120
ttcaatattc gcccttactc agagatggtg actgaccttg atgatgaagt tggatctcca   6180
gcagaagagt ttaaagcgtt tgcagcagac acagggatga acaggagcca atcagagtac   6240
tgcaatgtgg gcaccaagac atatctgacc aatcacccgg ctaaaaagtt cgttttgac    6300 ttcatgcggg tcttaatcat agacaacctc tgtctcactc ctgccagcaa gcaaactcca   6360
ctaattgatc ttttgttgga ggcttcccct gaaaggtcta caagaactca gcaaaaagaa   6420
```

```
tttcaaactt acattttgga tagcgtgatg gaccatttgc ttgcagctga tgtgttatta    6480
ggggaagatg catctctgcc tattaccagt ggaggaagct accaggtatt ggtgaacaat    6540
gtgttttatt tcacacagcg tgtggtggac aagctttggc aaggcatgtt caacaaagaa    6600
tctaaacttc ttatagattt tataattcaa ctaattgcac agtcaaagag aagatcacag    6660
ggattgtcac tggatgcagt gtatcattgc ctcaatagga ccatcttgta ccagttctca    6720
cgggcacaca aaaccgttcc tcagcaagta gctctgcttg attcactcag gtcctcact     6780 gtaaacagaa acttgatcct gggacctggg aaccatgacc aagaattcat tagctgtctg    6840
gcccactgct tgataaatct acatgttgga agcaacgtgg atggatttgg actggaagca    6900
gaagcccgca tgaccacatg gcacattatg atcccctcgg acattgaacc agatggtagt    6960
tacagccaag atattagtga agggcgtcag cttctcataa aagctgtcaa cagagttttgg   7020 actgaactga tacatagtaa gaaacaagtc ttagaggaac ttttcaaagt aactctacct    7080
gtgaatgaaa ggggccacgt ggacatagct acagcaaggc cactcattga agaagctgcc    7140
ctgaagtgct ggcagaatca tttggcccat gaaaagaaat gcataagtcg aggagaagct    7200
ttagcgccca ccacacagtc caaattatcc cgtgtcagca gtggctttgg tctttccaag    7260
ttaacaggat caagaaggaa tcgaaaagaa agtggtctta ataaacacag tcttccacc    7320 caggagattt cgcagtggat gtttactcac attgctgttg ttcgtgactt agtagataca    7380
caatataaag aatatcagga gcgtcagcag aatgccctga gtacgtgac agaagagtgg    7440 tgtcagatcg agtgcgagct gttgagggag cggggggctgt ggggccctcc catcggctcc    7500
cacctcgaca gtggatgct ggagatgaca aagggccct gcaggatgag gaaaaagatg      7560
gtgcgaaatg atatgtttta taaccattac ccttacgtgc cagaaactga gcaagagaca    7620
aatgtggcgt ctgagatccc aagtaaacag cctgagacac ccgatgatat tcctcaaaag    7680
aaacctgctc gatatagaag agccgtaagt tatgacagta aagagtacta catgcgactg    7740
gcctctggca atcccgccat tgtccaagac gccattgtgg agagttcaga aggtgaagct    7800
gctcagcaag aaccagagca tgggggaagac actattgcta aagtcaaagg tttggtcaag    7860
cctcctctaa aacgctcccg atctgcacct gatggaggag atgaggagaa ccaggagcag    7920
ctacaagacc agattgctga gggcagctcc atagaagagg aggagaaaac agataatgct    7980
accttactgc gcctgttaga ggaaggagaa aagatccaac acatgtaccg ctgtgctcga    8040
gtccagggcc tagataccag tgaggggctc cttctttttg gtaaagagca tttttatgtg    8100
attgatggat ttaccatgac agcaaccagg gaaataagag atattgaaac cttacctcca    8160
aatatgcatg agcctattat tcctagagga gccaggcaag gccctagtca actcaagaga    8220
acatgcagca tttttgcata tgaagatatc aaggaagttc ataaaaggag atatctcctg    8280
cagcctattg ctgtggaagt tttctctgga gatggacgga attacctcct tgcttttcag    8340
aaaggaatca gaaacaaagt ctatcaaagg tttttggctg tagtgccatc tctaacggac    8400
agttcagaat ctgtatctgg gcaacgacca aaacgagtg tggagcaggg atctgggtta    8460
cttagcactt tggttggaga gaagtctgtg actcagagat gggagagagg tgaaatcagc    8520
aacttccaat atttgatgca tttgaacact ttggctggca gatcatataa tgatctcatg    8580
cagtatcctg tcttcccctg gatccttgca gattatgact cagaggaggt ggatcttact    8640
aatcccaaga cgtttagaaa cctggctaag ccaatgggag cacaaacaga tgaacgatta    8700
gctcagtata agaagcggta taagactgg gaggatccta atggagaaac tcctgcatac     8760
cactatggga cccactattc atctgcaatg attgtggcct cataccttgt aaggatggag    8820
```

```
cctttcacac agatattctt aaggctacag ggtggccact ttgacctggc tgaccggatg    8880
tttcacagtg tgcgcgaggc ctggtattca gcgtcaaagc acaatatggc agatgtaaaa    8940
gaacttatcc cagagttctt ttatttacca gaattcctgt tcaattccaa caactttgat    9000
ctaggctgta aacaaaatgg caccaagctt ggagatgtta tccttccacc ctgggcaaaa    9060
ggggacccac gagaattcat cagagtccat cgtgaggctt tggagtgtga ttacgtgagt    9120
gcccatctac atgagtggat tgacttaatc ttcggttata aacagcaagg ccctgctgca    9180
gtagaagctg taaatgtctt ccatcatctt ttttatgagg gtcaagtgga tatctacaac    9240
atcaatgacc cactaaagga gacagccaca attgggttca ttaataactt cggtcagatc    9300
cctaaacagt tatttaaaaa acctcatcca ccaaagcgag tgagaagtcg actcaatgga    9360
gacaatgcag gaatctctgt cctaccagga tctacaagtg acaagatctt ttttcatcat    9420
ctagacaact tgaggccttc tctaacacct gtaaagaac  tcaaagaacc tgtaggacaa    9480
atcgtatgta cagataaagg tattcttgcg gtggaacaga ataaggttct tatcccacca    9540
acctggaata aaacttttgc ttggggctat gcagacctca gttgcagact gggaacctat    9600
gagtcagaca aggccatgac tgtttatgaa tgcttgtctg agtggggcca gattctctgt    9660
gcaatctgcc ccaaccccaa gctggtcatc acgggtggaa caagcacggt tgtgtgtgtg    9720
tgggagatgg gcacctccaa agaaaaggcc aagaccgtca ccctcaaaca ggccttactg    9780
ggccacactg ataccgtcac ctgcgccaca gcatcattag cctatcacat aattgtcagt    9840
gggtcccgtg atcgaacctg tatcatttgg gatttgaaca aactgtcatt tctaacccag    9900
cttcgagggc atcgagctcc agtttctgct ctttgtatca atgaattaac aggggacatt    9960
gtgtcctgcg ctggcacata tatccatgtg tggagcatca atgggaaccc tatcgtgagt   10020
gtcaacacgt tcacaggtag gagccagcag atcatctgct gctgcatgtc ggagatgaac   10080
gaatgggaca cgcagaacgt catagtgaca ggacactcag atggagtggt tcggttttgg   10140
agaatggaat ttttgcaagt tcctgaaaca ccagctcctg agcctgctga agtcctagaa   10200
atgcaggaag actgtccaga agcacaaata gggcaggaag cccaagacga ggacagcagt   10260
gattcagaag cagatgagca gagcatcagc caggacccta aggacactcc aagccaaccc   10320
agcagcacca gccacaggcc ccgggcagcc tcctgccgcg caacagccgc ctggtgtact   10380
gacagtggct ctgacgactc cagacgctgg tccgaccagc tcagtctaga tgagaaagac   10440
ggcttcatat ttgtgaacta ttcagagggc cagaccagag cccatctgca gggccccctt   10500
agccaccccc accccaatcc cattgaggtg cggaattaca gcagattgaa acctgggtac   10560
cgatgggaac ggcagctggt gttcaggagt aagctgacta tgcacacagc ctttgatcga   10620
aaggacaatg cacacccagc tgaggtcact gccttggcca tctccaagga tcacagtagg   10680
atcctcgttg gtgacagtcg aggccgagtt ttcagctggt ctgtgagtga ccagccaggc   10740
cgttctgctg ctgatcactg ggtgaaggat gaaggtggtg acagctgctc aggctgctcg   10800
gtgaggtttt cactcacaga aagacgacac cattgcagga actgtggtca gctcttctgc   10860
cagaagtgca gtcgctttca atctgaaatc aaacgcttga aaatctcatc cccggtgcgt   10920
gtttgtcaga actgttatta taacttacag catgagagag ttcagaaga tgggcctcga   10980
aattgttgaa gattcaacaa gctgagtgga gaccatggtc tgtagacccc ttcccgattc   11040
tcctgtccca gcttggaagg cattgaaaac agtctccgtt tacacatctc ttcataccac   11100
gtgtttgaag tgttaaaatt caaagggatc attgaataaa acgggtgtag agtacaggaa   11160
```

-continued

```
tggggcagac gcgattcagg tgaacagcac aagaagaata tgaggtggtt cctaggagca    11220
acactttcga cctccagttc tccctgatga cagtagctgt ctccaagaga aaaatcctca    11280
cttattaact ctcttttctt gcatctcatt tttatagagc tactcatcct tatttggaaa    11340
aaccaacaac aaaaaaggct tttagaaaat ggttgtaaat ctgacttctt tgcaagtaac    11400
tatgtatatt gtaaatagat ataaaaggcc ttttttctaa ataaggactt aactgcctgt    11460
aacatgaaac ttcaaactaa accactaact caatgaacta cttatggttt gtctgacatc    11520
cctcacttac caattaatta taaatatgtt tttttaaatc cccaaagaca ttatctgtgg    11580 tcttttttc ctttcaagct cagcctgtgt gcctgatgtc atttcttca agttgcccac    11640 agtatctcca cttaaactag gctagtaacc aaaataatgt ggaccttctt taggaaacag    11700
tgtgggagaa taggagtcca gccgtaagat aaactggaaa tatttgggcg tcttgtacct    11760
ggctacgcac cacctcagtg ttgttcctac ataaacaggg cccctttta acttgtatgt    11820 ggactgctgt ttggtcaaag ataccttct tagcattgca gaaaggtggt cagatgacca    11880
gtgtagtgca ggaaacagcc ctgtctcaac taatggaaat atatttgcat gtaacccaaa    11940
attagcttat cttgcatga acataataag tatgtgtctt tggtgacact aatgttctac    12000
tatagcttat tttcaaacaa ggggtaaaaa aaggaaagaa agaagtgtac agaattaaca    12060
tataactttt gttgtaaaac tgaatcatgt cagaactgct taaaattaac ctttaccatt    12120
taatgtcatc tacctgaaaa cagtgagatt tatactgtat caatgtctat ttttttgttt    12180
ttgctatgaa tataattaca gtatttttaat atttagttat ttaattttgtt ctactagttg    12240 gatacagaac acacaaatcc aggggattta aagctggaag gggctaagag attagtttac    12300
agagaaaagg cttggtggtg ggattttttt aaatgtgtgt tatgtacata tatatatata    12360
tataatatat attaaaaatg aaacaattaa tctagatttt aacatttttca gaaacttagt    12420 gataacatta tgaacaattc taaaagccct gtgatttgaa aaatatagaa tcattaatgg    12480
cccaagatag gccttcacac cttcacaggt gcgaaaggaa aggccttcac accctcacag    12540
aggcatcatg caaaggacag cggctttggc ttttccaatt ttccatcttt aggccctggt    12600
gagaggcaca cttatgcact aaaatgcaca tatatgcaca tgcattcaaa ataggcatt    12660 tggtacaatg gtgatcttgt acctgatggg ctgaaaccag cttaagaaca aatttgttct    12720
tcctgatatg ataactaggt ctccaagaga aaatagaaag gctgctttag tgccttacgc    12780
ttactaaatt taaatcttta tttacctggg tttgagccta cagtctattt atgattacat    12840
atcaaaattg attaaaacac ttccatttct aaaagttcaa atatacttgt taataaaagg    12900
attatcggca ttaatacttt aatttaaaga aaagttgtgt tctgtttttcc tttctgtgtc    12960 ttactccccc cacactctcc ctcccccatc accatcttca attctaataa ataatgctga    13020
tgttcaacag ttgcagaaat tgtgctatta tgtaactgtg ggccttgccc ctgtctggcc    13080
ctctagatga tttgtagcag tgttattcta cactttttaa aagaagcgtc ctcctttgt    13140 ccatgaatca tgtttacccc atacccagtg gcagaggtgt tctttaaaga cttgaatata    13200
tgaatgtgtg tgtgtagtta cttaaaggtt attcctcttt gtaataggaa actatatggg    13260
atgaacactt ttaaactttc cgacacaact tccattacta actttctaac agaacttcca    13320
taactagaag gtggaaacca aaaccctcat ggtagtattt cctctggcag ctggtgctgt    13380
gggcaactgt tttgttcaat cgggtttctt ttcttttgc ctctaatgca gaaatcaaca    13440
gaatcactca cacatacaag tacactcaca tacataaact aattatttct ctggatatct    13500
ttctgtgttc catgtaaatt tatttaccaa catctattgt caacatgtac atctacctta    13560
```

```
gtatggtctg cattcttttt ctgagagtac ctcatagggc tcctgcctga tctttgtagt   13620
ttgttcattc atccatccac ctgttcattt gttcatccat gtattctaac atttctatgt   13680
agtgtgcaac tctaatgtca tgcttttgaa gaagagaata gctgcccata gcagccatcc   13740
gtctggataa tagcaaaaca ctctagataa gttattttgc actttcttat gtataaagtt   13800
ggtagaaact tattttttgct ttgtatcatt taaatacatt ttgttttggt aaatgaactg   13860
tgtataaaat atttatgccg ttaaaactgt ttttagaaag tatttttaat ttcagcaagt   13920
ttggttactt gttgcatgac tcttaacaca gctgactttt tgtgtcagtg caatgtatat   13980 ttttttgtcct gttattaact tgtaagccct agtaatggcc aattatttgt acagcaacag   14040
aagtaaattg aagatactgg ctaagactgg attgattgtg gactttata ctatattgca   14100 gaaaccaata tctgtttctt ggtggttatg taaaagacct gaagaattac tatctagtgt   14160
gcagtctgtg atatctgaat gttcattgta tatttgtctc tgatgcaaaa aggtagagta   14220
acacaattac aatacatgat taaatgcaat agtccaggta cttaagtaat ttttttttca   14280
tttcaaataa atacctattt accaccaaaa gaaagaaaaa aaaaaaaaa              14329
```

<210> SEQ ID NO 50
<211> LENGTH: 12778
<212> TYPE: DNA
<213> ORGANISM: Homo sapiens

<400> SEQUENCE: 50

```
cgcggcccga gcgcctcttt tcgggattaa aagcgccgcc agctcccgcc gccgccgccg     60
tcgccagcag cgccgctgca gccgccgccg ccggagaagc aaccgctggg cggtgagatc    120
cccctagaca tgcggctcgg gggcgggcag ctggtgtcag aggagctgat gaacctgggc    180
gagagcttca tccagaccaa cgaccgtcg ctgaagctct tccagtgcgc cgtctgcaac    240
aagttcacga cggacaacct ggacatgctg ggcctgcaca tgaacgtgga gcgcagcctg    300
tcggaggacg agtggaaggc ggtgatgggg gactcatacc agtgcaagct ctgccgctac    360
aacacccagc tcaaggccaa cttccagctg cactgcaaga cagacaagca cgtgcagaag    420
taccagctgg tggcccacat caaggagggc ggcaaggcca acgagtggag gctcaagtgt    480
gtggccatcg gcaaccccgt gcacctcaag tgcaacgcct gtgactacta caccaacagc    540
ctggagaagc tgcggctgca cacggtcaac tccaggcacg aggccagcct gaagttgtac    600
aagcacctgc agcagcatga gagtggtgta gaaggtgaga gctgctacta ccactgcgtt    660
ctgtgcaact actccaccaa ggccaagctc aacctcatcc agcatgtgcg ctccatgaag    720
caccagcgaa gcgagagcct gcgaaagctg cagcggctgc agaagggcct tccagaggag    780
gacgaggacc tgggcagat cttcaccatc cgcaggtgcc cctccacgga cccagaagaa    840
gccattgaag atgttgaagg acccagtgaa acagctgctg atccagagga gcttgctaag    900
gaccaagagg gcggagcatc gtccagccaa gcagagaagg agctgacaga ttctcctgca    960
acctccaaac gcatctcctt cccaggtagc tcagagtctc ccctctcttc gaagcgacca   1020
aaaacagctg aggagatcaa accggagcag atgtaccagt gtccctactg caagtacagt   1080
aatgccgatg tcaaccggct ccgggtgcat gccatgacga gcactcggt gcaacccatg   1140 cttcgctgcc ccctgtgcca ggacatgctc aacaacaaga tccacctcca gctgcacctc   1200
acccacctcc acagcgtggc acctgactgc gtggagaagc tcattatgac ggtgaccacc   1260 cctgagatggg tgatgccaag cagcatgttc ctcccagcag ctgttccaga tcgagatggg   1320
```

```
aattccaatt tggaagaggc aggaaagcag cctgaaacct cagaggatct gggaagaac    1380 atcttgccat ccgcaagcac agagcaaagc ggagatttga aaccatcccc tgctgaccca    1440
ggctctgtga gagaagactc aggcttcatc tgctggaaga aggggtgcaa ccaggttttc    1500
aaaacttctg ctgcccttca gacgcatttt aatgaagtgc atgccaagag gcctcagctg    1560
ccggtgtcag atcgccatgt gtacaagtac cgctgtaatc agtgtagcct ggccttcaag    1620
accattgaaa agttgcagct ccattctcag taccatgtga tcagagctgc caccatgtgc    1680
tgtctttgtc agcgcagttt ccgaactttc caggctctga gaagcacct tgagacaagc    1740 cacctggagc tgagtgaggc tgacatccaa cagctttatg gtggcctgct ggccaatggg    1800
gacctcctgg caatgggaga ccccactctg gcagaggacc ataccataat tgttgaggaa    1860
gacaaggagg aagagagtga cttggaagat aaacagagcc caacgggcag tgactctggg    1920
tcagtacaag aagactcggg ctcagagcca aagagagctc tgcctttcag aaaaggtccc    1980 aatttttacta tggaaaagtt cctagaccct tctcgccctt acaagtgtac cgtctgcaag    2040
gaatctttca ctcaaaagaa tatcctgcta gtacactaca attctgtctc ccacctgcat    2100
aagttaaaga gagcccttca agaatcagca accggtcagc cagaacccac cagcagccca    2160
gacaacaaac cttttaagtg taacacttgt aatgtggcct acagccagag ttccactctg    2220
gagatccata tgaggtctgt gttacatcaa accaaggccc gggcagccaa gctggaggct    2280
gcaagtggca gcagcaatgg gactgggaac agcagcagta tttccttgag ctcctccacg    2340
ccaagtcctg tgagcaccag tggcagtaac acctttacca cctccaatcc aagcagtgct    2400
ggcattgctc caagctctaa cttactaagc caagtgccca ctgagagtgt agggatgcca    2460
cccctgggga atcctattgg tgccaacatt gcttcccctt cagagcccaa agaggccaat    2520
cggaagaaac tggcagatat gattgcatcc aggcagcagc aacaacagca gcagcaacag    2580
caacaacaac aacaacaaca acaacaacaa gcacaaacgc tggcccaggc ccaggctcaa    2640
gttcaagctc acctgcagca ggagctgcag caacaggctg ccctgatcca gtctcagctg    2700 tttaaccca ccctccttcc tcacttcccc atgacaactg agaccctgct gcaactacag    2760
cagcagcagc acctcctctt ccctttctac atccccagtg ctgagttcca gcttaaccccc    2820 gaggtgagct tgccagtgac cagtggggca ctgacactga ctgggacagg cccaggcctg    2880
ctggaagatc tgaaggctca ggttcaggtc ccacagcaga gccatcagca gatcttgccg    2940
cagcagcagc agaaccaact ctctatagcc cagagtcact ctgccctcct tcagccaagc    3000
cagcaccccg aaaagaagaa caaattggtc atcaaagaaa aggaaaaaga aagccagaga    3060
gagagggaca gcgccgaggg gggagagggc aacaccggtc cgaaggaaac actgccagat    3120
gccttgaagg ccaaagagaa gaaagagttg caccagggg gtggttctga gccttccatg    3180
ctccctccac gcattgcttc agatgccaga gggaacgcca ccaaggccct gctggagaac    3240
tttggctttg agttggtcat ccagtataat gagaacaagc agaaggtgca gaaaaagaat    3300
gggaagactg accagggaga gaacctggaa aagctcgagt gtgactcctg cggcaagttg    3360
ttttccaaca tcttgatttt aaagagtcat caagagcacg ttcatcagaa ttacttttcct    3420 ttcaaacagc tcgagaggtt tgccaaacag tacagagacc actacgataa actgtaccca    3480
ctgaggcccc agacccaga gccaccacca cctcccccctc cacccccctcc acccccactt    3540 ccggcagcgc cgcctcagcc ggcgtccaca ccagccatcc ccgcatcagc cccacccatc    3600
acctcaccta caattgcacc ggcccagcca tcagtgccgc tcacccagct ctccatgccg    3660
atggagctgc ccatcttctc gccgctgatg atgcagacga tgccgctgca gaccttgccg    3720
```

```
gctcagctac ccccgcagct gggacctgtg gagcctctgc ctgcggacct ggcccaactc    3780
taccagcatc agctcaatcc aaccctgctc cagcagcaga acaagaggcc tcgcaccagg    3840
atcacagatg atcagctccg agtcttgcgg caatattttg acattaacaa ctcccccagt    3900
gaagagcaaa taaagagat ggcagacaag tccggttgc cccagaaagt gatcaagcac      3960
tggttcagga acactctctt caaagagagg cagcgtaaca aggactcccc ttacaacttc    4020
agtaatcctc ctatcaccag cctggaggag ctcaagattg actcccggcc ccttcgccg    4080
gaacctccaa agcaggagta ctggggaagc aagaggtctt caagaacaag gtttacggac    4140
taccagctga gggtcttaca ggacttcttc gatgccaatg cttacccaaa ggatgatgaa    4200
tttgagcaac tctctaattt actgaaccctt ccaacccgag tgatagtggt gtggtttcag    4260
aatgcccgac agaaggccag gaagaattat gagaatcagg gagagggcaa agatggagag    4320
cggcgtgagc ttacaaatga tagatacatt cgaacaagca acttgaacta ccagtgcaaa    4380
aaatgtagcc tggtgtttca gcgcatcttt gatctcatca agcaccagaa gaagctgtgt    4440
tacaaggatg aggatgagga ggggcaggac gacagccaaa atgaggattc catggatgcc    4500
atggaaatcc tgacgcctac cagctcatcc tgcagtaccc cgatgccctc acaggcttac    4560
agcgccccag caccatcagc caataataca gcttcctccg ctttcttgca gcttacagcg    4620
gaggctgagg aactggccac cttcaattca aaaacagagg caggcgatga gaaaccaaag    4680
ctggcggaag ctcccagtgc acagccaaac caaacccaag aaaagcaagg acaaccaaag    4740
ccagagctgc agcagcaaga gcagcccgag cagaagacca cactccccca gcagaagctc    4800
ccccagctgg tgtccctgcc ttcgttgcca cagcctcctc cacaagcgcc ccctccacag    4860
tgccccttac cccagtcgag ccccagtcct tcccagctct cccacctgcc cctcaagccc    4920
ctccacacat caactcctca acagctcgca aacctaccctc ctcagctaat cccctaccag    4980
tgtgaccagt gtaagttggc atttccgtca tttgagcact ggcaggagca tcagcagctc    5040
cacttcctga gcgcgcagaa ccagttcatc cacccccagt ttttggacag gtccctggat    5100
atgcctttca tgctctttga tcccagtaac ccactcctgg ccagccagct gctctctggg    5160
gccatacctc agattccagc aagctcagcc acttctcctt caactccaac ctccacaatg    5220
aacactctca agaggaagct ggaggaaaag gccagtgcaa gccctggcga aaacgacagt    5280
gggacaggag gagaagagcc tcagagagac aagcgtttga gaacaaccat cacaccggaa    5340
caactagaaa ttctctacca gaagtatcta ctggattcca atccgactcg aaagatgttg    5400
gatcacattg cacacgaggt gggcttgaag aaacgtgtgg tacaagtctg gtttcagaac    5460
acccgagctc gggaaaggaa aggacagttc cgggctgtag cccagcgca ggcccacagg    5520
agatgccctt tttgcagagc gctcttcaaa gccaagactg ctcttgaggc tcatatccgg    5580
tcccgtcact ggcatgaagc caagagagct ggctacaacc taactctgtc tgcgatgctc    5640
ttagactgtg atgggggact ccagatgaaa ggagatattt ttgacggaac tagcttttcc    5700
cacctacccc caagcagtag tgatggtcag ggtgtccccc tctcacctgt gagtaaaacc    5760
atggaattgt cacccagaac tcttctaagc ccttcctcca ttaaggtgga agggattgaa    5820
gactttgaaa gcccctccat gtcctcagtt aatctaaact ttgaccaaac taagctggac    5880
aacgatgact gttcctctgt caacacagca atcacagata ccacaactgg agacgagggc    5940
aacgcagata acgacagtgc aacgggaata gcaactgaaa ccaaatcctc ttctgcaccc    6000
aacgaagggt tgaccaaagc ggccatgatg gcaatgtctg agtatgaaga tcggttgtca    6060
```

```
tctggtctgg tcagcccggc cccgagcttt tatagcaagg aatatgacaa tgaaggtaca    6120
gtggactaca gtgaaacctc aagccttgca gatccctgct ccccgagtcc tggtgcgagt    6180
ggatctgcag gcaaatctgg tgacagcgga gatcggcctg ggcagaaacg ttttcgcact    6240
caaatgacca atctgcagct gaaggtcctc aagtcatgct ttaatgacta caggacaccc    6300
actatgctag aatgtgaggt cctgggcaat gacattggac tgccaaagag agtcgttcag    6360
gtctggttcc agaatgcccg ggcaaaagaa aagaagtcca agttaagcat ggccaagcat    6420
tttggtataa accaaacgag ttatgaggga cccaaaacag agtgcacttt gtgtggcatc    6480
aagtacagcg ctcggctgtc tgtacgtgac catatctttt cccaacagca tatctccaaa    6540
gttaaagaca ccattggaag ccagctggac aaggagaaag aatactttga cccagccacc    6600
gtacgtcagt tgatggctca acaagagttg gaccggatta aaaaggccaa cgaggtcctt    6660
ggactggcag ctcagcagca agggatgttt gacaacaccc ctcttcaggc ccttaacctt    6720
cctacagcat atccagcgct ccagggcatt cctcctgtgt tgctcccggg cctcaacagc    6780
ccctccttgc caggctttac tccatccaac acagctttaa cgtctcctaa gccgaacttg    6840
atgggtctgc ccagcacaac tgttccttcc cctggcctcc ccacttctgg attaccaaat    6900
aaaccgtcct cagcgtcgct gagctcccca accccagcac aagccacgat ggcgatgggc    6960
cctcagcaac ccccccagca gcagcagcag cagcagcaac cacaggtgca gcagcctccc    7020
ccgccgccag cagcccagcc gccacccaca ccacagctcc cactgcaaca gcagcagcaa    7080
cgcaaggaca agacagtga gaaagtaaag gagaaggaaa aggcacacaa agggaaggg    7140
gaaccctgc ctgtccccaa gaaggagaaa ggagaggccc ccacggcaac tgcagccacg    7200
atctcagccc cgctgcccac catggagtat gcggtagacc ctgcacagct gcaggccctg    7260
caggccgcgt tgacttcgga ccccacagca ttgctcacaa gccagttcct tccttacttt    7320
gtaccaggct tttctcctta ttatgctccc cagatccctg gcgccctgca gagcgggtac    7380
ctgcagccta tgtatggcat ggaaggcctg ttcccctaca gccctgcact gtcgcaggcc    7440
ctgatggggc tgtccccagg ctccctactg cagcagtacc agcaatacca gcagagtctg    7500
caggaggcaa ttcagcagca gcagcagcgg caactacagc agcagcagca gcaaaaagtg    7560
cagcagcagc agcccaaagc aagccaaacc ccagtccccc ccggggctcc ttccccagac    7620
aaagaccctg ccaaagaatc ccccaaacca gaagaacaga aaaacacccc ccgtgaggtg    7680
tccccctcc tgccgaaact ccctgaagag ccagaagcag aaagcaaaag tgcggactcc    7740
ctctacgacc ccttcattgt tccaaaggtg cagtacaagt tggtctgccg caagtgccag    7800
gcgggcttca gcgacgagga ggcagcgagg agccacctga agtccctctg cttcttcggc    7860
cagtctgtgg tgaacctgca agagatggtg cttcacgtcc ccaccggcgg cggcggcggt    7920
ggcagtggcg gcggcggcgg cggtggcggc ggcggcggcg gcggcggctc gtaccactgc    7980
ctggcgtgcg agagcgcgct ctgtggggag gaagctctga gtcaacatct cgagtcggcc    8040
ttgcacaaac acagaacaat cacgagagca gcaagaaacg ccaaagagca ccctagttta    8100
ttacctcact ctgcctgctt ccccgatcct agcaccgcat ctacctcgca gtctgccgct    8160
cactcaaacg acagcccccc tccccgtcg gcgccgccc cctcctccgc ttcccccac    8220
gcctccagga agtcttggcc gcaagtggtc tcccgggctt cggcagcgaa gccccttct    8280
tttcctcctc tctcctcatc ttcaacggtt acctcaagtt catgcagcac ctcagggtt    8340
cagccctcga tgccaacaga cgactattcg gaggagtctg acacggatct cagccaaaag    8400
tccgacggac cggcgagccc ggtggagggt cccaaagacc ccagctgccc caaggacagt    8460
```

```
ggtctgacca gtgtaggaac ggacaccttc agattgtaag ctttgaagat gaacaataca   8520
aacaaatgaa tttaaataca aaaattaata acaaaccaat ttcaaaaata gactaactgc   8580
aattccaaag cttctaacca aaaaacaaaa aaaaaaaaaa aaagaaaaaa aagaaaaagc   8640
gtgggttgtt ttcccatata cctatctatg ccggtgattt tacattcttg tcttttctt    8700 ttcttttaat attaaaaaaa aaaaaaaagc cctaaccctg ttacattgtg tccttttgaa   8760
ggtactattg gtctgggaaa cagaagtccg cagggcctcc ctaatgtctt tggagcttaa   8820 acccttgta tatttgcccc ttttcaataa acgccccacg ctgatagcac agaggagccc    8880
ggcatgcact gtatgggaaa gcagtccacc ttgttacagt tttaaatttc ttgctatctt   8940
agcattcaga taccaatggc ttgctaaaag aaaaaaagaa atgtaatgtc ttttttattct  9000 caggtcaatc gctcacactt tgttttcaga atcattgttt tatatattat tgttttttca   9060
gttttttttt tttttttgt tccagaaaag attttttgtt ttgttaactt aaaaatgggc    9120
agaaagtatt caagaaaaac aatgtgaact gctttagctt tctggggatt tttaaggata   9180
gcttttctgc tgaagccaat ttcaagggga aaagttaagc actcccactt tcaaaaaaaa   9240
aaaaaaataa taccccacac acacaaagag tgttgaggac ttgtagctta aaaaaaataa   9300
gttttaaaaa ctgactttct gtatttatga tagatatgac cattttggt gttgagtaga    9360 ttgttgcatt ggaaatgaac tgaagcagta tggtagattt aaaaggaaaa aaaaaaaaaa   9420 acctttgtg tacatttagc tttttgtatg gtccagctga cagctcctca tttgatgttg    9480
tcttgttcat tcctagcaga tgatagattg caatccgttg attcgcctaa gcttttctcc   9540
ccttgtccct taattccact ttctctttct tgtcccttaa ttccacttc tctttccttc    9600 tcccacctcc cgtcctataa tctcccactt aaggtagctg ccttcattc ttagagggag    9660 ctgcagaatt attttataaa actaaagaaa gaatttcaag ggattctagg ggtcattagg   9720
atcctcacag attattttg gttggggagt tgaaactttt taaaggcata taattctagt    9780
tacctgtgtc tgttagcttt gtgcatttat tttttattta tccttctttt ggcttttttt   9840
tctttgtacc ccttcttttc ctccttgttt ggtaggagct tcaaatattc tttttttttc   9900
tatactaaag gatttgtttc catttgtgta attggctgtg tacttttctt ttctaaaaaa   9960 agttttggt tagggatttg gttttggtt ttgtgtttgt tttttctttc ctctctcaga    10020
aaaaaaaatt tcatgcttta aataaaatcc aaagacacac cctttcactg ctgatgcaga  10080
aaaaagggaa agggttcttg ttacttgaga atttgtttct gatttaaaca aacaagactt   10140
agtttaataa aagaaagaga aaacaaaag attcccaggt tgttatgtgc ttcttctgca    10200
agcagagagg caaatgttaa tgacaattcc atataccaaa agacacattt tttacttcaa   10260
agttttgtcc ttgtgttagg cagtctgagc agcgagtgat ccagagcgca gccaacaaag   10320
cagcagatag cagtgtacag aaagcaaaaa aggaactgta tgtgaggcac ttgtttctgt   10380
taatatccat attcctgtta acacacaccc tttctcatgt aaaagaaaa ataaataaat    10440 ggtctgaact ttgaaaactt tgtgctgcta aaacatagat tttggagaca aataaataga   10500
tgctttgctg tttcactttc atagctaaac atcaacagaa accatctccc cttgccccca   10560
aagtgtgaaa tccttcttcc cttcgttttc ttccttatgt ttcaaaaggg aactttgaag   10620
actgtgaata caggttccat tggtcacctt tcgggcttct ttccccagtg ctgaagccac   10680
tcatcgactt tgcaaaagac tggagcattc caagatctga aaatggattt tttttctttt   10740
tttctttttt agccgggact attttatttt tatgaatttg tttttagttt aatgaaatag   10800
```

```
tagatcctga aatgttgtac atatttctaa ctaggctgat gcacagtgca aattcctttt    10860
ttaattgttt tttttaagta gaaatactaa agaaagaata ccatctaact attcatacca    10920
gtatccagtt gtagcataag gtgtcaaaag caagtacgca aaacatttac tgttttaaca    10980
agctatttcc ttttaacaag aaatcttgta tttcttcctg tgtttgagat gaacattttt    11040
aaatttaaaa gttgtacagt ttttttgttt ccattatttt atcttgtttg taactctatg    11100
aaatatatat atatatattt tttgccattt aactgttgta tgttactctg tgtctgtacc    11160
atatagaaaa aaaattgttt ttgttttttgg ttctctatgt gatatcagtt aacaatgtaa    11220
cactagcttt acctgtcaaa ttctgctagg tcttctctga aaacgttgtt tttaaaaatg    11280
atattgcttg gtaatagtgc aatttctatc cttttccctc cccccctcaac ttttaagttc    11340 ttttctttat aattttgctg cccccctccct gatggtttgg gttttttgttt ttgttttttgt    11400 ttttttttttt catggagcta ctatgccatc ctccctctgt gaggcagagt gactgtcagt    11460
gttttgttat gccatgcctt gagctgtggg tgtttggcga caataaggtg gttgaataga    11520
ttggctgagc acacttccac ccacctagtg ttctcagagg ggttatgtga ttgtttcaac    11580
ctggagtggg ttgcacccctt aatgctttcc tctgcaacta aaccgcccac atatatgttc    11640
attgaaaaaa gtaagaataa ttctcagcac taacccagaa gtagcaaagc agtcagtgat    11700
ggtgaacatt agaggtcaaa catgagttag atgtttgtgg gctgacagcc atcgtggcta    11760
tgaccagtac tatttacaaa gcatgaattc actacaatgc tcaactgttt gtttagcttt    11820
atctcacttg gggaatttat tcctgtctgc tgcattgtag gtagctgggt aggatatatt    11880
tccacttgct ttttaaaatta gttcttcacc tccattgaca ctcgtttttt ggttttctcc    11940
ctatagtgtg ggttggtgct agacaccagt ctgacccaca gaatgggagt tatttcatcc    12000
atctttcctc catccttcca aaaaccacat atctacacaa ggaaaaattt aatacatcta    12060
ggaatttttt ttttaattac aagctattta aagagatgaa tgtggccaaa gttttacaca    12120
attgaaaata aagtaaaaca gacggcatgt gtttaaacct gagtttatca ggcatggcag    12180
gaagttgcag gagagagagg cagtgaccca agccagtgca cttgatgttc atggacatat    12240 attttttttta aataataaat taaaacattt taaatagaag cataaattga gttgtttgtt    12300
ggcgctgaga tactgcccac tgtgaaacaa gctttgact agttttttgt ttgtttactt     12360
tcttcagggg ggaggggggc aagtttgggt aggaaagaaa gcataaatga acgtgaccct    12420
gaggtgaaga ggtatatgaa cagcctttgc aatgtacaaa agaaaaaaaa aacaaaaaac    12480
aacaaaaaaa atagagcaag tgaaaccaaa aatgatgttc ttggtgtttt tctataatgt    12540
agtcttgtta gcttttttgt tactgtaaca atgctgatct cgaactgtac caaaatacat    12600
ggagactaac aaacagaacc acatggaact ttcaaactga aaaaaaaatt tgtcacaaaa    12660
actttgttgt catagttaag ttgattgtag atggtaattg aatatactcc tttgaaaata    12720
tttcatcaag tatgtttcct gctcattgtg atacattaaa aaaaaaatat gagcaaaa     12778
```

<210> SEQ ID NO 51
<211> LENGTH: 4826
<212> TYPE: DNA
<213> ORGANISM: Homo sapiens

<400> SEQUENCE: 51

```
gggcgcgggc agctctgcgt ccgaagctgc tccgacgccg tcgctgggac caagatggac        60
ctcccggcgc tgctccccgc ccgactgcg cgcggagggc aacatggcgg cggcccggc        120 ccgctccgcc gagccccagc gccgctcggc gcgagcccg cgcgccgccg cctgctactg       180
```

```
gtgcggggcc ctgaagatgg cgggcccggg gcgcggcccg gggaggcctc cgggccaagc    240
ccgccgcccg ccgaggacga cagcgacggc gactctttct tggtgctgct ggaagtgccg    300
cacggcggcg ctgccgccga ggctgccgga tcacaggagg ccgagcctgg ctcccgtgtc    360
aacctggcga gccgcccga gcagggcccc agcggcccgg ccgccccccc cggccctggc    420
gtagccccgg cgggcgccgt caccatcagc agccaggacc tgctggtgcg tctcgaccgc    480
ggcgtcctcg cgctgtctgc gccgcccggc cccgcaaccg cgggcgccgc cgctccccgc    540
cgcgcgcccc aggcctccgg ccccagcacg cccggctacc gctgccccga ccgcagtgc     600 gcgctggcct tcgccaagaa gcaccagctc aaggtgcacc tgctcacgca cggcggcggt    660
cagggccggc ggcccttcaa gtgcccactg gagggctgtg gttgggcctt cacaacgtcc    720
tacaagctca agcggcacct gcagtcgcac gacaagctgc ggcccttcgg ctgtccagtg    780
ggcggctgtg gcaagaagtt cactacggtc tataacctca aggcgcacat gaagggccac    840
gagcaggaga gcctgttcaa gtgcgaggtg tgcgccgagc gcttccccac gcacgccaag    900
ctcagctccc accagcgcag ccacttcgag cccgagcgcc cttacaagtg tgactttccc    960
ggctgtgaga agacatttat cacagtgagt gccctgtttt cccataaccg agcccacttc   1020
agggaacaag agctctttc  ctgctccttt cctgggtgca gcaagcagta tgataaagcc   1080
tgtcggctga aaattcacct gcggagccat acaggtgaaa gaccatttat ttgtgactct   1140
gacagctgtg gctggacctt caccagcatg tccaaacttc taaggcacag aaggaaacat   1200
gacgatgacc ggaggtttac ctgccctgtc gagggctgtg ggaaatcatt caccagagca   1260
gagcatctga aaggccacag cataacccac ctaggcacaa agccgttcga gtgtcctgtg   1320
gaaggatgtt gcgcgaggtt ctccgctcgt agcagtctgt acattcactc taagaaacac   1380
gtgcaggatg tgggtgctcc gaaaagccgt tgcccagttt ctacctgcaa cagactcttc   1440
acctccaagc acagcatgaa ggcgcacatg gtcagacagc acagccggcg ccaagatctc   1500
ttacctcagc tagaagctcc gagttctctt actcccagca gtgaactcag cagcccaggc   1560
caaagtgagc tcactaacat ggatcttgct gcactcttct ctgacacacc tgccaatgct   1620
agtggttctg caggtgggtc ggatgaggct ctgaactccg gaatcctgac tattgacgtc   1680
acttctgtga gctcctctct gggagggaac ctccctgcta ataatagctc cctagggccg   1740
atggaacccc tggtcctggt ggcccacagt gatattcccc caagcctgga cagccctctg   1800
gttctcggga cagcagccac ggttctgcag cagggcagct tcagtgtgga tgacgtgcag   1860
actgtgagtg caggagcatt aggctgtctg gtggctctgc ccatgaagaa cttgagtgac   1920
gacccactgg ctttgacctc caatagtaac ttagcagcac atatcaccac accgacctct   1980
tcgagcaccc cccgagaaaa tgccagtgtc ccggaactgc tggctccaat caaggtggag   2040
ccggactcgc cttctcgccc aggagcagtt gggcagcagg aaggaagcca tgggctgccc   2100
cagtccacgt tgcccagtcc agcagagcag cacggtgccc aggacacaga gctcagtgca   2160
ggcactggca acttctattt ggtatgaagc actctattca gtcaccacca tataggtcac   2220
ttctctcata ctcggtcttg aggatattct ggattaatcc tttctatgca gacgtttctg   2280
gtttacaaaa ggacgcagcc ctggactaca agtctgaac  tgacaagttc ttatgacctt   2340
gacaaatcac cttaacccat ctgagcctta aattctcatt tatttcctgc ataaggagat   2400
ttggctaaat gctttctgag gtcctttgga gtcctgtggc tccatggtaa tgtgctcctt   2460
tccttgaaga ttgggggttt tgtaatgttg agatactttg cctctatgct tgtcagctca   2520
```

```
tgaccagtcc tagaagagga gtcgagacat aagccacctt cagaggttca atggaaactt    2580
taaaaccata ccaaactctt tttttaaaatt agaattaaca agaaaaaaaa aaagggtggg    2640
gtttatgagc cttagttctt ggaggattat aagagtactt ccccagtttt gaggctggac    2700
agttaatata cttatatca attatacatt aatataatt taatttaaaa taatttaaag    2760
attcttagga gatagtctga cttcctgac ctagatggga atgatcagat agggattttt    2820
tttgtggcac aggctaaatt tgatggtgac atttatattg ttgagaatgt tacatcttat    2880
tttaccacaa cttttaaaaa atgttacatc ttttgcagta ggatcagttg tgaggcacat    2940
agtagctgag ctccatggaa gccacctttc atttctttca gtcagagagg aggacagtct    3000
ctgtctctgc atttctggtg tcttgcttgt cggtggcaga gccatgcttg ccggcatttg    3060
cttaggcggc catagtagtt gctaagtgta caggtgactg ggcagggatg ggaggtggcc    3120
acaggtcaga gacaagtgct cagtcagtcc ctggtgccag gactgtgtgc ctcggtgcct    3180
tgggaaatgg aagctccctg gtgcagctgc agctgtgggt ggaggtagag aagccagcaa    3240
gaccttggtc ttaaccccgt gttcattttc ttgctagctg tgtgacgttg ggctacctcg    3300
cttctctgag tacaaatggt gtgtggtgaa tgggtcccag gtatgctacg agctttgagg    3360
gctgctcttt ttctcttcat agcgataagt gttaaactgt cttcttagg aaacgttcac    3420 agacttgcaa cagctgatgt cctctgagta ctgtctgact ccctcaggca agttcctgaa    3480
ttcagtacca tcattattat tttgtgtaa gactttgaca aagtatagcc cctgccacca    3540
gagcagcctg tacagtgggt ctctaaggtg ggacctgccc cgggcctgcc atgcacgtgt    3600
gtgaaacagc gtgaaaagtg tcgcggtaag gtgaccctgg gttacccagg caaggctcgg    3660
tgtttgtttc agaaagcaga gaagtatgta attgatttta aaagtttctg tttaaaatat    3720
ttggctatgt tttagactat gaaggaatga actttgcttc tctggataag aaagtcacat    3780
acattgttcc agctccaagt ttgttcggcc ctcgccacaa gtggatgtag cgtttggccc    3840
tttgtgtgcc ttgctggtga ctctggtttt gggagctcgg atatgtccca gaagcaggct    3900
tatggcactt ctgtagctcc cttgctaccc ttcctttgtg tctagataag tgactgacat    3960
gcttttcttt ggtctcagga aagtgggggc tcagcaagaa ctgattaccg agccattcaa    4020
ctagccaagg aaaaaaagca gagaggagcg gggagcaatg caggtgaggc cgtgtgtgct    4080
gcagccggac gagcaagggc ctgagggttc tctgtcactg ttactggcag aagaaacaca    4140
gcaggtgttt ctgtgctctt ggtttttactt ttctgttcag aatacccttt tatcaactcc    4200 ttagtttttat ttgaacttaa gggaaaaaat tagtaacaaa attcccagca tcagtatgaa    4260
catattttat ttgcctaaac aagctttgtg aaagttaagc gttcaaacac cagtgtcagt    4320
tacctggaag gctactaagg taaataagca aagcaggcca gttgtcagga aagcagagat    4380
tgtgcctggt gctgaatggc cttggggcct gatcttggca tggcagagac ctggggactg    4440
ccactgtccc caggtacgtg tacatggagc caaactgtgt gtcctgtggc attgtcagag    4500
ttatgttgaa atcttatttg aaaatgttag caacttactt gcattttttaa agaccaaaca    4560 agagctggta acctatggcc tcaagcatct gtccttccta aaaatggaat agtgggatgt    4620
agtgcttaat ggaaactgct aaatcttttt ctaaaaacta acagtggatt tttaaaatat    4680
attgtttttt gtgtatttca tttgtccttt gtatttatct aaaagggttg atatgatttt    4740
atatcttgct ctctattcct aatagtatta tgacttctta tttaaaataa ataacaattg    4800 ccggtttttct gttaaaaaaa aaaaa                                         4826
```

<210> SEQ ID NO 52
<211> LENGTH: 4344
<212> TYPE: DNA
<213> ORGANISM: Homo sapiens

<400> SEQUENCE: 52

| | | | | | |
|---|---|---|---|---|---|
| gttggcagag | cagttgtcct | ggatggcgga | gccttgggtt | ccggggggcct | gggacctgca | 60 |
| actctttcta | caagatatca | agttattcta | gtacaaccat | ataaataaat | aatacctgaa | 120 |
| gtctcagtgt | aacatggaca | attaacagtg | atgacagata | aatacagacg | catgggatc | 180 |
| aaatactagg | caaaacgctt | tttaaaagtg | tatcaggctt | ttaagaaaca | ctgcaggatc | 240 |
| ctgtctatct | taatgctgat | agagctcagc | taaaaattta | ggaggttcta | gtattcttca | 300 |
| tggctgaagc | tgagagagtc | tgaaaccctg | atgcttaagc | tccattctag | atcatagctc | 360 |
| caactccttc | aggatataag | gaaaagagat | tatatttcca | caatgataga | tctttggttg | 420 |
| tacaggtttc | ccaatgagtg | gatcatgatg | accgtattgt | agggacttgc | catagtatgg | 480 |
| ctgcttcccg | atctactcgt | gttacaagat | caacagtggg | gttaaacggc | ttggatgaat | 540 |
| cttttttgtgg | tagaactttta | aggaatcgta | gcattgcgca | tcctgaagaa | atctcttcta | 600 |
| attctcaagt | acgatcaaga | tcaccaaaga | agagaccaga | gcctgtgcca | attcagaaag | 660 |
| gaaataataa | tgggagaacc | actgatttaa | aacagcagag | tacccgagaa | tcatgggtaa | 720 |
| gccctaggaa | aagaggactt | tcttcttcag | aaaaggataa | catagaaagg | caggctatag | 780 |
| aaaattgtga | gagaaggcaa | acagaacctg | tttcaccagt | tttaaaaga | attaagcgtt | 840 |
| gtcttagatc | tgaagcacca | aacagttcag | aagaagattc | tcctataaaa | tcagacaagg | 900 |
| agtcagtaga | acagaggagt | acagtagtgg | acaatgatgc | agattttcaa | gggactaaac | 960 |
| gagcttgtcg | atgtcttata | ctggatgatt | gtgagaaaag | ggaaattaaa | aggtgaatg | 1020 |
| tcagtgagga | agggccactt | aattctgcag | tagttgaaga | aatcacaggc | tatttggctg | 1080 |
| tcaatggtgt | tgatgacagt | gattcagctg | ttataaactg | tgatgactgt | cagcctgatg | 1140 |
| ggaacactaa | acaaaatagc | attggttcct | atgtgttaca | ggaaaaatca | gtagctgaaa | 1200 |
| atggggatac | ggatacccaa | acttcaatgt | tccttgatag | taggaaggag | gacagttata | 1260 |
| tagaccataa | ggtgccttgc | acagattcac | aagtgcaggt | caagttggag | gaccacaaaa | 1320 |
| tagtaactgc | ctgcttgcct | gtggaacatg | ttaatcagct | gactactgag | ccagctacag | 1380 |
| ggccctttttc | tgaaactcag | tcatctttaa | gggattctga | ggaggaagta | gatgtggtgg | 1440 |
| gagatagcag | tgcctcaaaa | gagcagtgta | aagaaaacac | caataacgaa | ctggacacaa | 1500 |
| gtcttgagag | tatgccagcc | tccggagaac | ctgaaccatc | tcctgttcta | gactgtgttt | 1560 |
| cagctcaaat | gatgtctttta | tcagaacctc | aagaacatcg | ttatactctg | agaacctcac | 1620 |
| cacgaagggc | agccctacc | agaggtagtc | ccactaaaaa | cagttctcct | tacagagaaa | 1680 |
| atggacaatt | tgaggagaat | aatcttagtc | ctaatgaaac | aaatgcaact | gttagtgata | 1740 |
| atgtaagtca | atctcctaca | aatcctggtg | aaatttctca | aaatgaaaaa | gggatatgtt | 1800 |
| gtgactctca | aaataatgga | agtgaaggag | taagtaaacc | accctcagag | gcaagactca | 1860 |
| atattggaca | tttgccatct | gccaaagaga | gtgccagtca | gcacattaca | gaagaggaag | 1920 |
| atgatgatcc | tgatgtttat | tactttgaat | cagatcatgt | ggcactgaaa | cacaacaaag | 1980 |
| attatcagag | actattacag | acgattgctg | tactcgaggc | tcagcgttct | caagcagtcc | 2040 |
| aagaccttga | aagtttaggc | aggcaccaga | gagaagcact | gaaaaatccc | attggatttg | 2100 |
| tggaaaaact | ccagaagaag | gctgatattg | ggcttccata | tccacagaga | gttgttcaat | 2160 |

```
tgcctgagat cgtatgggac caatataccc atagccttgg gaattttgaa agagaattta    2220
aaaatcgtaa aagacatact agaagagtta agctagtttt tgataaagta ggtttacctg    2280
ctagaccaaa aagtccttta gatcctaaga aggatggaga gtccctttca tattctatgt    2340
tgcctttgag tgatggtcca gaaggctcaa gcagtcgtcc tcagatgata agaggacgct    2400
tgtgtgatga taccaaacct gaaacattta accagttgtg gactgttgaa gaacagaaaa    2460
agctggaaca gctactcatc aaatacccctc ctgaagaagt agaatctcga cgctggcaga    2520
agatagcaga tgaattgggc aacaggacag caaaacaggt tgccagccga gtacagaagt    2580
atttcataaa gctaactaaa gctggcattc cagtaccagg cagaacacca aacttatata    2640
tatactccaa aaagtcttca acaagcagac gacagcaccc tcttaataag catctcttta    2700
agccttccac tttcatgact tcacatgaac cgccagtgta tatggatgaa gatgatgacc    2760
gatcttgttt tcatagccac atgaacactg ctgttgaaga tgcatcagat gacgaaagta    2820
ttcctatcat gtataggaat ttacctgaat ataaagaact attacagttt aaaaagttaa    2880
agaagcagaa acttcagcaa atgcaagctg aaagtggatt tgtgcaacat gtgggcttta    2940
agtgtgataa ctgtggcata gaacccatcc agggtgttcg gtggcattgc caggattgtc    3000
ctccagaaat gtctttggat ttctgtgatt cttgttcaga ctgtctacat gaaacagata    3060
ttcacaagga agatcaccaa ttagaaccta tttataggtc agagacattc ttagacagag    3120
actactgtgt gtctcagggc accagttaca attaccttga cccaaactac tttccagcaa    3180
acagatgaca tggaagagaa catcatttac tagtcctctt caacacatag caatggtatc    3240
attgttaatt atgtgcacag tttggaaaga ttctctgctt tcccagaaat gacactcaca    3300
gcatgagagc ttcctgagtg ttctcgtcaa gtacagctct gcaccgttgt ggctctagat    3360
cactgttcag cagctgaaca ttcctggtga gcaaaggttt ccctggtgaa tttttcacca    3420
ctgcgtttta ggtggtgatc ttaaatgggt gagatggaac gagagcacac attaaagaga    3480
gagtaaattc caaaggtttc aaagaacttg gtcataaata tgataatgag aagacaaagt    3540
atttatatta aaacagttta gtagccttca gttttgtgaa aatagttttc agcacagaaa    3600
ctgacttctt tagacaaagt tttaaccaat gatggtgttt gcttctagga tatacactt    3660
aaaagaactc actgtcccag tggtggtcat tgatggcctt tagtaaattg gagctgctta    3720
atcatattga tatctaattt cttttaacca caatgaattg tccttaatta ccaacagtga    3780
agcactacag gaggcaactg tggcattgct tccttaacca gctcatggtg tgtgaatgtt    3840
ataaaattgt cactcagata tattttttaa atgtaatgtt atataagatg atcatgtgat    3900
gtgtacaaac tatggtgaaa agtgccagtg gtagtaactg tgtaaagttt ctaattcaca    3960
acattaattc ctttaaaata cacagccttc tgcctctgta tttggagttg tcagtacaac    4020
tcatcaaaga aaactgccta atataaaaat catatatatg gtaataattt ccctcttttg    4080
tagtctgcac aagatccata aaagattgta tttttattac tatttaaaca agtgattaaa    4140
tttagtctgc acagtgagca agggttcaca tgcattcttt tatactgctg gattttgttg    4200
tgcatcatt aaaacatttt gtatgtttct tcttatctgt gtatacagta tgttcttgaa    4260
tgatgttcat ttgtcaggag aactgtgaga aataaactat gtggatactg tctgtttata    4320
ttaaaagaaa aaaaaaaaa aaaa                                            4344
```